(12) United States Patent
Cao et al.

(10) Patent No.: US 8,697,662 B2
(45) Date of Patent: Apr. 15, 2014

(54) METHODS FOR TREATING KAPOSI SARCOMA

(75) Inventors: Liangxian Cao, Parlin, NJ (US); Thomas W. Davis, South Orange, NJ (US); Samit Hirawat, Chatham, NJ (US); Harry H. Miao, Wellsley, MA (US); Langdon Miller, Seattle, WA (US); Marla L. Weetall, Morristown, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 13/321,233

(22) PCT Filed: May 27, 2010

(86) PCT No.: PCT/US2010/036287
§ 371 (c)(1),
(2), (4) Date: Mar. 9, 2012

(87) PCT Pub. No.: WO2010/138652
PCT Pub. Date: Dec. 2, 2010

(65) Prior Publication Data
US 2012/0157400 A1    Jun. 21, 2012

Related U.S. Application Data

(60) Provisional application No. 61/181,651, filed on May 27, 2009.

(51) Int. Cl.
*A61K 31/437* (2006.01)

(52) U.S. Cl.
USPC .......................................................... 514/43

(58) Field of Classification Search
USPC .......................................................... 514/43
See application file for complete search history.

(56) References Cited

U.S. PATENT DOCUMENTS

| | | | |
|---|---|---|---|
| 3,328,412 | A | 6/1967 | Atkinson et al. |
| 5,206,377 | A | 4/1993 | McAfee |
| 5,314,908 | A | 5/1994 | McAfee |
| 5,500,431 | A | 3/1996 | Audia et al. |
| 5,760,051 | A | 6/1998 | Audia et al. |
| 5,866,587 | A | 2/1999 | de Nanteuil et al. |
| 6,090,945 | A | 7/2000 | Audia et al. |
| 6,093,723 | A | 7/2000 | Miao et al. |
| 6,720,331 | B2 | 4/2004 | Yeh et al. |
| 7,341,749 | B2 | 3/2008 | Hall et al. |
| 7,601,840 | B2 | 10/2009 | Moon et al. |
| 7,767,689 | B2 | 8/2010 | Moon et al. |
| 7,872,133 | B2 | 1/2011 | Ohmoto et al. |
| 8,076,352 | B2 | 12/2011 | Cao et al. |
| 8,076,353 | B2 | 12/2011 | Cao et al. |
| 8,367,694 | B2 | 2/2013 | Moon et al. |
| 8,372,860 | B2 | 2/2013 | Moon et al. |
| 2003/0040527 | A1 | 2/2003 | Yeh et al. |
| 2003/0130293 | A1 | 7/2003 | Bamdad |
| 2004/0116458 | A1 | 6/2004 | Sawyer et al. |
| 2005/0143371 | A1 | 6/2005 | Meyers et al. |
| 2005/0282849 | A1 | 12/2005 | Moon et al. |
| 2006/0241084 | A1 | 10/2006 | Roifman et al. |
| 2007/0254878 | A1 | 11/2007 | Cao et al. |
| 2008/0103164 | A1 | 5/2008 | Gudmundsson et al. |
| 2008/0103213 | A1 | 5/2008 | Kurzrock et al. |
| 2008/0293766 | A1 | 11/2008 | Diamond et al. |
| 2009/0017021 | A1 | 1/2009 | Davis et al. |
| 2010/0125065 | A1 | 5/2010 | Moon et al. |
| 2010/0158858 | A1 | 6/2010 | Cao et al. |
| 2010/0179132 | A1 | 7/2010 | Moon et al. |
| 2011/0160190 | A1 | 6/2011 | Moon et al. |
| 2012/0157401 | A1 | 6/2012 | Cao et al. |
| 2012/0157402 | A1 | 6/2012 | Cao et al. |
| 2012/0178707 | A1 | 7/2012 | Cao et al. |
| 2012/0202763 | A1 | 8/2012 | Almstead et al. |
| 2012/0202801 | A1 | 8/2012 | Cao et al. |

FOREIGN PATENT DOCUMENTS

| | | |
|---|---|---|
| EP | 0357122 A2 | 3/1990 |
| EP | 0549916 A2 | 7/1993 |
| FR | 2662940 A1 | 12/1991 |
| JP | 3-287586 | 12/1991 |
| JP | 4275221 | 9/2002 |
| WO | WO 91/18604 | 12/1991 |
| WO | WO 94/10175 | 5/1994 |
| WO | WO 95/26723 | 10/1995 |
| WO | WO 97/37658 | 10/1997 |
| WO | WO 02/062339 A1 | 8/2002 |
| WO | WO 02/064590 A2 | 8/2002 |
| WO | WO 02/064591 A2 | 8/2002 |
| WO | WO 03/020279 | 3/2003 |

(Continued)

OTHER PUBLICATIONS

Belzil C. Therapeutic potential for inhibition of HIV activation. Lethbridge Undergrad Res J vol. 1, No. 2, pp. 1-9, 2006.*
U.S. Appl. No. 13/274,412, filed Oct. 17, 2011, Cao et al.
Begum et al., 1996, "Chemistry and biological activity of a tryptamine and beta-carboline series of bases", Drug Research; 12(46):1163-1168.
Berrougui et al., 2005, "Cytotoxic activity of methanolic extract and two alkaloids extracted from seeds of *Peganum harmala* L", Journal of Natural Remedies; 5(1):41-45.
Boyer et al., 2002, "Small molecule inhibitors of KDR (VEGFR-2) kinase: an overview of structure activity relationships", Current Topics in Medicinal Chemistry; 2(9):973-1000.
Cao et al., 2005, "Synthesis and in vitro cytotoxic evaluation of 1,3-disubstituted and 1,3,9-trisubstituted beta-carboline derivatives", European Journal of Medicinal Chemistry; 40(3):249-257.
Database WPI Accession No. 1992-376264, Abstract of JP 4275221, 1992, Taisho Pharm. Co., Ltd.
Fuhrmann-Benzakein et al., 2000, "Elevated levels of angiogenic cytokines in the plasma of cancer patients", International Journal of Cancer; 85(1):40-45.

(Continued)

*Primary Examiner* — Wu-Cheng Winston Shen
*Assistant Examiner* — Yih-Horng Shiao
(74) *Attorney, Agent, or Firm* — Jones Day

(57) ABSTRACT

Methods for treating Kaposi's sarcoma involving the administration of a compound that selectively inhibits pathological production of human VEGF are described. The compound can be administered as a single-agent therapy or in combination with one or more additional therapies to a human in need of such treatment.

18 Claims, 37 Drawing Sheets

(56) References Cited

FOREIGN PATENT DOCUMENTS

| | | |
|---|---|---|
| WO | WO 03/033496 A1 | 4/2003 |
| WO | WO 03/099821 A1 | 12/2003 |
| WO | WO 2004/113336 A1 | 12/2004 |
| WO | WO 2005/007672 A2 | 1/2005 |
| WO | WO 2005/009370 A2 | 2/2005 |
| WO | WO 2005/070930 A2 | 8/2005 |
| WO | WO 2005/089764 A1 | 9/2005 |
| WO | WO 2005/115470 A2 | 12/2005 |
| WO | WO 2006/015035 A1 | 2/2006 |
| WO | WO 2006/058088 A2 | 6/2006 |
| WO | WO 2006/113703 A2 | 10/2006 |
| WO | WO 2007/002051 A1 | 1/2007 |
| WO | WO 2008/127714 A1 | 10/2008 |

OTHER PUBLICATIONS

Hirawat et al., 2006, "51 Poster Phase 1 single-dose safety, PK, and food-effect study of PTC299, a novel VEGF expression inhibitor for treatment of solid tumors", European Journal of Cancer, Suppl; 4(12):19-20.

Hirawat et al., 2007, "Phase 1 studies assessing the safety, PK, and VEGF-modulating effects of PTC299, a novel VEGF expression inhibitor", Journal of Clinical Oncology ASCO Annual Meeting Proceedings Part 1; 25(18s):Abstract 3562.

International Search Report of International application PCT/US2010/036287, mailed Oct. 15, 2010.

Ishida et al., 1999, "Antitumor Agents 201. Cytotoxicity of harmine and beta-carboline analogs", Bioorganic & Medicinal Chemistry Letters; 9(23):3319-3324.

Nicolaus et al., 1983, "Symbiotic approach to drug design", Decision Making in Drug Research; pp. 173-186.

Venkov et al., 1999, "Synthesis of 2-acyltetrahydro-β-carbolines by an intramolecular α-amidoalkylation reaction", Synthetic Communications; 29(3):487-494.

Written Opinion of International application PCT/US2010/036287, mailed Oct. 15, 2010.

Ardill et al., 1990, "X=Y—ZH compounds as potential 1,3-dipoles. Part 29. The iminium ion route to azomelhine ylides. Reaction of cyclic secondary amines with mono- and bi-functional aldehydes," Tetrahedron 45(18):6449-6466.

Audia et al., 1996, "Potent, Selective Tetrahydro-beta-carboline Antagonists of the Serotonin 2B ($5HT_{2B}$) Contractile Receptor in the Rat Stomach Fundus," J. Med. Chem. 39:2773-2780.

Cleaveland et al., "Identitication of a Novel Inhibitor (Nsc 665564) of Dihydroorotate Dehydrogenase With a Potency Equivalent to Brequinar," Biochemical and Biophysical Research Communications 223(3):654-659 (1996).

Database Accession No. 84862, 570837, 578504, 585452, 690268 (XRN) accompanied by Aghbalian et al., 1972, "Synthesis Based on Harmine and Tetrahydroharmine," Armyanskii Khimicheskii Zhurnal 25:689-692; Partial European Search Report for EP11178488 dated May 9, 2012, p. 4.

Database REAXYS [Online], Elsevier Information Systems GmbH, Frankfurt/Main; XP002675485, Database Accession No. 84862, 230057, 306267 (XRN), accompanied by Fischer, 1897, "Über Harmin und Harmalin," Ber. Dtsch. Chem. Ges. 30(3):2481-2489; Fischer, 1901, "Chemische Studien der Alkaloids der Steppenraute (*Peganum harmala*)," Chem. Zentralbl. 72(1):957-959; Partial European Search Report for EP11178488 dated May 9, 2012, p. 2.

Database REAXYS [Online], Elsevier Information Systems GmbH, Frankfurt/Main; XP002675486, Database Accession No. 207280, 3918373 (XRN), accompanied by Fischer, 1914, "Über Harmin und Harmalin," Ber. Dtsch. Chem. Ges. 47:99-107 ; Partial European Search Report for EP11178488 dated May 9, 2012, p. 3.

Formagio et al., 2009, "Synthesis and antiviral activity of β-carboline derivatives bearing a substituted carbohydrazide at C-3 against poliovirus and herpes simplex virus (HSV-1)," Eur. J. Med. Chem. 44:4695-4701.

Hino et al., 1990, "2-Hydroxy-1-substituted-1,2,3,4-tetrahydro-β-carbolines. The Pictet-Spengler Reaction of N-Hydroxytryptamine with Aldehydes," Chem. Pharm. Bull. 38(1):59-64.

Lakhontov et al., 1958, "Reduction of Derivatives of Harmine with Sodium Borohydride to Derivatives of Py-Tetrahydroharmine" Zhurnal Obshchei Khimii 28(11):3139-3141.

Ishida et al., 1999, "Antitumor agents 201. Cytotoxicity of harmine and beta-carboline analogs," Bioorganic Med. Chem. Letters; 9: 3319-3324.

Jiang et al., 2003, "Potassium Superoxide as an Alternative Reagent For Winterfeldt Oxidation of β-Carbolines," Organic Letters 5(1):43-46.

Kawashima et al., 1995, "Synthesis and Pharmacological Evaluation 1,2,3,4-Tetrahydro-β-Carboline Derivatives," Chem. Pharm. Bull. 43(5):783-787.

Kawate et al., 1999, "Chiral Auxiliary Approach to the Asymmetric Pictet-Spengler Reaction of Tryptamines," Heterocycles 50(2):1033-1039.

Lehmann et al., 1987, "Lactamisation of 4.9-Dihydropyrano [3.4-b] indol-1(3H)-ones.—A New Synthetic Route to the beta-Carboline Ring System," Archiv der Pharmazie 320(1):30-36.

Lehnert et al., 1994, "DNA topoisomerase II inhibition by substituted 1,2,3,4-tetrahydro-β-carboline derivatives," Bioorganic & Medicinal Chemistry Letters 4(20):2411-2416.

McNulty et al., 1991, "Diastereoselective Pictet-Spengier reaction of L-(Boc) prolinai: a biomimetic synthesis of eudistomins H and I, and woodinine," Tetrahedron Letters 32(37):4875-4878.

Miller et al., 2010, "Substituted tetrahydro-β-carbolines as potential agents lorthe treatment of human papillornavirus infection," Bioorg. Med. Chem. Lett. 20:256-259.

Rubtsov et al., 1959, "Synthesis of Py—N—Alkyltetrahydroharmines" Zhurnal Obshchei Khimii 29:3232-3235.

Saiga et al., 1987, "Synthesis of 1,2,3,4-tearahydro-beta-carboline derivatives as hepatoprotective agents, III, Introduction of substituents onto methyl 1,2,3,4-tetrahydro-beta-carboline-2-carbodithioate," Chem. Pharm. Bull. 35(8), 3284-3291.

Schoenenberger et al., 1986, "Fragmentation of Optically Active (1-Phenylethyl)- and (1-Naphthylethyl) ureas in Refluxing Alcohols: Easy Preparation of Optically Active Amines of High Optical Purity," Helvetica Chimica Acta 69(6):1486-1497.

Siddiqui et al., 1992, "Preparation of Tetrahydrohannine Analogues—Their Antibacterial, Bronchodilator and Cytotoxic Activity and Effect on Central Nervous System," Proc. Pakistan Acad. Sci. 29(4):285-298.

Soe et al., 1995,"Asymmetric Pictet-Spengler Reaction with a Chiral N-(β-3-indolyl)-ethyl-1-methylbenzylamine," Tetrahedron Letters 36(11):1857-1860.

Solomina et al., 1990, "Synthesis and Pharmacological Properties of 1-R-2-[3'-R'-Amino-2-Hydroxypropyl]-1,2,3,4-Tetrahydro-β-Carbolines," Pharmaceutical Chemistry Journal, 24(4):272-275.

Tsuji et al., 2002, "Pictet-Spengler Reaction of Nitrones and Imines Catalyzed by Yb(OTf)$_3$-TMSCI" Chem. Lett. 4: 428-429.

Wu et al., 2002, "A Versatile Linkage Strategy for Solid-Phase Synthesis of N,N-Dimethyltryptamines and β-Carbolines," Organic Letters 4(23):4033-4036.

Yamada et al., 1998, "Chiral Lewis Acid-Mediated Enantioselective Pictet-Spengler Reaction of $N_b$-Hydroxytryptamine with Aldehydes," J. Org. Chem. 63(18):6348-6354.

Office Action mailed May 9, 2013 for U.S. Appl. No. 13/321,213, filed Mar. 23, 2012.

Office Action mailed Oct. 8, 2013 for U.S. Appl. No. 13/321,271, filed Mar. 23, 2012.

Office Action mailed Sep. 9, 2013 for U.S. Appl. No. 13/321,257, filed Apr. 25, 2012.

Saaristo et al., 2000, "Mechanisms of angiogenesis and their use in the inhibition of tumor growth and metastasis," Oncogene 19:6122-6129.

Notice of Allowance mailed Dec. 6, 2013 for U.S. Appl. No. 13/321,213.

* cited by examiner

A. Vehicle

B. Compound #10-Treated

A.

B.

A.

B:

A:

B.

A. Tumor VEGF Levels

B. Size-Normalized VEGF Levels

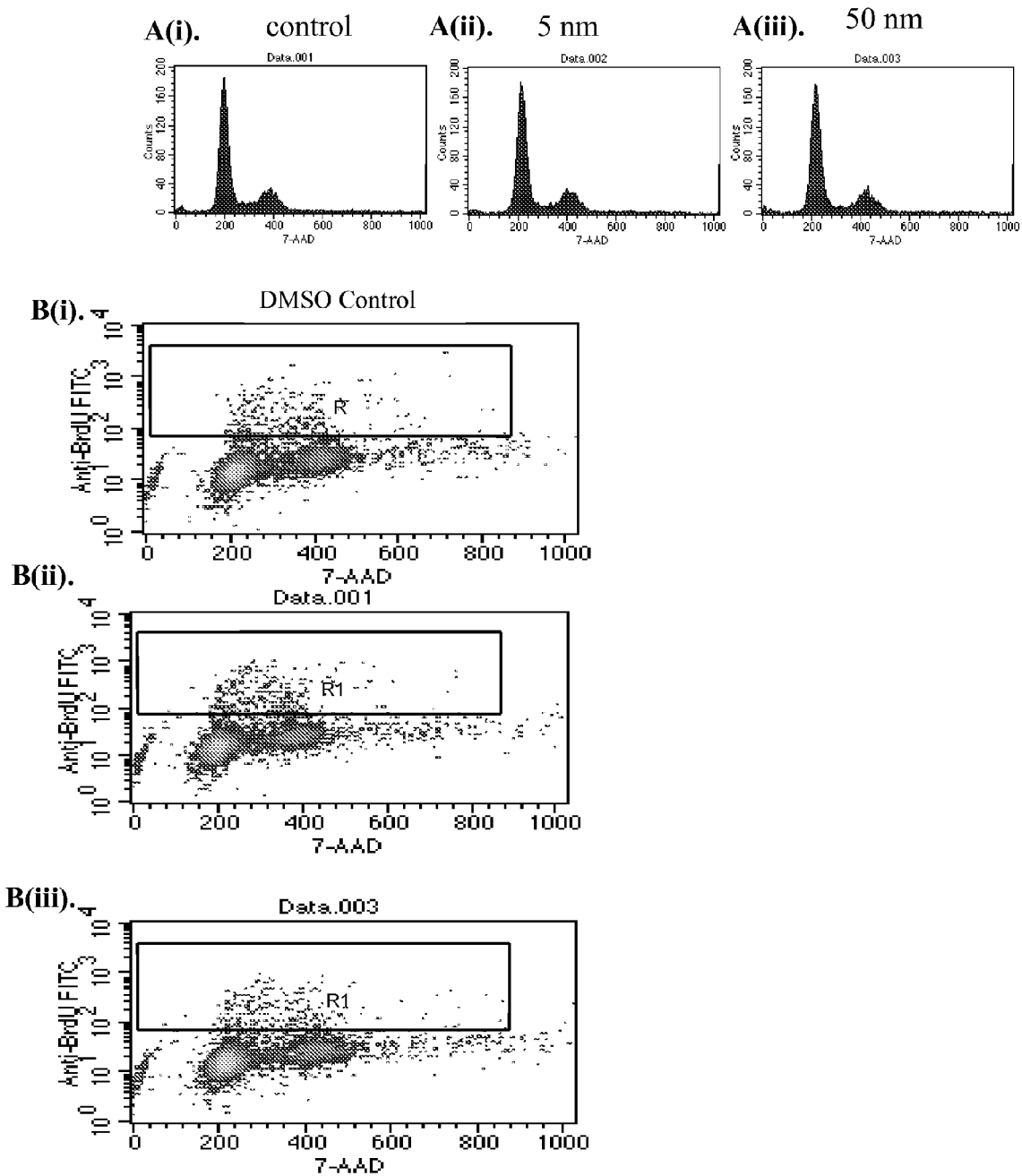
Fig. 31A-B

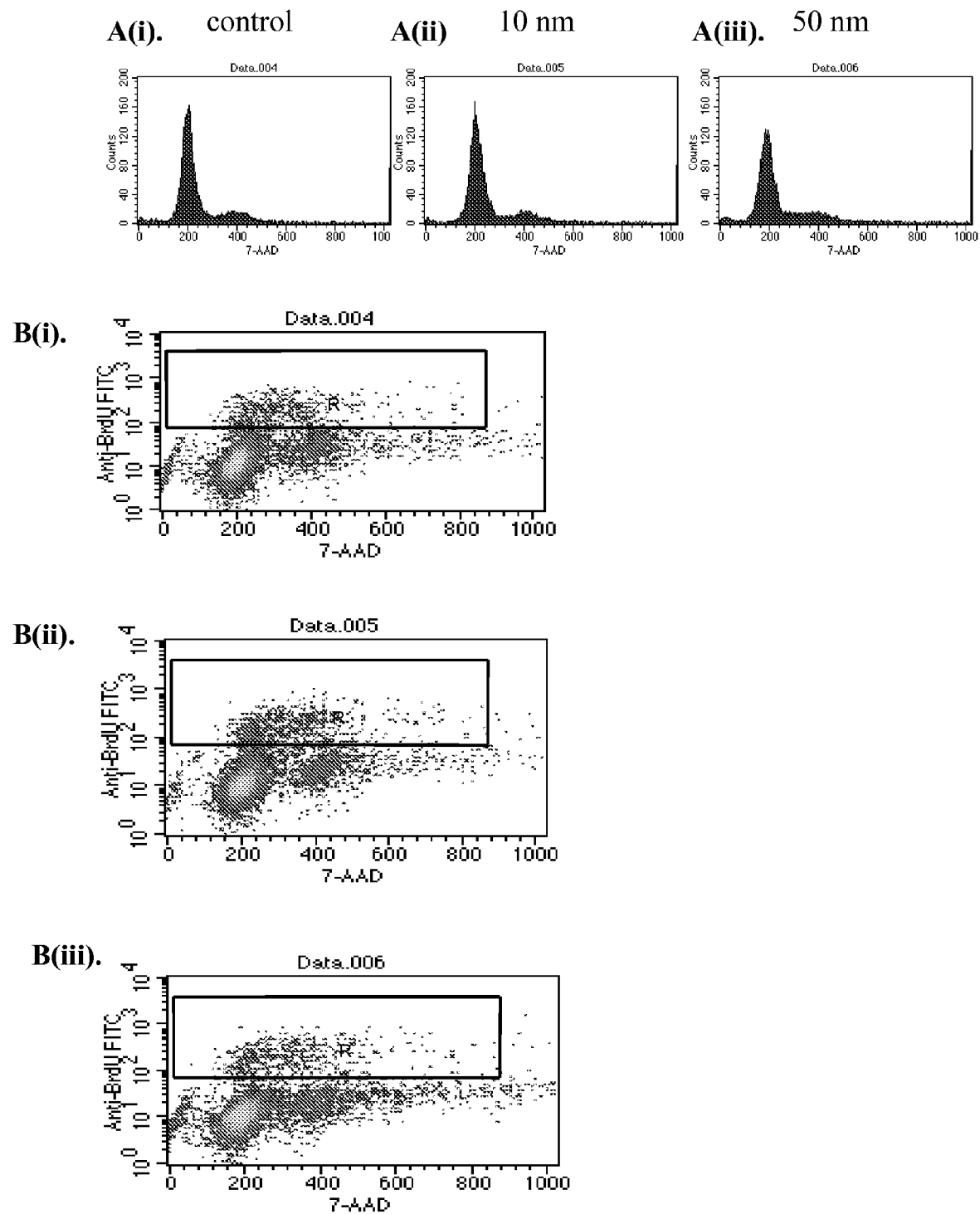
Fig. 32A-B

METHODS FOR TREATING KAPOSI SARCOMA

CROSS REFERENCE TO RELATED APPLICATIONS

This application is a national stage application of International Application No. PCT/US2010/036287, filed May 27, 2010, which claims the benefit of priority to U.S. Provisional Patent Application No. 61/181,651, filed May 27, 2009, each of which is incorporated herein by reference in its entirety and for all purposes.

1. INTRODUCTION

Methods for treating Kaposi sarcoma (KS) involving the administration of a compound that selectively inhibits pathological production of human vascular endothelial growth factor (VEGF) are described. The compound can be administered as a single-agent therapy or in combination with one or more additional therapies to a human in need of such treatment.

2. BACKGROUND

2.1 Kaposi Sarcoma

KS is a cancer that develops from the cells that line lymph or blood vessels. It was first described in 1872 by the Hungarian dermatologist Moritz Kaposi. Before the advent of widespread infection with the human immunodeficiency virus (HIV) and the acquired immunodeficiency syndrome (AIDS) epidemic, it was considered a rare condition.

Most KS cases in the US develop in people infected with HIV. It has been estimated that an HIV-infected person has a 20,000-fold increased risk of developing KS compared with people without HIV. AIDS patients with KS increased the rate of KS in the US more than 20 times, peaking at 47 cases per million people (per year) in the early 1990s. Early in the AIDS epidemic, patients infected with HIV in the US were estimated to have a 1 in 2 chance of developing KS. With new treatments for AIDS, KS has become less common in the US, with about 7 cases per million people each year (American Cancer Society website; www.cancer.org/docroot/CRI/CRI_2_3x.asp?dt=21; information last revised Mar. 14, 2006).

KS cells form purple, brown or red lesions on the skin that are usually papular (i.e, palpable or raised). In many cases, these skin lesions do not cause any symptoms; in other cases, they may cause painful swelling, especially in the legs, groin area or skin around the eyes. KS can cause serious problems, and can even become life-threatening when the lesions are in the lungs, liver or digestive tracts. Lesions in the digestive tract may cause blockage, resulting in nausea, vomiting, abdominal pain and occasionally bleeding. Lesions in the lungs can cause difficulty breathing.

KS is caused by the KS herpesvirus (KSHV), which is also called human herpesvirus 8. Infection with KSHV is necessary, but insufficient for KS development. KSHV is more prevalent in the HIV-infected population than in the general population in the US. Contributing factors, such as immunosuppression and AIDS, as well as others, are required for disease development (Horenstein et al., 2008; J. Cutan. Pathol. 35(Suppl. 2): 40-44).

KSHV infection is much more common in some parts of the world, such as subequatorial Africa, where over 30% of the population carries KSHV antibodies. In some areas in Africa, the virus seems to spread from mother to child. Seropositivity for the virus ranges from 10% to 25% in the Mediterranean area. In other regions of the world where KSHV is not endemic, the seroprevalence is around 2-5%. (Horenstein et al., 2008; J. Cutan. Pathol. 35(Suppl. 2): 40-44).

KSHV appears to be transmitted through saliva, as is the case for other human herpesviruses. Sexual transmission through semen has also been suggested (Horenstein et al., 2008; J. Cutan. Pathol. 35(Suppl. 2): 40-44). The virus may also be transmitted through organ donation. Some cases of KSHV have been reported in injection drug users and are thought to be spread when needles are contaminated with infected blood. The transmission of KSHV through blood appears to be rare and occurs much less than HIV transmission.

KSHV has a long latency period, like most herpesviruses. Several KSHV genes show oncogenic properties, modifying cell proliferation, apoptosis and angiogenesis. Proteins encoded by these genes, such as vGPCR, LANA-1, vCyclin, vFLIP and vIL-6 play an important role in the pathogenesis of KS (Horenstein et al., 2008; J. Cutan. Pathol. 35(Suppl. 2): 40-44).

2.2 Types of Kaposi Sarcoma

The different types of KS are defined by the different populations in which the disease develops, but the changes within the KS cells are very similar.

Classic (or Mediterranean) KS occurs in elderly people of Mediterranean, Eastern European, and Middle Eastern heritage and occurs more commonly in men than in women. Patients typically have one or more lesions on the legs, ankles, or the soles of the feet. In comparison with other types of KS, the lesions in this type do not grow as quickly, and new lesions do not develop as often. People who get classic KS come from areas where KSHV infection is more common than in the US or Northern Europe. The immune system of people with classic KS is not as weakened as those who have epidemic KS (see below); however, old age may naturally weaken the immune system, thus making people more likely to develop KS if they already have a KSHV infection.

Endemic KS occurs in people living in Equatorial Africa and is sometimes called African KS. KSHV infection is much more common in Africa than in other parts of the world, increasing the chance of developing KS. There appear to be other factors in Africa that contribute to the development of KS since the disease affects a broader group of people that includes children and women. Endemic KS tends to occur in younger people (usually under age 40). Rarely, a more aggressive form of endemic KS is seen in children before puberty. This type usually affects the lymph nodes and other organs and can lead to death within a year. In some parts of Africa, KS is currently considered the most common cancer (Horenstein et al., 2008; J. Cutan. Pathol. 35(Suppl. 2): 40-44).

The most common type of KS in the United States is epidemic or AIDS-related KS. This type of KS develops in individuals who are infected with HIV, the virus that causes AIDS. The severe immunosuppression caused by AIDS increases the likelihood of the development of KS in individuals already infected with KSHV. This more aggressive form of KS was first noted in young homosexual men in the 1970s. In addition to departing from the usual ethnic predisposition, the disease manifested with lesions that occurred at any site and that tended to spread more rapidly to the lymph nodes and visceral organs, such as the gastrointestinal and respiratory tracts (Horenstein et al., 2008; J. Cutan. Pathol. 35(Suppl. 2): 40-44). Gastrointestinal (GI) involvement is generally asymptomatic and does not affect prognosis, while lung involvement frequently is symptomatic and adversely affects prognosis (Vanni et al., 2006; Cancer Treatment Reviews; 32:445-455). The disease progressed very rapidly and many patients died within one year, despite drug chemotherapy regimens (Horenstein et al., 2008; J. Cutan. Pathol. 35(Suppl. 2): 40-44). Treatment of HIV infection with highly active antiretroviral therapy (HAART) has decreased the incidence of epidemic KS and can often keep advanced KS from developing. The clinical course of AIDS-KS is variable, ranging from a very indolent process requiring little, if any therapy, to a rapidly progressive and fatal disease (Vanni et al., 2006; Cancer Treatment Reviews; 32:445-455).

When KS develops in people whose immune systems have been suppressed after an organ transplant it is called iatrogenic, or transplant-associated KS or immunosuppression-associated KS. Most transplant patients take immunosuppressant drugs, such as rapamycin, to prevent organ rejection. The immunosuppression caused by these drugs increases the likelihood that individuals infected with KSHV will develop KS. Stopping the immune suppressing drugs or lowering their dose often makes KS lesions disappear or get smaller.

2.3 Histogenesis and Diagnosis of Kaposi Sarcoma

Despite its name, KS is not considered a true sarcoma, which comprises a tumor arising from the mesenchymal tissue. KS is a highly vascular tumor that arises as a cancer of the lymphatic endothelium. Tumors have dense vascular channels that leak blood cells into the surrounding tissue, giving the tumor its dark color and characteristic bruise-like appearance. KS lesions contain tumor cells with a characteristic abnormal elongated shape, called spindle cells. KSHV proteins are detected in spindle cells.

The first sign of KS is usually the development of skin lesions. The lesions can develop anywhere in the body, but most often, they arise on the legs, nose, feet, external portions of the ears, mouth or genitals. About 1 in 3 people with AIDS-related KS will develop mouth and throat lesions. KS lesions are often present in the GI tract when the patient is first diagnosed, particularly if the immune system is severely suppressed, due to AIDS. Sometimes lesions in the GI tract can develop in the absence of skin lesions. While often asymptomatic, lesions in the GI tract may lead to bowel obstruction and require surgery to unblock the intestine. Swelling of the lymph nodes, called lymphedema, due to blockage caused by KS, can also occur in the absence of skin lesions.

The histopathologic features of all four variants of KS are indistinguishable and the diagnosis using histology differs according to the stage and form of KS (Horenstein et al., 2008; J. Cutan. Pathol. 35(Suppl. 2): 40-44). A biopsy will reveal the presence of the spindle cells in suspected KS lesions. In addition, bronchoscopy can be performed if KS is suspected in the lungs. Gastrointestinal endoscopy can be performed if KS is suspected in the GI tract.

Immunohistochemistry has become the standard for identifying KS, as it is easier and more reliable than other methods. The LANA-1 monoclonal antibody allows the identification of all types of lesions and KSHV-positive lymphomas. Polymerase-chain reaction has been extensively used as a method to identify KSHV. In situ hybridization (ISH) may also be used for the detection of KSHV sequences (Horenstein et al., 2008; J. Cutan. Pathol. 35(Suppl. 2): 40-44).

Unlike most other forms of cancer, there is no officially accepted system for staging all types of KS. Most types of cancer staging systems are based mostly on the size of the primary lesion and how far the cancer has spread from that lesion. KS doesn't generally develop just in a single area so this staging approach isn't used.

The AIDS Clinical Trials Group (ACTG) system for KS in AIDS patients was developed to predict survival and treatment outcome. The outlook for patients with AIDS-related KS is influenced at least as much by their immunological status and the presence of other HIV-related illnesses, as by the tumor burden itself (Vanni et al., 2006; Cancer Treatment Reviews; 32:445-455). For this reason, the ACTG system uses the "TIS" staging criteria (tumor, immunological status and systemic illnesses). The three criteria consist of:

1) the extent of the tumor (T);
2) the status of the immune system (I), as measured by the number of CD4 cells; and
3) the extent of involvement within the body or systemic illness (S).

Under each heading, there are two subgroups identified by either a zero (0), which means good risk or a one (1), which means poor risk.

2.4 Treatment of Kaposi Sarcoma

KS is not curable, but it can be effectively palliated for many years, and this is typically the aim of current treatments. Treatment for KS is more effective today than it was a couple of decades ago. Choices about the best treatment options for each patient are based on the function of the immune system, as well as the number, location and size of the KS lesions. The patient's general condition is also a major factor. The presence and severity of other serious medical conditions can make some treatments a poor choice. Surgery is generally not recommended, as KS can appear in wound edges.

Treatment of any immunodeficiency and/or related infections is a very important part of the treatment of KS. Therefore, effective treatment of AIDS patients with highly active antiretroviral therapy (HAART) is associated with regression in size and number of existing lesions. For many patients with KS, HAART may be the only treatment needed for the cancer. The risk of developing new lesions is lower when antiviral medicines such as ganciclovir or foscarnet are used in patients who test positive for KSHV. However, existing lesions are relatively resistant to treatment with antiviral agents. Patients presenting with AIDS-KS often have other opportunistic life-threatening diseases. The prevention and effective treatment of these diseases, such as bacterial infections, is also important in slowing down the progression of KS.

Local treatment is most useful when there are just a few lesions in a very visible area, such as the face. The drawback of local therapy is that it doesn't keep lesions from developing.

Local treatment includes topical treatment with alitretinoin, a first-generation retinoid, available as a gel under the name Panretin®. Another type of local treatment is cryosurgery, whereby a probe cooled with liquid nitrogen is used to freeze the lesion. Photodynamic treatment is also an option for KS patients. In this case, patients are given a drug that has greater build-up in tumor cells than in normal cells. About 48 hours after the patient takes the drug, light is used to activate the drug and kill the cancer cells.

Intralesional chemotherapy, whereby a small amount of a chemotherapy drug is injected directly into the KS lesion, allows patients to avoid many of the typical side effects seen with systemic chemotherapy. The most common drug used for intralesional chemotherapy in KS is called vinblastine.

Similar to local treatment, radiation therapy can be used to treat KS when the disease is only in a few areas. Radiation treatments are used to reduce symptoms like pain and swelling, as well as to treat lesions that are unsightly. Radiation treatment can induce side effects, such as skin changes, nausea, vomiting and fatigue.

In general, systemic treatment for KS is indicated in patients with rapidly progressive mucocutaneous disease, causing lymphedema, ulceration and pain, as well as those with symptomatic visceral involvement and/or pulmonary involvement and debilitating KS-related symptoms (Vanni et al., 2006; Cancer Treatment Reviews; 32:445-455). Many chemotherapeutic agents have been tested and used in treatment of AIDS-KS, either as a single therapy or as a combination therapy. Even without the use of HAART, response rates of KS to single agents have varied widely, from 21% to 80% and the median duration of response varies from 1 to 9 months (Vanni et al., 2006; Cancer Treatment Reviews; 32:445-455).

Liposomal anthracyclines are used most often to treat KS. This formulation has been developed to prolong anthracyline circulation time in plasma and decrease their toxicity. The two liposomal anthracyclines used in the US to treat KS are doxorubicin (Doxil®) and daunorubicin (DaunoXome®). These drugs have become the first choice for KS treatment, especially in advanced or rapidly proliferating AIDS-KS, and have been used in several studies in AIDS-KS patients (Vanni et al., 2006, Cancer Treatment Reviews; 32:445-455). Overall, liposomal anthracyclines have good efficacy and are generally well tolerated. Myelosuppression remains the most important dose-limiting toxicity; neuropathy and alopecia occur infrequently and anthracycline-induced cardiotoxicity is rare.

Other chemotherapy drugs that are used to treat KS include paclitaxel (Taxol®) and vinorelbine (Navelbine). Paclitaxel is a microtubule-stabilizing drug known to inhibit Bcl-2 anti-apoptotic activity and to be highly effective in the treatment of certain neoplasms. It has been the subject of several studies with AIDS-KS patients (Vanni et al., 2006, Cancer Treatment Reviews; 32:445-455). Paclitaxel is well tolerated, but the higher prevalence rates of alopecia, myalgia, arthralgia and bone marrow suppression make it less attractive than liposomal anthracyclines as initial treatment for disseminated KS (Vanni et al., 2006; Cancer Treatment Reviews; 32:445-455).

Other chemotherapy drugs that have been used in the past include bleomycin, vinblastine, vincristine and etoposide. Several combination have been investigated using these drugs (Vanni et al., 2006; Cancer Treatment Reviews; 32:445-455). The combination of vincristine and bleomycin with or without doxorubicin (ABV or BV) has been supplanted by liposomal anthracyclines and paclitaxel for reasons of efficacy and toxicity. These chemotherapeutic agents have also been evaluated as single therapy in AIDS-KS patients (Vanni et al., 2006; Cancer Treatment Reviews; 32:445-455). Etoposide was one of the first drugs shown to be active against AIDS-KS. These drugs are still used in many developing countries where liposomal anthracyclines and paclitaxel are too costly and/or unavailable, and where the bulk of AIDS-KS cases exist (Vanni et al., 2006; Cancer Treatment Reviews; 32:445-455). Response rates for these agents have varied widely in these studies. Reasons for the variation in response rates may be the different prognostic factors of the patients enrolled, the lack of universally applied criteria for evaluation of response and the differences in the number of patients enrolled (Vanni et al., 2006; Cancer Treatment Reviews; 32:445-455). Most of the studies using the "old" chemotherapeutic agents were conducted in the pre-HAART era. Therefore, one can speculate that these response rates may become higher in AIDS-KS patients who are being treated with HAART.

Interferon has been seen as an attractive treatment option since the early AIDS-KS cases. The response rate to interferon as a single agent, in selected populations, varies from 20% to 60% (Vanni et al., 2006; Cancer Treatment Reviews; 32:445-455). In appropriately selected patients, the duration of the response can be relatively long, and could average 6-12 months for partial responders and up to 2 years for complete responders. However, interferon is not an appropriate therapy for patients with rapidly progressive KS, debilitating symptoms or symptomatic visceral disease, as the time to response is relatively long (8-12 weeks) (Vanni et al., 2006; Cancer Treatment Reviews; 32:445-455). In addition, myelosuppression, frequent hepatic toxicity and constitutional symptoms limit its use.

2.4.1 Role of HAART in AIDS-KS Treatment

The incidence of KS among patients infected with HIV has diminished since the beginning of the HAART era. Recent studies have shown that AIDS-KS in patients receiving HAART manifests less aggressively than in patients not on HAART (Vanni et al., 2006; Cancer Treatment Reviews; 32:445-455). HAART has also been associated with longer survival time and longer time to treatment failure in patients who have received chemotherapy (Vanni et al., 2006; Cancer Treatment Reviews; 32:445-455). HAART is often the only anti-cancer therapy in the early stages of the disease (T0) and/or for slowly proliferating disease. When patients develop rapidly proliferating disease, chemotherapy is used as a first-line therapy with or without anti-retroviral therapy, followed by maintenance with HAART (Vanni et al., 2006; Cancer Treatment Reviews; 32:445-455). Thus, HAART may be useful for the less aggressive stage of the disease as well as the more advanced stage of the disease as a maintenance therapy.

Two studies have shown that non-nucleoside reverse transcriptase inhibitor (NNRTI)-based HAART is as effective as protease inhibitor-based HAART in preventing KS (Vanni et al., 2006; Cancer Treatment Reviews; 32:445-455). It has been suggested that protease inhibitor-based therapy, in addition to controlling HIV viral load and restoring patients' immunity, may contribute directly to tumor regression. Nude mice treated with similar doses of two protease inhibitors, indinavir and saquinavir, as AIDS patients, demonstrated a reduction in the number and size of macroscopic KS-like angioproliferative lesions (Sgadari et al., 2003. Lancet Oncol. 4: 537-47). Another protease inhibitor, ritonavir, demonstrated in-vitro inhibition of activation and proliferation of primary endothelial cells and decreased production of TNF-α, IL-6, IL-8 and VEGF (Pati et al., 2002. Blood. 99:3771-3779).

It appears that HAART may also contribute to KSHV latency. Uncontrolled HIV replication leads to the expression of the HIV Tat protein, which in turn regulates KSHV growth. Reduction of the viral load with HAART will thus lead to a reduction in the expression of the Tat protein, which in turn will result in KSHV latency and tumor regression. (Vanni et al., 2006; Cancer Treatment Reviews; 32:445-455).

3. SUMMARY

Methods for treating KS are described involving the administration of compounds having the formulas set forth herein ("Compound") to a human subject in need of such treatment. Preferably, the Compound used in the therapeutic method demonstrates one or more of the following activities as determined in cell culture and/or animal model systems, such as those described herein: (a) selective inhibition of the pathological production of human VEGF; (b) inhibition of tumor angiogenesis, tumor-related inflammation, tumor-related edema and/or tumor growth; and/or (c) prolongation of the G1/S phase of cell cycle.

The Compound can be administered as a single agent therapy to a human in need of such treatment. Alternatively, the Compound can be administered in combination with one or more additional therapies to a human in need of such treatment. Such therapies may include the use of anti-cancer agents (e.g., cytotoxic agents, anti-angiogenesis agents, tyrosine kinase inhibitors, or other enzyme inhibitors).

Despite differences in the classifications of KS types, the therapies described herein should be effective because they are aimed at interfering with basic mechanisms required for manifestation of each type of KS—i.e., uncontrolled growth of KS tumors or vascularity, inflammation, or edema associated with KS tumors. While not bound by any theory, the therapies described are based, in part, on the pharmacodynamic activities of the Compounds as measured in cell culture and in animal models; in particular, these include: (a) selective inhibition of the pathological production of human VEGF; (b) inhibition of tumor angiogenesis, tumor-related inflammation, tumor-related edema and/or tumor growth; and/or (c) prolongation of the G1/S phase of the cell cycle of tumor cells.

These pharmacologic activities contribute to limiting solid tumor growth or tumor-related inflammation or edema in several ways. For example, inhibition of pathological production of human VEGF by the tumor will inhibit tumor angiogenesis, thereby limiting vascularization and further growth of solid tumors. In KS, antiangiogenic effects may result in minimizing the dark, bruise-like discoloration associated with the tumor lesions. An additional benefit is achieved for tumors that respond to VEGF as a growth factor—in such cases, the Compound can limit proliferation of such tumor cells independent of their angiogenic status, that is angiogenesis and vascularization need not be present for the Compound to limit proliferation of the tumor cells. Because the process of tumorigenesis can result in inflammation and edema, a Compound may limit such inflammation or edema. Finally, the prolongation of cell cycle may contribute to the induction of apoptotic death of the tumor cells, and/or allow for increased efficacy when the Compound is used in combination with a therapy or therapies (e.g., chemotherapeutic agents or radiation) that interfere with nucleic acid synthesis during the cell cycle (e.g., G1/S phase).

Thus, in specific embodiments, the methods for treating KS can result in inhibition or reduction of the pathological production of human VEGF (including intratumoral VEGF production), thus reducing human VEGF concentrations in biological specimens of an afflicted subject; inhibition of tumor angiogenesis, tumor-related inflammation or edema and/or tumor growth in the subject; stabilization or reduction of tumor volume or tumor burden in the subject; stabilization or reduction of peritumoral inflammation or edema in the subject; reduction of the concentrations of angiogenic or inflammatory mediators in biological specimens (e.g., plasma, serum, cerebral spinal fluid, urine, or any other biofluids); and/or a delayed or prolonged G1/S phase of the cell cycle (i.e., the period between the late resting or pre-DNA synthesis phase, and the early DNA synthesis phase) in tumor cells of the subject.

Existing antiangiogenic therapies that have been developed for other diseases (e.g., certain cancers, retinopathies including macular degeneration and the like) are directed at neutralizing VEGF activity (e.g., using anti-VEGF antibodies), or inhibiting downstream effects of VEGF signaling (e.g., using tyrosine kinase inhibitors to block the signaling activity of the VEGF receptor). As a result, these existing antiangiogenic therapies neutralize or inhibit physiological or homeostatic VEGF, as well as pathologically-produced human VEGF, activity, resulting in side effects that, while tolerated for the treatment of life-threatening cancers or to prevent or slow the development of blindness, may not be acceptable for the treatment of KS. Since the Compounds used in the therapeutic methods described herein selectively inhibit pathologic production of human VEGF (e.g., by the tumor), and do not disturb the production of human VEGF under physiological conditions, side effects that are unacceptable for the treatment of KS should be reduced.

The efficacy of the therapeutic intervention is supported by the data presented herein, demonstrating that: the Compounds inhibit the pathological production of human VEGF (see Section 9.1 et. seq., infra); the Compounds inhibit tumor angiogenesis and tumor growth (see Section 9.2 et. seq., infra); the Compounds delay cell cycle by prolonging the G1/S phase (see Section 9.3 et. seq., infra); and the Compounds can be administered safely to human subjects (see Section 10.2 et. seq., infra).

3.1 Definitions

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, $18^{th}$ eds., Mack Publishing, Easton Pa. (1990) or *Remington: The Science and Practice of Pharmacy*, $19^{th}$ eds., Mack Publishing, Easton Pa. (1995).

As used herein, the term "alkyl" generally refers to saturated hydrocarbyl radicals of straight or branched configuration including, but not limited to methyl, ethyl, n-propyl, isopropyl, n-butyl, isobutyl, sec-butyl, tert-butyl, n-pentyl, n-hexyl, n-heptyl, octyl, n-octyl, and the like. In some embodiments, alkyl substituents can be $C_1$ to $C_8$, $C_1$ to $C_6$, or $C_1$ to $C_4$ alkyl. Alkyl may be optionally substituted where allowed by available valences, for example, with one or more halogen or alkoxy substituents. For instance, halogen substituted alkyl may be selected from haloalkyl, dihaloalkyl, trihaloalkyl and the like.

As used herein, the term "cycloalkyl" generally refers to a saturated or partially unsaturated non-aromatic carbocyclic ring. Representative examples of cycloalkyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, indanyl and the like. Cycloalkyl may be optionally substituted where allowed by available valences. In certain embodiments, cycloalkyl is selected from $C_3$-$C_{20}$cycloalkyl, $C_3$-$C_{14}$cycloalkyl, $C_5$-$C_8$cycloalkyl, $C_3$-$C_8$cycloalkyl and the like.

As used herein, the term "alkenyl" generally refers to linear or branched alkyl radicals having one or more carbon-carbon double bonds, such as $C_2$ to $C_8$ and $C_2$ to $C_6$ alkenyl, including 3-propenyl and the like, and may be optionally substituted where allowed by available valences.

As used herein, the term "alkynyl" generally refers to linear or branched alkyl radicals having one or more carbon-carbon triple bonds, such as $C_2$ to $C_8$ and $C_2$ to $C_6$ alkynyl, including hex-3-yne and the like and may be optionally substituted where allowed by available valences.

As used herein, the term "aryl" refers to a monocarbocyclic, bicarbocyclic or polycarbocyclic aromatic ring structure. Included in the scope of aryl are aromatic rings having from six to twenty carbon atoms. Aryl ring structures include compounds having one or more ring structures, such as mono-, bi-, or tricyclic compounds. Examples of aryl include phenyl, tolyl, anthracenyl, fluorenyl, indenyl, azulenyl, phenanthrenyl (i.e., phenanthrene), napthyl (i.e., napthalene) and the like. In certain embodiments, aryl may be optionally substituted where allowed by available valences. In one embodiment, aryl is an optionally substituted phenyl or naphthyl.

As used herein, the term "heteroaryl" refers to monocyclic, bicyclic or polycyclic aromatic ring structures in which one or more atoms in the ring, is an element other than carbon (heteroatom). Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, heteroaryl may be selected from ring structures that contain one or more heteroatoms, two or more heteroatoms, three or more heteroatoms, or four or more heteroatoms. In one embodiment, the heteroaryl is a 5 to 10 membered or 5 to 12 membered heteroaryl. Heteroaryl ring structures may be selected from those that contain five or more atoms, six or more atoms, or eight or more atoms. Examples of heteroaryl ring structures include, but are not limited to: acridinyl, benzimidazolyl, benzoxazolyl, benzofuranyl, benzothiazolyl, benzothienyl, 1,3-diazinyl, 1,2-diazinyl, 1,2-diazolyl, 1,4-diazanaphthalenyl, furanyl, furazanyl, imidazolyl, indazolyl, indolyl, isoxazolyl, isoquinolinyl, isothiazolyl, isoindolyl, oxadiazolyl, oxazolyl, purinyl, pyridazinyl, pyrazolyl, pyridinyl, pyrazinyl, pyrimidinyl, pyrrolyl, quinazolinyl, quinolinyl, quinoxalinyl, thiazole-2 (3H) imine, 1,3,4,-thiadiazole-2(3H)-imine-yl, thiazolyl, thiophenyl, 1,3,5-triazinyl, 1,2,4-triazinyl, 1,2,3-triazinyl, tetrazolyl and the like. In certain embodiments, heteroaryl may be optionally substituted where allowed by available valences.

As used herein, the term "heteroaryl" refers to monocyclic, bicyclic or polycyclic aromatic ring structures in which one or more atoms in the ring, is an element other than carbon (heteroatom). Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, heteroaryl may be selected from ring structures that contain one or more heteroatoms, two or more heteroatoms, three or more heteroatoms, or four or more heteroatoms. In one embodiment, the heteroaryl is a 5 to 10 membered or 5 to 12 membered heteroaryl. Heteroaryl ring structures may be selected from those that contain five or more atoms, six or more atoms, or eight or more atoms. Examples of heteroaryl ring structures include, but are not limited to: acridinyl, benzimidazolyl, benzoxazolyl, benzofuranyl, benzothiazolyl, benzothienyl, 1,3-diazinyl, 1,2-diazinyl, 1,2-diazolyl, 1,4-diazanaphthalenyl, furanyl, furazanyl, imidazolyl, indazolyl, indolyl, isoxazolyl, isoquinolinyl, isothiazolyl, isoindolyl, oxadiazolyl, oxazolyl, purinyl, pyridazinyl, pyrazolyl, pyridinyl, pyrazinyl, pyrimidinyl, pyrrolyl, quinazolinyl, quinolinyl, quinoxalinyl, thiazole-2 (3H) imine, 1,3,4,-thiadiazole-2(3H)-imine-yl, thiazolyl, thiophenyl, 1,3,5-triazinyl, 1,2,4-triazinyl, 1,2,3-triazinyl, tetrazolyl and the like. In certain embodiments, heteroaryl may be optionally substituted where allowed by available valences.

As used herein, the term "alkoxy" generally refers to a structure of the formula: —O—R. In certain embodiments, R may be an optionally substituted straight or branched alkyl, such as a $C_1$ to $C_5$ alkyl.

As used herein, the term "alkylthio" generally refers to a structure of the formula: —S—R. In certain embodiments, R may be an optionally substituted straight or branched alkyl, such as a $C_1$ to $C_5$ alkyl.

As used herein, the term "amino" generally refers to a structure of the formula: —NRR'. In certain embodiments, R and R' independently may be H or an optionally substituted straight or branched alkyl, such as a $C_1$ to $C_5$ alkyl. In one embodiment, "thiazoleamino" refers to an amino, wherein at least one of R or R' is a 2-thiazolyl, 3-thiazolyl or 4-thiazolyl. In one embodiment, "alkylamino" refers to an amino, wherein at least one of R or R' is an optionally substituted straight or branched $C_1$ to $C_5$ alkyl.

As used herein, the term "acetamino" generally refers to a structure of the formula: —NR(C(=O)CH$_3$), wherein R may be H or an optionally substituted straight or branched alkyl, such as a $C_1$ to $C_5$ alkyl.

As used herein, the term "acetamide" generally refers to a structure of the formula: C(=O)NH$_2$.

As used herein, the term "sulfonyl" generally refers to a structure of the formula: —SO$_2$R, wherein R can be H or an optional substituent including, but not limited to straight or branched $C_1$ to $C_6$ alkyl, aryl, heteroaryl, cycloalkyl, or heterocycle. In one embodiment, "alkylsulfonyl" refers to a structure of the formula: —SO$_2$R, wherein R is an optionally substituted straight or branched $C_1$ to $C_6$ alkyl.

As used herein, the term "oxo" generally refers to a structure of the formula: (=O).

As used herein, the term "phenyloxy" generally refers to a structure of the formula: —O-phenyl, wherein phenyl can be optionally substituted.

For the purposes of this disclosure, the terms "halogen" or "halo" refer to substituents independently selected from fluorine, chlorine, bromine, and iodine.

As used herein, the terms "Compound" or "Compound provided herein" generally refer to a compound described in Section 5.1 or Example 6. In one embodiment, the terms refer to a compound of Formula I, II, III or IV. In another embodiment, the terms refer to a compound of Formula Ia, IIa, IIIa or IVa. In a specific embodiment, the terms refer to a compound depicted in Table 1. In one embodiment, the terms refer to a Compound disclosed in WO2005/089764, e.g., Compounds in the table on pages 26-98; WO2006/113703, e.g., Compounds in the table on pages 29-102; WO2008/127715, e.g., Compounds in the table on pages 52-126; WO2008/127714, e.g., Compounds in the table on pages 48-123; and U.S. Provisional Patent Application 61/181,653, entitled: METHODS FOR TREATING CANCER AND NON-NEOPLASTIC CONDITIONS, filed May 27, 2009, all of which are herewith incorporated by reference in their entirety. In one embodiment, the terms refer to a particular enantiomer, such as an R or S enantiomer of a "Compound" or "Compound provided herein". In one embodiment, the terms refer to an R or S enantiomer of a compound of Formula I, II, III or IV. In another embodiment, the terms refer to an R or S enantiomer of a compound of Formula Ia, IIa, IIIa or IVa. In a specific embodiment, the terms refer to an R or S enantiomer of a compound depicted in Table 1. The "Compound" or "Compound provided herein" may comprise one or more asymmetric carbon atoms, i.e. n asymmetric carbon atoms, having either R or S configuration as determined by a person skilled in the art. It is understood that the terms "Compound" or "Compound provided herein" encompass all possible stereoisomers that may be generated based on all asymmetric carbon atoms. For example, if a Compound has two (n=2) assymetric carbon atoms, the terms "Compound" or "Compound provided herein" encompass all four, i.e. $2^n=2^2=4$, stereoisomers (R,S; R,R; S,S; S;R). The "Compound" or "Compound provided herein" may be a substantially pure (e.g., about 90%, about 95%, about 98%, about 99%, or about 99.9% pure) single stereoisomer or a mixture of two or more stereoisomers.

As used herein, the terms "self-microemulsifying drug delivery system" (SMEDDS) or "self-emulsifying drug delivery system" (SEDDS) mean a composition that contains an active agent herein defined in intimate admixture with pharmaceutically acceptable excipients such that the system is capable of dissolving the active agent to the desired concentration and producing colloidal structures by spontaneously forming a microemulsion when diluted with an aqueous medium, for example water, or in gastric juices. The colloidal structures can be solid or liquid particles including droplets and nanoparticles. In a SEDDS or SMEDDS system the type of microemulsion produced will be either clear or turbid depending on drug loading and the type of surfactant used.

As used herein, "microemulsion" means a slightly opaque, opalescent, non-opaque or substantially non-opaque colloidal dispersion (i.e. "clear") that is formed spontaneously or substantially spontaneously when its components are brought into contact with an aqueous medium. A microemulsion is thermodynamically stable and typically contains dispersed droplets of a mean diameter less than about 200 nm (2000 Å). Generally microemulsions comprise droplets or liquid nanoparticles that have a mean diameter of less than about 150 nm (1500 Å); typically less than 100 nm, generally greater than 10 nm, wherein the dispersion may be thermodynamically stable over a time period of up to about 24 hours.

As used herein, the terms "pathologic," "pathological" or "pathologically-induced," in the context of the production of VEGF described herein, refer to the stress-induced expression of VEGF protein. In one embodiment, oncongenic transformation-induced expression of VEGF protein by tumor cells or other cells in the tumor environment is encompassed by the terms. In another embodiment, hypoxia-induced expression of VEGF protein in a chronic or traumatic inflammatory condition is encompassed by the terms. In another embodiment, in response to environmental stimuli, cells that disregulate or overproduce VEGF protein is also encompassed by the terms. As applicable, expression of VEGF protein supports inflammation, angiogenesis and tumor growth. The inhibition or reduction in pathological production of VEGF protein by a Compound can be assessed in cell culture and/or animal models as described herein.

As used herein, the term "about" means a range around a given value wherein the resulting value is substantially the same as the expressly recited value. In one embodiment, "about" means within 25% of a given value or range. For example, the phrase "about 70% by weight" comprises at least all values from 52% to 88% by weight. In another embodiment, the term "about" means within 10% of a given value or range. For example, the phrase "about 70% by weight" comprises at least all values from 63% to 77% by weight. In another embodiment, the term "about" means within 7% of a given value or range. For example, the phrase "about 70% by weight" comprises at least all values from 65% to 75% by weight.

As used herein the term "Kaposi sarcoma" or "KS" refers to any form of KS, including classic (or Mediterranean) KS, endemic KS, AIDS-related (epidemic) KS, or iatrogenic (transplant-associated) KS or immunosuppression-associated KS.

As used herein, the terms "therapies" and "therapy" can refer to any protocol(s), method(s), compositions, formulations, and/or agent(s) that can be used in the prevention, treatment, management, or amelioration of KS or a symptom thereof. In certain embodiments, the terms "therapies" and "therapy" refer to drug therapy, adjuvant therapy, radiation therapy, biological therapy, supportive therapy, and/or other therapies useful in treatment, management, prevention, or amelioration of KS or a symptom thereof. In certain embodiments, the term "therapy" refers to a therapy other than a Compound or pharmaceutical composition thereof. In specific embodiments, an "additional therapy" and "additional therapies" refer to a therapy other than a treatment using a Compound or pharmaceutical composition. In a specific embodiment, a therapy includes the use of a Compound as an adjuvant therapy, for e.g., using a Compound in conjunction with a drug therapy, biological therapy, and/or supportive therapy.

As used herein, the term "effective amount" in the context of administering a Compound to a subject refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of KS or one or more symptoms associated therewith; (ii) the reduction in the duration of one or more symptoms associated with KS; (iii) the prevention in the recurrence of KS or one or more symptoms associated with KS; (iv) the regression of KS tumors and/or one or more symptoms associated therewith; (v) the reduction in hospitalization of a subject; (vi) the reduction in hospitalization length; (vii) the increase in the survival of a subject; (viii) the inhibition of the progression of KS tumors and/or one or more symptoms associated therewith; (ix) the enhancement or improvement of the therapeutic effect of another therapy; (x) a reduction or elimination of the KS cell population; (xi) a reduction in the growth of a tumor associated with KS; (xii) a decrease in tumor size (e.g, volume or diameter); (xiii) a reduction in the formation of a newly formed tumor; (xiv) eradication, removal, or control of primary, regional and/or metastatic tumors associated with KS; (xv) ease in removal of tumors by reducing vascularization prior to surgery; (xvi) a decrease in the number or size of metastases; (xvii) a reduction in mortality; (xviii) an increase in the tumor-free survival rate of patients; (xix) an increase in relapse free survival; (xx) an increase in the number of patients in remission; (xxi) a decrease in hospitalization rate; (xxii) the size of the tumor is maintained and does not increase or increases by less than the increase of a tumor after administration of a standard therapy as measured by conventional methods available to one of skill in the art, such as photography, magnetic resonance imaging (MRI), dynamic contrast-enhanced MRI (DCE-MRI), X-ray, computed tomography (CT Scan) or a positron emission tomography (PET) scan; (xxiii) the prevention of the development or onset of one or more symptoms associated with KS; (xxiv) an increase in the length of remission in patients;

(xxv) the reduction in the number of symptoms associated with KS; (xxvi) an increase in symptom-free survival of KS patients; (xxvii) inhibition or reduction in pathological production of VEGF; (xxviii) stabilization or reduction of peritumoral inflammation or edema in a subject; (xxix) reduction of the concentration of VEGF or other angiogenic or inflammatory mediators (e.g., cytokines or interleukins) in biological specimens (e.g., plasma, serum, cerebral spinal fluid, urine, or any other biofluids); (xxx) reduction of the concentration of P1GF, VEGF-C, VEGF-D, VEGF-R, IL-6, IL-8 and/or IL-10 in biological specimens (e.g., plasma, serum, cerebral spinal fluid, urine, or any other biofluids); (xxxi) inhibition or decrease in tumor metabolism or perfusion; (xxxii) inhibition or decrease in angiogenesis or vascularization; and/or (xxxiii) improvement in quality of life as assessed by methods well known in the art, for e.g., a questionnaire. In specific embodiments, an "effective amount" of a Compound refers to an amount of a Compound specified herein, e.g., in section 5.4 below.

As used herein, the term "human infant" refers to a newborn to 1 year old year human.

As used herein, the term "human toddler" refers to a human that is 1 year to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "subject" and "patient" are used interchangeably to refer to an individual. In a specific embodiment, the individual is a human. See Section 5.3. infra for more information concerning patients treated for KS in accordance with the methods provided herein.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

4. DESCRIPTION OF FIGURES

FIG. 1. ELISA Evaluation of Inhibition of Soluble $VEGF_{121/165}$ Production by Compound #10 during Hypoxia or Normoxia in HeLa Cells. The results shown are from assays performed in triplicate. The acronyms have the following definitions: ELISA=enzyme-linked immunosorbent assay; SE=standard error; and, VEGF=vascular endothelial growth factor.

FIG. 2. ELISA Evaluation of Inhibition of Soluble $VEGF_{121/165}$ Production by Compound #10 during Hypoxia or Normoxia in Keratinocytes. The results shown are from assays performed in duplicate. The acronyms have the following definitions: ELISA=enzyme-linked immunosorbent assay; SE=standard error; and, VEGF=vascular endothelial growth factor.

FIG. 3. In Cell Western Evaluation of Inhibition of Matrix Associated $VEGF_{189/206}$ Production in HT1080 Cells. The results shown are from assays performed in duplicate. The acronyms have the following definitions: SE=standard error; and, VEGF=vascular endothelial growth factor.

FIG. 4. Western Blot Evaluation of Inhibition of Matrix Associated $VEGF_{189/206}$ Production in HT1080 Cells.

FIG. 5. Reduction of Intratumoral VEGF by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; SE=standard error; and, VEGF=vascular endothelial growth factor.

FIG. 6. Reduction of Tumor Induced Plasma VEGF by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; SE=standard error; and, VEGF=vascular endothelial growth factor.

FIG. 7A-B. Inhibition of Tumor Angiogenesis by Compound #10 in Nude Mice Bearing HT1080 Xenografts. FIG. 7A. The effect of vehicle on an immunostain using an anti-murine CD31 antibody specific for endothelial cells. FIG. 7B. The effect of Compound #10 on an immunostain using an anti-murine CD31 antibody specific for endothelial cells.

FIG. 8. Inhibition of Tumor Growth by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; and, SE=standard error.

FIG. 9. Time Course of Inhibition of Tumor Growth by Compound #10, Bevacizumab, and Doxorubicin in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; IP=intraperitoneal; QD=1 time per day; and, SE=standard error.

FIG. 10A-B. Time Course of Inhibition of Tumor Induced Plasma VEGF Concentrations by Compound #10, Bevacizumab, and Doxorubicin in Nude Mice Bearing HT1080 Xenografts. FIG. 10A. The effect on absolute values of plasma human VEGF concentrations. FIG. 10A. The effect on values of plasma human VEGF concentrations expressed as a ratio relative to tumor volume. The symbol "*" represents a p value of p<0.05, signifying that the differences in treated mice were significantly different from tumor size in vehicle-treated mice (ANOVA, followed by individual comparisons to vehicle). The acronyms have the following definitions: IP=intraperitoneal; QD=once per day; SE=standard error; and, VEGF=vascular endothelial growth factor.

FIG. 11A-B. Inhibition of Tumor Growth by Compound #10 at 5 Weeks in Nude Mice Bearing Orthotopically Implanted SKNEP or SY5Y Xenograft. FIG. 11A. The effect on weight of an SY5Y tumor for mice treated with vehicle and Compound #10. FIG. 11B. The effect on weight of an SKNEP tumor for mice treated with vehicle and Compound #10. The symbol "*" represents a p value of p<0.05, signifying that the differences in treated mice were significantly different from tumor size in vehicle-treated mice (Student's t-test). The acronyms have the following definitions: SE=standard error.

FIG. 12A-G. Cell Cycle Effects in HT1080 Cells by Compound #10 Concentration. Histograms depicting relative DNA content in HT1080 cells under normoxic conditions after treatment with varying concentrations of Compound #10 compared to vehicle. FIG. 12A. Histogram showing the effect of treatment with vehicle. FIG. 12B-G. Histograms showing the effect of treatment with Compound #10 at 0.3 nm, 1 nm, 3 nm, 10 nm, 30 nm and 100 nm, respectively. The acronyms have the following definitions: $G_1$=gap 1 phase (resting or pre-DNA synthesis phase—2 chromosomes present); $G_2$=gap 2 phase (gap between DNA synthesis and mitosis—4 chromosomes present); S=synthesis phase (DNA synthesis ongoing); and, PI=propidium iodide.

FIG. 13A-F. Cell Cycle Effects in HT1080 Cells by Time from Discontinuation of Compound #10. Histograms depicting relative DNA content in HT1080 cells under normoxic conditions after discontinuation of treatment with Compound #10 compared to vehicle. FIG. 13A. Histogram showing the effect of treatment with vehicle. FIGS. 13B-F. Histograms showing the effect of discontinuation of treatment with Compound #10 at 0 hours, 2 hours, 5 hours, 8 hours and 26 hours, respectively. The acronyms have the following definitions: $G_1$=gap 1 phase (resting or pre-DNA synthesis phase—2 chromosomes present); $G_2$=gap 2 phase (gap between DNA synthesis and mitosis—4 chromosomes present); S=synthesis phase (DNA synthesis ongoing); and, PI=propidium iodide.

FIG. 14. BrdU Labeling of Cells from HT1080 Xenografts Grown in Nude Mice. The effect of treatment with Compound #10 compared to vehicle and a positive and negative control, doxorubicin and bevcizumab, respectively. The tumors with adequate BrdU staining (≥3%) were included in analyses. The symbol "*" represents a p value of p<0.05, signifying that the differences in treated mice were significantly different from tumor size in vehicle-treated mice (ANOVA, followed by Dunnett's test relative to vehicle). The acronyms have the following definitions: ANOVA=analysis of variance; BrdU=bromodeoxyuridine; and, SE=standard error.

FIG. 15. Plasma Concentrations of Compound #10 by Dose Level after Stage 1 of a Study in Healthy Volunteers. The acronyms have the following definitions: BID=2 times per day; and, SD=standard deviation.

FIG. 16. Plasma Concentrations of Compound #10 by Dose Level after Stage 2 of a Study in Healthy Volunteers. The acronyms have the following definitions: TID=3 times per day; and, SD=standard deviation.

FIG. 17A-B. FIG. 17A: Absolute Physiologic VEGF A Plasma and Serum Concentrations: Stage 1 of Multiple dose Study; FIG. 17B: Change from Baseline in Physiologically-Induced VEGF-A Plasma and Serum VEGF Concentrations: Stage 1 of Multiple-dose Study. The acronyms have the following definitions: VEGF=vascular endothelial growth factor; and, SEM=standard error of the mean.

FIG. 18A-B. FIG. 18A: Absolute VEGF-A Plasma and Serum Concentrations: Stage 2 of Multiple-dose Study; FIG. 18B: Change from Baseline in VEGF-A Plasma and Serum VEGF Concentrations: Stage 2 of Multiple-dose Study. The acronyms have the following definitions: VEGF=vascular endothelial growth factor; and, SEM=standard error of the mean.

FIG. 19. Change in Total Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error.

FIG. 20. Change in Necrotic Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error.

FIG. 21. Change in Non-Necrotic Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error.

FIG. 22. Change in fBV Induced by Compound #10 in Non Necrotic Tissue in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: fBV=fractional blood volume; and, SE=standard error.

FIG. 23. Change in $K_{trans}$ Induced by Compound #10 in Non Necrotic Tissue in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: $K_{trans}$=volume transfer coefficient; and, SE=standard error.

FIG. 24A-B. Cell Cycle Delay After Overnight Exposure to Compound 1205. Histograms depicting relative DNA content in HT1080 cells under normoxic conditions after treatment with Compound 1205 compared to vehicle. FIG. 24A. Histogram showing the effect of treatment with Compound 1205 at 10 nm. FIG. 24B. Histogram showing the effect of treatment with vehicle.

FIG. 25. Dose Response of Compound 1205 and Compound #10: Inhibition of the Production of Hypoxia-Induced VEGF in HeLa Cells.

FIG. 26. Inhibition of HT1080 Tumor Growth by Compound #10, 1205 and 1330. The symbol "++" represents a p value of p=0.051, signifying the difference in tumor size in Compound #10 treated mice from tumor size in vehicle-treated mice (Student's t-test) on Day 11. The symbol "**" represents a p value of p<0.05, signifying that the differences in tumor size in Compound 1205 (S,S diastereoisomer) treated mice were significantly different from tumor size in vehicle-treated mice and that the differences in tumor size in Compound 1205 (S,S diastereoisomer) treated mice were significantly different from tumor size in Compound 1330 (R,S diastereoisomer)-treated mice (ANOVA, multiple comparisons).

FIG. 27A-B. Effect of Compound 1205 on Intra-Tumor Human VEGF Levels. FIG. 27A. Effect of treatment with vehicle and Compound 1205 on intra-tumor VEGF levels for Study #21 (target tumor size: 1200 $mm^3$) and Study #23 (target tumor size: 1500 $mm^3$). FIG. 27B. Intra-tumor VEGF levels normalized to tumor size.

FIG. 28. Effect of Compound 1205 on Levels of Homeostatic Plasma Human VEGF for Study #21 and Study #23.

FIG. 29A-F. Treatment of BrdU labeled HT1080 cells with increasing doses of Compound #10. FIG. 29A. The effect of DMSO control on percentage of cells residing in S-phase. FIGS. 29B-F. The effect of increasing concentration of Compound #10 at 1 nm, 3 nm, 10 nm, 30 nm and 100 nm, respectively, on percentage of cells residing in S-phase.

FIG. 30A-B. FIG. 30A. The percentage of cells incorporating BrdU. FIG. 30B. The relative level of BrdU at each Compound #10 concentration.

FIG. 31A-B-C. BrdU Histogram and Quantification: FIG. 31(A). Histograms of DNA content demonstrating that the cell cycle distribution for HT1080 spheroids treated for 24 hours is not affected by exposure to Compound #10; FIG. 31(A)(i). Data.001 shows the control results; FIG. 31(A)(ii). Data.002 shows the results of exposure at 5 nm Compound #10; and, FIG. 31(A)(iii). Data.003 shows the results of exposure at 50 nm Compound #10. FIG. 31(B). BrdU quantification indicating the fraction of cells actively synthesizing DNA; FIG. 31(B)(i). The effect of the DMSO control; FIG. 31(B)(ii). Represents the Data.001 results; and, FIG. 31(B)(iii). Represents the Data.003 results. FIG. 31(C) A graphical representation of the percentage of cells that incorporated BrdU (i.e., the cells in S-phase) after treatment with Compound #10 at various concentrations.

FIG. 32A-B-C. BrdU Histogram and Quantification: FIG. 32(A). Histograms of DNA content demonstrating that the cell cycle distribution for HT1080 spheroids treated for 48 hours is not affected by exposure to Compound #10; FIG. 32(A)(i). Data.004 shows the control results; FIG. 32(A)(ii). Data.005 shows the results of exposure at 10 nm Compound #10; and, FIG. 32(A)(iii). Data.006 shows the results of exposure at 50 nm Compound #10. FIG. 32(B). BrdU quantification indicating the fraction of cells actively synthesizing DNA; FIG. 32(B)(i). Represents the Data.004 results; FIG. 32(B)(ii). Represents the Data.005 results; and, FIG. 32(B)(iii). Represents the Data.006 results. FIG. 32(C) A graphical representation of the percentage of cells that incorporated BrdU (i.e., the cells in S-phase) after treatment with Compound #10 at various concentrations.

FIG. 33. The effect of Compound #10 on Anchorage Independent Colony Formation.

FIG. 34. The effect of Compound #10 administration on the clinical endpoint for reduction of cutaneous lesion size and quantity in patients with Kaposi Sarcoma. The administration of Compound #10 reduced the number of raised lesions in patients labeled PR, where the "*" symbol represents that the number of raised lesions was significantly reduced (i.e., ≥50%). The administration of Compound #10 also reduced lesion size in patients. The acronym EOC refers to "End of Cycle," at which "Best Change" occurred.

FIG. 35A-B. The effect of Compound #10 administration on the clinical endpoint for serum and plasma VEGF-A levels in patients. FIG. 35A. The administration of Compound #10 provided a dose responsive reduction in serum VEGF-A levels in patients. The acronym EOS refers to "End of Study." FIG. 35B. The administration of Compound #10 provided a dose responsive reduction in plasma VEGF-A levels in patients. The acronym EOS refers to "End of Study."

5. DETAILED DESCRIPTION

Presented herein are methods for treating KS. In one aspect, the methods for treating KS involve the administration of a Compound, as a single-agent therapy, to a patient in need thereof. In a specific embodiment, presented herein is a method for treating KS, comprising administering to a patient in need thereof an effective amount of a Compound, as a single-agent. In another embodiment, presented herein is a method for treating KS, comprising administering to a patient in need thereof a pharmaceutical composition comprising a Compound, as the single active ingredient, and a pharmaceutically acceptable carrier, excipient or vehicle.

In another aspect, the methods for treating KS involve the administration of a Compound in combination with another therapy (e.g., one or more additional therapies that do not comprise a Compound, or that comprise a different Compound) to a patient in need thereof. Such methods may involve administering a Compound prior to, concurrent with, or subsequent to administration of the additional therapy. In certain embodiments, such methods have an additive or synergistic effect. In a specific embodiment, presented herein is a method for treating KS, comprising administering to a patient in need thereof an effective amount of a Compound and an effective amount of another therapy.

In certain embodiments, the concentration of VEGF or other angiogenic or inflammatory mediators in biological specimens (e.g., plasma, serum, cerebral spinal fluid, urine or any other biofluids) of a patient is monitored before, during and/or after a course of treatment involving the administration of a Compound or a pharmaceutical composition thereof to the patient. In certain embodiments, the tumoral blood flow or metabolism, or peritumoral inflammation or edema in a patient is monitored before, during and/or after a course of treatment involving the administration of a Compound or a pharmaceutical composition. The dosage, frequency and/or length of administration of a Compound or a pharmaceutical composition thereof to a patient may also be modified as a result of the concentration of VEGF or other angiogenic or inflammatory mediators, or tumoral blood flow or metabolism, or peritumoral inflammation or edema as assessed by imaging techniques. Alternatively, changes in one or more of these monitoring parameters (e.g., concentration of VEGF or other angiogenic or inflammatory mediators, or tumoral blood flow or metabolism, or peritumoral inflammation or edema) might indicate that the course of treatment involving the administration of the Compound or pharmaceutical composition thereof is effective in treating KS.

In a specific embodiment, presented herein is a method for treating KS, comprising: (a) administering to a patient in need thereof one or more doses of a Compound or a pharmaceutical composition thereof; and (b) monitoring the concentration of VEGF or other angiogenic, or inflammatory mediators (e.g., detected in biological specimens such as plasma, serum, cerebral spinal fluid, urine or other biofluids), or monitoring tumoral blood flow or metabolism, or peritumoral edema before and/or after step (a). In specific embodiments, step (b) comprises monitoring the concentration of one or more inflammatory mediators including, but not limited to, cytokines and interleukins such as IL-6, IL-8 and IL-10. In particular embodiments, step (b) comprises monitoring the concentration of VEGF-R1, VEGF-R2, P1GF, VEGF-C, and/or VEGF-D. In certain embodiments, the monitoring step (b) is carried out before and/or after a certain number of doses (e.g., 1, 2, 4, 6, 8, 10, 12, 14, 15, or 20 doses, or more doses; or 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks), of administering the Compound. In certain embodiments, one or more of these monitoring parameters are detected prior to administration of the Compound or pharmaceutical composition thereof. In specific embodiments, a decrease in the concentration of VEGF or other angiogenic or inflammatory mediators or a change in tumoral blood flow or metabolism, or peritumoral inflammation or edema following administration of the Compound or pharmaceutical composition thereof indicates that the course of treatment is effective for treating KS. In some embodiments, a change in the concentration of VEGF or other angiogenic or inflammatory mediators or a change in tumoral blood flow or metabolism, or peritumoral inflammation or edema following administration of the Compound or pharmaceutical composition thereof may indicate that the dosage, frequency and/or length of administration of the Compound or a pharmaceutical composition thereof may be adjusted (e.g., increased, reduced or maintained).

The concentration of VEGF or other angiogenic or inflammatory mediators or a change in tumor blood flow or metabolism, or peritumoral inflammation or edema of a patient may be detected by any technique known to one of skill in the art. In certain embodiments, the method for detecting the concentration of VEGF or other angiogenic or inflammatory mediators in a patient involves obtaining a tissue or fluid sample from the patient and detecting the concentration of VEGF or the other angiogenic or the inflammatory mediators in the biological sample (e.g., from plasma serum sample, cerebral spinal fluid, urine or other biofluids) that has been subjected to certain types of treatment (e.g., centrifugation) and detection by use of immunological techniques, such as ELISA. In a specific embodiment, the ELISA described herein, e.g., in the working examples in Section 9 et seq., may be used to detect the concentration of VEGF or other angiogenic or inflammatory mediators, in a biological sample (e.g., from plasma serum, cerebral spinal fluid, urine or any other biofluids) that has been subjected to certain types of treatment (e.g., centrifugation). Other techniques known in the art that may be used to detect the concentration of VEGF or other angiogenic or inflammatory mediators, in a biological sample, include multiplex or proteomic assays. In a specific embodiment, photography, a CT scan, an MRI scan, or a PET scan may be used to detect the tumor size, color, blood flow, metabolism, or peritumoral edema or inflammation.

In specific embodiments, the methods for treating KS provided herein alleviate or manage one, two or more symptoms associated with KS. Alleviating or managing one, two or more symptoms of KS may be used as a clinical endpoint for efficacy of a Compound for treating KS. In some embodiments, the methods for treating KS provided herein reduce the duration and/or severity of one or more symptoms associated with KS. In some embodiments, the methods for treating KS provided herein inhibit the onset, progression and/or recurrence of one or more symptoms associated with KS. In some embodiments, the methods for treating KS provided herein reduce the number of symptoms associated with KS.

Symptoms associated with KS include, but are not limited to: purple, brown or red lesions on the skin that are usually papular; painful swelling, especially in the legs, groin area or skin around the eyes; lesions in the lungs; lesions in the liver; lesions in the digestive tract; blockage in the digestive tract; nausea; vomiting; abdominal pain; bleeding; difficulty breathing; lymphedema; KSHV-positive lesions or lymphomas; a CD4+ cell count <150/µL; tumor-associated edema; and tumor-associated ulceration.

In specific embodiments, the methods for treating KS provided herein inhibit or reduce pathological production of human VEGF. In specific embodiments, the methods for treating KS provided herein selectively inhibit pathologic production of human VEGF (e.g., by the tumor), but do not disturb the physiological activity of human VEGF protein. Preferably, the methods for treating KS provided herein do not significantly inhibit or reduce physiological or homeostatic production of human VEGF. For example, blood pressure, protein levels in urine, and bleeding are maintained within normal ranges in treated subjects. In a specific embodiment, the treatment does not result in adverse events as defined in Cancer Therapy Evaluation Program, Common Terminology Criteria for Adverse Events, Version 3.0, DCTD, NCI, NIH, DHHS Mar. 31, 2003 (http://cstep.cancer.gov), publish date Aug. 9, 2006, which is incorporated by reference herein in its entirety. In other embodiments, the methods for treating KS provided herein do not result in adverse events of grade 2 or greater as defined in the Cancer Therapy Evaluation Program, Common Terminology Criteria for Adverse Events, Version 3.0, supra. In specific embodiments, the methods for treating KS provided herein selectively inhibit pathologic production of human VEGF (e.g., by the tumor), and do not disturb the physiological activity of the human VEGF protein.

In specific embodiments, the methods for treating KS provided herein inhibit or reduce pathological angiogenesis and/or tumor growth. In certain embodiments, the methods for treating KS provided herein prolong or delay the G1/S or late G1/S phase of cell cycle (i.e., the period between the late resting or pre-DNA synthesis phase, and the early DNA synthesis phase).

In particular embodiments, the methods for treating KS provided herein inhibit, reduce, diminish, arrest, or stabilize a tumor associated with KS or a symptom thereof. In other embodiments, the methods for treating KS provided herein inhibit, reduce, diminish, arrest, or stabilize the blood flow, metabolism, peritumoral inflammation or peritumoral edema in a tumor associated with KS or a symptom thereof. In some embodiments, the methods for treating KS provided herein reduce, ameliorate, or alleviate the severity of KS and/or a symptom thereof. In particular embodiments, the methods for treating KS provided herein cause the regression of a KS tumor, tumor blood flow, tumor metabolism, or peritumoral edema and/or a symptom associated with KS. In other embodiments, the methods for treating KS provided herein reduce hospitalization (e.g., the frequency or duration of hospitalization) of a subject diagnosed with KS. In some embodiments, the methods for treating KS provided herein reduce hospitalization length of a subject diagnosed with KS. In certain embodiments, the methods provided herein increase the survival of a subject diagnosed with KS. In particular embodiments, the methods for treating KS provided herein inhibit or reduce the progression of one or more tumors or a symptom associated therewith. In specific embodiments, the methods for treating KS provided herein enhance or improve the therapeutic effect of another therapy (e.g., an anti-cancer agent, radiation, chemotherapy, or surgery). In certain embodiments, the methods for treating KS involve the use of a Compound as an adjuvant therapy. In certain embodiments, the methods for treating KS provided herein improve the ease in removal of tumors (e.g., enhance respectability of the tumors) by reducing vascularization prior to surgery. In particular embodiments, the methods for treating KS provided herein reduce vascularization after surgery, for example, reduce vascularization of the remaining tumor mass not removed by surgery. In some embodiments, the methods for treating KS provided herein prevent recurrence, e.g., recurrence of vascularization and/or tumor growth.

In specific embodiments, the methods for treating KS provided herein reduce or eliminate one, two, or more of the following: skin lesions, nausea, vomiting, abdominal pain, bleeding, difficulty breathing and lymphedema. In some embodiments, the methods for treating KS provided herein reduce the growth of a tumor associated with KS. In certain embodiments, the methods for treating KS provided herein eradicate, remove, or control primary, regional and/or metastatic tumors associated with KS. In other embodiments, the methods for treating KS provided herein decrease the number or size of lesions associated with KS. In particular embodiments, the methods for treating KS provided herein reduce the mortality of subjects diagnosed with KS. In other embodiments, the methods for treating KS provided herein increase the tumor-free survival rate of patients diagnosed with KS. In some embodiments, the methods for treating KS provided herein increase relapse-free survival. In certain embodiments, the methods for treating KS provided herein increase the number of patients in remission or decrease the hospitalization rate. In other embodiments, the methods for treating KS provided herein maintain the size of the tumor so that it does not increase, or so that it increases by less than the increase of a tumor after administration of a standard therapy as measured by methods available to one of skill in the art, such as measurement of a lesion, photography, X-ray, CT Scan, MRI, PET Scan, bronchoscopy, and endoscopy. In other embodiments, the methods for treating KS provided herein prevent the development or onset of KS, or a symptom associated therewith. In other embodiments, the methods for treating KS provided herein increase the length of remission in patients. In particular embodiments, the methods for treating KS provided herein increase symptom-free survival of KS patients. In some embodiments, the methods for treating KS provided herein do not cure KS in patients, but prevent the progression or worsening of the disease. In specific embodiments, the methods for treating KS achieve one or more of the clinical objectives or endpoints set forth in the working examples in Section 11 et seq. In particular embodiments, the methods for treating KS achieve one or more of the following: (i) inhibition or reduction in pathological production of VEGF; (ii) stabilization or reduction of peritumoral inflammation or edema in a subject; (iii) reduction of the concentration of VEGF or other angiogenic or inflammatory mediators (e.g., cytokines or interleukins) in biological specimens (e.g., plasma, serum, cerebral spinal fluid, urine, or any other biofluids); (iv) reduction of the concentration of P1GF, VEGF-C, VEGF-D, VEGF-R, IL-6, IL-8 and/or IL-10 in biological specimens (e.g., plasma, serum, cerebral spinal fluid, urine, or any other biofluids); (v) inhibition or decrease in tumor metabolism or perfusion; (vi) inhibition or decrease in angiogenesis or vascularization; and/or (vii) improvement in quality of life as assessed by methods well known in the art, for e.g, a questionnaire.

In certain aspects, the methods for treating KS provided herein reduce the tumor size (e.g., volume or diameter) in a subject as determined by methods well known in the art, e.g., MRI. Three dimensional volumetric measurement performed by MRI has been shown to be sensitive and consistent in assessing tumor size (see, e.g., Harris et al., Neurosurgery, June 2008, 62(6): 1314-9), and thus may be employed to assess tumor shrinkage in the methods provided herein. In specific embodiments, the methods for treating KS provided herein reduce the tumor size (e.g., volume or diameter) in a subject by at least about 20% as assessed by methods well known in the art, e.g., MRI. In certain embodiments, the methods for treating KS provided herein reduce the tumor size (e.g., volume or diameter) in a subject by at least about 10%, 15%, 20%, 25%, 30%, 35%, 40%, 45%, 50%, 55%, 60%, 65%, 80%, 85%, 90%, 95%, or 100%, relative to the tumor size prior to administration of a Compound, as assessed by methods well known in the art, e.g., MRI. In particular embodiments, the methods for treating KS provided herein reduce the tumor size (e.g., volume or diameter) in a subject by at least an amount in a range of from about 10% to about 100%, relative to the tumor size prior to administration of a Compound, as assessed by methods well known in the art. In particular embodiments, the methods for treating KS provided herein reduce the tumor size (e.g., volume or diameter) in a subject by an amount in a range of from about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 40% to 100%, or any range in between, relative to the tumor size prior to administration of a Compound, as assessed by methods well known in the art, e.g., MRI.

In particular aspects, the methods for treating KS provided herein inhibit or decrease tumor perfusion in a subject as assessed by methods well known in the art, e.g., dynamic contrast-enhanced MRI (DCE-MRI). Standard protocols for DCE-MRI have been described (see., e.g., Morgan et al., J. Clin. Oncol., Nov. 1, 2003, 21(21):3955-64; Leach et al., Br. J. Cancer, May 9, 2005, 92(9):1599-610; Liu et al., J. Clin. Oncol., August 2005, 23(24): 5464-73; and Thomas et al., J. Clin. Oncol., Jun. 20, 2005, 23(18):4162-71) and can be applied in the methods provided herein. In specific embodiments, the methods for treating KS provided herein inhibit or decrease tumor perfusion in a subject by at least about 5%, 10%, 15%, 20%, 25%, 30%, 35%, 40%, 45%, 50%, 55%, 60%, 65%, 80%, 85%, 90%, 95%, or 100%, relative to tumor perfusion prior to administration of a Compound, as assessed by methods well known in the art, e.g., DCE-MRI. In particular embodiments, the methods for treating KS provided herein inhibit or decrease tumor perfusion in a subject in the range of from about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 40% to 100%, or any range in between, relative to tumor perfusion prior to administration of a Compound, as assessed by methods well known in the art, e.g., DCE-MRI.

In particular aspects, the methods for treating KS provided herein inhibit or decrease tumor metabolism in a subject as assessed by methods well known in the art, e.g., PET scanning Standard protocols for PET scanning have been described and can be applied in the methods provided herein. In specific embodiments, the methods for treating KS provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95% or 100%, relative to tumor metabolism observed prior to administration of a Compound, as assessed by methods well known in the art, e.g., PET scanning. In particular embodiments, the methods for treating KS provided herein inhibit or decrease tumor metabolism in a subject in the range of about 10% to 100%, or any range in between, relative to tumor metabolism observed prior to administration of a Compound, as assessed by methods well known in the art, e.g., PET scan.

In specific aspects, the methods for treating KS provided herein decrease the concentration of VEGF or other angiogenic or inflammatory mediators (e.g., cytokines or interleukins, such as IL-6) in a subject as assessed by methods well known in the art, e.g., ELISA. In specific embodiments, the methods for treating KS provided herein decrease the concentration of VEGF or other angiogenic or inflammatory mediators (e.g., cytokines or interleukins, such as IL-6) in a subject by at least about 5%, 10%, 15%, 20%, 25%, 30%, 35%, 40%, 45%, 50%, 55%, 60%, 65%, 80%, 85%, 90%, 95% or 100%, relative to the respective concentration observed prior to administration of a Compound, as assessed by methods well known in the art, e.g., ELISA. In particular embodiments, the methods for treating KS provided herein decrease the concentration of VEGF or other angiogenic or inflammatory mediators (e.g., cytokines or interleukins, such as IL-6) in a subject in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective concentration observed prior to administration of a Compound, as assessed by methods well known in the art, e.g., ELISA.

In specific aspects, the methods for treating KS provided herein decrease the concentrations of P1GF, VEGF-C, VEGF-D, VEGFR-1, VEGFR-2, IL-6, IL-8, and/or IL-10 in a subject as assessed by methods well known in the art, e.g., ELISA. In specific embodiments, the methods for treating KS provided herein decrease the concentrations of P1GF, VEGF-C, VEGF-D, VEGFR-1, VEGFR-2, IL-6, IL-8, and/or IL-10 in a subject by at least about 5%, 10%, 15%, 20%, 25%, 30%, 35%, 40%, 45%, 50%, 55%, 60%, 65%, 80%, 85%, 90%, 95% or 100%, relative to the respective concentration observed prior to administration of a Compound, as assessed by methods well known in the art, e.g., ELISA. In particular embodiments, the methods for treating KS provided herein decrease the concentrations of P1GF, VEGF-C, VEGF-D, VEGFR-1, VEGFR-2, IL-6, IL-8, and/or IL-10 in a subject in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective concentration observed prior to administration of a Compound, as assessed by methods well known in the art, e.g., ELISA.

In specific embodiments, the methods for treating KS provided herein inhibit or decrease pathological production of VEGF by at least about 5%, 10%, 15%, 20%, 25%, 30%, 35%, 40%, 45%, 50%, 55%, 60%, 65%, 80%, 85%, 90%, 95% or 100%, relative to the pathological production of VEGF observed prior to administration of a Compound, as assessed by methods well known in the art, e.g., ELISA. In particular embodiments, the methods for treating KS provided herein inhibit or decrease pathological production of VEGF in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the pathological production of VEGF observed prior to administration of a Compound, as assessed by methods well known in the art, e.g., ELISA.

In certain embodiments, the methods for treating KS provided herein reduce or inhibit KSHV gene transcription or reduce KSHV mRNA levels in tumor biopsies from a subject with KS by about 5%, 10%, 15%, 20%, 25%, 35%, 45%, 50%, 55%, 65%, 70%, 75%, 80%, 85%, 90%, 95% or 100%, or any range in between, relative to the respective KSHV gene transcription level or KSHV mRNA levels observed prior to administration of a Compound, as determined using an assay described herein or others known to one of skill in the art. In particular embodiments, the methods for treating KS provided herein reduce or inhibit KSHV gene transcription or reduce KSHV mRNA levels in tumor biopsies from a subject with KS by 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between relative to the respective KSHV gene transcription level or KSHV mRNA levels observed prior to administration of a Compound, as determined using an assay described herein or others known to one of skill in the art.

In other embodiments, the methods for treating KS provided herein reduce or inhibit KSHV replication or reduce the number of copies of KSHV in circulating peripheral blood mononuclear cells (PBMC) in a subject with KS by about 5%, 10%, 15%, 20%, 25%, 35%, 45%, 50%, 55%, 65%, 70%, 75%, 80%, 85%, 90%, 95% or 100%, or any range in between, relative to the respective KSHV replication level or number of KSHV copies in circulating PBMC observed prior to administration of a Compound, as determined using an assay described herein or others known to one of skill in the art. In particular embodiments, the methods for treating KS provided herein reduce or inhibit KSHV replication or reduce the number of copies of KSHV in circulating PBMC in a subject with KS by about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective KSHV replication level or number of KSHV copies in circulating PBMC observed prior to administration of a Compound, as determined using an assay described herein or others known to one of skill in the art.

In certain embodiments, the methods for treating KS provided herein inhibit or reduce HIV plasma RNA levels in a subject with KS by about 5%, 10%, 15%, 20%, 25%, 35%, 45%, 50%, 55%, 65%, 70%, 75%, 80%, 85%, 90%, 95% or 100% in a subject with KS relative to the respective HIV plasma RNA levels observed prior to administration of a Compound, as determined using an assay described herein or others known to one of skill in the art. In particular embodiments, the methods for treating KS provided herein inhibit or reduce HIV plasma RNA levels in a subject with KS by about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective HIV plasma RNA levels observed prior to administration of a Compound, as determined using an assay described herein or others known to one of skill in the art.

In certain embodiments, the methods for treating KS provided herein decrease the expression of VEGF, VEGFR-2, VEGFR-3, phospho-Akt, KSHV LANA, orf59, p53 and HIF-1α in tumor biopsies from a subject with KS by about 5%, 10%, 15%, 20%, 25%, 35%, 45%, 50%, 55%, 65%, 70%, 75%, 80%, 85%, 90%, 95% or 100%, relative to the respective expression of VEGF, VEGFR-2, VEGFR-3, phospho-Akt, KSHV LANA, orf59, p53 and HIF-1α observed prior to administration of a Compound, as determined using an assay described herein or others known to one of skill in the art. In particular embodiments, the methods for treating KS provided herein decrease the expression of VEGF, VEGFR-2, VEGFR-3, phospho-Akt, KSHV LANA, orf59, p53 and HIF-1α in tumor biopsies from a subject with KS by about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 100%, or any range in between, relative to the respective expression of VEGF, VEGFR-2, VEGFR-3, phospho-Akt, KSHV LANA, orf59, p53 and HIF-1α observed prior to administration of a Compound, as determined using an assay described herein or others known to one of skill in the art.

In other embodiments, the methods for treating KS provided herein increase CD4 counts in a subject with KS by about 5%, 10%, 15%, 20%, 25%, 35%, 45%, 50%, 55%, 65%, 70%, 75%, 80%, 85%, 90%, 95% or 100% relative to the respective CD4 counts observed prior to administration of a Compound, as determined using an assay described herein or others known to one of skill in the art. In particular embodiments, the methods for treating KS provided herein increase CD4 counts in a subject with KS by about 1 fold to 2 fold, 1 fold to 3 fold, 1 fold to 5 fold, 1 fold to 10 fold, 1 fold to 20 fold, 1 fold to 50 fold, 1 fold to 100 fold, or any range in between, relative to the respective CD4 counts observed prior to administration of a Compound, as determined using an assay described herein or others known to one of skill in the art. In particular embodiments, the methods for treating KS provided herein increase CD4 counts in a subject with KS by about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective CD4 counts observed prior to administration of a Compound, as determined using an assay described herein or others known to one of skill in the art.

In specific embodiments, the methods for treating KS provided herein inhibit or reduce angiogenesis or vascularization, by at least about 5%, 10%, 15%, 20%, 25%, 30%, 35%, 40%, 45%, 50%, 55%, 60%, 65%, 80%, 85%, 90%, 95%, or 100%, relative to angiogenesis or vascularization observed prior to administration of a Compound, as assessed by methods well known in the art, e.g., photography, MRI scan, CT scan, PET scan. In particular embodiments, the methods for treating KS provided herein inhibit or reduce angiogenesis or vascularization, in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to angiogenesis or vascularization observed prior to administration of a Compound, as assessed by methods well known in the art, e.g., MRI scan, CT scan, PET scan.

In specific embodiments, the methods for treating KS provided herein inhibit or reduce inflammation, by at least about 5%, 10%, 15%, 20%, 25%, 30%, 35%, 40%, 45%, 50%, 55%, 60%, 65%, 80%, 85%, 90%, 95%, or 100%, or any percentage in between, relative to inflammation observed prior to administration of a Compound, as assessed by methods well known in the art, e.g., CT scan, MRI scan or PET scan. In particular embodiments, the methods for treating KS provided herein inhibit or reduce inflammation, in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to inflammation observed prior to administration of a Compound, as assessed by methods well known in the art, e.g., CT scan, MRI scan or PET scan.

In specific embodiments, the methods for treating KS provided herein inhibit or reduce edema, by at least about 5%, 10%, 15%, 20%, 25%, 30%, 35%, 40%, 45%, 50%, 55%, 60%, 65%, 80%, 85%, 90%, 95%, or 100%, or any percentage in between, relative to edema observed prior to administration of a Compound, as assessed by methods well known in the art, e.g., CT scan, MRI scan or PET scan. In particular embodiments, the methods for treating KS provided herein inhibit or reduce edema, in the range of about 5% to 10%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to edema observed prior to administration of a Compound, as assessed by methods well known in the art, e.g., CT scan, MRI scan or PET scan.

In specific embodiments, the methods for treating KS provided herein minimize the severity and/or frequency of one or more side effects observed with current anti-angiogenesis therapies. In certain embodiments, the methods for treating KS provided herein do not cause one or more side effects observed with current anti-angiogenesis therapies. Such side effects include, but are not limited to, bleeding, arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, and heart failure.

5.1 Compounds

In one embodiment, provided herein are Compounds having Formula (I):

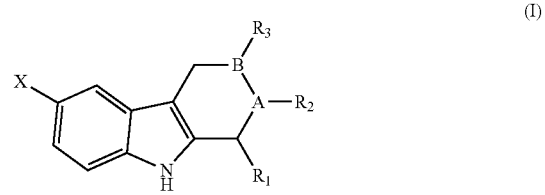

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with aryl;

A is CH or N;

B is CH or N, with the proviso that at least one of A or B is N, and that when A is N, B is CH;

$R_1$ is hydroxyl; $C_1$ to $C_8$ alkyl optionally substituted with alkylthio, 5 to 10 membered heteroaryl, or aryl optionally substituted with one or more independently selected $R_o$ substituents; $C_2$ to $C_8$ alkyenyl; $C_2$ to $C_8$ alkynyl; 3 to 12 membered heterocycle optionally substituted with one or more substituents independently selected from halogen, oxo, amino, alkylamino, acetamino, thio, or alkylthio; 5 to 12 membered heteroaryl optionally substituted with one or more substituents independently selected from halogen, oxo, amino, alkylamino, acetamino, thio, or alkylthio; or aryl, optionally substituted with one or more independently selected $R_o$ substituents;

$R_o$ is a halogen; cyano; nitro; sulfonyl optionally substituted with $C_1$ to $C_6$ alkyl or 3 to 10 membered heterocycle; amino optionally substituted with $C_1$ to $C_6$ alkyl, —C(O)—$R_b$, —C(O)O—$R_b$, sulfonyl, alkylsulfonyl, 3 to 10 membered heterocycle optionally substituted with —C(O)O—$R_n$; —C(O)—NH—$R_b$; 5 to 6 membered heterocycle; 5 to 6 membered heteroaryl; $C_1$ to $C_6$ alkyl optionally substituted with one or more substituents independently selected from hydroxyl, halogen, amino, or 3 to 12 membered heterocycle wherein amino and 3 to 12 membered heterocycle are optionally substituted with one or more $C_1$ to $C_4$ alkyl substituents optionally substituted with one or more substituents independently selected from $C_1$ to $C_4$ alkoxy, amino, alkylamino, or 5 to 10 membered heterocycle; —C(O)—$R_n$; or —O$R_a$;

$R_a$ is hydrogen; $C_2$ to $C_8$ alkylene; —C(O)—$R_n$; —C(O)O—$R_b$; —C(O)—NH—$R_b$; $C_3$-$C_{14}$cycloalkyl; aryl; heteroaryl; heterocyclyl; $C_1$ to $C_8$ alkyl optionally substituted with one or more substituents independently selected from hydroxyl, halogen, $C_1$ to $C_4$ alkoxy, amino, alkylamino, acetamide, —C(O)—$R_b$, —C(O)O—$R_b$, aryl, 3 to 12 membered heterocycle, or 5 to 12 membered heteroaryl, further wherein the alkylamino is optionally substituted with hydroxyl, $C_1$ to $C_4$ alkoxy, or 5 to 12 membered heteroaryl optionally substituted with $C_1$ to $C_4$ alkyl, further wherein the acetamide is optionally substituted with $C_1$ to $C_4$ alkoxy, sulfonyl, or alkylsulfonyl, further wherein the 3 to 12 membered heterocycle is optionally substituted with $C_1$ to $C_4$ alkyl optionally substituted with hydroxyl, —C(O)—$R_n$, —C(O)O—$R_n$, or oxo, further wherein the amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with C₁ to C₆ alkyl, wherein pyridine and thiazole are each optionally substituted with C₁ to C₄ alkyl;

$R_b$ is hydroxyl; amino; alkylamino optionally substituted with hydroxyl, amino, alkylamino, C₁ to C₄ alkoxy, 3 to 12 membered heterocycle optionally substituted with one or more independently selected C₁ to C₆ alkyl, oxo, —C(O)O—$R_n$, or 5 to 12 membered heteroaryl optionally substituted with C₁ to C₄ alkyl; C₁ to C₄ alkoxy; C₂ to C₈ alkenyl; C₂ to C₈ alkynyl; aryl, wherein the aryl is optionally substituted with one or more substituents independently selected from halogen or C₁ to C₄ alkoxy; 5 to 12 membered heteroaryl; 3 to 12 membered heterocycle optionally substituted with one or more substituents independently selected from acetamide, —C(O)O—$R_n$, 5 to 6 membered heterocycle, or C₁ to C₆ alkyl optionally substituted with hydroxyl, C₁ to C₄ alkoxy, amino, or alkylamino; or C₁ to C₈ alkyl optionally substituted with one or more substituents independently selected from C₁ to C₄ alkoxy, aryl, amino, or 3 to 12 membered heterocycle, wherein the amino and 3 to 12 membered heterocycle are optionally substituted with one or more substituents independently selected from C₁ to C₆ alkyl, oxo, or —C(O)O—$R_n$;

$R_2$ is hydrogen; hydroxyl; 5 to 10 membered heteroaryl; C₁ to C₈ alkyl optionally substituted with hydroxyl, C₁ to C₄ alkoxy, 3 to 10 membered heterocycle, 5 to 10 membered heteroaryl, or aryl; —C(O)—$R_c$; —C(O)O—$R_d$; —C(O)—N($R_dR_d$); —C(S)—N($R_dR_d$); —C(S)—O—$R_e$; —S(O₂)—$R_e$; —C(NR$_e$)—S—$R_e$; or —C(S)—S—$R_f$;

$R_c$ is hydrogen; amino optionally substituted with one or more substituents independently selected from C₁ to C₆ alkyl or aryl; aryl optionally substituted with one or more substituents independently selected from halogen, haloalkyl, hydroxyl, C₁ to C₄ alkoxy, or C₁ to C₆ alkyl; —C(O)—$R_n$; 5 to 6 membered heterocycle optionally substituted with —C(O)—$R_n$; 5 to 6 membered heteroaryl; thiazoleamino; C₁ to C₈ alkyl optionally substituted with one or more substituents independently selected from halogen, C₁ to C₄ alkoxy, phenyloxy, aryl, —C(O)—$R_n$, —O—C(O)—$R_n$, hydroxyl, or amino optionally substituted with —C(O)O—$R_n$;

$R_d$ is independently hydrogen; C₂ to C₈ alkenyl; C₂ to C₈ alkynyl; aryl optionally substituted with one or more substituents independently selected from halogen, nitro, C₁ to C₆ alkyl, —C(O)O—$R_e$, or —OR$_e$; or C₁ to C₈ alkyl optionally substituted with one or more substituents independently selected from halogen, C₁ to C₄ alkyl, C₁ to C₄ alkoxy, phenyloxy, aryl, 5 to 6 membered heteroaryl, —C(O)—$R_n$, —C(O)O—$R_n$, or hydroxyl, wherein the aryl is optionally substituted with one or more substituents independently selected from halogen or haloalkyl;

$R_e$ is hydrogen; C₁ to C₆ alkyl optionally substituted with one or more substituents independently selected from halogen or alkoxy; or aryl optionally substituted with one or more substituents independently selected from halogen or alkoxy;

$R_f$ is C₁ to C₆ alkyl optionally substituted with one or more substituents independently selected from halogen, hydroxyl, C₁ to C₄ alkoxy, cyano, aryl, or —C(O)—$R_n$, wherein the alkoxy is optionally substituted with one or more C₁ to C₄ alkoxy substituents and the aryl is optionally substituted with one or more substituents independently selected from halogen, hydroxyl, C₁ to C₄ alkoxy, cyano, or C₁ to C₆ alkyl;

$R_n$ is hydroxyl, C₁ to C₄ alkoxy, amino, or C₁ to C₆ alkyl;

$R_3$ is hydrogen or —C(O)—$R_g$; and $R_g$ is hydroxyl; amino optionally substituted with cycloalkyl or 5 to 10 membered heteroaryl; or 5 to 10 membered heterocycle, wherein the 5 to 10 membered heterocycle is optionally substituted with —C(O)—$R_n$.

In one embodiment, the compound of Formula (I) is other than:
(R)-1-(benzo[d][1,3]dioxol-5-yl)-2,3,4,9-tetrahydro-1H-pyrido[3,4-b]indole,
1-(benzo[d][1,3]dioxol-5-yl)-N-benzyl-3,4-dihydro-1H-pyrido[3,4-b]indole-2(9H)-carbothioamide,
(R)-1-(benzo[d][1,3]dioxol-5-yl)-N-benzyl-3,4-dihydro-1H-pyrido[3,4-b]indole-2(9H)-carbothioamide,
1-phenyl-2,3,4,9-tetrahydro-1H-pyrido[3,4-b]indole,
(R)-1-(benzo[d][1,3]dioxol-5-yl)-N-benzyl-3,4-dihydro-1H-pyrido[3,4-b]indole-2(9H)-carboxamide,
N-benzyl-1-phenyl-3,4-dihydro-1H-pyrido[3,4-b]indole-2(9H)-carboxamide,
N,1-diphenyl-3,4-dihydro-1H-pyrido[3,4-b]indole-2(9H)-carboxamide,
N-(naphthalen-1-yl)-1-phenyl-3,4-dihydro-1H-pyrido[3,4-b]indole-2(9H)-carboxamide,
1-(benzo[d][1,3]dioxol-5-yl)-N-cyclohexyl-3,4-dihydro-1H-pyrido[3,4-b]indole-2(9H)-carboxamide,
1-(benzo[d][1,3]dioxol-5-yl)-N-phenyl-3,4-dihydro-1H-pyrido[3,4-b]indole-2(9H)-carboxamide,
1-(3-chloro-4-methoxyphenyl)-N-phenyl-3,4-dihydro-1H-pyrido[3,4-b]indole-2(9H)-carboxamide,
(R)-1-(benzo[d][1,3]dioxol-5-yl)-N-((R)-1-phenylethyl)-3,4-dihydro-1H-pyrido[3,4-b]indole-2(9H)-carboxamide,
(R)-1-(benzo[d][1,3]dioxol-5-yl)-N-((S)-1-phenylethyl)-3,4-dihydro-1H-pyrido[3,4-b]indole-2(9H)-carboxamide,
(R)-1-(benzo[d][1,3]dioxol-5-yl)-N-benzoyl-3,4-dihydro-1H-pyrido[3,4-b]indole-2(9H)-carboxamide,
(R)-N-(1-(benzo[d][1,3]dioxol-5-yl)-2,3,4,9-tetrahydro-1H-pyrido[3,4-b]indole-2-carbonothioyl)benzamide,
benzyl 1-(benzo[d][1,3]dioxol-5-yl)-3,4-dihydro-1H-pyrido[3,4-b]indole-2(9H)-carboxylate,
(R)-benzyl 1-(benzo[d][1,3]dioxol-5-yl)-3,4-dihydro-1H-pyrido[3,4-b]indole-2(9H)-carboxylate,
methyl 1-phenyl-3,4-dihydro-1H-pyrido[3,4-b]indole-2(9H)-carboxylate,
methyl 5-oxo-5-(1-phenyl-3,4-dihydro-1H-pyrido[3,4-b]indol-2(9H)-yl)pentanoate,
5-(1-(3-chloro-4-methoxyphenyl)-3,4-dihydro-1H-pyrido[3,4-b]indol-2(9H)-yl)-5-oxopentanoic acid,
5-(1-(benzo[d][1,3]dioxol-5-yl)-3,4-dihydro-1H-pyrido[3,4-b]indol-2(9H)-yl)-5-oxopentanoic acid,
3-(2-aminophenyl)-1-(1-(benzo[d][1,3]dioxol-5-yl)-3,4-dihydro-1H-pyrido[3,4-b]indol-2(9H)-yl)propan-1-one,
(R)-1-(benzo[d][1,3]dioxol-5-yl)-N-(2-chlorobenzyl)-3,4-dihydro-1H-pyrido[3,4-b]indole-2(9H)-carbothioamide,
(R)-1-(benzo[d][1,3]dioxol-5-yl)-N-(2,4-dichlorobenzyl)-3,4-dihydro-1H-pyrido[3,4-b]indole-2(9H)-carbothioamide,
(R)-1-(benzo[d][1,3]dioxol-5-yl)-N-(2-fluorobenzyl)-3,4-dihydro-1H-pyrido[3,4-b]indole-2(9H)-carbothioamide,
(R)-1-(benzo[d][1,3]dioxol-5-yl)-N-((S)-1-phenylethyl)-3,4-dihydro-1H-pyrido[3,4-b]indole-2(9H)-carbothioamide,
(R)-4-((1-(benzo[d][1,3]dioxol-5-yl)-2,3,4,9-tetrahydro-1H-pyrido[3,4-b]indole-2-carbothioamido)methyl)benzoic acid,
(R)-methyl 4-((1-(benzo[d][1,3]dioxol-5-yl)-2,3,4,9-tetrahydro-1H-pyrido[3,4-b]indole-2-carbothioamido)methyl)benzoate,
(R)-3-((1-(benzo[d][1,3]dioxol-5-yl)-2,3,4,9-tetrahydro-1H-pyrido[3,4-b]indole-2-carbothioamido)methyl)benzoic acid, (R)-methyl 3-((1-(benzo[d][1,3]dioxol-5-yl)-2,3,4,9-tetrahydro-1H-pyrido[3,4-b]indole-2-carbothioamido)methyl)benzoate,
(R)-1-(benzo[d][1,3]dioxol-5-yl)-N-(4-chloro-3-(trifluoromethyl)phenyl)-3,4-dihydro-1H-pyrido[3,4-b]indole-2 (9H)-carbothioamide,
(R)-1-(benzo[d][1,3]dioxol-5-yl)-N-(2-(trifluoromethyl)phenyl)-3,4-dihydro-1H-pyrido[3,4-b]indole-2(9H)-carbothioamide,
(R)-1-(benzo[d][1,3]dioxol-5-yl)-N-(3-fluorobenzyl)-3,4-dihydro-1H-pyrido[3,4-b]indole-2(9H)-carbothioamide,
(R)-1-(benzo[d][1,3]dioxol-5-yl)-N-(4-chlorobenzyl)-3,4-dihydro-1H-pyrido[3,4-b]indole-2(9H)-carbothioamide,
(R)-1-(benzo[d][1,3]dioxol-5-yl)-N-(3,4-dichlorobenzyl)-3,4-dihydro-1H-pyrido[3,4-b]indole-2(9H)-carbothioamide,
(R)-1-(benzo[d][1,3]dioxol-5-yl)-N-(4-fluorobenzyl)-3,4-dihydro-1H-pyrido[3,4-b]indole-2(9H)-carbothioamide,
(R)-1-(benzo[d][1,3]dioxol-5-yl)-N-(3,4-dimethylbenzyl)-3,4-dihydro-1H-pyrido[3,4-b]indole-2(9H)-carbothioamide,
(R)-1-(benzo[d][1,3]dioxol-5-yl)-N-(3-chlorobenzyl)-3,4-dihydro-1H-pyrido[3,4-b]indole-2(9H)-carbothioamide,
(R)-1-(benzo[d][1,3]dioxol-5-yl)-N-(naphthalen-1-ylmethyl)-3,4-dihydro-1H-pyrido[3,4-b]indole-2(9H)-carbothioamide,
(3,4-difluorophenyl)-(1-phenyl-1,3,4,9-tetrahydro-β-carbolin-2-yl)-methanone,
6-methoxy-1,2,3,4-tetrahydronorharmane,
1,2,3,4-tetrahydronorharman-3-carboxylic acid,
6-methoxy-1,2,3,4-tetrahydronorharman-1-carboxylic acid,
1-(4-methoxyphenyl)-1,2,3,4-tetrahydronorharman-3-carboxylic acid,
1-methyl-1,2,3,4-tetrahydronorharman-3-carboxylic acid,
1-methyl-1,2,3,4-tetrahydronorharman-1,3-dicarboxylic acid,
1-(diethylmethyl)-1,2,3,4-tetrahydronorharman-3-carboxylic acid,
(6-bromo-1,2,3,4-tetrahydronorharman-1-yl)-3-propionic acid,
1-isobutyl-1,2,3,4-tetrahydronorharman-3-carboxylic acid,
1-phenyl-1,2,3,4-tetrahydronorharman-3-carboxylic acid,
1-propyl-1,2,3,4-tetrahydronorharman-3-carboxylic acid,
1-methyl-1-methoxycarbonyl-6-benzyloxy-1,2,3,4-tetrahydronorharmane,
1-methyl-1-methoxycarbonyl-6-methoxy-1,2,3,4-tetrahydronorharmane,
1-methyl-1-methoxycarbonyl-6-hydroxy-1,2,3,4-tetrahydronorharmane,
1-methyl-1-methoxycarbonyl-6-chloro-1,2,3,4-tetrahydronorharmane,
1-methyl-1-methoxycarbonyl-6-bromo-1,2,3,4-tetrahydronorharmane,
1-methyl-2-N-acetyl-6-methoxy-1,2,3,4-tetrahydro-β-carboline,
2-N-acetyl-1,2,3,4-tetrahydro-β-carboline,
1-methyl-2-N-acetyl-6-methoxy-1,2,3,4-tetrahydro-β-carboline,
4-chlorobenzyl (1S,3R)-1-(2,4-dichlorophenyl)-1,2,3,4-tetrahydro-β-carboline-3-carboxamide,
(3R)-1-(1-benzylindol-3-yl)-2-tert-butoxycarbonyl-1,2,3,4-tetrahydro-β-carboline-3-carboxylic acid,
(3R)-1-(1-butylindol-3-yl)-2-tert-butoxycarbonyl-1,2,3,4-tetrahydro-β-carboline-3-carboxylic acid,
(1S,3R)-1-(indol-3-yl)-2-tert-butoxycarbonyl-1,2,3,4-tetrahydro-β-carboline-3-carboxylic acid,
(1S,3R)-1-(1-methylindol-3-yl)-2-tert-butoxycarbonyl-1,2,3,4-tetrahydro-β-carboline-3-carboxylic acid,
benzothiazol-2-yl (1S,3R)-1-cyclohexyl-2-tert-butoxycarbonyl-1,2,3,4-tetrahydro-β-carboline-3-carboxylic acid,
benzothiazol-2-yl (1S,3R)-1-cyclohexyl-1,2,3,4-tetrahydro-β-carboline-3-carboxylic acid,
1-(4-chlorophenyl)-1,2,3,4-tetrahydro-β-carboline,
1-(4-bromophenyl)-1,2,3,4-tetrahydro-β-carboline,
1-(4-nitrophenyl)-1,2,3,4-tetrahydro-β-carboline,
1-(4-dimethylaminophenyl)-1,2,3,4-tetrahydro-β-carboline,
1-(4-diethylaminophenyl)-1,2,3,4-tetrahydro-β-carboline,
1-(2,4-dimethoxyphenyl)-1,2,3,4-tetrahydro-β-carboline,
1-(3,4-dimethoxyphenyl)-1,2,3,4-tetrahydro-β-carboline,
1-(2,5-dimethoxyphenyl)-1,2,3,4-tetrahydro-β-carboline,
1-(3,5-dimethoxyphenyl)-1,2,3,4-tetrahydro-β-carboline,
1-(3,4,5-trimethoxyphenyl)-1,2,3,4-tetrahydro-β-carboline,
1-(4-nitrobenzo[d][1,3]dioxol-5-yl)-1,2,3,4-tetrahydro-β-carboline,
1-(2-fluorenyl)-1,2,3,4-tetrahydro-β-carboline,
1-(9-ethyl-9H-carbazol-3-yl)-1,2,3,4-tetrahydro-β-carboline,
6-chloro-1-(4-methylphenyl)-2,3,4,9-tetrahydro-1H-β-carboline,
methyl 6-chloro-1-(4-methylphenyl)-1,3,4,9-tetrahydro-2H-β-carboline-2-carboxylate,
6-chloro-1-(4-methylphenyl)-2-(3-phenylpropanoyl)-2,3,4,9-tetrahydro-1H-β-carboline,
phenylmethyl 6-chloro-1-(4-methylphenyl)-1,3,4,9-tetrahydro-2H-β-carboline-2-carboxylate,
6-fluoro-1-(4-methylphenyl)-2,3,4,9-tetrahydro-1H-β-carboline,
methyl 6-fluoro-1-(4-methylphenyl)-1,3,4,9-tetrahydro-2H-β-carboline-2-carboxylate,
6-fluoro-1-(4-methylphenyl)-2-(3-phenylpropanoyl)-2,3,4,9-tetrahydro-1H-β-carboline,
phenylmethyl 6-fluoro-1-(4-methylphenyl)-1,3,4,9-tetrahydro-2H-β-carboline-2-carboxylate,
6-bromo-1-(4-methylphenyl)-2,3,4,9-tetrahydro-1H-β-carboline,
methyl 6-bromo-1-(4-methylphenyl)-1,3,4,9-tetrahydro-2H-β-carboline-2-carboxylate,
6-bromo-1-(4-methylphenyl)-2-(3-phenylpropanoyl)-2,3,4,9-tetrahydro-1H-β-carboline,
phenylmethyl 6-bromo-1-(4-methylphenyl)-1,3,4,9-tetrahydro-2H-β-carboline-2-carboxylate,
(1R)-6-chloro-1-(4-methylphenyl)-2-(3-phenylpropanoyl)-2,3,4,9-tetrahydro-1H-β-carboline,
(1S)-6-chloro-1-(4-methylphenyl)-2-(3-phenylpropanoyl)-2,3,4,9-tetrahydro-1H-β-carboline,
1-(4-methylphenyl)-2-(methylsulfonyl)-2,3,4,9-tetrahydro-1H-β-carboline,
2-acetyl-1-(4-methylphenyl)-2,3,4,9-tetrahydro-1H-β-carboline,
1-(4-methylphenyl)-2-(3-phenylpropanoyl)-2,3,4,9-tetrahydro-1H-β-carboline,
6-(methyloxy)-1-(4-methylphenyl)-2-(3-phenylpropanoyl)-2,3,4,9-tetrahydro-1H-β-carboline,
6-methyl-1-(4-methylphenyl)-2-(3-phenylpropanoyl)-2,3,4,9-tetrahydro-1H-β-carboline,
(1R/1S)-1-(2,3-dihydro-1-benzofuran-5-yl)-2,3,4,9-tetrahydro-1H-β-carboline, or
1-(1,3-benzodioxol-5-yl)-2-(2-pyrimidinyl)-2,3,4,9-tetrahydro-1H-β-carboline.

As will be evident to one of skill in the art, Compounds provided herein comprise at least one stereocenter, and may exist as a racemic mixture or as an enantiomerically pure composition. In one embodiment, a Compound provided herein is the (S) isomer, in an enantiomerically pure composition. In certain embodiments, the enantiomeric excess (e.e.) is about 90%, about 95%, about 99% or about 99.9% or greater.

In another embodiment, provided herein are Compounds having Formula (II):

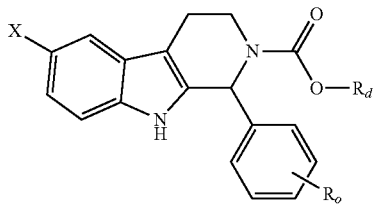

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, $C(O)R_b$, $-C(O)O-R_b$, alkylsulfonyl, morpholinyl or tetrahydropyranyl; $C_1$ to $C_6$ alkyl optionally substituted with one or more substituents independently selected from hydroxyl, halogen or amino; $C(O)-R_n$; or $-OR_a$;

$R_a$ is hydrogen; $C_2$ to $C_8$ alkenyl; $-C(O)-R_n$; $-C(O)O-R_b$; $-C(O)-NH-R_b$; $C_1$ to $C_8$ alkyl optionally substituted with one or more substituents independently selected from hydroxyl, halogen, $C_1$ to $C_4$ alkoxy, $C_1$ to $C_4$ alkoxy $C_1$ to $C_4$ alkoxy, amino, alkylamino, dialkylamino, acetamide, $-C(O)-R_b$, $-C(O)O-R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene or tetrazole;

wherein amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

wherein alkylamino and dialkylamino are each optionally substituted on alkyl with hydroxyl, $C_1$ to $C_4$ alkoxy, imidazole, pyrazole, pyrrole or tetrazole; and, wherein morpholinyl, thiomorpholinyl, pyrrolidinyl, piperidinyl, piperazinyl and oxiranyl are each optionally substituted with $-C(O)-R_n$, $-C(O)O-R_1$, or $C_1$ to $C_4$ alkyl, wherein $C_1$ to $C_4$ alkyl is optionally substituted with hydroxyl;

$R_b$ is hydroxyl; amino; alkylamino, optionally substituted on alkyl with hydroxyl, amino, alkylamino or $C_1$ to $C_4$ alkoxy; $C_1$ to $C_4$ alkoxy; $C_2$ to $C_8$ alkenyl; $C_2$ to $C_8$ alkynyl; aryl optionally substituted with one or more substituents independently selected from halogen and $C_1$ to $C_4$ alkoxy; furan; or $C_1$ to $C_8$ alkyl optionally substituted with one or more substituents independently selected from $C_1$ to $C_4$ alkoxy, aryl, amino, morpholinyl, piperidinyl or piperazinyl;

$R_d$ is aryl optionally substituted with one or more substituents independently selected from halogen, nitro, $C_1$ to $C_6$ alkyl, $-C(O)O-R_e$, and $-OR_e$;

$R_e$ is hydrogen; $C_1$ to $C_6$ alkyl optionally substituted with one or more substituents independently selected from halogen and alkoxy; or phenyl, wherein phenyl is optionally substituted with one or more substituents independently selected from halogen and alkoxy; and $R_n$ is hydroxyl, $C_1$ to $C_4$ alkoxy, amino or $C_1$ to $C_6$ alkyl.

In another embodiment, provided herein are Compounds having Formula (II):

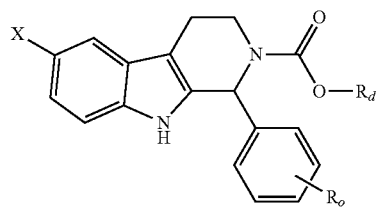

or a pharmaceutically acceptable salt, racemate or stereoisomer thereof, wherein, X is halogen;

$R_1$ is halogen, substituted or unsubstituted $C_1$ to $C_8$ alkyl or $OR_a$;

$R_a$ is H, $C_1$ to $C_8$ alkyl optionally substituted with one or more substituents independently selected from hydroxyl and halogen; and $R_d$ is phenyl optionally substituted with one or more alkoxy or halogen substituents.

In one embodiment, X is chloro or bromo.

In one embodiment, $R_d$ is chloro or bromo.

In one embodiment, $R_o$ is $OR_a$.

In one embodiment, $R_a$ is methyl, ethyl, propyl, isopropyl, butyl, or pentyl, each optionally substituted with one or more hydroxyl substituents.

In another embodiment, provided herein are Compounds having Formula (II):

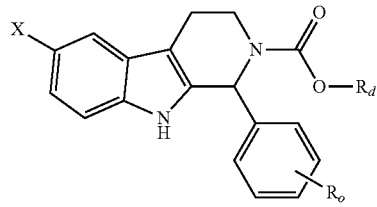

or a pharmaceutically acceptable salt, racemate or stereoisomer thereof, wherein, X is halogen;

$R_o$ is halogen, substituted or unsubstituted $C_1$ to $C_8$ alkyl or $OR_a$;

$R_a$ is H, or $C_1$ to $C_8$ alkyl optionally substituted with one or more substituents independently selected from hydroxyl and halogen; and $R_d$ is phenyl optionally substituted with one or more halogen substituents.

In another embodiment, provided herein are Compounds having Formula (III):

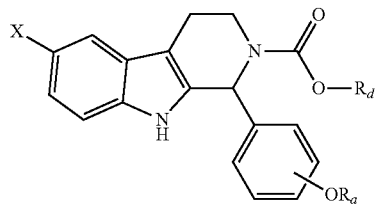
(III)

or a pharmaceutically acceptable salt, racemate or stereoisomer thereof, wherein,
X is halogen;
$R_a$ is H, $C_1$ to $C_8$ alkyl optionally substituted with one or more substituents independently selected from hydroxyl and halogen; and
$R_d$ is phenyl substituted with one or more halogen substituents.

In another embodiment, provided herein are Compounds having Formula (IV):

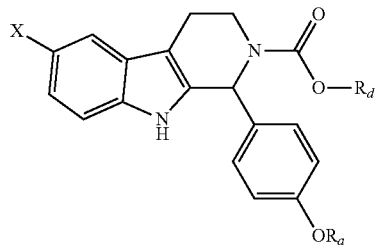
(IV)

or a pharmaceutically acceptable salt, racemate or stereoisomer thereof, wherein,
X is halogen;
$R_a$ is H, $C_1$ to $C_8$ alkyl optionally substituted with one or more substituents independently selected from hydroxyl and halogen; and
$R_d$ is phenyl substituted with one or more halogen substituents.

In another embodiment, provided herein are Compounds having Formula (IV):

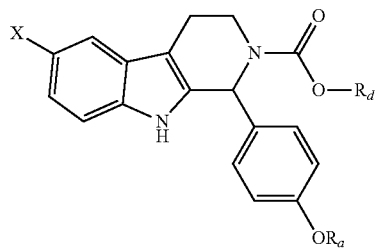
(IV)

or a pharmaceutically acceptable salt, racemate or stereoisomer thereof, wherein, X is halogen;
$R_a$ is H, $C_1$ to $C_8$ alkyl optionally substituted with one or more substituents independently selected from hydroxyl and halogen; and
$R_d$ is phenyl substituted on a para position with a halogen substituent.

In another embodiment, the Compounds set forth above having a formula selected from Formula (Ia), Formula (IIa), Formula (IIIa) and Formula (IVa):

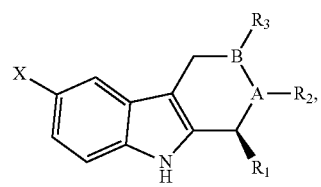
(Ia)

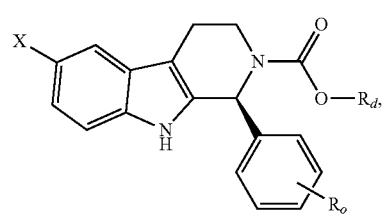
(IIa)

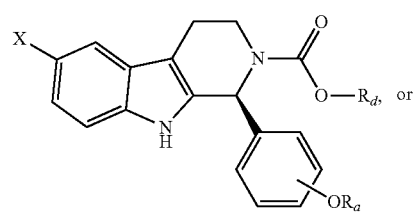
(IIIa), or

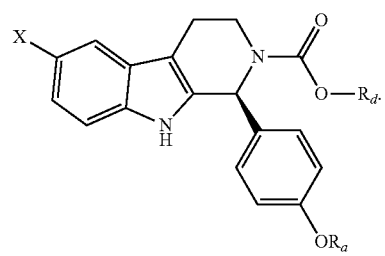
(IVa)

Illustrative examples of Compounds or a pharmaceutically acceptable salt, racemate or stereoisomer thereof provided herein include:

TABLE 1
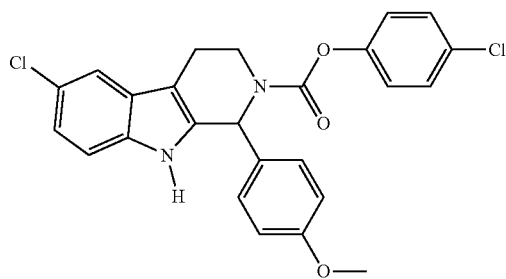
10
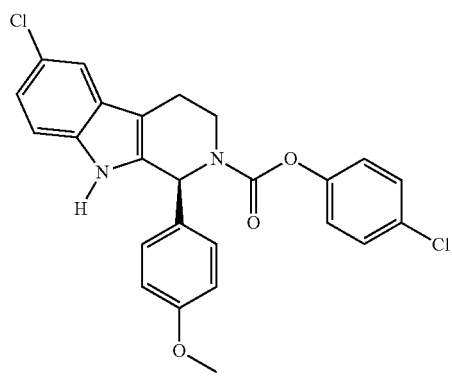 [SMILES: COc1ccc([C@H]2c3[nH]c4ccc(Cl)cc4c3CCN2C(=O)Oc2ccc(Cl)cc2)cc1]
10
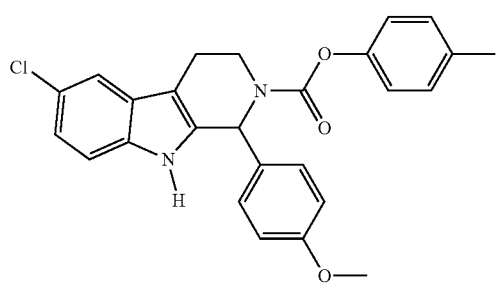 [SMILES: COc1ccc(C2c3[nH]c4ccc(Cl)cc4c3CCN2C(=O)Oc2ccc(C)cc2)cc1]
17
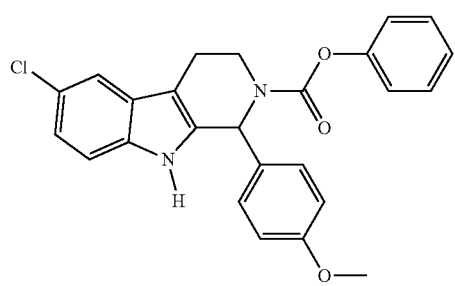 [SMILES: COc1ccc(C2c3[nH]c4ccc(Cl)cc4c3CCN2C(=O)Oc2ccccc2)cc1]
60
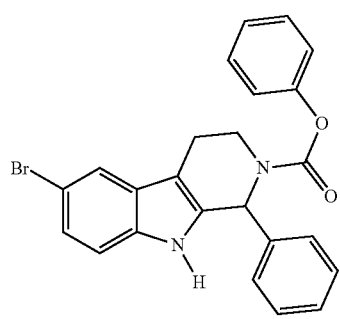 [SMILES: O=C(Oc1ccccc1)N1CCc2c([nH]c3ccc(Br)cc23)C1c1ccccc1]
76

TABLE 1-continued
| | |
|---|---|
| 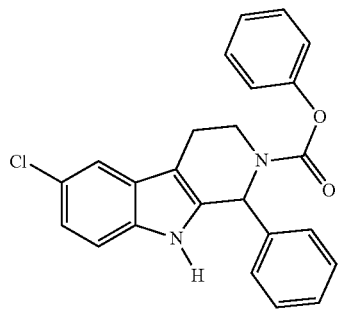 [SMILES: O=C(Oc1ccccc1)N1CCc2c([nH]c3ccc(Cl)cc23)C1c1ccccc1] | 121 |
| 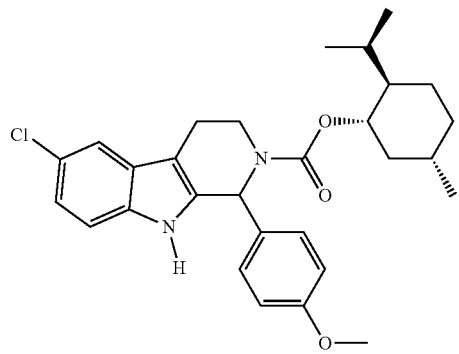 | 192 |
| 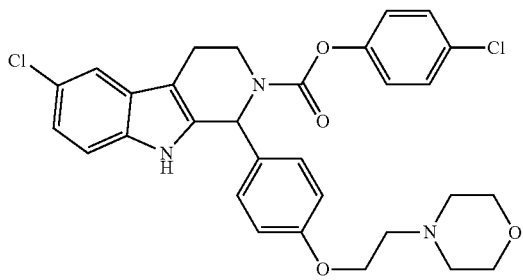 [SMILES: O=C(Oc1ccc(Cl)cc1)N1CCc2c([nH]c3ccc(Cl)cc23)C1c1ccc(OCCN2CCOCC2)cc1] | 331 |
| 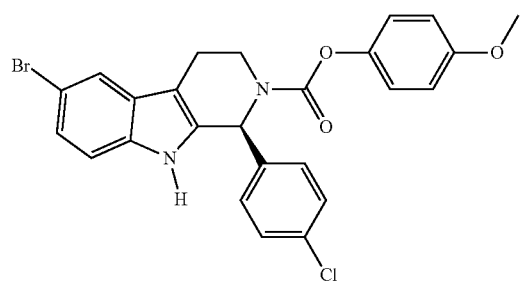 [SMILES: COc1ccc(OC(=O)N2CCc3c([nH]c4ccc(Br)cc34)[C@@H]2c2ccc(Cl)cc2)cc1] | 332 |
| 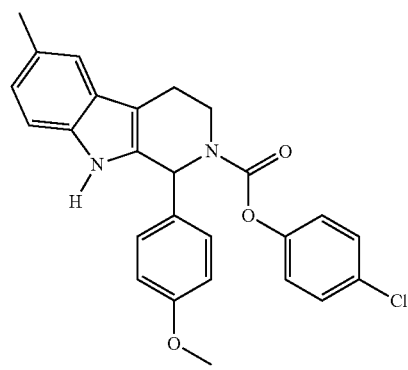 [SMILES: COc1ccc(C2c3[nH]c4ccc(C)cc4c3CCN2C(=O)Oc2ccc(Cl)cc2)cc1] | 341 |

TABLE 1-continued
| | |
|---|---|
| 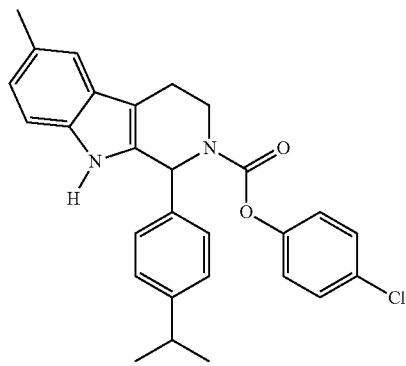 [SMILES: Cc1ccc2[nH]c3c(c2c1)CCN(C(=O)Oc1ccc(Cl)cc1)C3c1ccc(C(C)C)cc1] | 344 |
| 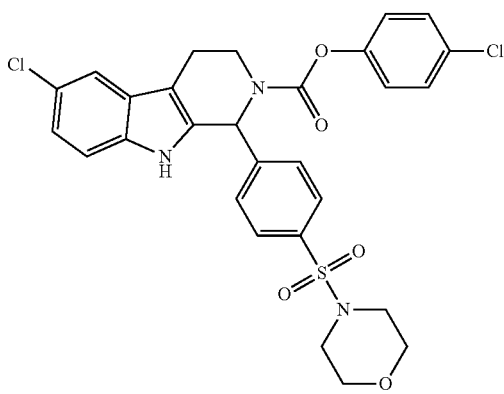 [SMILES: O=C(Oc1ccc(Cl)cc1)N1CCc2c([nH]c3ccc(Cl)cc23)C1c1ccc(S(=O)(=O)N2CCOCC2)cc1] | 346 |
| 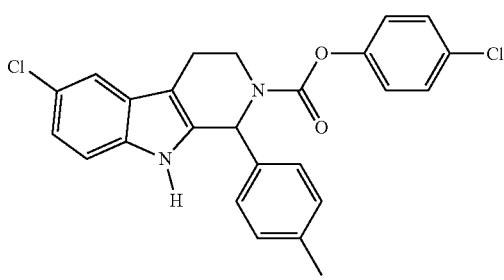 [SMILES: Cc1ccc(C2c3[nH]c4ccc(Cl)cc4c3CCN2C(=O)Oc2ccc(Cl)cc2)cc1] | 347 |
| 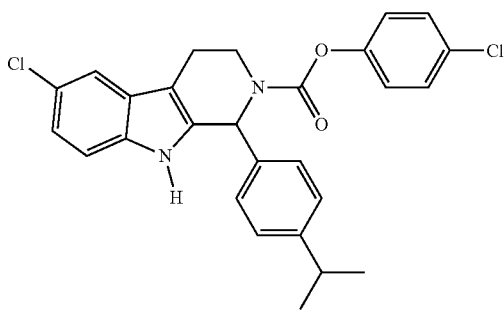 [SMILES: CC(C)c1ccc(C2c3[nH]c4ccc(Cl)cc4c3CCN2C(=O)Oc2ccc(Cl)cc2)cc1] | 348 |

TABLE 1-continued
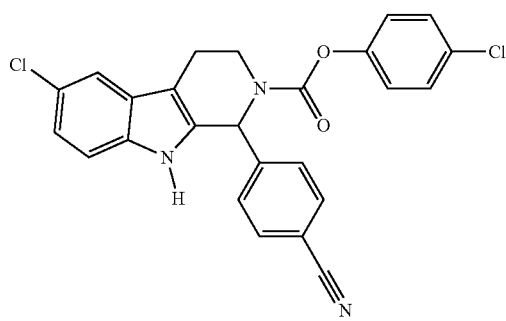 [SMILES: N#Cc1ccc(C2c3[nH]c4ccc(Cl)cc4c3CCN2C(=O)Oc2ccc(Cl)cc2)cc1] 350
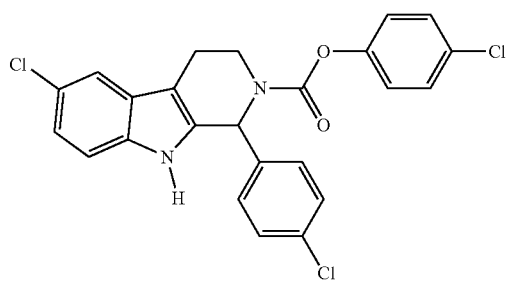 [SMILES: O=C(Oc1ccc(Cl)cc1)N1CCc2c([nH]c3ccc(Cl)cc23)C1c1ccc(Cl)cc1] 351
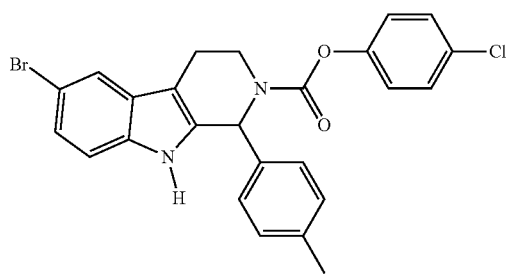 353
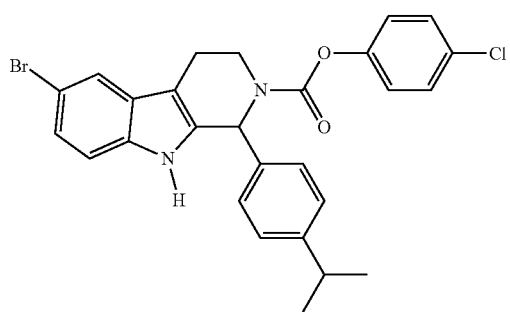 354
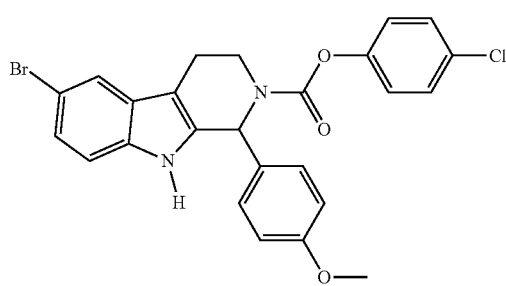 355

TABLE 1-continued
| | |
|---|---|
| 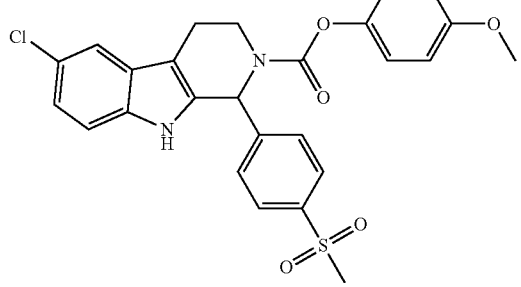 | 359 |
| 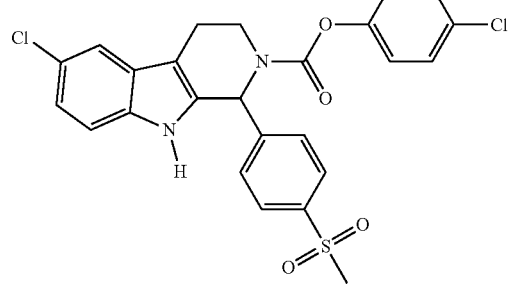 | 360 |
| 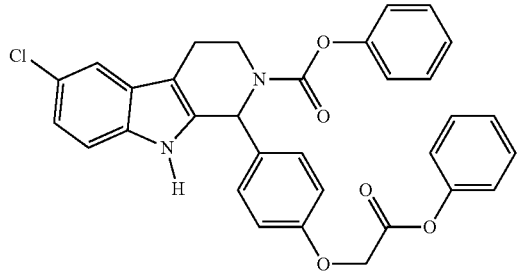 [SMILES: O=C(COc1ccc(C2c3[nH]c4ccc(Cl)cc4c3CCN2C(=O)Oc2ccccc2)cc1)Oc1ccccc1] | 366 |
| 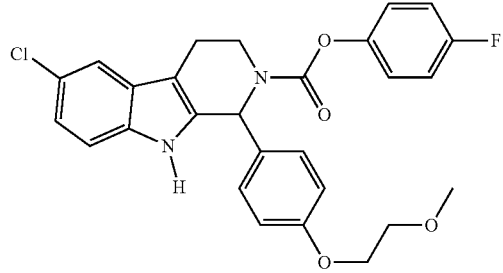 [SMILES: COCCOc1ccc(C2c3[nH]c4ccc(Cl)cc4c3CCN2C(=O)Oc2ccc(F)cc2)cc1] | 388 |
| 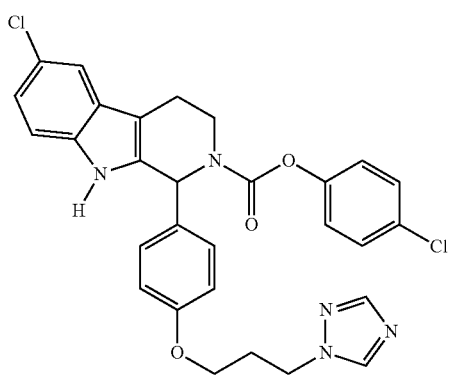 [SMILES: O=C(Oc1ccc(Cl)cc1)N1CCc2c([nH]c3ccc(Cl)cc23)C1c1ccc(OCCCn2cncn2)cc1] | 391 |

TABLE 1-continued
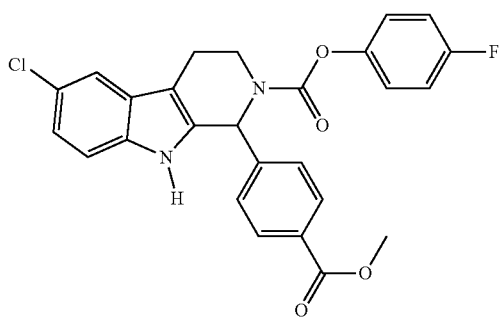
395
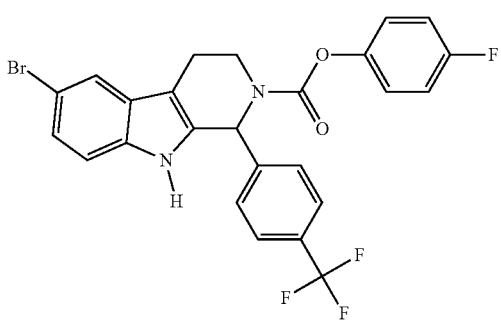 [SMILES: O=C(Oc1ccc(F)cc1)N1CCc2c([nH]c3ccc(Br)cc23)C1c1ccc(C(F)(F)F)cc1]
397
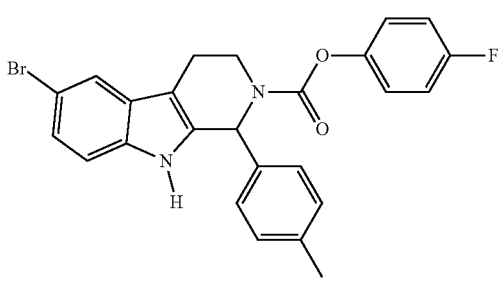 [SMILES: Cc1ccc(C2c3[nH]c4ccc(Br)cc4c3CCN2C(=O)Oc2ccc(F)cc2)cc1]
398
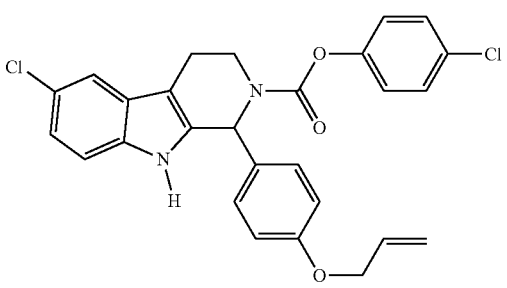 [SMILES: C=CCOc1ccc(C2c3[nH]c4ccc(Cl)cc4c3CCN2C(=O)Oc2ccc(Cl)cc2)cc1]
400
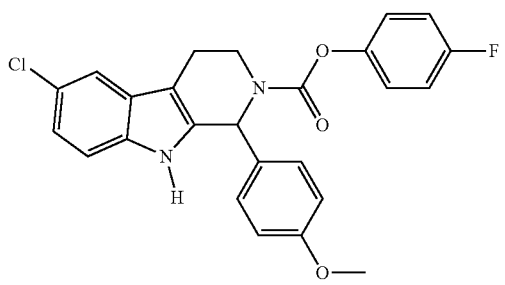 [SMILES: COc1ccc(C2c3[nH]c4ccc(Cl)cc4c3CCN2C(=O)Oc2ccc(F)cc2)cc1]
401

TABLE 1-continued
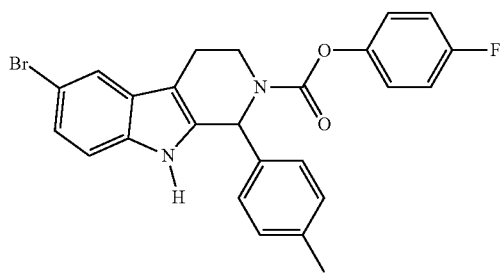 [SMILES: Cc1ccc(C2c3[nH]c4ccc(Br)cc4c3CCN2C(=O)Oc2ccc(F)cc2)cc1] 403
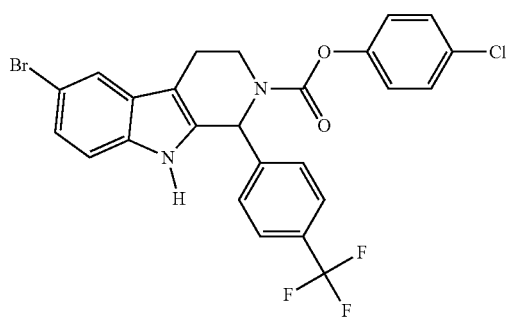 [SMILES: O=C(Oc1ccc(Cl)cc1)N1CCc2c([nH]c3ccc(Br)cc23)C1c1ccc(C(F)(F)F)cc1] 405
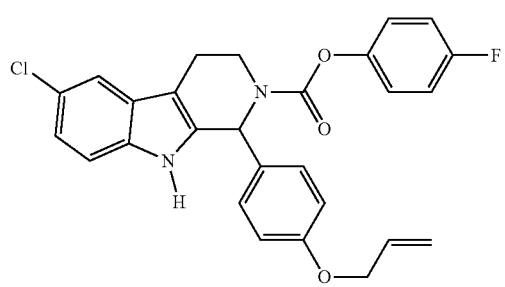 [SMILES: C=CCOc1ccc(C2c3[nH]c4ccc(Cl)cc4c3CCN2C(=O)Oc2ccc(F)cc2)cc1] 409
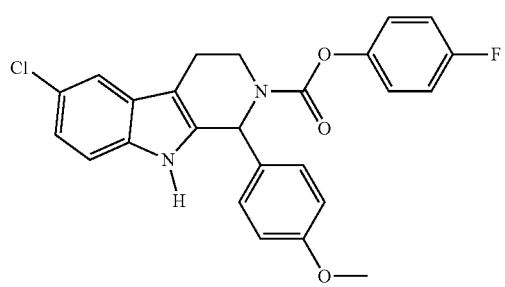 [SMILES: COc1ccc(C2c3[nH]c4ccc(Cl)cc4c3CCN2C(=O)Oc2ccc(F)cc2)cc1] 410
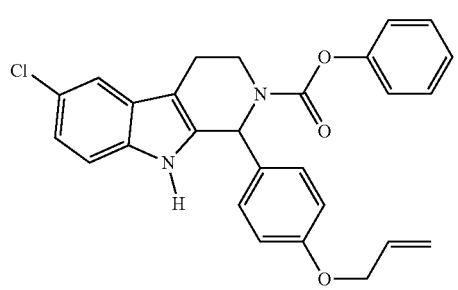 [SMILES: C=CCOc1ccc(C2c3[nH]c4ccc(Cl)cc4c3CCN2C(=O)Oc2ccccc2)cc1] 413

TABLE 1-continued
| | |
|---|---|
| 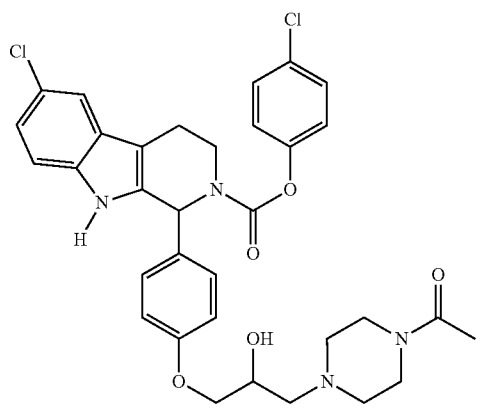 [SMILES: CC(=O)N1CCN(CC(O)COc2ccc(C3c4[nH]c5ccc(Cl)cc5c4CCN3C(=O)Oc3ccc(Cl)cc3)cc2)CC1] | 415 |
| 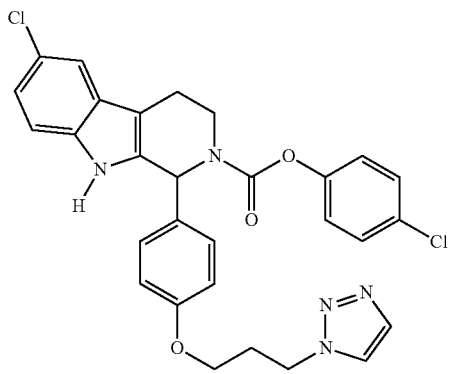 [SMILES: O=C(Oc1ccc(Cl)cc1)N1CCc2c([nH]c3ccc(Cl)cc23)C1c1ccc(OCCCn2ccnn2)cc1] | 417 |
| 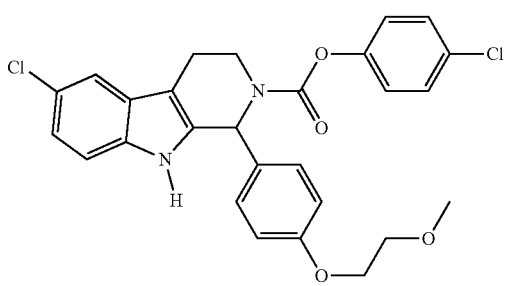 [SMILES: COCCOc1ccc(C2c3[nH]c4ccc(Cl)cc4c3CCN2C(=O)Oc2ccc(Cl)cc2)cc1] | 418 |
| 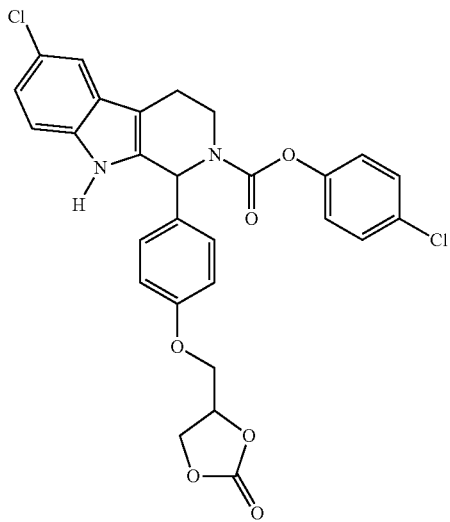 [SMILES: O=C1OCC(COc2ccc(C3c4[nH]c5ccc(Cl)cc5c4CCN3C(=O)Oc3ccc(Cl)cc3)cc2)O1] | 421 |

TABLE 1-continued
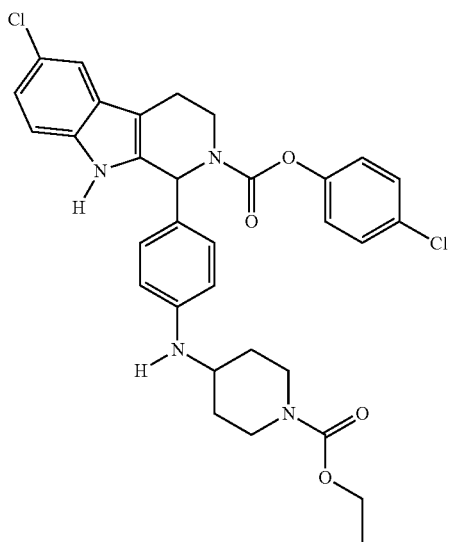 [SMILES: CCOC(=O)N1CCC(Nc2ccc(C3c4[nH]c5ccc(Cl)cc5c4CCN3C(=O)Oc3ccc(Cl)cc3)cc2)CC1]
422
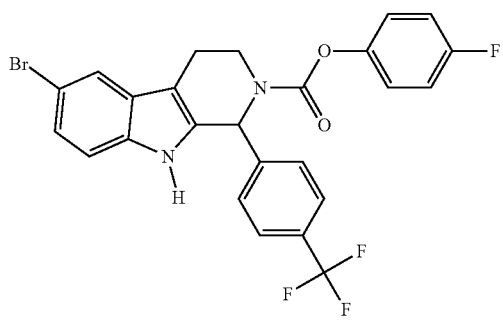 [SMILES: O=C(Oc1ccc(F)cc1)N1CCc2c([nH]c3ccc(Br)cc23)C1c1ccc(C(F)(F)F)cc1]
426
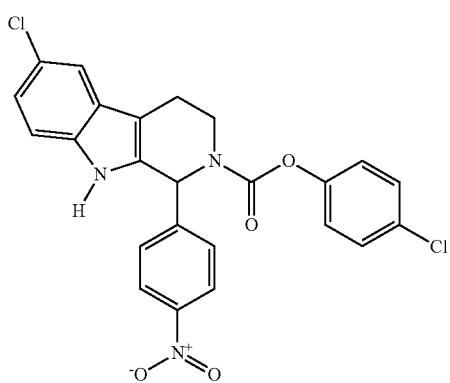 [SMILES: O=C(Oc1ccc(Cl)cc1)N1CCc2c([nH]c3ccc(Cl)cc23)C1c1ccc([N+](=O)[O-])cc1]
427
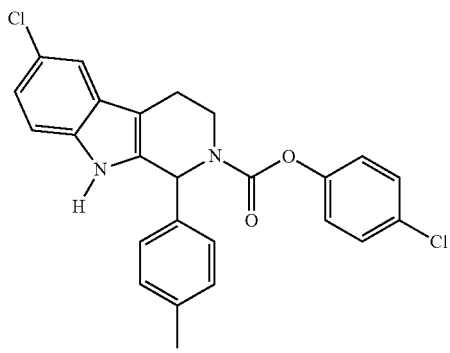 [SMILES: Cc1ccc(C2c3[nH]c4ccc(Cl)cc4c3CCN2C(=O)Oc2ccc(Cl)cc2)cc1]
428

TABLE 1-continued
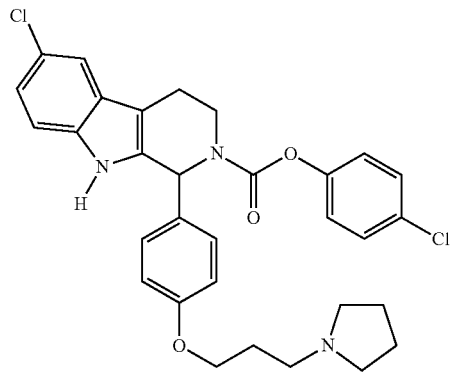 [SMILES: O=C(Oc1ccc(Cl)cc1)N1CCc2c([nH]c3ccc(Cl)cc23)C1c1ccc(OCCCN2CCCC2)cc1]
429
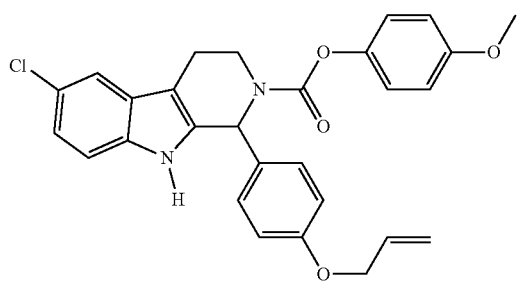 [SMILES: C=CCOc1ccc(C2c3[nH]c4ccc(Cl)cc4c3CCN2C(=O)Oc2ccc(OC)cc2)cc1]
432
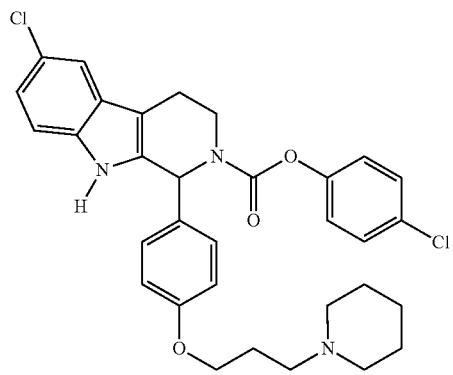 [SMILES: O=C(Oc1ccc(Cl)cc1)N1CCc2c([nH]c3ccc(Cl)cc23)C1c1ccc(OCCCN2CCCCC2)cc1]
433
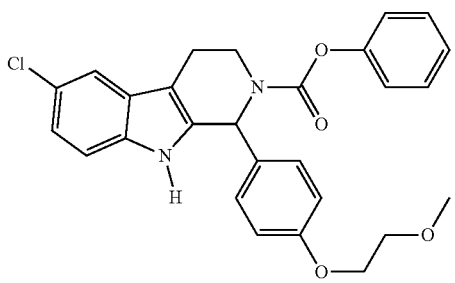 [SMILES: COCCOc1ccc(C2c3[nH]c4ccc(Cl)cc4c3CCN2C(=O)Oc2ccccc2)cc1]
436

TABLE 1-continued
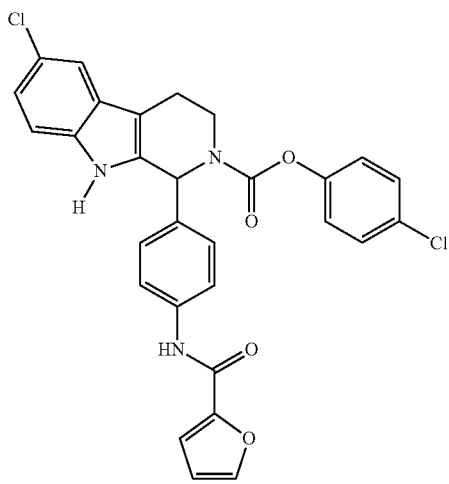 [SMILES: O=C(Nc1ccc(C2c3[nH]c4ccc(Cl)cc4c3CCN2C(=O)Oc2ccc(Cl)cc2)cc1)c1ccco1]
437
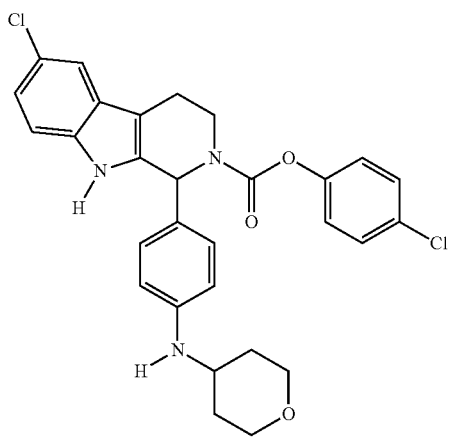 [SMILES: O=C(Oc1ccc(Cl)cc1)N1CCc2c([nH]c3ccc(Cl)cc23)C1c1ccc(NC2CCOCC2)cc1]
440
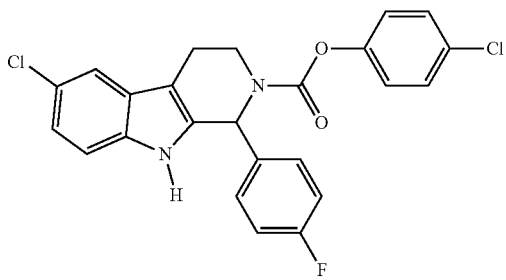
444
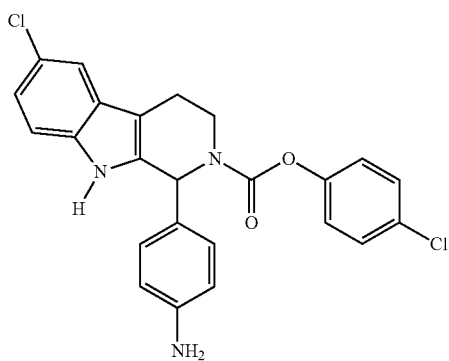 [SMILES: Nc1ccc(C2c3[nH]c4ccc(Cl)cc4c3CCN2C(=O)Oc2ccc(Cl)cc2)cc1]
446

TABLE 1-continued
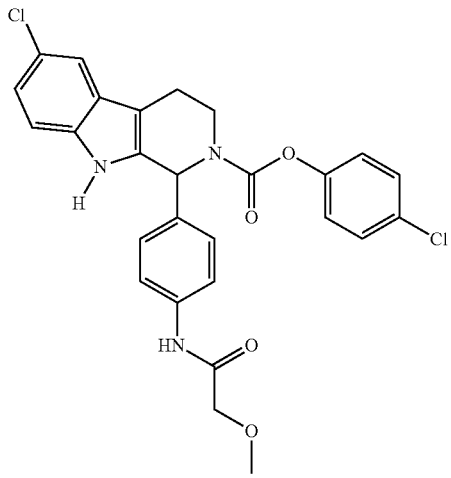 [SMILES: COCC(=O)Nc1ccc(C2c3[nH]c4ccc(Cl)cc4c3CCN2C(=O)Oc2ccc(Cl)cc2)cc1]
448
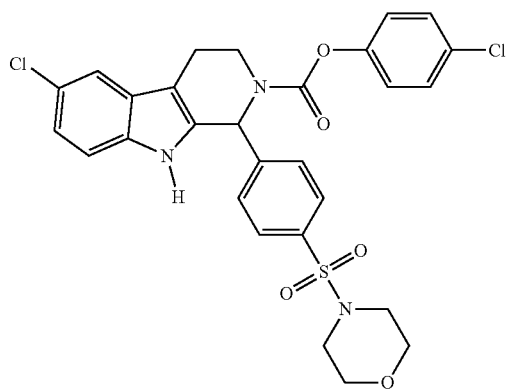 [SMILES: O=C(Oc1ccc(Cl)cc1)N1CCc2c([nH]c3ccc(Cl)cc23)C1c1ccc(S(=O)(=O)N2CCOCC2)cc1]
450
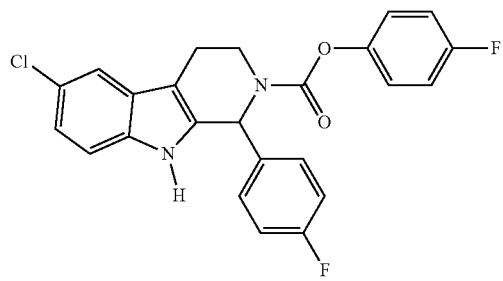 [SMILES: O=C(Oc1ccc(F)cc1)N1CCc2c([nH]c3ccc(Cl)cc23)C1c1ccc(F)cc1]
452
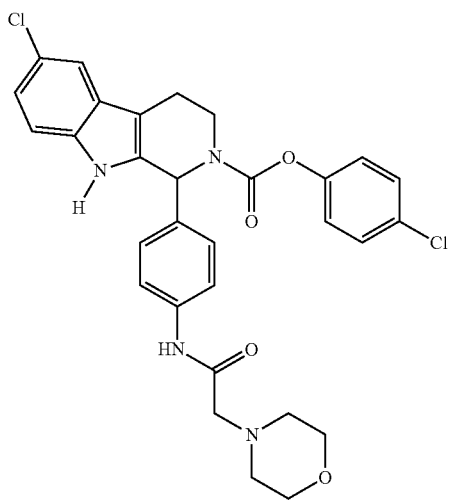 [SMILES: O=C(CN1CCOCC1)Nc1ccc(C2c3[nH]c4ccc(Cl)cc4c3CCN2C(=O)Oc2ccc(Cl)cc2)cc1]
454

TABLE 1-continued
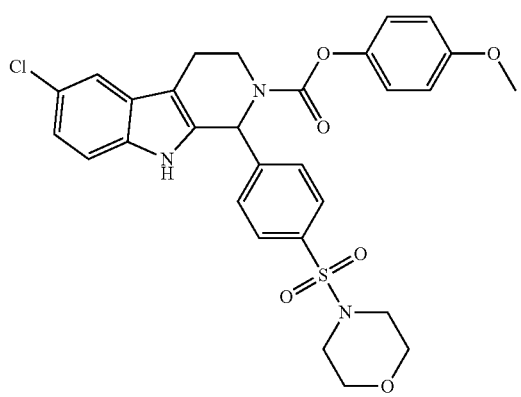 [SMILES: COc1ccc(OC(=O)N2CCc3c([nH]c4ccc(Cl)cc34)C2c2ccc(S(=O)(=O)N3CCOCC3)cc2)cc1]
455
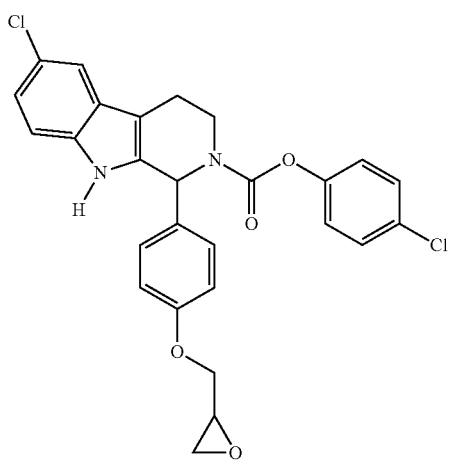 [SMILES: O=C(Oc1ccc(Cl)cc1)N1CCc2c([nH]c3ccc(Cl)cc23)C1c1ccc(OCC2CO2)cc1]
460
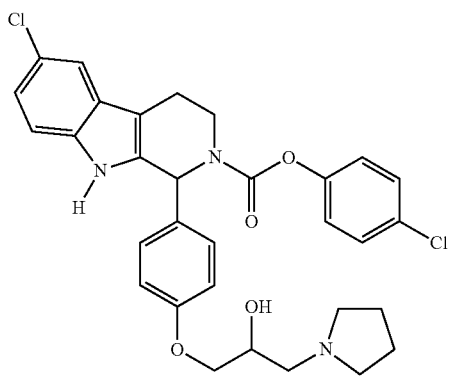 [SMILES: O=C(Oc1ccc(Cl)cc1)N1CCc2c([nH]c3ccc(Cl)cc23)C1c1ccc(OCC(O)CN2CCCC2)cc1]
462

TABLE 1-continued
| | |
|---|---|
| 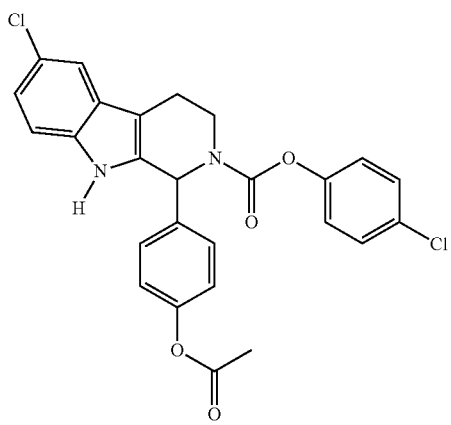 [SMILES: CC(=O)Oc1ccc(C2c3[nH]c4ccc(Cl)cc4c3CCN2C(=O)Oc2ccc(Cl)cc2)cc1] | 463 |
| 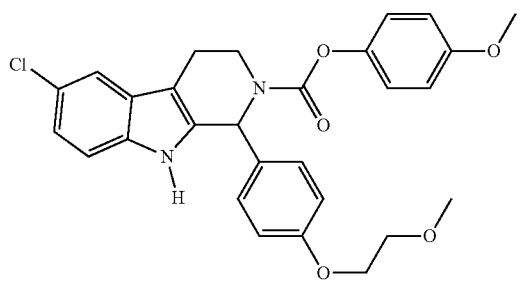 [SMILES: COCCOc1ccc(C2c3[nH]c4ccc(Cl)cc4c3CCN2C(=O)Oc2ccc(OC)cc2)cc1] | 465 |
| 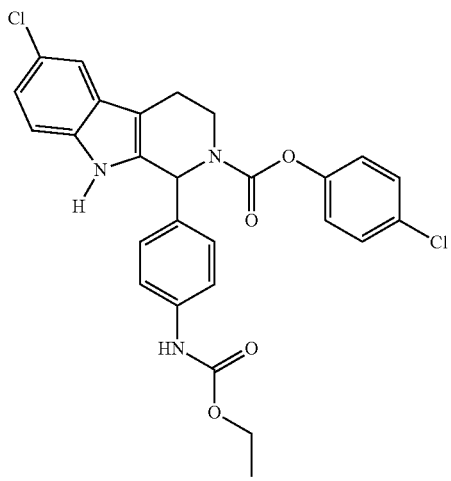 [SMILES: CCOC(=O)Nc1ccc(C2c3[nH]c4ccc(Cl)cc4c3CCN2C(=O)Oc2ccc(Cl)cc2)cc1] | 467 |
| 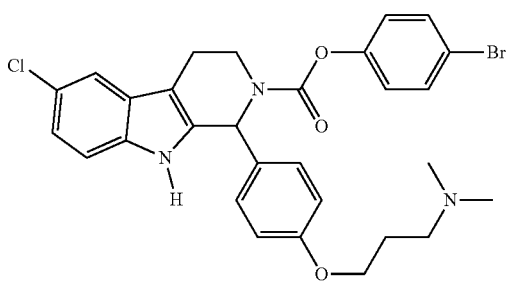 [SMILES: CN(C)CCCOc1ccc(C2c3[nH]c4ccc(Cl)cc4c3CCN2C(=O)Oc2ccc(Br)cc2)cc1] | 468 |

TABLE 1-continued
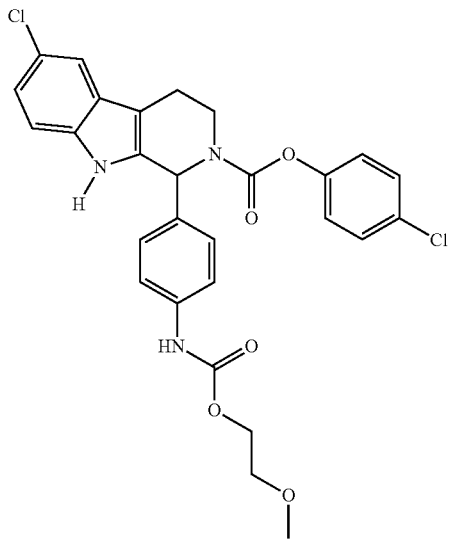 [SMILES: COCCOC(=O)Nc1ccc(C2c3[nH]c4ccc(Cl)cc4c3CCN2C(=O)Oc2ccc(Cl)cc2)cc1]
470
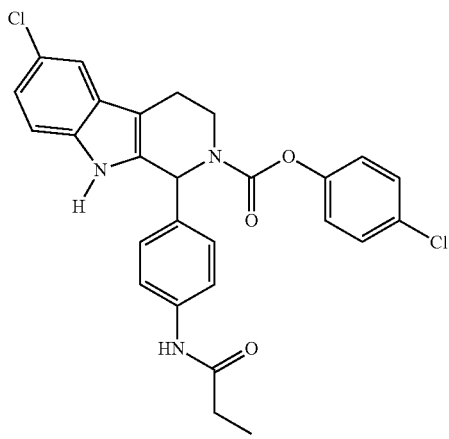 [SMILES: CCC(=O)Nc1ccc(C2c3[nH]c4ccc(Cl)cc4c3CCN2C(=O)Oc2ccc(Cl)cc2)cc1]
471
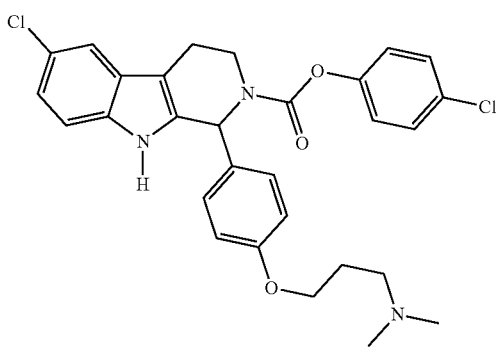 [SMILES: CN(C)CCCOc1ccc(C2c3[nH]c4ccc(Cl)cc4c3CCN2C(=O)Oc2ccc(Cl)cc2)cc1]
479

TABLE 1-continued
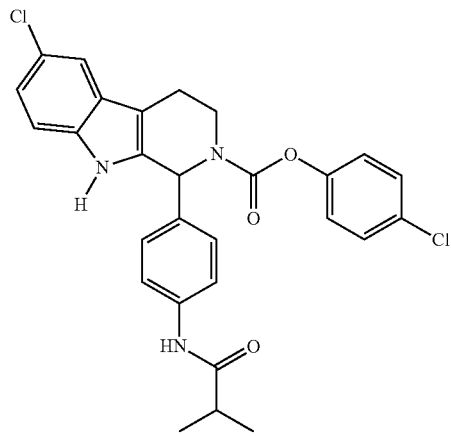 [SMILES: CC(C)C(=O)Nc1ccc(C2c3[nH]c4ccc(Cl)cc4c3CCN2C(=O)Oc2ccc(Cl)cc2)cc1]
482
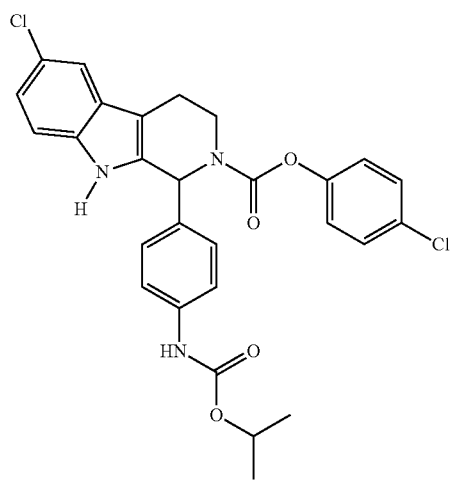 [SMILES: CC(C)OC(=O)Nc1ccc(C2c3[nH]c4ccc(Cl)cc4c3CCN2C(=O)Oc2ccc(Cl)cc2)cc1]
489
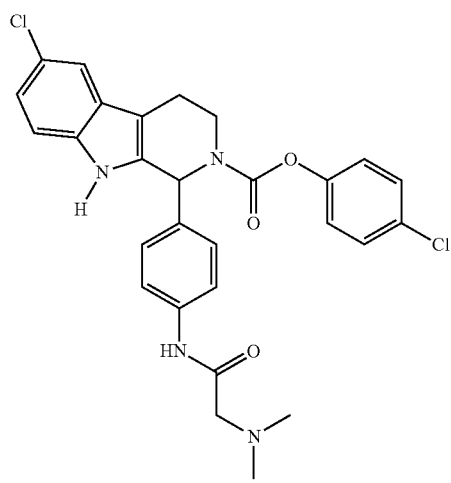 [SMILES: CN(C)CC(=O)Nc1ccc(C2c3[nH]c4ccc(Cl)cc4c3CCN2C(=O)Oc2ccc(Cl)cc2)cc1]
491

TABLE 1-continued
| | |
|---|---|
| 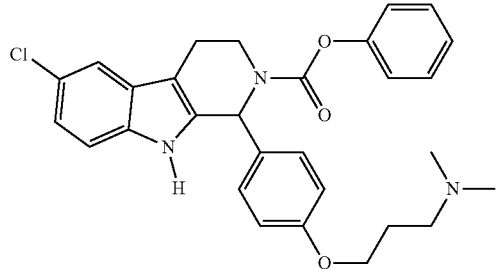 [SMILES: CN(C)CCCOc1ccc(C2c3[nH]c4ccc(Cl)cc4c3CCN2C(=O)Oc2ccccc2)cc1] | 493 |
| 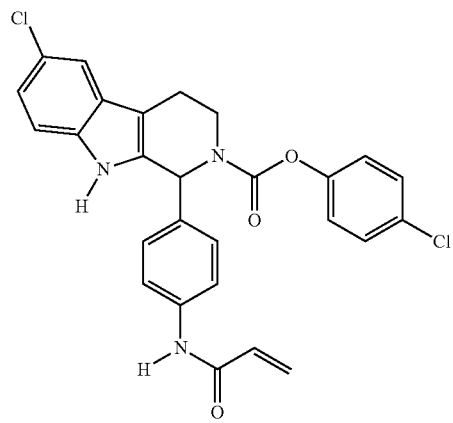 [SMILES: C=CC(=O)Nc1ccc(C2c3[nH]c4ccc(Cl)cc4c3CCN2C(=O)Oc2ccc(Cl)cc2)cc1] | 500 |
| 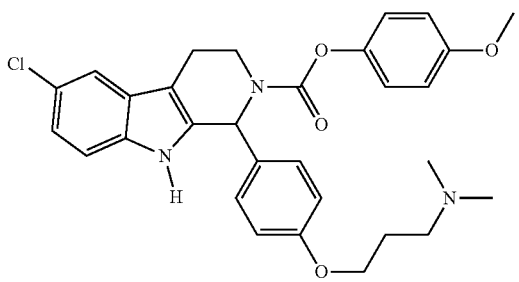 [SMILES: COc1ccc(OC(=O)N2CCc3c([nH]c4ccc(Cl)cc34)C2c2ccc(OCCCN(C)C)cc2)cc1] | 501 |
| 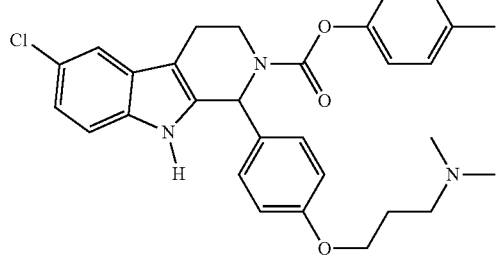 | 502 |
| 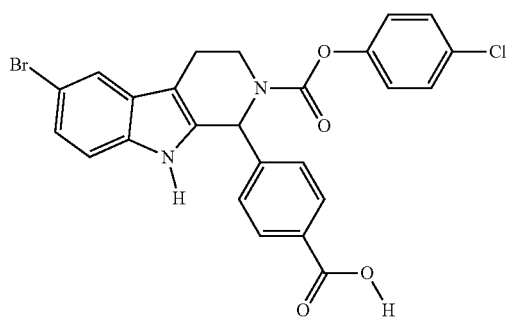 [SMILES: O=C(O)c1ccc(C2c3[nH]c4ccc(Br)cc4c3CCN2C(=O)Oc2ccc(Cl)cc2)cc1] | 519 |

TABLE 1-continued
| | |
|---|---|
| 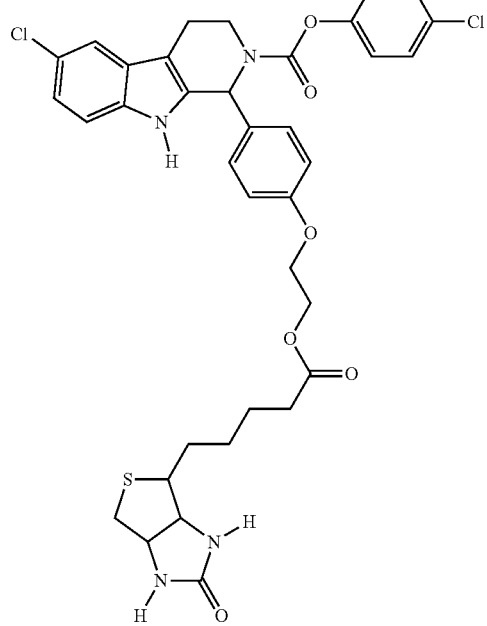 | 544 |
| 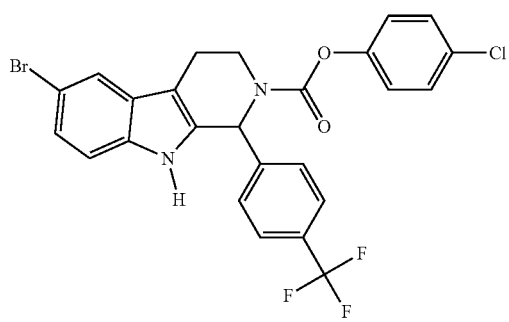 | 570 |
| 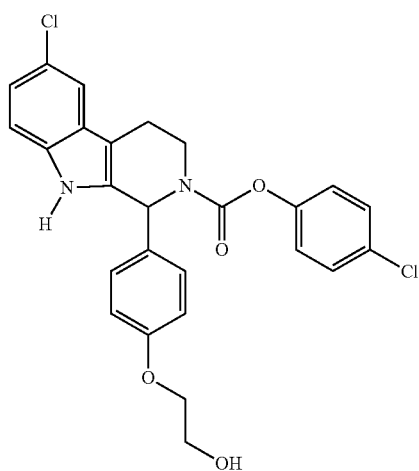 [SMILES: O=C(Oc1ccc(Cl)cc1)N1CCc2c([nH]c3ccc(Cl)cc23)C1c1ccc(OCCO)cc1] | 571 |

TABLE 1-continued
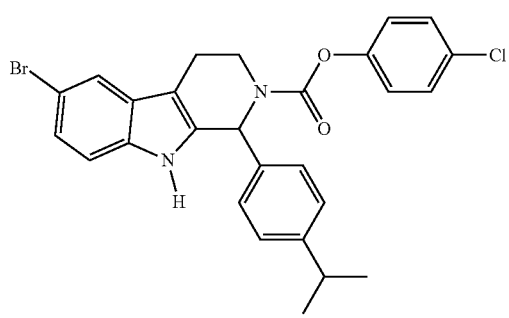
572
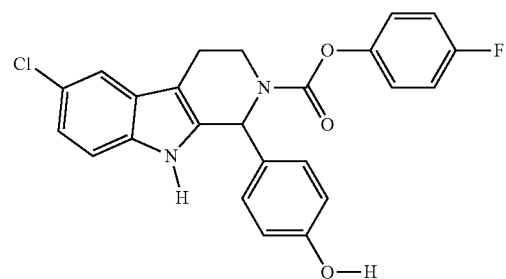 [SMILES: O=C(Oc1ccc(F)cc1)N1CCc2c([nH]c3ccc(Cl)cc23)C1c1ccc(O)cc1]
575
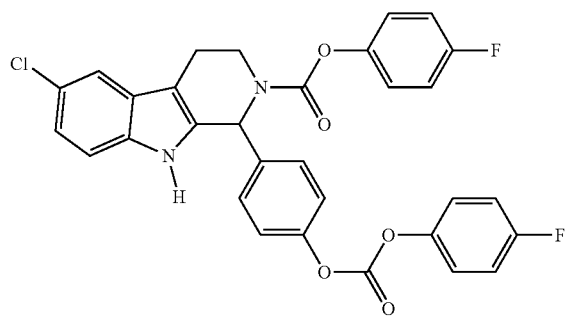 [SMILES: O=C(Oc1ccc(F)cc1)Oc1ccc(C2c3[nH]c4ccc(Cl)cc4c3CCN2C(=O)Oc2ccc(F)cc2)cc1]
576
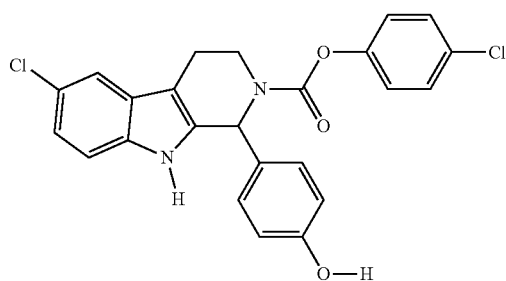 [SMILES: O=C(Oc1ccc(Cl)cc1)N1CCc2c([nH]c3ccc(Cl)cc23)C1c1ccc(O)cc1]
577
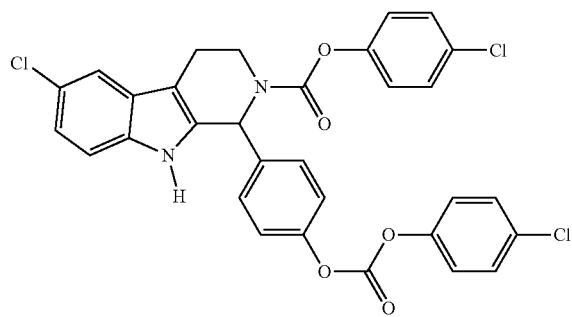 [SMILES: O=C(Oc1ccc(Cl)cc1)Oc1ccc(C2c3[nH]c4ccc(Cl)cc4c3CCN2C(=O)Oc2ccc(Cl)cc2)cc1]
578

TABLE 1-continued
| | |
|---|---|
| 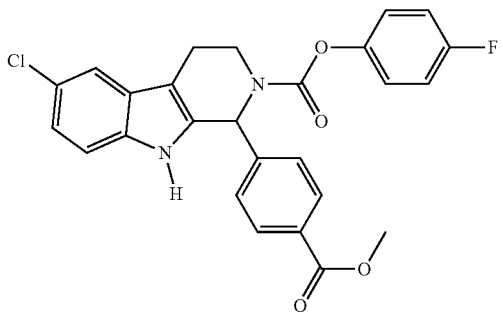 [SMILES: COC(=O)c1ccc(C2c3[nH]c4ccc(Cl)cc4c3CCN2C(=O)Oc2ccc(F)cc2)cc1] | 579 |
| 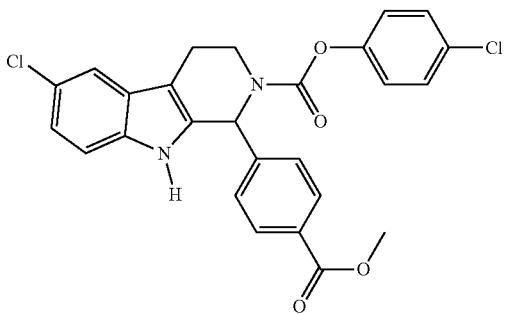 [SMILES: COC(=O)c1ccc(C2c3[nH]c4ccc(Cl)cc4c3CCN2C(=O)Oc2ccc(Cl)cc2)cc1] | 580 |
| 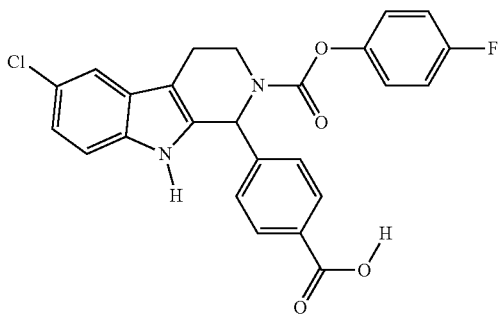 [SMILES: O=C(O)c1ccc(C2c3[nH]c4ccc(Cl)cc4c3CCN2C(=O)Oc2ccc(F)cc2)cc1] | 581 |
| 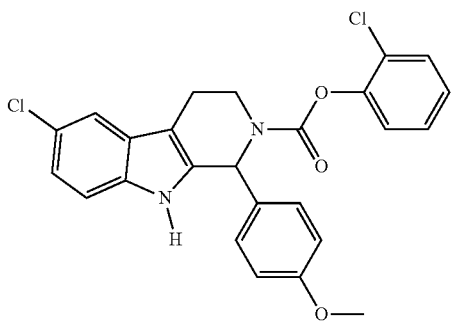 [SMILES: COc1ccc(C2c3[nH]c4ccc(Cl)cc4c3CCN2C(=O)Oc2ccccc2Cl)cc1] | 587 |
| 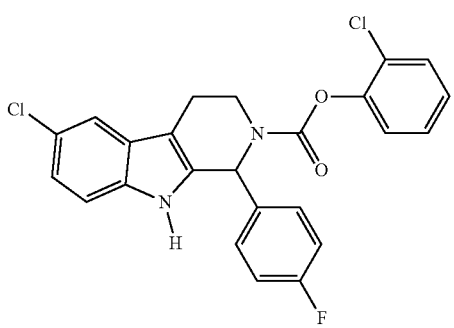 [SMILES: O=C(Oc1ccccc1Cl)N1CCc2c([nH]c3ccc(Cl)cc23)C1c1ccc(F)cc1] | 588 |

TABLE 1-continued
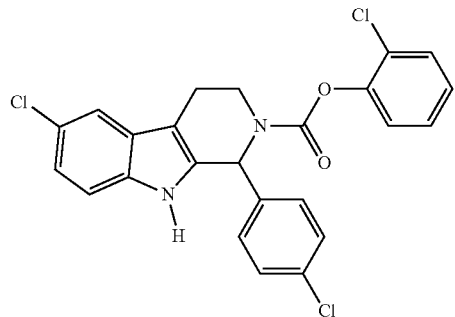
589
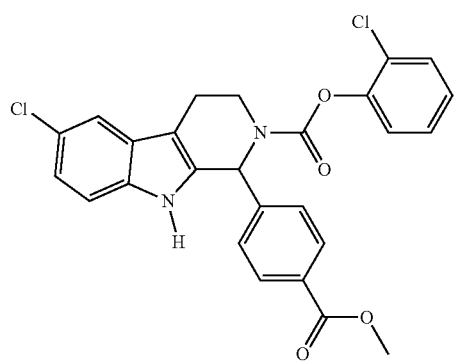 [SMILES: COC(=O)c1ccc(C2c3[nH]c4ccc(Cl)cc4c3CCN2C(=O)Oc2ccccc2Cl)cc1]
590
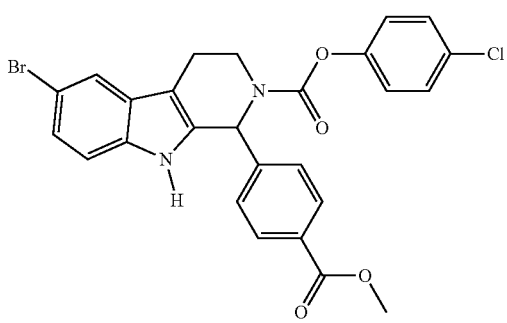 [SMILES: COC(=O)c1ccc(C2c3[nH]c4ccc(Br)cc4c3CCN2C(=O)Oc2ccc(Cl)cc2)cc1]
591
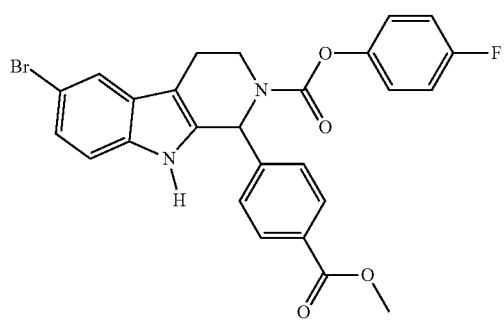
592

TABLE 1-continued
| | |
|---|---|
| 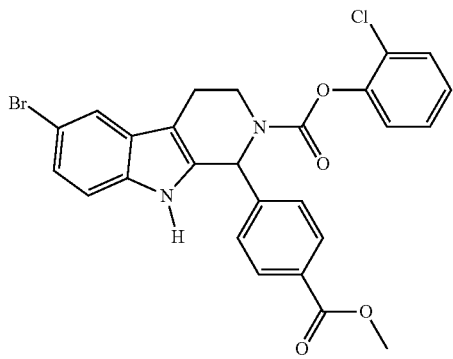 | 593 |
| 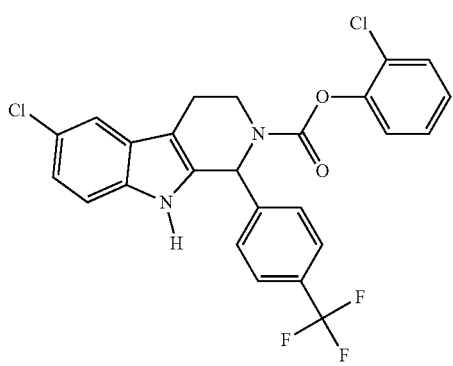 [SMILES: O=C(Oc1ccccc1Cl)N1CCc2c([nH]c3ccc(Cl)cc23)C1c1ccc(C(F)(F)F)cc1] | 594 |
| 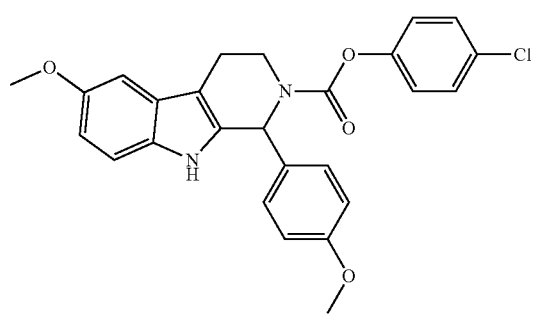 [SMILES: COc1ccc(C2c3[nH]c4ccc(OC)cc4c3CCN2C(=O)Oc2ccc(Cl)cc2)cc1] | 614 |
| 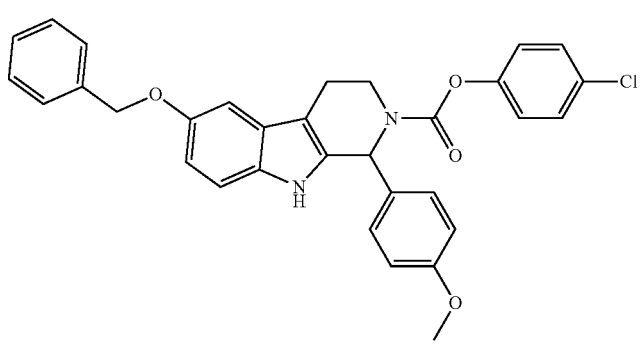 [SMILES: COc1ccc(C2c3[nH]c4ccc(OCc5ccccc5)cc4c3CCN2C(=O)Oc2ccc(Cl)cc2)cc1] | 616 |

TABLE 1-continued
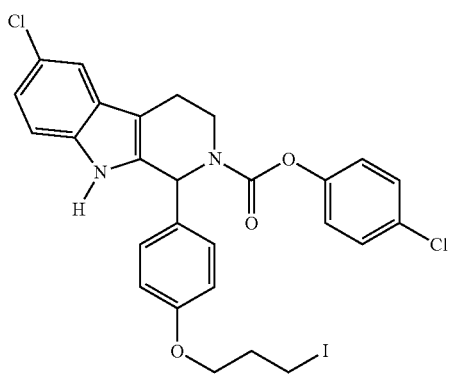 [SMILES: O=C(Oc1ccc(Cl)cc1)N1CCc2c([nH]c3ccc(Cl)cc23)C1c1ccc(OCCCI)cc1]
617
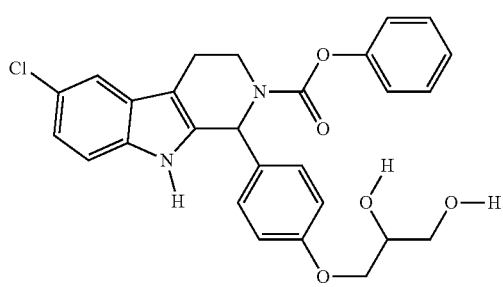 [SMILES: O=C(Oc1ccccc1)N1CCc2c([nH]c3ccc(Cl)cc23)C1c1ccc(OCC(O)CO)cc1]
626
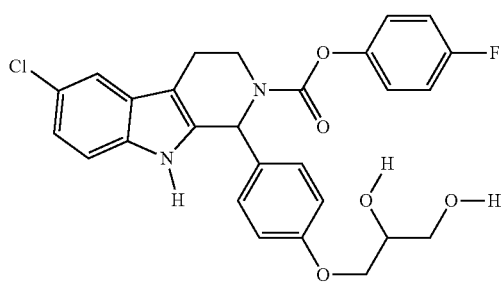 [SMILES: O=C(Oc1ccc(F)cc1)N1CCc2c([nH]c3ccc(Cl)cc23)C1c1ccc(OCC(O)CO)cc1]
627
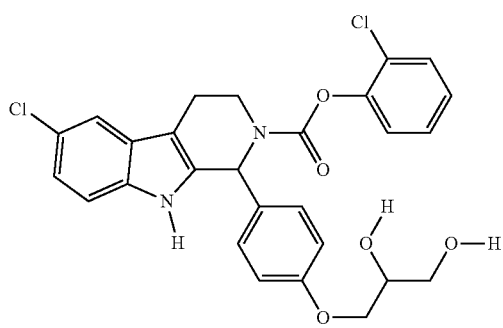 [SMILES: O=C(Oc1ccccc1Cl)N1CCc2c([nH]c3ccc(Cl)cc23)C1c1ccc(OCC(O)CO)cc1]
628
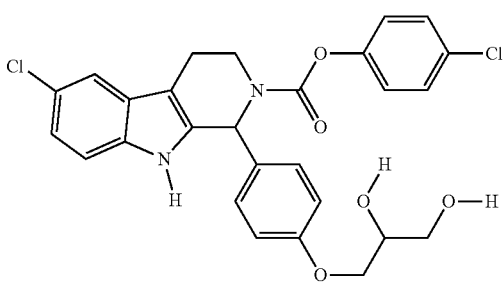 [SMILES: O=C(Oc1ccc(Cl)cc1)N1CCc2c([nH]c3ccc(Cl)cc23)C1c1ccc(OCC(O)CO)cc1]
629

TABLE 1-continued
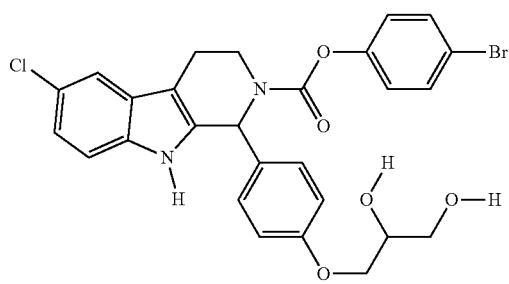 [SMILES: O=C(Oc1ccc(Br)cc1)N1CCc2c([nH]c3ccc(Cl)cc23)C1c1ccc(OCC(O)CO)cc1]
630
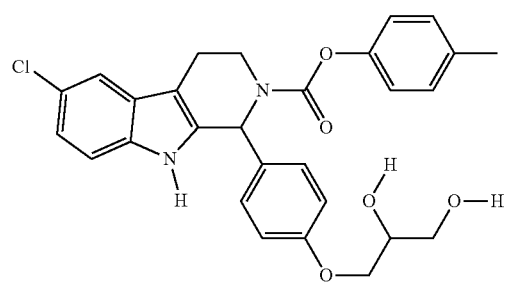 [SMILES: Cc1ccc(OC(=O)N2CCc3c([nH]c4ccc(Cl)cc34)C2c2ccc(OCC(O)CO)cc2)cc1]
631
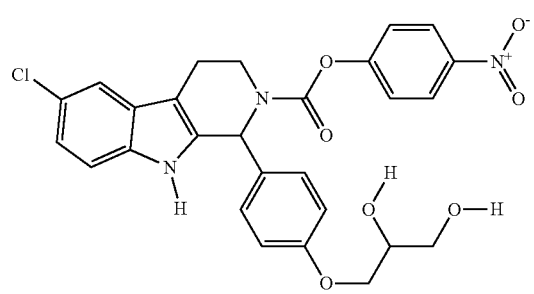 [SMILES: O=C(Oc1ccc([N+](=O)[O-])cc1)N1CCc2c([nH]c3ccc(Cl)cc23)C1c1ccc(OCC(O)CO)cc1]
632
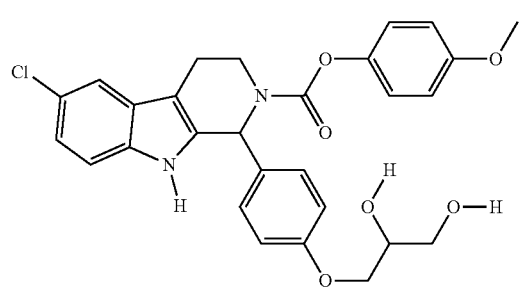 [SMILES: COc1ccc(OC(=O)N2CCc3c([nH]c4ccc(Cl)cc34)C2c2ccc(OCC(O)CO)cc2)cc1]
635
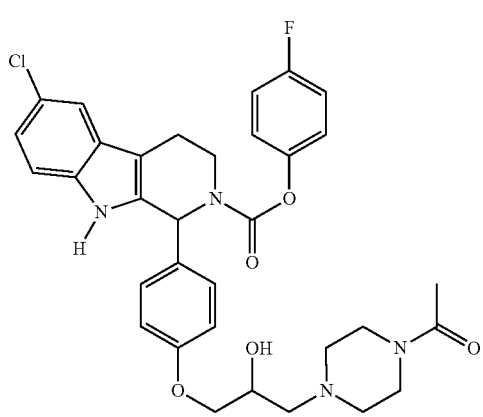 [SMILES: CC(=O)N1CCN(CC(O)COc2ccc(C3c4[nH]c5ccc(Cl)cc5c4CCN3C(=O)Oc3ccc(F)cc3)cc2)CC1]
637

TABLE 1-continued
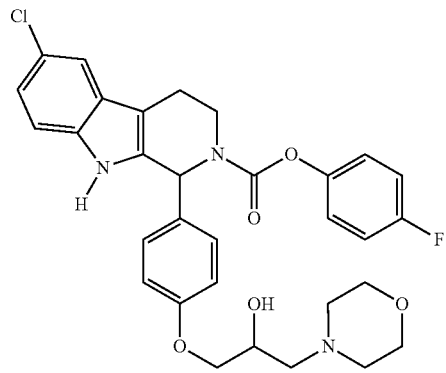 [SMILES: O=C(Oc1ccc(F)cc1)N1CCc2c([nH]c3ccc(Cl)cc23)C1c1ccc(OCC(O)CN2CCOCC2)cc1] 638
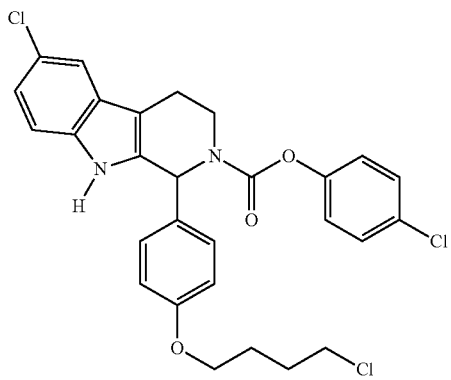 [SMILES: O=C(Oc1ccc(Cl)cc1)N1CCc2c([nH]c3ccc(Cl)cc23)C1c1ccc(OCCCCCl)cc1] 660
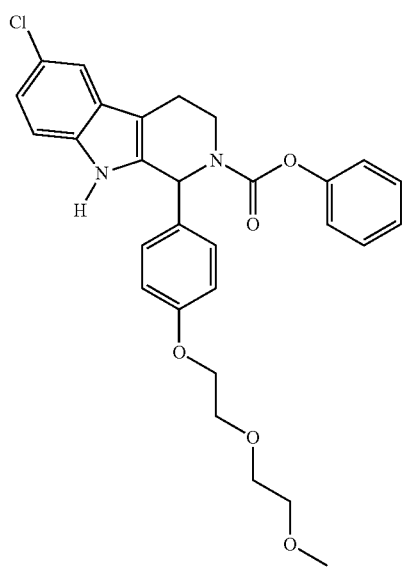 [SMILES: COCCOCCOc1ccc(C2c3[nH]c4ccc(Cl)cc4c3CCN2C(=O)Oc2ccccc2)cc1] 670

TABLE 1-continued
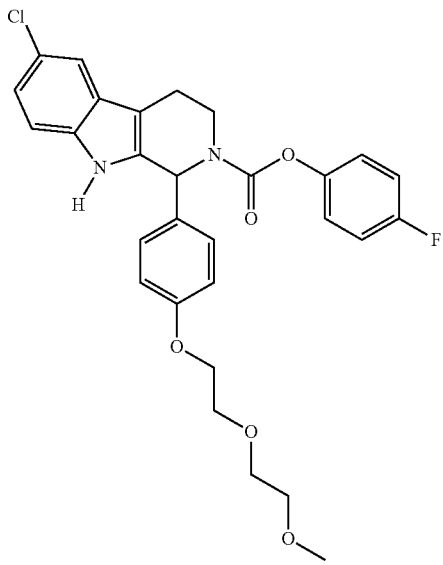 [SMILES: COCCOCCOc1ccc(C2c3[nH]c4ccc(Cl)cc4c3CCN2C(=O)Oc2ccc(F)cc2)cc1]
673
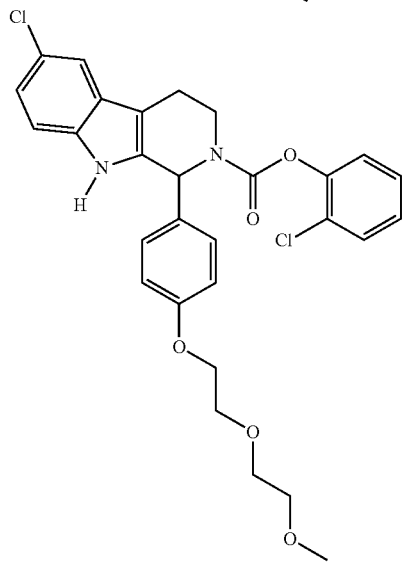
674
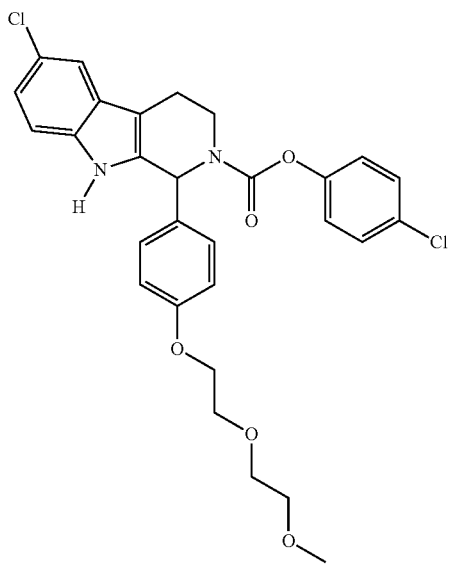 [SMILES: COCCOCCOc1ccc(C2c3[nH]c4ccc(Cl)cc4c3CCN2C(=O)Oc2ccc(Cl)cc2)cc1]
675

TABLE 1-continued
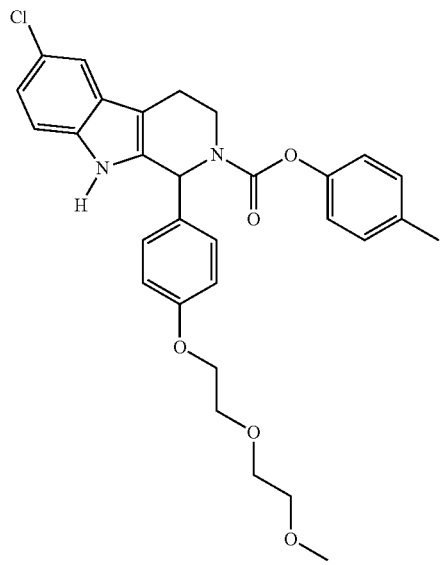 [SMILES: COCCOCCOc1ccc(C2c3[nH]c4ccc(Cl)cc4c3CCN2C(=O)Oc2ccc(C)cc2)cc1]
677
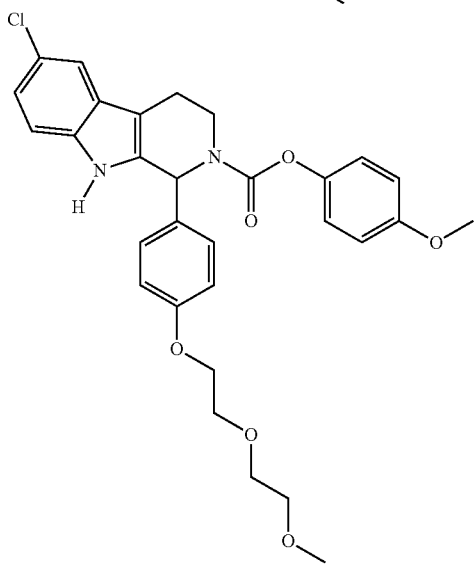
678
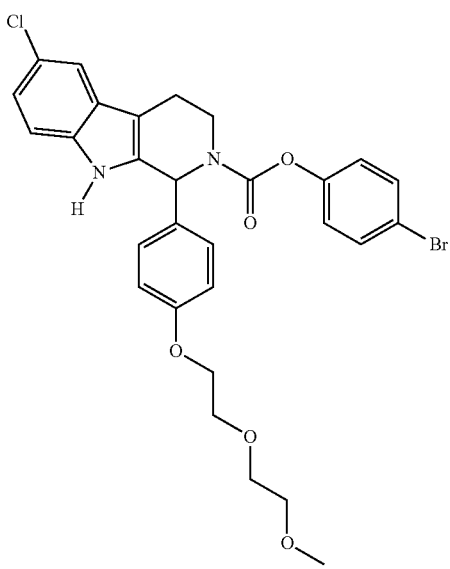 [SMILES: COCCOCCOc1ccc(C2c3[nH]c4ccc(Cl)cc4c3CCN2C(=O)Oc2ccc(Br)cc2)cc1]
680

TABLE 1-continued
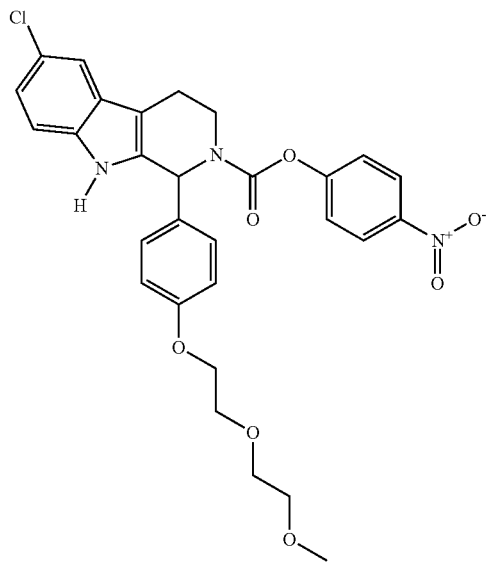 [SMILES: COCCOCCOc1ccc(C2c3[nH]c4ccc(Cl)cc4c3CCN2C(=O)Oc2ccc([N+](=O)[O-])cc2)cc1]
681
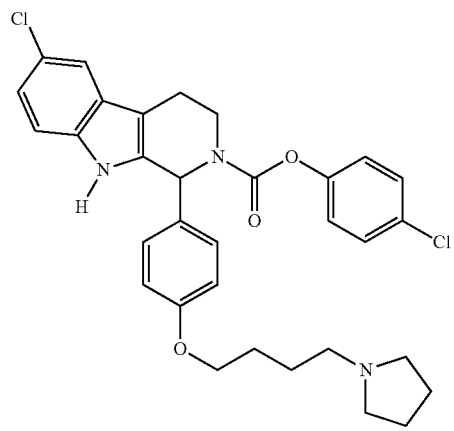 [SMILES: O=C(Oc1ccc(Cl)cc1)N1CCc2c([nH]c3ccc(Cl)cc23)C1c1ccc(OCCCCN2CCCC2)cc1]
698
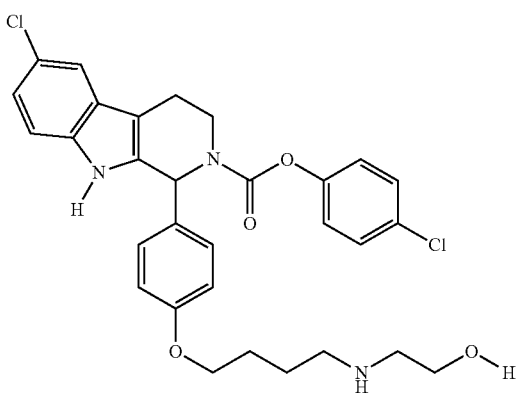 [SMILES: O=C(Oc1ccc(Cl)cc1)N1CCc2c([nH]c3ccc(Cl)cc23)C1c1ccc(OCCCCNCCO)cc1]
699

TABLE 1-continued
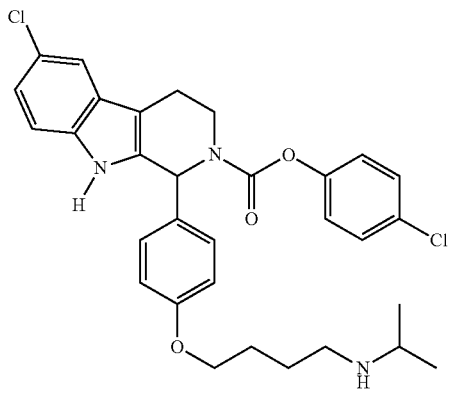 [SMILES: CC(C)NCCCCOc1ccc(C2c3[nH]c4ccc(Cl)cc4c3CCN2C(=O)Oc2ccc(Cl)cc2)cc1]
700
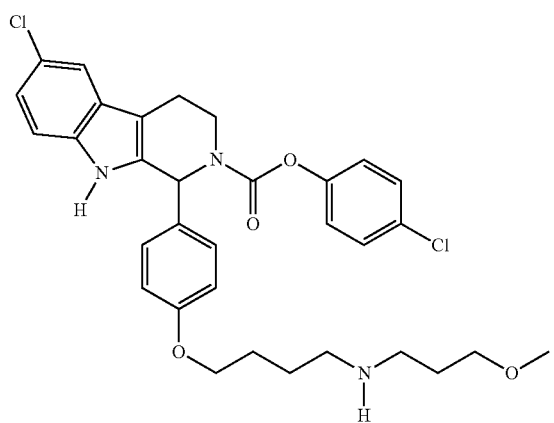 [SMILES: COCCCNCCCCOc1ccc(C2c3[nH]c4ccc(Cl)cc4c3CCN2C(=O)Oc2ccc(Cl)cc2)cc1]
701
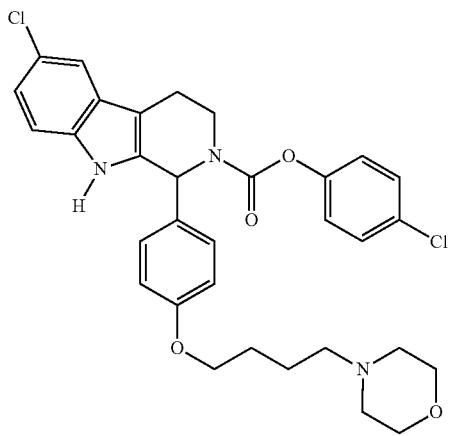 [SMILES: O=C(Oc1ccc(Cl)cc1)N1CCc2c([nH]c3ccc(Cl)cc23)C1c1ccc(OCCCCN2CCOCC2)cc1]
702

TABLE 1-continued
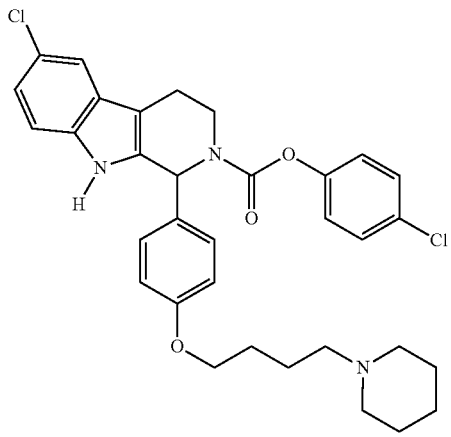 [SMILES: O=C(Oc1ccc(Cl)cc1)N1CCc2c([nH]c3ccc(Cl)cc23)C1c1ccc(OCCCCN2CCCCC2)cc1]
703
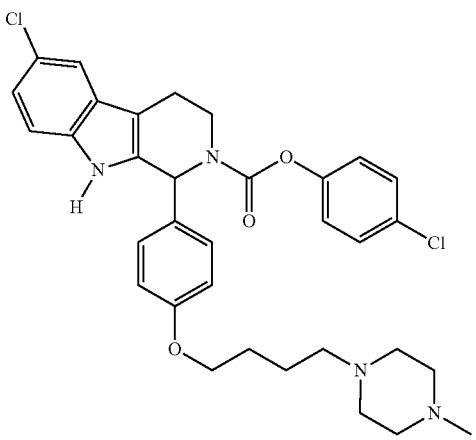 [SMILES: CN1CCN(CCCCOc2ccc(C3c4[nH]c5ccc(Cl)cc5c4CCN3C(=O)Oc3ccc(Cl)cc3)cc2)CC1]
704
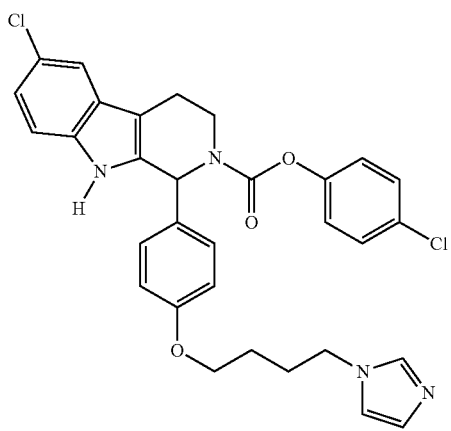 [SMILES: O=C(Oc1ccc(Cl)cc1)N1CCc2c([nH]c3ccc(Cl)cc23)C1c1ccc(OCCCCn2ccnc2)cc1]
705

TABLE 1-continued
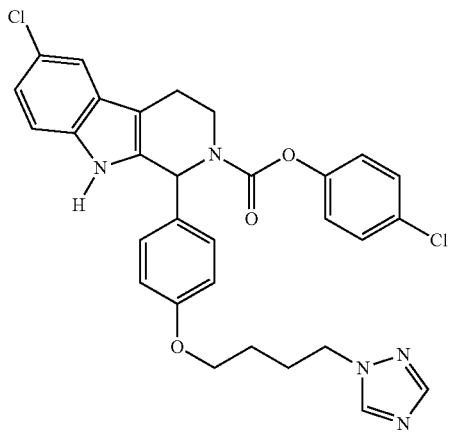 [SMILES: O=C(Oc1ccc(Cl)cc1)N1CCc2c([nH]c3ccc(Cl)cc23)C1c1ccc(OCCCCn2cncn2)cc1] 706
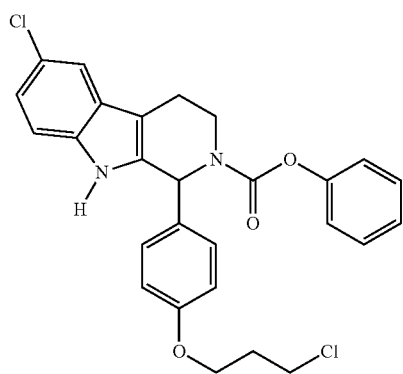 [SMILES: O=C(Oc1ccccc1)N1CCc2c([nH]c3ccc(Cl)cc23)C1c1ccc(OCCCCl)cc1] 710
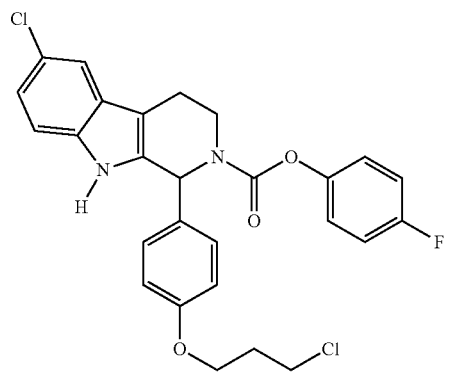 [SMILES: O=C(Oc1ccc(F)cc1)N1CCc2c([nH]c3ccc(Cl)cc23)C1c1ccc(OCCCCl)cc1] 712
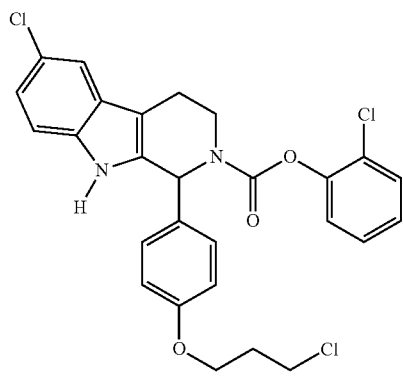 [SMILES: O=C(Oc1ccccc1Cl)N1CCc2c([nH]c3ccc(Cl)cc23)C1c1ccc(OCCCCl)cc1] 713

TABLE 1-continued
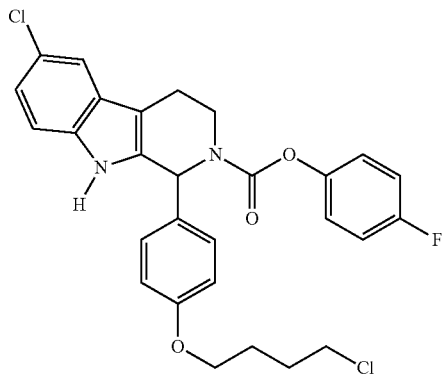 [SMILES: O=C(Oc1ccc(F)cc1)N1CCc2c([nH]c3ccc(Cl)cc23)C1c1ccc(OCCCCCl)cc1]
719
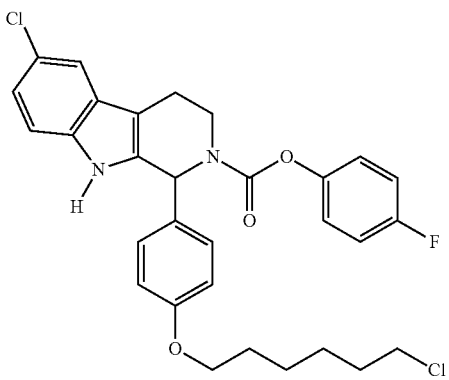 [SMILES: O=C(Oc1ccc(F)cc1)N1CCc2c([nH]c3ccc(Cl)cc23)C1c1ccc(OCCCCCCCl)cc1]
723
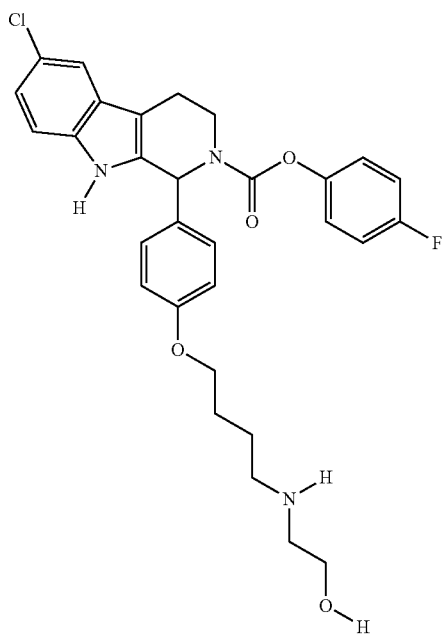 [SMILES: O=C(Oc1ccc(F)cc1)N1CCc2c([nH]c3ccc(Cl)cc23)C1c1ccc(OCCCCNCCO)cc1]
735

TABLE 1-continued
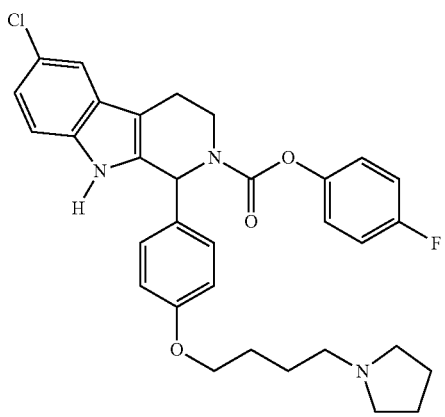 [SMILES: O=C(Oc1ccc(F)cc1)N1CCc2c([nH]c3ccc(Cl)cc23)C1c1ccc(OCCCCN2CCCC2)cc1]
736
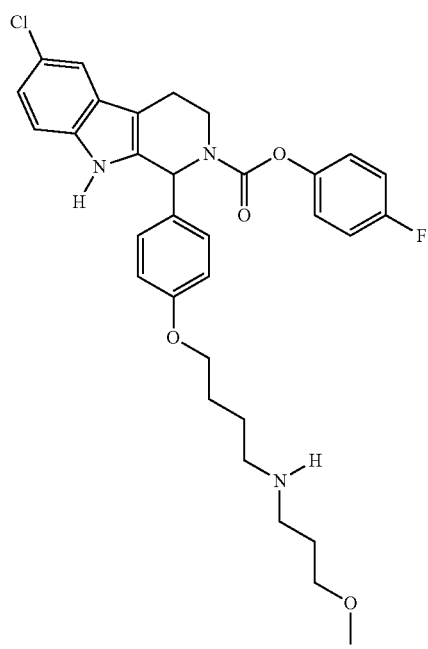 [SMILES: COCCCNCCCCOc1ccc(C2c3[nH]c4ccc(Cl)cc4c3CCN2C(=O)Oc2ccc(F)cc2)cc1]
737
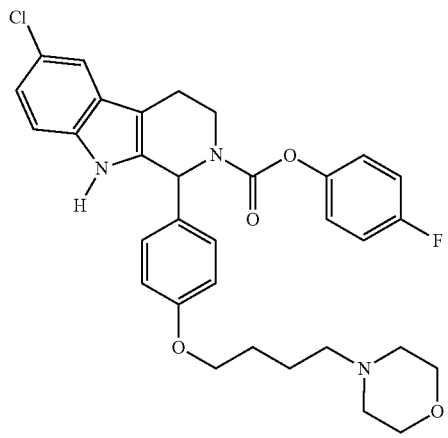 [SMILES: O=C(Oc1ccc(F)cc1)N1CCc2c([nH]c3ccc(Cl)cc23)C1c1ccc(OCCCCN2CCOCC2)cc1]
738

TABLE 1-continued
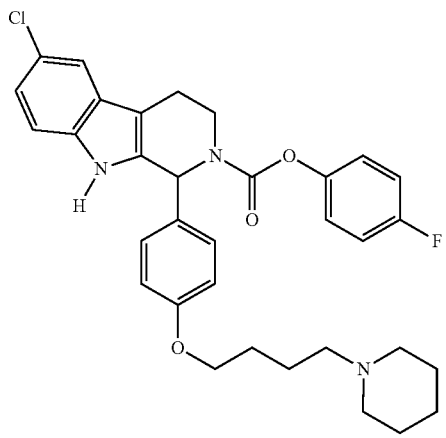 [SMILES: O=C(Oc1ccc(F)cc1)N1CCc2c([nH]c3ccc(Cl)cc23)C1c1ccc(OCCCCN2CCCCC2)cc1]
739
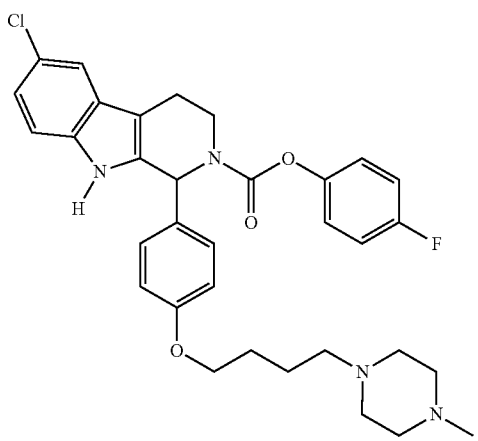
740
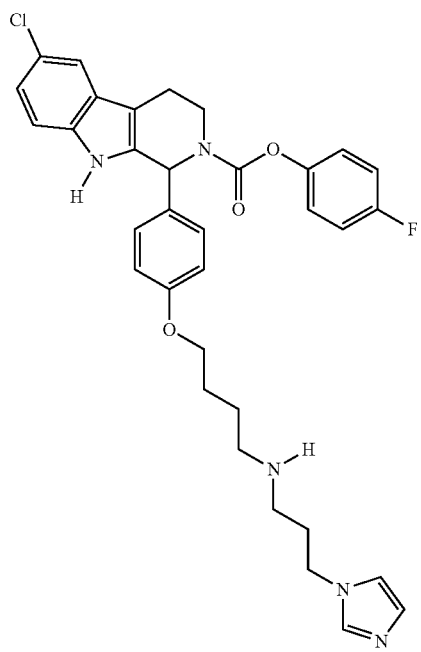 [SMILES: O=C(Oc1ccc(F)cc1)N1CCc2c([nH]c3ccc(Cl)cc23)C1c1ccc(OCCCCNCCCn2ccnc2)cc1]
741

TABLE 1-continued
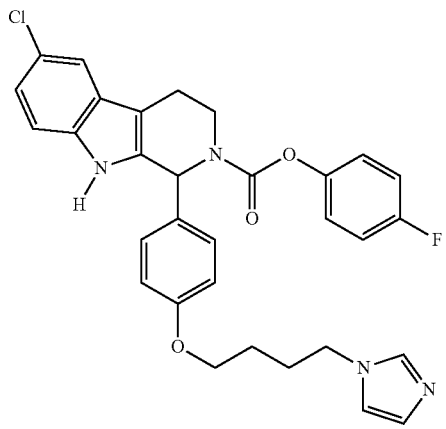 [SMILES: O=C(Oc1ccc(F)cc1)N1CCc2c([nH]c3ccc(Cl)cc23)C1c1ccc(OCCCCn2ccnc2)cc1]
742
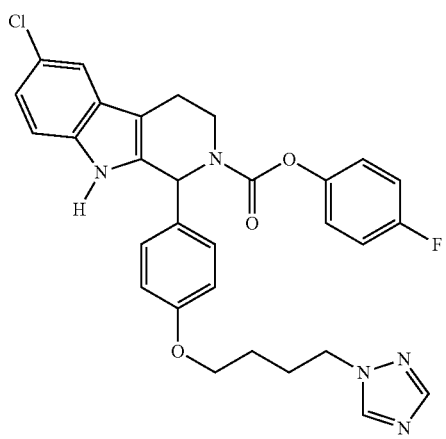 [SMILES: O=C(Oc1ccc(F)cc1)N1CCc2c([nH]c3ccc(Cl)cc23)C1c1ccc(OCCCCn2cncn2)cc1]
743
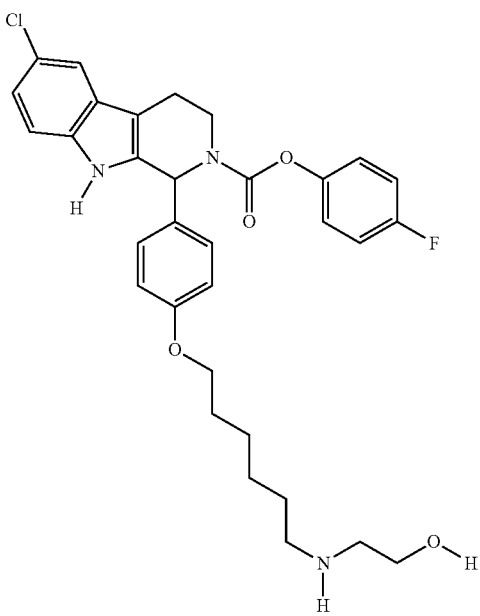 [SMILES: O=C(Oc1ccc(F)cc1)N1CCc2c([nH]c3ccc(Cl)cc23)C1c1ccc(OCCCCCCNCCO)cc1]
772

TABLE 1-continued
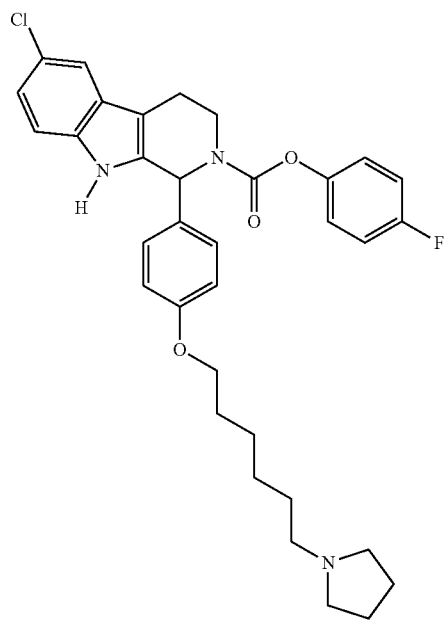 [SMILES: O=C(Oc1ccc(F)cc1)N1CCc2c([nH]c3ccc(Cl)cc23)C1c1ccc(OCCCCCCN2CCCC2)cc1]
773
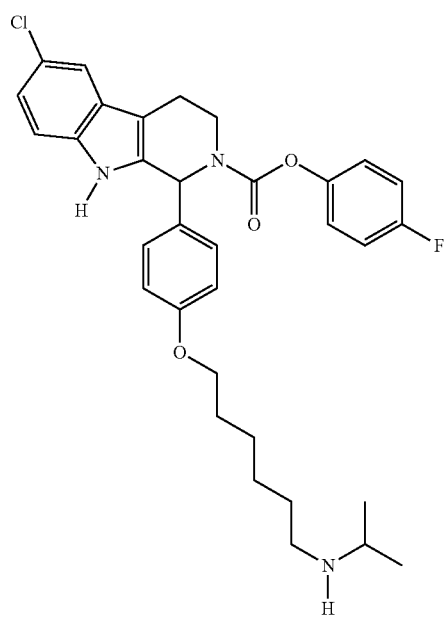 [SMILES: CC(C)NCCCCCCOc1ccc(C2c3[nH]c4ccc(Cl)cc4c3CCN2C(=O)Oc2ccc(F)cc2)cc1]
774

TABLE 1-continued
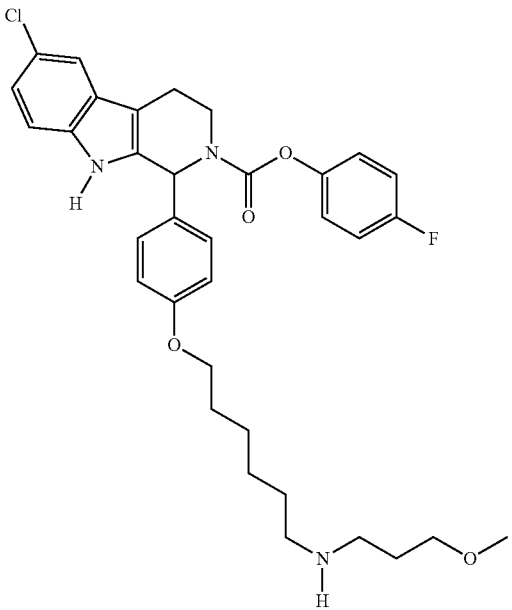 [SMILES: COCCCNCCCCCCOc1ccc(C2c3[nH]c4ccc(Cl)cc4c3CCN2C(=O)Oc2ccc(F)cc2)cc1]
775
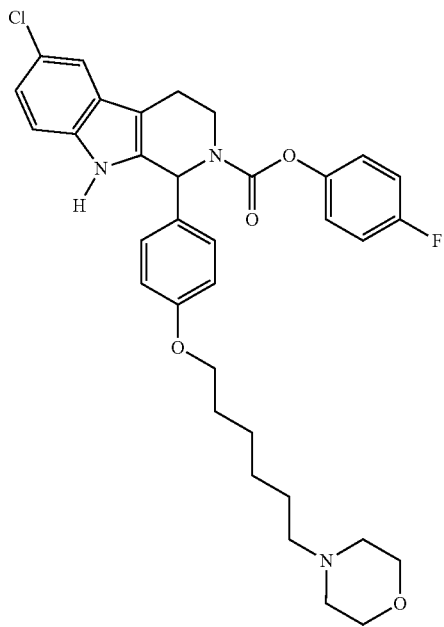
776

TABLE 1-continued
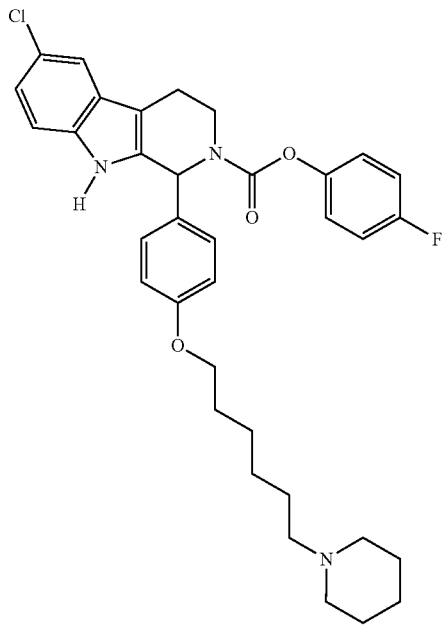 [SMILES: O=C(Oc1ccc(F)cc1)N1CCc2c([nH]c3ccc(Cl)cc23)C1c1ccc(OCCCCCCN2CCCCC2)cc1]
777
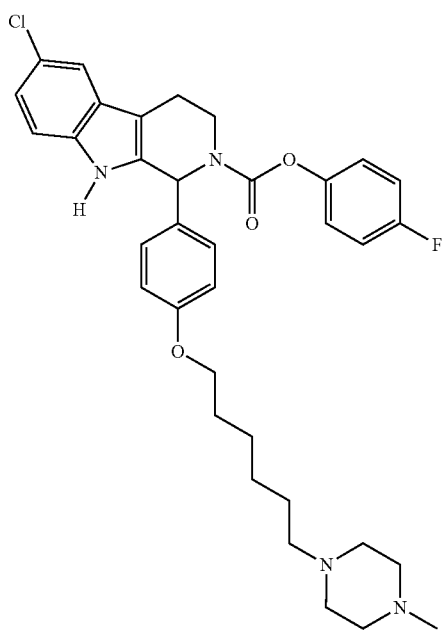 [SMILES: CN1CCN(CCCCCCOc2ccc(C3c4[nH]c5ccc(Cl)cc5c4CCN3C(=O)Oc3ccc(F)cc3)cc2)CC1]
778

TABLE 1-continued
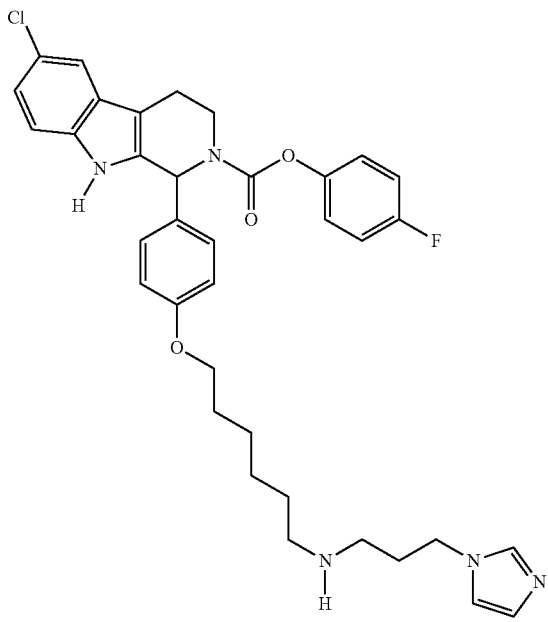 [SMILES: O=C(Oc1ccc(F)cc1)N1CCc2c([nH]c3ccc(Cl)cc23)C1c1ccc(OCCCCCCNCCCn2ccnc2)cc1]
779
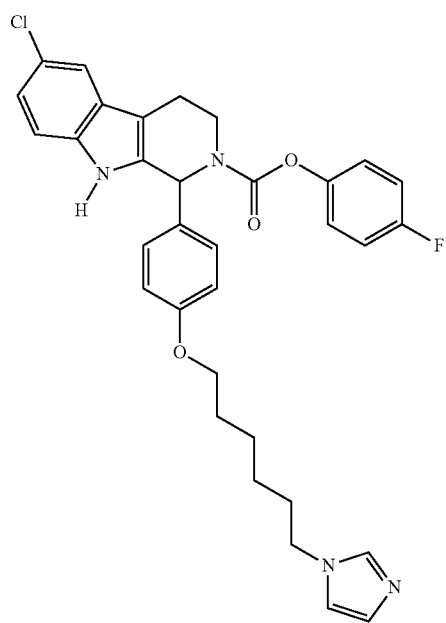 [SMILES: O=C(Oc1ccc(F)cc1)N1CCc2c([nH]c3ccc(Cl)cc23)C1c1ccc(OCCCCCCn2ccnc2)cc1]
780

TABLE 1-continued
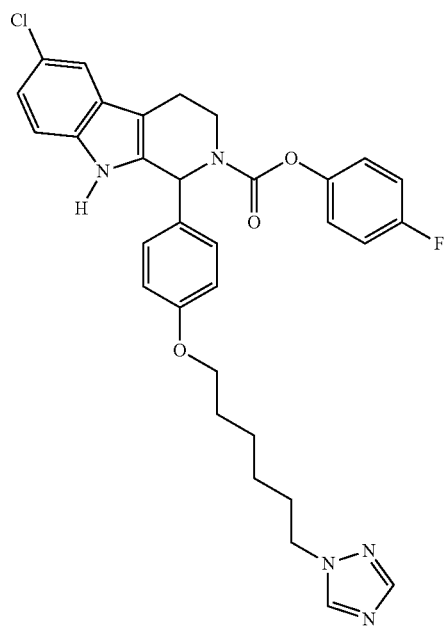 [SMILES: O=C(Oc1ccc(F)cc1)N1CCc2c([nH]c3ccc(Cl)cc23)C1c1ccc(OCCCCCCn2cncn2)cc1]
781
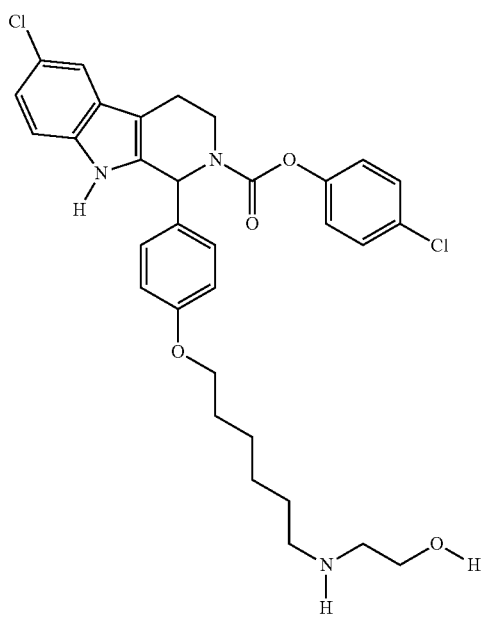
782

TABLE 1-continued
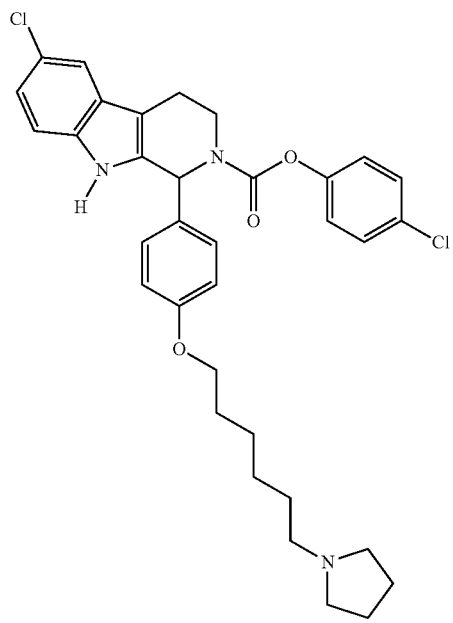 [SMILES: O=C(Oc1ccc(Cl)cc1)N1CCc2c([nH]c3ccc(Cl)cc23)C1c1ccc(OCCCCCCN2CCCC2)cc1]
783
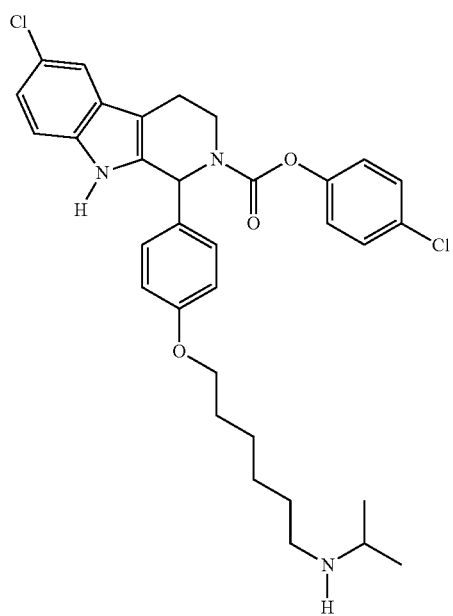 [SMILES: CC(C)NCCCCCCOc1ccc(C2c3[nH]c4ccc(Cl)cc4c3CCN2C(=O)Oc2ccc(Cl)cc2)cc1]
784

TABLE 1-continued
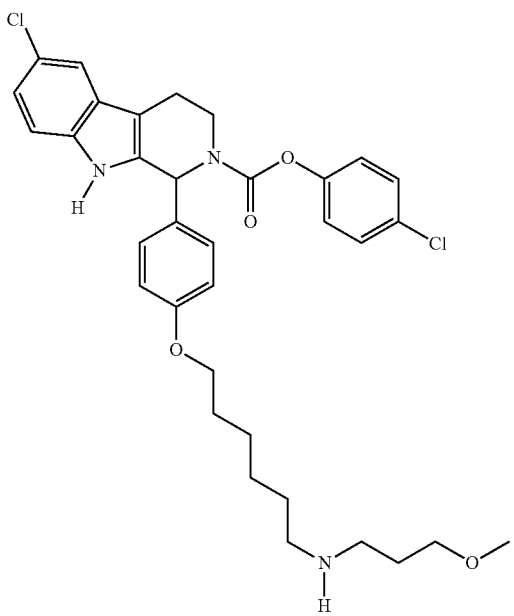
785
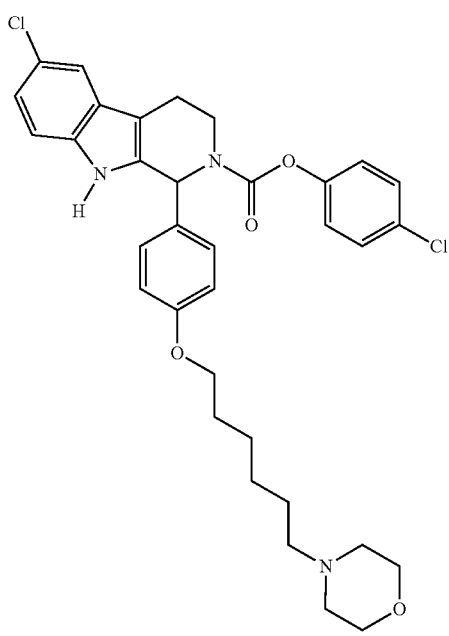
786

TABLE 1-continued
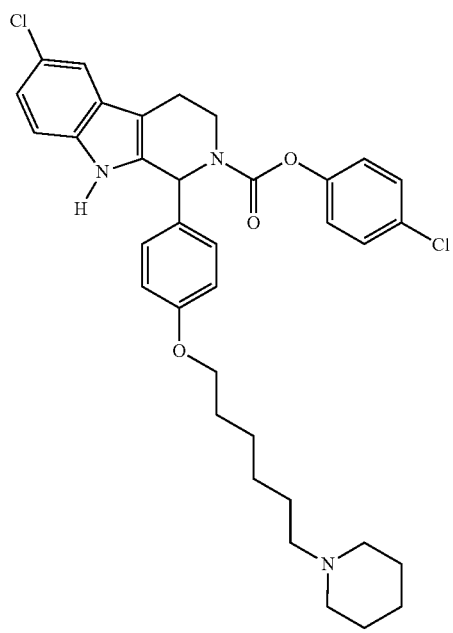 [SMILES: O=C(Oc1ccc(Cl)cc1)N1CCc2c([nH]c3ccc(Cl)cc23)C1c1ccc(OCCCCCCN2CCCCC2)cc1]
787
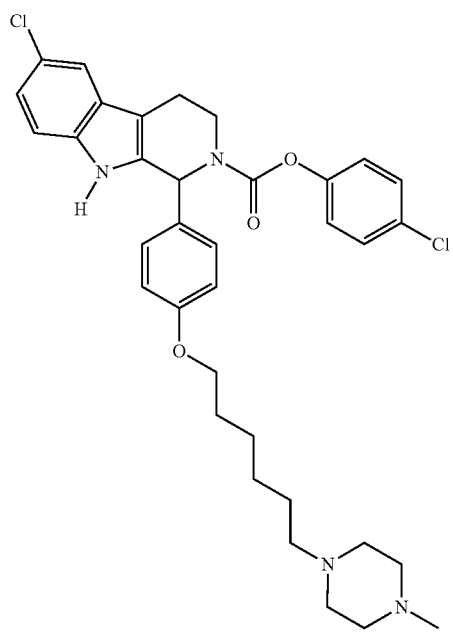 [SMILES: CN1CCN(CCCCCCOc2ccc(C3c4[nH]c5ccc(Cl)cc5c4CCN3C(=O)Oc3ccc(Cl)cc3)cc2)CC1]
788

TABLE 1-continued
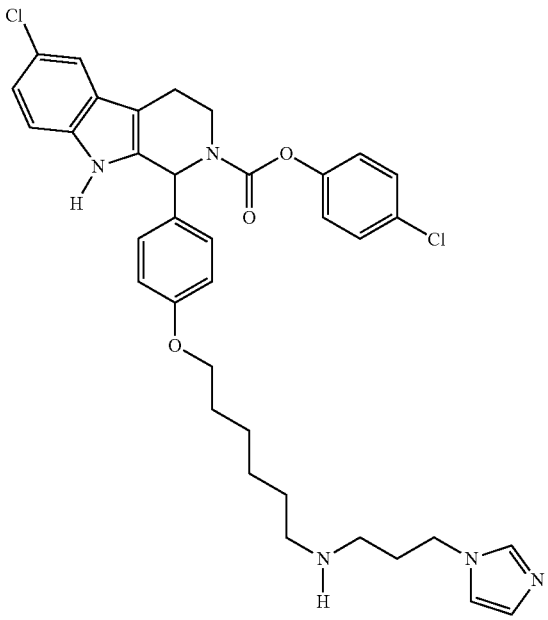 [SMILES: O=C(Oc1ccc(Cl)cc1)N1CCc2c([nH]c3ccc(Cl)cc23)C1c1ccc(OCCCCCCNCCCn2ccnc2)cc1]
789
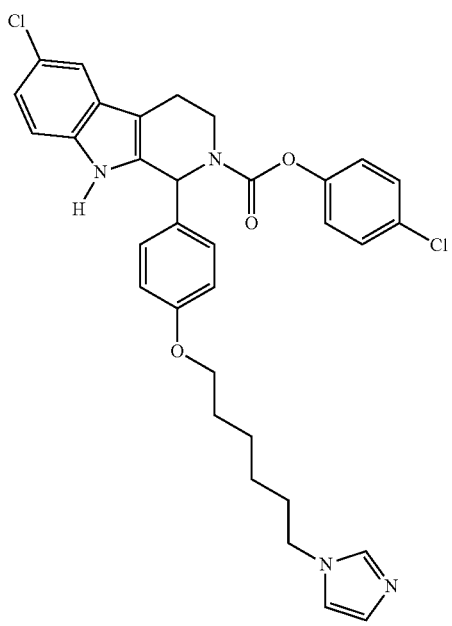 [SMILES: O=C(Oc1ccc(Cl)cc1)N1CCc2c([nH]c3ccc(Cl)cc23)C1c1ccc(OCCCCCCn2ccnc2)cc1]
790

TABLE 1-continued
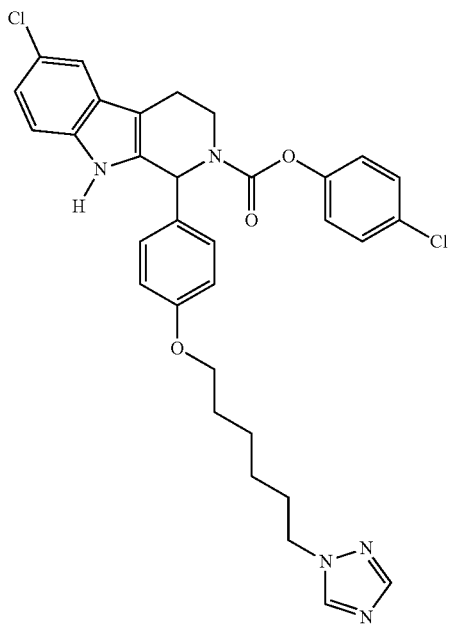 [SMILES: O=C(Oc1ccc(Cl)cc1)N1CCc2c([nH]c3ccc(Cl)cc23)C1c1ccc(OCCCCCCn2cncn2)cc1]
791
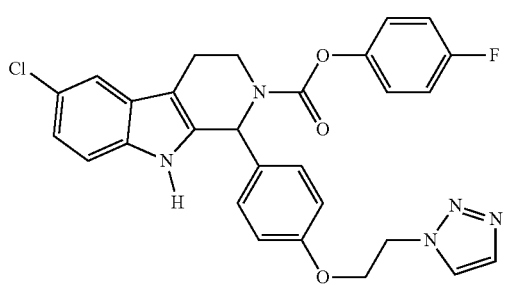
833
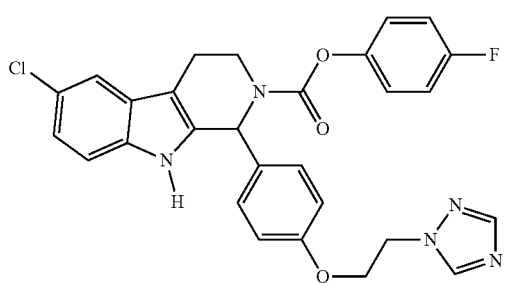 [SMILES: O=C(Oc1ccc(F)cc1)N1CCc2c([nH]c3ccc(Cl)cc23)C1c1ccc(OCCn2cncn2)cc1]
834
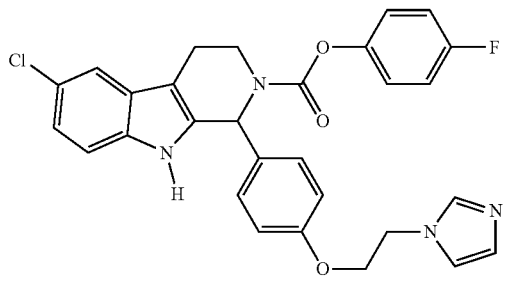
835

TABLE 1-continued
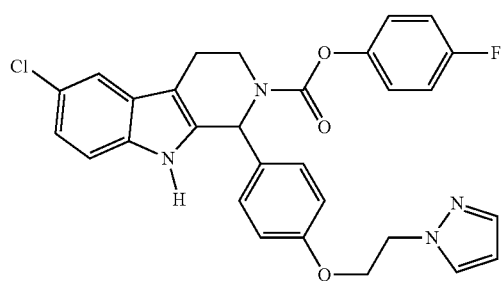 [SMILES: O=C(Oc1ccc(F)cc1)N1CCc2c([nH]c3ccc(Cl)cc23)C1c1ccc(OCCn2cccn2)cc1] 836
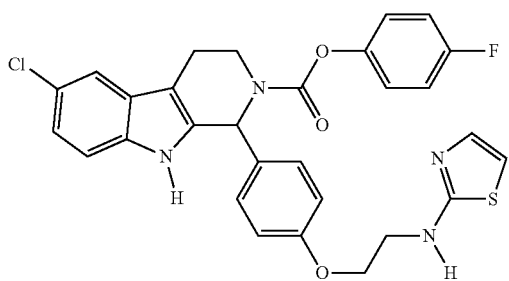 [SMILES: O=C(Oc1ccc(F)cc1)N1CCc2c([nH]c3ccc(Cl)cc23)C1c1ccc(OCCNc2nccs2)cc1] 837
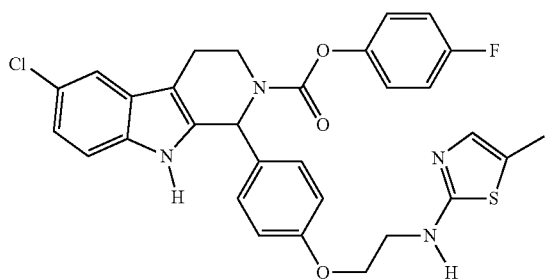 [SMILES: Cc1cnc(NCCOc2ccc(C3c4[nH]c5ccc(Cl)cc5c4CCN3C(=O)Oc3ccc(F)cc3)cc2)s1] 838
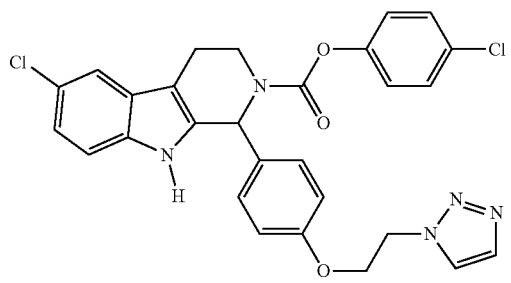 839
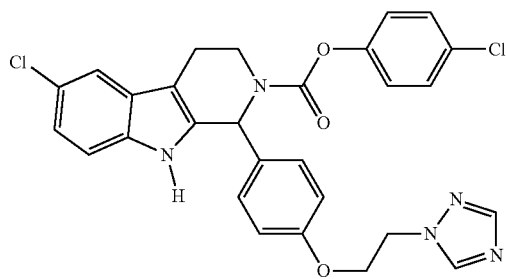 [SMILES: O=C(Oc1ccc(Cl)cc1)N1CCc2c([nH]c3ccc(Cl)cc23)C1c1ccc(OCCn2cncn2)cc1] 840

TABLE 1-continued
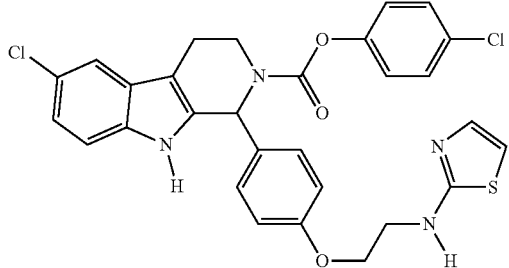 [SMILES: O=C(Oc1ccc(Cl)cc1)N1CCc2c([nH]c3ccc(Cl)cc23)C1c1ccc(OCCNc2nccs2)cc1] 841
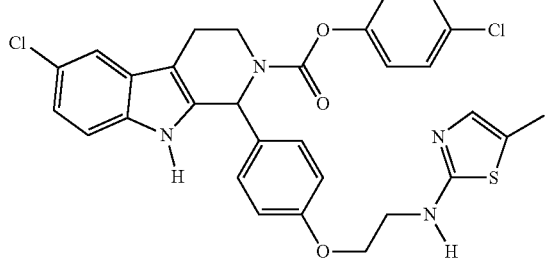 842
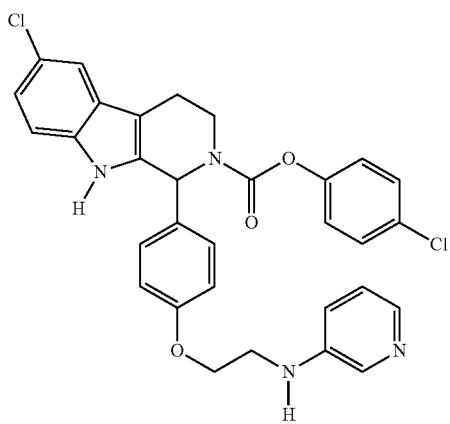 [SMILES: O=C(Oc1ccc(Cl)cc1)N1CCc2c([nH]c3ccc(Cl)cc23)C1c1ccc(OCCNc2cccnc2)cc1] 843
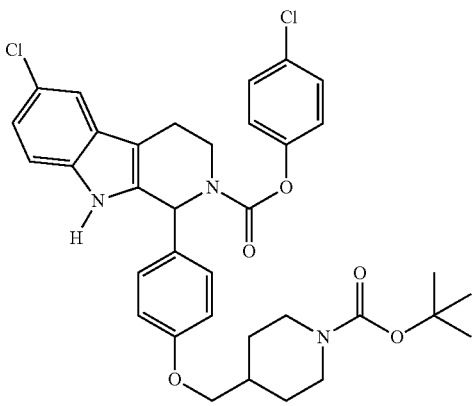 [SMILES: CC(C)(C)OC(=O)N1CCC(COc2ccc(C3c4[nH]c5ccc(Cl)cc5c4CCN3C(=O)Oc3ccc(Cl)cc3)cc2)CC1] 845

TABLE 1-continued
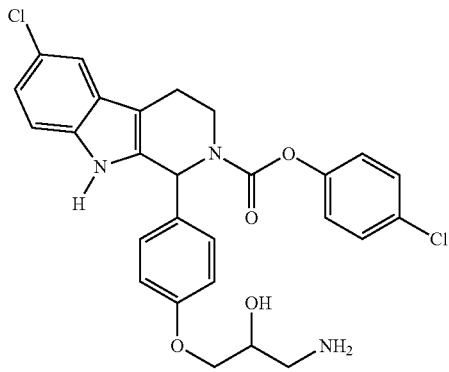 [SMILES: NCC(O)COc1ccc(C2c3[nH]c4ccc(Cl)cc4c3CCN2C(=O)Oc2ccc(Cl)cc2)cc1]
846
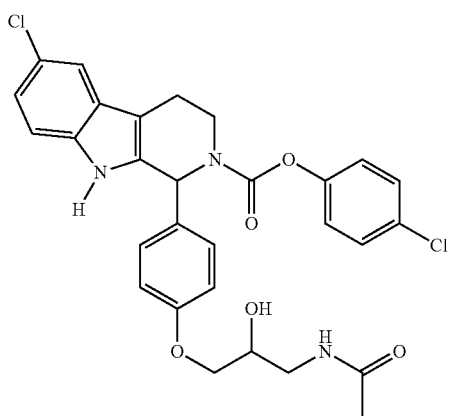 [SMILES: CC(=O)NCC(O)COc1ccc(C2c3[nH]c4ccc(Cl)cc4c3CCN2C(=O)Oc2ccc(Cl)cc2)cc1]
847
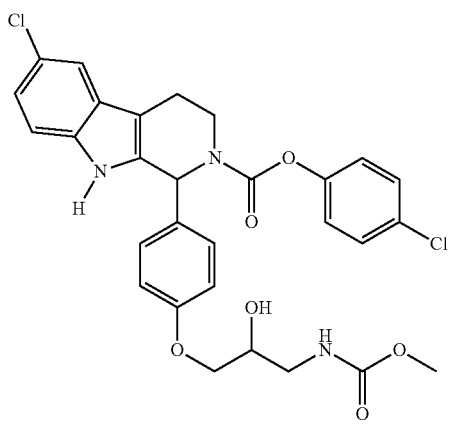 [SMILES: COC(=O)NCC(O)COc1ccc(C2c3[nH]c4ccc(Cl)cc4c3CCN2C(=O)Oc2ccc(Cl)cc2)cc1]
848
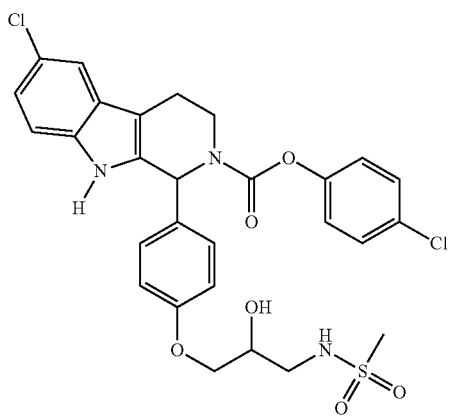 [SMILES: CS(=O)(=O)NCC(O)COc1ccc(C2c3[nH]c4ccc(Cl)cc4c3CCN2C(=O)Oc2ccc(Cl)cc2)cc1]
849

TABLE 1-continued
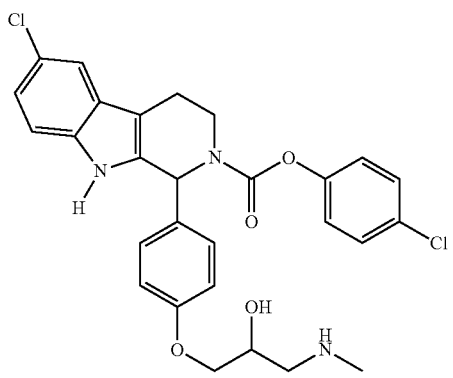 [SMILES: CNCC(O)COc1ccc(C2c3[nH]c4ccc(Cl)cc4c3CCN2C(=O)Oc2ccc(Cl)cc2)cc1]
850
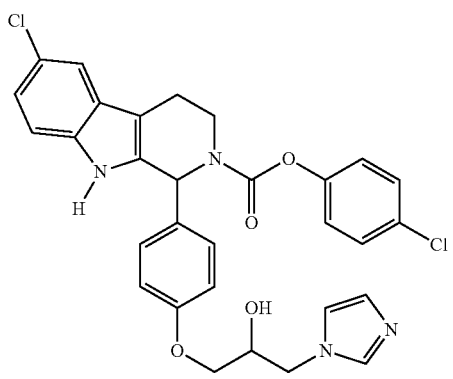 [SMILES: O=C(Oc1ccc(Cl)cc1)N1CCc2c([nH]c3ccc(Cl)cc23)C1c1ccc(OCC(O)Cn2ccnc2)cc1]
867
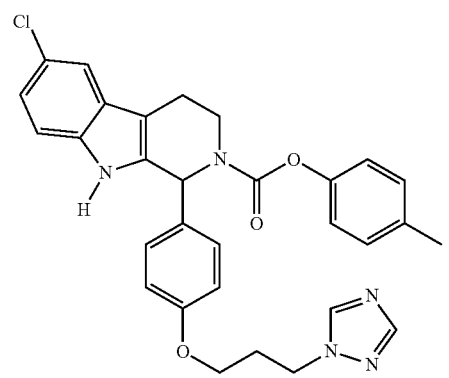 [SMILES: Cc1ccc(OC(=O)N2CCc3c([nH]c4ccc(Cl)cc34)C2c2ccc(OCCCn3cncn3)cc2)cc1]
882
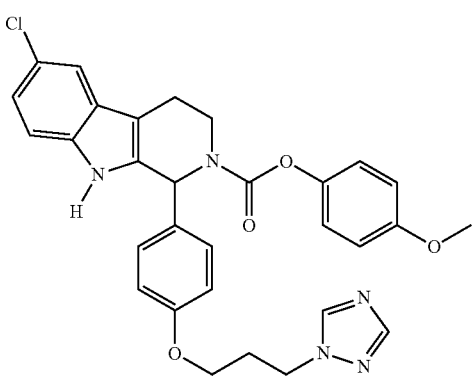
888

TABLE 1-continued
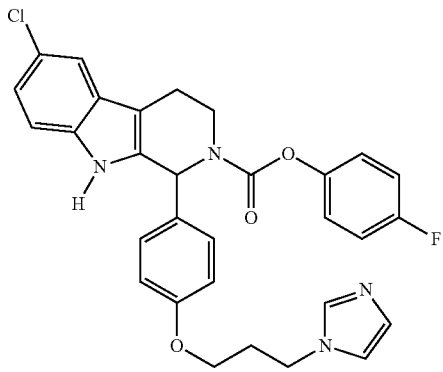 [SMILES: O=C(Oc1ccc(F)cc1)N1CCc2c([nH]c3ccc(Cl)cc23)C1c1ccc(OCCCn2ccnc2)cc1]
889
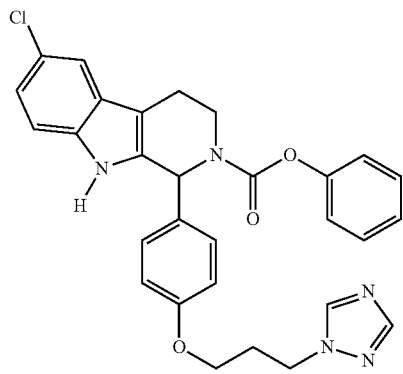
891
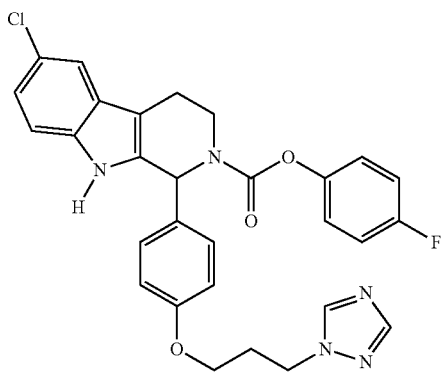 [SMILES: O=C(Oc1ccc(F)cc1)N1CCc2c([nH]c3ccc(Cl)cc23)C1c1ccc(OCCCn2cncn2)cc1]
892
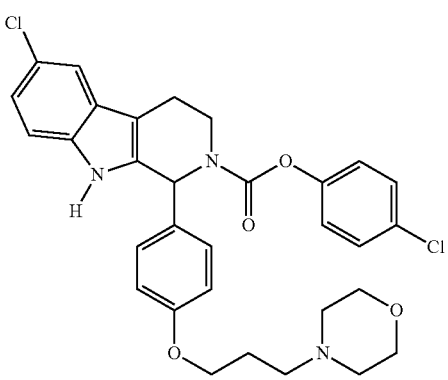 [SMILES: O=C(Oc1ccc(Cl)cc1)N1CCc2c([nH]c3ccc(Cl)cc23)C1c1ccc(OCCCN2CCOCC2)cc1]
894

TABLE 1-continued
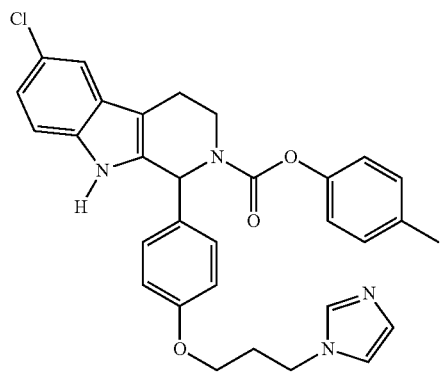 [SMILES: Cc1ccc(OC(=O)N2CCc3c([nH]c4ccc(Cl)cc34)C2c2ccc(OCCCn3ccnc3)cc2)cc1]
900
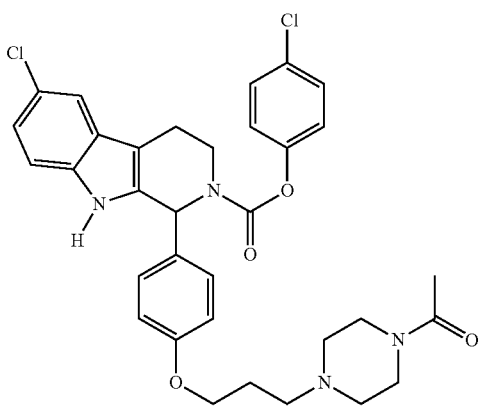 [SMILES: CC(=O)N1CCN(CCCOc2ccc(C3c4[nH]c5ccc(Cl)cc5c4CCN3C(=O)Oc3ccc(Cl)cc3)cc2)CC1]
903
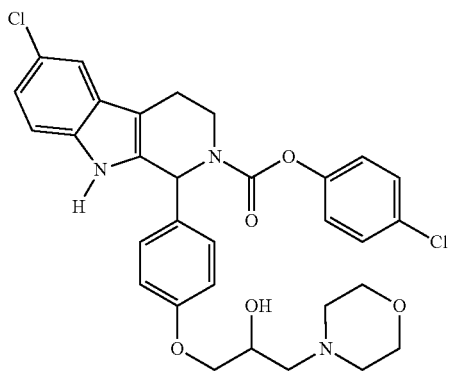 [SMILES: O=C(Oc1ccc(Cl)cc1)N1CCc2c([nH]c3ccc(Cl)cc23)C1c1ccc(OCC(O)CN2CCOCC2)cc1]
904
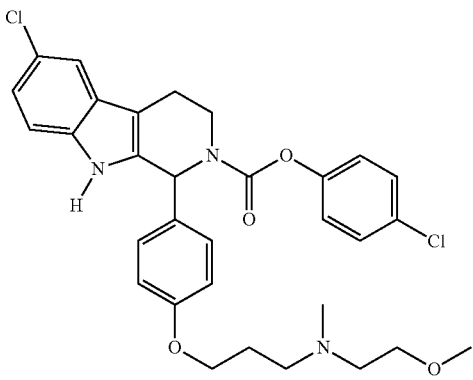 [SMILES: COCCN(C)CCCOc1ccc(C2c3[nH]c4ccc(Cl)cc4c3CCN2C(=O)Oc2ccc(Cl)cc2)cc1]
908

TABLE 1-continued
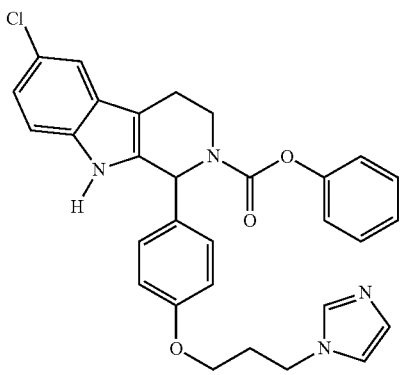 [SMILES: O=C(Oc1ccccc1)N1CCc2c([nH]c3ccc(Cl)cc23)C1c1ccc(OCCCn2ccnc2)cc1]
911
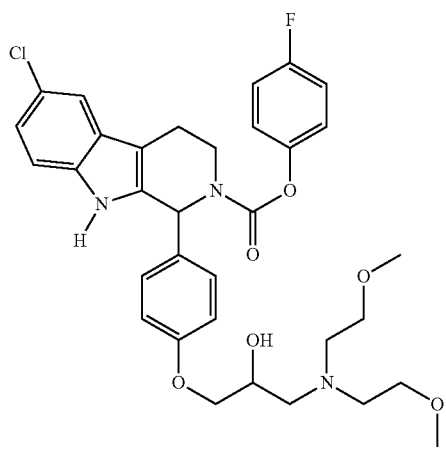 [SMILES: COCCN(CCOC)CC(O)COc1ccc(C2c3[nH]c4ccc(Cl)cc4c3CCN2C(=O)Oc2ccc(F)cc2)cc1]
913
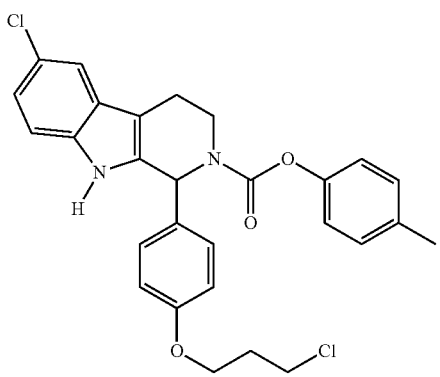 [SMILES: Cc1ccc(OC(=O)N2CCc3c([nH]c4ccc(Cl)cc34)C2c2ccc(OCCCCl)cc2)cc1]
915
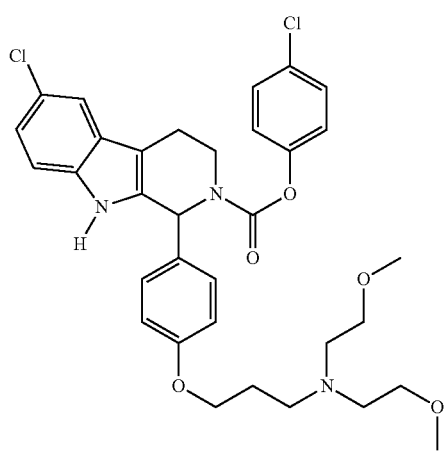 [SMILES: COCCN(CCCOc1ccc(C2c3[nH]c4ccc(Cl)cc4c3CCN2C(=O)Oc2ccc(Cl)cc2)cc1)CCOC]
916

TABLE 1-continued
| | |
|---|---|
| 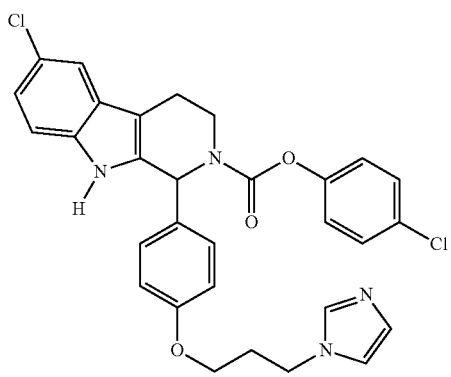 [SMILES: O=C(Oc1ccc(Cl)cc1)N1CCc2c([nH]c3ccc(Cl)cc23)C1c1ccc(OCCCn2ccnc2)cc1] | 917 |
| 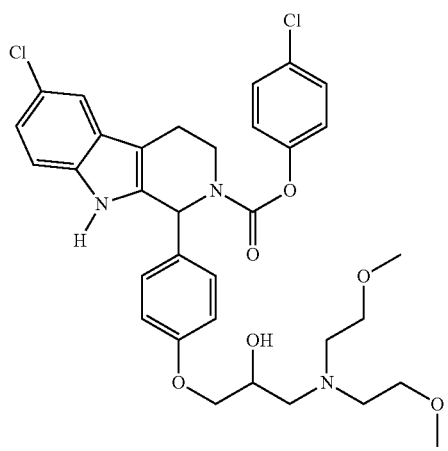 [SMILES: COCCN(CCOC)CC(O)COc1ccc(C2c3[nH]c4ccc(Cl)cc4c3CCN2C(=O)Oc2ccc(Cl)cc2)cc1] | 918 |
| 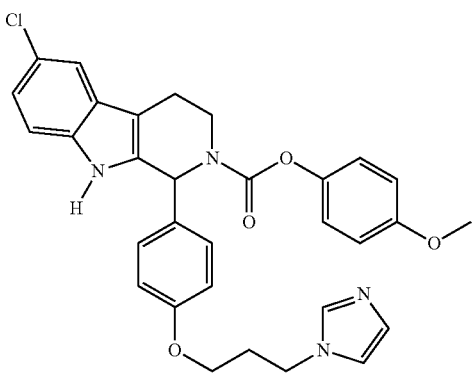 [SMILES: COc1ccc(OC(=O)N2CCc3c([nH]c4ccc(Cl)cc34)C2c2ccc(OCCCn3ccnc3)cc2)cc1] | 920 |
| 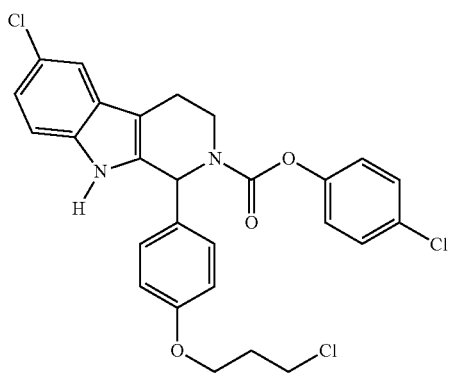 [SMILES: O=C(Oc1ccc(Cl)cc1)N1CCc2c([nH]c3ccc(Cl)cc23)C1c1ccc(OCCCCl)cc1] | 921 |

TABLE 1-continued
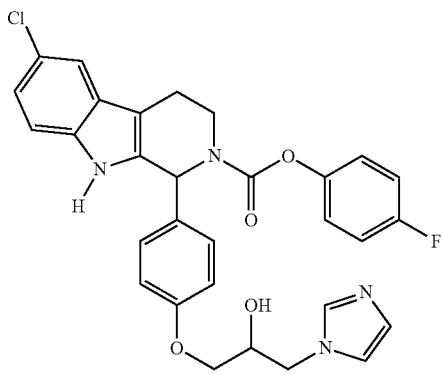 [SMILES: O=C(Oc1ccc(F)cc1)N1CCc2c([nH]c3ccc(Cl)cc23)C1c1ccc(OCC(O)Cn2ccnc2)cc1]
922
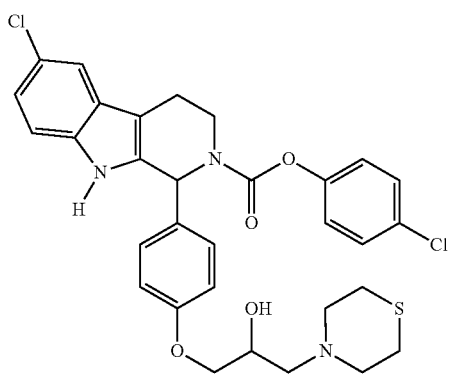
923
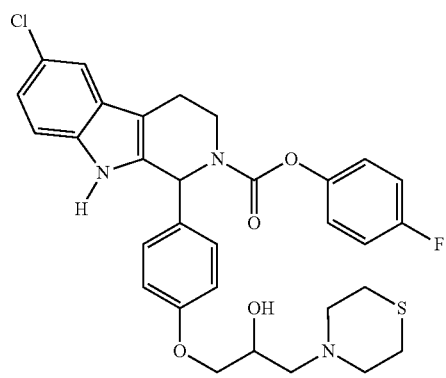 [SMILES: O=C(Oc1ccc(F)cc1)N1CCc2c([nH]c3ccc(Cl)cc23)C1c1ccc(OCC(O)CN2CCSCC2)cc1]
925
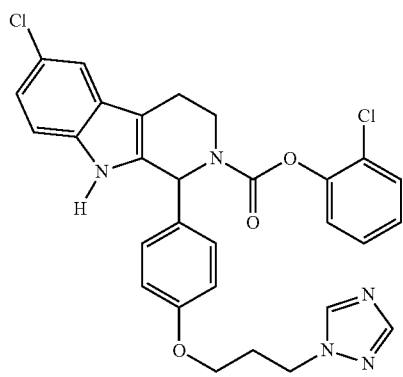
926

TABLE 1-continued
| | |
|---|---|
| 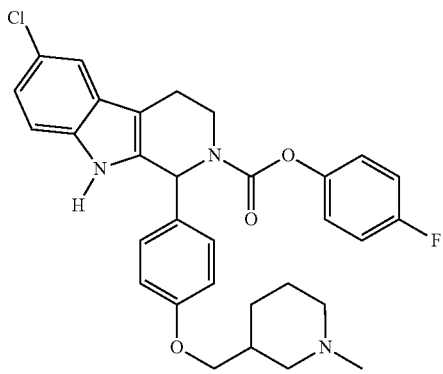 [SMILES: CN1CCCC(COc2ccc(C3c4[nH]c5ccc(Cl)cc5c4CCN3C(=O)Oc3ccc(F)cc3)cc2)C1] | 932 |
| 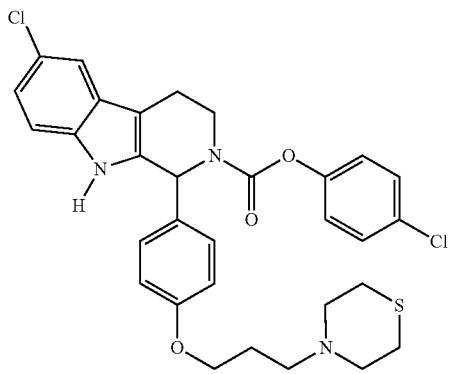 [SMILES: O=C(Oc1ccc(Cl)cc1)N1CCc2c([nH]c3ccc(Cl)cc23)C1c1ccc(OCCCN2CCSCC2)cc1] | 933 |
| 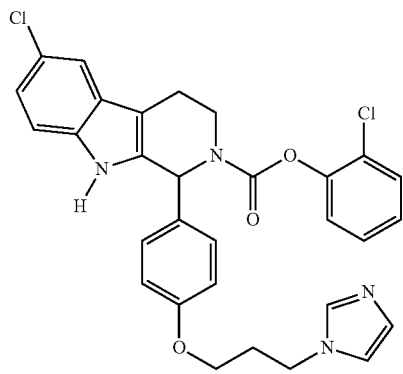 [SMILES: O=C(Oc1ccccc1Cl)N1CCc2c([nH]c3ccc(Cl)cc23)C1c1ccc(OCCCn2ccnc2)cc1] | 934 |
| 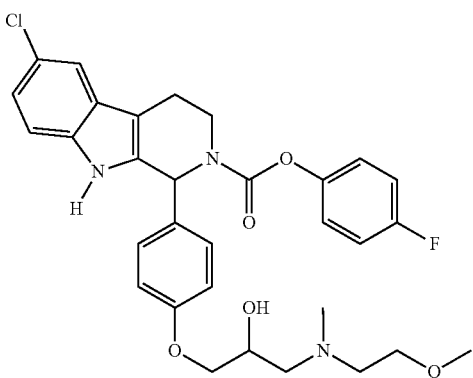 [SMILES: COCCN(C)CC(O)COc1ccc(C2c3[nH]c4ccc(Cl)cc4c3CCN2C(=O)Oc2ccc(F)cc2)cc1] | 936 |

TABLE 1-continued
| | |
|---|---|
| 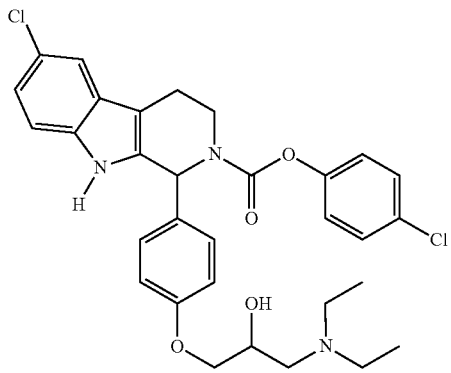 [SMILES: CCN(CC)CC(O)COc1ccc(C2c3[nH]c4ccc(Cl)cc4c3CCN2C(=O)Oc2ccc(Cl)cc2)cc1] | 938 |
| 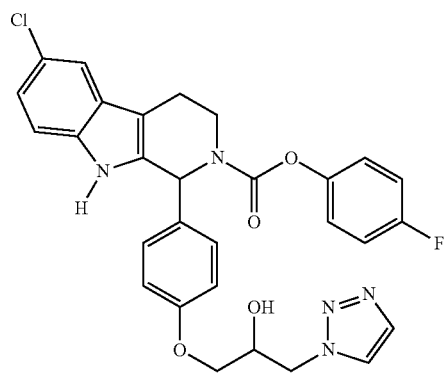 | 941 |
| 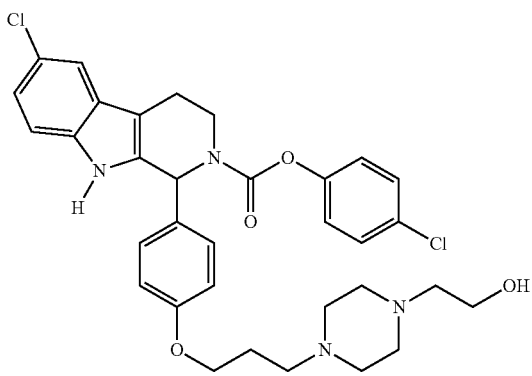 [SMILES: O=C(Oc1ccc(Cl)cc1)N1CCc2c([nH]c3ccc(Cl)cc23)C1c1ccc(OCCCN2CCN(CCO)CC2)cc1] | 942 |
| 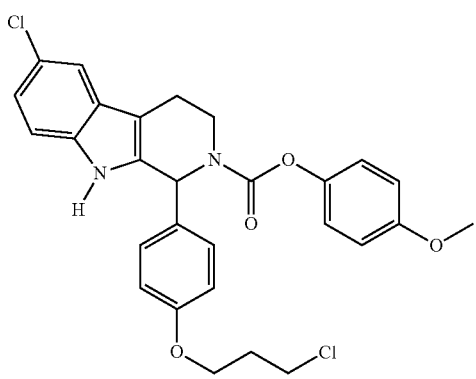 [SMILES: COc1ccc(OC(=O)N2CCc3c([nH]c4ccc(Cl)cc34)C2c2ccc(OCCCCl)cc2)cc1] | 944 |

TABLE 1-continued
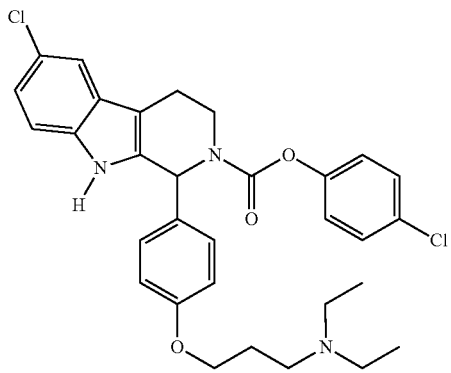 [SMILES: CCN(CC)CCCOc1ccc(C2c3[nH]c4ccc(Cl)cc4c3CCN2C(=O)Oc2ccc(Cl)cc2)cc1] 946
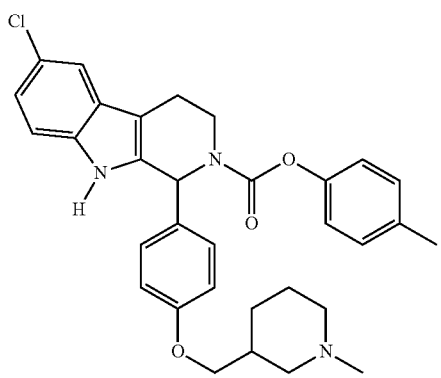 [SMILES: Cc1ccc(OC(=O)N2CCc3c([nH]c4ccc(Cl)cc34)C2c2ccc(OCC3CCCN(C)C3)cc2)cc1] 951
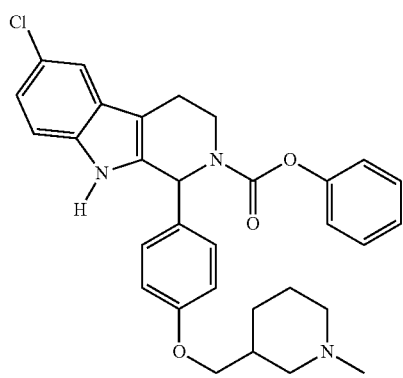 [SMILES: CN1CCCC(COc2ccc(C3c4[nH]c5ccc(Cl)cc5c4CCN3C(=O)Oc3ccccc3)cc2)C1] 952
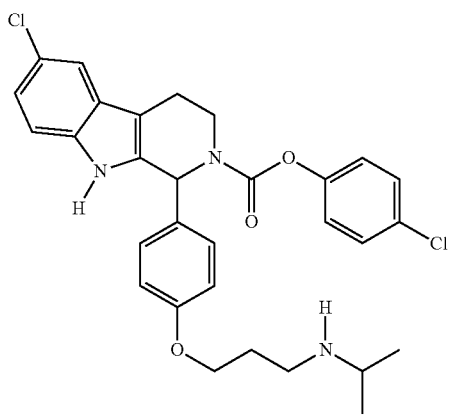 [SMILES: CC(C)NCCCOc1ccc(C2c3[nH]c4ccc(Cl)cc4c3CCN2C(=O)Oc2ccc(Cl)cc2)cc1] 953

TABLE 1-continued
| | |
|---|---|
| 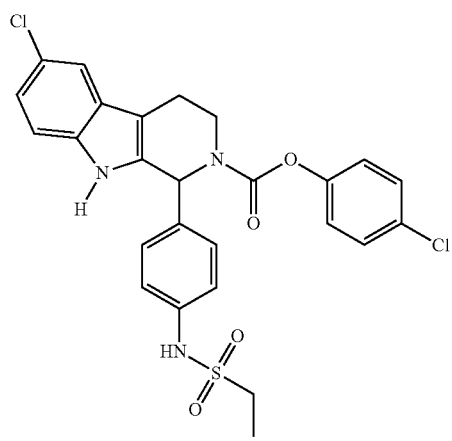 [SMILES: CCS(=O)(=O)Nc1ccc(C2c3[nH]c4ccc(Cl)cc4c3CCN2C(=O)Oc2ccc(Cl)cc2)cc1] | 958 |
| 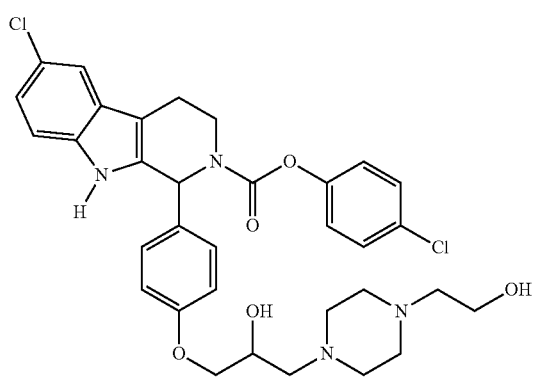 [SMILES: O=C(Oc1ccc(Cl)cc1)N1CCc2c([nH]c3ccc(Cl)cc23)C1c1ccc(OCC(O)CN2CCN(CCO)CC2)cc1] | 960 |
| 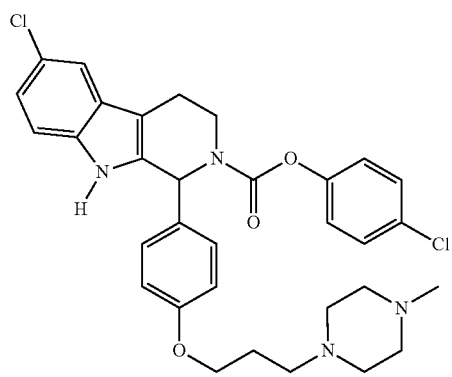 [SMILES: CN1CCN(CCCOc2ccc(C3c4[nH]c5ccc(Cl)cc5c4CCN3C(=O)Oc3ccc(Cl)cc3)cc2)CC1] | 961 |
| 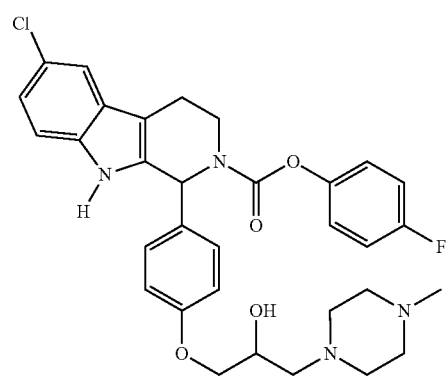 | 963 |

TABLE 1-continued
| | |
|---|---|
| 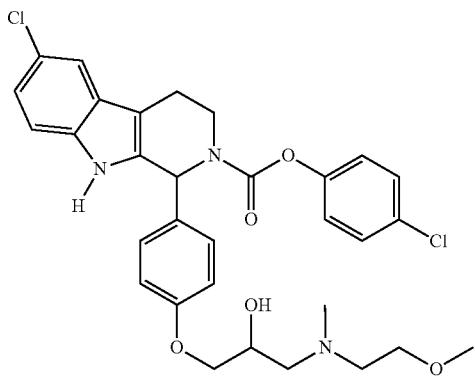 [SMILES: COCCN(C)CC(O)COc1ccc(C2c3[nH]c4ccc(Cl)cc4c3CCN2C(=O)Oc2ccc(Cl)cc2)cc1] | 964 |
| 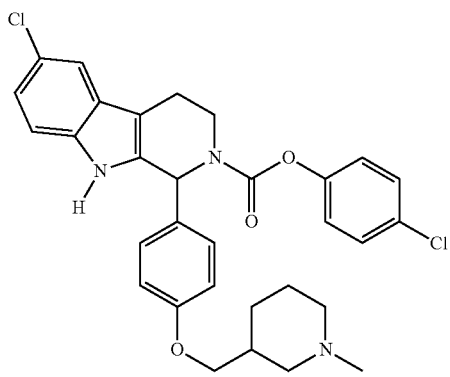 [SMILES: CN1CCCC(COc2ccc(C3c4[nH]c5ccc(Cl)cc5c4CCN3C(=O)Oc3ccc(Cl)cc3)cc2)C1] | 966 |
| 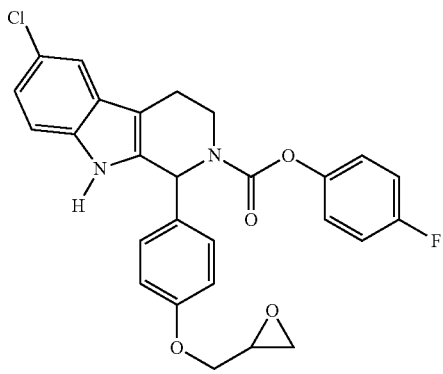 [SMILES: O=C(Oc1ccc(F)cc1)N1CCc2c([nH]c3ccc(Cl)cc23)C1c1ccc(OCC2CO2)cc1] | 967 |
| 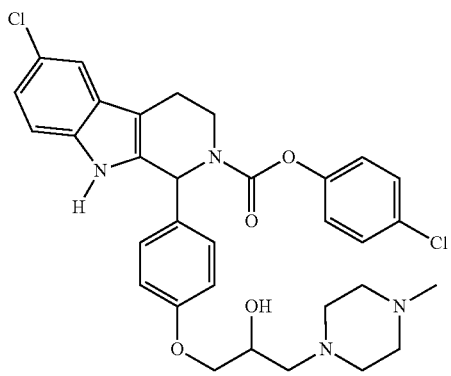 [SMILES: CN1CCN(CC(O)COc2ccc(C3c4[nH]c5ccc(Cl)cc5c4CCN3C(=O)Oc3ccc(Cl)cc3)cc2)CC1] | 970 |

TABLE 1-continued
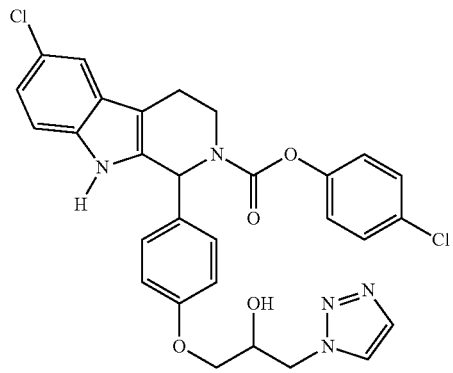 [SMILES: O=C(Oc1ccc(Cl)cc1)N1CCc2c([nH]c3ccc(Cl)cc23)C1c1ccc(OCC(O)Cn2ccnn2)cc1]
973
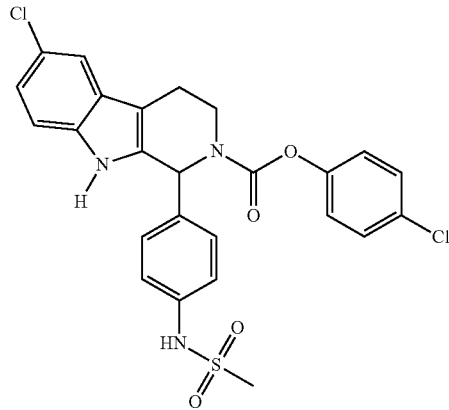 [SMILES: CS(=O)(=O)Nc1ccc(C2c3[nH]c4ccc(Cl)cc4c3CCN2C(=O)Oc2ccc(Cl)cc2)cc1]
974
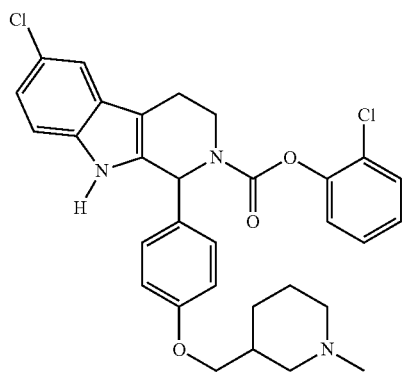 [SMILES: CN1CCCC(COc2ccc(C3c4[nH]c5ccc(Cl)cc5c4CCN3C(=O)Oc3ccccc3Cl)cc2)C1]
976
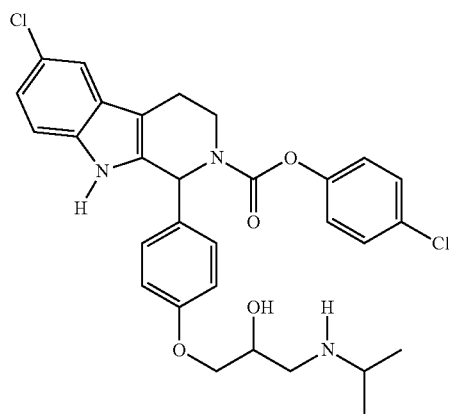 [SMILES: CC(C)NCC(O)COc1ccc(C2c3[nH]c4ccc(Cl)cc4c3CCN2C(=O)Oc2ccc(Cl)cc2)cc1]
977

TABLE 1-continued
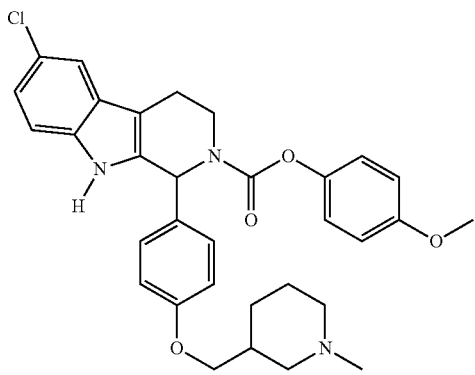 [SMILES: COc1ccc(OC(=O)N2CCc3c([nH]c4ccc(Cl)cc34)C2c2ccc(OCC3CCCN(C)C3)cc2)cc1]
981
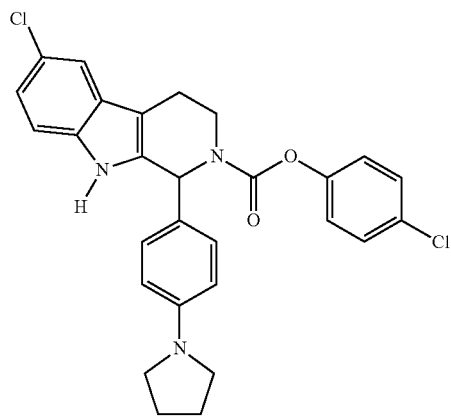 [SMILES: O=C(Oc1ccc(Cl)cc1)N1CCc2c([nH]c3ccc(Cl)cc23)C1c1ccc(N2CCCC2)cc1]
984
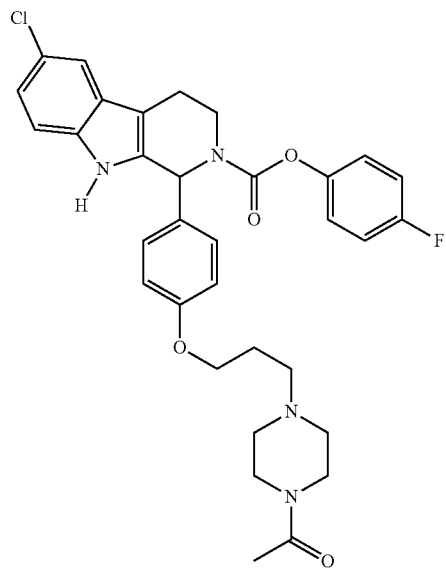 [SMILES: CC(=O)N1CCN(CCCOc2ccc(C3c4[nH]c5ccc(Cl)cc5c4CCN3C(=O)Oc3ccc(F)cc3)cc2)CC1]
988

TABLE 1-continued
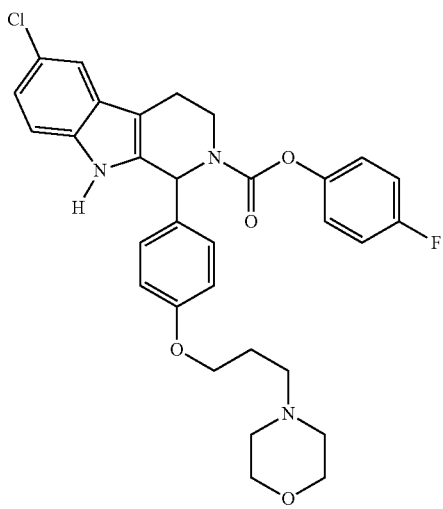 [SMILES: O=C(Oc1ccc(F)cc1)N1CCc2c([nH]c3ccc(Cl)cc23)C1c1ccc(OCCCN2CCOCC2)cc1]
989
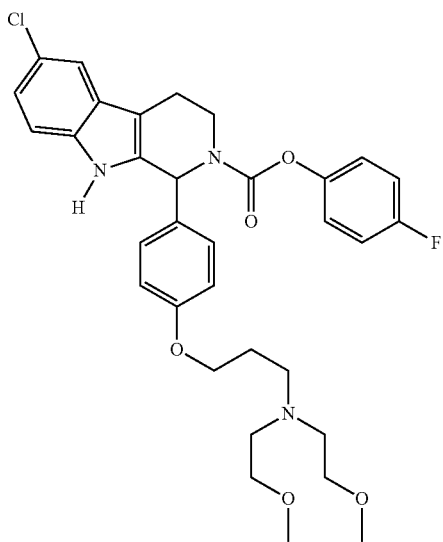 [SMILES: COCCN(CCCOc1ccc(C2c3[nH]c4ccc(Cl)cc4c3CCN2C(=O)Oc2ccc(F)cc2)cc1)CCOC]
990
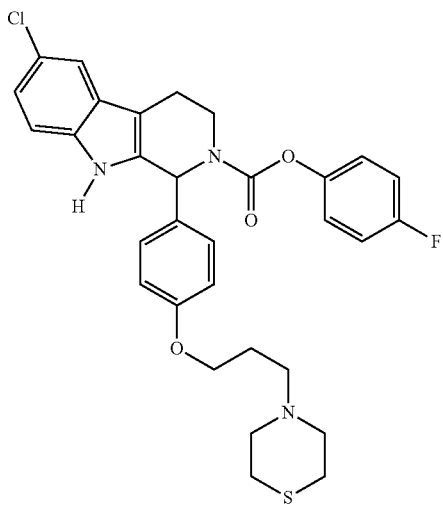 [SMILES: O=C(Oc1ccc(F)cc1)N1CCc2c([nH]c3ccc(Cl)cc23)C1c1ccc(OCCCN2CCSCC2)cc1]
991

TABLE 1-continued
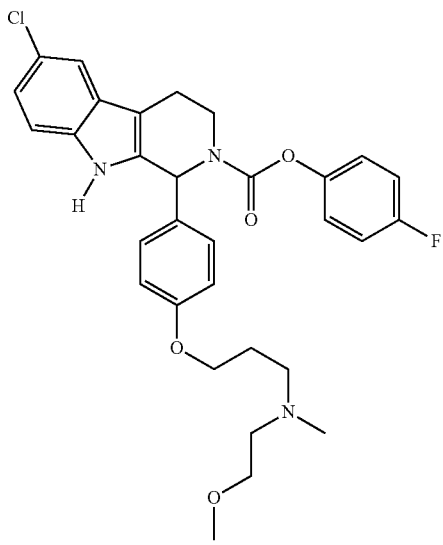 [SMILES: COCCN(C)CCCOc1ccc(C2c3[nH]c4ccc(Cl)cc4c3CCN2C(=O)Oc2ccc(F)cc2)cc1]
992
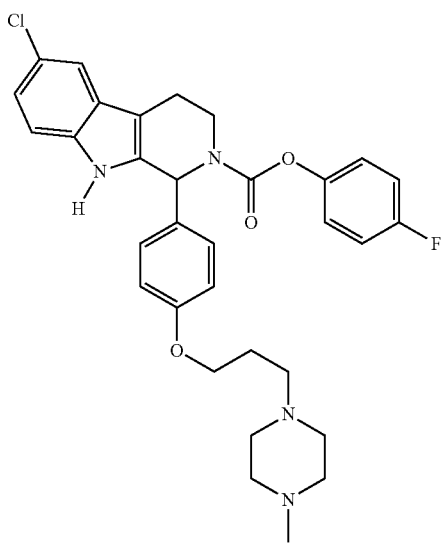 [SMILES: CN1CCN(CCCOc2ccc(C3c4[nH]c5ccc(Cl)cc5c4CCN3C(=O)Oc3ccc(F)cc3)cc2)CC1]
993
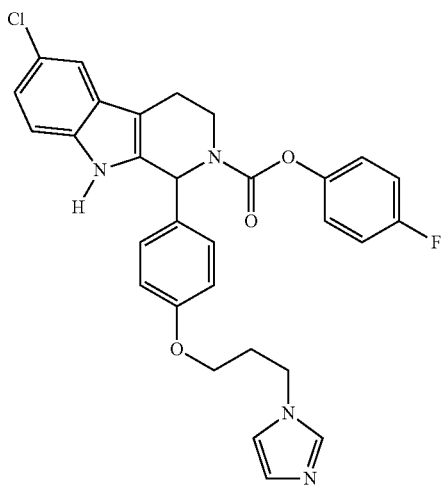 [SMILES: O=C(Oc1ccc(F)cc1)N1CCc2c([nH]c3ccc(Cl)cc23)C1c1ccc(OCCCn2ccnc2)cc1]
994

TABLE 1-continued
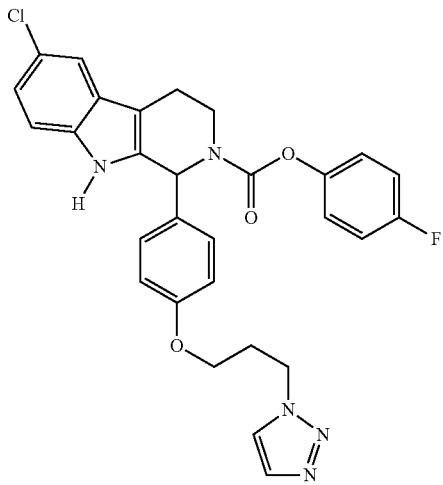 [SMILES: O=C(Oc1ccc(F)cc1)N1CCc2c([nH]c3ccc(Cl)cc23)C1c1ccc(OCCCn2ccnn2)cc1]
995
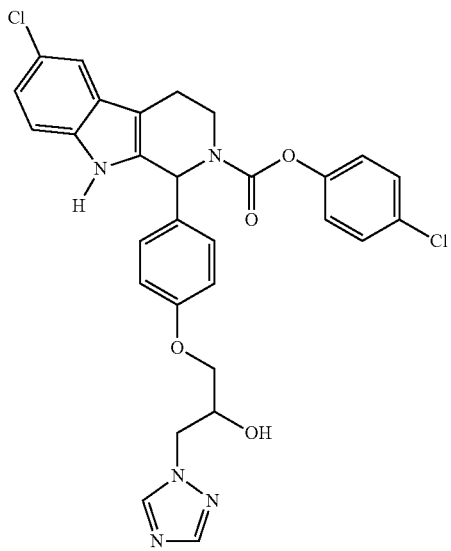 [SMILES: O=C(Oc1ccc(Cl)cc1)N1CCc2c([nH]c3ccc(Cl)cc23)C1c1ccc(OCC(O)Cn2cncn2)cc1]
996
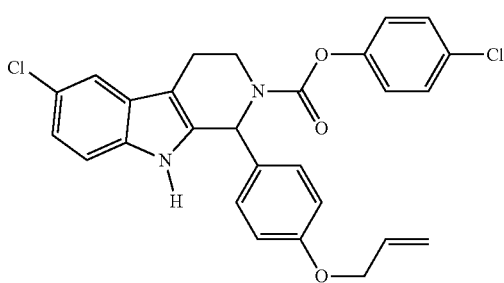 [SMILES: C=CCOc1ccc(C2c3[nH]c4ccc(Cl)cc4c3CCN2C(=O)Oc2ccc(Cl)cc2)cc1]
999

TABLE 1-continued
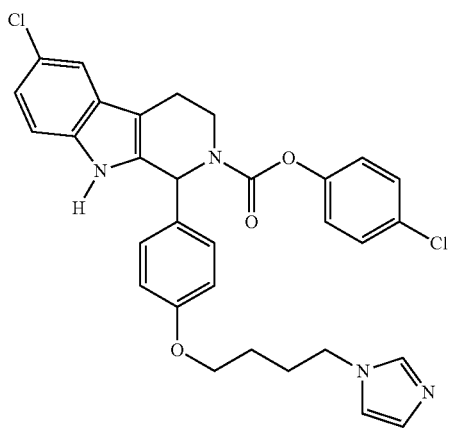 [SMILES: O=C(Oc1ccc(Cl)cc1)N1CCc2c([nH]c3ccc(Cl)cc23)C1c1ccc(OCCCCn2ccnc2)cc1]
1001
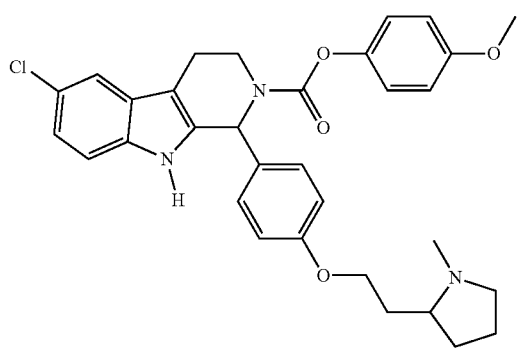 [SMILES: COc1ccc(OC(=O)N2CCc3c([nH]c4ccc(Cl)cc34)C2c2ccc(OCCC3CCCN3C)cc2)cc1]
1005
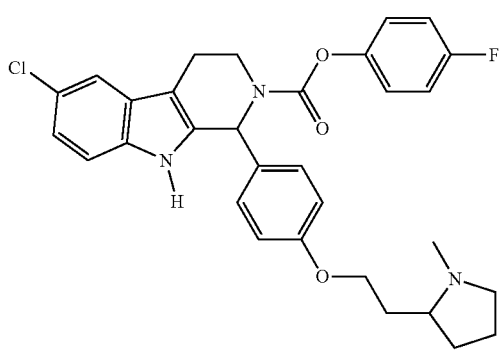 [SMILES: CN1CCCC1CCOc1ccc(C2c3[nH]c4ccc(Cl)cc4c3CCN2C(=O)Oc2ccc(F)cc2)cc1]
1008
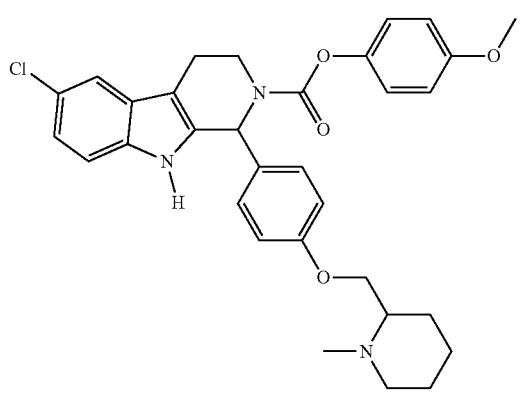 [SMILES: COc1ccc(OC(=O)N2CCc3c([nH]c4ccc(Cl)cc34)C2c2ccc(OCC3CCCCN3C)cc2)cc1]
1009

TABLE 1-continued
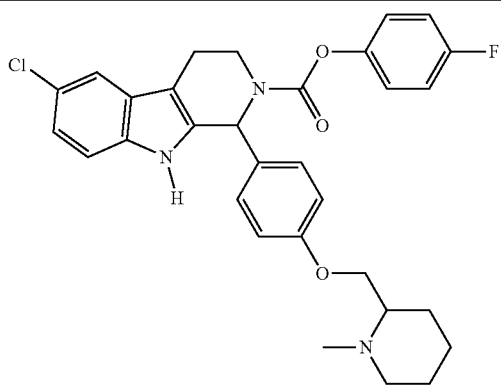
1011
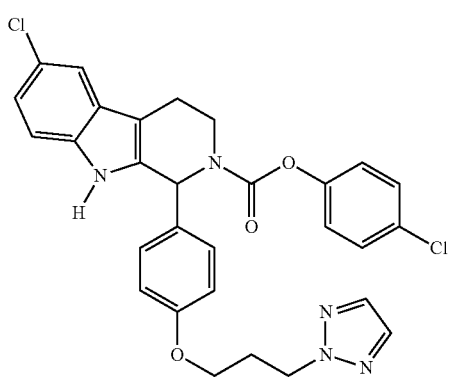
1016
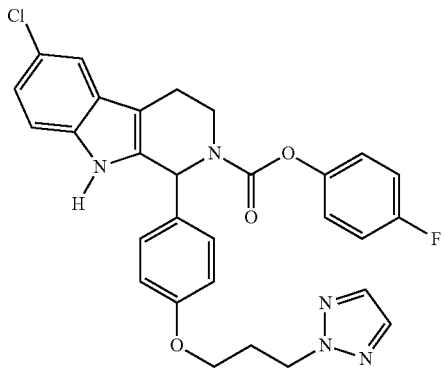 [SMILES: O=C(Oc1ccc(F)cc1)N1CCc2c([nH]c3ccc(Cl)cc23)C1c1ccc(OCCCn2nccn2)cc1]
1017
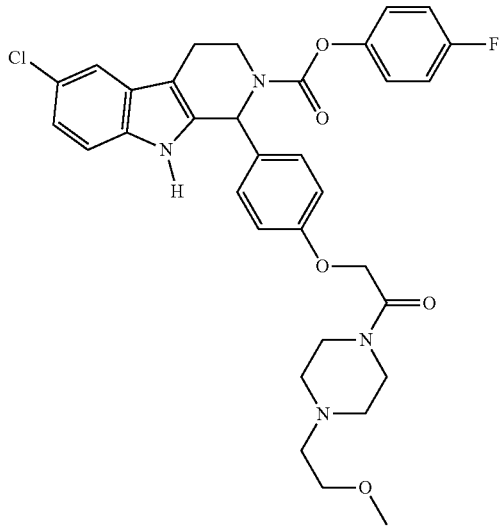 [SMILES: COCCN1CCN(C(=O)COc2ccc(C3c4[nH]c5ccc(Cl)cc5c4CCN3C(=O)Oc3ccc(F)cc3)cc2)CC1]
1021

TABLE 1-continued
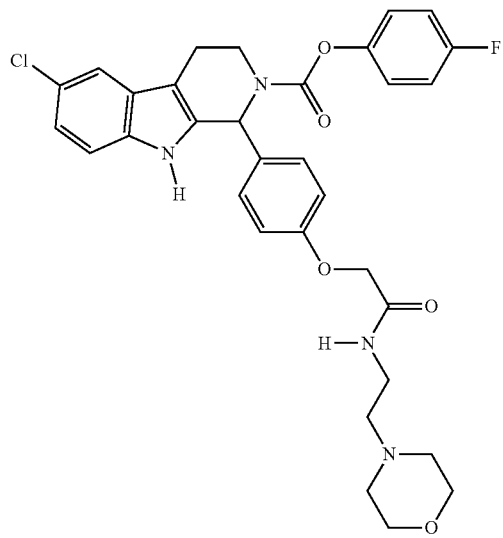 [SMILES: O=C(COc1ccc(C2c3[nH]c4ccc(Cl)cc4c3CCN2C(=O)Oc2ccc(F)cc2)cc1)NCCN1CCOCC1]
1022
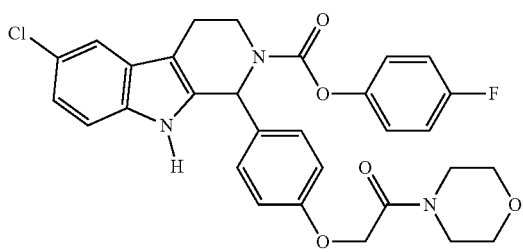 [SMILES: O=C(COc1ccc(C2c3[nH]c4ccc(Cl)cc4c3CCN2C(=O)Oc2ccc(F)cc2)cc1)N1CCOCC1]
1023
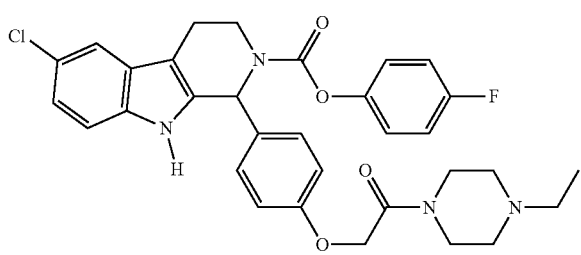 [SMILES: CCN1CCN(C(=O)COc2ccc(C3c4[nH]c5ccc(Cl)cc5c4CCN3C(=O)Oc3ccc(F)cc3)cc2)CC1]
1024
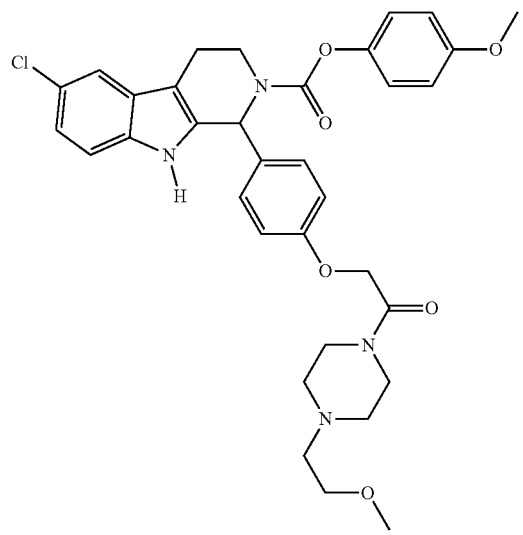 [SMILES: COCCN1CCN(C(=O)COc2ccc(C3c4[nH]c5ccc(Cl)cc5c4CCN3C(=O)Oc3ccc(OC)cc3)cc2)CC1]
1025

TABLE 1-continued
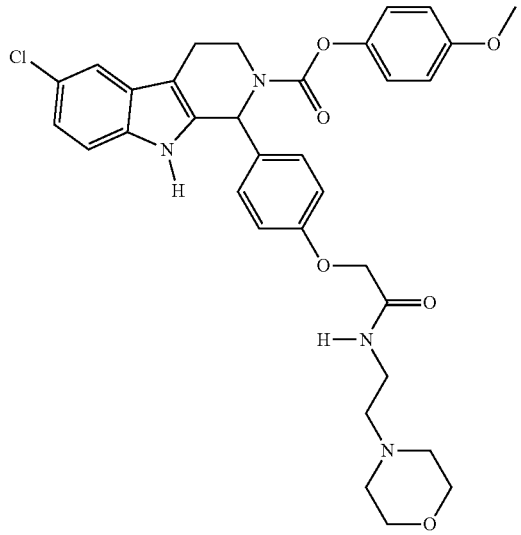 [SMILES: COc1ccc(OC(=O)N2CCc3c([nH]c4ccc(Cl)cc34)C2c2ccc(OCC(=O)NCCN3CCOCC3)cc2)cc1] 1026
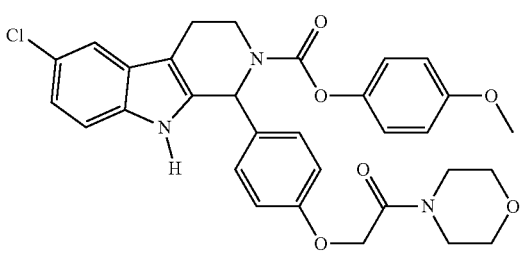 [SMILES: COc1ccc(OC(=O)N2CCc3c([nH]c4ccc(Cl)cc34)C2c2ccc(OCC(=O)N3CCOCC3)cc2)cc1] 1027
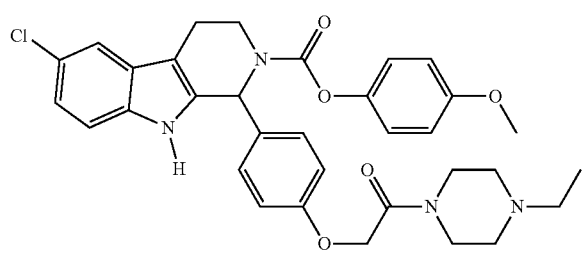 [SMILES: CCN1CCN(C(=O)COc2ccc(C3c4[nH]c5ccc(Cl)cc5c4CCN3C(=O)Oc3ccc(OC)cc3)cc2)CC1] 1028
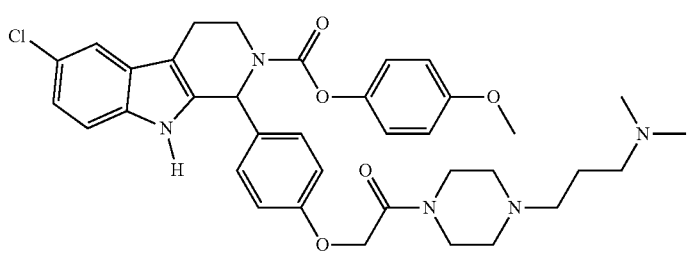 [SMILES: COc1ccc(OC(=O)N2CCc3c([nH]c4ccc(Cl)cc34)C2c2ccc(OCC(=O)N3CCN(CCCN(C)C)CC3)cc2)cc1] 1029

TABLE 1-continued
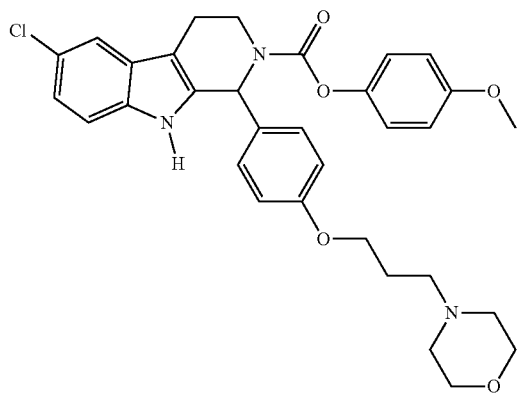 [SMILES: COc1ccc(OC(=O)N2CCc3c([nH]c4ccc(Cl)cc34)C2c2ccc(OCCCN3CCOCC3)cc2)cc1]
1030
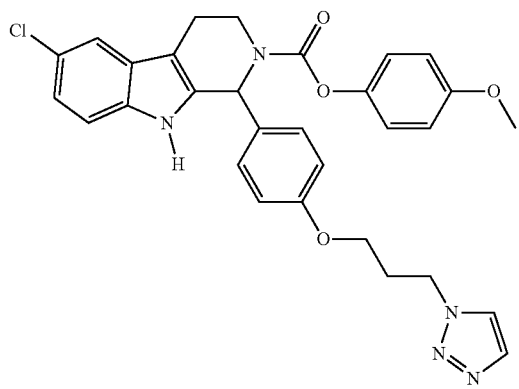 [SMILES: COc1ccc(OC(=O)N2CCc3c([nH]c4ccc(Cl)cc34)C2c2ccc(OCCCn3ccnn3)cc2)cc1]
1031
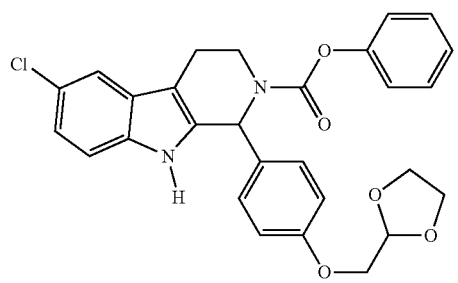 [SMILES: O=C(Oc1ccccc1)N1CCc2c([nH]c3ccc(Cl)cc23)C1c1ccc(OCC2OCCO2)cc1]
1050
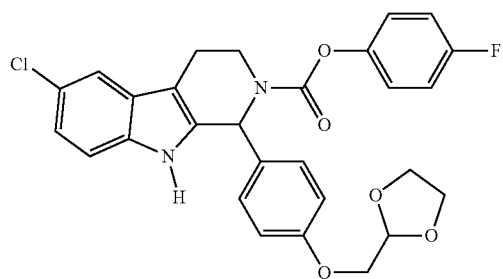 [SMILES: O=C(Oc1ccc(F)cc1)N1CCc2c([nH]c3ccc(Cl)cc23)C1c1ccc(OCC2OCCO2)cc1]
1051

TABLE 1-continued
| | |
|---|---|
| 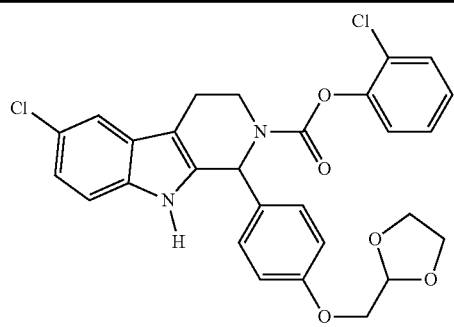 | 1052 |
| 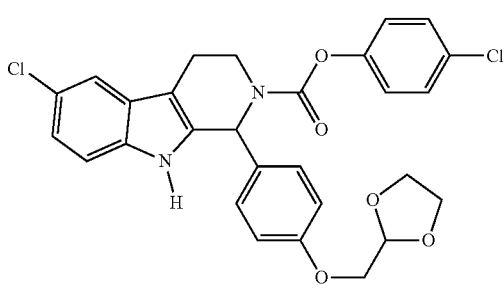 [SMILES: O=C(Oc1ccc(Cl)cc1)N1CCc2c([nH]c3ccc(Cl)cc23)C1c1ccc(OCC2OCCO2)cc1] | 1053 |
| 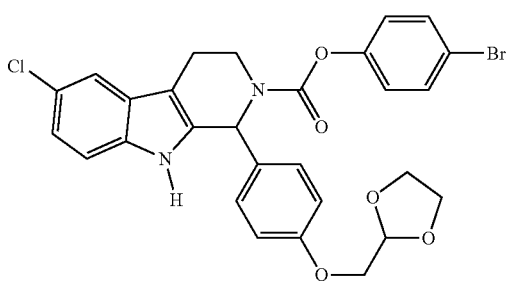 [SMILES: O=C(Oc1ccc(Br)cc1)N1CCc2c([nH]c3ccc(Cl)cc23)C1c1ccc(OCC2OCCO2)cc1] | 1054 |
| 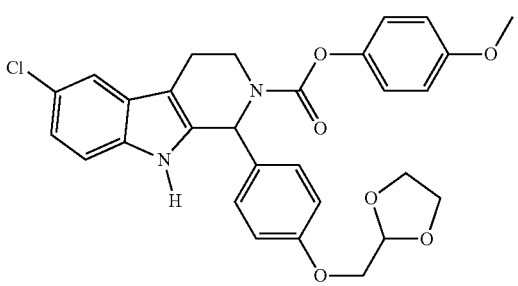 [SMILES: COc1ccc(OC(=O)N2CCc3c([nH]c4ccc(Cl)cc34)C2c2ccc(OCC3OCCO3)cc2)cc1] | 1055 |
| 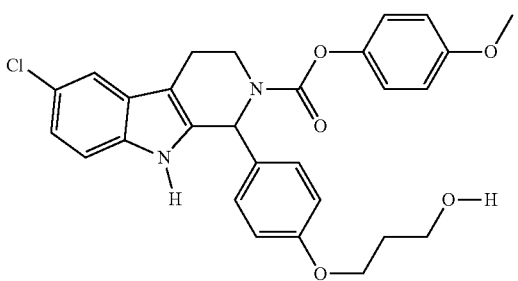 [SMILES: COc1ccc(OC(=O)N2CCc3c([nH]c4ccc(Cl)cc34)C2c2ccc(OCCCO)cc2)cc1] | 1058 |

TABLE 1-continued
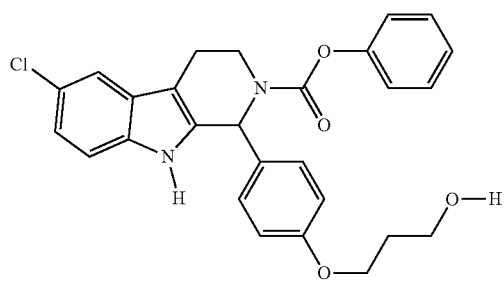 [SMILES: O=C(Oc1ccccc1)N1CCc2c([nH]c3ccc(Cl)cc23)C1c1ccc(OCCCO)cc1]
1062
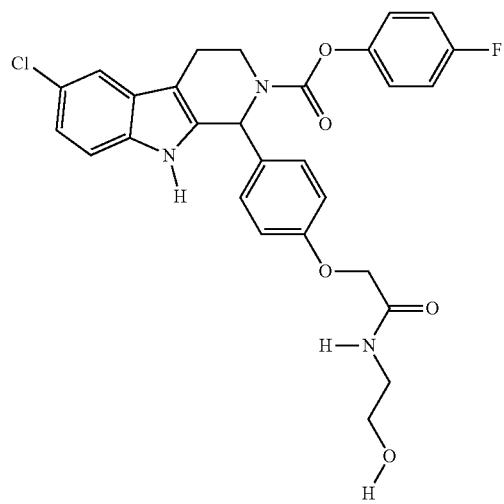 [SMILES: O=C(COc1ccc(C2c3[nH]c4ccc(Cl)cc4c3CCN2C(=O)Oc2ccc(F)cc2)cc1)NCCO]
1063
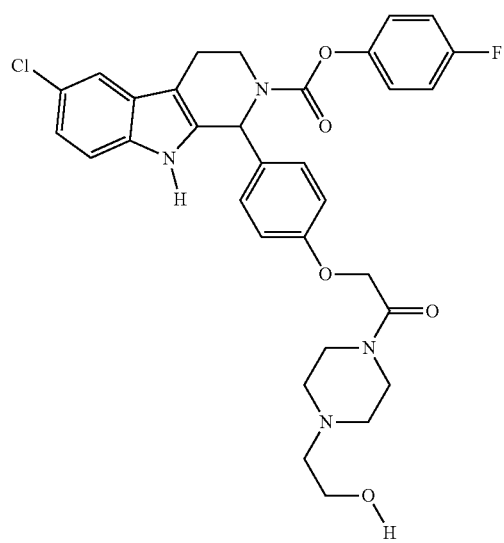 [SMILES: O=C(COc1ccc(C2c3[nH]c4ccc(Cl)cc4c3CCN2C(=O)Oc2ccc(F)cc2)cc1)N1CCN(CCO)CC1]
1064

TABLE 1-continued
| | |
|---|---|
| 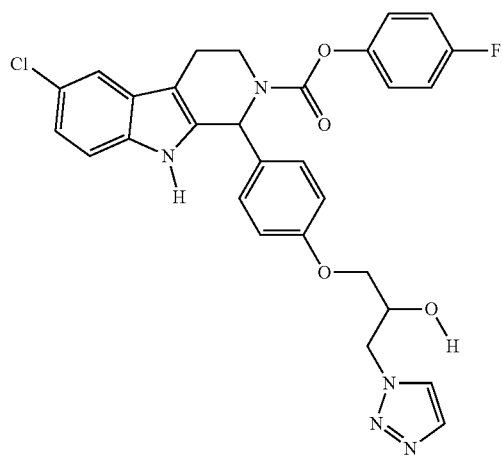 [SMILES: O=C(Oc1ccc(F)cc1)N1CCc2c([nH]c3ccc(Cl)cc23)C1c1ccc(OCC(O)Cn2ccnn2)cc1] | 1066 |
| 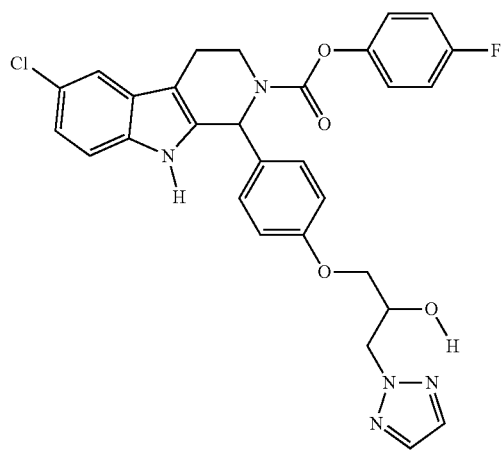 [SMILES: O=C(Oc1ccc(F)cc1)N1CCc2c([nH]c3ccc(Cl)cc23)C1c1ccc(OCC(O)Cn2nccn2)cc1] | 1067 |
| 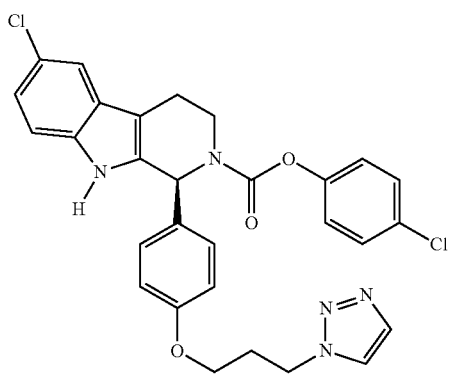 [SMILES: O=C(Oc1ccc(Cl)cc1)N1CCc2c([nH]c3ccc(Cl)cc23)[C@@H]1c1ccc(OCCCn2ccnn2)cc1] | 1068 |
| 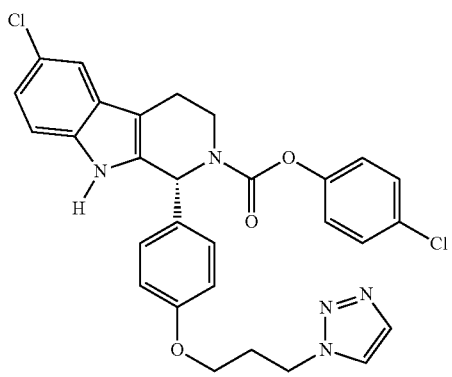 | 1069 |

TABLE 1-continued
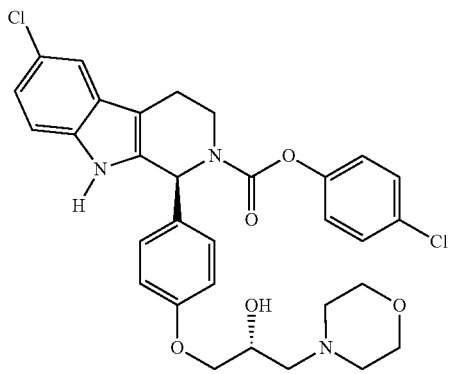 [SMILES: O=C(Oc1ccc(Cl)cc1)N1CCc2c([nH]c3ccc(Cl)cc23)[C@@H]1c1ccc(OC[C@H](O)CN2CCOCC2)cc1]
1070
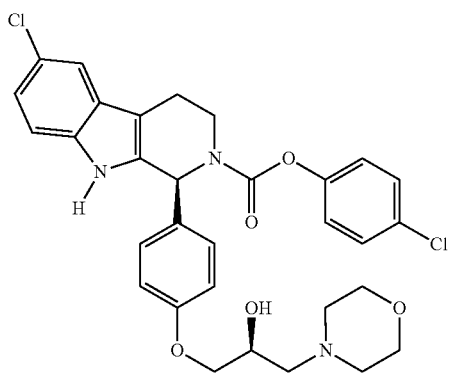 [SMILES: O=C(Oc1ccc(Cl)cc1)N1CCc2c([nH]c3ccc(Cl)cc23)[C@@H]1c1ccc(OC[C@@H](O)CN2CCOCC2)cc1]
1071
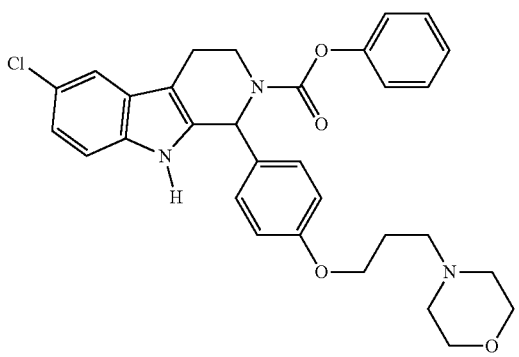 [SMILES: O=C(Oc1ccccc1)N1CCc2c([nH]c3ccc(Cl)cc23)C1c1ccc(OCCCN2CCOCC2)cc1]
1075
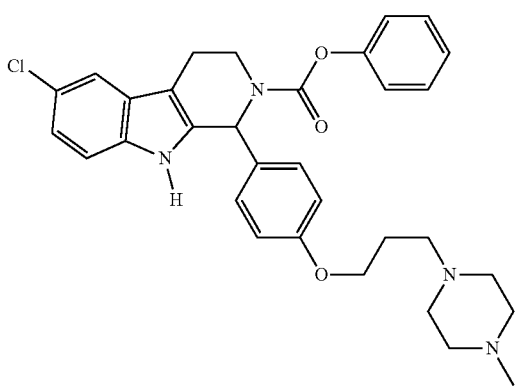 [SMILES: CN1CCN(CCCOc2ccc(C3c4[nH]c5ccc(Cl)cc5c4CCN3C(=O)Oc3ccccc3)cc2)CC1]
1076

TABLE 1-continued
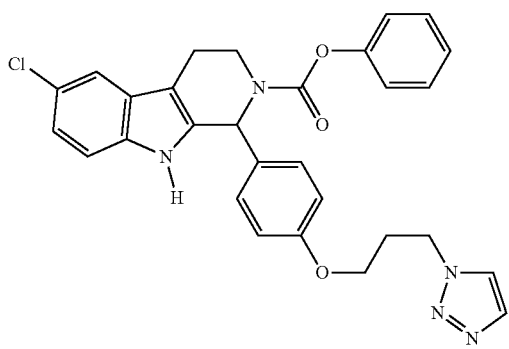 [SMILES: O=C(Oc1ccccc1)N1CCc2c([nH]c3ccc(Cl)cc23)C1c1ccc(OCCCn2ccnn2)cc1]
1077
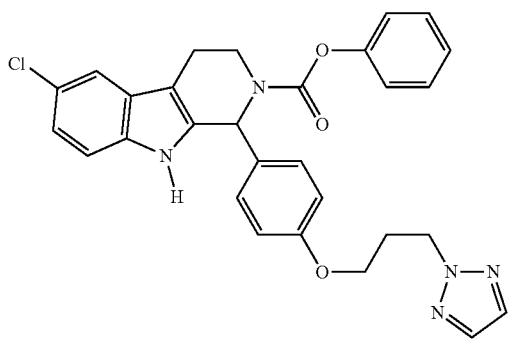 [SMILES: O=C(Oc1ccccc1)N1CCc2c([nH]c3ccc(Cl)cc23)C1c1ccc(OCCCn2nccn2)cc1]
1078
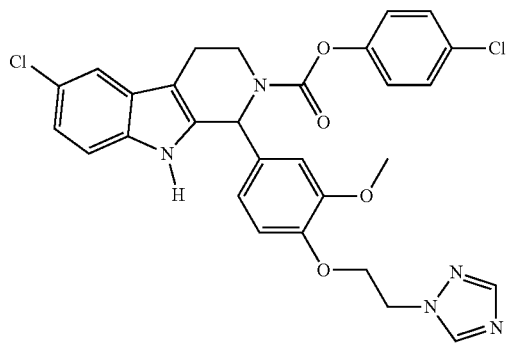 [SMILES: COc1cc(C2c3[nH]c4ccc(Cl)cc4c3CCN2C(=O)Oc2ccc(Cl)cc2)ccc1OCCn1cncn1]
1086
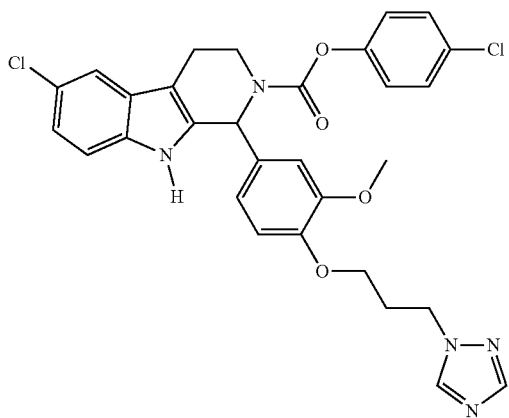 [SMILES: COc1cc(C2c3[nH]c4ccc(Cl)cc4c3CCN2C(=O)Oc2ccc(Cl)cc2)ccc1OCCCn1cncn1]
1087

TABLE 1-continued
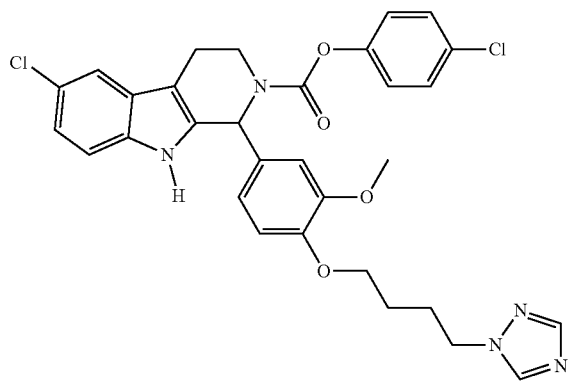 [SMILES: COc1cc(C2c3[nH]c4ccc(Cl)cc4c3CCN2C(=O)Oc2ccc(Cl)cc2)ccc1OCCCCn1cncn1]
1088
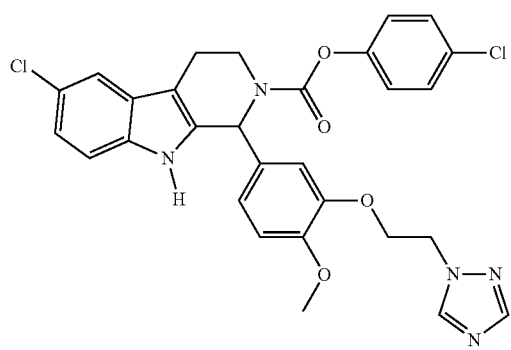 [SMILES: COc1ccc(C2c3[nH]c4ccc(Cl)cc4c3CCN2C(=O)Oc2ccc(Cl)cc2)cc1OCCn1cncn1]
1089
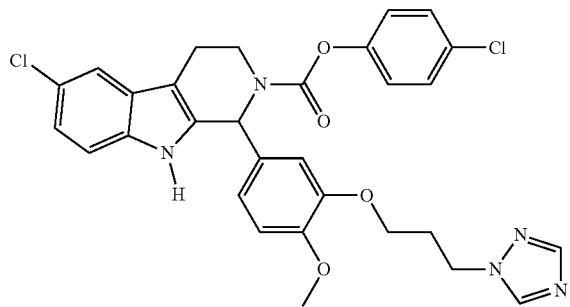 [SMILES: COc1ccc(C2c3[nH]c4ccc(Cl)cc4c3CCN2C(=O)Oc2ccc(Cl)cc2)cc1OCCCn1cncn1]
1090
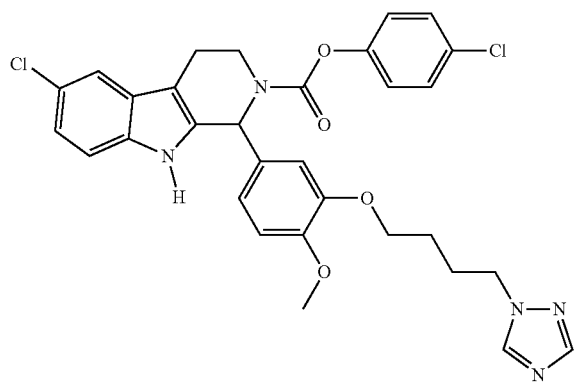 [SMILES: COc1ccc(C2c3[nH]c4ccc(Cl)cc4c3CCN2C(=O)Oc2ccc(Cl)cc2)cc1OCCCCn1cncn1]
1091

TABLE 1-continued
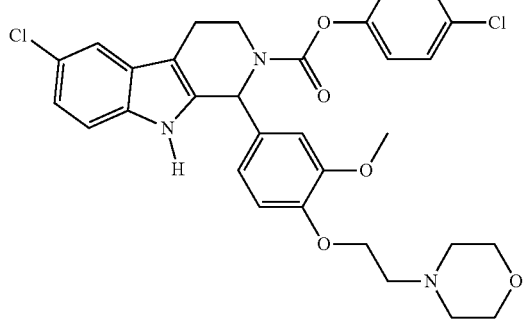
1092
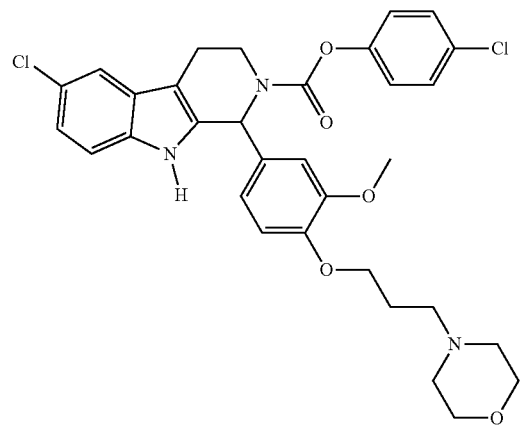 [SMILES: COc1cc(C2c3[nH]c4ccc(Cl)cc4c3CCN2C(=O)Oc2ccc(Cl)cc2)ccc1OCCCN1CCOCC1]
1093
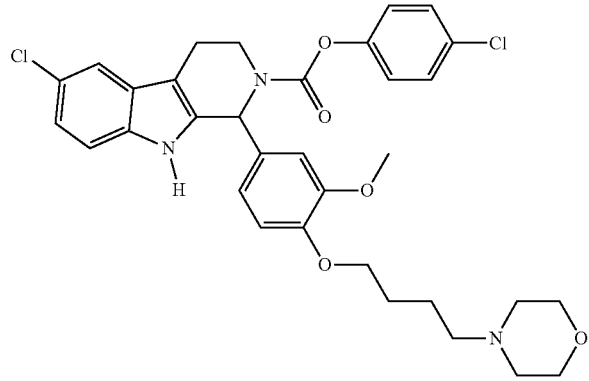 [SMILES: COc1cc(C2c3[nH]c4ccc(Cl)cc4c3CCN2C(=O)Oc2ccc(Cl)cc2)ccc1OCCCCN1CCOCC1]
1094
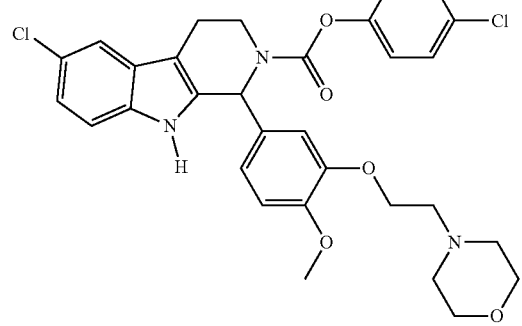
1095

TABLE 1-continued
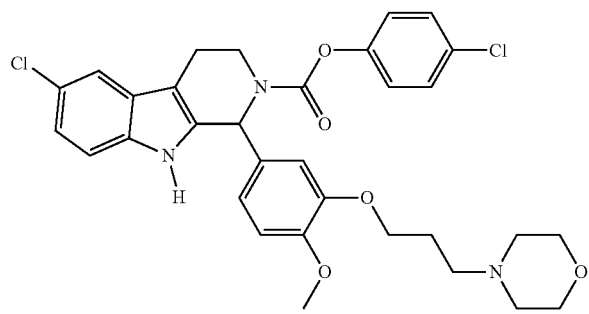 [SMILES: COc1ccc(C2c3[nH]c4ccc(Cl)cc4c3CCN2C(=O)Oc2ccc(Cl)cc2)cc1OCCCN1CCOCC1]
1096
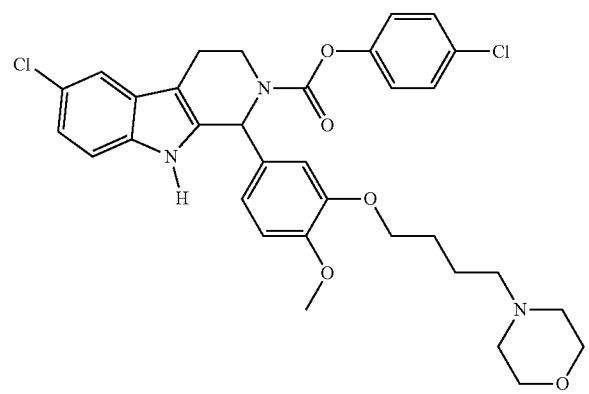 [SMILES: COc1ccc(C2c3[nH]c4ccc(Cl)cc4c3CCN2C(=O)Oc2ccc(Cl)cc2)cc1OCCCCN1CCOCC1]
1097
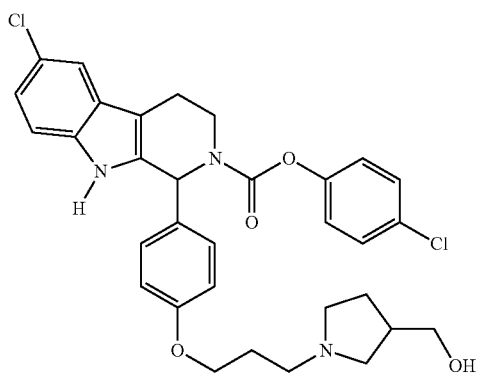 [SMILES: O=C(Oc1ccc(Cl)cc1)N1CCc2c([nH]c3ccc(Cl)cc23)C1c1ccc(OCCCN2CCC(CO)C2)cc1]
1098
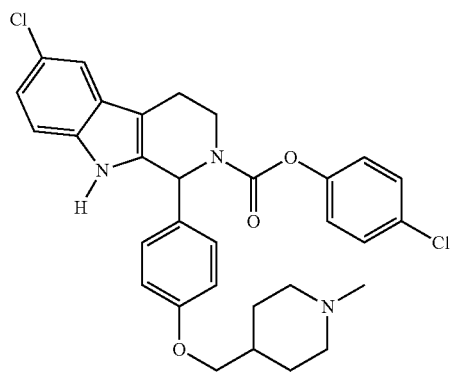 [SMILES: CN1CCC(COc2ccc(C3c4[nH]c5ccc(Cl)cc5c4CCN3C(=O)Oc3ccc(Cl)cc3)cc2)CC1]
1099

TABLE 1-continued
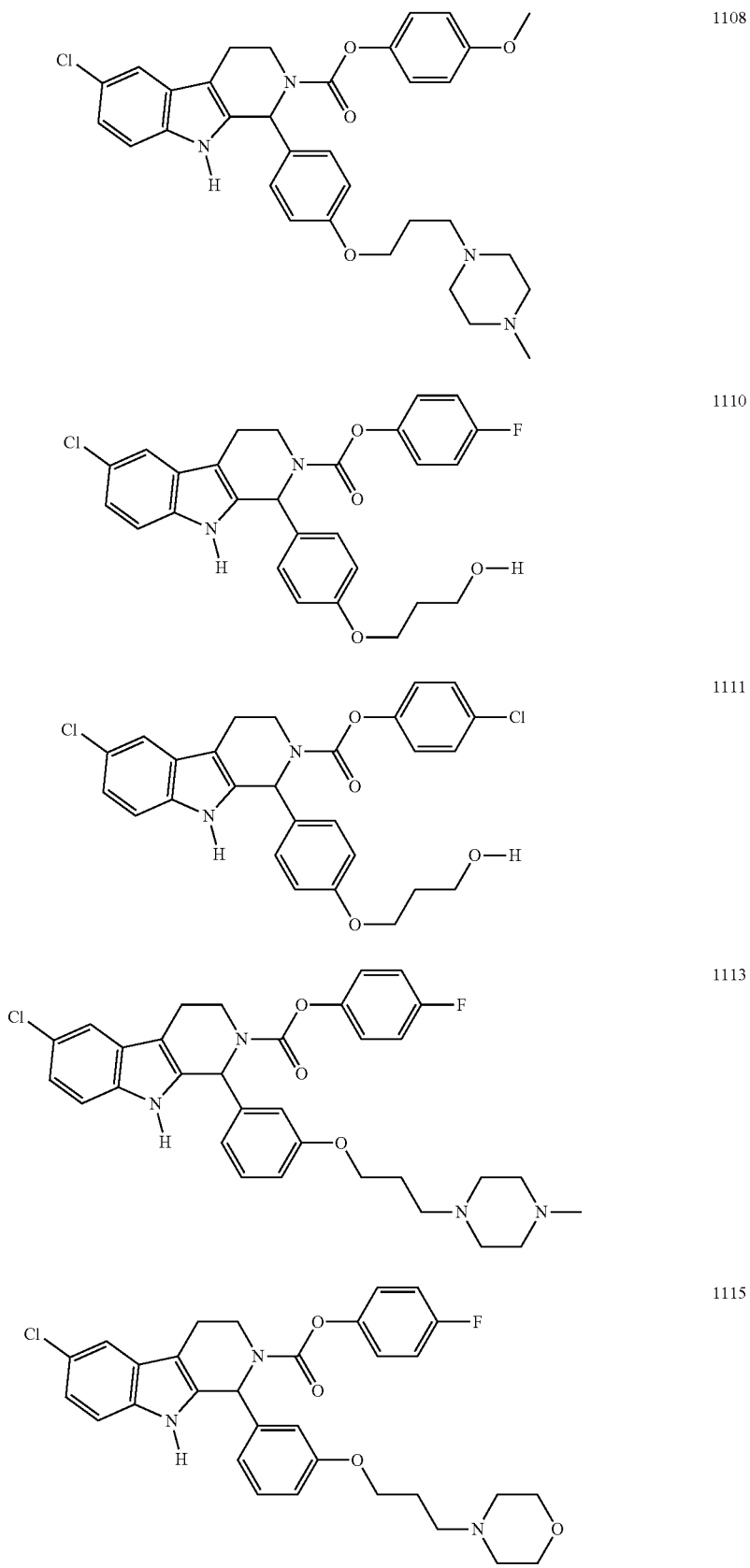
1108
1110
1111
1113
1115

TABLE 1-continued
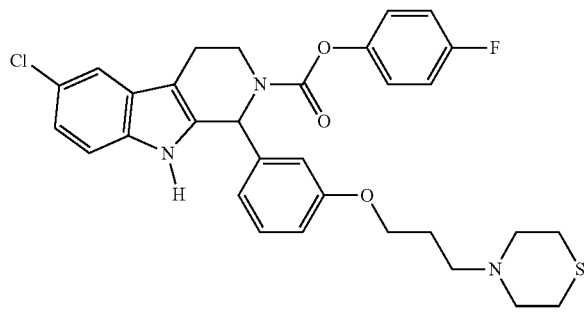 [SMILES: O=C(Oc1ccc(F)cc1)N1CCc2c([nH]c3ccc(Cl)cc23)C1c1cccc(OCCCN2CCSCC2)c1]
1117
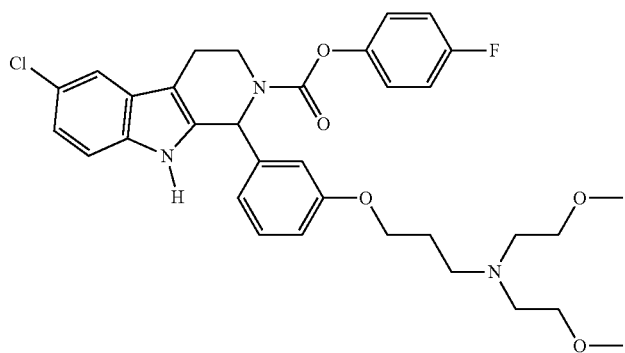 [SMILES: COCCN(CCCOc1cccc(C2c3[nH]c4ccc(Cl)cc4c3CCN2C(=O)Oc2ccc(F)cc2)c1)CCOC]
1119
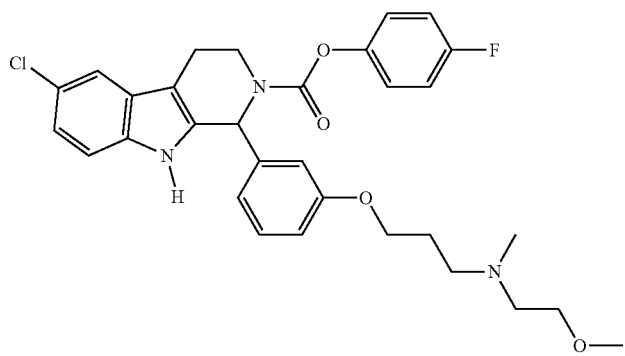 [SMILES: COCCN(C)CCCOc1cccc(C2c3[nH]c4ccc(Cl)cc4c3CCN2C(=O)Oc2ccc(F)cc2)c1]
1121
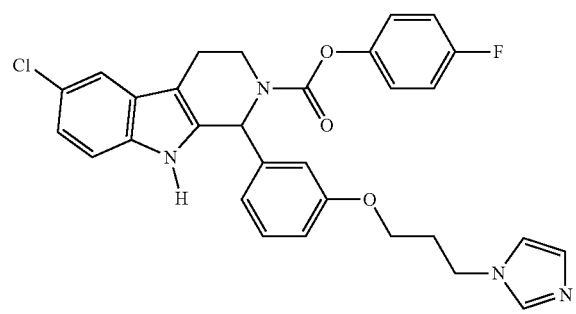 [SMILES: O=C(Oc1ccc(F)cc1)N1CCc2c([nH]c3ccc(Cl)cc23)C1c1cccc(OCCCn2ccnc2)c1]
1123
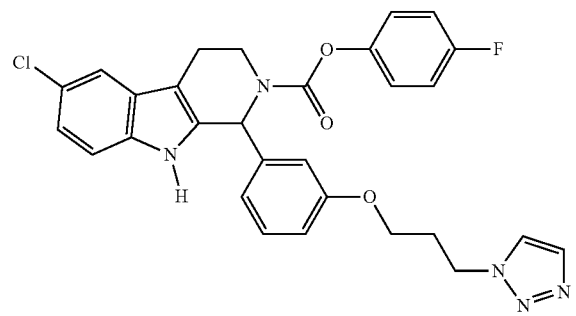 [SMILES: O=C(Oc1ccc(F)cc1)N1CCc2c([nH]c3ccc(Cl)cc23)C1c1cccc(OCCCn2ccnn2)c1]
1125

TABLE 1-continued
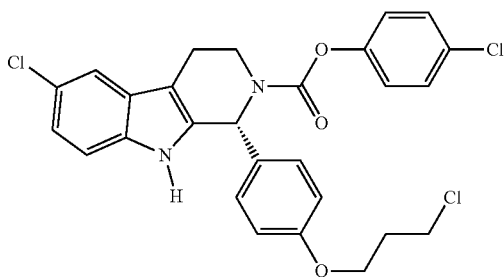 [SMILES: O=C(Oc1ccc(Cl)cc1)N1CCc2c([nH]c3ccc(Cl)cc23)[C@H]1c1ccc(OCCCCl)cc1]
1126
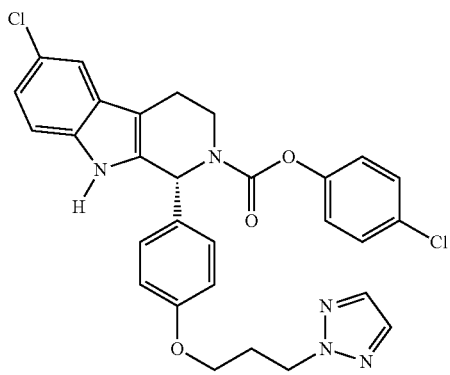
1127
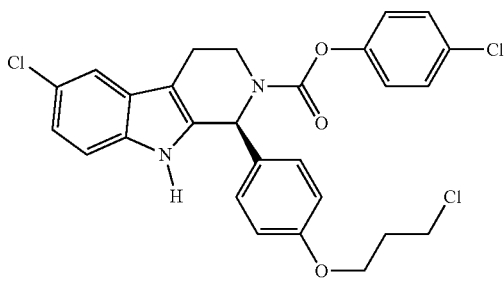 [SMILES: O=C(Oc1ccc(Cl)cc1)N1CCc2c([nH]c3ccc(Cl)cc23)[C@@H]1c1ccc(OCCCCl)cc1]
1128
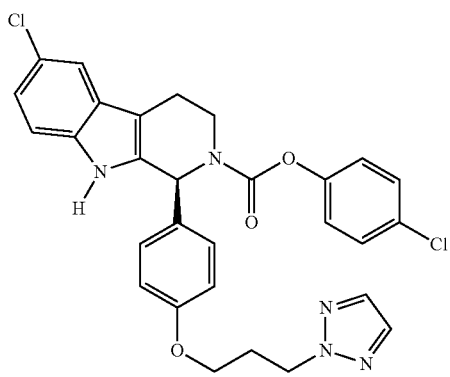 [SMILES: O=C(Oc1ccc(Cl)cc1)N1CCc2c([nH]c3ccc(Cl)cc23)[C@@H]1c1ccc(OCCCn2nccn2)cc1]
1129

TABLE 1-continued
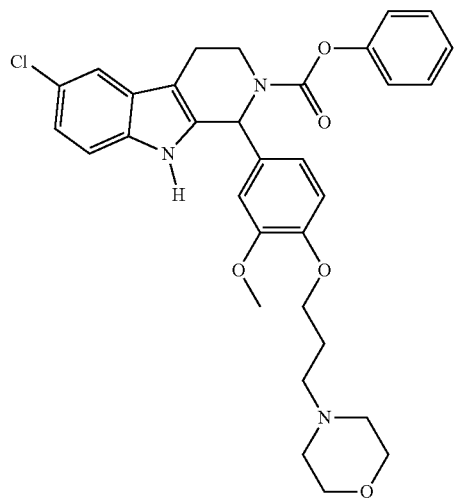 [SMILES: COc1cc(C2c3[nH]c4ccc(Cl)cc4c3CCN2C(=O)Oc2ccccc2)ccc1OCCCN1CCOCC1]
1130
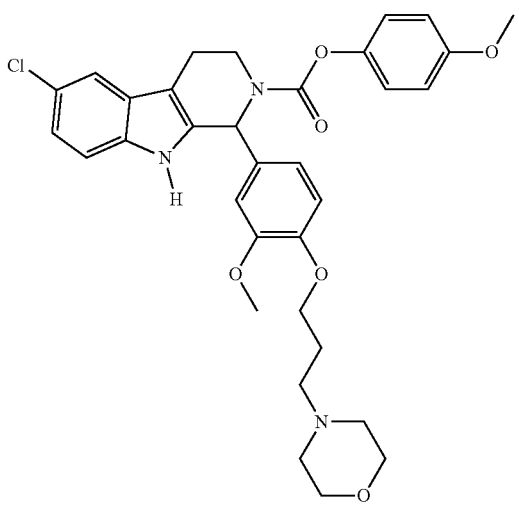 [SMILES: COc1ccc(OC(=O)N2CCc3c([nH]c4ccc(Cl)cc34)C2c2ccc(OCCCN3CCOCC3)c(OC)c2)cc1]
1131
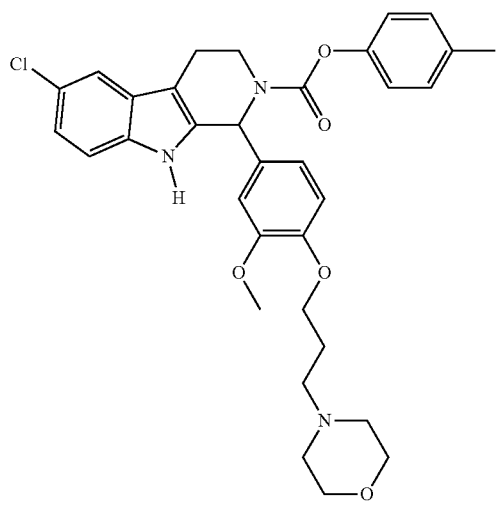 [SMILES: COc1cc(C2c3[nH]c4ccc(Cl)cc4c3CCN2C(=O)Oc2ccc(C)cc2)ccc1OCCCN1CCOCC1]
1132

TABLE 1-continued
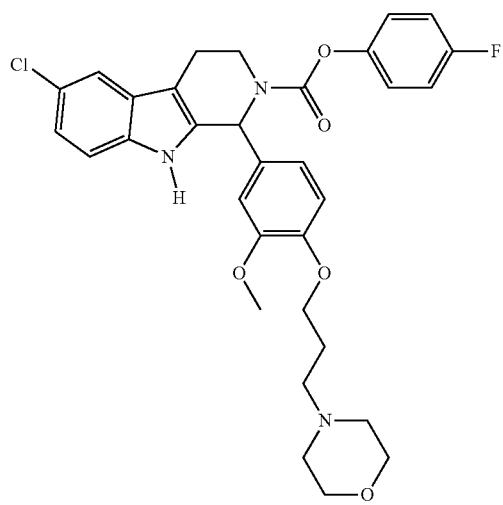 [SMILES: COc1cc(C2c3[nH]c4ccc(Cl)cc4c3CCN2C(=O)Oc2ccc(F)cc2)ccc1OCCCN1CCOCC1]
1133
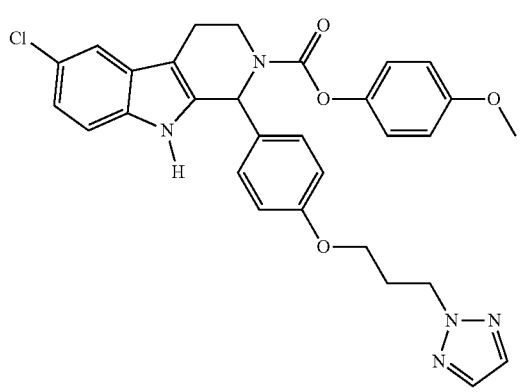 [SMILES: COc1ccc(OC(=O)N2CCc3c([nH]c4ccc(Cl)cc34)C2c2ccc(OCCCn3nccn3)cc2)cc1]
1134
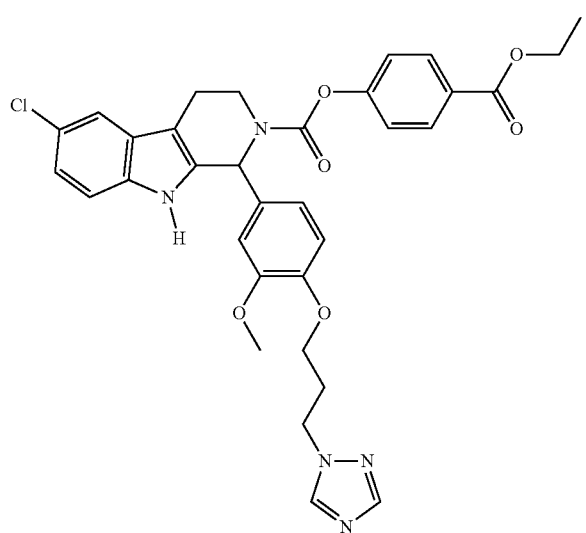 [SMILES: CCOC(=O)c1ccc(OC(=O)N2CCc3c([nH]c4ccc(Cl)cc34)C2c2ccc(OCCCn3cncn3)c(OC)c2)cc1]
1043

TABLE 1-continued
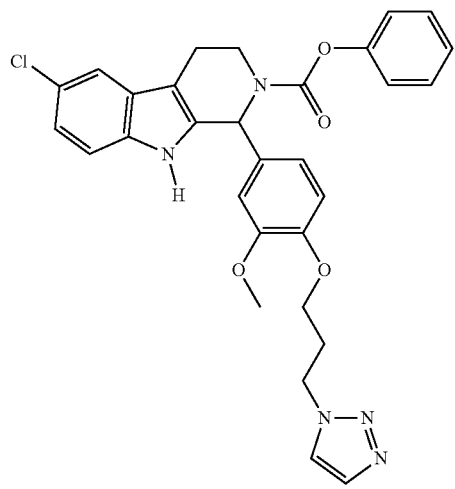 [SMILES: COc1cc(C2c3[nH]c4ccc(Cl)cc4c3CCN2C(=O)Oc2ccccc2)ccc1OCCCn1ccnn1]
1144
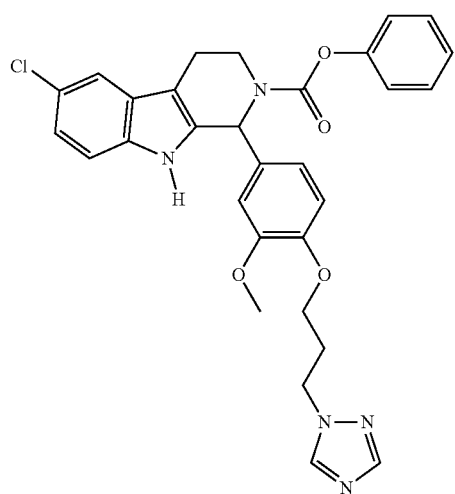 [SMILES: COc1cc(C2c3[nH]c4ccc(Cl)cc4c3CCN2C(=O)Oc2ccccc2)ccc1OCCCn1cncn1]
1145
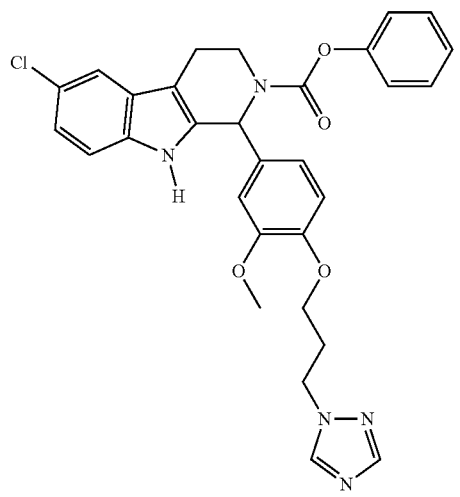 [SMILES: COc1cc(C2c3[nH]c4ccc(Cl)cc4c3CCN2C(=O)Oc2ccccc2)ccc1OCCCn1cncn1]
1150

TABLE 1-continued
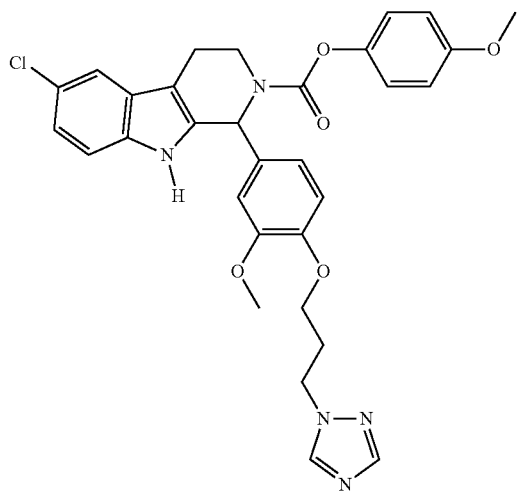 [SMILES: COc1ccc(OC(=O)N2CCc3c([nH]c4ccc(Cl)cc34)C2c2ccc(OCCCn3cncn3)c(OC)c2)cc1]
1151
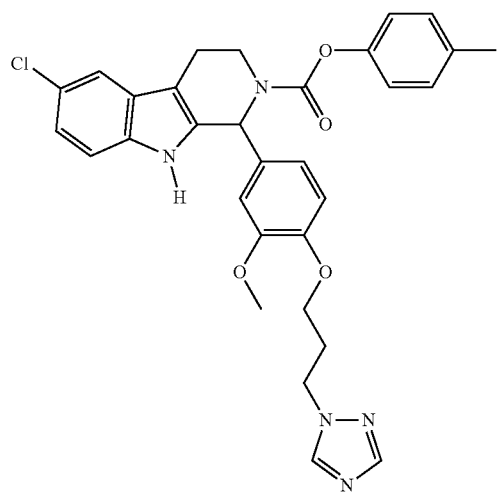 [SMILES: COc1cc(C2c3[nH]c4ccc(Cl)cc4c3CCN2C(=O)Oc2ccc(C)cc2)ccc1OCCCn1cncn1]
1152
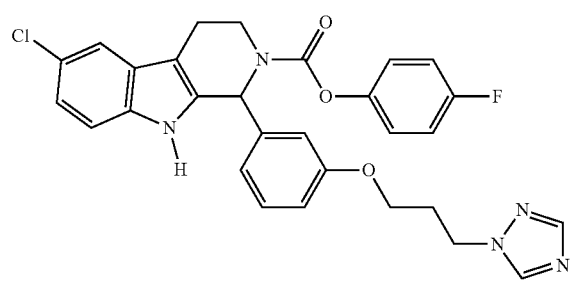 [SMILES: O=C(Oc1ccc(F)cc1)N1CCc2c([nH]c3ccc(Cl)cc23)C1c1cccc(OCCCn2cncn2)c1]
1155
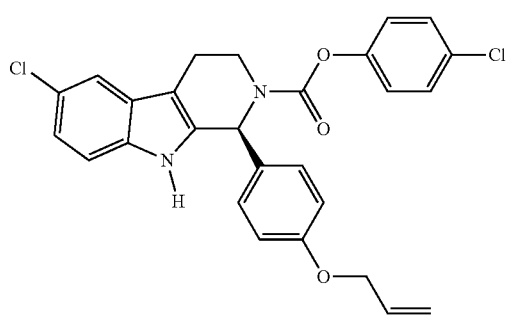 [SMILES: C=CCOc1ccc([C@H]2c3[nH]c4ccc(Cl)cc4c3CCN2C(=O)Oc2ccc(Cl)cc2)cc1]
1159

TABLE 1-continued
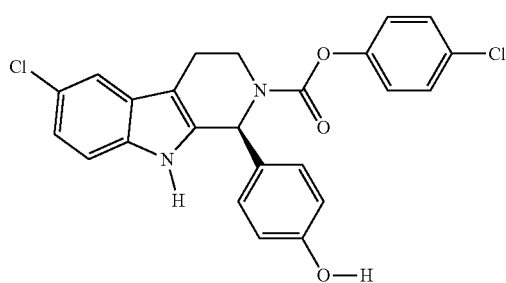 [SMILES: O=C(Oc1ccc(Cl)cc1)N1CCc2c([nH]c3ccc(Cl)cc23)[C@@H]1c1ccc(O)cc1]
1160
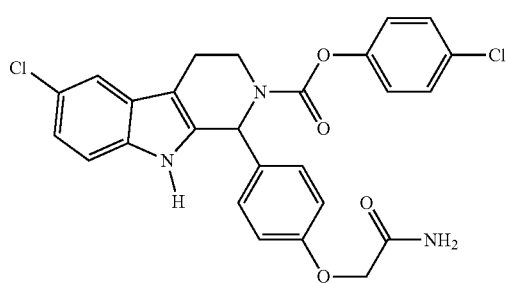 [SMILES: NC(=O)COc1ccc(C2c3[nH]c4ccc(Cl)cc4c3CCN2C(=O)Oc2ccc(Cl)cc2)cc1]
1161
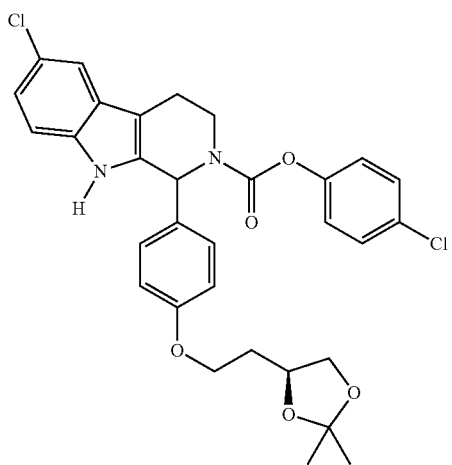
1162
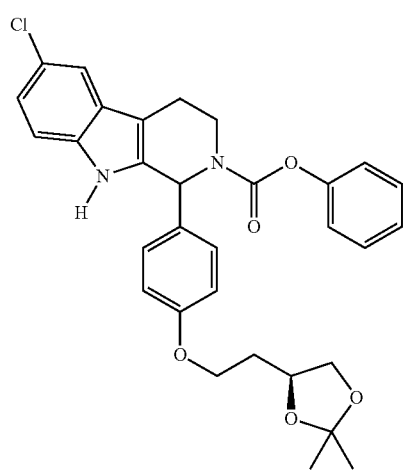 [SMILES: CC1(C)OC[C@H](CCOc2ccc(C3c4[nH]c5ccc(Cl)cc5c4CCN3C(=O)Oc3ccccc3)cc2)O1]
1168

TABLE 1-continued
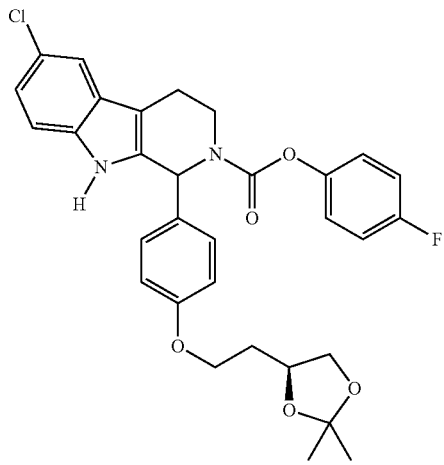 [SMILES: CC1(C)OC[C@H](CCOc2ccc(C3c4[nH]c5ccc(Cl)cc5c4CCN3C(=O)Oc3ccc(F)cc3)cc2)O1]
1169
1170
1171

TABLE 1-continued
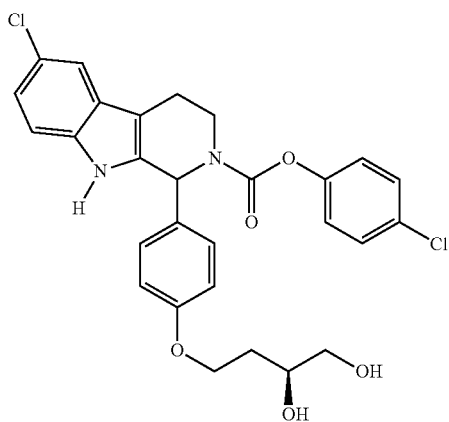
1172
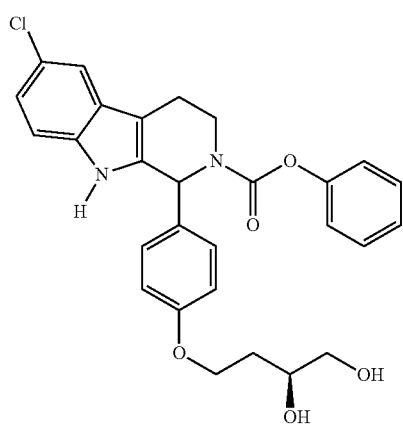 [SMILES: O=C(Oc1ccccc1)N1CCc2c([nH]c3ccc(Cl)cc23)C1c1ccc(OCC[C@H](O)CO)cc1]
1178
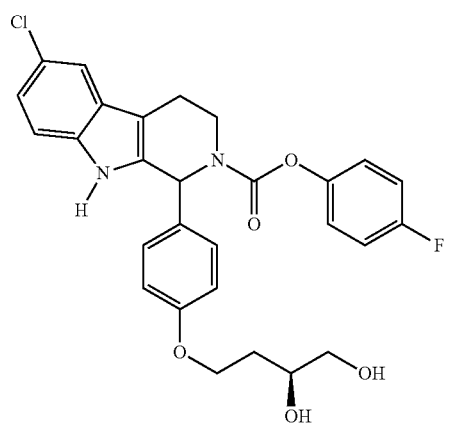 [SMILES: O=C(Oc1ccc(F)cc1)N1CCc2c([nH]c3ccc(Cl)cc23)C1c1ccc(OCC[C@H](O)CO)cc1]
1179

TABLE 1-continued
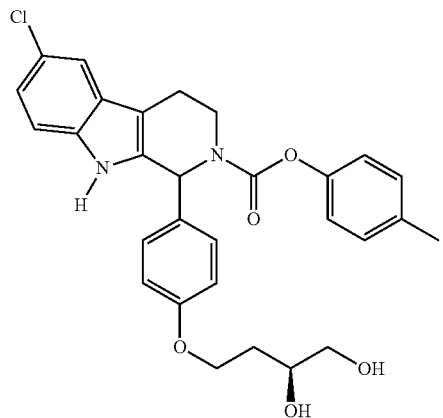 [SMILES: Cc1ccc(OC(=O)N2CCc3c([nH]c4ccc(Cl)cc34)C2c2ccc(OCC[C@H](O)CO)cc2)cc1]
1180
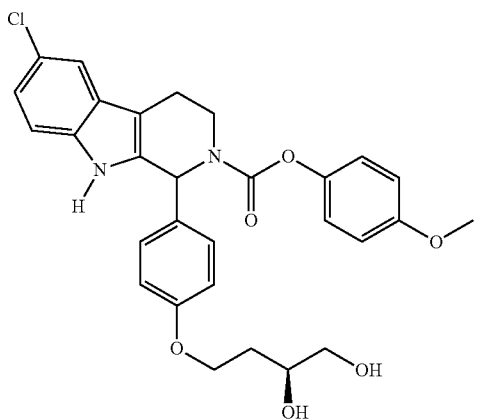 [SMILES: COc1ccc(OC(=O)N2CCc3c([nH]c4ccc(Cl)cc34)C2c2ccc(OCC[C@H](O)CO)cc2)cc1]
1181
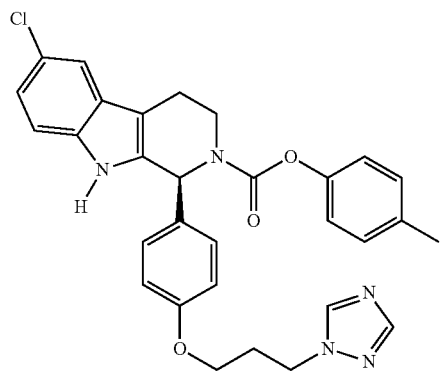 [SMILES: Cc1ccc(OC(=O)N2CCc3c([nH]c4ccc(Cl)cc34)[C@@H]2c2ccc(OCCCn3cncn3)cc2)cc1]
1182
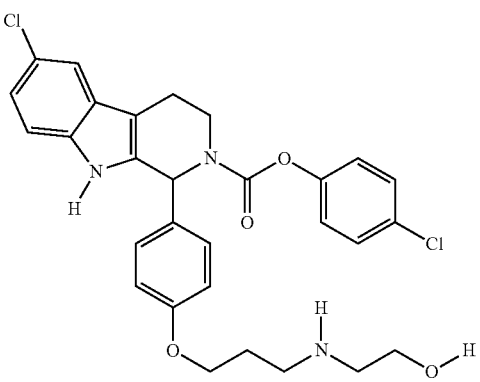 [SMILES: O=C(Oc1ccc(Cl)cc1)N1CCc2c([nH]c3ccc(Cl)cc23)C1c1ccc(OCCCNCCO)cc1]
1183

TABLE 1-continued
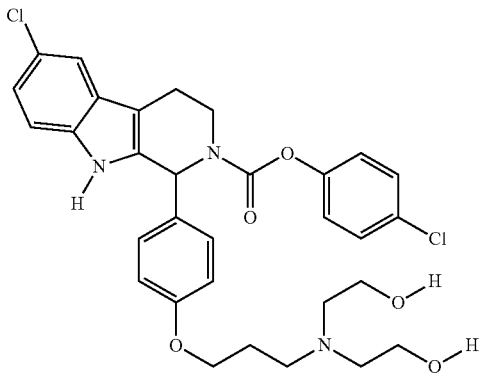 [SMILES: O=C(Oc1ccc(Cl)cc1)N1CCc2c([nH]c3ccc(Cl)cc23)C1c1ccc(OCCCN(CCO)CCO)cc1]
1184
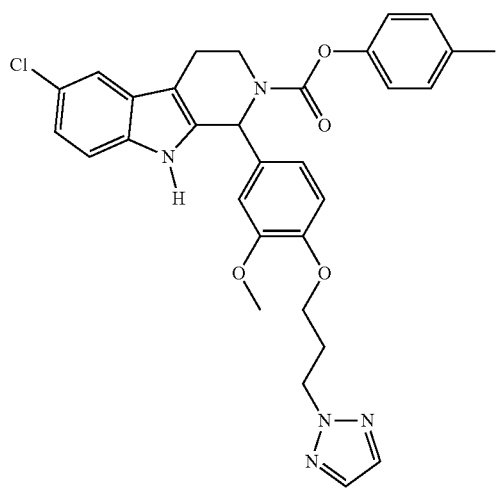 [SMILES: COc1cc(C2c3[nH]c4ccc(Cl)cc4c3CCN2C(=O)Oc2ccc(C)cc2)ccc1OCCCn1nccn1]
1194
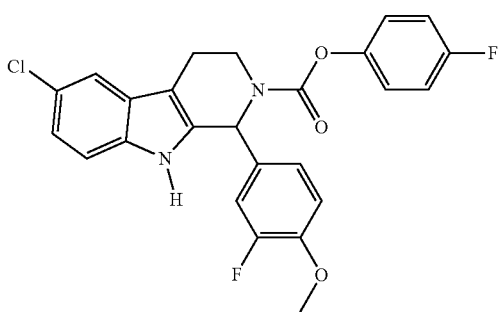 [SMILES: COc1ccc(C2c3[nH]c4ccc(Cl)cc4c3CCN2C(=O)Oc2ccc(F)cc2)cc1F]
1195
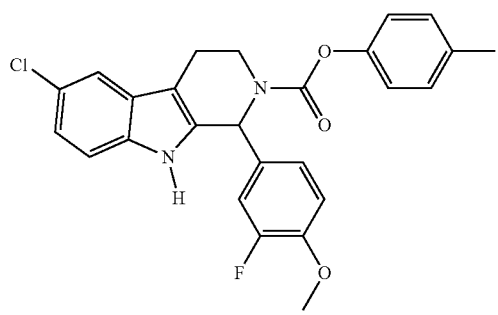 [SMILES: COc1ccc(C2c3[nH]c4ccc(Cl)cc4c3CCN2C(=O)Oc2ccc(C)cc2)cc1F]
1196

TABLE 1-continued
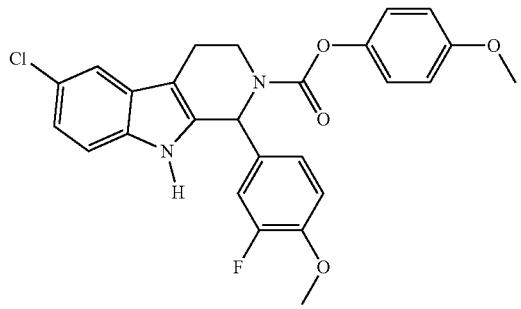 [SMILES: COc1ccc(OC(=O)N2CCc3c([nH]c4ccc(Cl)cc34)C2c2ccc(OC)c(F)c2)cc1]
1197
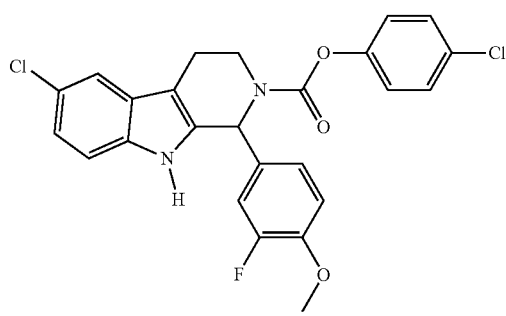 [SMILES: COc1ccc(C2c3[nH]c4ccc(Cl)cc4c3CCN2C(=O)Oc2ccc(Cl)cc2)cc1F]
1199
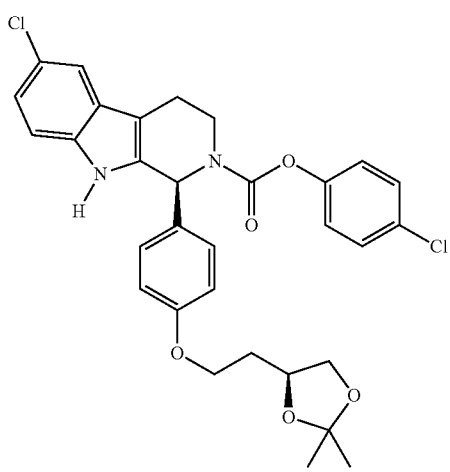 [SMILES: CC1(C)OC[C@H](CCOc2ccc([C@H]3c4[nH]c5ccc(Cl)cc5c4CCN3C(=O)Oc3ccc(Cl)cc3)cc2)O1]
1203
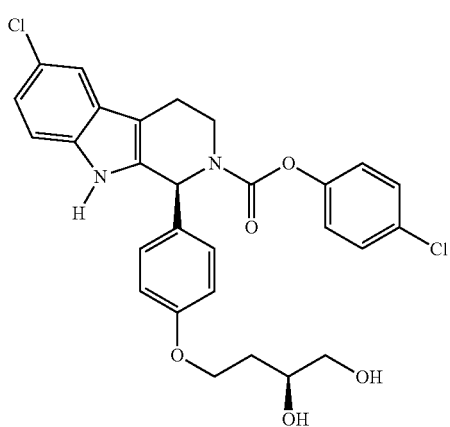 [SMILES: O=C(Oc1ccc(Cl)cc1)N1CCc2c([nH]c3ccc(Cl)cc23)[C@@H]1c1ccc(OCC[C@H](O)CO)cc1]
1205

TABLE 1-continued
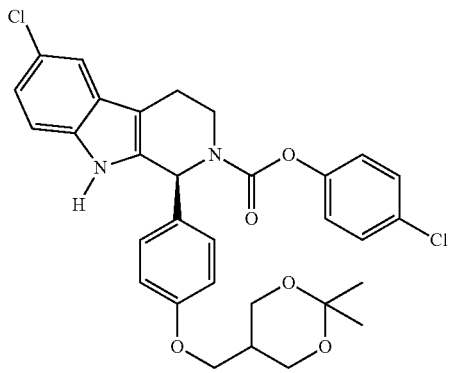 [SMILES: CC1(C)OCC(COc2ccc([C@H]3c4[nH]c5ccc(Cl)cc5c4CCN3C(=O)Oc3ccc(Cl)cc3)cc2)CO1]
1207
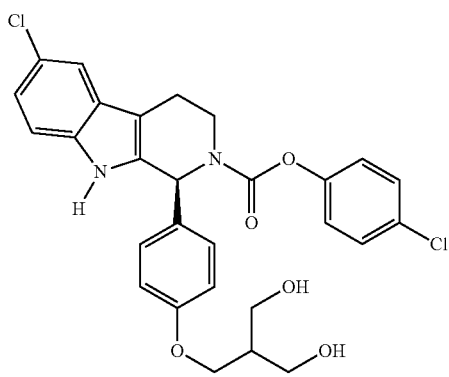 [SMILES: O=C(Oc1ccc(Cl)cc1)N1CCc2c([nH]c3ccc(Cl)cc23)[C@@H]1c1ccc(OCC(CO)CO)cc1]
1209
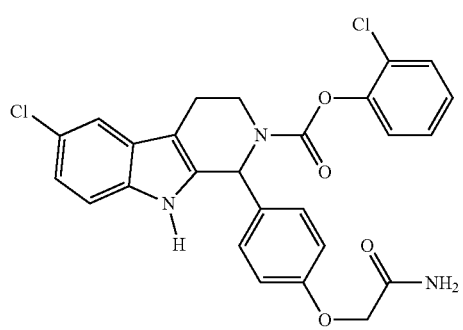 [SMILES: NC(=O)COc1ccc(C2c3[nH]c4ccc(Cl)cc4c3CCN2C(=O)Oc2ccccc2Cl)cc1]
1213
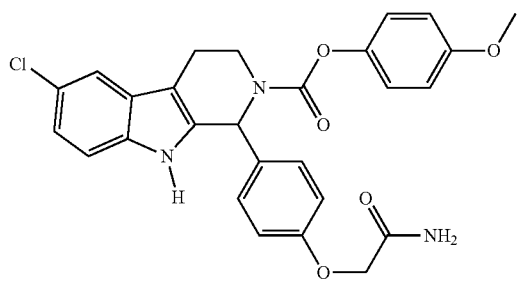 [SMILES: COc1ccc(OC(=O)N2CCc3c([nH]c4ccc(Cl)cc34)C2c2ccc(OCC(N)=O)cc2)cc1]
1216

TABLE 1-continued
| | |
|---|---|
| 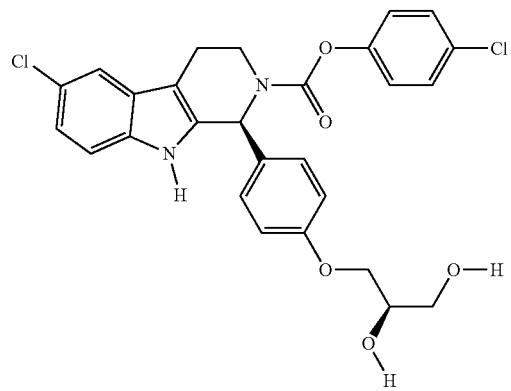 [SMILES: O=C(Oc1ccc(Cl)cc1)N1CCc2c([nH]c3ccc(Cl)cc23)[C@@H]1c1ccc(OC[C@H](O)CO)cc1] | 1223 |
| 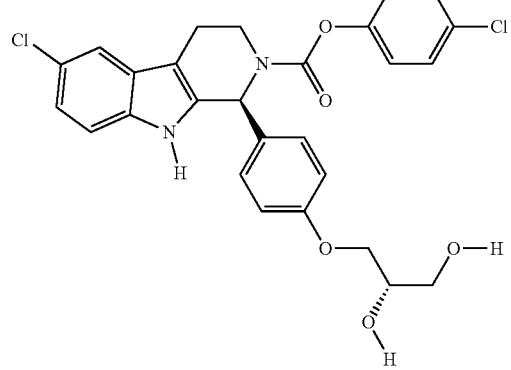 | 1224 |
| 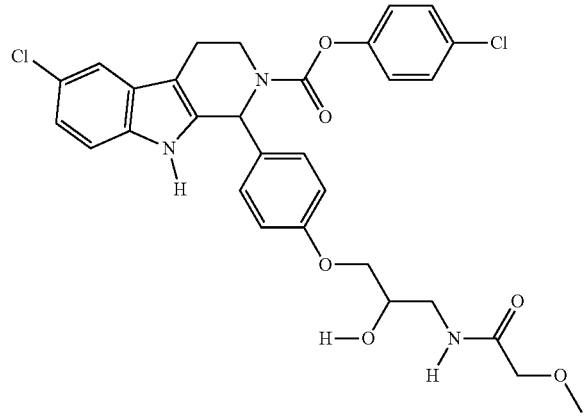 [SMILES: COCC(=O)NCC(O)COc1ccc(C2c3[nH]c4ccc(Cl)cc4c3CCN2C(=O)Oc2ccc(Cl)cc2)cc1] | 1225 |
| 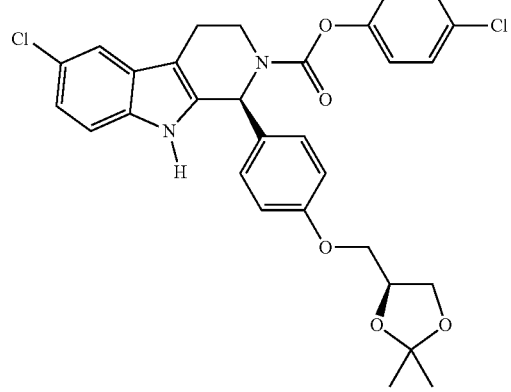 | 1227 |

TABLE 1-continued
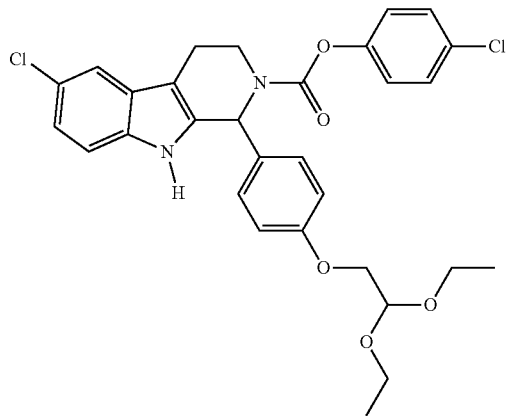 [SMILES: CCOC(COc1ccc(C2c3[nH]c4ccc(Cl)cc4c3CCN2C(=O)Oc2ccc(Cl)cc2)cc1)OCC]
1228
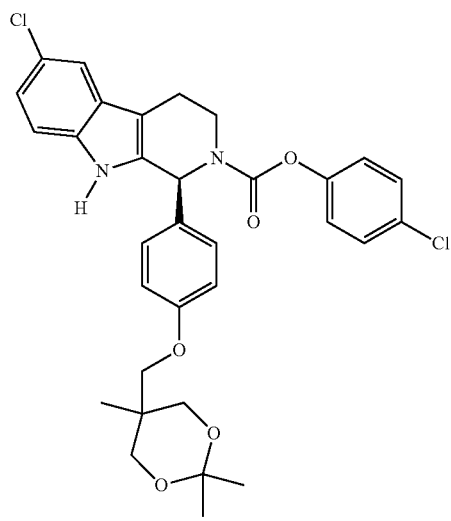 [SMILES: CC1(COc2ccc([C@H]3c4[nH]c5ccc(Cl)cc5c4CCN3C(=O)Oc3ccc(Cl)cc3)cc2)COC(C)(C)OC1]
1229
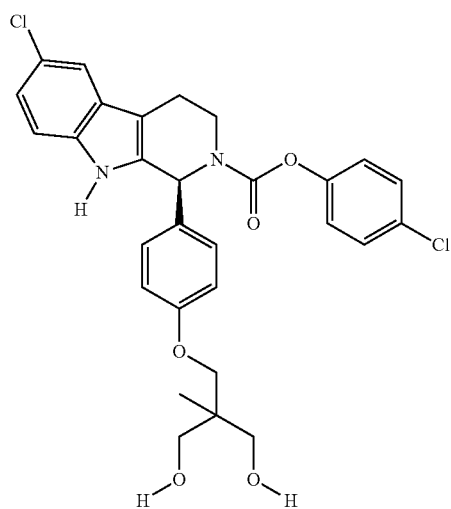 [SMILES: CC(CO)(CO)COc1ccc([C@H]2c3[nH]c4ccc(Cl)cc4c3CCN2C(=O)Oc2ccc(Cl)cc2)cc1]
1230

TABLE 1-continued
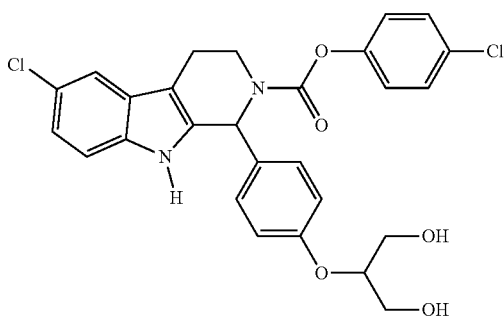 [SMILES: O=C(Oc1ccc(Cl)cc1)N1CCc2c([nH]c3ccc(Cl)cc23)C1c1ccc(OC(CO)CO)cc1]
1231
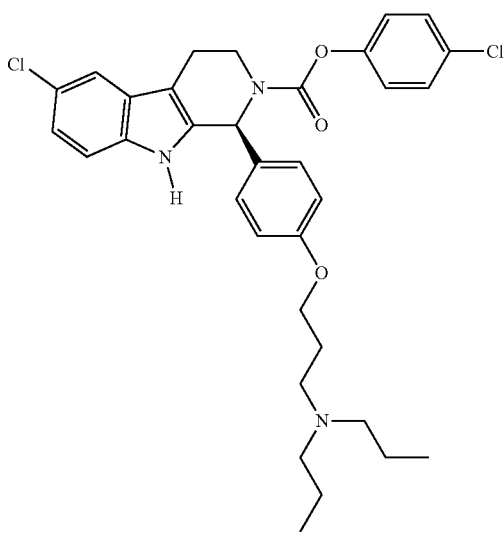 [SMILES: CCCN(CCC)CCCOc1ccc([C@H]2c3[nH]c4ccc(Cl)cc4c3CCN2C(=O)Oc2ccc(Cl)cc2)cc1]
1234
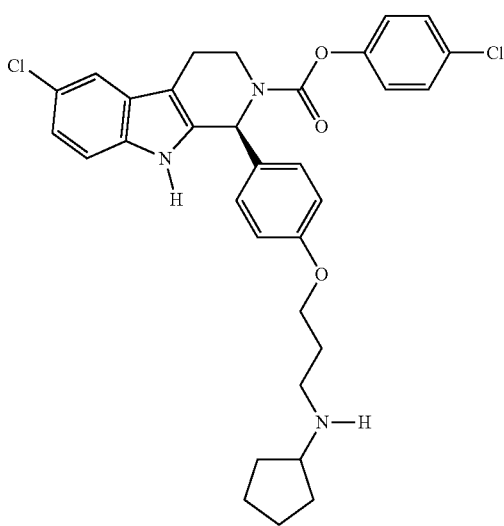 [SMILES: O=C(Oc1ccc(Cl)cc1)N1CCc2c([nH]c3ccc(Cl)cc23)[C@@H]1c1ccc(OCCCNC2CCCC2)cc1]
1235
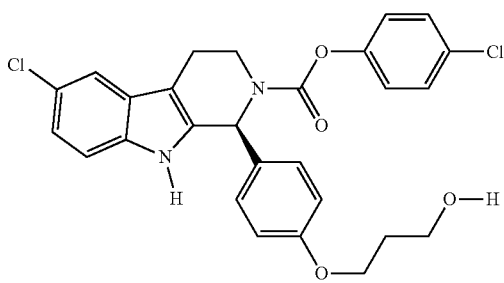 [SMILES: O=C(Oc1ccc(Cl)cc1)N1CCc2c([nH]c3ccc(Cl)cc23)[C@@H]1c1ccc(OCCCO)cc1]
1250

TABLE 1-continued
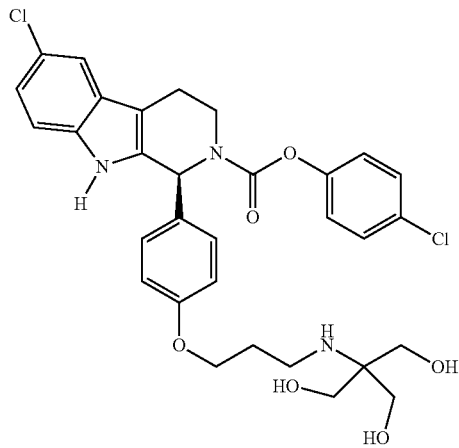 [SMILES: O=C(Oc1ccc(Cl)cc1)N1CCc2c([nH]c3ccc(Cl)cc23)[C@@H]1c1ccc(OCCCNC(CO)(CO)CO)cc1]
1255
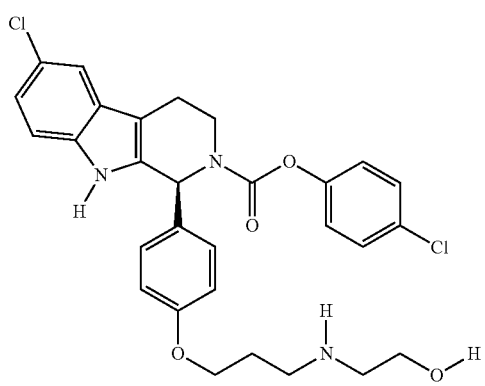 [SMILES: O=C(Oc1ccc(Cl)cc1)N1CCc2c([nH]c3ccc(Cl)cc23)[C@@H]1c1ccc(OCCCNCCO)cc1]
1257
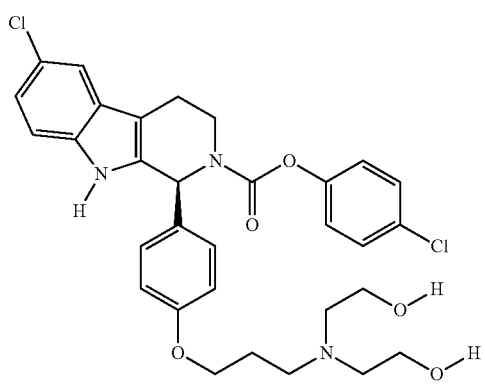 [SMILES: O=C(Oc1ccc(Cl)cc1)N1CCc2c([nH]c3ccc(Cl)cc23)[C@@H]1c1ccc(OCCCN(CCO)CCO)cc1]
1258
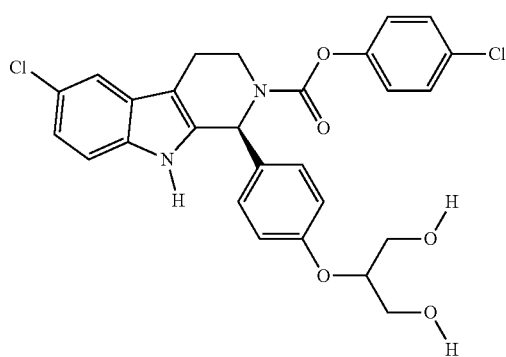 [SMILES: O=C(Oc1ccc(Cl)cc1)N1CCc2c([nH]c3ccc(Cl)cc23)[C@@H]1c1ccc(OC(CO)CO)cc1]
1259

TABLE 1-continued
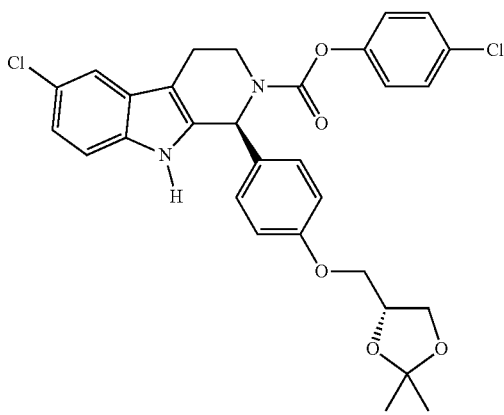 [SMILES: CC1(C)OC[C@@H](COc2ccc([C@H]3c4[nH]c5ccc(Cl)cc5c4CCN3C(=O)Oc3ccc(Cl)cc3)cc2)O1]
1260
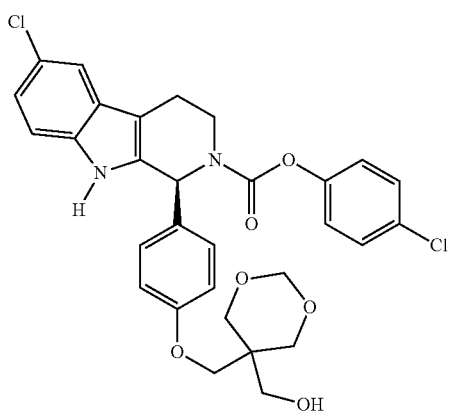 [SMILES: O=C(Oc1ccc(Cl)cc1)N1CCc2c([nH]c3ccc(Cl)cc23)[C@@H]1c1ccc(OCC2(CO)COCOC2)cc1]
1263
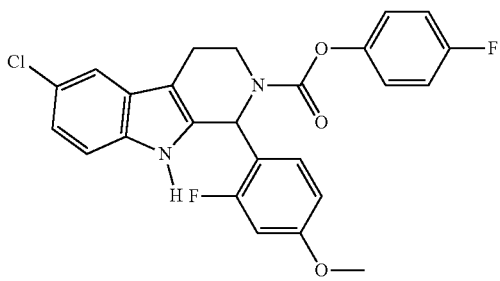 [SMILES: COc1ccc(C2c3[nH]c4ccc(Cl)cc4c3CCN2C(=O)Oc2ccc(F)cc2)c(F)c1]
1265
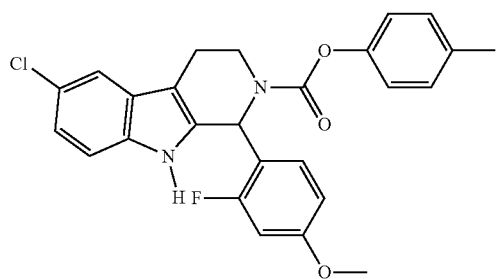 [SMILES: COc1ccc(C2c3[nH]c4ccc(Cl)cc4c3CCN2C(=O)Oc2ccc(C)cc2)c(F)c1]
1266

TABLE 1-continued
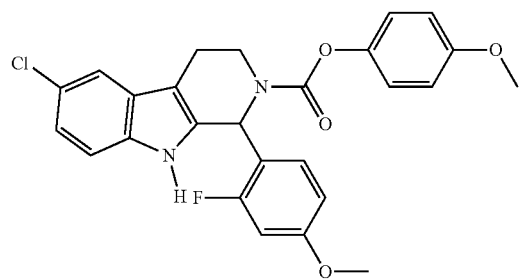 [SMILES: COc1ccc(OC(=O)N2CCc3c([nH]c4ccc(Cl)cc34)C2c2ccc(OC)cc2F)cc1]
1267
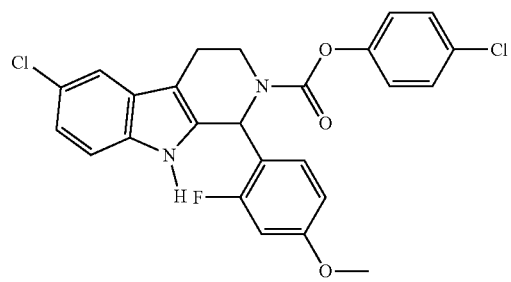 [SMILES: COc1ccc(C2c3[nH]c4ccc(Cl)cc4c3CCN2C(=O)Oc2ccc(Cl)cc2)c(F)c1]
1269
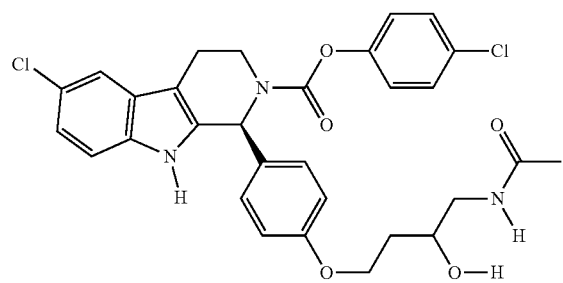 [SMILES: CC(=O)NCC(O)CCOc1ccc([C@H]2c3[nH]c4ccc(Cl)cc4c3CCN2C(=O)Oc2ccc(Cl)cc2)cc1]
1276
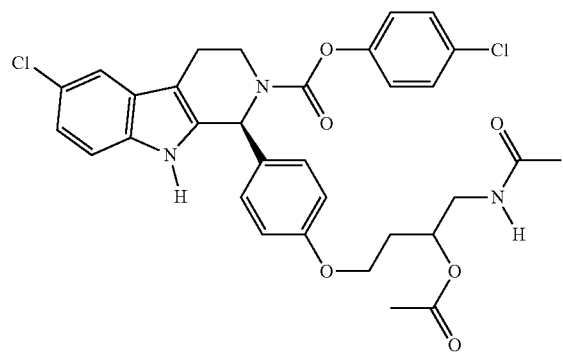 [SMILES: CC(=O)NCC(CCOc1ccc([C@H]2c3[nH]c4ccc(Cl)cc4c3CCN2C(=O)Oc2ccc(Cl)cc2)cc1)OC(C)=O]
1277
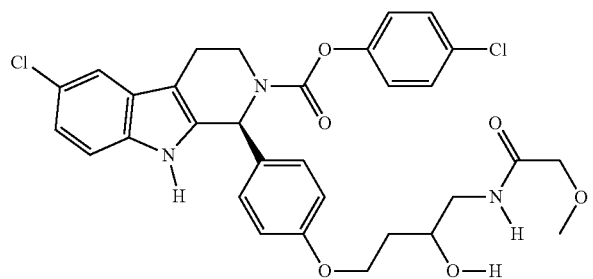 [SMILES: COCC(=O)NCC(O)CCOc1ccc([C@H]2c3[nH]c4ccc(Cl)cc4c3CCN2C(=O)Oc2ccc(Cl)cc2)cc1]
1278

TABLE 1-continued
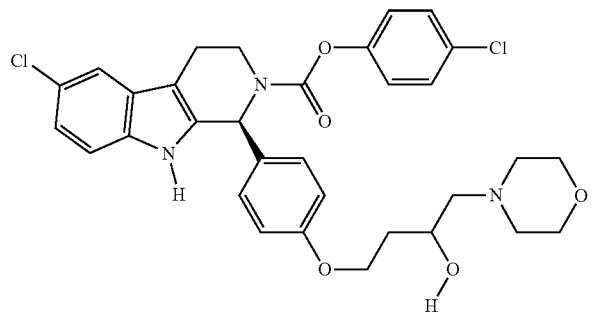
1279
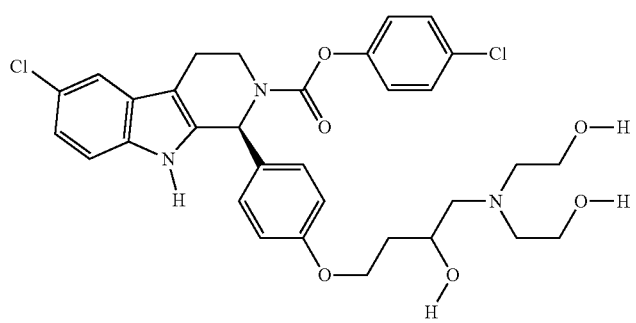
1280
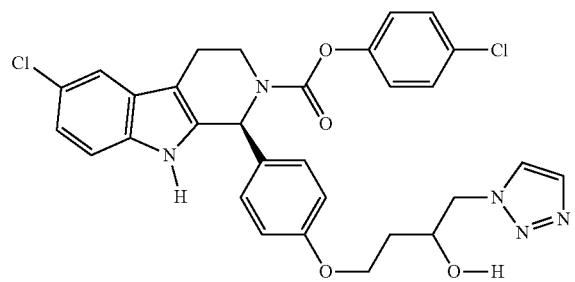 [SMILES: O=C(Oc1ccc(Cl)cc1)N1CCc2c([nH]c3ccc(Cl)cc23)[C@@H]1c1ccc(OCCC(O)Cn2ccnn2)cc1]
1281
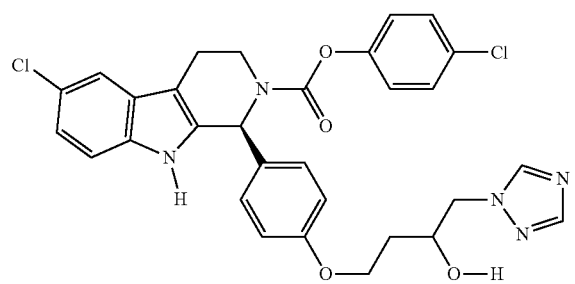 [SMILES: O=C(Oc1ccc(Cl)cc1)N1CCc2c([nH]c3ccc(Cl)cc23)[C@@H]1c1ccc(OCCC(O)Cn2cncn2)cc1]
1282
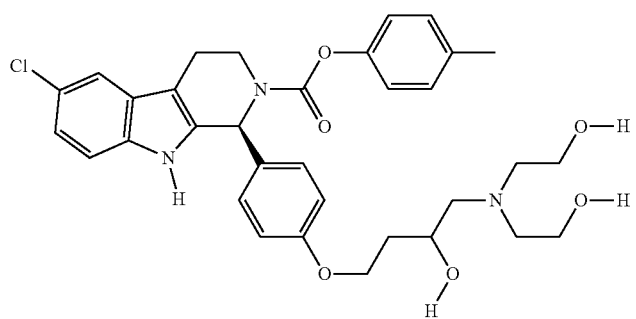
1288

TABLE 1-continued
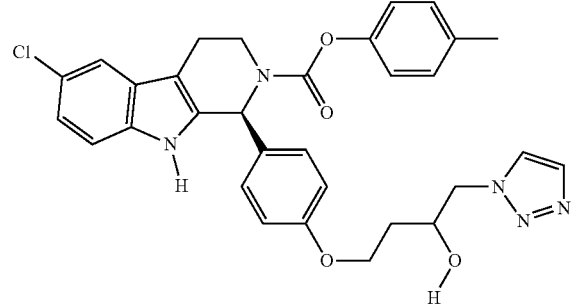 [SMILES: Cc1ccc(OC(=O)N2CCc3c([nH]c4ccc(Cl)cc34)[C@@H]2c2ccc(OCCC(O)Cn3ccnn3)cc2)cc1]
1289
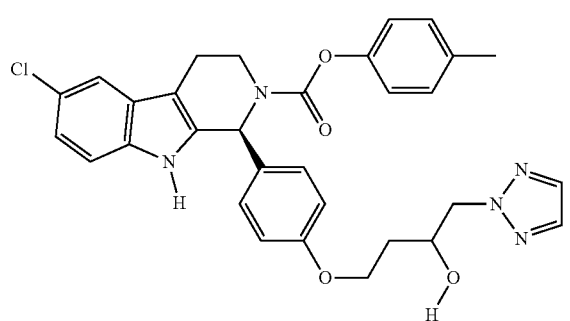 [SMILES: Cc1ccc(OC(=O)N2CCc3c([nH]c4ccc(Cl)cc34)[C@@H]2c2ccc(OCCC(O)Cn3nccn3)cc2)cc1]
1290
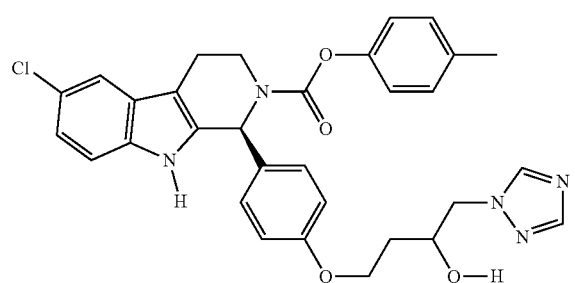 [SMILES: Cc1ccc(OC(=O)N2CCc3c([nH]c4ccc(Cl)cc34)[C@@H]2c2ccc(OCCC(O)Cn3cncn3)cc2)cc1]
1291
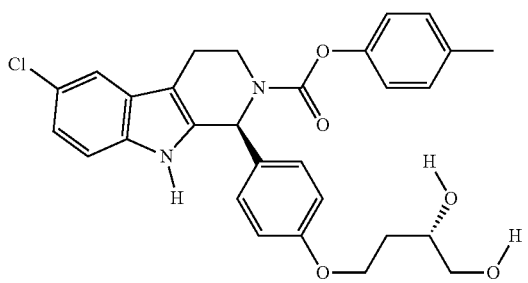 [SMILES: Cc1ccc(OC(=O)N2CCc3c([nH]c4ccc(Cl)cc34)[C@@H]2c2ccc(OCC[C@H](O)CO)cc2)cc1]
1292
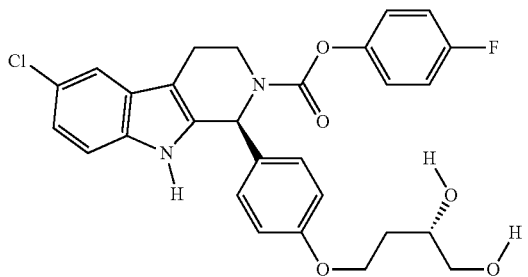 [SMILES: O=C(Oc1ccc(F)cc1)N1CCc2c([nH]c3ccc(Cl)cc23)[C@@H]1c1ccc(OCC[C@H](O)CO)cc1]
1293

TABLE 1-continued
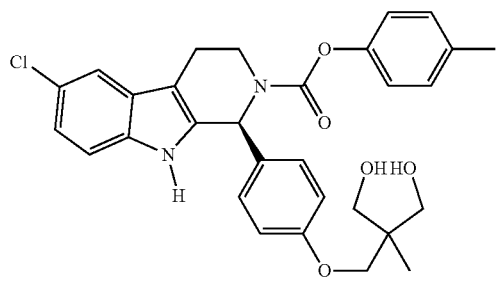 [SMILES: Cc1ccc(OC(=O)N2CCc3c([nH]c4ccc(Cl)cc34)[C@@H]2c2ccc(OCC(C)(CO)CO)cc2)cc1]
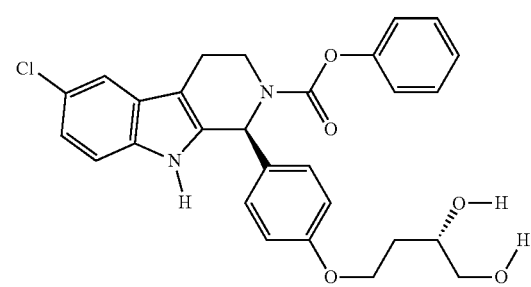 [SMILES: O=C(Oc1ccccc1)N1CCc2c([nH]c3ccc(Cl)cc23)[C@@H]1c1ccc(OCC[C@H](O)CO)cc1]
1299
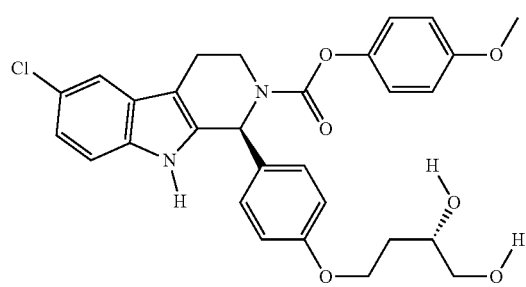 [SMILES: COc1ccc(OC(=O)N2CCc3c([nH]c4ccc(Cl)cc34)[C@@H]2c2ccc(OCC[C@H](O)CO)cc2)cc1]
1300
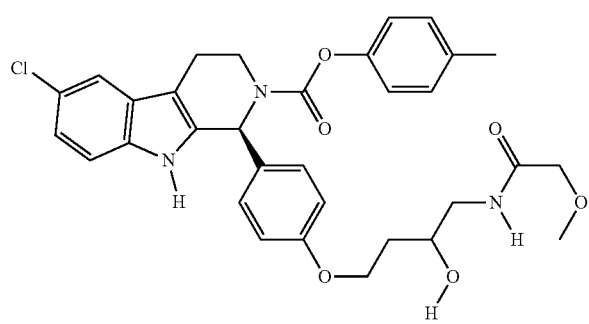 [SMILES: COCC(=O)NCC(O)CCOc1ccc([C@H]2c3[nH]c4ccc(Cl)cc4c3CCN2C(=O)Oc2ccc(C)cc2)cc1]
1301
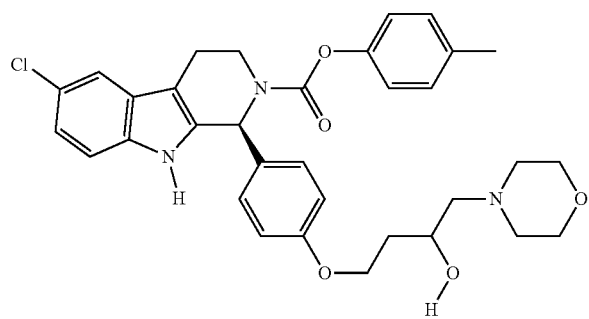 [SMILES: Cc1ccc(OC(=O)N2CCc3c([nH]c4ccc(Cl)cc34)[C@@H]2c2ccc(OCCC(O)CN3CCOCC3)cc2)cc1]
1302

TABLE 1-continued
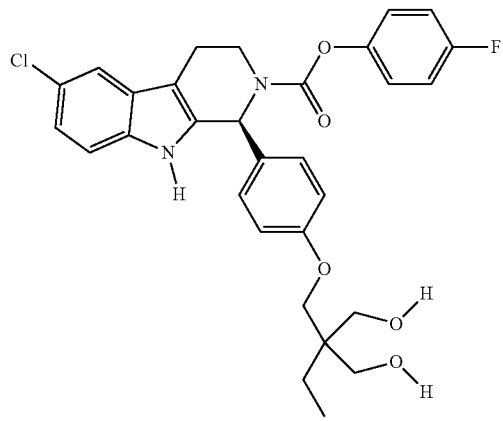 [SMILES: CCC(CO)(CO)COc1ccc([C@H]2c3[nH]c4ccc(Cl)cc4c3CCN2C(=O)Oc2ccc(F)cc2)cc1]
1328
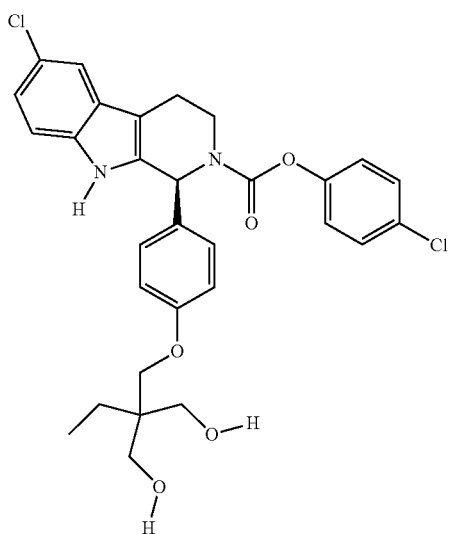 [SMILES: CCC(CO)(CO)COc1ccc([C@H]2c3[nH]c4ccc(Cl)cc4c3CCN2C(=O)Oc2ccc(Cl)cc2)cc1]
1329
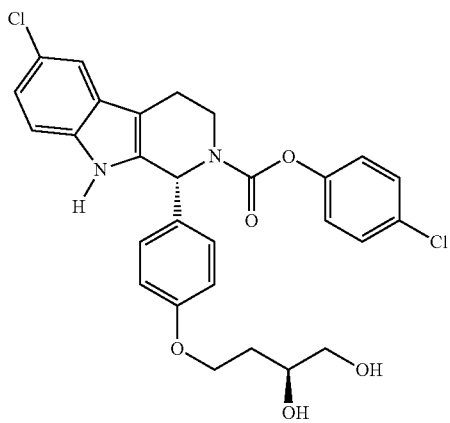 [SMILES: O=C(Oc1ccc(Cl)cc1)N1CCc2c([nH]c3ccc(Cl)cc23)[C@H]1c1ccc(OCC[C@H](O)CO)cc1]
1330

TABLE 1-continued
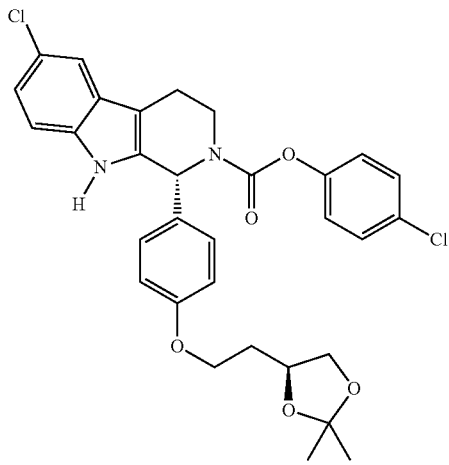 [SMILES: CC1(C)OC[C@H](CCOc2ccc([C@@H]3c4[nH]c5ccc(Cl)cc5c4CCN3C(=O)Oc3ccc(Cl)cc3)cc2)O1]
1331
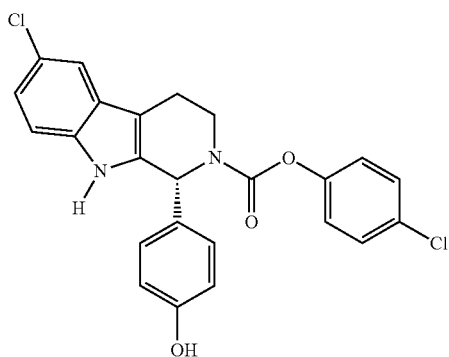 [SMILES: O=C(Oc1ccc(Cl)cc1)N1CCc2c([nH]c3ccc(Cl)cc23)[C@H]1c1ccc(O)cc1]
1332
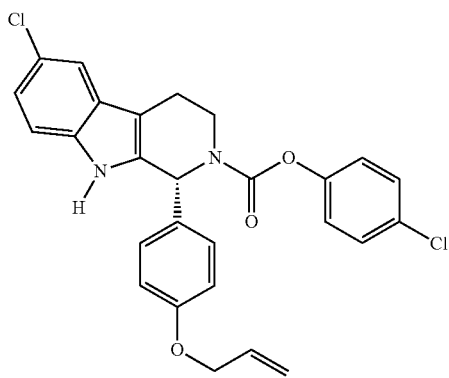 [SMILES: C=CCOc1ccc([C@@H]2c3[nH]c4ccc(Cl)cc4c3CCN2C(=O)Oc2ccc(Cl)cc2)cc1]
1333

TABLE 1-continued
| | |
|---|---|
| 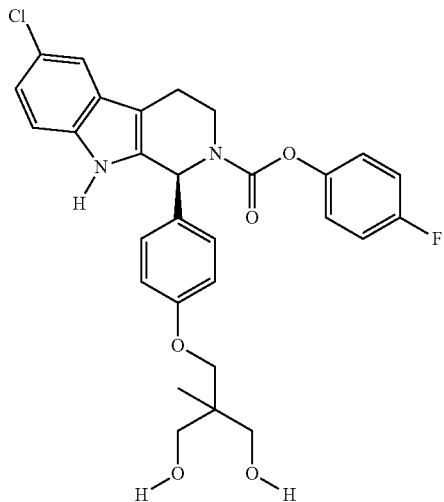 [SMILES: CC(CO)(CO)COc1ccc([C@H]2c3[nH]c4ccc(Cl)cc4c3CCN2C(=O)Oc2ccc(F)cc2)cc1] | 1335 |
| 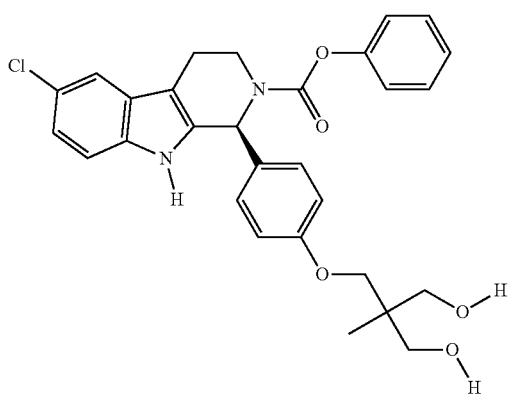 [SMILES: CC(CO)(CO)COc1ccc([C@H]2c3[nH]c4ccc(Cl)cc4c3CCN2C(=O)Oc2ccccc2)cc1] | 1336 |
| 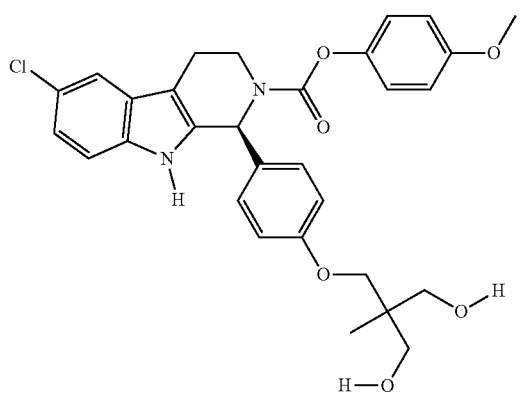 [SMILES: COc1ccc(OC(=O)N2CCc3c([nH]c4ccc(Cl)cc34)[C@@H]2c2ccc(OCC(C)(CO)CO)cc2)cc1] | 1337 |

TABLE 1-continued
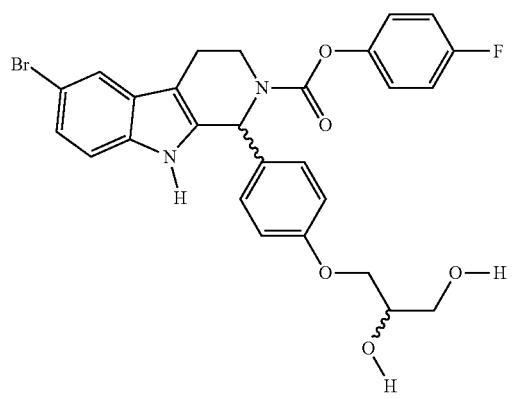 [SMILES: O=C(Oc1ccc(F)cc1)N1CCc2c([nH]c3ccc(Br)cc23)C1c1ccc(OCC(O)CO)cc1]
1343
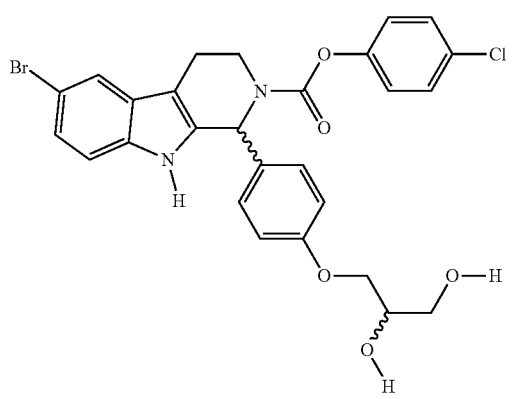 [SMILES: O=C(Oc1ccc(Cl)cc1)N1CCc2c([nH]c3ccc(Br)cc23)C1c1ccc(OCC(O)CO)cc1]
1344
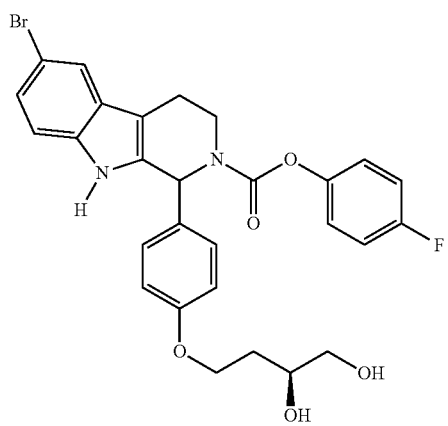
1348
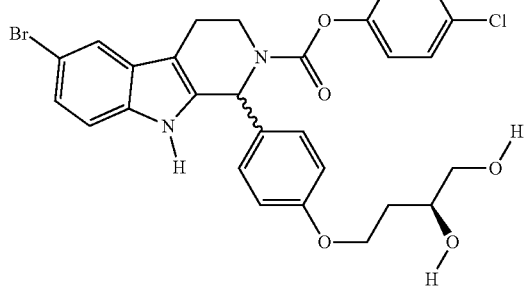
1349

TABLE 1-continued
| | |
|---|---|
| 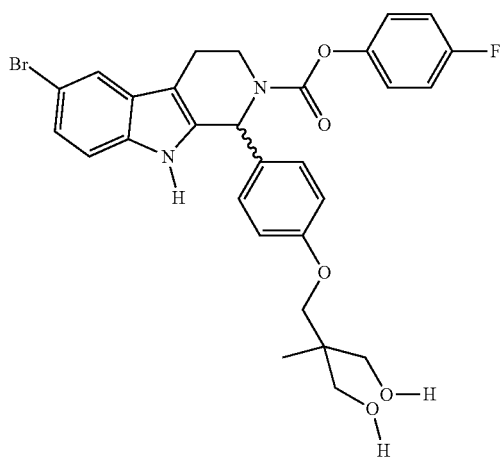 [SMILES: CC(CO)(CO)COc1ccc(C2c3[nH]c4ccc(Br)cc4c3CCN2C(=O)Oc2ccc(F)cc2)cc1] | 1352 |
| 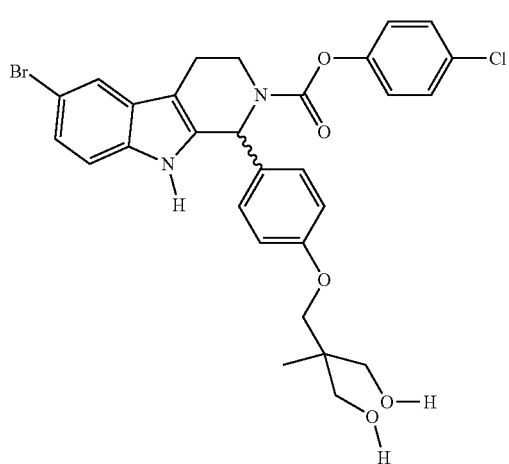 [SMILES: CC(CO)(CO)COc1ccc(C2c3[nH]c4ccc(Br)cc4c3CCN2C(=O)Oc2ccc(Cl)cc2)cc1] | 1353 |
| 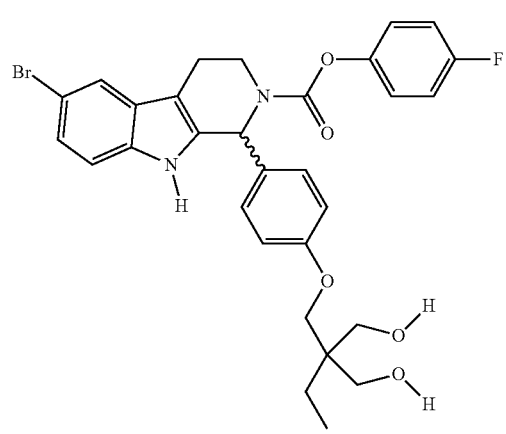 [SMILES: CCC(CO)(CO)COc1ccc(C2c3[nH]c4ccc(Br)cc4c3CCN2C(=O)Oc2ccc(F)cc2)cc1] | 1357 |

TABLE 1-continued
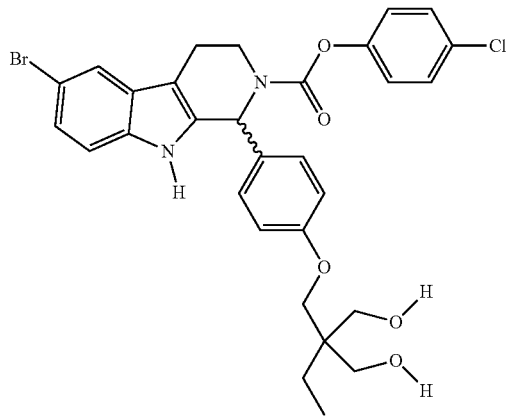 [SMILES: CCC(CO)(CO)COc1ccc(C2c3[nH]c4ccc(Br)cc4c3CCN2C(=O)Oc2ccc(Cl)cc2)cc1]
1358
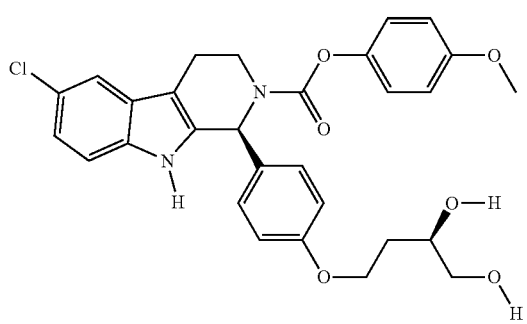 [SMILES: COc1ccc(OC(=O)N2CCc3c([nH]c4ccc(Cl)cc34)[C@@H]2c2ccc(OCC[C@@H](O)CO)cc2)cc1]
1361
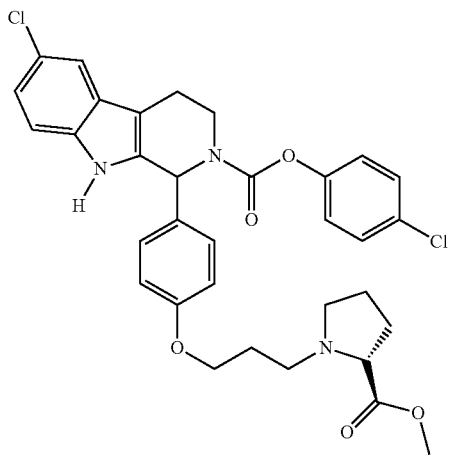
1362
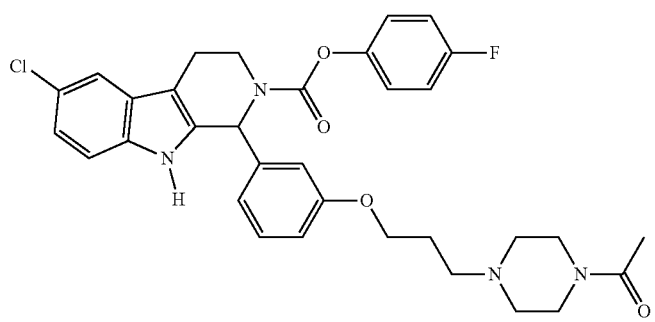 [SMILES: CC(=O)N1CCN(CCCOc2cccc(C3c4[nH]c5ccc(Cl)cc5c4CCN3C(=O)Oc3ccc(F)cc3)c2)CC1]
1364

TABLE 1-continued
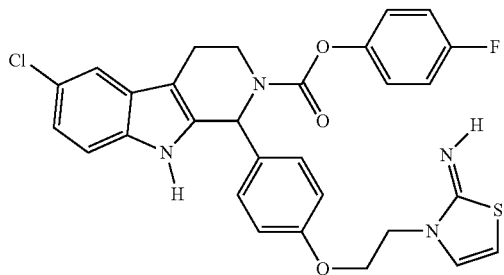 [SMILES: [H]/N=c1\sccn1CCOc1ccc(C2c3[nH]c4ccc(Cl)cc4c3CCN2C(=O)Oc2ccc(F)cc2)cc1]
1391
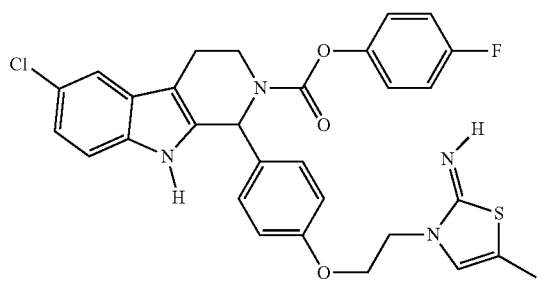 [SMILES: [H]/N=c1\sc(C)cn1CCOc1ccc(C2c3[nH]c4ccc(Cl)cc4c3CCN2C(=O)Oc2ccc(F)cc2)cc1]
1392
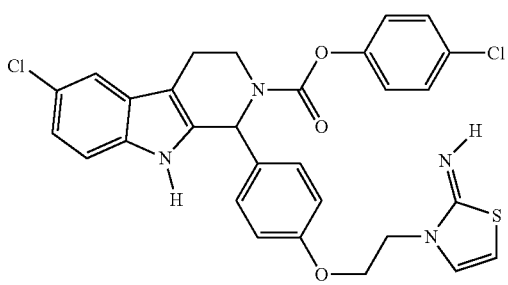 [SMILES: [H]/N=c1\sccn1CCOc1ccc(C2c3[nH]c4ccc(Cl)cc4c3CCN2C(=O)Oc2ccc(Cl)cc2)cc1]
1393
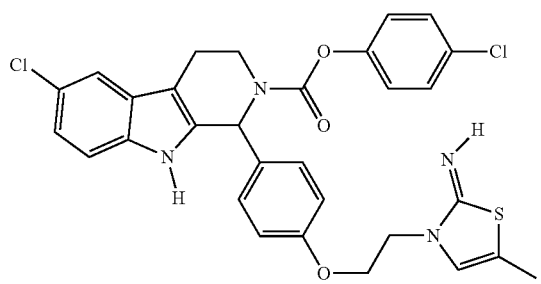 [SMILES: [H]/N=c1\sc(C)cn1CCOc1ccc(C2c3[nH]c4ccc(Cl)cc4c3CCN2C(=O)Oc2ccc(Cl)cc2)cc1]
1394
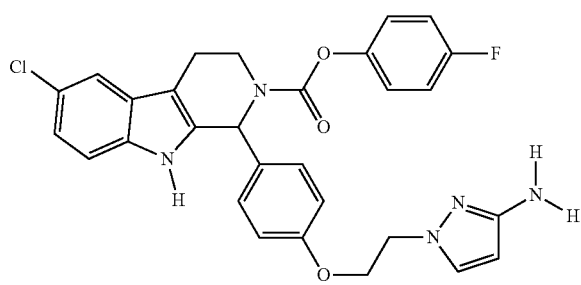 [SMILES: Nc1ccn(CCOc2ccc(C3c4[nH]c5ccc(Cl)cc5c4CCN3C(=O)Oc3ccc(F)cc3)cc2)n1]
1413

TABLE 1-continued
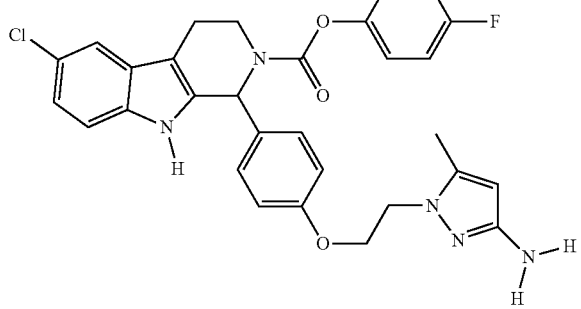
1414
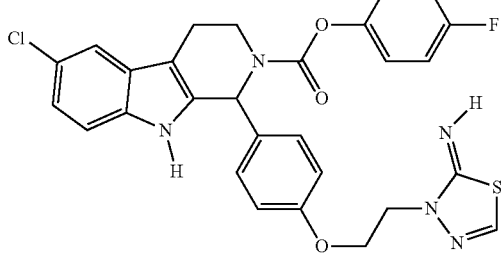
1415
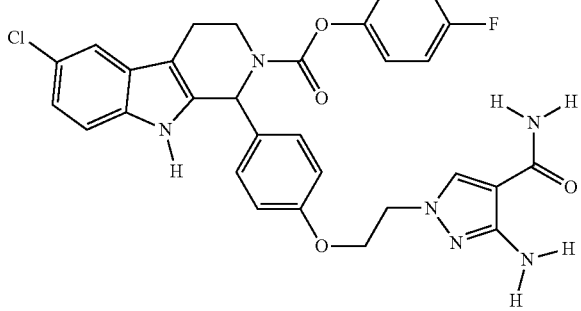
1416
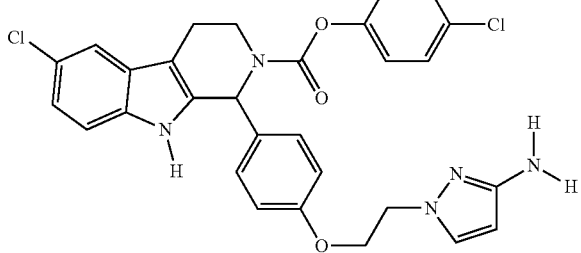
1417
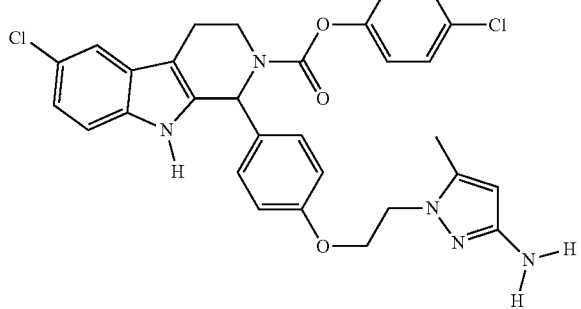
1418

TABLE 1-continued
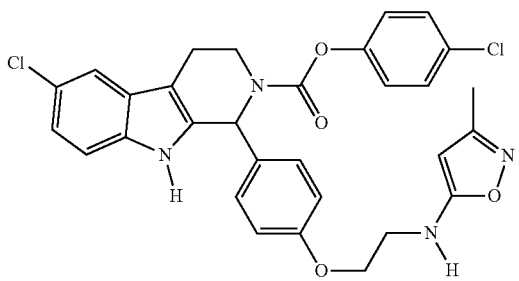 [SMILES: Cc1cc(NCCOc2ccc(C3c4[nH]c5ccc(Cl)cc5c4CCN3C(=O)Oc3ccc(Cl)cc3)cc2)on1]
1419
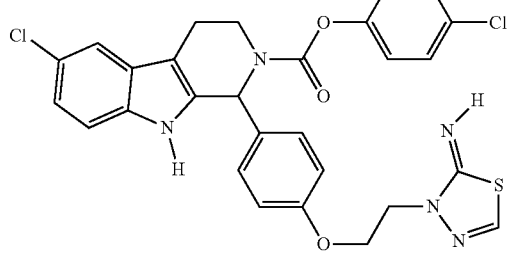
1420
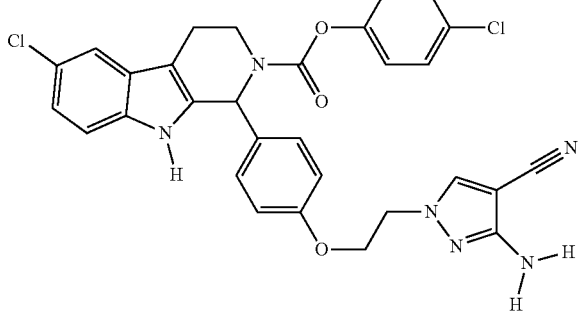
1421
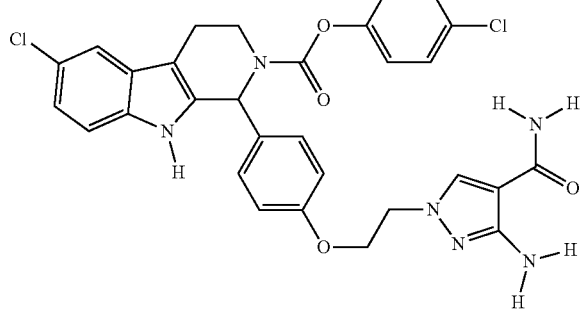
1422
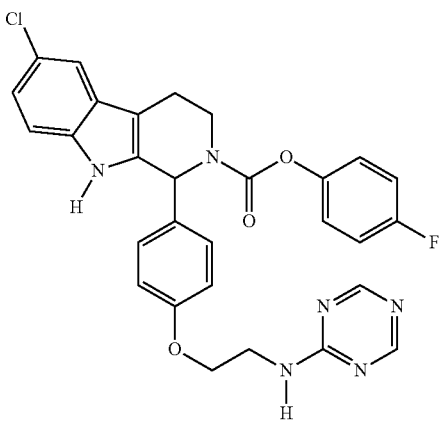 [SMILES: O=C(Oc1ccc(F)cc1)N1CCc2c([nH]c3ccc(Cl)cc23)C1c1ccc(OCCNc2ncncn2)cc1]
1440

TABLE 1-continued
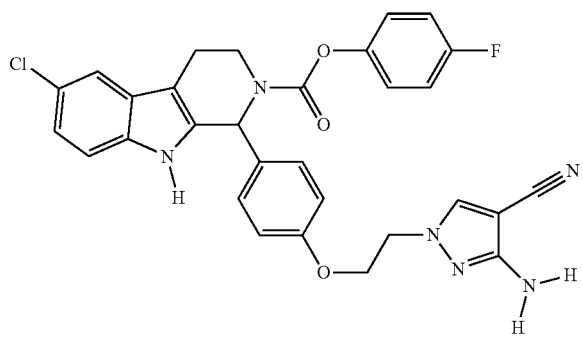 [SMILES: N#Cc1cn(CCOc2ccc(C3c4[nH]c5ccc(Cl)cc5c4CCN3C(=O)Oc3ccc(F)cc3)cc2)nc1N]
1441
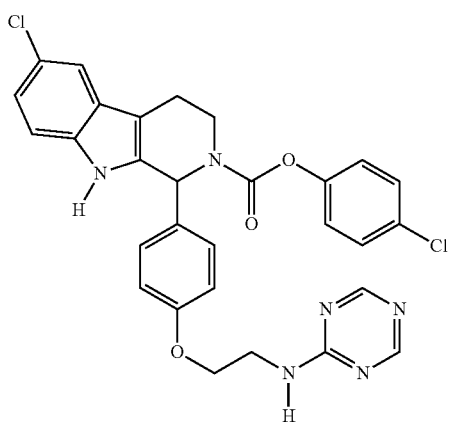 [SMILES: O=C(Oc1ccc(Cl)cc1)N1CCc2c([nH]c3ccc(Cl)cc23)C1c1ccc(OCCNc2ncncn2)cc1]
1442
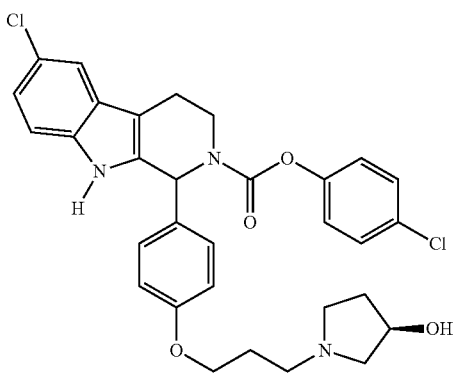 [SMILES: O=C(Oc1ccc(Cl)cc1)N1CCc2c([nH]c3ccc(Cl)cc23)C1c1ccc(OCCCN2CC[C@@H](O)C2)cc1]
1476
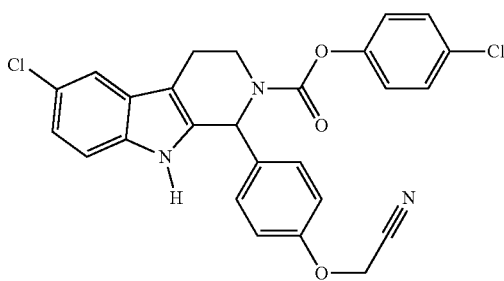
1520

TABLE 1-continued
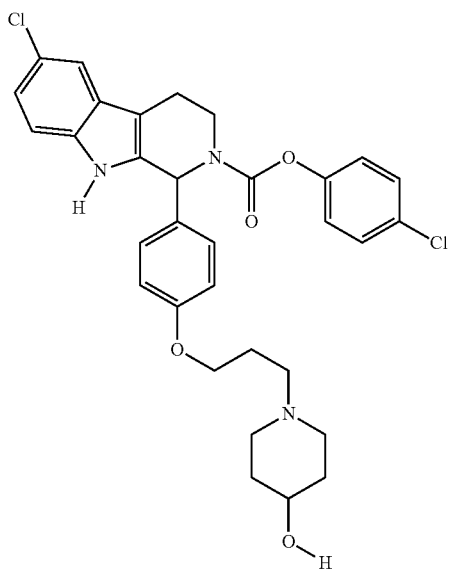 [SMILES: O=C(Oc1ccc(Cl)cc1)N1CCc2c([nH]c3ccc(Cl)cc23)C1c1ccc(OCCCN2CCC(O)CC2)cc1]
1537
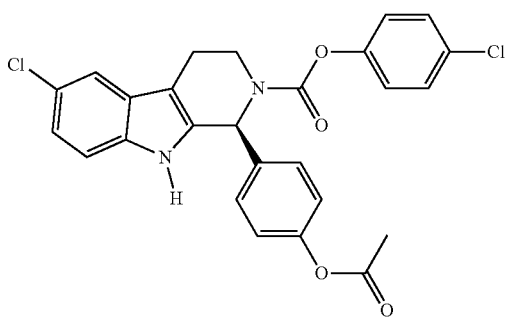 [SMILES: CC(=O)Oc1ccc([C@H]2c3[nH]c4ccc(Cl)cc4c3CCN2C(=O)Oc2ccc(Cl)cc2)cc1]
1538
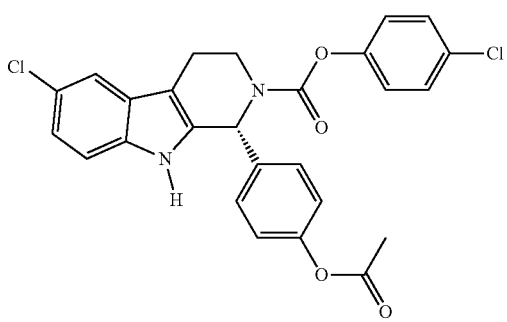 [SMILES: CC(=O)Oc1ccc([C@@H]2c3[nH]c4ccc(Cl)cc4c3CCN2C(=O)Oc2ccc(Cl)cc2)cc1]
1539
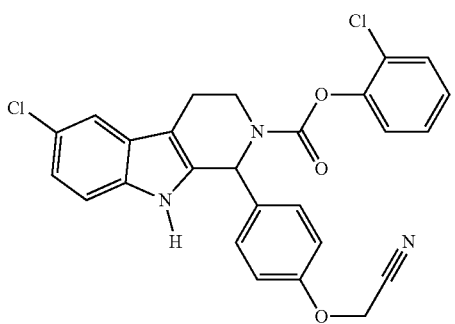 [SMILES: N#CCOc1ccc(C2c3[nH]c4ccc(Cl)cc4c3CCN2C(=O)Oc2ccccc2Cl)cc1]
1546

TABLE 1-continued
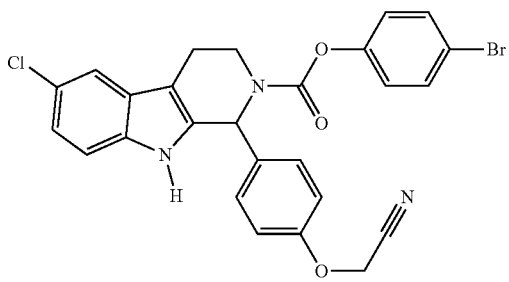 [SMILES: N#CCOc1ccc(C2c3[nH]c4ccc(Cl)cc4c3CCN2C(=O)Oc2ccc(Br)cc2)cc1]
1547
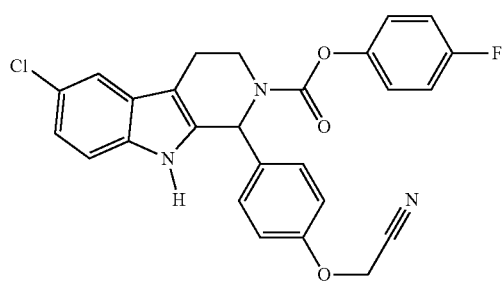 [SMILES: N#CCOc1ccc(C2c3[nH]c4ccc(Cl)cc4c3CCN2C(=O)Oc2ccc(F)cc2)cc1]
1548
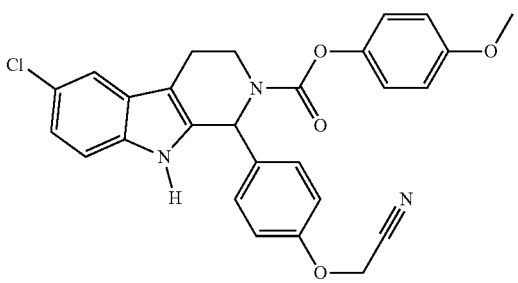 [SMILES: COc1ccc(OC(=O)N2CCc3c([nH]c4ccc(Cl)cc34)C2c2ccc(OCC#N)cc2)cc1]
1549
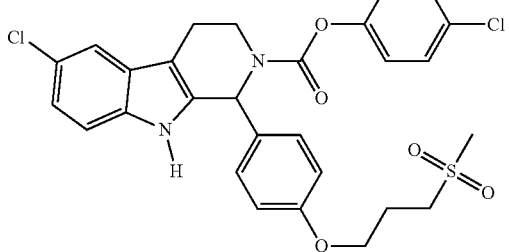
1551
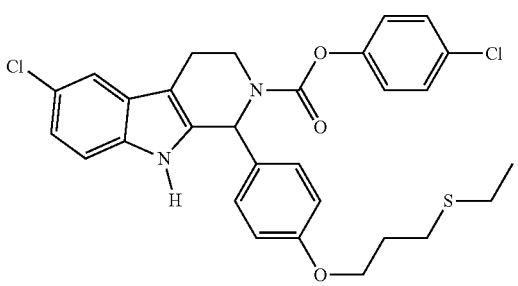 [SMILES: CCSCCCOc1ccc(C2c3[nH]c4ccc(Cl)cc4c3CCN2C(=O)Oc2ccc(Cl)cc2)cc1]
1552

TABLE 1-continued
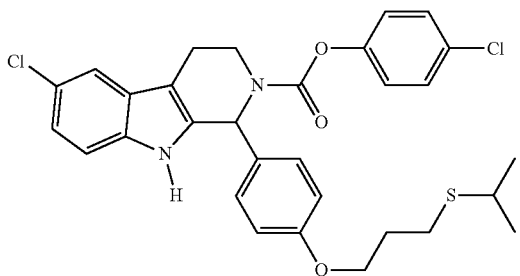 [SMILES: CC(C)SCCCOc1ccc(C2c3[nH]c4ccc(Cl)cc4c3CCN2C(=O)Oc2ccc(Cl)cc2)cc1]
1553
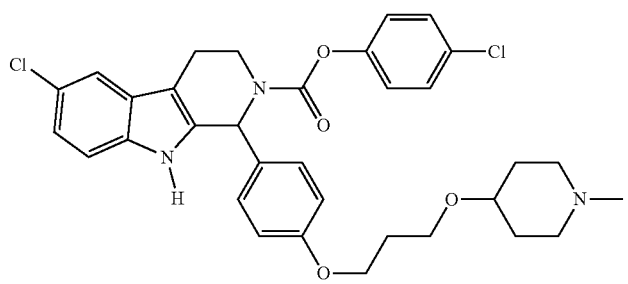 [SMILES: CN1CCC(OCCCOc2ccc(C3c4[nH]c5ccc(Cl)cc5c4CCN3C(=O)Oc3ccc(Cl)cc3)cc2)CC1]
1554
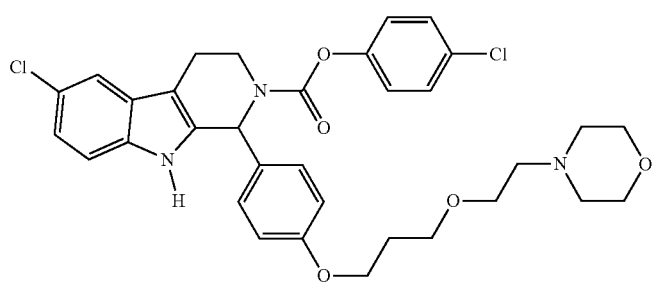 [SMILES: O=C(Oc1ccc(Cl)cc1)N1CCc2c([nH]c3ccc(Cl)cc23)C1c1ccc(OCCCOCCN2CCOCC2)cc1]
1555
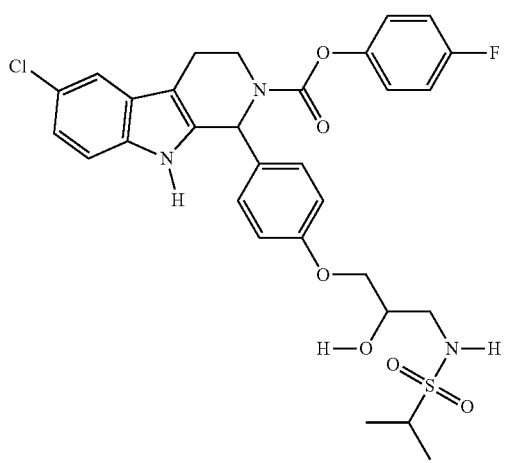 [SMILES: CC(C)S(=O)(=O)NCC(O)COc1ccc(C2c3[nH]c4ccc(Cl)cc4c3CCN2C(=O)Oc2ccc(F)cc2)cc1]
1557

TABLE 1-continued
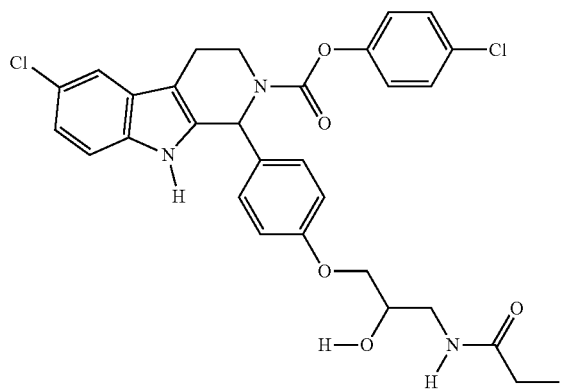 [SMILES: CCC(=O)NCC(O)COc1ccc(C2c3[nH]c4ccc(Cl)cc4c3CCN2C(=O)Oc2ccc(Cl)cc2)cc1]
1558
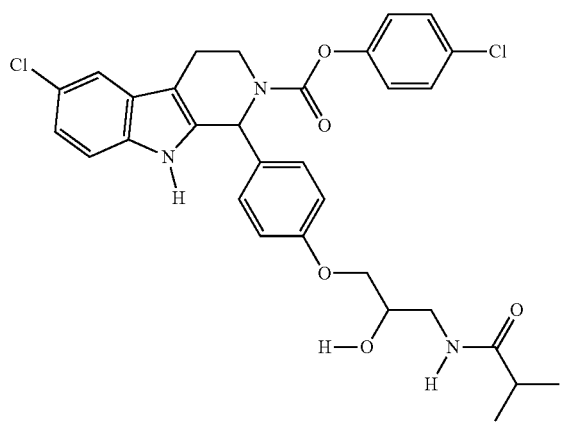 [SMILES: CC(C)C(=O)NCC(O)COc1ccc(C2c3[nH]c4ccc(Cl)cc4c3CCN2C(=O)Oc2ccc(Cl)cc2)cc1]
1559
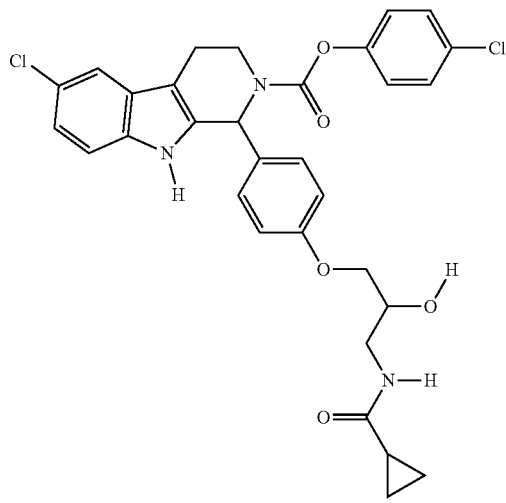 [SMILES: O=C(NCC(O)COc1ccc(C2c3[nH]c4ccc(Cl)cc4c3CCN2C(=O)Oc2ccc(Cl)cc2)cc1)C1CC1]
1560

TABLE 1-continued
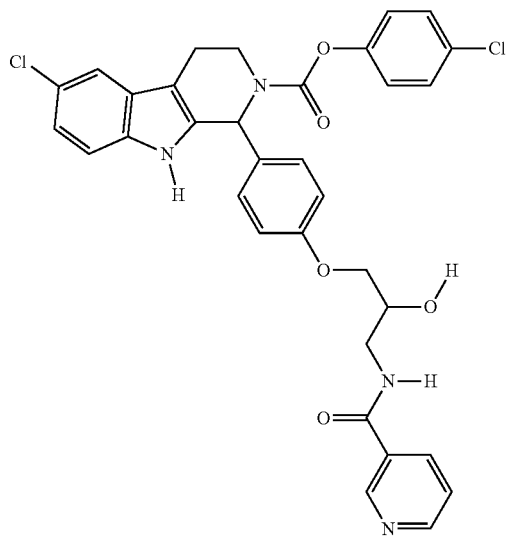 [SMILES: O=C(NCC(O)COc1ccc(C2c3[nH]c4ccc(Cl)cc4c3CCN2C(=O)Oc2ccc(Cl)cc2)cc1)c1cccnc1]
1561
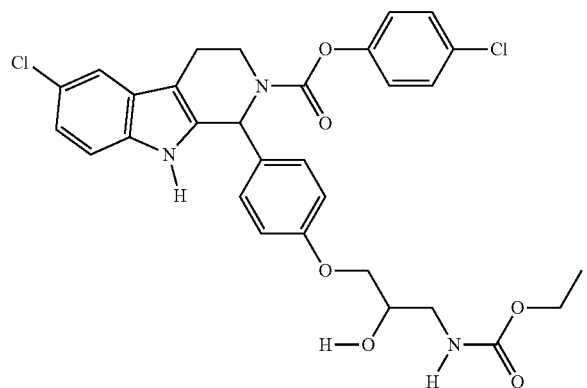 [SMILES: CCOC(=O)NCC(O)COc1ccc(C2c3[nH]c4ccc(Cl)cc4c3CCN2C(=O)Oc2ccc(Cl)cc2)cc1]
1562
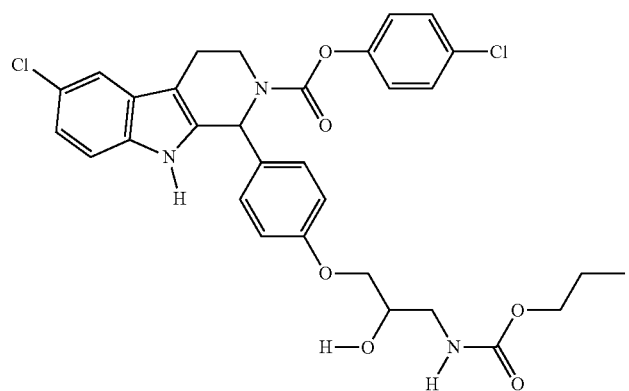 [SMILES: CCCOC(=O)NCC(O)COc1ccc(C2c3[nH]c4ccc(Cl)cc4c3CCN2C(=O)Oc2ccc(Cl)cc2)cc1]
1563

TABLE 1-continued
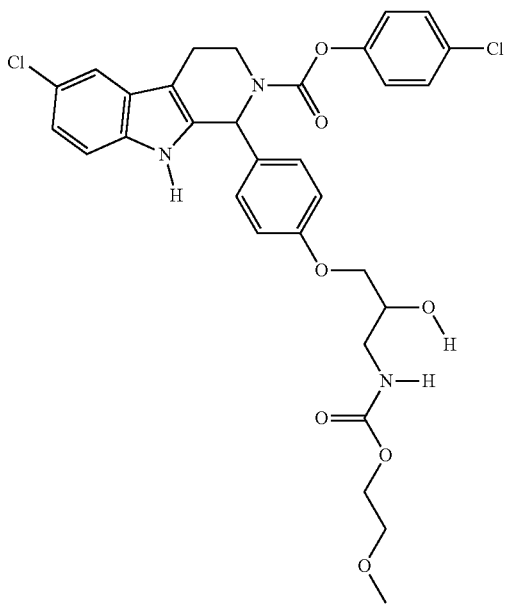 [SMILES: COCCOC(=O)NCC(O)COc1ccc(C2c3[nH]c4ccc(Cl)cc4c3CCN2C(=O)Oc2ccc(Cl)cc2)cc1]
1564
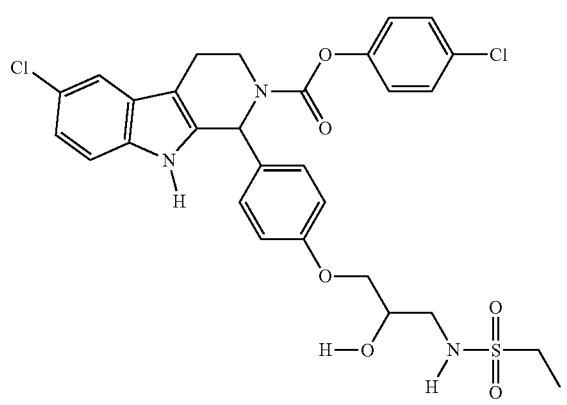 [SMILES: CCS(=O)(=O)NCC(O)COc1ccc(C2c3[nH]c4ccc(Cl)cc4c3CCN2C(=O)Oc2ccc(Cl)cc2)cc1]
1565
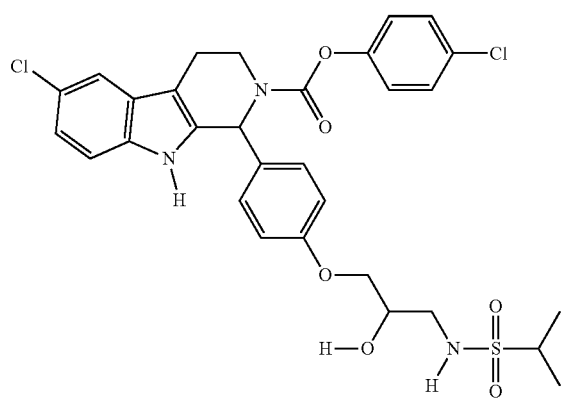 [SMILES: CC(C)S(=O)(=O)NCC(O)COc1ccc(C2c3[nH]c4ccc(Cl)cc4c3CCN2C(=O)Oc2ccc(Cl)cc2)cc1]
1566

TABLE 1-continued
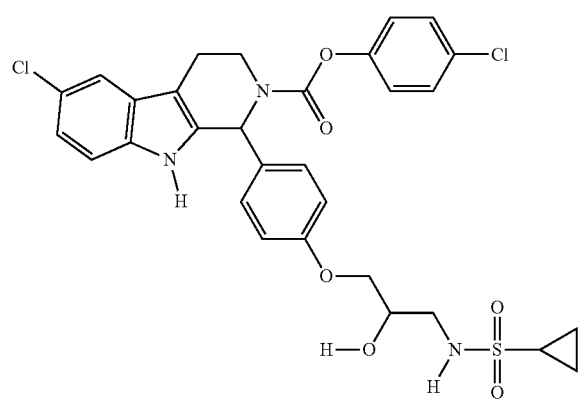 [SMILES: O=C(Oc1ccc(Cl)cc1)N1CCc2c([nH]c3ccc(Cl)cc23)C1c1ccc(OCC(O)CNS(=O)(=O)C2CC2)cc1]
1567
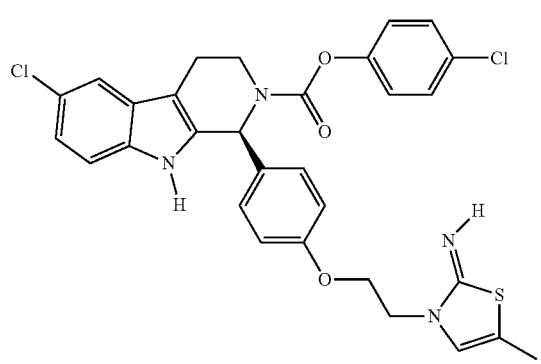 [SMILES: [H]/N=c1\sc(C)cn1CCOc1ccc([C@H]2c3[nH]c4ccc(Cl)cc4c3CCN2C(=O)Oc2ccc(Cl)cc2)cc1]
1568
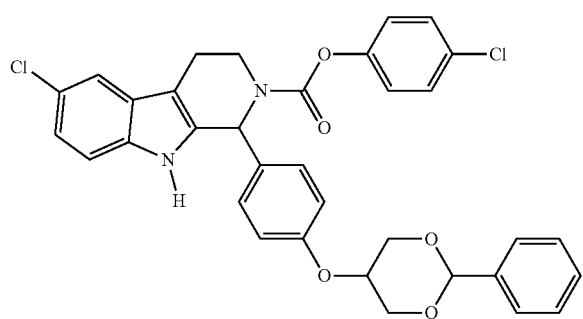 [SMILES: O=C(Oc1ccc(Cl)cc1)N1CCc2c([nH]c3ccc(Cl)cc23)C1c1ccc(OC2COC(c3ccccc3)OC2)cc1]
1569
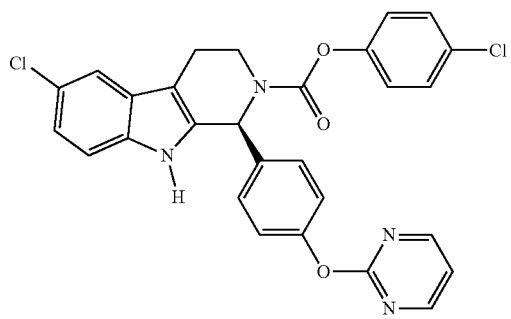 [SMILES: O=C(Oc1ccc(Cl)cc1)N1CCc2c([nH]c3ccc(Cl)cc23)[C@@H]1c1ccc(Oc2ncccn2)cc1]
1570

TABLE 1-continued
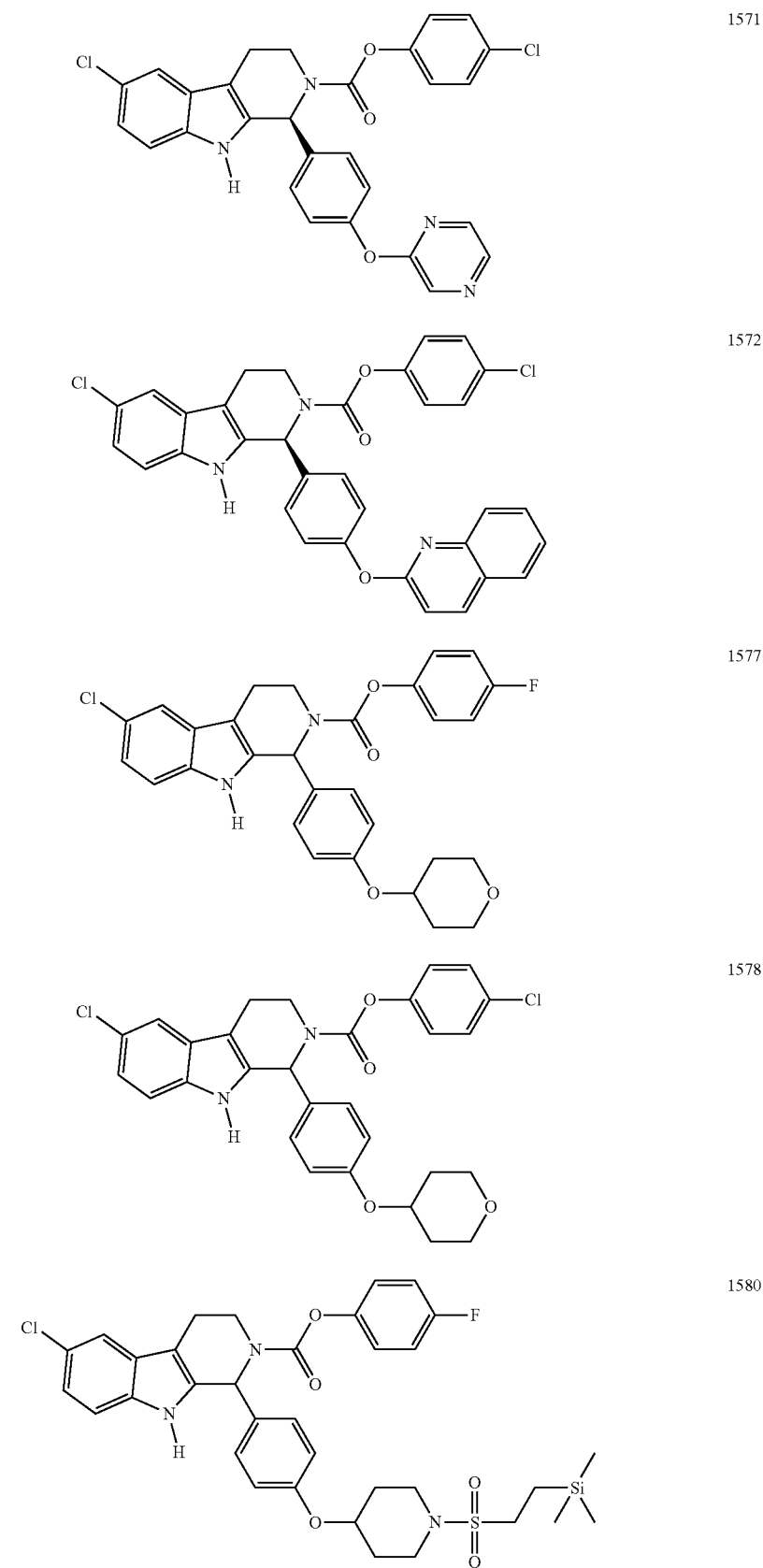

TABLE 1-continued
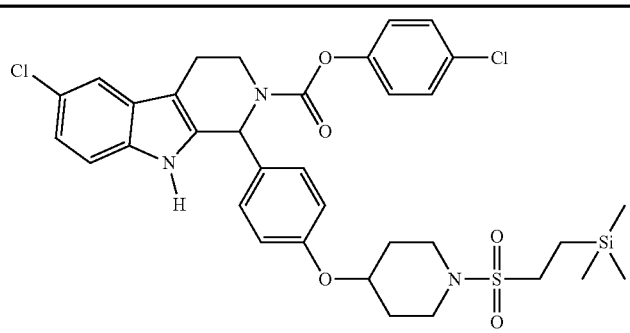
1581
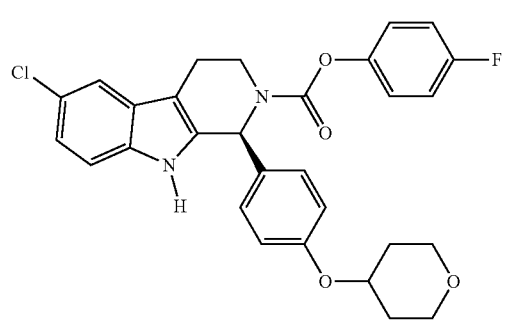 [SMILES: O=C(Oc1ccc(F)cc1)N1CCc2c([nH]c3ccc(Cl)cc23)[C@@H]1c1ccc(OC2CCOCC2)cc1]
1604
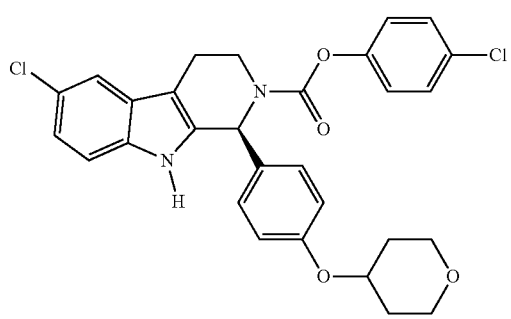 [SMILES: O=C(Oc1ccc(Cl)cc1)N1CCc2c([nH]c3ccc(Cl)cc23)[C@@H]1c1ccc(OC2CCOCC2)cc1]
1605
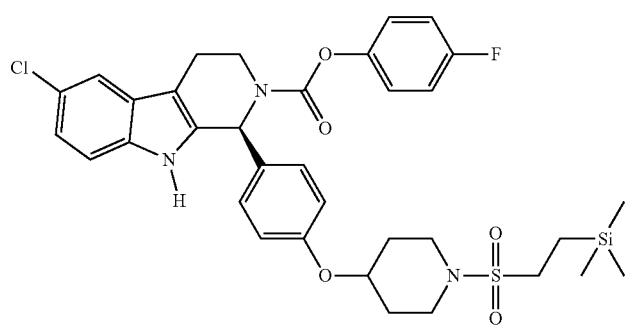 [SMILES: C[Si](C)(C)CCS(=O)(=O)N1CCC(Oc2ccc([C@H]3c4[nH]c5ccc(Cl)cc5c4CCN3C(=O)Oc3ccc(F)cc3)cc2)CC1]
1607

TABLE 1-continued
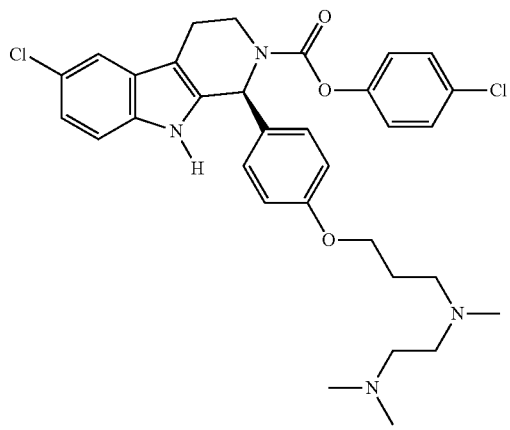 [SMILES: CN(C)CCN(C)CCCOc1ccc([C@H]2c3[nH]c4ccc(Cl)cc4c3CCN2C(=O)Oc2ccc(Cl)cc2)cc1]
1611
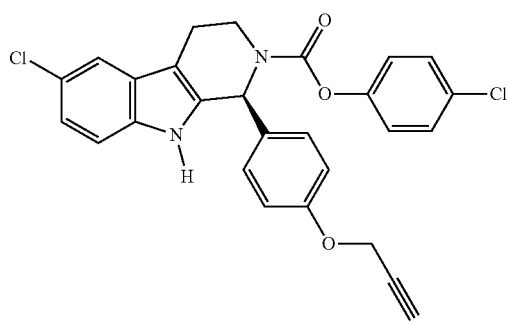 [SMILES: C#CCOc1ccc([C@H]2c3[nH]c4ccc(Cl)cc4c3CCN2C(=O)Oc2ccc(Cl)cc2)cc1]
1612
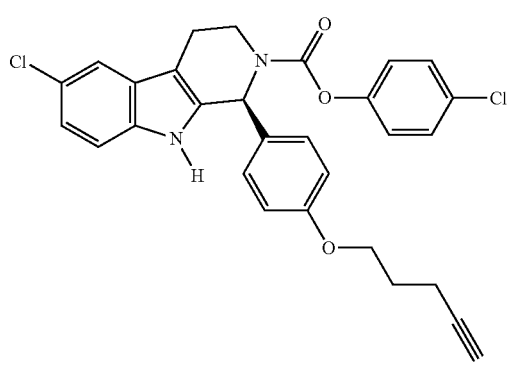 [SMILES: C#CCCCOc1ccc([C@H]2c3[nH]c4ccc(Cl)cc4c3CCN2C(=O)Oc2ccc(Cl)cc2)cc1]
1613
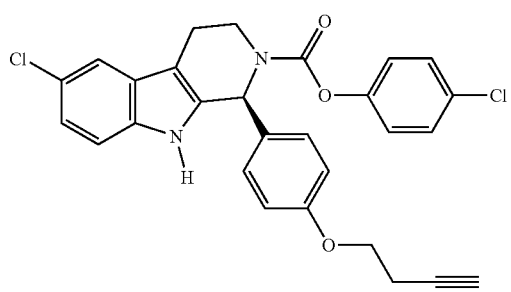 [SMILES: C#CCCOc1ccc([C@H]2c3[nH]c4ccc(Cl)cc4c3CCN2C(=O)Oc2ccc(Cl)cc2)cc1]
1614

TABLE 1-continued
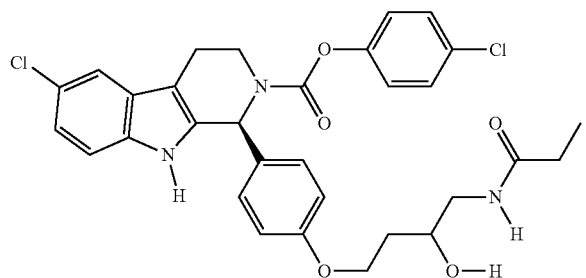
1625
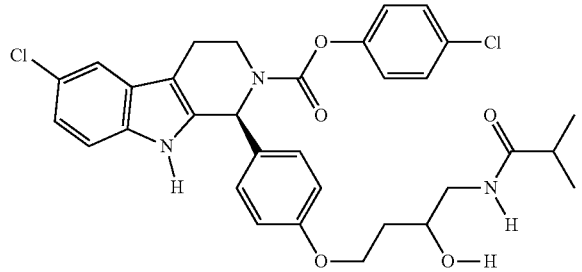 [SMILES: CC(C)C(=O)NCC(O)CCOc1ccc([C@H]2c3[nH]c4ccc(Cl)cc4c3CCN2C(=O)Oc2ccc(Cl)cc2)cc1]
1626
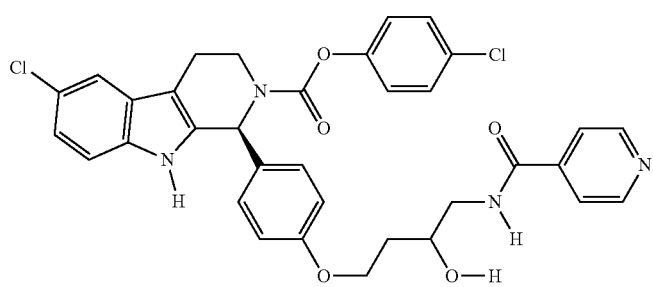 [SMILES: O=C(NCC(O)CCOc1ccc([C@H]2c3[nH]c4ccc(Cl)cc4c3CCN2C(=O)Oc2ccc(Cl)cc2)cc1)c1ccncc1]
1627
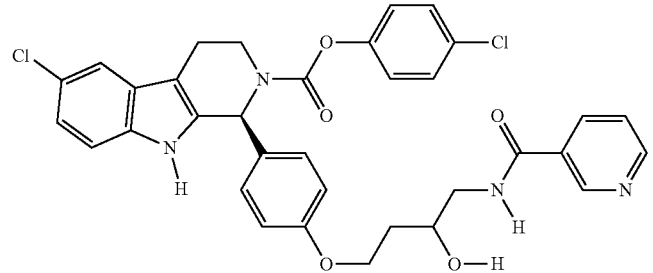 [SMILES: O=C(NCC(O)CCOc1ccc([C@H]2c3[nH]c4ccc(Cl)cc4c3CCN2C(=O)Oc2ccc(Cl)cc2)cc1)c1cccnc1]
1628
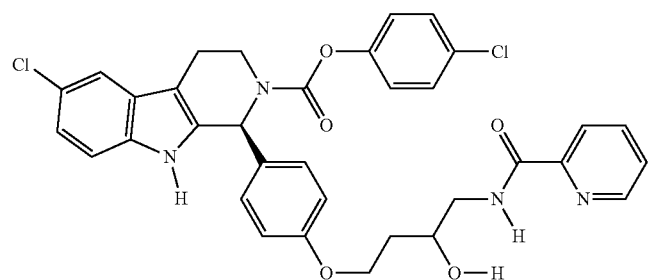 [SMILES: O=C(NCC(O)CCOc1ccc([C@H]2c3[nH]c4ccc(Cl)cc4c3CCN2C(=O)Oc2ccc(Cl)cc2)cc1)c1ccccn1]
1629

TABLE 1-continued
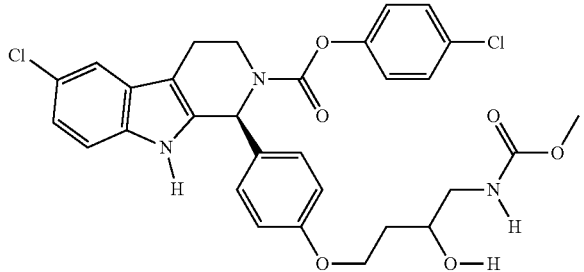 [SMILES: COC(=O)NCC(O)CCOc1ccc([C@H]2c3[nH]c4ccc(Cl)cc4c3CCN2C(=O)Oc2ccc(Cl)cc2)cc1]
1635
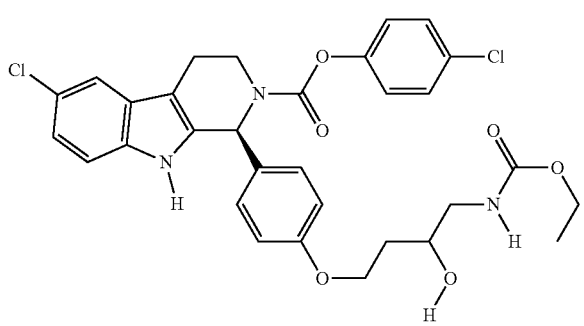
1636
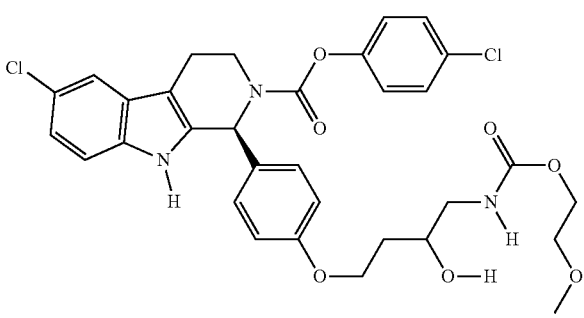 [SMILES: COCCOC(=O)NCC(O)CCOc1ccc([C@H]2c3[nH]c4ccc(Cl)cc4c3CCN2C(=O)Oc2ccc(Cl)cc2)cc1]
1637
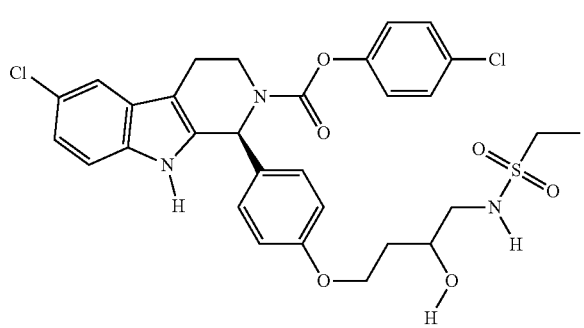 [SMILES: CCS(=O)(=O)NCC(O)CCOc1ccc([C@H]2c3[nH]c4ccc(Cl)cc4c3CCN2C(=O)Oc2ccc(Cl)cc2)cc1]
1638
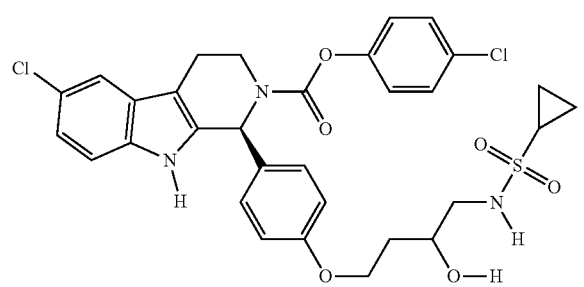 [SMILES: O=C(Oc1ccc(Cl)cc1)N1CCc2c([nH]c3ccc(Cl)cc23)[C@@H]1c1ccc(OCCC(O)CNS(=O)(=O)C2CC2)cc1]
1639

TABLE 1-continued
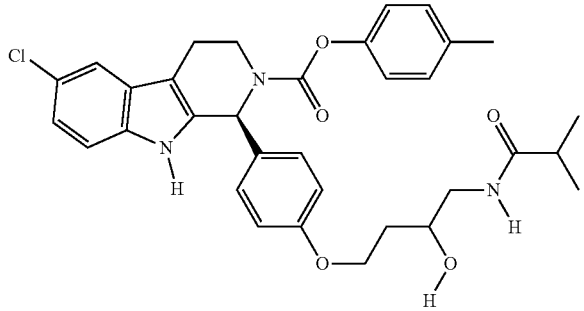 [SMILES: Cc1ccc(OC(=O)N2CCc3c([nH]c4ccc(Cl)cc34)[C@@H]2c2ccc(OCCC(O)CNC(=O)C(C)C)cc2)cc1]
1640
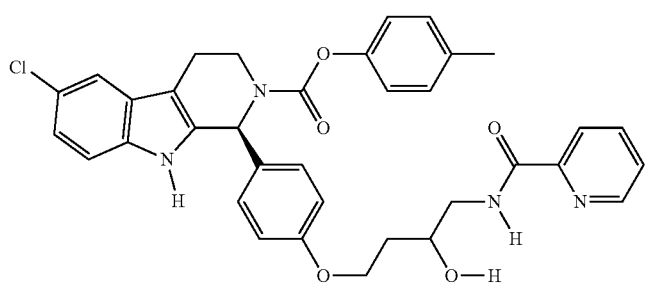 [SMILES: Cc1ccc(OC(=O)N2CCc3c([nH]c4ccc(Cl)cc34)[C@@H]2c2ccc(OCCC(O)CNC(=O)c3ccccn3)cc2)cc1]
1641
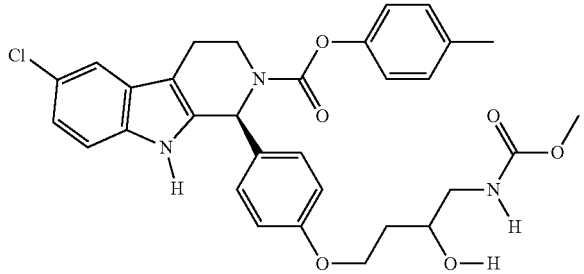 [SMILES: COC(=O)NCC(O)CCOc1ccc([C@H]2c3[nH]c4ccc(Cl)cc4c3CCN2C(=O)Oc2ccc(C)cc2)cc1]
1642
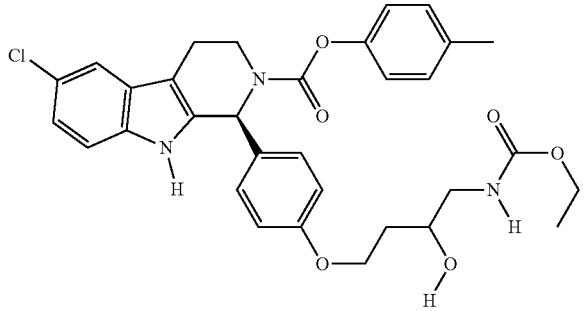 [SMILES: CCOC(=O)NCC(O)CCOc1ccc([C@H]2c3[nH]c4ccc(Cl)cc4c3CCN2C(=O)Oc2ccc(C)cc2)cc1]
1643
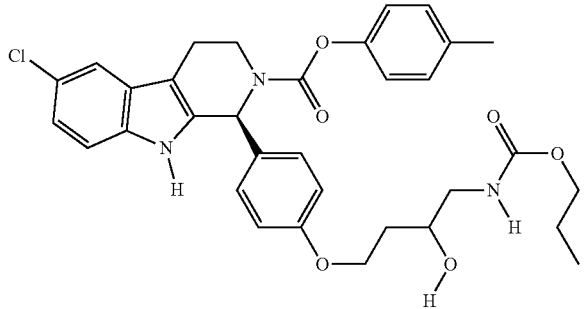 [SMILES: CCCOC(=O)NCC(O)CCOc1ccc([C@H]2c3[nH]c4ccc(Cl)cc4c3CCN2C(=O)Oc2ccc(C)cc2)cc1]
1644

TABLE 1-continued
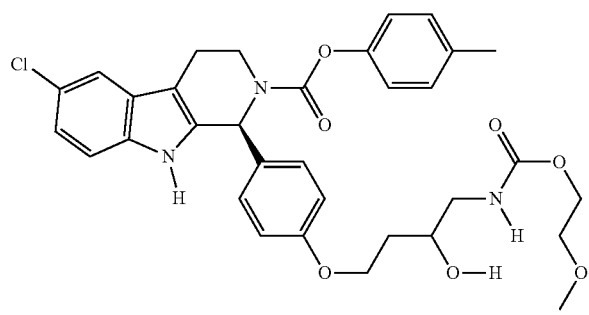 [SMILES: COCCOC(=O)NCC(O)CCOc1ccc([C@H]2c3[nH]c4ccc(Cl)cc4c3CCN2C(=O)Oc2ccc(C)cc2)cc1]
1645
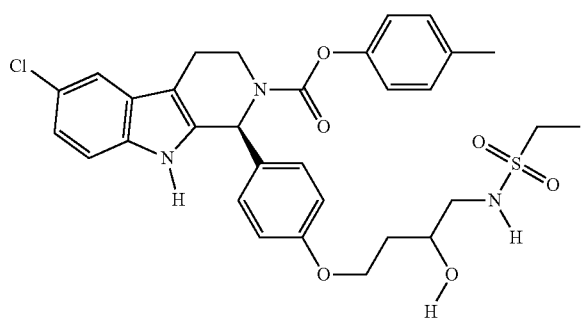 [SMILES: CCS(=O)(=O)NCC(O)CCOc1ccc([C@H]2c3[nH]c4ccc(Cl)cc4c3CCN2C(=O)Oc2ccc(C)cc2)cc1]
1646
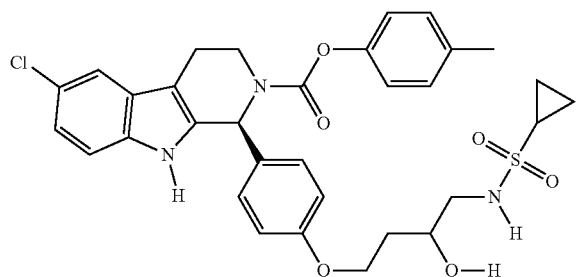 [SMILES: Cc1ccc(OC(=O)N2CCc3c([nH]c4ccc(Cl)cc34)[C@@H]2c2ccc(OCCC(O)CNS(=O)(=O)C3CC3)cc2)cc1]
1647
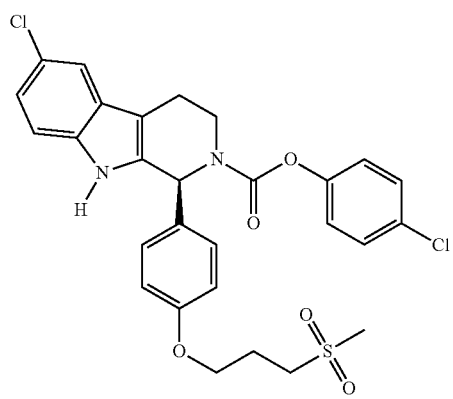 [SMILES: CS(=O)(=O)CCCOc1ccc([C@H]2c3[nH]c4ccc(Cl)cc4c3CCN2C(=O)Oc2ccc(Cl)cc2)cc1]
1648

TABLE 1-continued
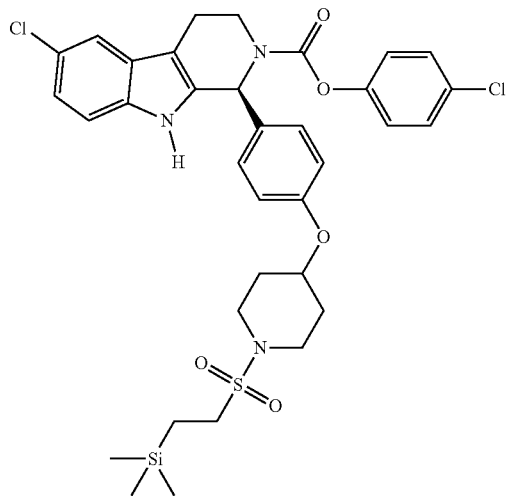 [SMILES: C[Si](C)(C)CCS(=O)(=O)N1CCC(Oc2ccc([C@H]3c4[nH]c5ccc(Cl)cc5c4CCN3C(=O)Oc3ccc(Cl)cc3)cc2)CC1]
1652
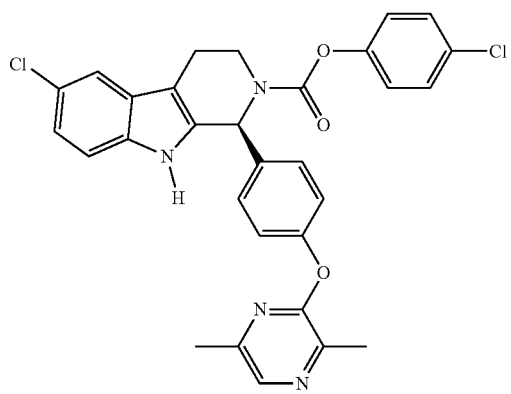 [SMILES: Cc1cnc(C)c(Oc2ccc([C@H]3c4[nH]c5ccc(Cl)cc5c4CCN3C(=O)Oc3ccc(Cl)cc3)cc2)n1]
1658
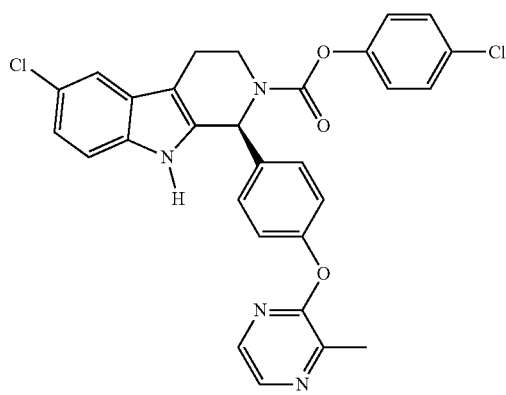 [SMILES: Cc1nccnc1Oc1ccc([C@H]2c3[nH]c4ccc(Cl)cc4c3CCN2C(=O)Oc2ccc(Cl)cc2)cc1]
1659

TABLE 1-continued
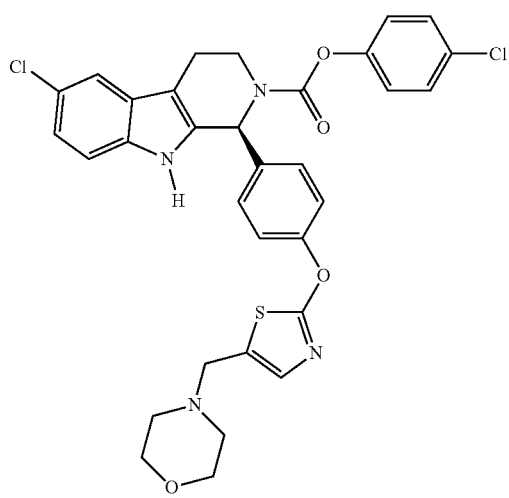 [SMILES: O=C(Oc1ccc(Cl)cc1)N1CCc2c([nH]c3ccc(Cl)cc23)[C@@H]1c1ccc(Oc2ncc(CN3CCOCC3)s2)cc1]
1660
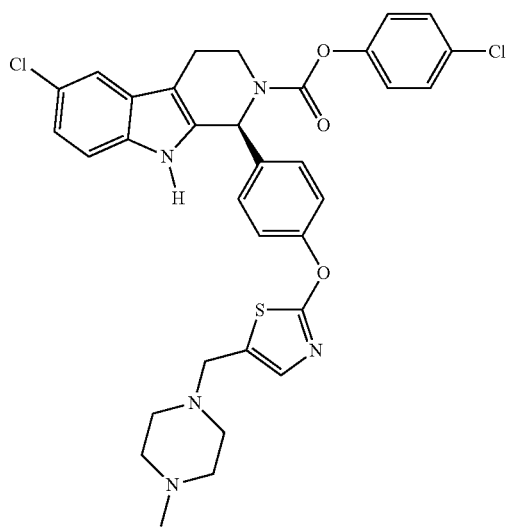 [SMILES: CN1CCN(Cc2cnc(Oc3ccc([C@H]4c5[nH]c6ccc(Cl)cc6c5CCN4C(=O)Oc4ccc(Cl)cc4)cc3)s2)CC1]
1661
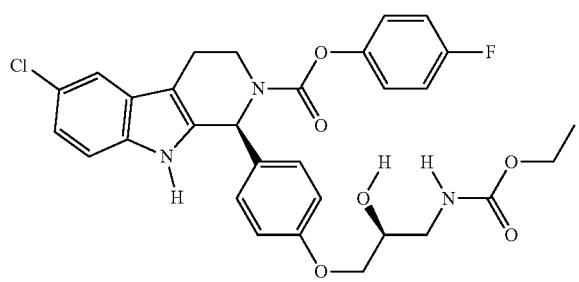 [SMILES: CCOC(=O)NC[C@H](O)COc1ccc([C@H]2c3[nH]c4ccc(Cl)cc4c3CCN2C(=O)Oc2ccc(F)cc2)cc1]
1663
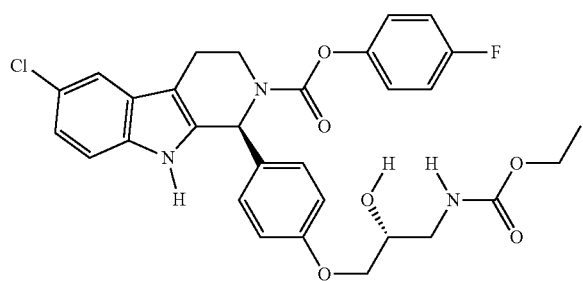 [SMILES: CCOC(=O)NC[C@@H](O)COc1ccc([C@H]2c3[nH]c4ccc(Cl)cc4c3CCN2C(=O)Oc2ccc(F)cc2)cc1]
1664

TABLE 1-continued
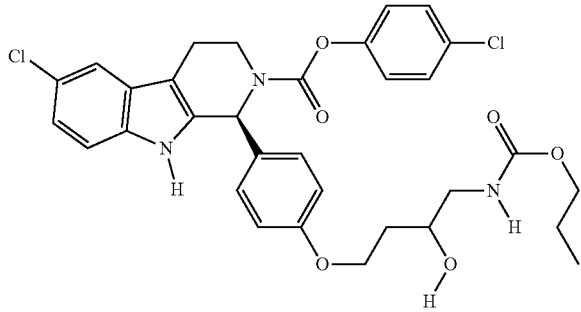
1666
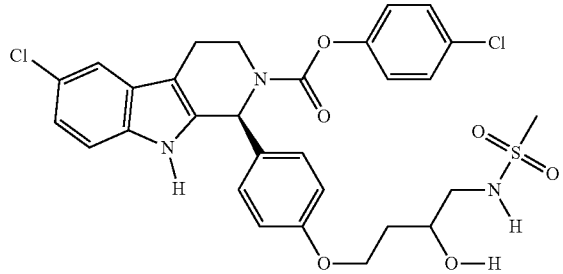 [SMILES: CS(=O)(=O)NCC(O)CCOc1ccc([C@H]2c3[nH]c4ccc(Cl)cc4c3CCN2C(=O)Oc2ccc(Cl)cc2)cc1]
1667
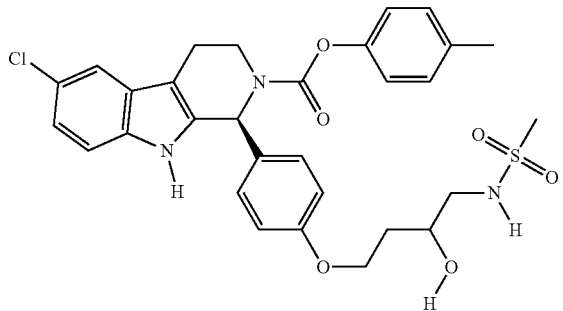 [SMILES: Cc1ccc(OC(=O)N2CCc3c([nH]c4ccc(Cl)cc34)[C@@H]2c2ccc(OCCC(O)CNS(C)(=O)=O)cc2)cc1]
1668
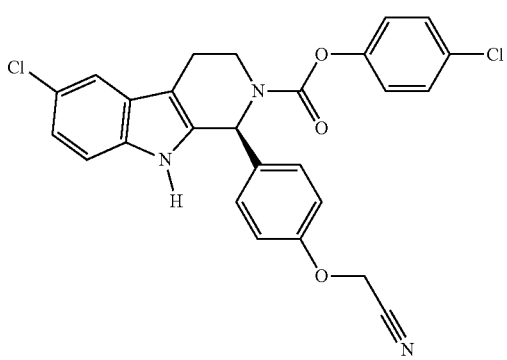 [SMILES: N#CCOc1ccc([C@H]2c3[nH]c4ccc(Cl)cc4c3CCN2C(=O)Oc2ccc(Cl)cc2)cc1]
1669
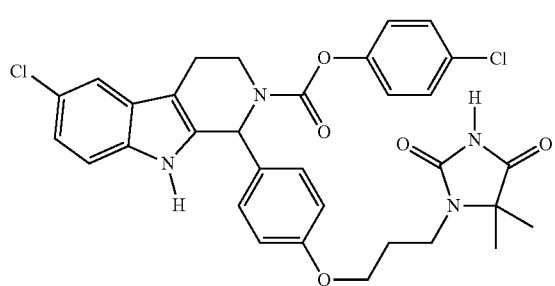 [SMILES: CC1(C)C(=O)NC(=O)N1CCCOc1ccc(C2c3[nH]c4ccc(Cl)cc4c3CCN2C(=O)Oc2ccc(Cl)cc2)cc1]
1671

TABLE 1-continued
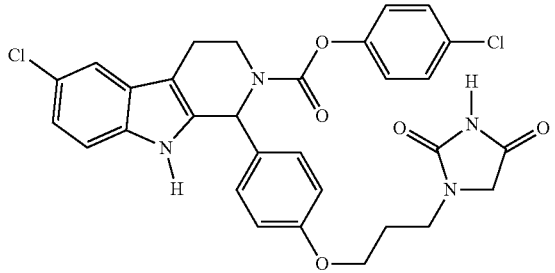 [SMILES: O=C1CN(CCCOc2ccc(C3c4[nH]c5ccc(Cl)cc5c4CCN3C(=O)Oc3ccc(Cl)cc3)cc2)C(=O)N1]
1672
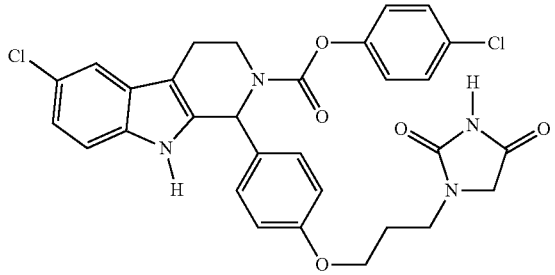 [SMILES: O=C1CN(CCCOc2ccc(C3c4[nH]c5ccc(Cl)cc5c4CCN3C(=O)Oc3ccc(Cl)cc3)cc2)C(=O)N1]
1673
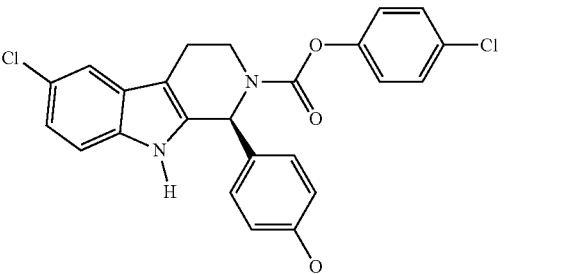
1674
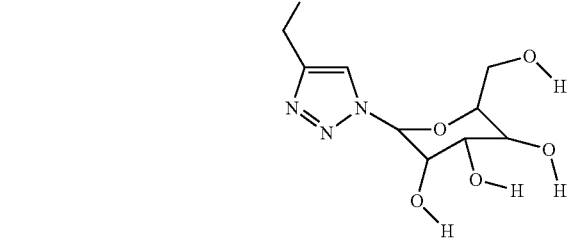
1675

TABLE 1-continued
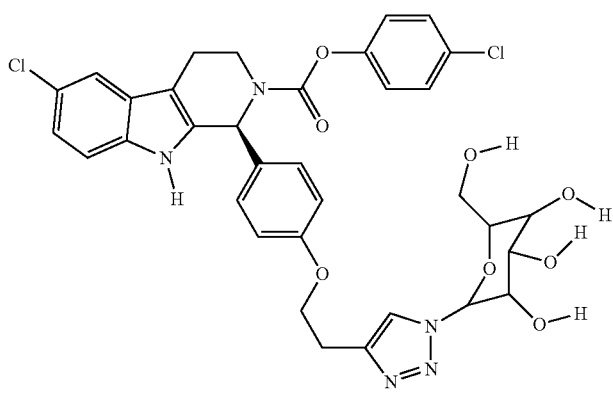 [SMILES: O=C(Oc1ccc(Cl)cc1)N1CCc2c([nH]c3ccc(Cl)cc23)[C@@H]1c1ccc(OCCc2cn(C3OC(CO)C(O)C(O)C3O)nn2)cc1]
1676
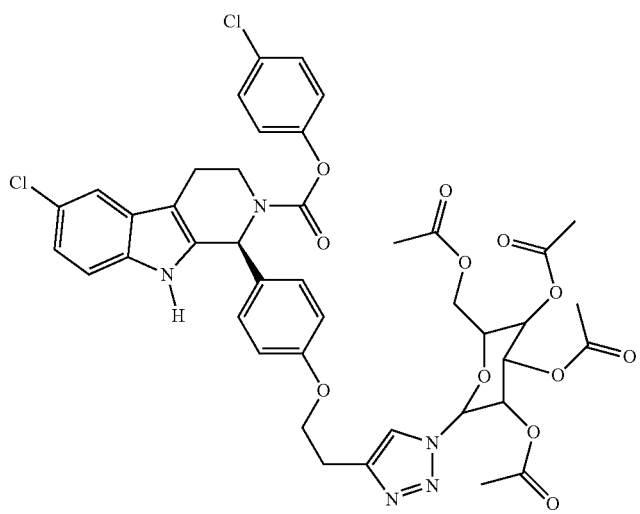 [SMILES: CC(=O)OCC1OC(n2cc(CCOc3ccc([C@H]4c5[nH]c6ccc(Cl)cc6c5CCN4C(=O)Oc4ccc(Cl)cc4)cc3)nn2)C(OC(C)=O)C(OC(C)=O)C1OC(C)=O]
1677
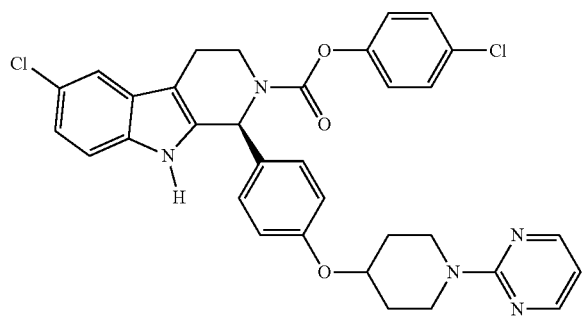 [SMILES: O=C(Oc1ccc(Cl)cc1)N1CCc2c([nH]c3ccc(Cl)cc23)[C@@H]1c1ccc(OC2CCN(c3ncccn3)CC2)cc1]
1681
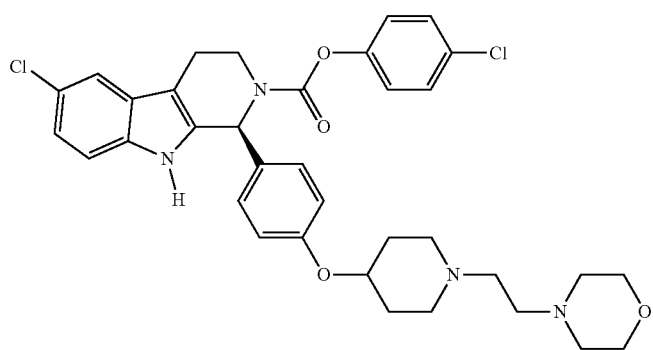 [SMILES: O=C(Oc1ccc(Cl)cc1)N1CCc2c([nH]c3ccc(Cl)cc23)[C@@H]1c1ccc(OC2CCN(CCN3CCOCC3)CC2)cc1]
1682

TABLE 1-continued
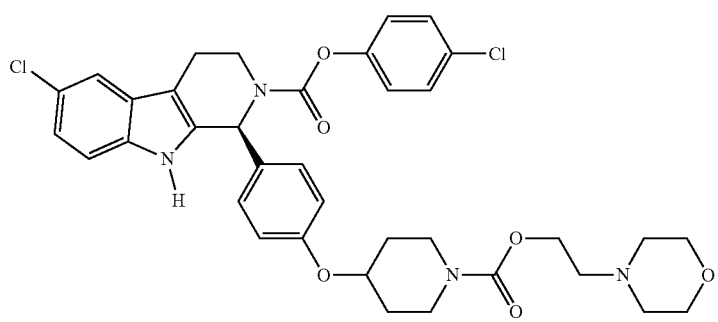 [SMILES: O=C(OCCN1CCOCC1)N1CCC(Oc2ccc([C@H]3c4[nH]c5ccc(Cl)cc5c4CCN3C(=O)Oc3ccc(Cl)cc3)cc2)CC1]
1693
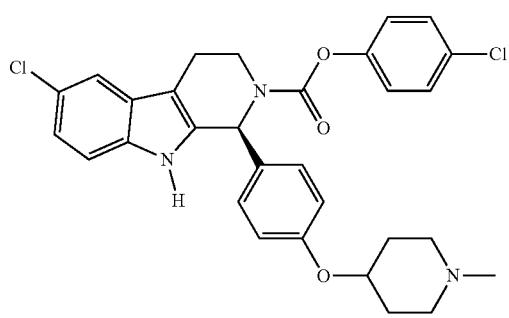 [SMILES: CN1CCC(Oc2ccc([C@H]3c4[nH]c5ccc(Cl)cc5c4CCN3C(=O)Oc3ccc(Cl)cc3)cc2)CC1]
1694
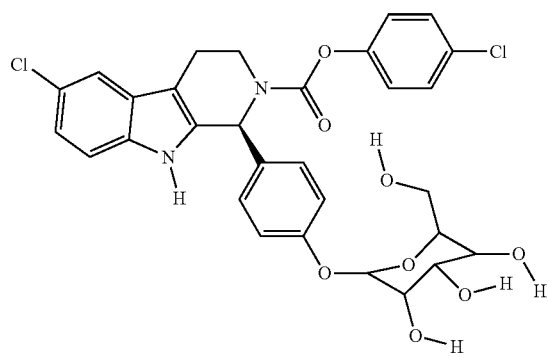 [SMILES: O=C(Oc1ccc(Cl)cc1)N1CCc2c([nH]c3ccc(Cl)cc23)[C@@H]1c1ccc(OC2OC(CO)C(O)C(O)C2O)cc1]
1695
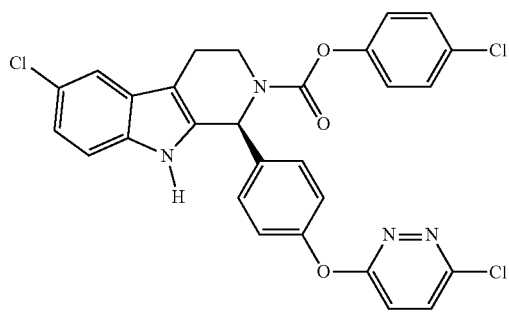 [SMILES: O=C(Oc1ccc(Cl)cc1)N1CCc2c([nH]c3ccc(Cl)cc23)[C@@H]1c1ccc(Oc2ccc(Cl)nn2)cc1]
1698

TABLE 1-continued
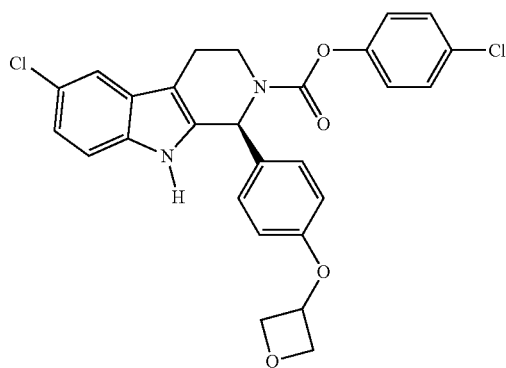 [SMILES: O=C(Oc1ccc(Cl)cc1)N1CCc2c([nH]c3ccc(Cl)cc23)[C@@H]1c1ccc(OC2COC2)cc1]
1701
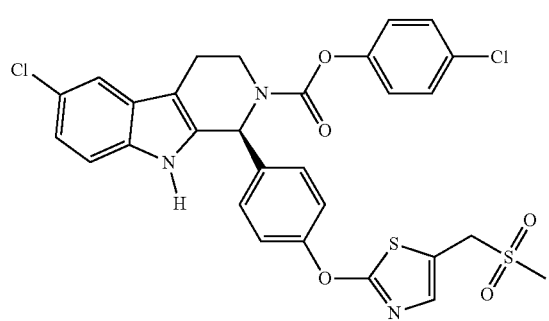 [SMILES: CS(=O)(=O)Cc1cnc(Oc2ccc([C@H]3c4[nH]c5ccc(Cl)cc5c4CCN3C(=O)Oc3ccc(Cl)cc3)cc2)s1]
1702
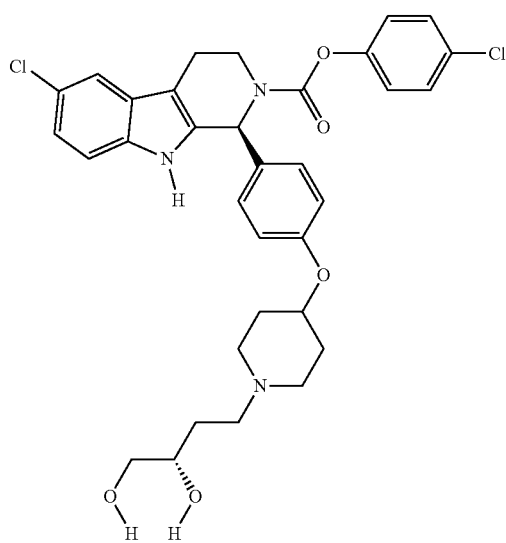 [SMILES: O=C(Oc1ccc(Cl)cc1)N1CCc2c([nH]c3ccc(Cl)cc23)[C@@H]1c1ccc(OC2CCN(CC[C@H](O)CO)CC2)cc1]
1703

TABLE 1-continued
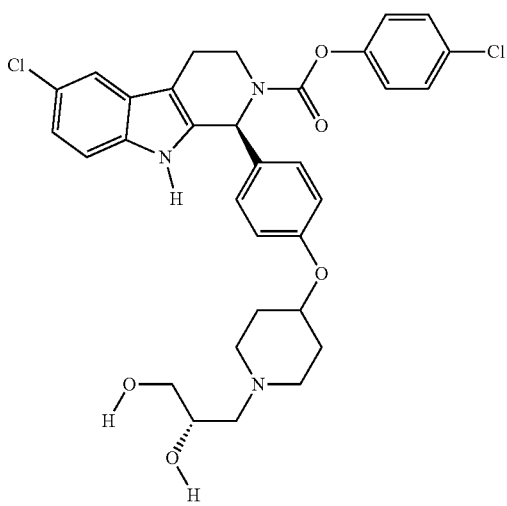 [SMILES: O=C(Oc1ccc(Cl)cc1)N1CCc2c([nH]c3ccc(Cl)cc23)[C@@H]1c1ccc(OC2CCN(C[C@H](O)CO)CC2)cc1]
1704
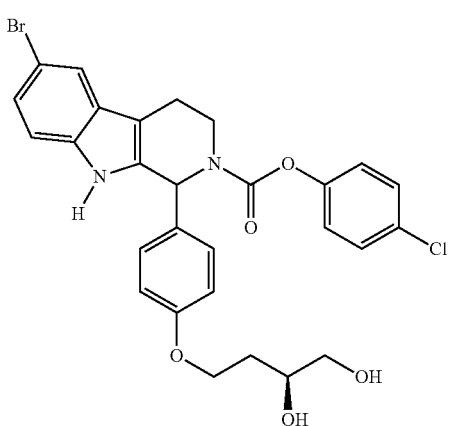 [SMILES: O=C(Oc1ccc(Cl)cc1)N1CCc2c([nH]c3ccc(Br)cc23)C1c1ccc(OCC[C@H](O)CO)cc1]
1725
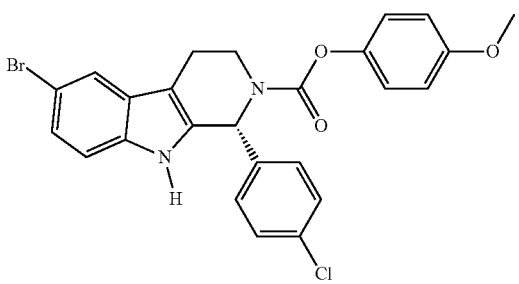 [SMILES: COc1ccc(OC(=O)N2CCc3c([nH]c4ccc(Br)cc34)[C@H]2c2ccc(Cl)cc2)cc1]
1726
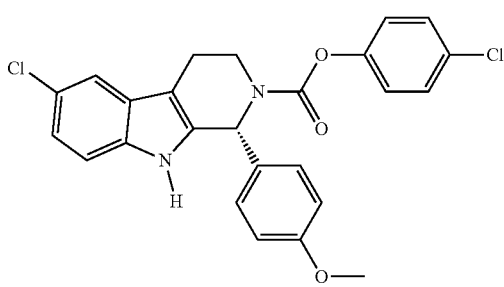 [SMILES: COc1ccc([C@@H]2c3[nH]c4ccc(Cl)cc4c3CCN2C(=O)Oc2ccc(Cl)cc2)cc1]
1727

TABLE 1-continued
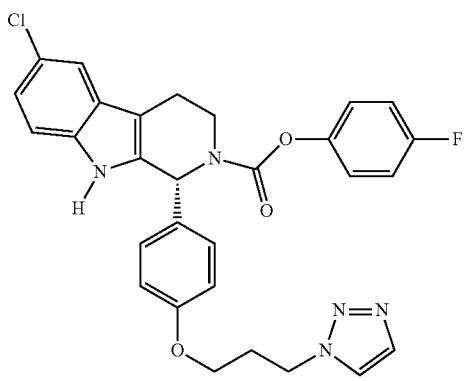 [SMILES: O=C(Oc1ccc(F)cc1)N1CCc2c([nH]c3ccc(Cl)cc23)[C@H]1c1ccc(OCCCn2ccnn2)cc1]
1728
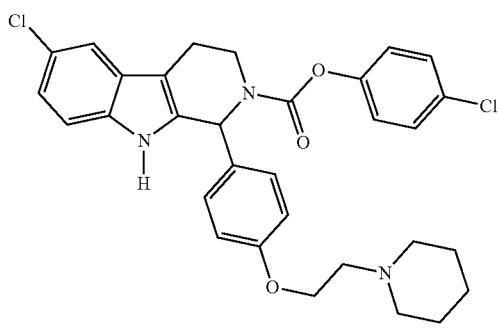 [SMILES: O=C(Oc1ccc(Cl)cc1)N1CCc2c([nH]c3ccc(Cl)cc23)C1c1ccc(OCCN2CCCCC2)cc1]
1729
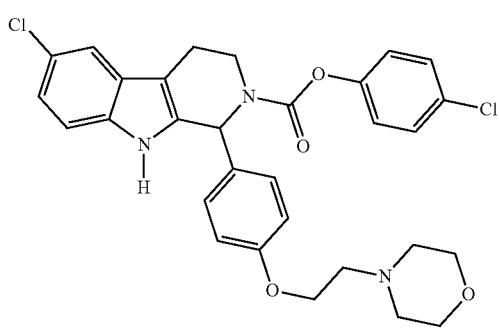 [SMILES: O=C(Oc1ccc(Cl)cc1)N1CCc2c([nH]c3ccc(Cl)cc23)C1c1ccc(OCCN2CCOCC2)cc1]
1730
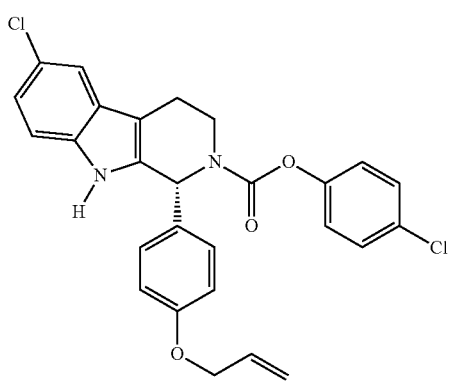 [SMILES: C=CCOc1ccc([C@@H]2c3[nH]c4ccc(Cl)cc4c3CCN2C(=O)Oc2ccc(Cl)cc2)cc1]
1731

TABLE 1-continued
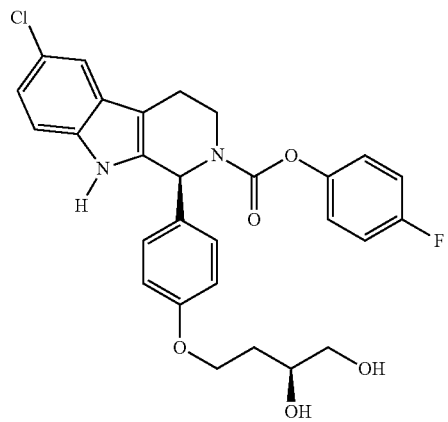 [SMILES: O=C(Oc1ccc(F)cc1)N1CCc2c([nH]c3ccc(Cl)cc23)[C@@H]1c1ccc(OCC[C@H](O)CO)cc1]
1732
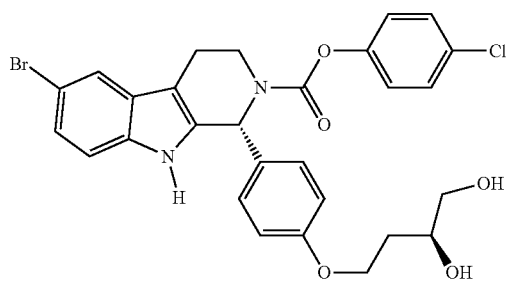 [SMILES: O=C(Oc1ccc(Cl)cc1)N1CCc2c([nH]c3ccc(Br)cc23)[C@H]1c1ccc(OCC[C@H](O)CO)cc1]
1733
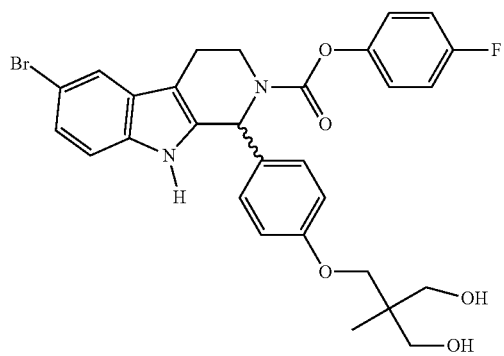 [SMILES: CC(CO)(CO)COc1ccc(C2c3[nH]c4ccc(Br)cc4c3CCN2C(=O)Oc2ccc(F)cc2)cc1]
1734
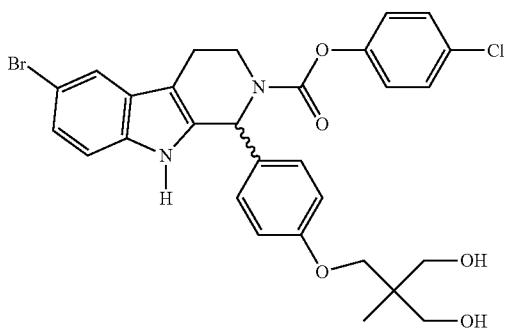 [SMILES: CC(CO)(CO)COc1ccc(C2c3[nH]c4ccc(Br)cc4c3CCN2C(=O)Oc2ccc(Cl)cc2)cc1]
1735

TABLE 1-continued
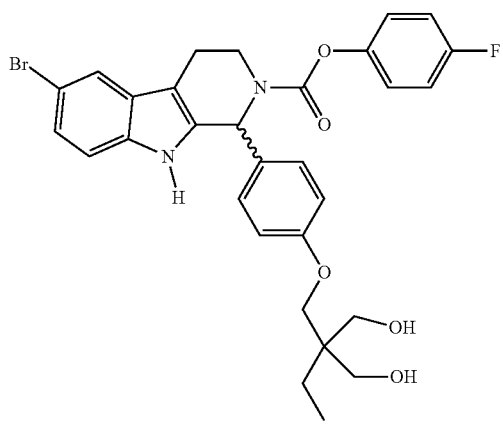 [SMILES: CCC(CO)(CO)COc1ccc(C2c3[nH]c4ccc(Br)cc4c3CCN2C(=O)Oc2ccc(F)cc2)cc1]
1736
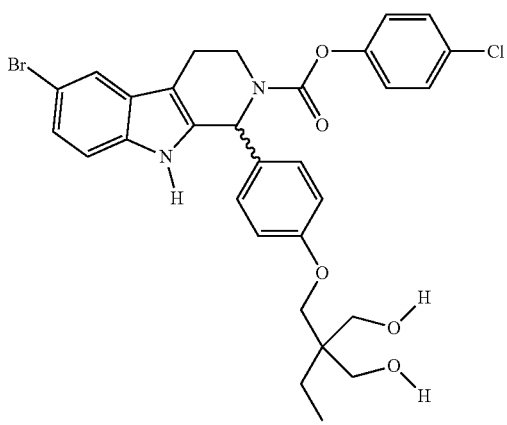 [SMILES: CCC(CO)(CO)COc1ccc(C2c3[nH]c4ccc(Br)cc4c3CCN2C(=O)Oc2ccc(Cl)cc2)cc1]
1737
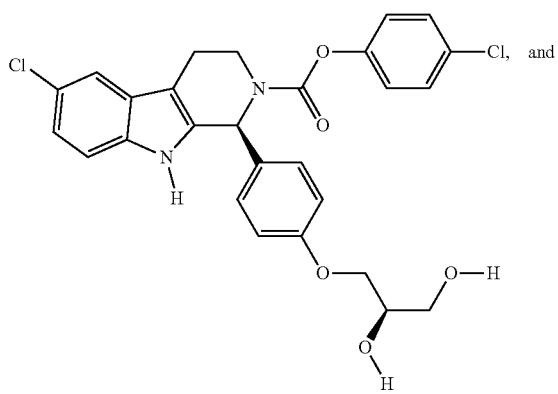 [SMILES: O=C(Oc1ccc(Cl)cc1)N1CCc2c([nH]c3ccc(Cl)cc23)[C@@H]1c1ccc(OC[C@H](O)CO)cc1 ; "and"]
1738
Cl, and
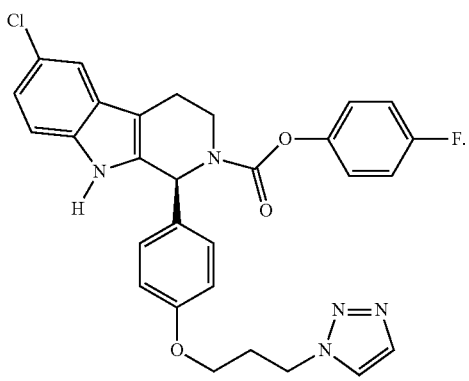 [SMILES: O=C(Oc1ccc(F)cc1)N1CCc2c([nH]c3ccc(Cl)cc23)[C@@H]1c1ccc(OCCCn2ccnn2)cc1]
1739

In a further embodiment, additional examples of the Compounds provided herein are disclosed in International Patent Application Publication No. WO2005/089764 ("'764 publication") on pages 26 to 98, and in copending U.S. Provisional Patent Application 61/181,653, entitled: METHODS FOR TREATING CANCER AND NON-NEOPLASTIC CONDITIONS, filed May 27, 2009, each of which are incorporated by reference herein in their entirety. Methods for preparing certain Compounds provided herein and the Compounds disclosed on pages 26 to 98 of the '764 publication are provided on pages 99 to 105 and 112 to 142 of the '764 publication and are incorporated by reference herein in their entirety and for all purposes. Methods for preparing certain Compounds provided herein and the Compounds disclosed in copending U.S. Provisional Patent Application 61/181,652, entitled: PROCESSES FOR THE PREPARATION OF SUBSTITUTED TETRAHYDRO BETA-CARBOLINES, filed May 27, 2009, are provided therein and are incorporated by reference herein in their entirety and for all purposes.

5.2 Pharmaceutical Properties and Formulations 5.2.1 Activity

Without being bound by any theory, Compounds described herein inhibit the translation of pathologically expressed human VEGF mRNA and, thus, inhibit the pathologic production of human VEGF protein. In particular, the Compounds act specifically through a mechanism dependent on the 5' untranslated region (UTR) of the human VEGF mRNA to inhibit the pathologic production of human VEGF protein. The activity of the Compounds tested is post-transcriptional since quantitative real-time polymerase chain reaction (PCR) assessments of mRNA have shown that the Compounds do not alter the levels of human VEGF mRNA. Analyses of the effects of the Compounds tested on ribosome association with VEGF transcripts indicate that the Compounds do not impede initiation of VEGF translation or promote dissociation of ribosomes from human VEGF mRNA.

5.2.1.1 Inhibition of Pathological VEGF Production

Compounds are described that reduce or inhibit pathologic production of human VEGF (also known as VEGF-A and vascular permeability factor (VPF)). Exemplary Compounds have been shown to reduce or inhibit tumor production of VEGF as measured in cell culture and/or preclinical tumor models. Furthermore, the Compounds tested do not affect homeostatic, physiologically produced plasma VEGF levels in healthy humans.

By way of background, the human VEGF-A gene encodes a number of different products (isoforms) due to alternative splicing. The VEGF-A isoforms include $VEGF_{121}$, $VEGF_{165}$, $VEGF_{189}$ and $VEGF_{206}$ having 121, 165, 189 and 206 amino acids, respectively. $VEGF_{165}$ and $VEGF_{121}$ isoforms are soluble, whereas $VEGF_{189}$ and $VEGF_{206}$ isoforms are sequestered within the extracellular matrix. The activity of the Compounds tested was assessed by measuring the concentrations of soluble VEGF and/or extracellular matrix bound-VEGF in cell culture systems. In preclinical tumor models, the activity of the Compounds tested was assessed by measuring the concentrations of soluble VEGF. The data indicate that the Compounds tested inhibit the production of soluble as well as matrix associated forms of tumor derived VEGF.

In particular, a Compound provided herein has been shown to selectively inhibit stress (e.g., hypoxia) induced production of soluble human VEGF isoforms in cell culture without affecting soluble human VEGF production under normoxic conditions (see Sections 9.1.1.1 and 9.1.1.2). Thus, the Compound was shown to preferentially inhibit pathological production of soluble human VEGF isoforms resulting from hypoxia while sparing homeostatic production of soluble isoforms in unperturbed cells. Accordingly, in specific embodiments, a Compound selectively inhibits or reduces the pathological production of a soluble human VEGF isoform over inhibiting or reducing physiological production of a soluble human VEGF isoform.

A Compound provided herein has also shown to selectively inhibit pathological production of VEGF in tumor cells that constitutively overproduce VEGF even under normoxic conditions. See Section 9.1.1.3. In these studies, to better assess the Compound's activity, the inhibition of the pathological production of matrix-bound human VEGF was measured. Thus, in one embodiment, a Compound selectively inhibits or reduces the pathological production of a matrix-bound human VEGF isoform over inhibiting or reducing physiological production of a matrix-bound human VEGF isoform.

The ability of a Compound provided herein to inhibit pathologic production of human VEGF in cell culture has been demonstrated for multiple human tumor cells from a variety of different tissues. See Table 4 (Section 9.1.1.4).

Exemplary Compounds inhibited intratumoral and pathologic plasma human VEGF production in animal models with pre-established human tumors. See Sections 9.1.2.1 to 9.1.2.3. In addition to reducing pathological induced human VEGF concentrations and edema, inflammation, pathological angiogenesis and tumor growth, a Compound provided herein has been shown to selectively reduce intratumoral levels of human growth factors and cytokines, such as IL-6, IL-8, osteopontin, MCP-1 and VEGF family members including human VEGF-C, VEGF-D and placental growth factor (P1GF). See Sections 9.1.2.1. In particular, the Compound shows a dose-dependent reduction in the concentration of intratumoral and pathologic plasma soluble human VEGF isoforms (see Section 9.1.2.2, in particular FIG. 5 and FIG. 6). Accordingly, in specific embodiments, a Compound provided herein, selectively inhibits or reduces the pathological production of one or more human VEGF family members. See Section 9.1.2.1.

5.2.1.2 Inhibition of Pathological Angiogenesis and Tumor Growth

Compounds are described that reduce or inhibit edema, inflammation, pathological angiogenesis and tumor growth. A Compound provided herein has been shown to have a profound effect on the architecture of the tumor vasculature in animal models with pre-established human tumors. The Compound reduced the total volume and diameter of blood vessels formed compared to vehicle treated subjects. See Section 9.2.1. The Compound also showed inhibition of tumor growth in the same model. A dose-response effect of the Compound that correlated with decreases in tumor and pathologic plasma VEGF concentrations was observed when tumor size was assessed. See Section 9.2.2. Thus, in one embodiment, the concentration of soluble pathologically produced VEGF in human plasma may be used to assess and monitor the pharmacodynamic effect of a Compound provided herein. In a specific embodiment, the concentration of either $VEGF_{121}$, $VEGF_{165}$, or both in human plasma may be used to assess and monitor the pharmacodynamic effect of a Compound provided herein.

In concert with a decrease in pathological tumor induced production of VEGF, a Compound provided herein demonstrated tumor regression or delay of tumor growth in various xenograft models, including models of breast cancer, neuroblastoma, and prostate cancer. See Section 9.2.5. Compounds that inhibit tumor growth in multiple preclinical models are more likely to have clinical efficacy. See Johnson et al., *Br. J. Cancer* 2001, 84(10):1424-31. Further, a Compound provided herein has shown activity in an orthotopic SY5Y neuroblastoma and SKNEP ewing sarcoma tumor model. In orthotopic tumor models, human tumor cells are implanted into the mouse in an organ that corresponds to the location of the human cells from which a tumor would arise. Such models may provide a better predictor of clinical efficacy than injection of tumors into the flanks of nude mice. See Hoffman, *Invest. New Drugs* 1999, 17(4):343-59. See Section 9.2.5.6.

An in vivo study in rats administered a $^{14}$C-radiolabeled Compound provided herein has been shown that the Compound penetrates all tissues investigated after oral administration. See Section 9.2.6 and Table 23. In one embodiment, a Compound provided herein is able to penetrate cells, tissues or organs that are surrounded by an endothelial cell barrier. In a specific embodiment, a Compound penetrates endothelial cell barriers, such as, but not limited to, the blood-brain barrier, the blood-eye barrier, the blood-testes barrier, blood-uterus barrier, or the blood-ovary barrier. The cells, tissues or organs surrounded by an endothelial cell barrier are, for example, cerebellum, cerebrum, ovary, testis, or the eye. The ability of a Compound to traverse such endothelial barriers makes it suited for the treatment of cancers, such as brain cancers, including but not limited to glioblastoma or neurofibromatosis.

5.2.1.3 Prolongation of Early $G_1$/Early S-Phase Cell Cycle Delay

Provided herein are Compounds that provoke a delay or prolongation of the cell cycle.

In addition to its effects on pathological VEGF production, a Compound provided herein induces a late $G_1$/early S-Phase cell cycle delay, i.e., between the late resting or pre-DNA synthesis phase, and the early in DNA synthesis phase in those tumor cell lines in which pathologic VEGF expression is decreased by the Compound. Further characterization indicates that this effect is concentration dependent, occurring at low nanomolar $EC_{50}$ values similar to those associated with reducing pathological VEGF production. See Section 9.3.1.1. The effect seen is reversible upon cessation of exposure to a Compound. See Section 9.3.1.2. The cell cycle delay and inhibition of pathological VEGF protein production occur in concert, linking these phenotypes in inflammation, pathological angiogenesis and tumor growth. Inhibition of pathological VEGF production in the same tumor cells used herein with small interfering RNA (siRNA) does not induce a delay or prolongation of the cell cycle (data not shown). Conversely, the use of mimosine, a DNA synthesis inhibitor that halts cell cycle progression at the $G_1$/S interface, does not delay or prolong the cell cycle or reduce VEGF production (data not shown). A Compound provided herein has demonstrated in an in vivo HT1080 xenograft model that the Compound delays cycling through the S-phase; an effect that is distinct from that of bevacizumab, which has no effect on tumor cell cycling. Thus, these experiments indicate that the effects of a Compound on the tumor cell cycle occur in parallel with its actions on pathological VEGF production in tumors.

5.2.2 Formulations 5.2.2.1 General Formulation Methods

The Compounds provided herein can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrant (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the Compound provided herein in the pharmaceutical composition may be at a level that will exercise the desired effect. Effective amounts contemplated are further discussed in Section 5.4.

The dose of a Compound provided herein to be administered to a patient is rather widely variable and can be subject to the judgment of a health-care practitioner. In general, a Compound provided herein can be administered one to four times a day. The dosage may be properly varied depending on the age, body weight and medical condition of the patient and the type of administration. In one embodiment, one dose is given per day. In any given case, the amount of the Compound provided herein administered will depend on such factors as the solubility of the active component, the formulation used and the route of administration.

A Compound provided herein can be administered orally, with or without food or liquid.

The Compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, the Compound provided herein is administered orally using a capsule dosage form composition, wherein the capsule contains the Compound provided herein without an additional carrier, excipient or vehicle.

In another embodiment, provided herein are compositions comprising an effective amount of a Compound provided herein and a pharmaceutically acceptable carrier or vehicle, wherein a pharmaceutically acceptable carrier or vehicle can comprise one or more excipients, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing a Compound provided herein with one or more suitable carriers or excipients and filling the proper amount of the mixture in capsules.

5.2.2.2 Lipid-Based Formulation Methods

One embodiment, provided herein is a SEDDS or SMEDDS system comprising a Compound provided herein (e.g., an effective amount of a composition provided herein), and a carrier medium comprising a lipophilic component, a surfactant, and optionally a hydrophilic component. In certain embodiments, the present disclosure provides a SEDDS or SMEDDS system comprising a Compound provided herein, and a carrier medium comprising one or more surfactants and optionally one or more additives.

In certain embodiments, the SEDDS or SMEDDS system is suitable for oral administration.

One embodiment, provided herein is a SEDDS or SMEDDS system comprising a representative Compound provided herein and a carrier medium that comprises a lipophilic component, a surfactant, optionally a hydrophilic component and optionally an additive.

In one embodiment, the SEDDS or SMEDDS system forms an o/w (oil-in-water) microemulsion when diluted with water.

In one embodiment, of a SEDDS or SMEDDS system provided herein is a microemulsion comprising a Compound provided herein. In certain embodiments, the microemulsion is an o/w (oil-in-water) microemulsion. In one embodiment, the microemulsion comprises a Compound provided herein, a lipophilic component, a surfactant, water, and optionally a hydrophilic component and optionally an additive. In one embodiment, the microemulsion comprises a Compound provided herein, a lipophilic component, a surfactant, and water. In one embodiment, the microemulsion comprises a Compound provided herein, a surfactant, water, and optionally an additive.

The colloidal structures of the microemulsion form spontaneously or substantially spontaneously when the components of the SEDDS or SMEDDS system are brought into contact with an aqueous medium, e.g., by simple shaking by hand for a short period of time, for example for about 10 seconds. The SEDDS or SMEDDS system provided herein is thermodynamically stable, e.g., for at least 15 minutes or up to 4 hours, even to 24 hours. Typically, the system contains dispersed structures, i.e., droplets or liquid nanoparticles of a mean diameter less than about 200 nm (2,000 Å), e.g., less than about 150 nm (1,500 Å), typically less than about 100 nm (1,000 Å), generally greater than about 10 nm (100 Å) as measured by standard light scattering techniques, e.g., using a MALVERN ZETASIZER 300™ particle characterizing machine. Solid drug particles of mean diameter greater than 200 nm may also be present. The proportion of particles present may be temperature dependent.

In accordance with the present disclosure, Compounds provided herein may be present in an amount of up to about 20% by weight of the SEDDS or SMEDDS system provided herein, e.g., from about 0.05% by weight. In one embodiment, the Compound provided herein is present in an amount of from about 0.05 to about 15% by weight of the composition, or in an amount of from about 0.1 to about 5% by weight of the SEDDS or SMEDDS system.

In some embodiments, the SEDDS or SMEDDS system provided herein further comprises a carrier medium having a lipophilic component and a surfactant. In other embodiments, the carrier medium also comprises a lipophilic component, a hydrophilic component and a surfactant. In further embodiments, the carrier medium may comprise a surfactant. In some embodiments, the carrier medium also comprises a surfactant and an additive. In certain embodiments, the Compound provided herein can reside in the lipophilic component or phase.

In some embodiments, the SEDDS or SMEDDS system, the carrier medium, and the microemulsion comprise one or more lipophilic substances. In certain embodiments, the SEDDS or SMEDDS system, the carrier medium, and the microemulsion comprise one or more hydrophilic substances. In other embodiments, the SEDDS or SMEDDS system, the carrier medium, and the microemulsion comprise one or more surfactants. In further embodiments, the SEDDS or SMEDDS system, the carrier medium, and the microemulsion comprise one or more additives.

The compositions provided herein can include a variety of additives including antioxidants, antimicrobial agents, enzyme inhibitors, stabilizers, preservatives, flavors, sweeteners and further components known to those skilled in the art.

A. Lipophilic Components

Lipophilic components include, but are not limited to:

A1) Medium Chain Fatty Acid Triglyceride

These include, but are not limited to, triglycerides of saturated fatty acid having 6 to 12, e.g. 8 to 10, carbon atoms. In one embodiment, the medium chain fatty acid triglycerides include, but are not limited to, those known and commercially available under the trade names ACOMED®, LABRAFAC®, MYRITOL®, CAPTEX®, NEOBEE®M 5 F, MIGLYOL® 810, MIGLYOL®812, MIGLYOL®818, MAZOL®, SEFSOL® 860, SEFSOL®870. In one embodiment, the lipophilic component is LABRAFAC®. In one embodiment, the lipophilic component is LABRAFAC®CC. In another embodiment, the lipophilic component is LABRAFAC®WL 1349.

A2) Propylene Glycol Mono Fatty Acid Esters

The fatty acid constituent may include, but is not limited to, both saturated and unsaturated fatty acids having a chain length of from e.g. $C_8$-$C_{12}$. In one embodiment, the fatty acid is propylene glycol mono ester of caprylic and lauric acid as commercially available, e.g. under the trade names SEFSOL® 218, CAPRYOL®90 or LAUROGLYCOL®90, from e.g. Nikko Chemicals Co., Ltd. or Gattefossé or Capmul PG-8 from Abitec Corporation.

A3) Propylene Glycol Mono- and Di-Fatty Acid Esters

These include, but are not limited to, Laroglycol FCC and Capryol PGMC.

A4) Propylene Glycol Diesters

These include, but are not limited to, propylene glycol di-fatty acid esters such as propylene glycol dicaprylate (which is commercially available under the trade name MIGLYOL® 840 from e.g. sasol; Fiedler, H. P. "Lexikon der Hilfsstoffe für Pharmazie, Kosmetik and angrenzende Gebiete", Edition Cantor, D-7960 Aulendorf, 4th revised and expanded edition (1996), volume 2, page 1008) or Captex 200 from Abitec Corporation.

A5) Propylene Glycol Monoacetate and Propylene Glycol

A6) Transesterified Ethoxylated Vegetable Oils

Transesterified ethoxylated vegetable oils are known and are commercially available under the trade name LABRAFIL® (H. Fiedler, loc. cit., vol 2, page 880). Examples are LABRAFIL® M 2125 CS (obtained from corn oil and having an acid value of less than about 2, a saponification value of 155 to 175, an HLB value of 3 to 4, and an iodine value of 90 to 110), and LABRAFIL® M 1944 CS (obtained from kernel oil and having an acid value of about 2, a saponification value of 145 to 175 and an iodine value of 60 to 90). LABRAFIL® M 2130 CS (which is a transesterification product of a $C_{12}$-$C_{18}$ glyceride and polyethylene glycol and which has a melting point of about 35 to about 40° C., an acid value of less than about 2, a saponification value of 185 to 200 and an iodine value of less than about 3) may also be used. LABRAFIL® lipophilic components can be obtained, for example, from Gattefossé (Paramus, N.J., USA).

In one embodiment, the alkylene polyol ethers or esters include products obtainable by transesterification of glycerides, e.g. triglycerides, with poly-($C_2$-$C_4$ alkylene) glycols, e.g. poly-ethylene glycols and, optionally, glycerol. Such transesterification products are generally obtained by alcoholysis of glycerides, e.g. triglycerides, in the presence of a poly-($C_2$-$C_4$ alkylene) glycol, e.g. polyethylene glycol and, optionally, glycerol (i.e. to effect transesterification from the glyceride to the poly-alkylene glycol/glycerol component, i.e. via poly-alkylene glycolysis/glycerolysis). In general such reaction is effected by reacting the indicated components (glyceride, polyalkylene glycol and, optionally, glycerol) at elevated temperature under an inert atmosphere with continuous agitation.

In one embodiment, the glycerides are fatty acid triglycerides, e.g. ($C_{10}$-$C_{22}$ fatty acid) triglycerides, including natural and hydrogenated oils, in particular vegetable oils. In one embodiment, vegetable oils include, for example, olive, almond, peanut, coconut, palm, soybean and wheat germ oils and, in particular, natural or hydrogenated oils rich in ($C_{12}$-$C_{18}$ fatty acid) ester residues. In one embodiment, polyalkylene glycol materials are polyethylene glycols, in particular polyethylene glycols having a molecular weight of from ca. 500 to ca. 4,000, e.g. from ca. 1,000 to ca. 2,000.

In one embodiment, alkylene polyol ethers or esters include, but are not limited to, mixtures of $C_3$-$C_5$ alkylene triol esters, e.g. mono-, di- and tri-esters in variable relative amount, and poly ($C_2$-$C_4$ alkylene) glycol mono- and di-esters, together with minor amounts of free $C_3$-$C_5$ alkylene triol and free poly-($C_2$-$C_5$ alkylene) glycol. As hereinabove set forth, in one embodiment, the alkylene triol moiety is glyceryl; in another embodiment, the polyalkylene glycol moieties include, but are not limited to, polyethylene glycol, in certain embodiments, having a molecular weight of from ca. 500 to ca. 4,000; and in another embodiment, the fatty acid moieties will be $C_{10}$-$C_{22}$ fatty acid ester residues, in certain embodiments, saturated $C_{10}$-$C_{22}$ fatty acid ester residues.

In one embodiment, the alkylene polyol ethers or esters include transesterification products of a natural or hydrogenated vegetable oil and a polyethylene glycol and, optionally, glycerol; or compositions comprising or consisting of glyceryl mono-, di- and tri-$C_{10}$-$C_{22}$ fatty acid esters and polyethylene glycol mono- and di-$C_{10}$-$C_{22}$ fatty esters (optionally together with, e.g. minor amounts of free glycerol and free polyethylene glycol).

In one embodiment, the alkylene polyol ethers or esters include, but are not limited, those commercially available under the trade name GELUCIRE® from e.g. Gattefossé, in particular the products:

a) GELUCIRE® 33/01, which has an m.p.=ca. 33-37° C. and a saponification value of about 230-255;

b) GELUCIRE® 39/01, m.p.=ca. 37.5-41.5° C., saponification value of about 225-245; and c) GELUCIRE® 43/01, m.p.=ca. 42-46° C., saponification value of about 220-240.

Products (a) to (c) above all have an acid value of maximum of 3. The SEDDS or SMEDDS system provided herein may include mixtures of such ethers or esters.

B. Surfactants

The SEDDS or SMEDDS system provided herein can contain one or more surfactants to reduce the emulsion's interfacial tension thereby providing thermodynamic stability. Surfactants may be complex mixtures containing side products or unreacted starting products involved in the preparation thereof, e.g. surfactants made by polyoxyethylation may contain another side product, e.g. polyethylene glycol.

In one embodiment, surfactants include, but are not limited to:

B1) Polyoxyethylene Mono Esters of a Saturated $C_{10}$ to $C_{22}$ Polymer

These include, but are not limited to, $C_{11}$ substituted e.g. hydroxy fatty acid; e.g. 12 hydroxy stearic acid PEG ester, e.g. of PEG about e.g. 600-900, e.g. 660 Daltons MW, e.g. SOLUTOL®HS15 from BASF (Ludwigshafen, Germany). SOLUTOL®HS15, according to the BASF technical information (July 2003), comprises polyglycol mono- and di-esters of 12-hydroxystearic acid (=lipophilic part) and about 30% of free polyethylene glycol (=hydrophilic part). A small part of the 12-hydroxy group can be etherified with polyethylene glycol. SOLUTOL® HS15 has a hydrogenation value of 90 to 110, a saponification value of 53 to 63, an acid number of maximum 1, an iodine value of maximum 2, and a maximum water content of about 0.5% by weight. In one embodiment, the surfactant is SOLUTOL® HS 15.

B2) Alkylene Polyol Ethers or Esters

In one embodiment, the alkylene polyol ethers or esters as described above for use in the pharmaceutical compositions provided herein include those commercially available under the trade name GELUCIRE® from e.g. Gattefossé (Paramus, N.J., USA), in particular the products:

a) GELUCIRE® 44/14, m.p.=ca. 42.5-47.5° C., saponification value of about 79-93;

b) GELUCIRE® 50/13, m.p.=ca. 46-51° C., saponification value of about 67-81;

Products (a) to (b) above both have an acid value of maximum of 2.

In one embodiment, the alkylene polyol ethers or esters have an iodine value of maximum 2. The SEDDS or SMEDDS system provided herein may further include mixtures of such ethers or esters.

GELUCIRE® products are inert semi-solid waxy materials with amphiphilic character. They are identified by their melting point and their HLB value. Most GELUCIRE® grades are saturated polyglycolised glycerides obtainable by polyglycolysis of natural hydrogenated vegetable oils with polyethylene glycols. They are composed of a mixture of mono-, di- and tri-glycerides and mono- and di-fatty acid esters of polyethylene glycol. In one embodiment, the $C_{10}$ glyceride is GELUCIRE® 44/14 which has a nominal melting point of 44° C. and an HLB of 14. GELUCIRE® 44/14 exhibits the following additional characterizing data: acid value of max. 2, iodine value of max. 2, saponification value of 79-93, hydroxyl value of 36-56, peroxide value of max. 6, alkaline impurities max. 80, water content max. 0.50, free glycerol content max. 3, monoglycerides content 3.0-8.0. (H. Fiedler, loc. cit., vol 1, page 676; manufacturer information).

In one embodiment, the surfactant is present in a range of from about 5 to about 99.9% by weight, or in a range of from about 30% to about 99.9% of the SEDDS or SMEDDS system provided herein.

In one embodiment, the surfactant comprises about 30% to about 70%, or about 40% to about 60% by weight of the carrier medium of the SEDDS or SMEDDS system provided herein.

In one embodiment, the SEDDS or SMEDDS system provided herein include additives e.g. antioxidants, flavors, sweeteners and other components known to those skilled in the art.

In one embodiment, the antioxidants include ascorbyl palmitate, butylated hydroxy anisole (BHA), 2,6-di-tert-butyl-4-methyl phenol (BHT) and tocopherols. In a further embodiment, the antioxidant is BHT.

In one embodiment, these additives may comprise about 0.005% to about 5% or about 0.01% to about 0.1% by weight of the total weight of the SEDDS or SMEDDS system. Antioxidants, or stabilizers typically provide up to about 0.005 to about 1% by weight based on the total weight of the composition. Sweetening or flavoring agents typically provide up to about 2.5% or 5% by weight based on the total weight of the composition.

The aforementioned additives can also include components that act as surfactants to solidify a liquid micro-emulsion pre-concentrate. These include solid polyethylene glycols (PEGs) and GELUCIRE® products, in one embodiment, the GELUCIRE® products include those such as GELUCIRE® 44/14 or GELUCIRE® 50/13.

When the SEDDS or SMEDDS system provided herein is combined with water or an aqueous solvent medium to obtain an emulsion, for example a microemulsion, the emulsion or microemulsion may be administered orally, for example in the form of a drinkable solution. The drinkable solution may comprise water or any other palatable aqueous system, such as fruit juice, milk and the like. In one embodiment, the relative proportion of the lipophilic component(s), the surfactant(s) and the hydrophilic component(s) lie within the "Microemulsion" region on a standard three way plot graph. The compositions will therefore be capable, on addition to an aqueous medium, of providing microemulsions, for example having a mean particle size of <200 nm.

In one embodiment, the carrier medium comprises about 30 to 70% by weight of one or more lipophilic components, wherein the one or more lipophilic components are a medium chain fatty acid triglyceride (A1), or a transesterified ethoxylated vegetable oil (A6). In a further embodiment, the medium chain fatty acid triglyceride (A1) is LABRAFAC® (Gattefossé, Paramus, N.J., USA). In another embodiment, the transesterified ethoxylated vegetable oil (A6) is LABRAFIL® (Gattefossé, Paramus, N.J., USA).

In one embodiment, the carrier medium comprises about 30 to 70% by weight of one or more surfactants, wherein the one or more surfactants are a polyoxyethylene mono ester ($C_5$), an alkylene polyol ether or ester ($C_{10}$), or a transesterified, polyoxyethylated caprylic-capric acid glyceride ($C_{13}$). In a further embodiment, the polyoxyethylene mono ester ($C_5$) is SOLUTOL® HS15 (BASF, Ludwigshafen, Germany). In another embodiment, the alkylene polyol ether or ester ($C_{10}$) is GELUCIRE®44/14 (Gattefosse, Paramus, N.J., USA). In yet another embodiment, the transesterified, polyoxyethylated caprylic-capric acid glyceride ($C_{13}$) is LABRASOL® (Gattefossé, Paramus, N.J., USA).

In one embodiment, the carrier medium comprises about 70% by weight LABRASOL®, about 18.3% by weight LABRAFAC® and about 11.7% by weight LABRAFIL®.

In one embodiment, the carrier medium comprises a range of about 65.1% to about 74.9% by weight LABRASOL®, a range of about 17.0% to about 19.6% by weight LABRAFAC® and a range of about 10.9% to about 12.5% by weight LABRAFIL®.

In one embodiment, the carrier medium comprises about 35% by weight LABRASOL®, about 35% by weight LABRAFAC® and about 30% by weight SOLUTOL® HS15.

In one embodiment, the carrier medium comprises a range of about 33.6% to about 37.4% by weight LABRASOL®, a range of about 33.6% to about 37.4% by weight LABRAFAC® and a range of about 27.9% to about 32.1% by weight SOLUTOL® HS15.

In one embodiment, the carrier medium comprises about 35% by weight LABRAFIL®, about 35% by weight LABRAFAC®, and about 30% by weight SOLUTOL®HS15.

In one embodiment, the carrier medium comprises a range of about 33.6% to about 37.4% by weight LABRAFIL®, a range of about 33.6% to about 37.4% by weight LABRAFAC®, and a range of about 27.9% to about 32.1% by weight SOLUTOL® HS15.

In one embodiment, the carrier medium comprises about 35% by weight GELUCIRE®44/14, about 35% by weight LABRAFAC®, and about 30% by weight SOLUTOL®HS15.

In one embodiment, the carrier medium comprises a range of about 33.6% to about 37.4% by weight GELUCIRE®44/14, a range of about 33.6% to about 37.4% by weight LABRAFAC®, and a range of about 27.9% to about 32.1% by weight SOLUTOL® HS15.

In one embodiment, provided herein is a SEDDS or SMEDDS system comprising a Compound provided herein, and a carrier medium comprising one or more surfactants. In one embodiment, the SEDDS or SMEDDS system additionally comprises an additive.

In one embodiment, the SEDDS or SMEDDS system comprises about 0.01% to about 5% by weight of a Compound provided herein.

In one embodiment, the dispersible pharmaceutical composition comprises about 95% to 99.09% by weight of one or more surfactants, wherein the one or more surfactants are selected from a group comprising an alkylene polyol ether or ester ($C_{10}$), and a polyoxyethylene mono ester ($C_5$). In a further embodiment, the alkylene polyol ether or ester ($C_{10}$) is GELUCIRE®44/14 (Gattefosse, Paramus, N.J., USA). In yet another embodiment, the polyoxyethylene mono ester ($C_5$) is SOLUTOL® HS15 (BASF, Ludwigshafen, Germany).

In one embodiment, the dispersible pharmaceutical composition comprises about 0.01% to about 0.1% by weight of an additive selected from a group comprising an antioxidant and a preservative. In a further embodiment, the additive is 2,6-di-tert-butyl-4-methylphenol (BHT).

In one embodiment, the SEDDS or SMEDDS system comprises about 0.28% by weight of a Compound provided herein, about 49.87% A by weight of GELUCIRE® 44/14, about 49.84% by weight of SOLUTOL® HS15 and about 0.01% by weight of BHT.

In one embodiment, the SEDDS or SMEDDS system comprises a range of about 0.26% to about 0.30% by weight of a Compound provided herein, a range of about 46.4% to about 53.4% by weight of GELUCIRE®44/14, a range of about 46.4% to about 53.3% by weight of SOLUTOL® HS15 and a range of about 0.009% to about 0.011% by weight of BHT.

In one embodiment, the SEDDS or SMEDDS system comprises about 1.43% by weight of a Compound provided herein, about 49.87% A by weight of GELUCIRE® 44/14, about 48.69% by weight of SOLUTOL® HS15 and about 0.01% by weight of BHT.

In one embodiment, the SEDDS or SMEDDS system comprises a range of about 1.33% to about 1.53% by weight of a Compound provided herein, a range of about 46.4% to about 53.4% by weight of GELUCIRE®44/14, a range of about 45.3% to about 52.1% by weight of SOLUTOL® HS15 and a range of about 0.009% to about 0.011% by weight of BHT.

In one embodiment, the SEDDS or SMEDDS system comprises about 2.67% by weight of a Compound provided herein, about 49.87% A by weight of GELUCIRE® 44/14, about 47.45% by weight of SOLUTOL® HS15 and about 0.01% by weight of BHT.

In one embodiment, the SEDDS or SMEDDS system comprises a range of about 2.48% to about 2.86% by weight of a Compound provided herein, a range of about 46.4% to about 53.4% by weight of GELUCIRE®44/14, a range of about 44.1% to about 50.8% by weight of SOLUTOL® HS15 and a range of about 0.009% to about 0.011% by weight of BHT.

In one embodiment, when the SEDDS or SMEDDS system provided herein is used to fill capsules for use in oral administration. The capsule may have a soft or hard capsule shell, for example, the capsule may be made of gelatine.

One group of SEDDS or SMEDDS systems provided herein may, on addition to water, provide aqueous microemulsions having an average particle size of about <200 nm (2,000 Å), about <150 nm (1,500 Å), or about <100 nm (1,000 Å).

In one embodiment, the SEDDS or SMEDDS systems provided herein exhibit advantageous properties when administered orally; for example in terms of consistency and high level of bioavailability obtained in standard bioavailability trials.

Pharmacokinetic parameters, for example, drug substance absorption and measured for example as blood levels, also can become more predictable and problems in administration with erratic absorption may be eliminated or reduced. Additionally pharmaceutical compositions provided herein are effective with biosurfactants or tenside materials, for example bile salts, being present in the gastro-intestinal tract. That is, pharmaceutical compositions provided herein are fully dispersible in aqueous systems comprising such natural tensides and thus capable of providing emulsion or microemulsion systems and/or particulate systems in situ which are stable. The function of pharmaceutical compositions provided herein upon oral administration remain substantially independent of and/or unimpaired by the relative presence or absence of bile salts at any particular time or for any given individual. Compositions provided herein may also reduce variability in inter- and intra-patient dose response.

In one embodiment, provided herein is a SEDDS or SMEDDS system comprising a Compound provided herein, and a carrier medium comprising one or more lipophilic components and one or more surfactants.

5.3 Patient Populations

In some embodiments, a subject treated for KS in accordance with the methods provided herein is a human who has or is diagnosed with KS. In specific embodiments, a subject treated for KS in accordance with the methods provided herein is a human who is KSHV-positive. In certain embodiments, a subject treated for KS in accordance with the methods provided herein is a human who has or is diagnosed with classic KS. In other embodiments, a subject treated for KS in accordance with the methods provided herein is a human who has or is diagnosed with endemic KS or African KS, either African cutaneous or African lymphadenopathic KS. In other embodiments, a subject treated for KS in accordance with the methods provided herein is a human who has or is diagnosed with AIDS-associated KS or epidemic KS. In other embodiments, a subject treated for KS in accordance with the methods provided herein is a human who has or is diagnosed with iatrogenic or immunosuppression-associated KS. In some embodiments, a subject treated for KS in accordance with the methods provided herein is a human who has or is diagnosed with KS who is at stage T0I0S0, T0I0S1, T0I1S1, T1I1S1, T1I0S1, T1I0S0, T1I1S0 or T0I1S0.

In certain embodiments, a subject treated for KS in accordance with the methods provided herein is a human predisposed or susceptible to KS. In some embodiments, a subject treated for KS in accordance with the methods provided herein is a human at risk of developing KS. In specific embodiments, a subject treated for KS in accordance with the methods provided herein is a human that meets one, two or more, or all of the criteria for subjects in the working examples in Section 11 et seq.

In specific embodiments, a subject treated for KS in accordance with the methods provided herein has one or more purple, brown or red lesions on the skin. In certain embodiments, a subject treated for KS in accordance with the methods provided herein has lesions on the skin that are present on, but not limited to, the feet, legs, hands, arms, face, neck, chest, shoulders and back. In specific embodiments, a subject treated for KS in accordance with the methods provided herein has at least five, previously non-radiated, measurable cutaneous lesions, which can be used as indicator lesions, and a sufficient number of non-indicator cutaneous lesions measuring ≥4×4 mm. In some embodiments, a subject treated for KS in accordance with the methods provided herein has lesions on the skin, with or without lymph node, oral cavity, throat, GI tract and/or lung involvement. GI and pulmonary involvement may be asymptomatic or minimally symptomatic. In certain embodiments, a subject treated for KS in accordance with the methods provided herein has one or more lesions in the oral cavity, lungs, throat, liver or digestive tract (GI tract). In other embodiments, a subject treated for KS in accordance with the methods provided herein does not have lesions on the skin, but has lesions in the lymph nodes and/or the oral cavity and/or the throat and/or the GI tract and/or the lungs and/or any other visceral organ. In particular embodiments, a subject treated for KS in accordance with the methods provided herein has one or more KSHV-positive lesions and/or lymphomas.

In one embodiment, a subject treated for KS in accordance with the methods provided herein has a Karnofsky performance status equal to or over 60. In another embodiment, a subject treated for KS in accordance with the methods provided herein has a Karnofsky performance status equal to or less than 60. In one embodiment, a subject treated for KS in accordance with the methods provided herein has a life expectancy equal to or less than 3 months. In another embodiment, a subject treated for KS in accordance with the methods provided herein has a life expectancy greater or equal to 3 months.

In one embodiment, a subject treated for KS in accordance with the methods provided herein is a human infant. In one embodiment, a subject treated for KS in accordance with the methods provided herein is an elderly human. In another embodiment, a subject treated for KS in accordance with the methods provided herein is a human adult. In another embodiment, a subject treated for KS in accordance with the methods provided herein is a human child. In another embodiment, a subject treated for KS in accordance with the methods provided herein is a human toddler. In a specific embodiment, a subject treated for KS in accordance with the methods provided herein is a human that is 18 years old or is older than 18 years old. In certain embodiments, a subject treated for KS in accordance with the methods provided herein is a female human that is not pregnant or is not breast-feeding. In other embodiments, a subject treated for KS in accordance with the methods provided herein is a human that is pregnant or will become pregnant, or is breastfeeding. In certain embodiments, a subject treated for KS in accordance with the methods provided herein is a male human. In some embodiments, a subject treated for KS in accordance with the methods provided herein is a female human.

In certain embodiments, a subject treated for KS in accordance with the methods provided herein is a human that is about 1 to about 12 months old, about 1 to about 10 years old, about 10 to about 12 years old, about 12 to about 18 years old, about 18 to about 30 years old, about 30 to about 40 years old, about 40 to about 50 years old, about 50 to about 60 years old, about 60 to about 70 years old, about 70 to about 80 years old, about 80 to about 90 years old, about 90 to about 100 years old, or any age in between.

In particular embodiments, a subject treated for KS in accordance with the methods provided herein is a human that is in an immunocompromised state or immunosuppressed state. In specific embodiments, a subject treated for KS in accordance with the methods provided herein is a human that is HIV-positive or has AIDS. In certain embodiments, a subject treated for KS in accordance with the methods provided herein is a human receiving or recovering from immunosuppressive therapy. In certain embodiments, a subject treated for KS in accordance with the methods provided herein is a human that has or is at risk of getting cancer (e.g., metastatic cancer), a viral infection, a fungal infection, a parasitic infection or a bacterial infection. In specific embodiments, a subject treated for KS in accordance with the methods provided herein is a human that is HIV-positive or has AIDS and has an opportunistic infection, such as Aspergillosis, *Bartonella henselae* infection, Candidiasis, Coccidioidomycosis, Cryptococcosis, Cryptosporidiosis, Cytomegalovirus disease, herpes simplex infection, histoplasmosis, microsporidiosis, *Mycobacterium avium* infection, *M. kansasii infection, Mycobacterium tuberculosis* infection, Nocardiosis, *Pneumocystis carinii* pneumonia, and *Salmonella septicemia*. In certain embodiments, a subject treated for KS in accordance with the methods provided herein is a human that is HIV-positive or has AIDS and cervical cancer, encephalopathy, isosporiasis, Burkitt's lymphoma, toxoplasmosis of brain, or wasting syndrome.

In certain embodiments, a subject treated for KS in accordance with the methods provided herein is a human who is, will or has undergone surgery, chemotherapy and/or radiation therapy. In specific embodiments, a subject treated for KS in accordance with the methods provided herein is a human who is, will or has undergone surgery to remove the KS lesion(s). In certain embodiments, a subject treated for KS in accordance with the methods provided herein is a human that has cystic fibrosis, pulmonary fibrosis or another condition affecting the lungs. In other embodiments, a subject treated for KS in accordance with the methods provided herein is a human that has, will have or has had a tissue or organ transplant.

In specific embodiments, a subject treated for KS in accordance with the methods provided herein is suffering from a condition, e.g., stroke or cardiovascular conditions that may require VEGF therapy, wherein the administration of anti-angiogenic therapies other than a Compound may be contraindicated. For example, in certain embodiments, a subject treated for KS in accordance with the methods provided herein has suffered from a stroke or is suffering from a cardiovascular condition. In some embodiments, a subject treated for KS in accordance with the methods provided herein is a human experiencing circulatory problems. In certain embodiments, a subject treated for KS in accordance with the methods provided herein is a human with diabetic polyneuropathy or diabetic neuropathy. In some embodiments, a subject treated for KS in accordance with the methods provided herein is a human receiving VEGF protein or VEGF gene therapy. In other embodiments, a subject treated for KS in accordance with the methods provided herein is not a human receiving VEGF protein or VEGF gene therapy.

In some embodiments, a subject treated for KS in accordance with the methods provided herein is administered a Compound or a pharmaceutical composition thereof, or a combination therapy before any adverse effects or intolerance to therapies other than the Compound develops. In some embodiments, a subject treated for KS in accordance with the methods provided herein is a refractory patient. In a certain embodiment, a refractory patient is a patient with a tumor that is refractory to a standard therapy (e.g., surgery, radiation, and/or drug therapy such as chemotherapy). In certain embodiments, a patient with cancer associated with KS, is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment of KS, using art-accepted meanings of "refractory" in such a context. In various embodiments, a patient with KS is refractory when one or more tumors associated with KS, have not decreased or have increased. In various embodiments, a patient with cancer associated with KS is refractory when one or more tumors metastasize and/or spreads to another organ. In some embodiments, a patient is in remission. In certain embodiments, a patient is experiencing recurrence of one or more tumors associated with KS.

In some embodiments, a subject treated for KS in accordance with the methods provided herein is a human that has proven refractory to therapies other than treatment with a Compound, but is no longer on these therapies. In certain embodiments, a subject treated for KS in accordance with the methods provided herein is a human already receiving one or more conventional anti-cancer therapies, such as surgery, drug therapy such as chemotherapy, or radiation. Among these patients are refractory patients, patients who are too young for conventional therapies, and patients with recurring tumors despite treatment with existing therapies.

In some embodiments, a subject treated for KS in accordance with the methods provided herein is a human susceptible to adverse reactions to conventional therapies. In some embodiments, a subject treated for KS in accordance with the methods provided herein is a human that has not received a therapy, e.g., drug therapy such as chemotherapy, surgery, or radiation therapy, prior to the administration of a Compound or a pharmaceutical composition thereof. In other embodiments, a subject treated for KS in accordance with the methods provided herein is a human that has received a therapy prior to administration of a Compound. In some embodiments, a subject treated for KS in accordance with the methods provided herein is a human that has experienced adverse side effects to the prior therapy or the prior therapy was discontinued due to unacceptable levels of toxicity to the human.

In some embodiments, a subject treated for KS in accordance with the methods provided herein has had no prior exposure to another anti-angiogenic therapy (e.g., an anti-VEGF monoclonal antibody, an anti-VEGFR monoclonal antibody, a tyrosine kinase inhibitor, or other angiogenesis pathway modulator). In particular embodiments, a subject treated for KS in accordance with the methods provided herein does not have uncontrolled hypertension, major bleeding, HIV infection or recent acute cardiovascular event. In some embodiments, a subject treated for KS in accordance with the methods provided herein is not, has not and/or will not receive a drug that is primarily metabolized by CYP2D6.

In particular embodiments, a subject treated for KS in accordance with the methods provided herein has not and will not have received a drug that is primarily metabolized by CYP2D6 1, 2, 3 or 4 weeks before receiving a Compound or a pharmaceutical composition thereof and 1, 2, 3 or 4 weeks after receiving the Compound or pharmaceutical composition. Examples of such drugs include, without limitation, some antidepressants (e.g., tricyclic antidepressants and selective serotonin uptake inhibitors), some antipsychotics, some beta-adrenergic receptor blockers, and certain anti-arrhythmics. Certain anti-retroviral agents, including ritonavir, lopinivir/ritonavir, and delavirdine, rely to some extent on CYP2D6 for their clearance.

In specific embodiments, a subject treated for KS in accordance with the methods provided herein is not, has not and/or will not receive tamoxifen. In particular embodiments, a subject treated for KS in accordance with the methods provided herein has not and will not have received tamoxifen 1, 2, 3 or 4 weeks before receiving a Compound or a pharmaceutical composition thereof and 1, 2, 3 or 4 weeks after receiving the Compound or pharmaceutical composition thereof. In specific embodiments, a subject treated for KS in accordance with the methods provided herein has received tamoxifen, e.g., for 1, 2, 3 or 4 weeks before receiving a Compound or a pharmaceutical composition thereof.

In certain embodiments, a subject treated for KS in accordance with the methods provided herein is not, has not and/or will not have received an anti-viral drug 1, 2, 3 or 4 weeks before receiving a Compound or a pharmaceutical composition thereof and 1, 2, 3 or 4 weeks after receiving the Compound or pharmaceutical composition thereof. In other embodiments, a subject treated for KS in accordance with the methods provided herein is, has and/or will have received an anti-viral drug 1, 2, 3 or 4 weeks before receiving a Compound or a pharmaceutical composition thereof and 1, 2, 3 or 4 weeks after receiving the Compound or pharmaceutical composition thereof. In specific embodiments, a subject treated for KS in accordance with the methods provided herein is not, has not and/or will not receive ritonavir, lopinivir/ritonavir, or delavirdine. In particular embodiments, a subject treated for KS in accordance with the methods provided herein has not and will not have received ritonavir, lopinivir/ritonavir, or delavirdine 1, 2, 3 or 4 weeks before receiving a Compound or a pharmaceutical composition thereof and 1, 2, 3 or 4 weeks after receiving the Compound or pharmaceutical composition. In other embodiments, a subject treated for KS in accordance with the methods provided herein is, has and/or will receive ritonavir, lopinivir/ritonavir, or delavirdine.

5.4 Dosage and Administration

In accordance with the methods for treating KS provided herein, a Compound or a pharmaceutical composition thereof can be administered to a subject in need thereof by a variety of routes in amounts which result in a beneficial or therapeutic effect. A Compound or pharmaceutical composition thereof may be orally administered to a subject in need thereof in accordance with the methods for treating KS provided herein. The oral administration of a Compound or a pharmaceutical composition thereof may facilitate subjects in need of such treatment complying with a regimen for taking the Compound or pharmaceutical composition. Thus, in a specific embodiment, a Compound or pharmaceutical composition thereof is administered orally to a subject in need thereof.

Other routes of administration include, but are not limited to, intravenous, intrathecal, intradermal, intramuscular, subcutaneous, intranasal, inhalation, transdermal, topical, transmucosal, intracranial, intratumoral, epidural and intra-synovial. In one embodiment, a Compound or a pharmaceutical composition thereof is administered systemically (e.g., parenterally) to a subject in need thereof. In another embodiment, a Compound or a pharmaceutical composition thereof is administered locally (e.g., intratumorally) to a subject in need thereof. In one embodiment, a Compound or a pharmaceutical composition thereof is administered via a route that permits the Compound to cross the blood-brain barrier (e.g., orally).

Evaluation has indicated that Compound #10 penetrates the blood-brain barrier. Table 32 provides brain tissue plasma concentration ratios determined by whole-body autoradiography at specified times after a single oral administration of $^{14}$C-Compound #10 to rats (50 mg/kg).

TABLE 32

| | Blood-Brain Barrier Penetration | | | | | | | | | |
|---|---|---|---|---|---|---|---|---|---|---|
| | 6 Hours | | 12 Hours | | 24 Hours | | 48 Hours | | 72 Hours | |
| Tissue | M | F | M | F | M | F | M | F | M | F |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Medulla | 1.60 | 1.42 | 1.98 | 3.82 | 1.83 | 1.69 | 1.20 | 2.01 | NA | 1.88 |
| Olfactory lobe | 1.42 | 1.38 | 1.35 | 2.45 | 1.23 | 1.13 | 0.967 | NA | NA | 3.33 |
| Pituitary gland | 4.06 | 4.27 | 3.22 | 5.48 | 2.72 | 2.33 | 0.890 | 3.68 | NA | 1.58 |
| Spinal cord | 1.14 | 0.898 | 1.24 | 1.92 | 1.75 | 1.60 | 1.43 | 1.60 | 1.84 | 2.75 |

In accordance with the methods for treating KS provided herein that involve administration of a Compound in combination with one or more additional therapies, the Compound and one or more additional therapies may be administered by the same route or a different route of administration.

The dosage and frequency of administration of a Compound or a pharmaceutical composition thereof is administered to a subject in need thereof in accordance with the methods for treating KS provided herein will be efficacious while minimizing any side effects. The exact dosage and frequency of administration of a Compound or a pharmaceutical composition thereof can be determined by a practitioner, in light of factors related to the subject that requires treatment. Factors which may be taken into account include the severity of the disease state, general health of the subject, age, weight, and gender of the subject, diet, time and frequency of administration, drug combination(s), reaction sensitivities, and tolerance/response to therapy. The dosage and frequency of administration of a Compound or a pharmaceutical composition thereof may be adjusted over time to provide sufficient levels of the Compound or to maintain the desired effect.

In certain embodiments, a Compound or a pharmaceutical composition thereof is administered to a subject in need thereof in accordance with the methods for treating KS provided herein at a dosage and a frequency of administration that achieves one or more of the following: (i) decreases the production and/or concentration of VEGF or other angiogenic or inflammatory mediators or changes tumor blood flow or metabolism, or peritumoral inflammation or edema in a subject with KS or an animal model with a pre-established human tumor; (ii) reduces or ameliorates the severity of KS and/or a symptom associated therewith in a subject with KS; (iii) reduces the number of symptoms and/or the duration of a symptom(s) associated with KS in a subject with KS; (iv) prevents the onset, progression or recurrence of a symptom associated with KS in a subject with KS; (v) reduces skin lesions associated with KS in a subject with KS; and/or (vi) enhances or improves the therapeutic effect of another therapy in a subject with KS or an animal model with a pre-established human tumor.

In certain embodiments, a Compound or a pharmaceutical composition thereof is administered to a subject in need thereof in accordance with the methods for treating KS provided herein at a dosage and a frequency of administration that results in one or more of the following: (i) regression of a tumor associated with KS and/or inhibition of the progression of a tumor associated with KS in a subject with KS or an animal model with a pre-established human tumor; (ii) reduction in the growth of a tumor associated with KS and/or a decrease in the tumor size (e.g., volume or diameter) of a tumor associated with KS in a subject with KS or an animal model with a pre-established human tumor; (iii) the size of a tumor associated with KS is maintained and/or the tumor does not increase or increases by less than the increase of a similar tumor after administration of a standard therapy as measured by conventional methods available to one of skill in the art, such as measurement of a lesion, photography, MRI, DCE-MRI, PET Scan, X-ray, and CT Scan; (iv) reduction in the formation of a tumor associated with KS in a subject with KS or an animal model with a pre-established human tumor; (v) eradication, removal, or control of primary, regional and/or metastatic tumors associated with KS in a subject with KS or an animal model with a pre-established human tumor; (vi) a decrease in the number or size of metastases associated with KS in a subject with KS or an animal model with a pre-established human tumor; and/or (vii) reduction in the growth of a pre-established tumor or decrease in the tumor size (e.g., volume or diameter) of a pre-established tumor in a subject with KS or an animal model with a pre-established human tumor.

In certain embodiments, a Compound or a pharmaceutical composition thereof is administered to a subject in need thereof in accordance with the methods for treating KS provided herein at a dosage and a frequency of administration that achieve one or more of the following: (i) inhibition or reduction in pathological production of VEGF; (ii) stabilization or reduction of peritumoral inflammation or edema in a subject; (iii) reduction of the concentration of VEGF or other angiogenic or inflammatory mediators (e.g., cytokines or interleukins) in biological specimens (e.g., plasma, serum, cerebral spinal fluid, urine, or any other biofluids); (iv) reduction of the concentration of P1GF, VEGF-C, VEGF-D, VEGFR-1, VEGFR-2, IL-6, IL-8 and/or IL-10 in biological specimens (e.g., plasma, serum, cerebral spinal fluid, urine, or any other biofluids); (v) inhibition or decrease in tumor metabolism or perfusion; (vi) inhibition or decrease in angiogenesis or vascularization; and/or (vii) improvement in quality of life as assessed by methods well known in the art, for e.g., a questionnaire.

In certain embodiments, a Compound or a pharmaceutical composition thereof is administered to a subject in need thereof in accordance with the methods for treating KS provided herein at a dosage and a frequency of administration that decrease the number of one, two, three or more, or all previously existing lesions by about 5%, 10%, 15%, 20%, 25%, 35%, 45%, 50%, 55%, 65%, 70%, 75%, 80%, 85%, 90%, 95% or 100% in a subject with KS or an animal model with a pre-established human tumor (e.g., a tumor associated with KS), relative to the number of lesions observed prior to administration of a Compound. In other embodiments, a Compound or a pharmaceutical composition thereof is administered to a subject in need thereof in accordance with the methods for treating KS provided herein at a dosage and a frequency of administration that decreases the number of raised lesions by about 5%, 10%, 15%, 20%, 25%, 35%, 45%, 50%, 55%, 65%, 70%, 75%, 80%, 85%, 90%, 95% or 100% in a subject with KS or an animal model with a pre-established human tumor (e.g., a tumor associated with KS), relative to the number of raised lesions observed prior to administration of a Compound. In certain embodiments, a Compound or a pharmaceutical composition thereof is administered to a subject in need thereof in accordance with the methods for treating KS provided herein at a dosage and a frequency of administration that completely flatten about 5%, 10%, 15%, 20%, 25%, 35%, 45%, 50%, 55%, 65%, 70%, 75%, 80%, 85%, 90%, 95% or 100% of all previously raised lesions in a subject with KS or an animal model with a pre-established human tumor (e.g., a tumor associated with KS). In certain embodiments, a Compound or a pharmaceutical composition thereof is administered to a subject in need thereof in accordance with the methods for treating KS provided herein at a dosage and a frequency of administration that decreases the sum of perpendicular diameters by about 5%, 10%, 15%, 20%, 25%, 35%, 45%, 50%, 55%, 65%, 70%, 75%, 80%, 85%, 90%, 95% or 100% in a subject with KS or an animal model with a pre-established human tumor (e.g., a tumor associated with KS), relative to the sum of perpendicular diameters observed prior to administration of a Compound.

In certain embodiments, a Compound or a pharmaceutical composition thereof is administered to a subject in need thereof in accordance with the methods for treating KS provided herein at a dosage and a frequency of administration that reduces or inhibits KSHV gene transcription or reduces KSHV mRNA levels in tumor biopsies from a subject with KS by about 5%, 10%, 15%, 20%, 25%, 35%, 45%, 50%, 55%, 65%, 70%, 75%, 80%, 85%, 90%, 95% or 100% relative to the respective KSHV gene transcription level or KSHV mRNA levels observed prior to administration of a Compound, as determined using an assay described herein (see, e.g., Example 11 et seq.) or others known to one of skill in the art. In other embodiments, a Compound or a pharmaceutical composition thereof is administered to a subject in need thereof in accordance with the methods for treating KS provided herein at a dosage and a frequency of administration that reduces or inhibits KSHV replication or reduces the number of copies of KSHV in circulating PBMC in a subject with KS by about 5%, 10%, 15%, 20%, 25%, 35%, 45%, 50%, 55%, 65%, 70%, 75%, 80%, 85%, 90%, 95% or 100% relative to the respective KSHV replication level or number of copies of KSHV in circulating PBMC observed prior to administration of a Compound, as determined using an assay described herein (see, e.g., Example 11 et seq.) or others known to one of skill in the art. In certain embodiments, a Compound or a pharmaceutical composition thereof is administered to a subject in need thereof in accordance with the methods for treating KS provided herein at a dosage and a frequency of administration that inhibits or reduces HIV plasma RNA levels by about 5%, 10%, 15%, 20%, 25%, 35%, 45%, 50%, 55%, 65%, 70%, 75%, 80%, 85%, 90%, 95% or 100% in a subject with KS relative to the HIV plasma RNA levels observed prior to administration of a Compound, as determined using an assay described herein or others known to one of skill in the art.

In certain embodiments, a Compound or a pharmaceutical composition thereof is administered to a subject in need thereof in accordance with the methods for treating KS provided herein at a dosage and a frequency of administration that decreases the expression of VEGF, VEGFR-2, VEGFR-3, phospho-Akt, KSHV LANA, orf59, p53 and HIF-1α in tumor biopsies from a subject with KS by about 5%, 10%, 15%, 20%, 25%, 35%, 45%, 50%, 55%, 65%, 70%, 75%, 80%, 85%, 90%, 95% or 100% relative to the respective expression level of VEGF, VEGFR-2, VEGFR-3, phospho-Akt, KSHV LANA, orf59, p53 and HIF-1α in tumor biopsies observed prior to administration of a Compound, as determined using an assay described herein or others known to one of skill in the art.

In certain embodiments, a Compound or a pharmaceutical composition thereof is administered to a subject in need thereof in accordance with the methods for treating KS provided herein at a dosage and a frequency of administration that alters cellular gene expression of one, two, three or more of the following genes in tumor biopsies from a subject with KS by about 5%, 10%, 15%, 20%, 25%, 35%, 45%, 50%, 55%, 65%, 70%, 75%, 80%, 85%, 90%, 95% or 100% relative to the respective cellular gene expression levels observed prior to administration of a Compound, as determined using an assay described herein or others known to one of skill in the art: IANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGFA, VEGFC, ANGPTL3, BAI1, COL4A3, IL8, LAMA5, NRP1, NRP2, STAB1, ANGPTL4, PECAM1, PF4, PROK2, SERPINF1, TNFAIP2, HAND2, SPHK1, CCL11, CCL2, CXCL1, CXCL10, CXCL3, CXCL5, CXCL6, CXCL9, IFNA1, IFNB1, IFNG, IL1B, IL6, MDK, TNF, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL11, CCL2, CDH5, COL18A1, EDG1, ENG, ITGAV, ITGB3, THBS1, THBS2, LECT1, LEP, MMP2, MMP9, PLAU, PLG, TIMP1, TIMP2, TIMP3, AKT1, HIF1A, HPSE, ID1, ID3, NOTCH4, and PTGS1.

In certain embodiments, a Compound or a pharmaceutical composition thereof is administered to a subject in need thereof in accordance with the methods for treating KS provided herein at a dosage and a frequency of administration that reduces the plasma and serum levels of VEGF, VEGF-C, VEGF-D, VEGF-R1, VEGF-R2, VEGF165b, P1GF, IL-6, IL-8 and IL-10, by about 5%, 10%, 15%, 20%, 25%, 35%, 45%, 50%, 55%, 65%, 70%, 75%, 80%, 85%, 90%, 95% or 100% in a subject with KS relative to the respective plasma and serum levels of VEGF, VEGF-C, VEGF-D, VEGF-R1, VEGF-R2, VEGF165b, P1GF, IL-6, IL-8 and IL-10 observed prior to administration of a Compound, as determined using an assay described herein or others known to one of skill in the art. In specific embodiments, a Compound or a pharmaceutical composition thereof is administered to a subject in need thereof in accordance with the methods for treating KS provided herein at a dosage and a frequency of administration that increases CD4 counts in a subject with KS by about 5%, 10%, 15%, 20%, 25%, 35%, 45%, 50%, 55%, 65%, 70%, 75%, 80%, 85%, 90%, 95% or 100% relative to the respective CD4 counts observed prior to administration of a Compound, as determined using an assay described herein or others known to one of skill in the art.

In one aspect, a method for treating KS presented herein involves the administration of a unit dosage of a Compound or a pharmaceutical composition thereof. The unit dosage may be administered as often as determined effective (e.g., once, twice or three times per day, every other day, once or twice per week, biweekly or monthly). In certain embodiments, a method for treating KS presented herein involves the administration to a subject in need thereof of a unit dose of a Compound or a pharmaceutical composition thereof that ranges from about 0.1 milligram (mg) to about 1000 mg, from about 1 mg to about 1000 mg, from about 5 mg to about 1000 mg, from about 10 mg to about 500 mg, from about 40 mg to about 500 mg, from about 80 mg to about 500 mg, from about 100 mg to about 500 mg, from about 150 mg to about 500 mg, from about 200 mg to about 500 mg, from about 250 mg to about 500 mg, from about 100 mg to about 1000 mg, or from about 500 mg to about 1000 mg, or any range in between. In some embodiments, a method for treating KS presented herein involves the administration to a subject in need thereof of a unit dose of a Compound or a pharmaceutical composition thereof of about 15 mg, 16, mg, 17 mg, 18 mg, 19 mg, 20 mg, 21, mg, 22 mg, 23 mg, 24 mg, 25 mg, 26 mg, 27 mg, 28 mg, 29 mg, 30 mg or 40 mg. In certain embodiments, a method for treating KS presented herein involves the administration to a subject in need thereof of a unit dose of a Compound or a pharmaceutical composition thereof of about 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg. In some embodiments, a method for treating KS presented herein involves the administration to a subject in need thereof of a unit dose of a Compound or a pharmaceutical composition thereof of at least about 0.1 mg, 1 mg, 5 mg, 10 mg, 20 mg, 30 mg, 40 mg, 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg or more. In certain embodiments, a method for treating KS presented herein involves the administration to a subject in need thereof of a unit dose of a Compound or a pharmaceutical composition thereof of less than about 35 mg, less than about 40 mg, less than about 45 mg, less than about 50 mg, less than about 60 mg, less than about 70 mg, or less than about 80 mg.

In specific embodiments, a method for treating KS presented herein involves the administration to a subject in need thereof of a unit dose of a Compound or a pharmaceutical composition thereof of about 20 mg to about 500 mg, about 40 mg to about 500 mg, about 40 mg to about 200 mg, about 40 mg to about 150 mg, about 75 mg to about 500 mg, about 75 mg to about 450 mg, about 75 mg to about 400 mg, about 75 mg to about 350 mg, about 75 mg to about 300 mg, about 75 mg to about 250 mg, about 75 mg to about 200 mg, about 100 mg to about 200 mg, or any range in between. In other specific embodiments, a method for treating KS presented herein involves the administration to a subject in need thereof of a unit dose of a Compound or a pharmaceutical composition thereof of about 20 mg, 25 mg, 30 mg, 35 mg, 40 mg, 50 mg, 60 mg, 75 mg, 80 mg, 90 mg, 100 mg, 125 mg, 140 mg, 150 mg, 160 mg, 165 mg, 170 mg, 175 mg, 200 mg, 210 mg, 215 mg or 225 mg. In some embodiments, a method for treating KS presented herein involves the administration to a subject in need thereof of a unit dose of a Compound or a pharmaceutical composition thereof of about 250 mg, 300 mg, 350 mg, 400 mg, 500 mg, 600 mg, 700 mg, 800 mg, 900 mg, or 1000 mg. In some embodiments, a unit dose of a Compound or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly.

In certain embodiments, a method for treating KS presented herein involves the administration to a subject in need thereof of a unit dose of a Compound or a pharmaceutical composition thereof that ranges from about 50 mg to about 500 mg per day. In some embodiments, a method for treating KS presented herein involves the administration to a subject in need thereof of a unit dose of a Compound or a pharmaceutical composition thereof that ranges from about 40 mg to about 500 mg per day, about 80 mg to about 500 mg per day, about 100 mg to about 500 mg per day, about 80 mg to about 400 mg per day, about 80 mg to about 300 mg per day, about 80 mg to about 200 mg per day, about 200 mg to about 300 mg per day, about 200 mg to about 400 mg per day, or any range in between.

In a specific embodiment, a method for treating KS presented herein involves the administration to a subject in need thereof of a unit dose of about 20 mg of a Compound or a pharmaceutical composition thereof twice per day. In a specific embodiment, a method for treating KS presented herein involves the administration to a subject in need thereof of a unit dose of about 40 mg of a Compound or a pharmaceutical composition thereof twice per day. In a specific embodiment, a method for treating KS presented herein involves the administration to a subject in need thereof of a unit dose of about 60 mg of a Compound or a pharmaceutical composition thereof twice per day. In another specific embodiment, a method for treating KS presented herein involves the administration to a subject in need thereof of a unit dose of about 80 mg of a Compound or a pharmaceutical composition thereof twice per day. In another specific embodiment, a method for treating KS presented herein involves the administration to a subject in need thereof of a unit dose of about 100 mg of a Compound or a pharmaceutical composition thereof twice per day. In accordance with such embodiments, the unit doses are preferably administered orally to the subject.

In specific embodiments, a method for treating KS presented herein involves the administration to a subject in need thereof of a Compound or a pharmaceutical composition at the dosage, frequency of administration and route of administration set forth in the working examples infra in Section 11 et seq.

In some embodiments, a method for treating KS presented herein involves the administration of a dosage of a Compound or a pharmaceutical composition thereof that is expressed as mg per meter squared (mg/m2). The mg/m2 for a Compound may be determined, for example, by multiplying a conversion factor for an animal by an animal dose in mg/kg to obtain the dose in mg/m2 for human dose equivalent. For regulatory submissions the FDA may recommend the following conversion factors: Mouse=3, Hamster=4.1, Rat=6, Guinea Pig=7.7. (based on Freireich et al., Cancer Chemother. Rep. 50(4):219-244 (1966)). The height and weight of a human may be used to calculate a human body surface area applying Boyd's Formula of Body Surface Area. In specific embodiments, a method for treating KS presented herein involves the administration to a subject in need thereof of an amount of a Compound or a pharmaceutical composition thereof in the range of from about 0.1 mg/m2 to about 1000 mg/m2, or any range in between.

Other non-limiting exemplary doses of a Compound that may be used in the methods for treating KS provided herein include mg or microgram (μg) amounts per kilogram (kg) of subject or sample weight per day such as from about 0.001 mg per kg to about 1500 mg per kg per day, from about 0.001 mg per kg to about 1400 mg per kg per day, from about 0.001 mg per kg to about 1300 mg per kg per day, from about 0.001 mg per kg to about 1200 mg per kg per day, from about 0.001 mg per kg to about 1100 mg per kg per day, from about 0.001 mg per kg to about 1000 mg per kg per day, from about 0.01 mg per kg to about 1500 mg per kg per day, from about 0.01 mg per kg to about 1000 mg per kg per day, from about 0.1 mg per kg to about 1500 mg per kg per day, from about 0.1 mg per kg to about 1000 mg per kg per day, from about 0.1 mg per kg to about 500 mg per kg per day, from about 0.1 mg per kg to about 100 mg per kg per day, or from about 1 mg per kg to about 100 mg per kg per day. In specific embodiments, oral doses for use in the methods provided herein are from about 0.01 mg to about 300 mg per kg body weight per day, from about 0.1 mg to about 75 mg per kg body weight per day, or from about 0.5 mg to 5 mg per kg body weight per day. In certain embodiments, oral doses for use in the methods provided herein involves the oral administration to a subject in need thereof of a dose of a Compound or a pharmaceutical composition thereof that ranges from about 80 mg to about 800 mg per kg per day, from about 100 mg to about 800 mg per kg per day, from about 80 mg to about 600 mg per kg per day, from about 80 mg to about 400 mg per kg per day, from about 80 mg to about 200 mg per kg per day, from about 200 mg to about 300 mg per kg per day, from about 200 mg to about 400 mg per kg per day, from about 200 mg to about 800 mg per kg per day, or any range in between. In certain embodiments, doses of a Compound that may be used in the methods provided herein include doses of about 0.1 mg/kg/day, 0.2 mg/kg/day, 0.3 mg/kg/day, 0.4 mg/kg/day, 0.5 mg/kg/day, 0.6 mg/kg/day, 0.7 mg/kg/day, 0.8 mg/kg/day, 0.9 mg/kg/day, 1 mg/kg/day, 1.5 mg/kg/day, 2 mg/kg/day, 2.5 mg/kg/day, 2.75 mg/kg/day, 3 mg/kg/day, 4 mg/kg/day, 5 mg/kg/day, 6 mg/kg/day, 6.5 mg/kg/day, 6.75 mg/kg/day, 7 mg/kg/day, 7.5 mg/kg/day, 8 mg/kg/day, 8.5 mg/kg/day, 9 mg/kg/day, 10 mg/kg/day, 11 mg/kg/day, 12 mg/kg/day, 13 mg/kg/day, 14 mg/kg/day or 15 mg/kg/day. In accordance with these embodiments, the dosage may be administered one, two or three times per day, every other day, or once or twice per week and the dosage may be administered orally.

In specific aspects, a method for treating KS presented herein involves the administration to a subject in need thereof of a Compound or a pharmaceutical composition thereof at a dosage that achieves a target plasma concentration of the Compound in a subject with KS or an animal model with a pre-established human tumor (e.g., tumor associated with KS). In a particular embodiment, a method for treating KS presented herein involves the administration to a subject in need thereof of a Compound or a pharmaceutical composition thereof at a dosage that achieves a plasma concentration of the Compound ranging from approximately 0.001 μg/mL to approximately 100 mg/mL, approximately 0.01 μg/mL to approximately 100 mg/mL, approximately 0.01 μg/mL to approximately 10 mg/mL, approximately 0.1 μg/mL to approximately 10 mg/mL, approximately 0.1 μg/mL to approximately 500 μg/mL, approximately 0.1 μg/mL to approximately 500 μg/mL, approximately 0.1 μg/mL to approximately 100 μg/mL, or approximately 0.5 μg/mL to approximately 10 μg/mL in a subject with KS or an animal model with pre-established human tumors (e.g., tumors associated with KS). To achieve such plasma concentrations, a Compound or a pharmaceutical composition thereof may be administered at doses that vary from 0.001 µg to 100,000 mg, depending upon the route of administration. In certain embodiments, subsequent doses of a Compound may be adjusted accordingly based on the plasma concentrations of the Compound achieved with initial doses of the Compound or pharmaceutical composition thereof administered to the subject.

In specific aspects, a method for treating KS presented herein involves the administration to a subject in need thereof of a Compound or a pharmaceutical composition thereof at a dosage that achieves a target plasma concentration of VEGF, P1GF, VEGF-C, VEGF-D, VEGFR-1, VEGFR-2, IL-6, IL-8, and/or IL-10 in a subject with KS or an animal model with a pre-established human tumor (e.g., tumor associated with KS). In a particular embodiment, a method for treating KS presented herein involves the administration to a subject in need thereof of a Compound or a pharmaceutical composition thereof at a dosage that achieves a plasma concentration of VEGF, P1GF, VEGF-C, VEGF-D, VEGFR-1, VEGFR-2, IL-6, IL-8, and/or IL-10 ranging from approximately 0.1 pg/mL to approximately 100 mg/mL, approximately 0.1 pg/mL to approximately 1 mg/mL, approximately 0.1 pg/mL to approximately 500 µg/mL, approximately 0.1 pg/mL to approximately 500 µg/mL, approximately 0.1 pg/mL to approximately 100 µg/mL, or approximately 4 pg/mL to approximately 10 µg/mL in a subject with KS or an animal model with a pre-established human tumor (e.g., tumor associated with KS). To achieve such plasma concentrations, a Compound or a pharmaceutical composition thereof may be administered at doses that vary from 0.1 pg to 100,000 mg, depending upon the route of administration. In certain embodiments, subsequent doses of a Compound or a pharmaceutical composition thereof may be adjusted accordingly based on the plasma concentrations of VEGF, P1GF, VEGF-C, VEGF-D, VEGFR-1, VEGFR-2, IL-6, IL-8, and/or IL-10 achieved with initial doses of the Compound or pharmaceutical composition thereof administered to the subject.

In specific aspects, a method for treating KS presented herein involves the administration to a subject in need thereof of a Compound or a pharmaceutical composition thereof at a dosage and/or a frequency of administration that achieves an imaging outcome indicating inhibition, stability, and/or reduction in a monitoring parameter such as tumor size, tumor perfusion, tumor metabolism, or peritumoral inflammation or edema, as assessed, e.g., by photography, MRI scan, DCE-MRI scan, PET scan, and/or CT scan. To achieve such imaging outcome, a Compound or a pharmaceutical composition thereof may be administered at doses that vary from 0.1 pg to 100,000 mg, depending upon the route and/or frequency of administration. In certain embodiments, subsequent doses of a Compound or a pharmaceutical composition thereof may be adjusted accordingly based on the imaging outcome achieved with initial doses of the Compound or pharmaceutical composition thereof administered to the subject, as assessed, e.g., by photography, MRI scan, DCE-MRI scan, PET scan, and/or CT scan.

In particular embodiments, a method for treating KS presented herein involves the administration to a subject in need thereof of a Compound or a pharmaceutical composition thereof at a dosage that achieves the desired tissue to plasma concentration ratios of the Compound as determined, e.g., by any imaging techniques known in the art such as whole-body autoradiography in a subject with KS or an animal model (such as an animal model with a pre-established human tumor, e.g., a tumor associated with KS). Table 23 lists exemplary tissue to plasma concentration ratios of a Compound as determined by whole-body autoradiography.

In some embodiments, a method for treating KS presented herein involves the administration to a subject in need thereof of one or more doses of an effective amount of a Compound or a pharmaceutical composition, wherein the effective amount may or may not be the same for each dose. In particular embodiments, a first dose of a Compound or pharmaceutical composition thereof is administered to a subject in need thereof for a first period of time, and subsequently, a second dose of a Compound is administered to the subject for a second period of time. The first dose may be more than the second dose, or the first dose may be less than the second dose. A third dose of a Compound may also be administered to a subject in need thereof for a third period of time.

In some embodiments, the dosage amounts described herein refer to total amounts administered; that is, if more than one Compound is administered, then, in some embodiments, the dosages correspond to the total amount administered. In a specific embodiment, oral compositions contain about 5% to about 95% of a Compound by weight.

The length of time that a subject in need thereof is administered a Compound or a pharmaceutical composition in accordance with the methods for treating KS presented herein will be the time period that is determined to be efficacious. In certain embodiments, a method for treating KS presented herein involves the administration of a Compound or a pharmaceutical composition thereof for a period of time until the severity and/or number of symptoms associated with KS decreases. In some embodiments, a method for treating KS presented herein involves the administration of a Compound or a pharmaceutical composition thereof for up to 48 weeks. In other embodiments, a method for treating KS presented herein involves the administration of a Compound or a pharmaceutical composition thereof for up to about 4 weeks, 8 weeks, 12 weeks, 16 weeks, 20 weeks, 24 weeks, 26 weeks (0.5 year), 52 weeks (1 year), 78 weeks (1.5 years), 104 weeks (2 years), or 130 weeks (2.5 years) or more. In certain embodiments, a method for treating KS presented herein involves the administration of a Compound or a pharmaceutical composition thereof for an indefinite period of time. In some embodiments, a method for treating KS presented herein involves the administration of a Compound or a pharmaceutical composition thereof for a period of time followed by a period of rest (i.e., a period wherein the Compound is not administered) before the administration of the Compound or pharmaceutical composition thereof is resumed. In specific embodiments, a method for treating KS presented herein involves the administration of a Compound or a pharmaceutical composition thereof in cycles, e.g., 1 week cycles, 2 week cycles, 3 week cycles, 4 week cycles, 5 week cycles, 6 week cycles, 8 week cycles, 9 week cycles, 10 week cycles, 11 week cycles, or 12 week cycles. In such cycles, the Compound or a pharmaceutical composition thereof may be administered once, twice, three times, or four times daily. In particular embodiments, a method for treating KS presented herein involves the administration of a Compound or a pharmaceutical composition thereof twice daily in 4 week cycles.

In specific embodiments, the period of time of administration of a Compound or pharmaceutical composition thereof may be dictated by one or more monitoring parameters, e.g., concentration of VEGF or other angiogenic or inflammatory mediators (e.g., cytokines or interleukins such as IL-6 or IL-8); tumor size, blood flow, or metabolism; peritumoral inflammation or edema. In particular embodiments, the period of time of administration of a Compound or pharmaceutical composition thereof may be adjusted based on one or more monitoring parameters, e.g., concentration of VEGF or other angiogenic or inflammatory mediators (e.g., cytokines or interleukins such as IL-6 or IL-8); tumor size, blood flow, or metabolism; and/or peritumoral inflammation or edema.

In certain embodiments, in accordance with the methods for treating KS presented herein, a Compound or a pharmaceutical composition thereof is administered to a subject in need thereof prior to, concurrently with, or after a meal (e.g., breakfast, lunch, or dinner). In specific embodiments, in accordance with the methods for treating KS presented herein, a Compound or a pharmaceutical composition thereof is administered to a subject in need thereof in the morning (e.g., between 5 am and 12 pm). In certain embodiments, in accordance with the methods for treating KS presented herein, a Compound or a pharmaceutical composition thereof is administered to a subject in need thereof at noon (i.e., 12 pm). In particular embodiments, in accordance with the methods for treating KS presented herein, a Compound or a pharmaceutical composition thereof is administered to a subject in need thereof in the afternoon (e.g., between 12 pm and 5 pm), evening (e.g., between 5 pm and bedtime), and/or before bedtime.

In specific embodiments, a dose of a Compound or a pharmaceutical composition thereof is administered to a subject once, twice, three times or four times every other day (i.e., on alternate days); once, twice, three times or four times every two days; once, twice, three times or four times every three days; once, twice, three times or four times every four days; once, twice, three times or four times every five days; once, twice, three times or four times once a week, biweekly or monthly.

5.5 Combination Therapy

Presented herein are combination therapies for the treatment of KS which involve the administration of a Compound in combination with one or more additional therapies to a subject in need thereof. In a specific embodiment, presented herein are combination therapies for the treatment of KS which involve the administration of an effective amount of a Compound in combination with an effective amount of another therapy to a subject in need thereof.

As used herein, the term "in combination," refers, in the context of the administration of a Compound, to the administration of a Compound prior to, concurrently with, or subsequent to the administration of one or more additional therapies (e.g., agents, radiation or surgery) for use in treating KS. The use of the term "in combination" does not restrict the order in which one or more Compounds and one or more additional therapies are administered to a subject. In specific embodiments, the interval of time between the administration of a Compound and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, a Compound and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering a Compound daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, a Compound and one or more additional therapies are cyclically administered to a subject. Cycling therapy involves the administration of the Compound for a period of time, followed by the administration of one or more additional therapies for a period of time, and repeating this sequential administration. In certain embodiments, cycling therapy may also include a period of rest where the Compound or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating KS provided herein comprise administering a Compound as a single agent for a period of time prior to administering the Compound in combination with an additional therapy. In certain embodiments, the methods for treating KS provided herein comprise administering an additional therapy alone for a period of time prior to administering a Compound in combination with the additional therapy.

In some embodiments, the administration of a Compound and one or more additional therapies in accordance with the methods presented herein have an additive effect relative the administration of the Compound or said one or more additional therapies alone. In some embodiments, the administration of a Compound and one or more additional therapies in accordance with the methods presented herein have a synergistic effect relative to the administration of the Compound or said one or more additional therapies alone.

As used herein, the term "synergistic," refers to the effect of the administration of a Compound in combination with one or more additional therapies (e.g., agents, radiation or surgery), which combination is more effective than the additive effects of any two or more single therapies (e.g., agents, radiation or surgery). In a specific embodiment, a synergistic effect of a combination therapy permits the use of lower dosages (e.g., sub-optimal doses) of a Compound or an additional therapy and/or less frequent administration of a Compound or an additional therapy to a subject. In certain embodiments, the ability to utilize lower dosages of a Compound or of an additional therapy and/or to administer a Compound or said additional therapy less frequently reduces the toxicity associated with the administration of a Compound or of said additional therapy, respectively, to a subject without reducing the efficacy of a Compound or of said additional therapy, respectively, in the treatment of KS. In some embodiments, a synergistic effect results in improved efficacy of a Compound and each of said additional therapies in treating KS. In some embodiments, a synergistic effect of a combination of a Compound and one or more additional therapies avoids or reduces adverse or unwanted side effects associated with the use of any single therapy.

The combination of a Compound and one or more additional therapies can be administered to a subject in the same pharmaceutical composition. Alternatively, a Compound and one or more additional therapies can be administered concurrently to a subject in separate pharmaceutical compositions. A Compound and one or more additional therapies can be administered sequentially to a subject in separate pharmaceutical compositions. A Compound and one or more additional therapies may also be administered to a subject by the same or different routes of administration.

The combination therapies provided herein involve administrating to a subject to in need thereof a Compound in combination with conventional, or known, therapies for KS. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference (61st ed. 1007) for information regarding therapies (e.g., agents, radiation or surgery) which have been or are currently being used for treating and/or managing KS. Current therapies for KS include surgery, radiation or drug therapy such as chemotherapy, antiviral therapy, and interferon. Other therapies for KS or a condition associated therewith are aimed at controlling or relieving symptoms, e.g., pain. Accordingly, in some embodiments, the combination therapies provided herein involve administrating to a subject in need thereof a pain reliever, or other therapy aimed at alleviating or controlling symptoms associated with KS or a condition associated therewith.

Specific examples of anti-cancer agents that may be used in combination with a Compound include, a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with a Compound include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as NOLVADEX®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with a Compound include microtubule disassembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capecitabine, gemcitabine (branded/marketed as GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of anti-angiogenic agents that may be used in combination with a Compound include VEGF antagonists, receptor antagonists, integrin antagonists (e.g., vitaxin, cilengitide, and S247), and VTAs/VDAs (e.g., fosbretabulin). VEGF antagonists include, but are not to, anti-VEGF antibodies (e.g., bevacizumab (branded/marketed as AVASTIN®) and ranibizumab (branded/marketed as LUCENTIS®)), VEGF traps (e.g., aflibercept), VEGF antisense or siRNA or miRNA, and aptamers (e.g., pegaptanib (branded/marketed as MACUGEN®)). Anti-angiogenic agents that are receptor antagonists include, but are not limited to, antibodies (e.g., ramucirumab) and kinase inhibitors (e.g., sunitinib, sorafenib, cediranib, panzopanib, vandetanib, axitinib, and AG-013958) such as tyrosine kinase inhibitors. Other non-limiting examples of anti-angiogenic agents include ATN-224, anecortave acetate (branded/marketed as RETAANE®), microtubule depolymerization inhibitor such as combretastatin A4 prodrug, and recombinant protein or protein fragment such as collagen 18 (endostatin).

Non-limiting examples of other therapies that may be administered to a subject in combination with a Compound include:

(1) a statin such as lovostatin (e.g., branded/marketed as MEVACOR®);
(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;
(3) a farnesyltransferase inhibitor agent such as tipifarnib (e.g., branded/marketed as ZARNESTRA®);
(4) an antifibrotic agent such as pirfenidone;
(5) a pegylated interferon such as PEG-interferon alpha-2b;
(6) a CNS stimulant such as methylphenidate (branded/marketed as RITALIN®;
(7) a HER-2 antagonist such as anti-HER-2 antibody (e.g., trastuzumab) or kinase inhibitor (e.g., lapatinib);

(8) an IGF-1 antagonist such as an anti-IGF-1 antibody (e.g., AVE1642 and IMC-A11) or an IGF-1 kinase inhibitor;

(9) EGFR/HER-1 antagonist such as an anti-EGFR antibody (e.g., cetuximab, panitumamab) or EGFR kinase inhibitor (e.g., erlotinib (e.g., branded/marketed as TARCEVA®), gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;

(19) immune modulator such as lenalidomide, pomalidomide, or thalidomide (e.g., branded/marketed as THALIDOMID®);

(20) kinase (eg, tyrosine kinase) inhibitor such as imatinib (e.g., branded/marketed as GLEEVEC®), dasatinib, erlotinib, nilotinib, gefitinib, sorafenib, sunitinib (e.g., branded/marketed as SUTENT®), lapatinib, AEE788, or TG100801;

(21) non-steroidal anti-inflammatory agent such as celecoxib (branded/marketed as CELEBREX®);

(22) human granulocyte colony-stimulating factor (G-CSF) such as filgrastim (branded/marketed as NEUPOGEN®);

(23) folinic acid or leucovorin calcium;

(24) integrin antagonist such as an integrin α5β1-antagonist (e.g., JSM6427);

(25) nuclear factor kappa beta (NF-κβ) antagonist such as OT-551, which is also an anti-oxidant;

(26) hedgehog inhibitor such as CUR61414, cyclopamine, GDC-0449, or anti-hedgehog antibody;

(27) histone deacetylase (HDAC) inhibitor such as SAHA (also known as vorinostat (branded/marketed as ZOLINZA®), PCI-24781, SB939, CHR-3996, CRA-024781, ITF2357, JNJ-26481585, or PCI-24781;

(28) retinoid such as isotretinoin (e.g., branded/marketed as ACCUTANE®);

(29) hepatocyte growth factor/scatter factor (HGF/SF) antagonist such as HGF/SF monoclonal antibody (e.g., AMG 102);

(30) synthetic chemical such as antineoplaston;

(31) anti-diabetic such as rosiglitazone maleate (e.g., branded/marketed as AVANDIA®);

(32) antimalarial and amebicidal drug such as chloroquine (e.g., branded/marketed as ARALEN®);

(33) synthetic bradykinin such as RMP-7;

(34) platelet-derived growth factor receptor inhibitor such as SU-101;

(35) receptor tyrosine kinase inhibitorsof Flk-1/KDR/VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy.

Non-limiting examples of other therapies that may be administered to a subject in combination with a Compound include: a synthetic nonapeptide analog of naturally occurring gonadotropin releasing hormone such as leuprolide acetate (branded/marketed as LUPRON®); a nonsteroidal, anti-androgen such as flutamide (branded/marketed as EULEXIN®) or nilutamide (branded/marketed as NILANDRON®); a non-steroidal androgen receptor inhibitor such as bicalutamide (branded/marketed as CASODEX®); steroid hormone such as progesterone; anti-fungal agent such as Ketoconazole (branded/marketed as NIZORAL®); glucocorticoid such as prednisone; estramustine phosphate sodium (branded/marketed as EMCYT®); and bisphosphonate such as pamidronate, alendronate, and risedronate.

Other specific examples of therapies that may be used in combination with a Compound include, but are not limited to, antibodies that specifically bind to a tumor specific antigen or tumor associated antigen, e.g., anti-EGFR/HER-1 antibodies.

Additional specific examples of therapies that may be used in combination with a Compound include, but are not limited to, agents associated with cancer immunotherapy, e.g., cytokines, interleukins, and cancer vaccines.

In certain embodiments, a Compound can be administered in combination with one or more antiviral agents. Antiviral agents include, but are not limited to, non-nucleoside reverse transcriptase inhibitors (e.g., delavirdine efavirenz, nevirapine), nucleoside reverse transcriptase inhibitors (e.g., AZT, ddI, ddC, 3TC, d4T), protease inhibitors (e.g., aprenavir, indinavir, ritonavir, and saquinavir), and fusion inhibitors (e.g., enfuvirtide). Specific examples of antiviral agents include amantadine, oseltamivir phosphate, rimantadine, zanamivir, delavirdine, efavirenz, nevirapine, abacavir, didanosine, emtricitabine, emtricitabine, lamivudine, stavudine, tenofovir DF, zalcitabine, zidovudine, amprenavir, atazanavir, fosamprenav, indinavir, lopinavir, nelfinavir, ritonavir, saquinavir, and enfuvirtide.

In certain embodiments, a Compound can be administered in combination with one or more antibacterial agents. Antibacterial agents include, but are not limited to, aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), glycopeptides, amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). In a specific embodiment, a Compound can be administered in combination with other protein synthesis inhibitors, such as streptomycin, neomycin, erythromycin, carbomycin, spiramycin. Other examples of antibiotics that a Compound can be administered in combination with include: ampicillin, amoxicillin, ciprofloxacin, gentamycin, kanamycin, neomycin, penicillin G, streptomycin, sulfanilamide, vancomycin, azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, trimethoprim, cycloserine, mupirocin, tuberin amphomycin, bacitracin, capreomycin, colistin, enduracidin, enviomycin, and 2,4 diaminopyrimidines (e.g., brodimoprim).

Other specific examples of therapies that may be used in combination with a Compound include, but are not limited to, alitretinoin, agents used in photodynamic treatment, antiemetics, antidepressants (tricyclic antidepressants, selective serotonin reuptake inhibitors, and others), antipsychotics, beta-adrenergic receptor blockers, anti-arrhythmics, erythropoietin, granulocyte colony stimulating factors (GCSF), antipyretics, analgesics, allergy medications, sleep medications, oral contraceptives, megestrol acetate, testosterone or any other medication that is indicated.

Specific examples of agents alleviating side-effects associated with KS, that can be used as therapies in combination with a Compound, include, but are not limited to: antiemetics, e.g., Ondansetron hydrochloride (branded/marketed as ZOFRAN®), Granisetron hydrochloride (branded/marketed as KYTRIL®), Lorazepam (branded/marketed as ATIVAN®) and Dexamethasone (branded/marketed as DECADRON®).

Other specific examples of therapies that may be used in combination with a Compound include, but are not limited to, antifungal drugs such as polyene antifungal drugs (Amphotericin, Nystatin, and Pimaricin), azole antifungal drugs (Fluconazole, Itraconazole, and Ketoconazole), allylamine antifungal drugs, for e.g., Naftifine and Terbinafine, and morpholine anti-fungal drugs, for e.g., Amorolfine, as well as antimetabolite antifungal drugs, such as 5-Fluorocytosine.

Specific examples of therapies that may be used in combination with a Compound include, but are not limited to, anti-helminthic drugs, such as Abamectin, Albendazole, Diethylcarbamazine, Mebendazole, Niclosamide, Ivermectin, Suramin, Thiabendazole, Pyrantel pamoate, Levamisole, piperazine, Praziquantel, Triclabendazole, Flubendazole, Fenbendazole, Octadepsipeptides (for e.g., Emodepside) and Amino Acetonitrile derivatives (for e.g., Monepantel). Other specific examples of therapies that may be used in combination with a Compound include, but are not limited to, anti-malarial drugs, such as Quinine and related agents, Chloroquine, Amodiaquine, Pyrimethamine, Sulphadoxine, Proguanil, Mefloquine, Atovaquone, Primaquine, Artemesinin and derivatives, Halofantrine, Doxycycline and Clindamycin.

In certain embodiments, combination therapies provided herein for treating KS comprise administering a Compound in combination with one or more agents used to treat and/or manage one or more of the following conditions: bleeding, arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, and heart failure.

In certain embodiments, combination therapies provided herein for treating KS comprise administering a Compound in combination with one or more current anti-angiogenesis agents and one or more agents used to treat and/or manage a side effect observed with one or more of the current anti-angiogenesis agents, such as bleeding, arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, or heart failure.

In certain embodiments, a Compound is not used in combination with a drug that is primarily metabolized by CYP2D6 (such as an antidepressant (e.g. a tricyclic antidepressant, a selective serotonin reuptake inhibitor and the like), an antipsychotic, a beta-adrenergic receptor blocker or certain types of anti-arrhythmics) to treat KS.

6. EXAMPLE

Preparation of Compounds Provided Herein

The following examples are presented by way of illustration not limitation.

Methods for preparing certain Compounds provided herein and the Compounds disclosed on pages 26 to 98 of the '764 publication are provided on pages 112 to 142 of the '764 publication and are incorporated by reference herein on pages 99 to 105 and in their entireties and for all purposes. Methods for preparing certain Compounds provided herein and the Compounds disclosed in copending U.S. Provisional Patent Application 61/181,652, entitled: PROCESSES FOR THE PREPARATION OF SUBSTITUTED TETRAHYDRO BETA-CARBOLINES, filed May 27, 2009, are provided therein and are incorporated by reference herein in their entirety and for all purposes.

7. EXAMPLE

Formulation of Compound #10

The following example illustrates how Compound #10 may be formulated for oral administration.

For clinical use, Compound #10 has been formulated using cGMPs. Compound #10 is intended for oral administration and is provided in size 00 color coded, hard gelatin capsules. As shown in Table 2, each capsule contains 2 mg (white), 10 mg (gray), or 20 mg (orange) of the Compound formulated by w/w % (weight/weight %) in a SEDDS or SMEDDS system. The formulated product in the capsules appears as an opaque, off white soft solid at room temperature. If warmed, the encapsulated system begins to soften at temperatures of 38 to 40° C. and eventually becomes a clear, yellow liquid at ≥44° C.

TABLE 2

Composition of Compound #10 Capsules

| Component | 2 mg Capsule (w/w %) | 10 mg Capsule (w/w %) | 20 mg Capsule (w/w %) |
|---|---|---|---|
| Compound #10 | 0.28 [0.26-0.30] | 1.43 [1.33-1.53] | 2.67 [2.48-2.86] |
| GELUCIRE ® 44/14 | 49.87 [46.4-53.4] | 49.87 [46.4-53.4] | 49.87 [46.4-53.4] |
| SOLUTOL ® HS15 | 49.84 [46.4-53.3] | 48.69 [45.3-52.1] | 47.45 [44.1-50.8] |
| BHT | 0.01 [0.009-0.011] | 0.01 [0.009-0.011] | 0.01 [0.009-0.011] |
| Total Weight (100%) (mg) | 700 | 700 | 750 |

8. EXAMPLE

Assay to Evaluate Effect on Hypoxia-Inducible Endogenous VEGF Expression

The ability of the Compounds to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a Compound. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using Cell Titer Glo (Promega) under the same conditions as the ELISA to ensure that the inhibition of VEGF expression was not due to the cytotoxicity. Dose-response curves may be plotted using percentage inhibition versus concentration of the Compound, and $EC_{50}$ and $CC_{50}$ values may be generated for each Compound with the maximal inhibition set as 100% and the minimal inhibition as 0%. In one embodiment, Compounds will have an $EC_{50}$ of less than 50, less than 10, less than 2, less than 0.5, or less than 0.01.

The $EC_{50}$ for a series of Compounds is provided in Table 3.

TABLE 3

| Compound | LC/MS [M + H] | LC/MS Retention Time (min) | ELISA $EC_{50}$ μM |
|---|---|---|---|
| 10 | 467.15 | 4.48 | ***** |
| #10 | 467.15 | 4.51 | ***** |
| 17 | 447.14 | 4.44 | ***** |
| 60 | 433.17 | 4.27 | **** |
| 76 | 449.26 | 4.3 | **** |
| 121 | 403.32 | 4.27 | **** |
| 142 | 462.15 | 4.11 | *** |
| 160 | 450.15 | 3.95 | *** |
| 186 | 462.19 | 3.81 | ** |
| 192 | 495.28 | 4.89 | ** |
| 331 | ~0.010 | 2.94 | * |
| #332 | ~0.010 | 4 | * |
| 341 | 447.26 | 4.25 | *** |
| 344 | 459.31 | 4.91 | **** |
| 346 | 587 | 4.04 | **** |
| 347 | 451.16 | 3.93 | ***** |
| 348 | 479.28 | 4.13 | ***** |
| 350 | 462.17 | 3.66 | ***** |
| 351 | 471.17 | 3.93 | **** |
| 353 | 497.16 | 3.94 | ***** |
| 354 | 525.2 | 4.19 | ***** |
| 355 | 511.21 | 3.81 | ***** |
| 359 | 511.25 | 3.64 | *** |

TABLE 3-continued

| Compound | LC/MS [M + H] | LC/MS Retention Time (min) | ELISA $EC_{50}$ μM |
|---|---|---|---|
| 360 | 516 | 3.82 | **** |
| 366 | 553.3 | 4.42 | * |
| 372 | 486.9 | 4.96 | * |
| 388 | 495.4 | 3.94 | ***** |
| 391 | 562.55 | 3.63 | ***** |
| 395 | 481.32 | 3.51 | ***** |
| 397 | 535.3 | 4.29 | ***** |
| 398 | 481.3 | 4.23 | ***** |
| 400 | 493.3 | 4.43 | ***** |
| 401 | 451.3 | 3.99 | ***** |
| 403 | 479.3 | 4.23 | ***** |
| 405 | 551.17 | 4.58 | ***** |
| 409 | 477.4 | 4.18 | ***** |
| 410 | 451.3 | 3.99 | ***** |
| 413 | 459.3 | 4.16 | ***** |
| 415 | 637.64 | 2.82 | ***** |
| 417 | 562.47 | 4.15 | ***** |
| 418 | 511.3 | 4.13 | ***** |
| 421 | 553.30 | 4.05 | ***** |
| 422 | 359.29 | 4.17 | ***** |
| 426 | 535.27 | 4.29 | ***** |
| 427 | 554.3 | 4.45 | ***** |
| 428 | 563.55 | 4.64 | ***** |
| 429 | 564.42 | 2.77 | ***** |
| 432 | 489.4 | 4.14 | ***** |
| 433 | 578.44 | 2.82 | ***** |
| 436 | 477.4 | 3.93 | ***** |
| 437 | 543.4 | 3.92 | ***** |
| 440 | 536.43 | 3.95 | ***** |
| 444 | 455.28 | 3.73 | **** |
| 446 | 383.3 | 4.10 | **** |
| 448 | 501.27 | 3.65 | **** |
| 450 | 587 | 4.04 | **** |
| 452 | 439.3 | 3.56 | **** |
| 454 | 579.3 | 2.75 | **** |
| 455 | 583 | 3.84 | **** |
| 460 | 509.30 | 4.16 | **** |
| 462 | 580.56 | 2.85 | **** |
| 463 | 495.44 | 4.13 | **** |
| 465 | 507.4 | 3.98 | **** |
| 467 | 524.2 | 4.02 | **** |
| 468 | 582.2 | 2.81 | **** |
| 470 | 554.3 | 3.90 | **** |
| 471 | 620.18 | 3.85 | **** |
| 479 | 538.3 | 2.76 | *** |
| 482 | 522.3 | 3.95 | *** |
| 489 | 538.3 | 4.15 | *** |
| 491 | 537.31 | 2.64 | *** |
| 493 | 504.3 | 2.68 | *** |
| 500 | 506.29 | 3.85 | *** |
| 501 | 534.3 | 2.68 | *** |
| 502 | 518.3 | 2.76 | *** |
| 519 | 527.2 | 3.88 | ** |
| 530 | 466.28 | 3.21 | ** |
| 536 | 482.29 | 3.29 | ** |
| 540 | 428.28 | 3.43 | ** |
| 543 | 466.34 | 3.29 | ** |
| 544 | 723.58 | 3.92 | ***** |
| 545 | 466.31 | 3.28 | ** |
| 554 | 482.32 | 3.41 | ** |
| 570 | 549.22 | 4.59 | ***** |

TABLE 3-continued

| Compound | LC/MS [M + H] | LC/MS Retention Time (min) | ELISA EC$_{50}$ μM |
|---|---|---|---|
| 571 | 497.13 | 3.50 | ** |
| 572 | 525.29 | 4.14 | ***** |
| 575 | 437.33 | 3.16 | ** |
| 576 | 575.43 | 3.71 | *** |
| 577 | 453.28 | 3.34 | *** |
| 578 | 610.45 | 3.94 | *** |
| 579 | 481.32 | 3.51 | ***** |
| 580 | 495.29 | 3.64 | ***** |
| 581 | 465.43 | 3.64 | * |
| 583 | 512.26 | 3.39 | *** |
| 584 | 466.37 | 3.34 | *** |
| 587 | 467.29 | 3.66 | *** |
| 588 | 455.26 | 3.69 | *** |
| 589 | 471.3 | 3.83 | *** |
| 590 | 495.31 | 3.64 | **** |
| 591 | 541.35 | 3.73 | ***** |
| 592 | 523.42 | 3.58 | ***** |
| 593 | 541.38 | 3.69 | **** |
| 594 | 505.38 | 3.83 | *** |
| 614 | 463 | 3.88 | ** |
| 616 | 540 | 4.17 | ** |
| 617 | 621.57 | 4.13 | **** |
| 626 | 493.6 | 3.48 | **** |
| 627 | 511.6 | 3.53 | ***** |
| 628 | 527.4 | 3.62 | *** |
| 629 | 527.5 | 3.72 | ***** |
| 630 | 573.5 | 3.75 | ***** |
| 631 | 507.6 | 3.65 | ***** |
| 632 | 538.6 | 3.53 | **** |
| 635 | 523.6 | 3.47 | **** |
| 637 | 621.62 | 2.77 | ***** |
| 638 | 580.56 | 2.80 | ***** |
| 660 | 543.7 | 4.92 | ***** |
| 670 | 521.6 | 4.02 | ***** |
| 673 | 539.6 | 4.02 | **** |
| 674 | 555.6 | 4.13 | **** |
| 675 | 555.6 | 4.22 | **** |
| 677 | 535.6 | 4.15 | **** |
| 678 | 551.6 | 3.98 | *** |
| 680 | 599.5 | 4.27 | ***** |
| 681 | 566.6 | 4.02 | **** |
| 698 | 578.5 | 2.43 | **** |
| 699 | 568.5 | 2.35 | **** |
| 700 | 566.6 | 2.45 | **** |
| 701 | 596.6 | 2.47 | **** |
| 702 | 594.6 | 2.43 | **** |
| 703 | 592.6 | 2.48 | **** |
| 704 | 607.6 | 2.20 | *** |
| 705 | 575.5 | 2.47 | **** |
| 706 | 576.5 | 3.58 | ***** |
| 710 | 495.45 | 4.42 | ***** |
| 712 | 513.50 | 4.42 | ***** |
| 713 | 529.46 | 4.62 | **** |
| 719 | 527.5 | 4.47 | ***** |
| 723 | 555.4 | 4.09 (non polar) | ***** |
| 735 | 552.5 | 2.98 | ***** |
| 736 | 562.5 | 3.15 | ***** |
| 737 | 580.6 | 3.17 | **** |
| 738 | 578.5 | 3.02 | ***** |
| 739 | 576.6 | 3.17 | ***** |
| 740 | 591.6 | 2.75 | *** |
| 741 | 616.5 | 2.62 | *** |
| 742 | 559.5 | 3.13 | ***** |
| 743 | 560.5 | 3.83 | ***** |
| 772 | 580.5 | 3.03 | ***** |
| 773 | 590.6 | 3.12 | ***** |
| 774 | 578.5 | 3.12 | **** |
| 775 | 608.6 | 3.05 | ***** |
| 776 | 606.5 | 3.05 | ***** |
| 777 | 604.6 | 3.12 | ***** |
| 778 | 619.6 | 2.77 | ***** |
| 779 | 644.5 | 2.63 | *** |
| 780 | 587.5 | 3.10 | ***** |
| 781 | 588.5 | 4.05 | ***** |
| 782 | 596.5 | 3.10 | ***** |
| 783 | 606.5 | 3.18 | ***** |
| 784 | 594.5 | 3.27 | ***** |
| 785 | 624.5 | 3.22 | ***** |
| 786 | 622.5 | 3.12 | ***** |
| 787 | 620.5 | 3.20 | ***** |
| 788 | 635.6 | 2.85 | **** |
| 789 | 660.5 | 2.68 | *** |
| 790 | 603.5 | 3.22 | ***** |
| 791 | 604.5 | 4.25 | ***** |
| 833 | 532.4 | 3.50 | *** |
| 834 | 532.4 | 3.42 | **** |
| 835 | 531.4 | 2.57 | *** |
| 836 | 531.4 | 3.67 | **** |
| #837 | 563.4 | 2.93 | ***** |
| #838 | 577.4 | 2.82 | ***** |
| 839 | 548.3 | 3.63 | **** |
| 840 | 548.3 | 3.58 | **** |
| #841 | 579.3 | 3.08 | ***** |
| #842 | 593.3 | 2.95 | ***** |
| #843 | 573.4 | 2.75 | ***** |
| 845 | 648.48 | 4.45 | *** |
| 846 | 526.45 | 2.57 | *** |
| 847 | 568.37 | 3.40 | **** |
| 848 | 585.30 | 3.57 | ***** |
| 849 | 604.37 | 3.52 | **** |
| 850 | 540.39 | 2.60 | *** |
| 851 | 495.06 | 4.37 | ***** |
| 853 | 549.09 | 4.38 | ***** |
| 854 | 523.17 | 4.73 | ***** |
| 855 | 455.19 | 4.15 | **** |
| 857 | 505.16 | 4.30 | ***** |
| 860 | 467.2 | 4.13 | ***** |
| 861 | 451.12 | 4.10 | **** |
| 862 | 471.17 | 4.32 | ***** |
| 863 | 514.55 | 4.38 | ***** |
| 867 | 577.43 | 2.85 | **** |
| 882 | 542.51 | 3.87 | ***** |
| 888 | 558.54 | 3.70 | ***** |
| 889 | 545.55 | 2.93 | ***** |
| 891 | 528.49 | 3.69 | ***** |
| 892 | 546.50 | 3.75 | ***** |
| 894 | 580.47 | 2.72 | ***** |
| 900 | 541.55 | 3.00 | ***** |
| 903 | 621.39 | 2.72 | ***** |
| 904 | 596.54 | 2.85 | ***** |
| 908 | 582.43 | 2.79 | ***** |
| 911 | 527.54 | 2.88 | ***** |
| 913 | 626.6 | 2.88 | ***** |
| 915 | 509.56 | 4.63 | ***** |
| 916 | 626.40 | 2.82 | ***** |
| 917 | 561.46 | 2.95 | ***** |
| 918 | 642.56 | 2.85 | ***** |
| 920 | 557.57 | 2.87 | ***** |
| 921 | 527.39 | 4.52 | ***** |
| 922 | 561.53 | 2.85 | ***** |
| 923 | 612.51 | 2.92 | ***** |
| 925 | 596.54 | 2.88 | ***** |
| 926 | 5.62 | 3.85 | ***** |
| 932 | 548.49 | 3.17 | ***** |
| 933 | 596.37 | 2.79 | ***** |
| 934 | 561.53 | 2.95 | ***** |
| 936 | 582.6 | 2.83 | ***** |
| 938 | 582.53 | 2.85 | ***** |
| 941 | 562.55 | 3.63 | ***** |
| 942 | 623.35 | 2.73 | **** |
| 944 | 525.56 | 4.36 | **** |
| 946 | 566.53 | 2.77 | **** |
| 951 | 544.53 | 3.27 | **** |
| 952 | 530.53 | 3.12 | **** |
| 953 | 552.46 | 2.90 | **** |
| 958 | 542.36 | 3.84 | **** |
| 960 | 639.57 | 2.70 | **** |
| 961 | 593.52 | 2.64 | **** |
| 963 | 593.61 | 2.72 | **** |
| 964 | 598.55 | 2.83 | **** |
| 966 | 564.45 | 3.32 | **** |
| 967 | 491.57 | 4.00 | **** |
| 970 | 609.54 | 2.72 | **** |
| 973 | 578.47 | 3.80 | **** |

TABLE 3-continued

| Compound | LC/MS [M + H] | LC/MS Retention Time (min) | ELISA EC$_{50}$ μM |
|---|---|---|---|
| 974 | 528.34 | 3.79 | *** |
| 976 | 564.46 | 3.23 | *** |
| 977 | 568.53 | 2.85 | *** |
| 981 | 560.51 | 3.12 | *** |
| 984 | 5.06.19 | 3.97 | ** |
| 988 | 605.62 | 2.52 | ***** |
| 989 | 564.61 | 2.55 | ***** |
| 990 | 610.62 | 2.67 | ***** |
| 991 | 580.58 | 2.60 | *** |
| 992 | 566.61 | 2.60 | *** |
| 993 | 577.61 | 2.45 | ***** |
| 994 | 545.54 | 2.57 | ***** |
| 995 | 546.57 | 3.53 | ***** |
| 996 | 578.46 | 3.71 | ***** |
| 999 | 493.3 | 4.43 | ***** |
| 1001 | 575.5 | 2.98 | **** |
| 1005 | 560.3 | 4.55 | ** |
| 1008 | 548.2 | 4.79 | *** |
| 1009 | 468.1 | 3.90 | *** |
| 1011 | 560.2 | 5.54 | *** |
| 1016 | 560.51 | 4.23 | * |
| 1017 | 544.39 | 4.08 | ***** |
| 1021 | 621.2 | 4.35 | *** |
| 1022 | 607.2 | 5.05 | *** |
| 1023 | 586.1 | 5.93 | **** |
| 1024 | 591.2 | 5.01 | *** |
| 1025 | 633.2 | 4.29 | *** |
| 1026 | 619.2 | 4.24 | **** |
| 1027 | M − 1: 574.1 | 5.03 | *** |
| 1028 | 603.2 | 4.23 | *** |
| 1029 | 660.2 | 3.87 | * |
| 1030 | 576.2 | 5.29 | **** |
| 1031 | 558.0 | 4.69 | ***** |
| 1050 | 505.33 | 3.85 | ***** |
| 1051 | 523.4 | 3.88 | ***** |
| 1052 | 539.3 | 3.97 | **** |
| 1053 | 537.5 | 4.00 | ***** |
| 1054 | 583.4 | 4.07 | ***** |
| 1055 | 535.4 | 3.82 | **** |
| 1058 | 507.0 | 5.88 | ***** |
| 1062 | 477.1 | 5.53 | ***** |
| 1063 | 560.1 | 5.47 | **** |
| 1064 | 607.1 | 4.84 | **** |
| 1066 | 562.55 | 3.63 | ***** |
| 1067 | 562.1 | 5.33 | **** |
| 1068 | 562.1 | 5.70 | ***** |
| 1069 | 562.27 | 3.9 | ***** |
| 1070 | 596.24 | 2.40 | ***** |
| 1071 | 598.21 | 2.48 | ***** |
| 1075 | 546.3 | 4.55 | **** |
| 1076 | 559.3 | 4.08 | *** |
| 1077 | 528.1 | 5.51 | **** |
| 1078 | 528.1 | 4.74 | **** |
| 1086 | 577.9 | 3.73 | **** |
| 1087 | 591.9 | 3.78 | **** |
| 1088 | 605.9 | 3.87 | **** |
| 1089 | 577.9 | 3.75 | ** |
| 1090 | 591.9 | 3.80 | ** |
| 1091 | 605.9 | 3.85 | ** |
| 1092 | 595.9 | 2.45 | **** |
| 1093 | 610.0 | 2.47 | **** |
| 1094 | 624.0 | 2.48 | **** |
| 1095 | 596.0 | 2.47 | ** |
| 1096 | 610.0 | 2.47 | ** |
| 1097 | 624.0 | 2.50 | *** |
| 1098 | 594.57 | 2.47 | **** |
| 1099 | 564.52 | 2.45 | **** |
| 1108 | 589.4 | 3.97 | **** |
| 1110 | M − 1: 493.1 | 5.48 | ***** |
| 1111 | 509.1 | 4.84 | ***** |
| 1113 | 577.4 | 34.06 | ** |
| 1115 | 564.3 | 4.61 | **** |
| 1117 | 580.3 | 4.79 | **** |
| 1119 | 610.3 | 4.85 | *** |
| 1121 | 566.3 | 4.74 | * |
| 1123 | 545.2 | 4.65 | *** |
| 1125 | 546.1 | 5.84 | ** |
| 1126 | 530.8 | 4.3 | ** |
| 1127 | 562.24 | 4.20 | *** |
| 1128 | 530.8 | 4.32 | ***** |
| 1129 | 562.26 | 4.13 | ***** |
| 1130 | 576.3 | 4.668 | **** |
| 1131 | 606.0 | 4.646 | **** |
| 1132 | 590.5 | 4.826 | **** |
| 1134 | 558.1 | 3.68 | ***** |
| 1143 | 510 | 4.300 | **** |
| 1144 | 558.5 | 4.711 | *** |
| 1145 | 558.5 | 5.05 | **** |
| 1150 | 558.5 | 4.664 | **** |
| 1151 | 588.5 | 4.616 | *** |
| 1152 | 572.5 | 4.891 | **** |
| 1155 | 546.3 | 5.54 | *** |
| 1159 | 493 | 4.22 | ***** |
| 1160 | 453 | 3.73 | ***** |
| 1161 | 492 | 3.65 | ***** |
| 1162 | 579.17 | 4.28 | ***** |
| 1168 | 547.27 | 4.18 | ***** |
| 1169 | 565.24 | 4.17 | ***** |
| 1170 | 561.28 | 4.37 | ***** |
| 1171 | 577.28 | 4.13 | ***** |
| 1172 | 539.20 | 3.58 | ***** |
| 1178 | 507.19 | 3.37 | ***** |
| 1179 | 525.25 | 3.38 | ***** |
| 1180 | 521.23 | 3.52 | ***** |
| 1181 | 537.20 | 3.35 | ***** |
| 1182 | 542.27 | 3.70 | ***** |
| 1183 | 556.26 | 2.45 | ***** |
| 1184 | 600.38 | 2.43 | ***** |
| 1194 | 572.5 | 5.237 | ***** |
| 1195 | 469.5 | 5.192 | **** |
| 1196 | 465 | 5.373 | **** |
| 1197 | 481 | 5.156 | **** |
| 1199 | 485 | 5.407 | **** |
| 1203 | 581.24 | 4.40 | ***** |
| 1205 | 539.29 | 3.58 | ***** |
| 1207 | 581.24 | 4.35 | ***** |
| 1209 | 539.26 | 3.67 | ***** |
| 1213 | 510 | 3.45 | *** |
| 1216 | 506 | 3.37 | **** |
| 1223 | 527.2 | 3.52 | ***** |
| 1224 | 527.0 | 3.53 | ***** |
| 1225 | 597.9 | 4.69 | **** |
| 1227 | 565.2 | 4.18 | ***** |
| 1228 | 567.2 | 4.37 | ***** |
| 1229 | 595.39 | 4.47 | ***** |
| 1230 | 555.24 | 3.73 | ***** |
| 1231 | 528 | 3.48 | **** |
| 1234 | 594.00 | 5.135 | ***** |
| 1235 | 578.0 | 4.785 | **** |
| 1250 | 511.07 | 3.93 | ***** |
| 1255 | 614.35 | 2.35 | *** |
| 1257 | 554.26 | 2.42 | **** |
| 1258 | 600.14 | 2.43 | ***** |
| 1259 | 527.2 | 3.50 | **** |
| 1260 | 565.2 | 4.18 | ***** |
| 1263 | 583.00 | 3.85 | ***** |
| 1265 | 469.0 | 5.478 | **** |
| 1266 | 465.0 | 5.667 | ***** |
| 1267 | 481.0 | 5.426 | **** |
| 1269 | 485.0 | 5.723 | ***** |
| 1276 | M + 23: 604.2 | 4.47 | ***** |
| 1277 | M + 23: 646.2 | 4.83 | ***** |
| 1278 | M + 23: 634.2 | 4.60 | ***** |
| 1279 | 610.2 | 5.28 | ***** |
| 1280 | 628.2 | 5.22 | **** |
| 1281 | M + 23: 614.1 | 4.65 | ***** |
| 1282 | 592.0 | 5.90 | ***** |
| 1288 | 608.2 | 4.51 | **** |
| 1289 | M + 23: 594.2 | 4.80 | ***** |
| 1290 | M + 23: 594.2 | 5.18 | ***** |
| 1291 | M + 23: 594.2 | 4.88 | ***** |
| 1292 | M − 1: 519.2 | 5.53 | ***** |
| 1293 | M − 1: 523.2 | 5.34 | ***** |
| 1297 | 535.31 | 3.67 | **** |

TABLE 3-continued

| Compound | LC/MS [M + H] | LC/MS Retention Time (min) | ELISA EC$_{50}$ μM |
|---|---|---|---|
| 1299 | M − 1: 505.2 | 5.28 | ***** |
| 1300 | M − 1: 535.2 | 4.55 | ***** |
| 1301 | M + 23: 614.2 | 5.96 | **** |
| 1302 | 590.2 | 5.37 | *** |
| 1328 | 553.4 | 3.65 | ***** |
| 1329 | 569.3 | 3.83 | ***** |
| 1330 | 539.28 | 3.60 | * |
| 1331 | 581.25 | 4.50 | * |
| 1332 | 451.27 | 3.75 | * |
| 1333 | 499.40 | 3.90 | * |
| 1335 | M − 1: 573.0 | 4.82 | **** |
| 1336 | M − 1: 519.1 | 5.76 | **** |
| 1337 | M − 1: 549.2 | 4.33 | **** |
| 1343 | 555.1 | 3.53 | ***** |
| 1344 | 571.0 | 3.70 | ***** |
| 1348 | 569.1 | 3.60 | ***** |
| 1349 | 585.0 | 3.77 | ***** |
| 1352 | 583.1 | 3.72 | ***** |
| 1353 | 599.0 | 3.88 | ***** |
| 1357 | 597.2 | 3.77 | ***** |
| 1358 | 613.2 | 3.93 | ***** |
| 1361 | M − 1: 535.2 | 5.42 | **** |
| 1362 | 622.57 | 2.53 | ***** |
| 1364 | 605.3 | 4.41 | *** |
| 1391 | 563.4 | 2.93 | ***** |
| 1392 | 577.4 | 2.82 | ***** |
| 1393 | 579.4 | 3.08 | ***** |
| 1394 | 593.3 | 2.95 | ***** |
| 1413 | 546.4 | 3.23 | ***** |
| 1414 | 560.4 | 2.83 | ***** |
| 1415 | 564.4 | 3.65 | ***** |
| 1416 | 589.5 | 3.40 | *** |
| 1417 | 562.4 | 3.42 | ***** |
| 1418 | 576.41 | 2.95 | **** |
| 1419 | 577.4 | 4.05 | **** |
| 1420 | 580.3 | 3.83 | ***** |
| 1421 | 587.4 | 3.88 | ***** |
| 1422 | 605.4 | 3.55 | **** |
| 1440 | 558.9 | 3.65 | ***** |
| 1441 | 571.5 | 3.75 | **** |
| 1442 | 574.9 | 3.85 | ***** |
| 1476 | 580.56 | 2.43 | *** |
| 1520 | 492 | 3.87 | ***** |
| 1537 | 594.23 | 2.40 | ***** |
| 1538 | 495.2 | 3.95 | ***** |
| 1539 | 495.08 | 3.95 | *** |
| 1546 | 492 | 3.85 | *** |
| 1547 | 534, 536 | 3.93 | ***** |
| 1548 | 474 | 3.75 | **** |
| 1549 | 488 | 3.77 | **** |
| 1551 | 573 | 3.83 | ***** |
| 1552 | 555 | 4.68 | ***** |
| 1553 | 569 | 4.88 | ***** |
| 1554 | 608 | 2.40 | * |
| 1555 | 624 | 3.80 | ***** |
| 1557 | M − 1: 614.2 | 4.52 | ** |
| 1558 | M + 23: 604.2 | 4.57 | **** |
| 1559 | 596.1 | 4.88 | **** |
| 1560 | M + 23: 616.2 | 4.82 | **** |
| 1561 | 631.1 | 4.15 | **** |
| 1562 | M − 1: 596.0 (cal: 597.1) | 4.98 | **** |
| 1563 | M − 1: 610.0 | 5.25 | **** |
| 1564 | M + 23: 650.2 | 4.83 | ***** |
| 1565 | M − 1: 616.1 | 4.83 | **** |
| 1566 | M − 1: 630.1 | 4.85 | *** |
| 1567 | M + 23: 652.1 | 4.93 | *** |
| 1568 | 593.2 | 2.43 | **** |
| 1569 | 615 | 4.52 | ***** |
| 1570 | 531 | 3.90 | ***** |
| 1571 | 531 | 4.00 | ***** |
| 1572 | 580 | 4.53 | ***** |
| 1577 | 521 | 3.93 | ***** |
| 1578 | 537 | 4.12 | ***** |
| 1580 | 684 | 4.32 | ***** |
| 1581 | 700 | 4.60 | ***** |
| 1604 | 521 | 3.95 | ***** |
| 1605 | 537 | 4.13 | ***** |
| 1607 | 684 | 4.30 | ***** |
| 1611 | 595.2 | 24.453 | ***** |
| 1612 | 491.365 | 5.676 | ***** |
| 1613 | 519.5 | 5.932 | ***** |
| 1614 | 505.5 | 5.775 | ***** |
| 1625 | M + 23: 618.2 | 4.61 | ***** |
| 1626 | M + 23: 632.2 | 4.76 | ***** |
| 1627 | M + 23: 667.2 | 3.96 | ***** |
| 1628 | M + 23: 667.1 | 4.03 | ***** |
| 1629 | M + 23: 667.1 | 4.92 | ***** |
| 1635 | M + 23: 620.1 | 4.73 | ***** |
| 1636 | M + 23: 634.1 | 4.92 | ***** |
| 1637 | M + 23: 664.1 | 5.03 | ***** |
| 1638 | M + 23: 654.1 | 5.03 | ***** |
| 1639 | M + 23: 666.1 | 5.10 | ***** |
| 1640 | M + 23: 612.2 | 4.93 | ***** |
| 1641 | M + 23: 647.2 | 5.13 | ***** |
| 1642 | M + 23: 600.1 | 4.92 | ***** |
| 1643 | M + 23: 614.2 | 5.12 | ***** |
| 1644 | M + 23: 628.2 | 5.35 | ***** |
| 1645 | M + 23: 644.2 | 4.91 | ***** |
| 1646 | M + 23: 634.2 | 4.88 | ***** |
| 1647 | M + 23: 646.2 | 4.99 | ***** |
| 1648 | 571 | 3.80 | ***** |
| 1652 | 700 | 4.53 | ***** |
| 1658 | 559 | 4.25 | ***** |
| 1659 | 545 | 4.12 | ***** |
| 1660 | 635 | 2.80 | ***** |
| 1661 | 650 | 2.47 | ***** |
| 1663 | 580.0 | 4.59 | ***** |
| 1664 | 579.9 | 4.84 | ***** |
| 1666 | M + 23: 648.1 | 5.44 | ***** |
| 1667 | M + 23: 640.1 | 4.55 | ***** |
| 1668 | M + 23: 620.1 | 5.45 | **** |
| 1669 | 492.1 | 13.380 | ***** |
| 1671 | 623.3 | 3.85 | ***** |
| 1672 | 593.34 | 3.70 | ***** |
| 1673 | 605.18 | 3.82 | ***** |
| 1674 | 696 | 3.33 | ** |
| 1675 | 864 | 3.88 | *** |
| 1676 | 710 | 3.33 | * |
| 1677 | 878 | 3.90 | *** |
| 1681 | 614 | 4.42 | ***** |
| 1682 | 649 | 2.33 | ***** |
| 1693 | 693 | 2.53 | ***** |
| 1694 | 550 | 2.40 | ***** |
| 1695 | 615 | 3.13 | ** |
| 1698 | 567.19 | 4.02 | ***** |
| 1701 | 509 | 3.87 | ***** |
| 1702 | 628 | 3.80 | ***** |
| 1703 | 624 | 2.35 | ** |
| 1704 | 610 | 2.40 | **** |

(S) Isomer prepared and tested.
Where in:
1 star, >1 uM (1000 nM)
2 stars, 0.2 to 1 uM (200 nM to 1000 nM)
3 stars, 0.04 uM to 0.2 uM (40 nM to 200 nM)
4 stars, 0.008 uM to 0.04 uM (8 nM to 40 nM)
5 stars, <0.008 uM (<8 nM)

LC/MS for certain Compounds was performed on either a Waters 2795 or 2690 model separations module coupled with a Waters Micromass ZQ mass spectrometer using a Waters Xterra MS C$_{18}$ 4.6×50 mm reverse phase column (detection at 254 nM). The methods employed a gradient of acetonitrile (ACN) in water at 2 mL/min at ambient temperature as shown in Table 3a. The mobile phase was buffered with a 0.1 N formic acid.

The standard 6 minute method maintains a constant 85/5/10 ratio of water/ACN/1% aqueous formic acid from 0 minutes to 0.5 minutes. The method runs a linear gradient from 85/5/10 at 0.5 minutes to 0/90/10 at 3.5 minutes. The method holds at 0/90/10 until 4.5 minutes then immediately drops back down to 85/5/10 and holds there until 6 minutes.

The non-polar 6 minute method maintains a constant 60/30/10 ratio of water/ACN/1% aqueous formic acid from 0 minutes to 0.5 minutes. The method runs a linear gradient from 60/30/10 at 0.5 minutes to 0/90/10 at 3.5 minutes. The method holds at 0/90/10 until 4.5 minutes then immediately drops back down to 60/30/10 and holds there until 6 minutes.

The polar 6 minute method maintains a constant 90/0/10 ratio of water/ACN/1% aqueous formic acid from 0 minutes to 0.5 minutes. The method runs a linear gradient from 90/0/10 at 0.5 minutes to 20/70/10 at 3.5 minutes. The method holds at 20/70/10 until 4.5 minutes then immediately drops back down to 90/0/10 and holds there until 6 minutes.

TABLE 3a

| Time | % Acetonitrile | % Water | % 1% Aq. Formic Acid | Gradient |
|---|---|---|---|---|
| Standard | | | | |
| 0.00 | 5 | 85 | 10 | |
| 0.50 | 5 | 85 | 10 | hold |
| 3.50 | 90 | 0 | 10 | linear hold |
| 4.50 | 5 | 85 | 10 | instant |
| 6.00 | 5 | 85 | 10 | hold |
| Non-Polar | | | | |
| 0.00 | 30 | 60 | 10 | |
| 0.50 | 30 | 60 | 10 | hold |
| 3.50 | 90 | 0 | 10 | linear hold |
| 4.50 | 30 | 60 | 10 | instant |
| 6.00 | 30 | 60 | 10 | hold |
| Polar | | | | |
| 0.00 | 0 | 90 | 10 | |
| 0.50 | 0 | 90 | 10 | hold |
| 3.50 | 70 | 20 | 10 | linear hold |
| 4.50 | 0 | 90 | 10 | instant |
| 6.00 | 0 | 90 | 10 | hold |

LC/MS for Compounds 1611 and 1669 was performed using a $C_{18}$-BDS 5 (250×4.6 mm) column with a 0.7 mL/min flow rate. The following solvent gradient was employed using 0.1% TFA/water as solvent A and acetonitrile as solvent B: 20% B for 0-20 minutes, 70% B for 20-30 minutes, 100% B for 30-40 minutes, 20% B for 40-50 minutes.

9. EXAMPLE

Compound Pharmacodynamics

The examples that follow demonstrate that the Compounds tested can inhibit the pathological production of human VEGF, and suppress edema, inflammation, pathological angiogenesis and tumor growth tumor growth. Compounds tested have been shown to inhibit the pathological production of human VEGF by multiple human tumor cells and/or human tumors in animal models with pre-established human tumors.

9.1 Inhibition of Pathological Production of VEGF
9.1.1 Cell Based Assays
9.1.1.1 Compound #10 and Compound 1205 Inhibit Pathological VEGF Production in Transformed Cells Grown Under Hypoxic Conditions This example demonstrates the selective inhibition of Compound #10 and Compound 1205 on pathological VEGF production in transformed HeLa cells grown under stressed conditions while sparing VEGF production in HeLa cells grown under non-stressed conditions.

Experimental Design. HeLa (human cervical carcinoma) cell cultures were established under normoxic conditions (21% oxygen). HeLa cells increase VEGF production 4- to 5-fold in response to hypoxia. In one experimental design, vehicle (0.5% DMSO) alone, or a range of concentrations of Compound #10 was added to the HeLa cell cultures and the cells were incubated for 48 hours under either hypoxic (1% oxygen) or normoxic conditions. In another experimental design, vehicle (0.5% DMSO) alone, or a range of concentrations of Compound #10, Compound 1205, or Compound 1330 was added to the culture medium and the cells were incubated for 48 hours. At the completion of treatment, the conditioned media were collected and the VEGF protein levels were assayed in an enzyme-linked immunosorbent assay (ELISA) with primary antibodies that recognize the soluble $VEGF_{121}$ and $VEGF_{165}$ isoforms (R & D Systems, Minneapolis, Minn., USA). To ensure that decreases in VEGF concentration were not due to cytotoxicity, cultures were assayed using a standard assay (CELLTITER-GLO® Luminescent Cell Viability Assay; Promega, Madison, Wis., USA) that measures total cellular adenosine triphosphate (ATP) concentrations as an indicator of cell viability.

Results. FIG. 1 shows the concentrations of VEGF in conditioned media across the Compound #10 dose range tested. In the absence of Compound #10, media from hypoxic cells had substantial concentrations of VEGF (mean 1379 pg/mL). Compound #10 treatment induced dose dependent reductions in VEGF concentrations in the media, resulting in a maximal 87% decrease in VEGF concentration (to a mean of 175 pg/mL). By contrast, media from normoxic cells had relatively low concentrations of VEGF (mean 257 pg/mL) in the absence of Compound #10, and showed only a 39% decrease in VEGF concentrations (to a mean of 157 pg/mL) in the presence of Compound #10. No cytotoxicity was observed at any concentration tested. The data indicate that under stress conditions (with hypoxia), VEGF production was more sensitive to Compound #10 inhibition than under non-stress conditions (with normoxia). This data indicates that Compound #10 selectively inhibits or reduces pathological tumor-related production of soluble VEGF isoforms while sparing physiological VEGF production of the same isoforms. The (R)-enantiomer of Compound #10 showed lower activity (data not shown).

FIG. 25 shows the concentrations of VEGF in conditioned media across the dose range tested for Compound #10, Compound 1205 and Compound 1330. The data indicate that Compound #10 and Compound 1205 inhibit stress-induced VEGF production.

9.1.1.2 Compound #10 Inhibits pathological VEGF Production in Nontransformed Cells Grown Under Hypoxic Conditions This example demonstrates the inhibition of Compound #10 is selective for the pathological production of soluble VEGF isoforms in nontransformed keratinocytes grown under stressed conditions and does not affect the production of soluble VEGF isoforms in nontransformed keratinocytes grown under non-stressed conditions.

Experimental Design. Nontransformed normal human keratinocyte cell cultures were established under normoxic conditions (21% oxygen). Vehicle (0.5% DMSO) alone, or a range of concentrations of Compound #10 was added to the cultures and the cells were incubated for 72 hours under either under hypoxic (1% oxygen) or normoxic conditions. At the completion of treatment, cells were assessed for viability with an ATP assay and conditioned media were evaluated for VEGF protein levels by ELISA (as described in Section 9.1.1.1).

Results. FIG. 2 shows the concentrations of VEGF in conditioned media across the Compound #10 dose range tested. In the absence of Compound #10, media from hypoxic keratinocytes had substantial concentrations of VEGF (mean 1413 pg/mL). Compound #10 treatment induced dose dependent reductions in VEGF concentrations in the media, resulting in a maximal 57% decrease in VEGF concentration (to a mean of 606 pg/mL). By contrast, media from normoxic cells had relatively low concentrations of VEGF (mean 242 pg/mL) in the absence of Compound #10 and showed only a 21% decrease in VEGF concentrations (to a mean of 192 pg/mL) in the presence of Compound #10. No toxicity was observed at any concentration tested.

This data indicates that Compound #10 selectively inhibits or reduces pathological production of soluble VEGF isoforms in nontransformed keratinocytes grown under stressed hypoxic conditions while sparing physiological VEGF production of the same isoforms in unperturbed cells.

9.1.1.3 Compound #10 Inhibits Matrix-Bound Tumor VEGF Production

This example demonstrates that Compound #10 inhibits the pathological production of matrix bound/cell associated $VEGF_{189}$ and $VEGF_{206}$ isoforms resulting from oncogenic transformation.

Experimental Design. HT1080 (human fibrosacoma) cell cultures were established under normoxic conditions (21% oxygen). HT1080 cells constitutively overproduce VEGF even under normoxic conditions. Vehicle (0.5% DMSO) alone or a range of concentrations of Compound #10 was added to the cultures, and the cells were incubated for 48 hours under normoxic conditions. At the completion of treatment, the cells were washed and harvested. Cells were incubated with a primary antibody that recognizes the $VEGF_{189}$ and $VEGF_{206}$ isoforms. Infrared-dye labeled antibodies were applied secondarily, and the amounts of $VEGF_{189}$ and $VEGF_{206}$ were determined using the IN-CELL WESTERN® assay and ODYSSEY® infrared imaging system (Li-Cor, Lincoln, Nebr., USA); results are expressed as percentage inhibition relative to vehicle treated controls. Conventional Western blotting using the same primary antibody was also performed to confirm the presence of the matrix associated isoforms; for these experiments actin was used as a loading control. Actin is a ubiquitous housekeeping protein that is not known to be post transcriptionally regulated.

Results. As shown in FIG. 3, Compound #10 induced a potent concentration-dependent inhibition of $VEGF_{189}$ and $VEGF_{206}$ isoforms. These results demonstrate that Compound #10 inhibits the production of matrix-associated as well as soluble forms of tumor-derived VEGF. As shown in FIG. 4, immunoblotting documented the presence of 2 bands at the expected location for $VEGF_{189}$ and $VEGF_{206}$, and confirmed a concentration-dependent Compound #10 effect in reducing the amounts of these isoforms. The activity of the (R) enantiomer was relatively lower.

This data shows that Compound #10 inhibits pathological production of the matrix bound/cell associated VEGF isoforms resulting from oncogene transformation.

9.1.1.4 Compound #10 Inhibits Soluble VEGF Production in Multiple Human Tumor Cell Lines This example demonstrates that Compound #10 inhibits soluble VEGF production in multiple human tumor cell lines.

Study Design. The activity of Compound #10 in suppressing VEGF production in a number of other human tumor cell lines has been assessed. These evaluations focused on cell lines that produce sufficient soluble VEGF (>200 pg/mL in conditioned media, either constitutively or under hypoxic stress) to allow assessment of Compound #10 activity by ELISA. In these experiments, cultures were established under normoxic conditions (21% oxygen). Cultures were then incubated for 48 hours with vehicle (0.5% DMSO) alone or with Compound #10 over a range of concentrations from 0.1 nM to 10 µM. Cells requiring induction of VEGF production were incubated under hypoxic conditions (1% oxygen). At the completion of treatment, the conditioned media were collected and assayed by ELISA (as described in Section 9.1.1.1) for soluble $VEGF_{121}$ and $VEGF_{165}$ isoforms; results were calculated as percentage inhibition relative to vehicle treated controls. $EC_{50}$ values were calculated from the dose concentration response curves.

Results. Compound #10 potently inhibited the production of soluble VEGF in 18 of the human tumor cell lines tested to date. The $EC_{50}$ values for cell lines showing VEGF inhibition are generally in the low nanomolar range, as presented in Table 4. Compound #10 did not show activity in several cell lines in which there was insufficient basal or inducible production of soluble VEGF. Other human cell lines that produce sufficient soluble VEGF in vitro or in vivo may be used, with appropriate adaptations, by those skilled in the art to measure inhibition of pathologically produced soluble human VEGF.

TABLE 4

Inhibition of Soluble VEGF Production by Compound #10 in Human Cell Lines - $EC_{50}$ Values by Cell Line.

| Tumor Type | Cell Line | VEGF Inhibition Approximate $EC_{50}$ (nM) |
|---|---|---|
| Breast | MDA-MB-231[a] | 5 |
|  | MDA-MB-468[a] | 5 |
| Cervical | HeLa[a] | 2 |
| Colorectal | HCT-116 | 10 |
| Epidermoid | A431 | 10 |
| Fibrosarcoma | HT1080 | 10 |
| Gastric | SNU-1 | 0.1 |
|  | AGS | 0.1 |
|  | Kato III[a] | 10 |
| Lung | NCI H460 | 10 |
|  | A549 | 50 |
|  | Calu-6[a] | 7 |
| Melanoma | A375[a] | 50 |
| Neuroblastoma | SY5Y[a] | 5 |
| Ovarian | SKOV3[a] | 10 |
| Pancreas | Capan-1[a] | 5 |
| Prostate | LNCaP[a] | 15 |
| Renal cell | HEK293 | 10 |

[a]Cell lines requiring incubation under hypoxic conditions (1% oxygen) to induce VEGF production.
Abbreviations:
$EC_{50}$ = effective concentration achieving 50% of peak activity;
VEGF = vascular endothelial growth factor 9.1.2 Animal Model Systems 9.1.2.1 Compound #10 Selectively Inhibits Pathological VEGF Production Relative to Other Human Angiogenic Factors This example demonstrates that Compound #10 selectively inhibits pathological VEGF production relative to other human angiogenic factors.

Experimental Design. In a series of experiments evaluating the effects of Compound #10 on intratumoral VEGF and tumor growth, intratumoral levels of VEGF-C, P1GF (Placental Growth Factor), FGF-2 (Fibroblast growth factor 2), survivin, PDGF (Platelet derived growth factor), and endostatin were also measured to assess the selectivity of Compound #10. VEGF-C and P1GF were analyzed to determine the in vivo effects of Compound #10 on other members of the VEGF family of angiogenic factors. All of these factors can be produced at tumor sites, and all may support tumor growth and metastases. See Yoon et al., Circ Res. 2003, 93(2):87 90; Ferrara et al., Nat. Rev. Drug Discov. 2004, 3(5):391 400; Luttun et al., Biochim. Biophys. Acta 2004, 1654(1):79 94; Saharinen et al., Trends Immunol. 2004, 25(7):387 95. There is also evidence that VEGF-A may stimulate production of P1GF by a post transcriptional mechanism. See Yao et al., FEBS Lett. 2005, 579(5):1227 34. VEGF-B was not assessed. The angiogenic growth factor FGF-2 was analyzed because it promotes tumor survival (see Bikfalvi et al., Angiogenesis 1998, 1(2):155 73), and has a 5'-UTR IRES. See Vagner at al., Mol. Cell. Biol. 1995, 15(1):35 44; Hellen et al., Genes Dev. 2001, 15(13):1593 612. The survivin protein was similarly evaluated because the survivin mRNA has an IRES. PDGF was assessed because this protein has angiogenic activity and its mRNA contains an IRES. See Sella et al., Mol. Cell. Biol. 1999, 19(8):5429 40; Hellen et al., supra. Endostatin was included because antiangiogenic treatment in vivo has shown that compensatory decreases in endogenous angiogenic inhibitors such as endostatin, thrombospondin, and angiostatin, results in a more pro angiogenic environment. See Sim, Angiogenesis, 1998, 2(1):37-48.

In all of these experiments, HT1080 cells ($5 \times 10^6$ cells/mouse) were implanted subcutaneously in male athymic nude mice. When tumors had become established, mice were divided into groups (10 mice/group). Treatments comprised Compound #10 (either alone or as the racemic mixture) or the corresponding vehicle alone, administered by oral gavage BID ("bis in die"; twice a day) on Monday through Friday and QD ("quaque die"; daily) on Saturday and Sunday over periods of 7 to 21 days (Table 5). Tumor size was measured by calipers at the beginning and end of treatment. At the completion of Compound administration, the mice were sacrificed, and excised tumors were assayed by ELISA for intratumoral VEGF or other angiogenic factors using methods analogous to those described in Section 9.1.1.1.

Results. As summarized in the studies shown in Table 5, Compound #10 universally inhibited the production of intratumoral VEGF A and tumor size. Compound #10 also reduced intratumoral P1GF in the experiments where this factor was measured; the results show a variable effect on VEGF-C. Compound #10 did not have statistically significant effects on levels of the other proteins tested, except for FGF 2 levels (as shown in Study 5). In Study 5, treatment was initiated when the tumors were quite large (~600 mm$^3$). The study was continued for 15-days, and the tumors had become quite bulky by the time intratumoral protein levels were analyzed. However, Compound #10 still decreased intratumoral VEGF levels by 78%, although FGF-2 levels were noted to be significantly elevated at the time of study termination. In Studies 2 and 3, endostatin levels were depressed by 22 to 30%, although these changes were not statistically significant. Collectively, these data indicate that Compound #10 is selective for suppression of VEGF family proteins.

TABLE 5

Study Design and Efficacy Information for Assessments of Selectivity for VEGF Inhibition by Compound #10 in Nude Mice Bearing HT1080 Xenografts.

| Parameter | | 1 | 2 | 3 | 4 | 5 | 6 | 7 |
|---|---|---|---|---|---|---|---|---|
| Animal number per group | | 10 | 10 | 10 | 10 | 10 | 7 | 10 |
| Compound #10 dose (mg/kg)[a] | | 1 | 5 | 5 | 5 | 5/50[b] | 5 | 10 |
| Administration | Route | Oral | Oral | Oral | Oral | Oral | Oral | Oral |
| | Schedule | BID[c] | BID[c] | BID[c] | BID[c] | BID[c] | QD[d] | QD[d] |
| Vehicle | | DMSO/PEG | DMSO/PEG | DMSO/PEG | DMSO/PEG | DMSO/PEG | L21[e] | L21[e] |
| Compound #10 Treatment duration (days) | | 28 | 7 | 10 | 9 | 15 | 21 | 42 |
| Vehicle-treatment duration (days) | | 14 | 7 | 10 | 9 | 10 | 21 | 10 |
| Initial mean tumor size (mm$^3$) | | 85 | 390 | 285 | 610 | 610 | 180 | 160 |
| Final mean Compound #10-treated tumor size (mm$^3$) | | 450 | 595 | 735 | 953 | 1922 | 750 | 1770 |
| Mean % difference relative to vehicle-treated animals[f] in: | | | | | | | | |
| Tumor size | | −58*[g] | −32* | −40* | −44* | −34*[h] | −51* | −63*[h] |
| Human VEGF-A (%) | | −57* | −81* | −95* | −85* | −78* | −95* | −42 |
| Human VEGF-C (%)[i] | | ND | −19 | −26 | ND | ND | −38* | +10 |
| Human PlGF (%)[i] | | ND | −67* | −59* | ND | ND | −73 | −65* |
| FGF-2 | | +3 | +3 | +5 | +15 | +31* | ND | ND |
| Survivin | | +7 | ND | ND | −9 | ND | ND | ND |
| PDGF | | +12 | ND | −30 | +23 | +20 | ND | ND |
| Endostatin | | ND | −30 | −22 | ND | ND | ND | ND |

*p < 0.05 (Student's t-test relative to vehicle)
[a]Some animals received racemic mixture; the dose is expressed as amount of Compound #10 in the mixture.
[b]Mice were treated with 5 mg/kg for the first 9 days and with 50 mg/kg for the last 6 days.
[c]Treatments were administered by oral gavage BID on Monday through Friday and QD on Saturday and Sunday for the number of days shown. All morning doses were given before 0830 hours. Evening doses were administered after 1630 hours (i.e., ≥8 hours after the morning dose).
[d]Treatments were administered by oral gavage QD in the morning before 0830 hours on Monday through Friday for the number of days shown.
[e]Vehicle was 35% Labrasol, 35% Labrafac and 30% Solutol).
[f]Calculated as [1-(treated/control)] × 100%
[g]Difference in tumor size is shown for Day 14, the day the vehicle-treated mice were taken off study.
[h]Difference in tumor size is shown for Day 10, the day the vehicle-treated mice were taken off study.
[i]Six mice per group in Compound #10-treated and vehicle-treated groups were analyzed
Abbreviations: BID = 2 times per day; QD = 1 time per day; DMSO = dimethyl sulfoxide; PEG-300 = polyethylene glycol (molecular weight 300); FGF-2 = basic fibroblast growth factor-2; PDGF = platelet-derived growth factor; PlGF = placental growth factor; VEGF = vascular endothelial growth factor; ND = not done 9.1.2.2 Compound #10 Dose-Dependently Reduces Tumor and Pathologically Produced Plasma Human VEGF Concentrations This example demonstrates that Compound #10 dose-dependently reduces intratumoral and pathologically produced plasma human VEGF concentrations in vivo.

Experimental Study Design. HT1080 cells ($5 \times 10^6$ cells/mouse) were implanted subcutaneously in male athymic nude mice. When tumors had become established (i.e., the mean tumor size had reached 180±75 mm³), mice were divided into 6 groups and treatment was assigned as shown in Table 6.

TABLE 6

Study Design for Dose Response Assessment in Nude Mice Bearing HT1080 Xenografts.

| Test Compound | Number of Animals | | Dose (mg/kg) | Administration[a] Route | Sched-ule | Dose Volume (mL/kg) | Dose Concen-tration (mg/mL) |
|---|---|---|---|---|---|---|---|
| | M | F | | | | | |
| Vehicle[b] | 10 | 0 | 0 | Oral | BID | 4 | 0 |
| Compound #10 | 10 | 0 | 0.3 | Oral | BID | 4 | 0.075 |
| Compound #10 | 10 | 0 | 1 | Oral | BID | 4 | 0.25 |
| Compound #10 | 10 | 0 | 3 | Oral | QD | 4 | 0.75 |
| Compound #10 | 10 | 0 | 3 | Oral | BID | 4 | 0.75 |
| Compound #10 | 10 | 0 | 10 | Oral | QD | 4 | 2.5 |

[a]Treatments were administered by oral gavage 7-days per week (except the 10-mg-QD regimen, which was administered daily on Monday through Friday) for a total of 18 days. All morning doses were given before 0830 hours. For BID schedules, evening doses were administered after 1630 hours (i.e., ≥8 hours after the morning dose).
[b]Vehicle was L21 (35% Labrasol, 35% Labrafac, and 30% Solutol).
Abbreviations: BID = 2 times per day; QD = 1 time per day Tumor size was measured using calipers at periodic intervals during the study (data shown in Section 9.2.2). Retro-orbital blood collection was performed to assess Compound #10 trough plasma concentrations after the first dose (just prior to the second dose) on Day 1, Day 4, and Day 9, and at study termination. The study was ended after 18 days, when the vehicle treated tumors reached a mean volume of ~1755 mm³. Retro-orbital terminal bleeding was performed at ~8 to 16 hours (depending upon the schedule of Compound administration) after the last dose to assess pathologic plasma human VEGF concentrations and trough Compound #10 plasma concentrations. Mice were sacrificed, and excised tumors were homogenized in buffer containing protease inhibitors. Both terminal intratumoral and pathologic plasma human VEGF levels were measured using an ELISA that recognizes human $VEGF_{121}$ and $VEGF_{165}$ (as described in Section 9.1.1.1). Intratumoral VEGF levels were normalized to the total tumor protein concentration, while pathologic plasma human VEGF levels were expressed in pg/mL of plasma. Plasma Compound #10 concentrations were evaluated by high performance liquid chromatography and with tandem mass spectroscopy (HPLC-MS/MS).

Results. As shown in FIG. 5 and FIG. 6, Compound #10 significantly suppressed pathologic human VEGF levels in tumors and in plasma in all Compound #10 dose groups. At the suboptimal Compound #10 dose of 0.3 mg/kg BID, partial reductions in both tumor and pathologic plasma human VEGF concentrations were observed, while human VEGF reductions were essentially maximal at all Compound #10 dose levels of ≥1 mg/kg BID. The correlation between pathologic plasma and tumor human VEGF levels in this animal model supports the potential utility of assessing pathologic plasma human VEGF levels to serve as a mechanism-specific, pharmacodynamic marker of Compound activity in the clinic.

The data shows that Compound #10 dose-dependently reduces intratumoral and pathologically produced plasma human VEGF concentrations in vivo.

9.1.2.3 Compound 1205 Reduces Tumor and Pathologically Produced Plasma Human VEGF Concentrations This example demonstrates that Compound 1205 reduces intratumoral and pathologically produced plasma human VEGF concentrations in vivo.

Experimental Design. HT1080 cells ($5 \times 10^6$ cells/mice) were implanted subcutaneously into male athymic nude mice. Treatment with vehicle alone or Compound 1205 was initiated when the median tumor volume was approximately 311±88 mm³. Table 7 and Table 9 (study design #21 and #23) provide the study design for assessing tumor and plasma pathologic VEGF concentrations—each group in each study included eight (8) mice. When the tumors in vehicle-treated mice had reached the target size of ~1200 mm³ for study #21 and ~1500 mm³ for study #23, all mice in the study were sacrificed, and excised tumors were homogenized in buffer containing protease inhibitors. Both intra-tumor and pathologic plasma human VEGF levels were measured using an ELISA that recognizes human $VEGF_{121}$ and $VEGF_{165}$. Intra-tumor VEGF levels were normalized to the total tumor protein concentration and pathologic plasma VEGF levels were expressed in pg/mL. Because smaller tumors produce less VEGF per mg of tumor protein, intra-tumor VEGF levels were normalized to tumor size. Table 9 provides the study design for assessing tumor and pathologic plasma VEGF.

Results. Treatment with Compound 1205 at 0.5 or 3 mg/kg for 14-days significantly reduced the levels of pathologic human VEGF measured in excised tumors (FIG. 27) and in plasma (FIG. 28) compared to levels measured in tumors and plasma from mice treated with vehicle. At the dose of 0.5 or 3 mg/kg QD, Compound 1205 inhibits both tumor and pathologic plasma human VEGF levels by more than 95%. Even with the reduction in tumor size in the treated groups, the volume normalized intra-tumor human VEGF levels were significantly reduced (FIG. 27; Table 7).

TABLE 7

Inhibition of Intra-Tumor and Pathologic Plasma Human VEGF by Compound 1205

| | Study #21 | | | Study #23 | |
|---|---|---|---|---|---|
| | Vehicle | Compound 1205 | | Vehicle | Compound 1205 |
| 1) Dose (mg/kg) | 0 | 0.5 | 3 | 0 | 1 |
| 2) Regimen | QD | QD | QD | QD | QD |
| 3) Test-Compound duration (days) | 14 | 14 | 14 | 14 | 14 |
| 4) Mean difference in human tumor VEGF (%) at Day 14 (Compound 1205) or Day 18 (Compound #10) | NA | 95%** | 98%** | NA | 95** |
| 5) Mean difference in human plasma VEGF (%) on Day 14 (Compound 1205) or on Day 18 (Compound #10) | NA | 97%** | 99% | NA | 100%** |

**p < 0.05 (ANOVA vs. vehicle).

9.2 Inhibition of Pathological Angiogenesis and Tumor Growth 9.2.1 Compound #10 Inhibits Tumor Angiogenesis This example demonstrates that Compound #10 reduces the total volume and diameter of tumor vessels.

Experimental Design. HT1080 cells ($5 \times 10^6$ cells/mouse) were implanted subcutaneously in male athymic nude mice. At a mean tumor size of 285±45 mm³, mice were divided into 2 groups and treatment was administered as shown in Table 8.

At the end of treatment, the mice were sacrificed. Excised tumors were assayed by ELISA for VEGF content as described in Section 9.1.1.1, and were sectioned and immunostained with an anti murine CD31 antibody that is specific for endothelial cells.

TABLE 8

Study Design for Assessment of Intratumoral Microvessel
Density in Nude Mice Bearing HT1080 Xenografts.

| Test Compound | Number of Animals M | F | Dose (mg/kg) | Administration[a] Route | Dose Schedule | Dose Volume (mL/kg) | Dose Concentration (mg/mL) |
|---|---|---|---|---|---|---|---|
| Vehicle[b] | 10 | 0 | 0 | Oral | BID | 8 | 0 |
| Racemic mixture[c] | 10 | 0 | 5[c] | Oral | BID | 8 | 0.625 |

[a]Treatments were administered by oral gavage BID on Monday through Friday and QD on Saturday and Sunday Treatments were administered by oral gavage BID on Monday through Friday and QD on Saturday and Sunday for a total of 10 days. All morning doses were given before 0830 hours. Evening doses were administered after 1630 hours (i.e., ≥8 hours after the morning dose).
[b]Vehicle was 5% DMSO and 95% PEG 300.
[c]Racemic material was used for this study at a dose of 10 mg/kg (1.25 mg/mL), resulting in a dose of the active Compound #10 enantiomer of 5 mg/kg (0.625 mg/mL).
Abbreviations: BID = 2 times per day; DMSO = dimethyl sulfoxide; PEG 300 = polyethylene glycol (molecular weight 300); QD = 1 time per day Results. Treatment with Compound #10 resulted in a mean 95% inhibition of tumor VEGF concentration. As shown in FIG. 7, this activity resulted in a profound effect on the architecture of the vasculature. Although the vessel count was unchanged, the total volume of tumor vessels and the diameters of vessels were visibly reduced. These findings are consistent with results from reports describing the effects of antiangiogenic therapies on larger tumors that have an existing vasculature. See Yuan et al., *Proc. Natl. Acad. Sci. USA.* 1996; 93(25):14765-70.

9.2.2 Compound #10 Inhibits Tumor Growth In Vivo

This example demonstrates that Compound #10 inhibits tumor growth in nude mice bearing HT1080 xenografts.

Experimental Design. The experimental design was reported in Section 9.1.2.2.

Results. The dose response effect of Compound #10 that correlated with decreases in tumor and pathologic human VEGF concentrations (see FIG. 5 and FIG. 6; Section 9.1.2.2) was also observed when assessing tumor size by treatment group over time. As depicted in FIG. 8, maximum antitumor activity was again observed at Compound #10 dose levels of ≥1 mg/kg BID. The dose of 1 mg/kg BID was associated with mean trough plasma concentrations of 0.13 µg/mL (0.28 µM) at 16 hours after the first day of dosing (n=3), and with steady state mean trough plasma concentrations of 0.82 µg/mL (1.76 µM) at 16 hours after the last dose on Day 18 (n=4). These data provide an indication of trough plasma concentrations that could be targeted when assessing the pharmacokinetics (PK) of a Compound in humans. In observing the animals, there was no overt toxicity associated with Compound #10 treatment. This data shows that Compound #10 inhibits tumor growth in nude mice bearing HT1080 xenografts.

9.2.3 Compound 1205 Inhibits Tumor Growth In Vivo

This example demonstrates that Compound 1205 inhibits tumor growth in nude mice bearing HT1080 xenografts.

Experimental Design. HT1080 cells ($5 \times 10^6$ cells/mouse) were implanted subcutaneously in male athymic nude mice. When tumors had become established (i.e., the mean tumor size had reached $311 \pm 88$ mm$^3$), mice were divided into 5 groups and treatment was administered as shown in Table 9 and 10. Compound 1330 is a relatively inactive (R,S) diastereomer of Compound 1205, which has (S,S) configuration. For comparison, Compound #10 was included in this study.

TABLE 9

Study Design for HT1080 Xenograft Studies Assessing
In vivo Efficacy of Compound 1205 and Compound #10.

| Test Compound | # of Animals Male | Dose (mg/kg) | Regimen | Dose Volume (mL/kg) | Dose Conc. (mg/mL) | Study # | Study Termination |
|---|---|---|---|---|---|---|---|
| Vehicle† | 8 | 0 | QD | 8 | 0 | 21 | All mice were taken off study |
| Compound 1205 | 8 | 0.5 | QD | 8 | 0.0625 | 21 | when tumors in vehicle |
| Compound 1205 | 8 | 3 | QD | 8 | 0.375 | 21 | reached 1200 mm$^3$ |
| Vehicle† | 8 | 0 | QD | 8 | 0 | 22 | (A) Vehicle-treated mice were |
| Compound 1205 | 8 | 0.5 | QD | 8 | 0.0625 | 22 | taken off study when the |
| Compound 1205 | 8 | 3 | QD | 8 | 0.375 | 22 | average tumor size of the group wais 1500 mm$^3$. (B) Each treated mouse was taken off study when its tumor was 1500 mm$^3$ |
| Vehicle† | 8 | 0 | QD | 8 | 0 | 23 | All mice were taken off study |
| Compound 1205 | 8 | 1 | QD | 8 | 0.125 | 23 | when tumors in vehicle reached 1500 mm$^3$ |
| Vehicle‡ | 8 | 0 | QD | 8 | 0 | 24a | A) Vehicle- and Compound |
| Compound 1205 | 8 | 10 | QD | 8 | 1.25 | 24a | 1330-treated mice were taken |
| Compound 1330Φ | 8 | 10 | QD | 8 | 1.25 | 24a | off study when the average tumor size of the group wais 1500 mm$^3$. (B) Each treated mouse was taken off study when its tumor was 1500 mm$^3$ |
| Vehicle† | 8 | 0 | QD | 8 | 0 | 24b | (A) Vehicle-treated mice were |
| Compound 1205 | 8 | 0.3 | QD | 8 | 0.0375 | 24b | taken off study when the average tumor size of the group wais 1500 mm$^3$. (B) Each treated mouse was taken off study when its tumor was 1500 mm$^3$ |

†Vehicle was 0.5% HPMC/1% Tween-80
‡Vehicle was L21 (35% Labrasol, 35% Labrafac, and 30% Solutol).
ΦInactive (R,S) diastereomer of Compound 1205
Abbreviations: BID = twice per day, QD = once per day Results. The results of the studies described in Table 10 and are shown in FIG. 26 for #24a. The data indicate that Compound 1205 (S,S diastereoisomer) inhibits tumor growth in an animal model with a pre-established human tumor. As shown in FIG. 26, treatment with Compound 1205 (S,S), but not with the (R,S) diastereomer Compound 1330, significantly delayed growth of HT1080 tumor cells in vivo. The growth of the tumors in mice treated with Compound 1330 overlapped with the growth of tumors in mice treated with 0.5% HPMC vehicle. This suggests that the relatively inactive (R,S) diastereomer (Compound 1330) does not appreciably isomerize to active Compound 1205 in vivo. Compound 1205 is active at doses as low as 0.3 mg/kg.

9.2.4 Time-Course Effects of Compound #10 on Tumor Size and Pathologically Produced Plasma Human VEGF Concentrations This example demonstrates that Compound #10 has a rapid onset for reducing xenograft tumor size and pathologically produced plasma human VEGF concentration.

Experimental Design. HT1080 cells ($5\times10^6$ cells/mouse) were implanted subcutaneously in male athymic nude mice.

TABLE 10

Effect of Compound 1205 and Compound #10 on Growth of HT1080 Tumor Cells In vivo.

| | Compound 1205 | | | | | | | Compound #10 |
|---|---|---|---|---|---|---|---|---|
| Study #[A] | 24b | 22 | 21 | 23 | 22 | 21 | 24a | 24a |
| Study Information | | | | | | | | |
| Dose (mg/kg) | 0.3 | 0.5 | 0.5 | 1 | 3 | 3 | 10 | 10 |
| Regimen | QD | QD | QD | QD | QD | QD | QD | QD |
| Dose (mg/kg/week) | 2.1 | 3.5 | 3.5 | 7 | 21 | 21 | 70 | 70 |
| Study design | Xeno | Xeno | PD | PD | Xeno | PD | Xeno | Xeno |
| Number of days that test compound was administered | 16[C] | 28[C] | 14 | 14 | 32[C] | 14 | 30[C] | 27[C] |
| Initial mean tumor size (mm$^3$) | 204 | 170 | 167 | 157 | 170 | 167 | 311 | 311 |
| Day that vehicle-treated mice were taken off study | 15 | 11 | 14 | 14 | 11 | 14 | 11 | 11 |
| Mean tumor size in vehicle-treated mice when taken off study | 1790 | 1390 | 1210 | 1500 | 1390 | 1210 | 1500 | 1500 |
| Final mean terminal tumor size in treatment group (mm$^3$) | 1540 | 1750 | 580 | 710 | 1840 | 379 | 1400 | 1460 |
| Results | | | | | | | | |
| Mean difference in tumor growth rate at the Day that the vehicle-treated tumors taken off study (%)[B] | 28% | 62%** | 61%** | 59%** | 75%** | 80%** | 76%** | 59%** |
| Difference vs. vehicle in median number of days to reach 1000 mm$^3$ (Days) | 0.7 | 11 | NA | NA | 14** | NA | 14** | 8** |

[A]See Table 9 for additional study information.
[B]% Difference in the rat of growth in compound-treated vs. vehicle-treated
**P < 0.05 (ANOVA vs. vehicle)
[C]Average time on study.
NA not applicable. The time to progression could not be calculated for PD (pharmacodynamic) studies.
Xeno Xenograft When tumors had become established (i.e., the mean tumor size had reached 585±150 mm$^3$), mice were divided into 4 treatment groups, as shown in Table 11.

TABLE 11

Study Design for Time Course Assessment in Nude Mice Bearing HT1080 Xenografts

| Test Compound | Number of Animals Per Time Point[a] | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 5 | 0 | 0 | Oral | QD | 4 | 0 |
| Compound #10 | 5 | 0 | 10 | Oral | QD | 4 | 2.50 |
| Doxorubicin | 5 | 0 | 6 | IP | Single bolus | 8 | 0.75 |
| Bevacizumab | 5 | 0 | 5 | IP | Single bolus | 8 | 0.625 |

[a]Treatments were initiated on Day 0 with 20 mice per group. On each day, 5 mice were sacrificed per group for analysis. Mice were treated with Compound #10 daily. Mice were treated with doxorubicin or bevacizumab on Day 0 only.
[b]Vehicle was L21 (35% Labrasol, 35% Labrafac, and 30% Solutol).
Abbreviations: IP = intraperitoneal; QD = 1 time per day Tumor size was measured by calipers immediately pretreatment and at the time of sacrifice on Day 1, 2, or 3 (5 mice per group per day). At sacrifice, the plasma was collected for assay of pathologic human VEGF concentration using an ELISA that recognizes human $VEGF_{121}$ and $VEGF_{165}$ (as described in Section 9.1.1.1).

Results. FIG. 9 shows the relative change in tumor size with time. In this short term study, the untreated tumors grew rapidly. Tumors from the vehicle treated mice had grown by 22% on Day 1, 42% on Day 2, and 79% on Day 3 ($p<0.05$ for each day, paired Student's t-test versus Day 0). All 3 treatments significantly reduced the rate of tumor growth by more than 50% over this 3 day period.

FIG. 10 displays an evaluation of pathologic plasma human VEGF concentrations. In Panel A, absolute values are expressed. In Panel B, values are expressed as a ratio relative to tumor volume because larger tumors tend to produce more VEGF. As shown in Panel A, pathologic plasma human VEGF concentrations from vehicle treated mice rose from Day 0 to Day 3. As indicated in Panel B, increases in pathologic plasma human VEGF in control mice were seen even when adjusting for the increase in tumor size that occurred over this time period. By contrast, pathologic plasma human VEGF levels from mice treated with Compound #10, doxorubicin, or bevacizumab were numerically lower than in control animals by Day 1. Pathologic plasma human VEGF concentrations continued to decline under the influence of Compound #10, consistent with an effect indicating the inhibition of VEGF production, while absolute and relative values in other treatment groups began to increase on Days 2 and 3. Thus, by Day 3 of treatment, Compound #10 was demonstrated to be as active as bevacizumab and more effective than doxorubicin in reducing tumor derived plasma VEGF levels. In addition, these data suggest that Compound #10 regulates tumor VEGF independent of tumor size.

9.2.5 Compound #10 Shows Antitumor Activity in Several Human Tumor Xenograft Models This example demonstrates that Compound #10 shows antitumor activity in several clinically relevant human tumor xenograft models.

Investigators at the National Cancer Institute (NCI) have shown that compounds that inhibit tumor growth in multiple nonclinical models are more likely to have clinical efficacy. See Johnson et al., Br. J. Cancer 2001, 84(10):1424 31. In each of these studies, human tumor cells were implanted and treatment was initiated some days later, only after tumors had developed a vasculature (i.e., when tumors were >100 $mm^3$). This method of waiting to begin treatment until after tumors are established is considered a more stringent and clinically relevant assessment of efficacy compared to beginning treatment immediately after tumor implantation. See Teicher, ed. Totowa, Tumor models in cancer research. Humana Press, 2002: 593-616.

9.2.5.1 Compound #10 Shows Inhibition of Tumor Growth in an T47D Estrogen-Sensitive Breast Cancer Xenograft Model This example demonstrates that Compound #10 shows antitumor activity in an T47D estrogen-sensitive breast cancer xenograft model.

Experimental Design. Estrogen pellets (0.72 mg/pellet) were implanted 30 days prior to cell implantation and again 60 days later. T47D estrogen-sensitive breast cancer cells ($5×10^6$ cells/mouse mixed 1:1 with MATRIGEL™) were implanted subcutaneously in female athymic nude mice. After 31 days, when the tumors had become established (i.e., the mean tumor size had reached 180±33 $mm^3$), mice were divided into 3 treatment groups, and treatment was administered as shown in Table 12. Tamoxifen was included as a positive control.

TABLE 12

Study Design for Assessment of Tumor Growth Inhibition in Nude Mice Bearing Estrogen Sensitive T47D Xenografts.

| Test Compound | Number of Animals | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 0 | 10 | 0 | Oral | QD | 4 | 0 |
| Compound #10 | 0 | 10 | 10 | Oral | QD | 4 | 2.5 |
| Tamoxifen | 0 | 10 | 10 | Oral | QD | 4 | 2.5 |

[a]Treatments were administered by oral gavage QD.
[b]Vehicle was L21 (35% Labrasol, 35% Labrafac, and 30% Solutol).
Abbreviations: QD = 1 time per day Tumor size was measured by calipers at periodic intervals. After 74 days of treatment, the mice were sacrificed. The tumors were not analyzed for intratumoral VEGF levels because of their small size at sacrifice.

Results. Results by treatment regimen are shown in Table 13. In this breast cancer xenograft model, Compound #10 resulted in a transient reduction and persistent delay in tumor growth relative to controls. Compound #10 appeared as active as tamoxifen in suppressing growth of this estrogen-sensitive cell line. In observing the animals, there was no evidence of toxicity associated with Compound #10 treatment.

TABLE 13

Efficacy Information for Assessment of Tumor Growth Inhibition in Nude Mice Bearing Estrogen Sensitive T47D Xenografts.

| Test Compound | Number of Animals | | Dose (mg/kg) | Schedule | Dose per Week (mg/kg) | Mean % Inhibition of Intratumoral VEGF vs Vehicle at Sacrifice | Mean % Inhibition of Tumor Size vs Vehicle at Day 74[a] |
|---|---|---|---|---|---|---|---|
| | M | F | | | | | |
| Vehicle[b] | 0 | 10 | 0 | QD | 0 | ND | NA |
| Compound #10 | 0 | 10 | 10 | QD | 70 | ND | 40 |
| Tamoxifen | 0 | 10 | 10 | QD | 70 | ND | 50 |

[a]Day 74 was the day on which mice were sacrificed.
[b]Vehicle was L21 (35% Labrasol, 35% Labrafac, and 30% Solutol).
Abbreviations: NA = Not applicable; ND = not determined; QD = 1 time per day; VEGF = vascular endothelial growth factor

9.2.5.2 Compound #10 Shows Inhibition of Tumor Growth in an MDA-MB 468 Estrogen Insensitive Breast Cancer Xenograft Model This example demonstrates that Compound #10 shows antitumor activity in an MDA-MB-468 estrogen-insensitive breast cancer xenograft model.

MDA-MB-468 estrogen-insensitive breast cancer cells ($5 \times 10^6$ cells/mouse mixed 1:1 with MATRIGEL™) were implanted subcutaneously in female athymic nude mice. After 6 days, tumors had become established (i.e., the mean tumor size had reached $185 \pm 26$ mm$^3$), mice were divided into 2 treatment groups, and treatment was administered as shown in Table 14.

TABLE 14

Study Design for Assessment of Tumor Growth Inhibition in Nude Mice Bearing Estrogen-Insensitive MDA-MB-468 Xenografts.

| Test Compound | Number of Animals | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 0 | 10 | 0 | Oral | QD | 4 | 0 |
| Compound #10 | 0 | 10 | 10 | Oral | QD | 4 | 2.5 |

[a]Treatments were administered QD continuously by oral gavage for at least 30 days.
[b]Vehicle was L21 (35% Labrasol, 35% Labrafac, and 30% Solutol).
Abbreviations: QD = 1 time per day Tumor size was measured by calipers at periodic intervals. When the individual tumor size in a mouse exceeded 1500 mm$^3$, that mouse was sacrificed and both tumor and plasma were assayed for pathologic VEGF concentration as described in Section 9.1.1.1.

Results. Results by treatment regimen are shown in Table 15. Compound #10 at 10 mg/kg significantly reduced intratumoral and plasma pathologic VEGF concentrations on the day on which the animals were sacrificed (range, Day 33 to 53) relative to controls (range, Day 9 to 15). In addition, Compound #10 reduced tumor size and prolonged the time to tumor progression (i.e., the time to reach $\geq 1000$ mm$^3$). In observing the animals, there was no evidence of toxicity associated with Compound #10 treatment.

9.2.5.3 Compound #10 Shows Reduction in Tumor Perfusion as Assessed by Dynamic Contrast-Enhanced Magnetic Resonance Imaging This example shows that Compound #10 reduces tumor perfusion as assessed by dynamic contrast-enhanced magnetic resonance imaging.

Experimental Design. Dynamic contrast-enhanced magnetic resonance imaging can be used preclinically and clinically to evaluate the anatomy of soft tissues, including the identification and accurate measurement of tumor volumes. In addition, evaluation of the intratumoral pharmacokinetics of contrast agents containing gadolinium can be used to measure vascular permeability characteristics. Coupling gadopentetate dimeglumine gadolinium to a small molecule like bovine serum albumin can reveal information about the necrotic (non-perfused) and non-necrotic (perfused) tumor volumes, and the percentage of vascular blood volume relative to the perfused tumor volume (known as the fractional blood volume [fBV]). Use of a macromolecular tracer, gadopentetate dimeglumine, can reveal information regarding the volume transfer coefficient ($K^{trans}$), a variable that represents a combination of vascular permeability, vascular surface area, and blood flow.

MDA MB 468 breast cancer cells ($5 \times 10^6$ cells/mouse mixed 1:1 with MATRIGEL™) were implanted subcutaneously in female athymic nude mice. After 13 days, when the tumors had become established (i.e., the mean tumor size reached ~400 mm$^3$), mice were divided into 2 treatment groups, and treatment was administered as shown in Table 16.

TABLE 16

Study Design for Assessment of Tumor Perfusion in Nude Mice Bearing MDA MB 468 Xenografts

| Test Compound | Number of Animals | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[a] | 0 | 8 | 0 | Oral | QD | 4 | 0 |
| Compound #10 | 0 | 8 | 10 | Oral | QD | 4 | 2.0 |

[a]Vehicle was L21 (35% Labrasol, 35% Labrafac, and 30% Solutol).
Abbreviations: QD = 1 time per day

TABLE 15

Efficacy Information for Assessment of Tumor Growth Inhibition in Nude Mice Bearing Estrogen Insensitive MDA-MB-468 Breast Cancer Xenografts.

| Test Compound | Number of Animals | | Dose (mg/kg) Schedule[a] | Dose per Week (mg/kg) | Mean % Inhibition of Intratumoral VEGF vs Vehicle at Sacrifice | Mean % Inhibition of Plasma pathologic VEGF vs Vehicle at Sacrifice | Mean % Inhibition of Tumor Size vs Vehicle at Day 12[b] | Median Time to Tumor Size $\geq 1000$ mm$^3$ (days) |
|---|---|---|---|---|---|---|---|---|
| | M | F | | | | | | |
| Vehicle[c] | 0 | 10 | 0/QD | 0 | — | — | — | 12 |
| Compound #10 | 0 | 10 | 10/QD | 70 | 61* | 75* | 65* | 25 |

*p < 0.05 (Student's t test relative to vehicle)
[a]Treatments were administered QD continuously by oral gavage for at least 30 days.
[b]Vehicle treated animal tumors reached $\geq 1500$ mm$^3$ between Day 9 and 15 and all vehicle treated animals were sacrificed by Day 15.
[c]Vehicle was L21 (35% Labrasol, 35% Labrafac, and 30% Solutol).
Abbreviations: M = Male; F = Female; QD = 1 time per day; VEGF = vascular endothelial growth factor; M = Male; F = Female Before each DCE-MRI scan, mice were injected intravenously with gadolinium-containing contrast dyes (bovine serum albumin-gadopentetate dimeglumine conjugate at ~0.03 mmol/kg followed by gadopentetate dimeglumine at ~0.2 mmol/kg). Baseline DCE-MRI measurements were taken on Day −1, test Compounds were administered on Day 0 through Day 5, and additional DCE-MRI measurements were taken on Days 1, 3, and 5. Image analyses were conducted with customized software. Total tumor volumes were measured by semi-automatically segmenting a region of interest around an anatomical image of the tumor. Tumor volumes of necrotic and non-necrotic tissues were measured by applying the same semi-automated segmentation process to a contrast dyed image. fBV and $K^{trans}$ were computed using a standard Kety PK model.

Results. As shown in FIG. 19, vehicle-treated animals had an increase in mean tumor volume from Day −1 to Day 5. By contrast, Compound #10 treated animals had little mean change. Differences in total tumor volumes in vehicle treated versus treated mice were apparent by Day 1 and were statistically significant by Day 3, confirming that Compound #10 begins to impede tumor growth rapidly after treatment initiation.

As shown in FIG. 20, vehicle-treated animals had a small mean change in necrotic (non perfused) tumor volume from Day −1 to Day 5. Consistent with an antivascular effect, Compound #10 rapidly increased the mean necrotic tumor volume, resulting in differences in necrotic tumor volumes between vehicle treated and treated groups that were statistically significant by Day 1.

Conversely, as shown in FIG. 21, most of the mean tumor volume increase depicted in FIG. 19 in vehicle-treated animals was due to growth of non-necrotic tumor tissue. By contrast, mean non-necrotic tumor volume in Compound #10-treated animals decreased from Day −1 to Day 5. Differences in non necrotic tumor volumes between vehicle-treated and treated groups were statistically significant by Day 1.

Tissue regions identified as necrotic have no measurable vascular permeability, limiting analysis of fBV to non-necrotic tumor regions (primarily in the tumor rim). As shown in FIG. 22, mean tumor fBV in vehicle-treated animals increased steadily from Day 1 to Day 5. Initially, mean tumor fBV also increased in Compound #10 treated mice but then declined after Day 3, resulting in a statistically significant difference relative to the vehicle-treated values on Day 5. These data indicate that Compound #10 inhibits tumor angiogenesis, increases tumor necrosis, decreases viable tumor, and decreases tumor microvessel density.

As for fBV, analysis of $K^{trans}$ was necessarily confined to non-necrotic tissue. As shown in FIG. 23, mean $K^{trans}$ increased in vehicle treated mice between Day −1 and Day 5, while the mean $K^{trans}$ decreased in Compound #10 treated mice over this same period. The relative changes in $K^{trans}$ in vehicle-treated compared to treated animals were statistically significant by Day 1. The data are consistent with Compound #10 inhibition of vascular permeability in the non-necrotic tumor rim.

9.2.5.4 Compound #10 Shows Inhibition of Tumor Growth in an SY5Y Neuroblastoma Xenograft Model This example demonstrates that Compound #10 shows antitumor activity in an SY5Y neuroblastoma xenograft model.

Experimental Design. SY5Y cells are derived from a human neuroblastoma, a childhood tumor arising in neural crest cells. SY5Y cells ($1\times10^7$ cells/mouse) were implanted subcutaneously in male athymic nude mice. After 7-days, tumors had become established (i.e., the mean tumor size had reached 387±10 mm$^3$), mice were divided into 2 groups, and treatment was administered as shown in Table 17.

TABLE 17

Study Design for Assessment of Tumor Growth Inhibition in Nude Mice Bearing SY5Y Xenografts

| Test Compound | Number of Animals | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 6 | 0 | 0 | Oral | QD | 4 | 0 |
| Compound #10 | 6 | 0 | 10 | Oral | QD | 4 | 2.5 |

[a]Treatments were administered by oral gavage 5 days per week (Monday through Friday) for up to 50 days.
[b]Vehicle was L22 (35% Labrafil, 35% Labrafac, and 30% Solutol).
Abbreviation: QD = 1 time per day Tumor size was measured by calipers at periodic intervals. When the average tumor size in a group exceeded 2000 mm$^3$, the mice in the group were sacrificed and excised tumors were assayed for intratumoral VEGF concentration as described in Section 9.1.1.1. Animals in which tumors did not reach 2000 mm$^3$ were sacrificed at Day 50.

Results. Results by treatment regimen are shown in Table 18. Compound #10 treatment was associated with a significant reduction in mean intratumoral VEGF concentration and essentially eliminated any increase in mean tumor size through 15-days of dosing, substantially prolonging the mean time until tumor progression (tumor size ≥1000 mm$^3$). In contrast, tumors in many control animals exceeded 2000 mm$^3$ by Day 17 and these animals had to be sacrificed. In view of the dramatic effect of Compound #10 treatment, Compound #10 treatment was stopped on Day 15 to determine whether these effects might be sustained after treatment withdrawal. Tumors from mice treated with Compound #10 continued to be smaller than tumors from vehicle treated mice, even after 28-days without treatment (data not shown). At Day 43, treatment with vehicle or Compound #10 was reinitiated for a further 6 days. There were not enough vehicle mice remaining in the study to assess if Compound #10 would be more effective than vehicle in terms of tumor growth inhibition after treatment reinitiation. However, as summarized in Table 18, even after the cessation of treatment for 28-days and then continued Compound #10 treatment for 6 days, intratumoral levels of VEGF were almost completely suppressed in the treated tumors. In observing the animals, there was no evidence of toxicity associated with Compound #10 treatment.

TABLE 18

Efficacy Information for Assessment of Tumor Growth
Inhibition in Nude Mice Bearing SY5Y Xenografts.

| Test Compound | Number of Animals M | F | Dose (mg/kg) | Schedule[a] | Dose per Week (mg/kg) | Mean % Inhibition of Intratumoral VEGF vs Vehicle at Sacrifice | Mean % Inhibition of Tumor Size vs Vehicle at Day 17[b] | Median Time to Tumor Size ≥1000 mm$^3$ (days) |
|---|---|---|---|---|---|---|---|---|
| Vehicle[c] | 6 | 0 | 0 | QD | 0 | 0 | 0 | 12 |
| Compound #10 | 6 | 0 | 50 | QD | 250 | 96* | 73* | 35 |

*p < 0.05 (Student's t-test relative to vehicle)
[a]Treatments were administered by oral gavage 5 days per week (Monday through Friday) for up to 50 days.
[b]Day 17 was day on which vehicle treated animal tumors had reached ≥2000 mm$^3$ and the mice were sacrificed.
[c]Vehicle was L22 (35% Labrafil, 35% Labrafac, and 30% Solutol).
Abbreviations: QD = 1 time per day; VEGF = vascular endothelial growth factor; M = Male; F = Female 9.2.5.5 Compound #10 Shows Inhibition of Tumor Growth in an LNCaP Prostate Cancer Xenograft Model This example demonstrates that Compound #10 shows antitumor activity in an LNCaP prostate cancer xenograft model.

Experimental Design. The LNCaP cell line is derived from a lymph node metastasis. LNCaP cells (1×10$^6$ cells/mouse mixed 1:1 with MATRIGEL™) were implanted subcutaneously in male athymic nude mice. After 43 days, tumors had become established (i.e., the mean tumor size had reached 260±35 mm$^3$), mice were divided into 2 treatment groups, and treatment was administered as shown in Table 19.

TABLE 19

Study Design for Assessment of Tumor Growth Inhibition in
Nude Mice Bearing Androgen-Sensitive LNCaP Xenografts.

| Test Compound | Number of Animals M | F | Dose (mg/kg) | Administration[a] Route | Schedule | Dose Volume (mL/kg) | Dose Concentration (mg/mL) |
|---|---|---|---|---|---|---|---|
| Vehicle[b] | 10 | 0 | 0 | Oral | M-W-F | 4 | 0 |
| Compound #10 | 10 | 0 | 10 | Oral | M-W-F | 4 | 2.5 |

[a]Treatments were administered M-W-F by oral gavage for at least 35 days.
[b]Vehicle was L21 (35% Labrasol, 35% Labrafac, and 30% Solutol).
Abbreviations: M-W-F = Monday-Wednesday-Friday Tumor size was measured by calipers at periodic intervals during the study. When the mean tumor size in a mouse exceeded 1500 mm$^3$, mice in that group were sacrificed and both tumor and plasma were assayed for pathologic VEGF concentration as described in Section 9.1.1.1.

Results. Results by treatment regimen are shown in Table 20. Relative to controls, Compound #10 at 10 mg/kg M-W-F reduced intratumoral VEGF concentrations adjusted for tumor size on the day on which the animals were sacrificed. In addition, Compound #10 prolonged the time to tumor progression (i.e., the time to reach ≥1000 mm$^3$). In observing the animals, there was no evidence of toxicity associated with Compound #10 treatment.

TABLE 20

Efficacy Information for Assessment of Tumor Growth Inhibition in Nude
Mice Bearing Androgen-Insensitive LNCaP Prostate Cancer Xenografts.

| Test Compound | Number of Animals M | F | Dose (mg/kg) | Schedule[a] | Dose per Week (mg/kg) | Mean % Inhibition of Intratumoral VEGF vs Vehicle at Sacrifice | Mean % Inhibition of Tumor Size vs Vehicle at Day 35[b] | Median Time to Tumor Size ≥1000 mm$^3$ (days) |
|---|---|---|---|---|---|---|---|---|
| Vehicle[c] | 10 | 0 | 0 | M-W-F | 0 | — | — | 27 |
| Compound #10 | 10 | 0 | 10 | M-W-F | 30 | 51[d] | 36 | 38 |

[a]Treatments were administered M-W-F by oral gavage for at least 35 days.
[b]Vehicle treated animal tumors reached ≥1500 mm3 by ~Day 30 and all vehicle-treated animals were sacrificed by Day 35.
[c]Vehicle was L21 (35% Labrasol, 35% Labrafac, and 30% Solutol).
[d]Adjusted for tumor size
Abbreviations: M-W-F = Monday-Wednesday-Friday; VEGF = vascular endothelial growth factor

9.2.5.6 Compound #10 Shows Inhibition of Tumor Growth in Orthotopic SY5Y Neuroblastoma and SKNEP Ewing Sarcoma Tumor Models This example demonstrates that Compound #10 shows antitumor activity in orthotopic SY5Y neuroblastoma and SKNEP Ewing sarcoma tumor models.

Experimental Design. In orthotopic tumor models, human tumor cells are implanted into the mouse in an organ that corresponds to the location from which the tumors arise. Such models may provide a better predictor of clinical efficacy than injection of tumors into the flanks of nude mice. See Hoffman, *Invest. New Drugs* 1999, 17(4):343-59. SY5Y neuroblastoma or SKNEP Ewing sarcoma tumor cells ($1 \times 10^6$ cells/mouse) were implanted into the kidney capsule of female athymic nude mice according to published methods. See Huang et al., *Proc. Natl. Acad. Sci. USA* 2003, 100(13):7785-90. One week after implantation of each type of tumor, mice were divided into 2 groups and were administered a test Compound as shown in Table 21.

TABLE 21

Study Design for Assessment of Tumor Growth Inhibition in Nude Mice Bearing SKNEP or SY5Y Orthotopic Xenografts.

| Tumor Type | Test Compound | Number of Animals M | Number of Animals F | Dose (mg/kg) | Administration[a] Route | Administration[a] Schedule | Dose Volume (mL/kg) | Dose Concentration (mg/mL) |
|---|---|---|---|---|---|---|---|---|
| SY5Y | Vehicle[b] | 0 | 15 | 0 | Oral | QD | 4 | 0 |
|  | Compound #10 | 0 | 15 | 30 | Oral | QD | 4 | 7.5 |
| SKNEP | Vehicle[b] | 0 | 15 | 0 | Oral | QD | 4 | 0 |
|  | Compound #10 | 0 | 15 | 30 | Oral | QD | 4 | 7.5 |

[a] Treatments were administered by oral gavage 5 days per week (Monday through Friday) for up to 5 weeks.
[b] Vehicle was L3 (70% Labrasol, 18.3% Labrafac, and 11.7% Labrafil).
Abbreviation: QD = 1 time per day After 5 weeks of treatment, the mice were sacrificed, and the weights of the tumors were assessed.

Results. As shown in FIG. 11, tumors from vehicle treated mice weighed about 3 to 4 grams at 5 weeks. By contrast, treatment with Compound #10, when evaluated at the same time point, completely prevented growth of both the SKNEP and the SY5Y tumors. In observing the animals, there was no evidence of toxicity associated with Compound #10 treatment.

9.2.6 Compound #10 Penetrates Disease Relevant Tissues

This example demonstrates that Compound #10 penetrates disease relevant tissues.

Experimental Design. The distribution of $^{14}$C-Compound #10 were evaluated following a single oral gavage administration of 50 mg/kg (~10 µCi/animal) of $^{14}$C-labeled Compound #10 to rats in a GLP study. For the quantitative whole-body autoradiography (QWBA) analysis, 1 animal/sex/timepoint was sacrificed at 6, 12, 24, 48, and 72 hours postdose as shown in Table 22.

TABLE 22

Study Design for $^{14}$C-Compound #10 Single Dose Tissue Distribution Assessment in Rats

| Number of Animals M | Number of Animals F | Compound #10 Dose[a] (mg/kg) | Dose Volume (mL/kg) | Dose Concentration (mg/mL) | Number of Animals per Timepoint | Dosing Day Sampled | Timepoints Relative to Dose (hours) |
|---|---|---|---|---|---|---|---|
| 5 | 5 | 50 | 1.25 | 40 | 1[b] | Day 1 | 6, 12, 24, 48, 72 |

[a] $^{14}$C-Compound #10 was administered as a single-dose by oral gavage in L23 vehicle (35% Gelucire, 35% Labrafac, and 30% Solutol).
[b] For 1 animal per sex at each timepoint, a blood sample was collected at the time of sacrifice for assessments of concentrations $^{14}$C-Compound #10 in blood, plasma, and tissues, and for calculation of tissue:plasma concentration ratios at the specified times postdose.
Abbreviations: F = female; M = male For the QWBA, the carcasses were prepared by immediately freezing them, embedding them in chilled carboxymethylcellulose, and freezing them into blocks. Appropriate cryomicrotome sections of the blocks at 40 μm thickness were collected on adhesive tape. Mounted sections were tightly wrapped and exposed on phosphorimaging screens along with plastic embedded autoradiographic standards. Exposed screens were scanned and the autoradiographic standard image data were sampled to create a calibrated standard curve. Specified tissues, organs, and fluids were analyzed. Tissue concentrations were interpolated from each standard curve as nanocuries per gram and then converted to μg equivalents/gram on the basis of the Compound #10 specific activity.

Results. All animals appeared healthy and exhibited no overt signs of toxicity throughout the study. In this study, absorbed radioactivity was rapidly distributed into the whole body with the $T_{max}$ in blood and plasma occurring at 4 hours postdose in both sexes. Excluding the gastrointestinal tract, $C_{max}$ values in most tissues occurred at 6 to 12 hours postdose, with the highest values occurring in lipomatous tissues such as adrenal gland, brown fat, and liver. By 72 hours postdose, discernable residual radioactivity remained concentrated in fatty tissues in both sexes.

As shown in Table 23, the tissue:plasma concentration ratios were greater than 1 in most tissues. At 72 hours postdose, the highest tissue:plasma concentration ratios were in fat with values ranging from 37.1 to 63.9 in both sexes. All other tissues had ratios less than 10 with the exception of female bone marrow, Harderian gland, ovary, and skin, which had values of 18.8, 12.0, 28.1, and 11.4, respectively. There were no remarkable gender related differences in absorption, distribution, and elimination of radioactivity.

TABLE 23

Tissue:Plasma Concentration Ratios Determined by Whole-Body Autoradiography at Specified Times after a Single Oral Administration of $^{14}$C-Compound #10 to Rats (50 mg/kg)

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Adrenal gland | 18.5 | 16.2 | 10.8 | 16.7 | 8.96 | 8.93 | 5.89 | 6.59 | 6.02 | 7.16 |
| Blood | 0.569 | 0.577 | 0.601 | 1.00 | NA | 0.613 | NA | NA | NA | 1.80 |
| Bone | NA | 0.362 | NA | 0.497 | NA | NA | NA | NA | NA | NA |
| Bone marrow | 2.71 | 4.85 | 4.01 | 13.0 | 3.48 | 4.63 | 2.91 | 7.05 | NA | 18.8 |
| Cecum | 4.18 | 7.44 | 4.80 | 5.70 | 2.56 | 2.10 | 2.39 | 3.49 | NA | 3.66 |
| Cecum contents | 98.7 | 40.5 | 21.9 | 40.3 | 4.91 | 7.20 | 4.98 | 2.74 | 5.01 | 3.04 |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Diaphragm | 5.48 | 4.35 | 4.98 | 6.58 | 2.89 | 3.06 | 2.04 | 3.09 | 1.75 | 3.50 |
| Epididymis | 0.862 | NA | 1.22 | NA | 2.13 | NA | 3.09 | NA | 3.09 | NA |
| Esophageal contents | NA | 0.231 | NA | NA | NA | NA | NA | NA | NA | 2.21 |
| Esophagus | 1.83 | 1.25 | 1.89 | 3.64 | 1.53 | 1.59 | NA | 2.76 | NA | 1.93 |
| Exorbital lacrimal gland | 3.46 | 3.45 | 5.56 | 8.15 | 4.72 | 3.85 | 3.44 | 3.90 | 3.91 | 3.51 |
| Eye | 0.279 | 0.275 | 0.291 | 0.606 | NA | NA | 0.847 | NA | NA | 1.72 |
| Fat (abdominal) | 13.3 | 4.05 | 20.7 | 9.61 | 27.8 | 38.2 | 47.7 | 58.4 | 62.1 | 60.8 |
| Fat (brown) | 15.5 | 14.2 | 25.4 | 46.1 | 34.4 | 34.0 | 37.0 | 58.4 | 37.1 | 63.9 |
| Fat (subcutaneous) | 4.66 | 5.11 | 15.4 | 12.9 | 22.9 | 31.7 | 35.6 | 50.0 | 52.2 | 56.6 |
| Gastric mucosa | 5.47 | 5.92 | 6.58 | 6.82 | 3.35 | 3.66 | 2.86 | 4.18 | 2.97 | 4.50 |
| Harderian gland | 3.06 | 2.53 | 5.02 | 7.61 | 8.92 | 7.80 | 10.5 | 14.7 | 9.54 | 12.0 |
| Intra-orbital lacrimal gland | 3.12 | 3.33 | 5.47 | 6.21 | 4.46 | 4.11 | 3.67 | 6.13 | NA | 8.76 |
| Kidney | 5.98 | 4.50 | 4.44 | 5.82 | 3.20 | 2.72 | 2.36 | 3.23 | 2.04 | 4.09 |
| Large intestinal contents | 26.2 | 138 | 61.7 | 256 | 21.9 | 20.8 | 12.1 | 5.44 | 5.80 | 7.51 |
| Large intestine | 2.65 | 2.43 | 3.06 | 5.94 | 1.81 | 2.10 | 1.58 | 1.69 | NA | 3.02 |
| Liver | 7.77 | 8.49 | 5.65 | 8.82 | 4.83 | 4.79 | 4.23 | 6.01 | 4.52 | 5.74 |
| Lung | 2.52 | 2.00 | 1.80 | 2.69 | 1.54 | 1.43 | 1.38 | 1.64 | NA | 2.46 |
| Medulla | 1.60 | 1.42 | 1.98 | 3.82 | 1.83 | 1.69 | 1.20 | 2.01 | NA | 1.88 |
| Muscle | 2.65 | 2.11 | 2.81 | 3.55 | 1.70 | 1.82 | 1.47 | 1.73 | NA | 2.54 |
| Myocardium | 5.31 | 5.89 | 3.90 | 7.03 | 2.82 | 2.88 | 2.43 | 3.95 | 1.97 | 4.15 |
| Nasal turbinates | 1.19 | 1.14 | 1.40 | 2.12 | 1.55 | 1.25 | 1.52 | 2.06 | NA | 2.58 |
| Olfactory lobe | 1.42 | 1.38 | 1.35 | 2.45 | 1.23 | 1.13 | 0.967 | NA | NA | 3.33 |
| Ovary | NA | 7.48 | NA | 17.6 | NA | 12.1 | NA | 11.3 | NA | 28.1 |
| Pancreas | 6.95 | 6.25 | 6.28 | 9.58 | 4.54 | 4.79 | 3.25 | 5.08 | 3.21 | 4.96 |
| Pituitary gland | 4.06 | 4.27 | 3.22 | 5.48 | 2.72 | 2.33 | 0.890 | 3.68 | NA | 1.58 |
| Preputial gland | 4.15 | 3.45 | 6.94 | 12.3 | 11.3 | 7.93 | 20.2 | NA | NA | NA |
| Prostate | 2.62 | NA | 2.61 | NA | 2.35 | NA | 1.09 | NA | 1.78 | NA |
| Renal cortex | 6.83 | 5.65 | 4.53 | 6.48 | 3.27 | 2.96 | 2.64 | 3.49 | 2.44 | 4.40 |
| Renal medulla | 5.35 | 3.70 | 4.21 | 5.06 | 3.04 | 2.53 | 1.75 | 2.84 | 1.68 | 3.60 |
| Salivary gland | 5.69 | 4.75 | 4.80 | 7.18 | 3.38 | 3.53 | 2.45 | 3.57 | 1.90 | 3.74 |
| Seminal vesicle | 0.780 | NA | 0.646 | NA | 0.691 | NA | NA | NA | NA | NA |
| Skin | 1.66 | 1.46 | 3.33 | 5.21 | 3.98 | 4.19 | 4.49 | 5.73 | 8.06 | 11.4 |
| Small intestinal contents | 7.35 | 7.81 | 15.2 | 15.1 | 1.67 | 3.35 | 3.68 | 2.80 | 1.69 | 3.34 |

TABLE 23-continued

Tissue:Plasma Concentration Ratios Determined by Whole-Body Autoradiography at Specified Times after a Single Oral Administration of $^{14}$C-Compound #10 to Rats (50 mg/kg)

| Tissue | 6 Hours M | 6 Hours F | 12 Hours M | 12 Hours F | 24 Hours M | 24 Hours F | 48 Hours M | 48 Hours F | 72 Hours M | 72 Hours F |
|---|---|---|---|---|---|---|---|---|---|---|
| Small intestine | 8.46 | 5.01 | 3.02 | 5.09 | 2.93 | 2.45 | 1.21 | 2.62 | 1.80 | 3.36 |
| Spinal cord | 1.14 | 0.898 | 1.24 | 1.92 | 1.75 | 1.60 | 1.43 | 1.60 | 1.84 | 2.75 |
| Spleen | 2.73 | 2.84 | 2.37 | 3.91 | 1.80 | 1.89 | 1.50 | 1.88 | NA | 2.84 |
| Stomach | 4.34 | 3.62 | 3.72 | 5.12 | 2.86 | 1.76 | 1.72 | 2.93 | 2.44 | 4.19 |
| Stomach contents | 6.51 | 3.36 | 1.10 | 1.01 | NA | NA | NA | NA | NA | NA |
| Testis | 0.642 | NA | 1.17 | NA | 1.88 | NA | 2.13 | NA | 1.90 | NA |
| Thymus | 2.11 | 1.98 | 2.50 | 3.94 | 1.98 | 1.84 | 1.58 | 1.65 | NA | 3.34 |
| Thyroid | 3.18 | 3.77 | 2.57 | 3.61 | 2.76 | 1.38 | 1.14 | 1.87 | NA | 3.05 |
| Urinary bladder | 1.63 | 1.45 | 0.786 | 1.89 | 1.56 | 1.02 | 1.23 | 1.38 | NA | 1.92 |
| Urine | 0.239 | 1.66 | 0.299 | 0.761 | NA | NA | NA | NA | NA | NA |
| Uterus | NA | 1.86 | NA | 4.97 | NA | 3.51 | NA | 3.51 | NA | 7.66 |

Abbreviations: F = female; M = male; NA = not applicable

This example demonstrates that Compound #10 penetrates disease relevant tissues.

9.3 Cell Cycle Delay 9.3.1 Cell Based Assays 9.3.1.1 Compound #10 and Compound 1205 Provoke a Late $G_1$/Early S-Phase Cell Cycle Delay This example demonstrates that a Compound induces a cell cycle delay at the $G_1$/S-phase border.

Experimental Design. During in vitro evaluations of Compound #10 and Compound 1205 effects on VEGF expression, an examination of the effect on tumor cell cycling was performed. HT1080 cells were incubated under normoxic conditions (21% oxygen) for 18 hours with vehicle (0.5% DMSO) alone, or with a range of concentrations of Compound #10 from 0.3 nM to 100 nM, or 10 nM of Compound 1205. Compounds shown in Table 24 were incubated under normoxic conditions for 18 hours with vehicle or Compound #10 at a single dose of 100 nM. After treatment, cells were trypsinized, and stained with propidium iodide (PI) dye to measure DNA content of individual cells by flow cytometry. Output comprised histograms showing relative DNA content in 10,000 cells.

Results. As shown in FIG. 12 and FIG. 24, Compound #10 and Compound 1205 induced a redistribution of the cycling characteristics of the cell population. An apparent dose response was observed for Compound #10. Starting at a concentration of 1 nM for Compound #10, an accumulation of cells in S phase can be observed. With higher concentrations of Compound #10, there is a progressive shift, such that a substantial proportion of the cells show a cell cycle delay at the $G_1$/S phase border. Concentrations of Compound #10 achieving these effects are consistent with those demonstrating inhibition of VEGF production (FIG. 1).

For additional Compounds shown in Table 24, the test results are expressed as the percentage of cells in the S-phase compared to a DMSO control (17.3% cells in S-Phase). While compounds which cause greater than 20% of the cells to accumulate in S-phase at 100 nM are considered active, a larger percentage of cells may be accumulated in S-phase at lower doses depending on the Compound, as shown in FIG. 12 for example.

TABLE 24

| Compound | % Cells In S-Phase |
|---|---|
| DMSO (Control) | 17.3 |
| 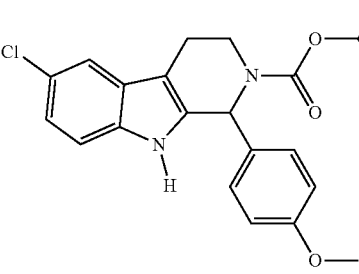 10 | 15.3 |
| 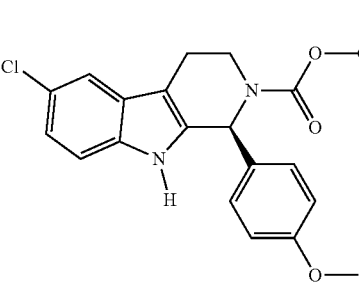 #10 | 26.1 |
| 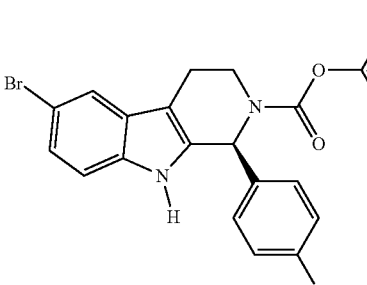 332 | 26.4 |

TABLE 24-continued

| Compound | % Cells In S-Phase |
|---|---|
| 1739 | 25.7 |
| 1205 | 20.0 |
| 1726 | 16.5 |
| 1727 | 16.8 |
| 1728 | 16.4 |
| 1159 | 17.2 |
| 1729 | 16.8 |
| 1730 | 16.4 |

TABLE 24-continued

| Compound | % Cells In S-Phase |
|---|---|
| 1731 | 17.9 |
| 1732 | 20.6 |
| 1330 | 17 |

9.3.1.2 The Effect of Compound #10 on the Cell Cycle is Reversible

This example demonstrates that the effect of Compound #10 on cell cycle delay is reversible.

Experimental Design. HT1080 cells were incubated under normoxic conditions (21% oxygen) for 14 hours with Compound #10 (100 nM) or with vehicle (0.5% DMSO) alone. Compound #10 was then washed out of the cultures and cells were harvested and analyzed by PI staining and flow cytometry (as described in Section 9.3.1.1) at 0, 2, 5, 8, and 26 hours after discontinuation of treatment.

Results. As shown in FIG. 13, treatment with Compound #10 caused the expected increase in the proportion of cells in late $G_1/S$ phase of the cell cycle (Time 0). At 2 hours after Compound #10 removal, a shift was beginning to occur; however, a large percentage of the cells remained delayed in $G_1/S$. By 5 to 8 hours, cells were clearly redistributing. By 26 hours after Compound #10 washout, the cells had resumed normal cycling.

9.3.1.3 Compound #10 Cell Cycle Delay is Coincident with the Inhibition of VEGF Production This example demonstrates that Compound #10 cell cycle delay is coincident with the inhibition of VEGF production.

Experimental Design. Several VEGF secreting cell lines were assayed for cell cycle effects. Actively proliferating cells were incubated for 18 hours under normoxic conditions (21% oxygen) with vehicle (0.5% DMSO) alone or with Compound #10 at concentrations of 10 nM or 100 nM. At the completion of treatment, cells were harvested and cellular DNA content was analyzed via PI staining and flow cytometry (as described in Section 9.3.1.1).

Results. In the same cell lines, treatment was undertaken for 48 hours with a range of concentrations of Compound #10 from 0.1 nM to 30 μM or with vehicle (0.5% DMSO) alone. The conditioned media were collected and assayed by ELISA for soluble $VEGF_{121}$ and $VEGF_{165}$ isoforms (as described in Section 9.1.1.1); results were calculated as percentage inhibition relative to vehicle treated controls. $EC_{50}$ values were calculated from the concentration response curves.

As shown in Table 25, Compound #10 cell cycle delay was coincident with the inhibition of VEGF production in all of the tested tumor types.

TABLE 25

Correlation of VEGF Inhibition and Cell Cycle Delay in Human Tumor Cell Lines

| Tumor Type | Cell Line | VEGF Inhibition $EC_{50}$ (nM) | Cell Cycle Delay at VEGF Inhibition $EC_{50}$ |
|---|---|---|---|
| Cervical | HeLa | 2 | Yes |
| Fibrosarcoma | HT1080 | 10 | Yes |
| Colorectal | HCT116 | 10 | Yes |
| Renal cell | HEK293 | 10 | Yes |
| Lung | NCI H460 | 10 | Yes |
| Glioblastoma | U-87MG | >30,000 | No |
| Pancreas | ASPC-1 | >30,000 | No |
|  | PL-45 | >30,000 | No |
|  | HPAF-2 | >30,000 | No |
|  | PC-3 | >30,000 | No |

Abbreviations:
$EC_{50}$ = effective concentration achieving 50% of peak activity;
VEGF = vascular endothelial growth factor

9.3.1.4 The Kinetics of S-Phase Transit Employing BrdU Incorporation into DNA This example demonstrates the rate and number of cells transiting the S-phase of the cell cycle.

Experimental Design. HT 1080 cells are exposed to BrdU (bromodeoxyuridine, a synthetic nucleoside that is an analogue of thymidine and is incorporated into DNA during the S phase of cell division) (FITC BrdU Flow Kit, BD Pharmingen catalog #552598). Cells are grown and treated as described in Section 9.3.1.3 above with the exception that one hour prior to harvesting by trypsinization, BrdU (final concentration 1 μM) is added to each culture for 1 hour. Cells actively replicating DNA during this brief time incorporate the BrdU into the DNA, which can then be quantitated. BrdU content is quantitated with using the FITC BrdU Flow Kit as instructed by the manufacturer. The process includes fixation (paraformaldehyde) and DNA staining with 7-AAD (7-amino-actinomycin D) followed by incubation with a fluoro-tagged anti-BrdU antibody that specifically recognizes BrdU incorporated into DNA. Dual channel FACS analysis permits assessment of both the DNA content of individual cells and the rate of transit across the S-phase, which is assessed based upon BrdU incorporation over the one hour treatment period.

Results. FIG. 29 indicates that an 18-hour treatment with increasing doses of Compound #10 causes a net increase in the percentage of cells residing in S-phase; however, individual cells incorporated less BrdU during the one-hour treatment period compared to DMSO control cells. The percentage of cells incorporating BrdU and the relative level of BrdU at each Compound #10 concentration is shown in FIG. 30. These results suggest that Compound #10 slows the transit of cells through the S-phase of the cell cycle.

9.3.1.5 The Effect of Compound #10 on the 3-Dimensional Growth of HT 1080 Cells

This example demonstrates the effect of a Compound provided herein on the 3-dimensional growth of HT1080 cells.

Experimental Design. HT1080 cells grown as a monolayer were trypsinized and seeded onto a 0.75% agar noble base to prevent the cells from attaching to the bottom of the tissue culture plate and to allow/promote the cells to self-adhere and grow as 3-dimensional spheroids. After 4 days the spheroids were established and the liquid growth medium was replaced with medium containing either 0.5% DMSO vehicle, or 10 nM or 50 nM of Compound #10 with 0.5% DMSO vehicle. The cells were incubated for 22 and 45 hours at 37° C., in the presence of a 10% $CO_2$ atmosphere. Spheroids were visually checked daily for morphological changes and a medium was replenished two times per week. At 22 and 45 hours after exposure to Compound #10, BrdU was added to a subset of the wells designated for FACS analysis and then returned to the incubator for 3 hours to permit cells synthesizing DNA (i.e. cells in S-phase) to incorporate the BrdU into the nascent strands of DNA. These pulse labeled spheroids were then harvested, washed and trypsinized (triple action solution, Gibco), pelleted and prepared for FACS analysis with a FITC BrdU Flow Kit, (BD Pharmingen). Cells were fixed and permeabilized with paraformadehyde and DNA stained with 7-AAD followed by incubation with an antibody which specifically recognizes BrDV incorporated into DNA. As described in Section 9.3.1.4. Cells were analyzed and sorted by 7-AAD signal (DNA content) to determine cell cycle phase, and BrdU content (percent actively synthesizing DNA).

Results. HT1080 spheroids prepared as above were treated with a Compound provided herein for 24 (FIG. 31) or 48 hours (FIG. 32). FIG. 31 and FIG. 32 show: (A) a histogram of DNA content demonstrating that the cell cycle distribution is not affected by exposure to the Compound provided herein; (B) BrdU quantification indicating the fraction of cells actively synthesizing DNA; and (C) a graphical representation of the percentage of cells that incorporated BrdU (i.e., the cells in S-phase), indicating that the percentage is not significantly altered by compound #10 treatment.

Spheroids, prepared as above, were treated with either vehicle alone (0.5% DMSO v/v final) added to the media or a Compounds provided herein (10 nM or 50 nM final concentration) in media to which vehicle has been added. The cells were photographed on day 5 of treatment to assess any gross morphological differences caused by exposure to Compound #10. Spheroids from all treatment groups looked indistinguishable from one another (data not shown). In addition, spheroids maintained in the presence of Compound #10 provided herein for three weeks also display no obvious morphological changes (data not shown).

9.3.1.6 Effect of Compound #10 on HT1080 Cell Viability and Mobility

This example demonstrates that Compound #10 inhibits or reduces the ability of cells to migrate out of spheroids of HT1080 cells.

Experimental Design. To assess the viability and motility of HT 1080 cells exposed to Compound #10, spheroids of HT1080 cells were prepared as in Section 9.3.1.5. The cells were cultured in media with vehicle only (0.5% DMSO) or in the presence of 50 nM Compound #10 present in media with vehicle added. After three weeks of treatment, treated spheroids were re-plated into wells without an agar base, thus allowing cells to migrate out onto the coated surface and grow as a two-dimensional (2-D) monolayer in the presence or absence of Compound #10 at 50 nM. Pictures were then taken 48 hours to assess the migration and proliferation of the cells across the well's surface.

Results. Cells from vehicle treated spheroids plated out in the absence of Compound #10 migrate to cover the entire surface of the tissue culture plate within the 48 hours. Spheroids grown for 3 weeks in the presence of Compound #10 and re-plated in the absence of the compound also migrate out of the spheroid to cover the surface of the tissue culture plate within 48 hours. This indicates that a three-week exposure to Compound #10 does not reduce either the proliferative or the migratory capacity of HT1080 cells.

Cells from control spheroids grown in the absence of Compound #10 and subsequently re-plated in the presence of 50 nM of Compound #10 are blocked in their ability to migrate out of the spheroid, and do not cover the surface of the tissue culture plate. Similarly, cells grown as spheroids in tissue culture media containing 50 nM of Compound #10 herein and re-plated in the presence of Compound #10 migrate much less than other groups. The data suggests that, even after three weeks of growth in three dimensions (3-D), the cell cycle delay and migratory inhibition of Compound #10 herein are still intact once the cells move into 2-D culture. The data further suggests that Compound #10 can act to inhibit the metastasis of cells from tumors.

9.3.1.7 Effect of Compound #10 on Anchorage-Independent Colony Formation in HT1080 Cells This example demonstrates that Compound #10 may reduce formation of colonies from HT1080 cells treated with Compound #10.

Experimental Design. HT1080 cells growing in monolayer were trypsinized, counted and suspended in a 0.35% agar noble/1× complete DMEM solution at 37° C. at a concentration of 2,500 cells/mL. One ml of this solution was layered over a semisolid base consisting of 0.5 mL of 0.75% agar noble/1× complete DMEM in a six well tissue culture plate. The top layer was permitted to solidify at room temperature, whereupon 1.5 mL of liquid medium (complete DMEM) containing 0.5% DMSO and 0, 5, 20 or 100 nM of Compound #10 was added to achieve a final concentration of 0, 2.5, 10 or 50 nM of Compound #10. Tissue culture plates were then returned to the incubator and colonies were allowed to form. The top medium layer was replaced periodically (every 3-4 days) with complete DMEM containing either 0.5% DMSO or Compound #10 (0, 2.5, 10 or 50 nm) and 0.5% DMSO. On day 18 the vehicle-treated wells had colonies of sufficient size to count (>50 cells/colony). At this time, for increased visualization, 1.5 mL of a 2× working volume of (3-(4,5-Dimethylthiazol-2-yl)-2,5-diphenyltetrazolium bromide, a tetrazole) (MTT, Invitrogen, Cat #C35007) was added and the plates were returned to the incubator for 2 hours until colonies were stained by conversion of the MTT to purple formazan crystals. Colonies were then visually counted under a dissecting microscope.

Results. FIG. 33 is a graphical representation of the average for each treatment group, which consists of two or three wells per group. There was a modest trend toward a reduced number of colonies formed from cells treated with 10 and 50 nM of Compound #10, but the results do not reach statistical significance (P=0.29 and 0.07, respectively).

9.3.2 Animal Model Systems 9.3.2.1 Compound #10 Induces S-phase Cell Delay in Dividing Tumor Cells In Vivo.

This example demonstrates that Compound #10 induces a S-phase cell delay in dividing tumor cells in vivo.

Experimental Design. HT1080 cells ($5 \times 10^6$ cells/mouse) were implanted subcutaneously in male athymic nude mice. When tumors had become established (i.e., the mean tumor size had reached 585±150 mm$^3$), mice were divided into 4 treatment groups, as shown in Table 26. Positive and negative controls for effects on tumor cell cycling included doxorubicin and bevacizumab, respectively.

After 1, 2, or 3 days of treatment with Compound #10, mice were injected with BrdU, a synthetic nucleoside that is an analogue of thymidine and is incorporated into DNA during the S phase of cell division. The mice were sacrificed 3 hours later, and the tumors collected. A single cell suspension was prepared from the tumor cells. The cells were permeabilized and an antibody to BrdU was used to stain cells that had entered S phase during the labeling period. The proportion of cells actively synthesizing DNA was determined by cell sorting.

TABLE 26

Study Design for Cell Cycle Effect Assessment in Nude Mice Bearing HT1080 Xenografts

| Test Compound | Number of Animals Per Time Point[a] M | Number of Animals Per Time Point[a] F | Dose (mg/kg) | Administration[a] Route | Administration[a] Schedule | Dose Volume (mL/kg) | Dose Concentration (mg/mL) |
|---|---|---|---|---|---|---|---|
| Vehicle[b] | 5 | 0 | 0 | Oral | QD | 4 | 0 |
| Compound #10 | 5 | 0 | 10 | Oral | QD | 4 | 2.50 |
| Doxorubicin | 5 | 0 | 6 | IP | Single bolus | 8 | 0.75 |
| Bevacizumab | 5 | 0 | 5 | IP | Single bolus | 8 | 0.625 |

[a]Treatments were initiated on Day 0 with 20 mice per group. On each day, 5 mice were sacrificed per group for analysis. Mice were treated with Compound #10 daily. Mice were treated with doxorubicin or bevacizumab on Day 0 only.
[b]Vehicle was L21 (35% Labrasol, 35% Labrafac, and 30% Solutol).
Abbreviations: IP = intraperitoneal; QD = 1 time per day As shown in FIG. 14, approximately 7 to 12% of the tumor cells from vehicle-treated mice were in S phase as indicated by the amount of BrdU incorporation. As the size of the tumors from vehicle treated mice increased with each succeeding treatment day, the percentage of cells showing BrdU incorporation decreased. On each treatment day, tumor cells from mice treated with Compound #10 demonstrated increased BrdU staining, consistent with a higher fraction of cells delayed in S phase. By contrast, treatment with doxorubicin decreased the percentage of tumor cells staining with BrdU, consistent with the arrest in the G1 phase of the cell cycle that is expected with this type of DNA-damaging agent. As also expected, bevacizumab had no effect on the proportion of cells in S phase.

When taken together with reductions in tumor derived plasma VEGF in these same animals (Section 9.2.3), these results are consistent with the previous in vitro results for Compound #10, suggesting that Compound #10 selectively induces a S phase cell delay in rapidly dividing tumor cells.

10. EXAMPLE

Clinical and Pre-Clinical Studies Compound #10

10.1 Pre-Clinical Studies

In vitro and in vivo safety pharmacology studies with Compound #10 demonstrate a favorable safety profile. Based on the safety pharmacology studies and results of electrocardiograms (ECGs) and blood pressures collected during 7- and 28-day toxicity studies in dogs, Compound #10 is unlikely to cause serious adverse effects on the central nervous, cardiovascular, and respiratory systems.

A functional observation battery in Sprague Dawley rats dosed daily for 7-days by oral gavage at dose levels of 40, 120, and 400 mg/kg revealed no adverse behavioral or neurological effects at any dose level.

Compound #10 was considered negative for meaningful inhibition of human-ether-a-go-go-related gene (hERG) current in a higher throughput hERG assay. In a cardiovascular safety pharmacology study in awake telemeterized male beagle dogs, single oral doses of 30, 60, and 120 mg/kg of Compound #10 induced no meaningful changes in cardiovascular or electrocardiographic (including QT interval) parameters. In addition, ECG analysis and blood pressure assessments were performed as part of 2 GLP toxicity and toxicokinetic studies of Compound #10 in beagle dogs, one with 7-days of dosing and one with 28-days of dosing followed by a 15-day recovery period. In these studies, oral dosing with Compound #10 at dose levels through 120 mg/kg/day for 7-days and through 60 mg/kg/day for 28-days did not have any toxicological effects on ECG or blood pressure results in dogs. At the end of dosing in the 28-day toxicity study in dogs, males in the 60 mg/kg/day group had a slightly higher (7%) mean uncorrected QT value which also was statistically significant in comparison to controls. However, QTc (QT interval corrected for heart rate) values in males in the 60 mg/kg/day group were comparable to controls.

In a respiratory safety pharmacology study in awake telemeterized male beagle dogs, single oral doses of 30, 60, and 120 mg/kg of Compound #10 induced no dose dependent or biologically significant changes in respiratory rate, core body temperature, arterial blood gases, arterial pH, or arterial bicarbonate.

10.1.1 Pharmacokinetics and Compound Metabolism in Animals

The absorption of Compound #10 was evaluated in nude mice, C57BL/6 mice, Sprague Dawley rats, and beagle dogs dosed by the oral route. The pharmacokinetic evaluations in mice were adjuncts to the primary pharmacodynamic xenograft studies. The evaluations in rats included toxicokinetic assessments in single-dose, 7-day, and 28-day toxicology studies as well as a mass-balance study after a single oral dose of $^{14}$C-Compound #10. The evaluations in dogs included toxicokinetic assessments in 7-day and 28-day toxicology studies. In the studies performed, rodents were dosed once daily with Compound #10 formulated in vehicle and administered via oral gavage. Dogs were dosed BID at ~12-hour intervals between doses with Compound #10 formulated in vehicle and loaded into gelatin capsules that were administered orally.

The results of the PK studies demonstrate that Compound #10 is orally bioavailable in mice, rats, and dogs. Compound #10 pharmacokinetic parameters have been evaluated in mice at the 1-mg/kg dose level that, when given BID, was associated with maximal antitumor activity in the HT1080 human tumor xenograft model. At Day 1, Compound #10 plasma trough concentration of ~0.10 to 0.15 μg/mL at 24 hours was established as the minimal mean target plasma concentration to be achieved in pharmacokinetic studies.

In all mice, rats, and dogs, the relationship between Compound #10 dose and plasma exposure describes a "bell-shaped curve," i.e., plasma exposures initially rise with dose but then decrease despite further increases in dose. These bell-shaped dose-exposure relationships are consistent with absorption saturation and/or possible precipitation of the Compound within the gastrointestinal tract at the highest dose levels. The dose exposure curves were used in the dose selection for the rat and dog toxicology studies and in the interpretation of the No-Observed-Adverse-Effect Levels (NOAELs) from these studies. In both rat and dog toxicology species, $C_{max}$ and AUC values at the NOAELs exceed those expected in subjects to be enrolled to the proposed Phase 1b clinical study in patients with advanced breast cancer.

In vitro plasma protein binding for $^{14}$C-radiolabeled Compound #10 was determined from plasma samples obtained from mice, rats, dogs, monkeys, and humans. $^{14}$C-radiolabeled Compound #10 was highly bound to proteins in the plasma in vitro, with an overall mean of ≥99.5% for all species. Protein binding was independent of concentration over the range of 0.05 to 50 μg/mL of $^{14}$C-radiolabeled Compound #10. Given the similarities in protein binding across species, these data suggest that cross-species exposure comparisons do not need to be adjusted to take protein binding into account.

When evaluated in human hepatic microsomes or in assays using human recombinant cytochrome P450 (CYP) isoenzymes, Compound #10 inhibits the activity of the CYP2D6 isoenzyme. No meaningful inhibition of CYP3A4, CYP1A2, CYP2C9, or CYPC19 was observed. These data suggest the possibility that Compound #10 may slow or alter the clearance of drugs that are primarily metabolized by CYP2D6. It is possible that in certain clinical trial subjects, such agents may need to be adjusted for dosing or replaced by alternative agents that are not metabolized by CYP2D6, particularly when such agents may have a low therapeutic index.

10.1.2 Toxicology

A comprehensive toxicology program has been completed for Compound #10, consisting of a single-dose oral study in rats, 7-day oral studies in rats and dogs, and 28-day oral studies in rats and dogs each with a 2-week recovery period. A battery of genotoxicity studies was also performed. For the toxicology studies conducted in vivo, the study design consisted of a vehicle control group and 3 dose levels of Compound #10. The L23 vehicle was used. In rats, the vehicle or Compound #10 formulated in vehicle was administered by oral gavage. In dogs, the vehicle alone or Compound #10 formulated in vehicle was loaded into gelatin capsules for oral administration of 2 equal doses ~12 hours apart (BID). All studies in the toxicology program were conducted according to GLP regulations.

In rats given single oral gavage doses of Compound #10 at doses of 100, 200, or 400 mg/kg, no notable clinical or clinical pathological toxicities were observed at any dose level. Because maximal exposure occurred at 100 mg/kg, this dose is considered the NOAEL for 1 day of dosing.

In the subsequent 7-day study, rats administered oral gavage Compound #10 doses of 40, 120, and 400 mg/kg/day. Maximal exposures occurred at a dose of 120 mg/kg/day. At this dose, notable changes included increases in mean prothrombin time (PT) and mean activated partial thromboplastin time (aPTT) in males but not in females. Elevations of about ~2.5-fold to about 3-fold in mean cholesterol levels and about 1.3-fold in mean glucose levels were also noted in males and females receiving Compound #10. Based on the collective toxicity and toxicokinetic findings, the NOAEL for 7-days of Compound #10 administration for male rats is 40 mg/kg/day and for female rats is 120 mg/kg/day.

In the 28-day study (with a 14-day recovery period), rats received oral gavage Compound #10 doses of 12, 40, and 120 mg/kg/day. Exposures were maximal at 120 mg/kg/day. Consistent with the 7-day study, the 28-day study showed reversible increases in mean PT and aPTT at Compound #10 doses of 40 and 120 mg/kg/day in males but not in females. Other chemistry changes included about 2- to about 3-fold elevations in mean cholesterol levels in all Compound #10 dose groups, and minimally increased glucose and alkaline phosphatase values in females and minimally increased chloride and minimally decreased potassium values in males dosed with Compound #10 at 40 and 120 mg/kg/day. Increased adrenal weights were observed at all dose levels; these changes correlated with adrenal cortical hypertrophy that was observed in males and females. The findings indicate an NOAEL for 28-days of Compound #10 administration in rats of 12 mg/kg/day.

In dogs given Compound #10 at doses of 10, 30, or 60 mg/kg/dose BID (20, 60, and 120 mg/kg/day) orally in L23 gelatin capsules for 7 consecutive days, exposures were maximal at 30 mg/kg/dose BID. Animals receiving Compound #10 had an increased incidence and frequency of soft stools in both males and females but no other notable treatment-related effects. Considering exposure values, the NOAEL for 7-days is considered to be 30 mg/kg/dose BID (60 mg/kg/day).

In the 28-day study (with a 15-day recovery period), dogs were administered Compound #10 doses of 5, 15, and 30 mg/kg/dose BID (10, 30, or 60 mg/kg/day) in gelatin capsules. Maximal exposures occurred at 30 mg/kg/dose BID (60 mg/kg/day). Compound #10 was clinically well tolerated in male and female dogs at the low- and mid-dose levels but at the high dose, adverse clinical findings, and decreased food consumption resulting in decreased body weights were observed. The target organ of toxicity was the small intestine. Microscopic findings of erosion, necrosis and/or ulceration of the mucosa, submucosal inflammation, epithelial hyperplasia of the mucosa of the crypts, and/or congestion of the Peyer's patches in the small intestine were seen in several dogs at the high dose. The findings in the small intestine did not reverse at the end of the 15-day recovery period. Based on the findings, the NOAEL for 28-days of Compound #10 administration in dogs is considered to be 15 mg/kg/dose BID (30 mg/kg/day).

Genotoxicity was assessed in a battery of in vitro and in vivo studies that included a bacterial reverse mutation study, a chromosome aberration study in Chinese hamster ovary (CHO) cells, and a micronucleus study in rats by the oral route. The in vitro studies were performed in the presence and absence of an exogenous metabolic activation system. There was no evidence of genotoxic effects with Compound #10 in these studies.

10.2 Clinical Studies:

Compound #10 has been evaluated in a Phase 1, escalating multiple-dose, safety, tolerability and PK study in healthy adult volunteers.

The study was performed under the oversight of the French health authorities. The study was not performed under an IND. The primary objective of the study was to determine a dose range and regimen for Compound #10 that safely achieves and maintains pharmacologically active target plasma concentrations (as determined from xenograft studies) and would be appropriate for use in subsequent Phase 1 or Phase 2 studies in patients with cancer. The secondary objective was to evaluate the safety profile of multiple doses of Compound #10 administered 2 times per day (BID) (Stage 1) or 3 times per day (TID) (Stage 2) in oral capsules, to characterize the multiple dose PK profile of Compound #10, and to assess the effect of Compound #10 on plasma and serum physiological VEGF concentrations.

Methods. The trial was a Phase 1, randomized, escalating multiple dose, single center study conducted in 2 stages. Stage 1 comprised a double blind, placebo controlled dose escalation with Compound #10 given BID. Stage 2 comprised a double blind, placebo controlled escalation of Compound #10 given TID. The number of subjects planned and enrolled for Stage 1: 24 subjects as 3 cohorts of 8 subjects, with each cohort comprising 4 males (3 Compound #10, 1 placebo) and 4 females (3 Compound #10, 1 placebo). The number of subjects planned and enrolled for Stage 2: 1 cohort of 8 subjects comprising 4 males (3 Compound #10, 1 placebo) and 4 females (3 Compound #10, 1 placebo).

Diagnosis and Main Criteria for Inclusion: Subjects were required to be healthy males or females, 18 to 65 years old, weighing 41 to 90 kg. Female subjects were required to be surgically sterile or post menopausal (as documented by an absence of menses for ≥1 year before screening).

Test and Reference Products: In Stage 1, Compound #10 was provided in gelatin capsules for oral administration. Capsules contained 2 mg or 20 mg of active substance. Cohorts of subjects assigned to active treatment received progressively higher Compound #10 doses of 0.3, 0.6, and 1.2 mg/kg BID (0.6, 1.2, and 2.4 mg/kg/day).

In Stage 2, Compound #10 was provided in gelatin capsules for oral administration. Capsules contained 20 mg or 25 mg of active substance. The cohort of subjects assigned to active treatment received a Compound #10 dose of 1.6 mg/kg TID (4.8 mg/kg/day).

Placebo gelatin capsules for oral administration were used as the reference product in both Stage 1 and Stage 2 of the study.

Duration of Treatment: Stage 1: Compound #10 or placebo was administered orally BID for 7 days (Day 1 through Day 7). Stage 2: Compound #10 or placebo was administered orally TID for 7 days (Day 1 through Day 7).

Criteria Used for Evaluation: Maximum tolerated dose; Safety as characterized by type, frequency, severity, timing, and relationship to study treatment of any adverse events, laboratory abnormalities, or electrocardiogram (ECG) abnormalities; PK profile of Compound #10 as described by plasma concentration time curves and by derived PK parameters; Plasma and serum VEGF concentrations.

Statistical Methods: The results were summarized by study stage, treatment, and dose.

Pharmacokinetics: Compound #10 concentrations and PK parameters were presented descriptively. Noncompartmental methods were used to compute $T_{max}$, $C_{max}$, and AUC. Dose proportionality and sex effect were evaluated using ANOVA on log transformed PK parameters using dose, sex, and dose by sex as fixed factors.

Plasma VEGF Concentrations: Plasma and serum VEGF concentrations and concentration changes from baseline were presented descriptively.

Results. As planned, 32 subjects were included in the study. In Stage 1, 8 subjects were enrolled to each of the 3 dose groups (3 males and 3 females receiving Compound #10 and 1 male and 1 female receiving placebo) resulting in enrollment of 24 subjects (12 males and 12 females). In Stage 2, 8 subjects (3 males and 3 females receiving Compound #10 and 1 male and 1 female receiving placebo) completed their participation in the study. No subject discontinued prematurely and all subjects completed the study. Subject characteristics for Stage 1 and Stage 2 are described in Table 27 below. Demographic characteristics in Stage 1 were generally similar between the Compound #10 and placebo groups. Characteristics in Stage 2 were generally similar to those in Stage 1.

TABLE 27

Subject Characteristics: Stage 1 and Stage 2 of Multiple-dose Study

| | Stage 1 | | Stage 2 | |
| --- | --- | --- | --- | --- |
| Characteristic | Compound #10 N = 18 | Placebo N = 6 | Compound #10 N = 6 | Placebo N = 2 |
| Gender, n | | | | |
| Male:Female | 9:9 | 3:3 | 3:3 | 1:1 |
| Median age, years [range] | | | | |
| Males | 34 [25-62] | 32 [21-38] | 38 [33-46] | 31 [NA] |
| Females | 57 [44-64] | 56 [53-62] | 56 [54-65] | 58 [NA] |
| Mean body weight, kg [range] | | | | |
| Males | 73 [67-90] | 88 [80-90] | 66 [52-70] | 78 [NA] |
| Females | 62 [46-72] | 55 [52-77] | 66 [51-67] | 70 [NA] |
| Race, n (%) | | | | |
| Caucasian | 14 (78) | 3 (50) | 5 (83) | 2 (100) |
| African/West Indian | 2 (11) | 2 (33) | — | — |
| Other | 2 (11) | 1 (17) | 1 (17) | — |

Abbreviations:
BID = 2 times per day,
TID = 3 times per day

Pharmacokinetics: Mean plasma concentration time profiles for Compound #10 are shown in FIG. 15 for Stage 1 and FIG. 16 or Stage 2. Compound #10 appeared in plasma after a ~30 minute lag time. On Day 1, mean maximum concentration ($C_{max}$) values after the second dose were almost double those of the first dose, while by Day 7, the mean Cmax values of the first and second daily doses appeared similar; this pattern suggests accumulation of Compound #10 concentrations over time rather than diurnal variation in exposures.

At all dose levels, the target trough plasma concentration of ~0.1 to 0.15 µg/mL established as maximally active in the HT1080 animal tumor model was achieved.

PK parameters for Compound #10 in plasma are shown in Table 28 below. The mean $T_{max}$ was in the range of ~3 hours. During Stage 1 and Stage 2, increases in mean values for $C_{max}$ and area under the concentration time curve over 24 hours ($AUC_{0-24}$) were generally dose proportional. When comparing Day 1 to Day 7, there was an increase in the mean $C_{max}$ and $AUC_{0-24}$ over time at all dose levels, indicating accumulation (~2-fold) when Compound #10 was dosed continuously. A 2-compartment model could be readily fit to all of the individual subject data throughout the 7 day course of treatment.

MTD was established and no dose limiting toxicities were observed through the highest dose level tested (1.6 mg/kg TID).

PK data indicated that Compound #10 is orally bioavailable. The mean $T_{max}$ was in the range of ~3 hours. Increases in $C_{max}$ and AUC were generally proportional with dose. There was ~2 fold accumulation when Compound #10 was dosed continuously. In this study, no significant differences in $C_{max}$ or $AUC_{0-24}$ values were observed between males and females. Target trough plasma concentrations of ≥100 to 150 ng/mL derived from preclinical human tumor xenograft models were achieved and maintained at all dose levels in the current study.

TABLE 28

Mean (SD) Compound #10 Pharmacokinetic Parameters: Stage 1 and Stage 2 Multiple dose Study

| Parameter, units | Stage 1 Compound #10 Dose mg/kg BID | | | | | | Stage 2 Compound #10 Dose mg/kg TID | |
|---|---|---|---|---|---|---|---|---|
| | 0.3 N = 6 | | 0.6 N = 6 | | 1.2 N = 6 | | 1.6 N = 6 | |
| | Day 1 | Day 7 | Day 1 | Day 7 | Day 1 | Day 7 | Day 1 | Day 7 |
| $T_{max}$ (after PM dose), hours | 3.16 (0.41) | 3.33 (0.52) | 3.17 (0.41) | 3.33 (0.52) | 3.00 (0.00) | 3.33 (0.52) | 2.50 (1.05) | 2.33 (1.37) |
| $C_{max}$ (after PM dose), µg/mL | 0.48 (0.15) | 0.59 (0.18) | 0.97 (0.24) | 1.16 (0.27) | 1.97 (0.29) | 2.47 (0.57) | 2.36 (0.46) | 4.65 (1.86) |
| $C_{24\,h}$, µg/mL | 0.094 (0.036) | 0.21 (0.09) | 0.26 (0.095) | 0.54 (0.21) | 0.41 (0.17) | 0.85 (0.32) | 1.33 (0.40) | 2.37 (0.62) |
| $AUC_{0-24}$, µg · hr/mL | 4.31 (1.20) | 8.44 (2.84) | 10.1 (2.60) | 18.6 (4.85) | 18.0 (3.97) | 32.9 (9.43) | 37.2 (5.90) | 78.6 (19.4) |
| Dose-normalized $C_{max}$, µg/mL/mg/kg | 0.79 (0.24) | 0.99 (0.29) | 0.81 (0.20) | 0.97 (0.22) | 0.82 (0.12) | 1.03 (0.24) | 0.51 (0.10) | 0.98 (0.38) |
| Dose-normalized $AUC_{0-24}$, µg · hr/mL/mg/kg | 7.2 (2.0) | 14.1 (4.7) | 8.4 (2.2) | 15.5 (4.1) | 7.5 (1.6) | 13.7 (3.9) | 7.7 (1.2) | 16.4 (4.0) |

Values represent male and female subjects combined.
Abbreviations: AUC = area under the concentration-time curve, $C_{24}$ = concentration at 24 hours after first daily dose, $C_{max}$ = maximum concentration, $T_{max}$ = time of maximum concentration; BID = 2 times per day, TID = 3 times per day Gender related differences were analyzed by ANOVA. In this study, no significant differences in $C_{max}$ or $AUC_{0-24}$ values were observed between males and females.

Circulating VEGF Concentrations

Plasma and serum VEGF A concentrations were assayed in all subjects. Mean absolute values and changes from baseline in plasma and serum VEGF A concentrations are plotted in FIG. 17A and FIG. 17B for Stage 1 and in FIG. 18A and FIG. 18B for Stage 2. When considering both stages of the study, no clear dose dependent effects of Compound #10 on physiological concentrations of circulating VEGF A were noted.

Summary and Conclusions

In this Phase 1 dose study of Compound #10 in healthy volunteer males and females, administration of Compound #10 for 7 consecutive days at doses of 0.3, 0.6, and 1.2 mg/kg BID (0.6, 1.2, and 2.4 mg/kg/day) and at 1.6 mg/kg TID (4.8 mg/kg/day) was well tolerated. Treatment emergent adverse events and laboratory abnormalities were generally Grade 1. The incidence or severity of these findings was not clearly greater in the Compound #10 group than in the placebo group and no dose dependency was apparent. Frequent ECG evaluations revealed no concerning rhythm, waveform, or interval changes. In particular, no meaningful QTc prolongation was observed. No serious adverse events or premature discontinuations due to adverse events occurred. Interventions for adverse events were minimal. None of the safety findings were deemed clinically significant by the investigator. No significant alterations in plasma or serum physiological VEGF-A concentrations were observed at any of the Compound #10 doses tested in this multiple dose study. The finding that Compound #10 did not affect physiological plasma or serum VEGF levels in healthy volunteers appears consistent with in vitro results suggesting that Compound #10 does not perturb physiological VEGF production, but acts selectively to inhibit pathological VEGF production (induced by hypoxia or tumor transformation). Lack of changes in circulating VEGF concentrations may correlate with the lack of Compound #10 toxicities (e.g., hypertension, bleeding, proteinuria) in this trial. Such toxicities have been classically associated with currently used drugs that inhibit VEGF signaling at endothelial cells.

Collectively, the safety and PK findings of this study in healthy volunteers indicate that the dosing regimens tested in this study can readily attain target trough plasma concentrations known to be active in nonclinical models of human disease and that oral BID administration of Compound #10 may offer safety and ease of use advantages over existing clinical methods of inhibiting VEGF signaling.

11. EXAMPLE

Protocol for Treating Patients

Subjects with HIV-associated KS may receive continuous daily treatment with a Compound being administered BID for up to 48 weeks. In a specific embodiment, the Compound is Compound #10 or Compound #1205. Response rate of HIV-associated KS to a Compound is an indicator of efficacy.

Clinical Objectives: Clinical objectives include:
1. Defining the safety and toxicity of a Compound in patients with HIV-associated KS.
2. Establishing the maximum safely tolerated dose of a Compound in patients with HIV-associated KS.
3. Estimating the response rate of HIV-associated KS to treatment with a Compound.

Other clinical objectives include:
1. Describing the pharmacokinetics of a Compound in patients with HIV-associated KS.
2. Describing the effects of a Compound on serum and plasma VEGF, VEGFR and cytokine profiles in patients with HIV-associated KS.
3. Describing the effects of a Compound on HIV and KSHV viral loads.
4. Describing the effects of a Compound on T-lymphocyte subsets (CD4 and CD8).
5. Describing the effects of a Compound on KS tumor biopsies with respect to expression of VEGF, VEGFR-2 and -3, phospho-Akt, p53, HIF-1α and proliferation, measured by Ki-67 staining
6. Describing the effects of a Compound on viral gene expression and cellular gene transcription in KS tumor biopsies using real-time QPCR-based profiling.
7. Evaluating tumor size, erythema or peritumoral inflammation or edema by calipers, photography, CT scan, MRI scan, or PET scan.

Subject Selection: The following eligibility criteria may be used to select subjects for whom treatment with a Compound is considered appropriate. All relevant medical and non-medical conditions are taken into consideration when deciding whether this treatment protocol is suitable for a particular subject.

Subjects should meet the following conditions to be eligible for the treatment protocol:
1. Biopsy-proven KS involving the skin, with or without lymph node, oral cavity, gastrointestinal (GI) tract and/or lung involvement. GI and pulmonary involvement are preferably asymptomatic or minimally symptomatic and not require systemic cytotoxic chemotherapy.
2. At least five measurable, previously non-radiated, cutaneous lesions should be present, which can be used as indicator lesions. Additionally, patients should have a sufficient number of non-indicator cutaneous lesions measuring ≥4×4 mm to obtain a total of four (4) 3-mm punch biopsies, two at baseline and two during the course of treatment.
3. Serologic documentation of HIV infection at any time prior administration of a Compound, as evidenced by positive ELISA, positive Western Blot, or other federally approved licensed HIV test, or a detectable blood level of HIV RNA.
4. Karnofsky performance status ≥60.
5. The following laboratory parameters within 21 days prior to administration of a Compound:
6. Hemoglobin ≥8 g/dL.
7. Absolute neutrophil count ≥1,000 cells/mm3.
8. Platelet count ≥75,000/mm3.
9. Creatinine ≤2.0 mg/dL.
10. Total bilirubin should be ≤1.5× upper limit of normal (ULN). If, however, the elevated bilirubin is felt to be secondary to indinavir or atazanavir therapy, patients may be allowed to enroll on protocol if the total bilirubin is ≤3.5 mg/dL provided that the direct bilirubin is normal.
11. AST (SGOT) and ALT (SGPT) ≤2.5×ULN.
12. INR and aPTT ≤ULN.
13. <2+ proteinuria.
14. Life expectancy ≥3 months.
15. Age ≥18 years.
16. Women of child-bearing potential should have a negative pregnancy test within 72 hours before initiation of administration of a Compound. Post menopausal women should be amenorrheic for at least 12 months to be considered of non-childbearing potential.
17. Patients must, in the opinion of the physician, be capable of complying with the protocol.
18. Antiretroviral therapy for HIV infection is not required, but may be recommended.

Compound Administration: Subjects may be administered a Compound at the following dose levels: 40 mg/dose BID, 80 mg/dose BID, and 100 mg/dose BID. A Compound may be orally administered each day on a BID schedule at approximately the same times each day. Ideally, doses should be taken at ~12-hour intervals (e.g., at ~7:00 AM and at ~7:00 PM). If convenient for the subject, the drug may be taken during or within ~30 minutes after a meal; however, administration with food is not required. Subjects may continue receiving repeated 4-week cycles of a Compound indefinitely or until termination. Compound administration may be terminated because of, e.g., tumor progression or other progression of KS, or a dose-limiting toxicity.

The dosage administered to a subject may be reduced to 80 mg/dose BID, 60 mg/dose BID, 40 mg/dose or 20 mg/dose if a dose-limiting toxicity (DLT) occurs. The dosage may be successively reduced if a DLT occurs. In other words, if a DLT occurs at 100 mg/dose BID, then the dosage may first be reduced to 40 mg/dose BID, and if a DLT occurs again then the dosage may be reduced to 20 mg/dose BID. A DLT may be defined as the occurrence of any of the following:
1. Grade ≥2: Compound-related vomiting despite maximal oral antiemetic therapy, or a requirement for intravenous antiemetics to control a Compound-related nausea and vomiting.
2. Grade ≥2: proteinuria.
3. Other Grade ≥3: Compound-related toxicities.

Events and Procedures: The following evaluations may be conducted on subjects:
1. Biopsy diagnostic of KS at any time prior to administration of a Compound.
2. Documentation of HIV infection at any time prior to administration of a Compound.
3. Chest X-ray to rule out pulmonary KS (should be done within 28 days prior to administration of a Compound). Pulmonary involvement should be asymptomatic or minimally symptomatic and not require systemic cytotoxic therapy in the judgment of the physician. Subjects with a positive chest X-ray or symptoms suggestive of pulmonary disease may have a chest CT performed at entry. Findings suggestive of pulmonary KS may be followed up with bronchoscopy to evaluate the presence and extent of pulmonary KS and evaluate for the presence of other pulmonary diseases.
4. Electrocardiogram within 21 days of administration of a Compound.

A medical history should be done within 21 days of administration of a Compound and may be done during the treatment course with a Compound (e.g., the first day of every 4 week cycle) and following such treatment. The medical history may include the following information:
1. Previous HIV-related and non-HIV related diagnoses.
2. Complete prior anti-HIV therapy, immune based therapy and prior anti-tumor therapy, including start dates of current anti-HIV therapy.
3. All prescription medications taken within the preceding 2 weeks.
4. An assessment of signs and symptoms occurring within the 2 weeks prior to administration of a Compound, including history of weight change.
5. Complete physical exam including the following prior to administration of a Compound and during the treatment course with a Compound (e.g., the first day of every 4 week cycle): vital signs (temperature, pulse, blood pressure, respiratory rate), height, weight, and Karnofsky performance status (see Table 29).
6. Laboratory studies should be obtained within 21 days prior to administration of a Compound and may be obtained during the treatment course with a Compound (e.g., the first day of every 4 week cycle or as needed) and following such treatment. Such laboratory studies may include the following:
7. Complete blood count with differential and platelets.
8. INR and aPTT.
9. Serum chemistries: liver enzymes (AST, ALT, alkaline phosphatase), BUN, creatinine, electrolytes (sodium, potassium, chloride, bicarbonate), calcium, phosphorus, total protein, glucose, albumin, bilirubin (direct and indirect), triglycerides and total cholesterol.
10. Blood for ACTH and cortisol.
11. Urinalysis.
12. For women of child bearing potential, a serum beta human chorionic gonadotropin (β-HCG) pregnancy test.
13. CD4 count.
14. Plasma HIV-1 RNA.
15. KS tumor assessments may be performed. Tumor measurements may include the following:
16. Identify marker lesions: Select five bi-dimensionally measurable marker lesions for assessing changes in lesion dimension. Select the largest lesions with clearly defined margins. If possible, marker lesions may be photographed. Additionally, patients may need a sufficient number of non-indicator cutaneous lesions measuring ≥4×4 mm to obtain a total of four (4) 3-mm punch biopsies, two at baseline and two during the course of treatment.
17. For subjects with <50 total skin and oral lesions, all lesions should be evaluated for changes in number and characteristics. For subjects with ≥50 total skin and oral lesions, up to three representative areas may be chosen for evaluating change in lesion numbers and characteristics (preferably an area with ≥5 lesions), with a total of at least 20 lesions.
    a Note that a representative area is a single extremity, the back, chest, or face that has lesions similar in characteristics, i.e., nodularity, size, color, and number, to those found on other parts of the body. A representative area does not need to be the area with the largest number of lesions but should contain lesions that are truly representative of those throughout the remainder of the body.
18. Staging Criteria (should be done within 28 days prior to administration of a Compound). KS staging may be based on the modified AIDS Clinical Trials Group (ACTG) Oncology Committee Staging Criteria (see Table 30).
19. KSHV viral load may be done prior to administration of a Compound, during the course of treatment with a Compound, and following such treatment.

TABLE 29

Karnofsky Performance Scale

| Karnofsky Performance Scale | | ECOG Performance Status Scale | |
|---|---|---|---|
| Percent | Description | Grade | Description |
| 100 | Normal, no complaints, no evidence of disease. | 0 | Normal activity. Fully active, able to carry on all pre-disease performance without restriction. |
| 90 | Able to carry on normal activity; minor signs or symptoms of disease. | | |
| 80 | Normal activity with effort; some signs or symptoms of disease. | 1 | Symptoms, but ambulatory. Restricted in physically strenuous activity, but ambulatory and able to carry out work of a light or sedentary nature (e.g., light housework, office work). |
| 70 | Cares for self, unable to carry on normal activity or to do active work. | | |
| 60 | Requires occasional assistance, but is able to care for most of his/her needs. | 2 | In bed <50% of the time. Ambulatory and capable of all self-care, but unable to carry out any work activities. Up and about more than 50% of waking hours. |
| 50 | Requires considerable assistance and frequent medical care. | | |
| 40 | Disabled, requires special care and assistance. | 3 | In bed >50% of the time. Capable of only limited self-care, confined to bed or chair more than 50% of waking hours. |
| 30 | Severely disabled, hospitalization indicated. Death not imminent. | | |
| 20 | Very sick, hospitalization indicated. Death not imminent. | 4 | 100% bedridden. Completely disabled. Cannot carry on any self-care. Totally confined to bed or chair. |
| 10 | Moribund, fatal processes progressing rapidly. | | |
| 0 | Dead. | 5 | Dead. |

TABLE 30

KS Staging Criteria

|  | GOOD RISK ($_0$) (All of the following) | POOR RISK ($_1$) (Any of the following) |
|---|---|---|
| Tumor (T) | Confined to skin and/or lymph nodes and/or minimal oral disease (such as nonnodular KS confined to the palate) | Tumor-associated edema or ulceration Extensive oral KS Gastrointestinal KS KS in other nonnodal viscera |
| Immune system (I) | CD4 cells ≥200/μL | CD4 cells <200/μL |
| Systemic illness (S) | No history of OI or thrush No "B" symptoms (e.g., unexplained fever, night sweats, >10% involuntary weight loss, or diarrhea persisting more than 2 weeks) Performance status ≥70 (Karnofsky) | History of OI and/or thrush "B" symptoms present Performance status <70 Other HIV-related illness (e.g., neurological disease, lymphoma) |

T0 = tumor confined to skin, lymph nodes and/or minimal oral disease.
T1 = any tumor falling under the "Poor Risk" criteria.
S0 = no history of OI or thrush, no "B" symptoms, and Karnofsky Performance status ≥70.
S1 = any "Poor Risk" systemic illness signs and symptoms.
Note:
Staging criteria taken from: Krown SE, Metroka C, Wernz JC. Kaposi's sarcoma in the acquired immunodeficiency syndrome: A proposal for uniform evaluation, response, and staging criteria. J Clin Oncol 1989; 7: 1201-1207. This criteria was adopted by the Oncology Committee.

Biopsy: A 3-mm punch biopsy of a non-indicator KS lesion may be performed at baseline and between Days 22 and 28 of cycle 1. Biopsies may be fixed in formalin and studied by immunohistochemistry (IHC) for expression of the following: VEGF, VEGFR-2, VEGFR-3, phospho-Akt, KSHV LANA, orf59, p53 and HIF-1α. Tumor cell proliferation may be assessed by Ki-67 staining Change in the intensity or distribution of a particular marker is evaluated. Ki 67 staining may be quantified as a percentage of tumor cells. All other immunohistochemical staining may be described with a score (0, 1+, 2+) and a description of the distribution of the signal (endothelial cells, spindle cells, infiltrating lymphocytes, etc.). Depending on the results of these assays, other potential immunohistochemical markers characteristic for KS may also be measured.

Without being bound by any theory, evaluation by IHC of the effects of a Compound on KSHV LANA and orf 59 is based on the hypothesis that either VEGF depletion directly, or VEGF inhibition-induced hypoxia indirectly, may induce KSHV lytic gene expression. Because reduction of VEGF production should reduce capillary-dependent oxygen flow to the tumor, this will, in turn, induce hypoxia. Hypoxia causes p53-dependent apoptosis but also, via HIF-1α, induces VEGF. HIF-1α and the cellular response to hypoxia are modulated by KSHV. Hence, p53, HIF-1α, and some of their representative targets may be characterized by IHC as secondary biological endpoints.

A separate 3-mm biopsy of a non-indicator KS lesion may be performed at baseline and again between Days 22 and 28 of cycle 1 to assess viral gene expression within tumor at the messenger RNA level. Real-time QPCR based profiling of KSHV transcription may be used to assess the effect of a Compound on changes in KSHV transcription.

In addition, as a control, a 3-mm skin biopsy from morphologically normal skin in the same anatomic location as the tumor specimen may be obtained at baseline only.

Pharmacokinetics of a Compound. Blood for pharmacokinetic (PK) assessments may be collected immediately pre-dose; and at, e.g., 1, 2, 3, 4, 5, 6, and 8 hours after the AM dose on Day 1 and again at, e.g., 1, 2, 3, 4, 5, 6, and 8 hours after the AM dose on Day 28 of cycle 1 (the Day 28/cycle 1 PK samples can be collected up to 3 days prior to Day 28). A PK sample may also be collected prior to the AM dose on Day 15 (±1 day) during cycle 1 and prior to the AM dose on Day 28 of cycle 2 (or Day 1 of cycle 3 if the subject's last dose of a Compound was the evening prior). Blood samples for a Compound PK assessments may not collected after cycle 2.

A blood sample may comprise ≤1 mL of venous blood drawn into a 5 mL Vacutainer® tube with $K_2$-EDTA as the anticoagulant. Immediately after collection, the tube should be gently inverted 8 to 10 times to mix the anticoagulant with the blood sample. The tube should be stored upright on ice until centrifugation; centrifugation and sample processing should ideally be performed within 1 hour of sample collection. The plasma sample fraction may be separated by placing the collection tube into a refrigerated centrifuge (4 to 8° C.) in a horizontal rotor (with a swing-out head) for a minimum of 15 minutes at 1500 to 1800 relative centrifugal force (RCF). The plasma fraction may be withdrawn by pipette and divided into 2 polypropylene freezing tubes (each tube receiving approximately equal aliquots). After processing, samples may be stored in a freezer at approximately −70° C.

Assaying secreted cytokines characteristic for KS: To measure the effect of a Compound on KS, serum and plasma may be evaluated for levels of VEGF, VEGF-C, VEGF-D, VEGF-R1, VEGF-R2, VEGF165b, P1GF, IL-6, IL-8 and IL-10 at baseline (pre-dose of a Compound on Day 1) and mid-cycle (e.g., Day 15) of cycle 1, on Day 1 of all subsequent cycles, and at the end of the study. Depending on the results of these assays, other potential serum markers characteristic for KS may also be measured.

Detection of Viral and Host RNA Levels in KS Tissues. Changes in gene expression are a fundamental hallmark of cancer progression and invaluable tool of cancer staging. In case of KS, KSHV/HHV-8 has been identified as the etiological agent and this assay is designed to identify KSHV genes that might change in response to therapy. Reverse-transcription (RT) coupled to amplification using polymerase chain reaction (PCR) may be used to measure the RNA levels of all KSHV/HHV-8 mRNAs in tumor biopsies. Secondly, a custom-made array for cellular targets, which is presumed to be regulated by VEGF, hypoxia or both, may be used.

A targeted array of 96 mRNAs that were previously shown to be involved in angiogenesis, endothelial cell remodeling or hypoxic responses may be used. This array is based upon PAHS-024 (SuperArray, Inc.). It may be modified based upon literature review but most likely includes growth factors and receptors ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGFA, VEGFC; adhesion molecules ANGPTL3, BAIL COL4A3, IL8, LAMA5, NRP1, NRP2, STAB1; proteases, inhibitors and other matrix proteins ANGPTL4, PECAM1, PF4, PROK2, SERPINF1, TNFAIP2; transcription factors and other proteins HAND2, SPHK1; cytokines and chemokines CCL11, CCL2, CXCL1, CXCL10, CXCL3, CXCL5, CXCL6, CXCL9, IFNA1, IFNB1, IFNG, IL1B, 1L6, MDK, TNF; other growth factors and receptors EDG1, EFNA1, EFNA3, EFNB2, EGF, EPHB4, FGFR3, HGF, IGF1, ITGB3, PDGFA, TEK, TGFA, TGFB1, TGFB2, TGFBR1; adhesion molecules CCL11, CCL2, CDH5, COL18A1, EDG1, ENG, ITGAV, ITGB3, THBS1, THBS2; proteases, inhibitors and other matrix proteins LECT1, LEP, MMP2, MMP9, PLAU, PLG, TIMP1, TIMP2, TIMP3; transcription factors and protein AKT1, HIF1A, HPSE, ID1, ID3, NOTCH4, PTGS1.

Reverse-transcription (RT) coupled to amplification using polymerase chain reaction (PCR) is widely recognized as the most sensitive method to detect the presence of specific RNAs. Real-time quantitative RT-PCR is used. This assay measures the amount of PCR product based on hybridization to a sequence-specific dual-labeled fluorogenic oligonucleotide (Taqman™) or intercalation of a fluorescent dye. Fluorescence is recorded at each cycle. So-called Ct-values indicate the cycle at which the fluorescence crosses a particular threshold (3 times standard deviation (SD) of the non-template control (NTC)). Hence, Ct-values indicate the abundance of a given mRNA on a log scale. A low Ct value represents a highly abundant target mRNA (Heid, Genome Res. 6:968-94, 1996).

Specifically, biopsies of KS preserved in RNA later (Ambion) at baseline and at indicated intervals after treatment may be used. Total RNA may be isolated using RNAzol (Tel-Test, Inc., Friendswood, Tex.) according to the supplier's protocol and reverse-transcribed using Mo-MuLV reverse transcriptase and 120 pmol random hexanucleotide primers (Taqman™RT, Applied Biosystems Inc., Foster City, Calif.). After incubation at 42° C. for 35 min, the reaction is stopped by heating to 95° C. for 5 min, the cDNA pool is diluted, and the resulting sample analyzed by real-time quantitative PCR using a dedicated Roche LC480 machine and universal cycle conditions. Commercial SYBR-green-based PCR (Roche Inc., Indianapolis, Ind.) as a uniform detection method is used.

Biopsies may be obtained by standard punch technique, using a THREE (3) mm punch. Tumor biopsies should be completely within the margins of the lesions. A second biopsy is obtained at baseline only from adjacent normal skin. Each specimen is immersed in 1.5 ml RNAlater (Ambion Inc. cat#AM7022) and stored at FOUR (4)° C. until shipment and labeled.

Description of KSHV Viral Load Assay. This assay may be used to quantify the burden of KSHV (Human Herpes virus Type 8, or Kaposi's sarcoma associated virus) present in circulating PBMC. Cells may be separated from whole blood by Ficoll centrifugation, DNA extracted from purified PBMC by column extraction, and the number of KSHV copies determined using a quantitative competitive DNA PCR assay. Results may be expressed in numbers of copies per million PBMC. The limit of detection for this assay depends upon the DNA available, but generally ≤50 copies/$10^6$ PBMC. Changes ≥1.7-fold are unlikely to be due to assay variation, but KSHV burden does not appear to be as constant as HIV viral load.

Definitions

The terms complete response or partial response may be used to characterize the efficacy of a Compound in treating KS.

Complete Response: Complete response (CR) may be defined as the absence of any detectable residual disease, including tumor-associated edema, persisting for at least 4 weeks. In subjects in whose pigmented (brown or tan) macular skin lesions persist after apparent CR, biopsy of at least one representative lesion is required in order to document the absence of malignant cells. In subjects known to have had visceral disease, an assessment at restaging with appropriate endoscopic or radiographic procedures should be made.

Partial Response: Partial response (PR) may be defined as no new lesions (skin or oral), or new visceral sites of involvement (or the appearance or worsening of tumor-associated edema or effusions); and
1. A 50% or greater decrease in the number of all previously existing lesions lasting for at least 4 weeks; or
2. Complete flattening of at least 50% of all previously raised lesions (i.e., 50% of all previously nodular or plaque-like lesion become macules); or
3. A 50% decrease in the sum of the products of the largest perpendicular diameters of the marker lesions.

Subjects with residual tumor-associated edema or effusion who otherwise meet the criteria for CR are classified as having a PR.

Stable Disease: Stable disease may be defined as any response not meeting the criteria for CR, PR, or progressive disease.

Progressive Disease: Progressive disease (PD) may be defined as follows:
For subjects with <50 cutaneous lesions:
1. ≥25% increase in the sum of perpendicular diameters of the indicator lesions; or
2. ≥25% increase in the total lesion count, or a minimum of 5 new lesions, whichever is greater; or
3. ≥25% increase in the number of raised lesions (minimum of 5 new raised lesions if there are very few raised lesions, for example ≤8), whichever is greater.

There are body sites where disease is particularly difficult to evaluate, and a few new lesions may be counted in spite of the fact that a subject is not actually progressing. For example, lesions of the foot, particularly those which are flat, are difficult to evaluate because their intensity may be variable based on how much edema is present, how much the person walked the day before, how long their feet have been in a dependent position prior to the physical exam, etc.

For subjects with >50 cutaneous lesions:
1. 25% increase in the sum of the perpendicular diameters of the indicator lesions; or
2. ≥25% increase in the total number of lesions in the prospectively defined anatomic sites containing representative numbers of lesions; or
3. A total of 5 new lesions in anatomic sites which were previously documented as having no evidence of cutaneous disease on the whole body diagram; or
4. ≥25% increase in the number of raised lesions (minimum of 5 raised lesions if there are very few raised lesions, for example <8) whichever is greater. Photographic documentation of "gross" or significant progression, particularly in areas that were not being followed, may be of particular value.

In order to classify a response as PR, the subject should have at least a PR in either the cutaneous or noncutaneous sites of disease and no evidence of progression as defined in the above criteria. In order to classify a response as a CR, the subject should have a CR in both the cutaneous (if applicable) and noncutaneous (if applicable) sites of disease and no evidence of progression as defined by the above criteria.

Noncutaneous Progression: PD includes new visceral sites of involvement or progression of visceral disease or the development of new or increasing tumor-associated edema or effusion lasting at least 1 week, which interferes with the subject's normal activities. Progressive visceral disease, for measurable and evaluable disease, should be analogous to non-KS response criteria.

Recurrent Disease: Recurrent disease may be defined as the appearance of tumor following documentation of a complete remission.

Time to Response: Time to response may be defined as time from the first dose of chemotherapy until documentation of first response.

Time to Progression: Time to progression may be defined as time from initiation of chemotherapy to documentation of first progression.

Response Duration. Response duration may be defined as the time from first documentation of response to documentation of first progression.

FIG. 34 shows the effect of Compound #10 administration on the clinical endpoint for reduction of cutaneous lesion size and quantity in patients with Kaposi Sarcoma. The administration of Compound #10 has reduced the number of raised lesions in patients labeled PR, where the "*" symbol represents that the number of raised lesions was significantly reduced (i.e., ≥50%). The administration of Compound #10 has also reduced lesion size in patients. The acronym EOC refers to "End of Cycle," at which best change has occurred.

12. EXAMPLE

Treatment in Disease Model

Figure 1:
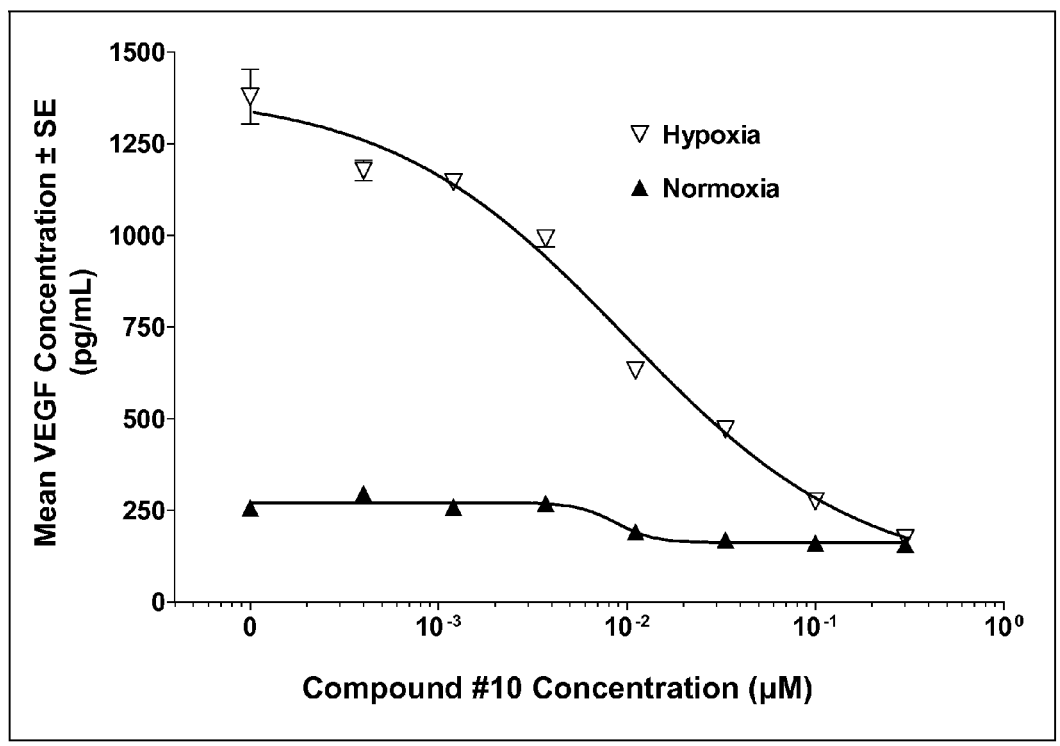
Figure 2:
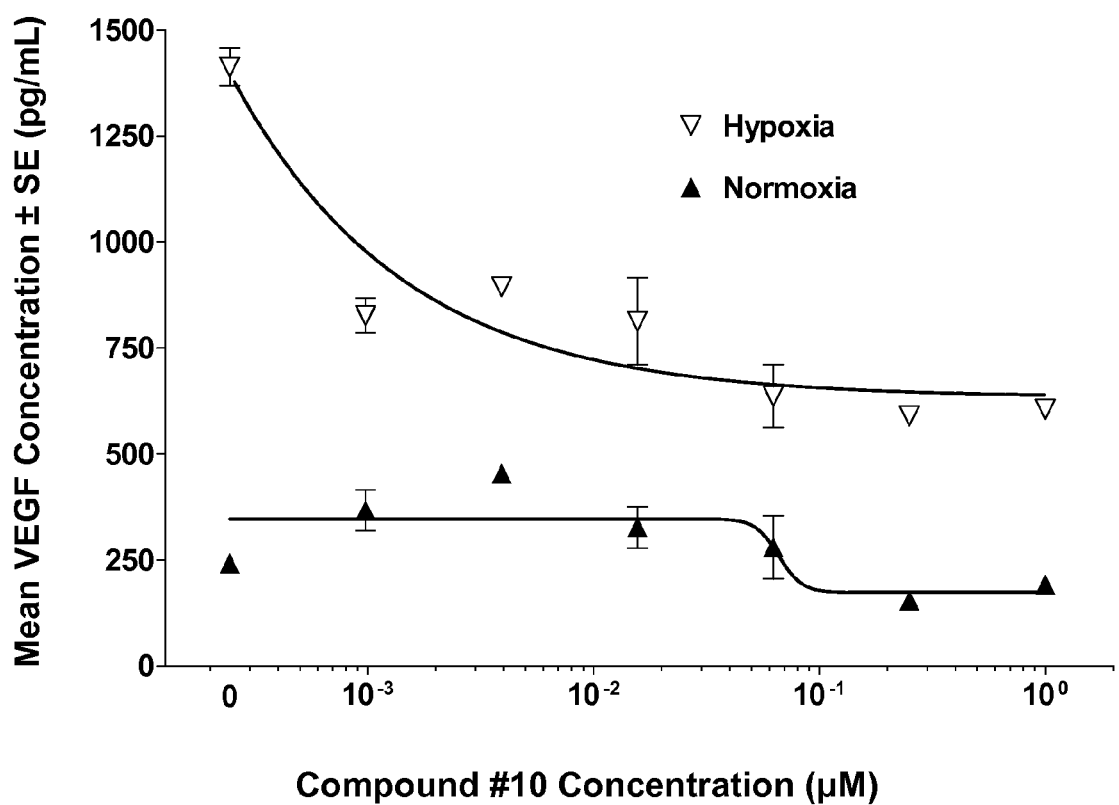
Figure 3:
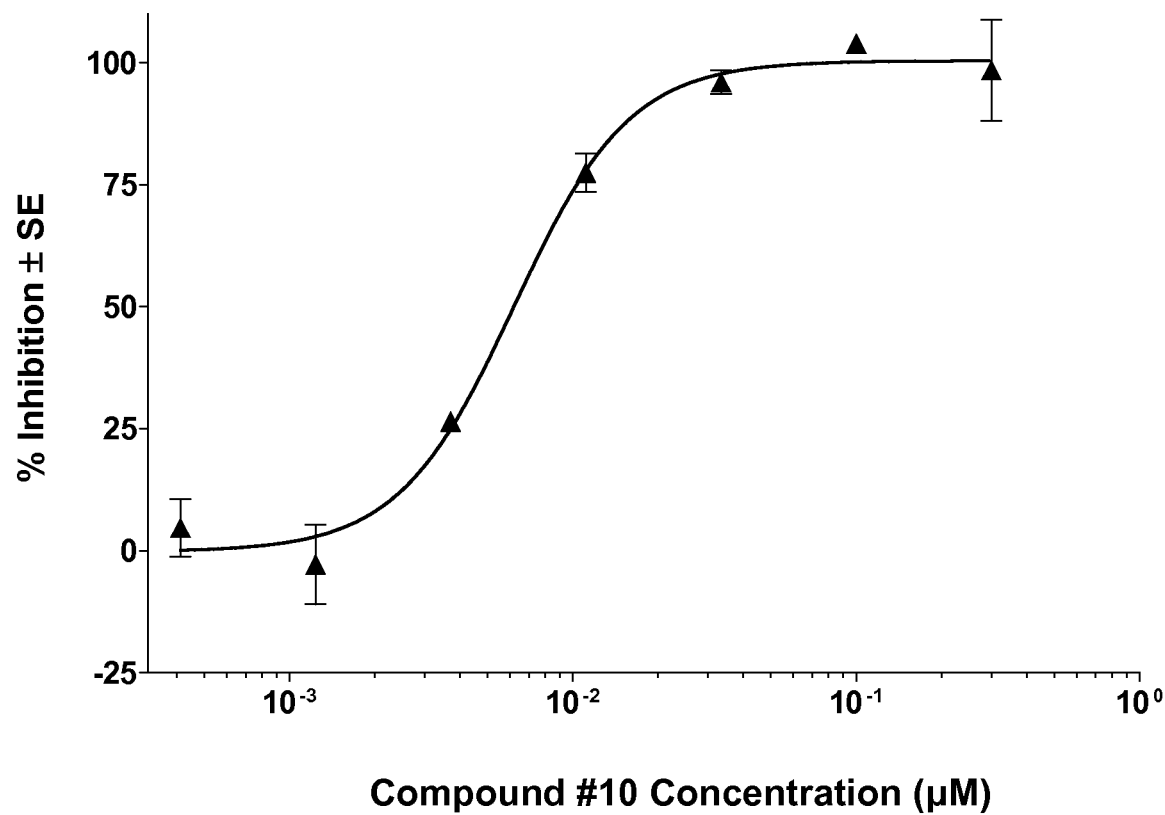
Figure 4:
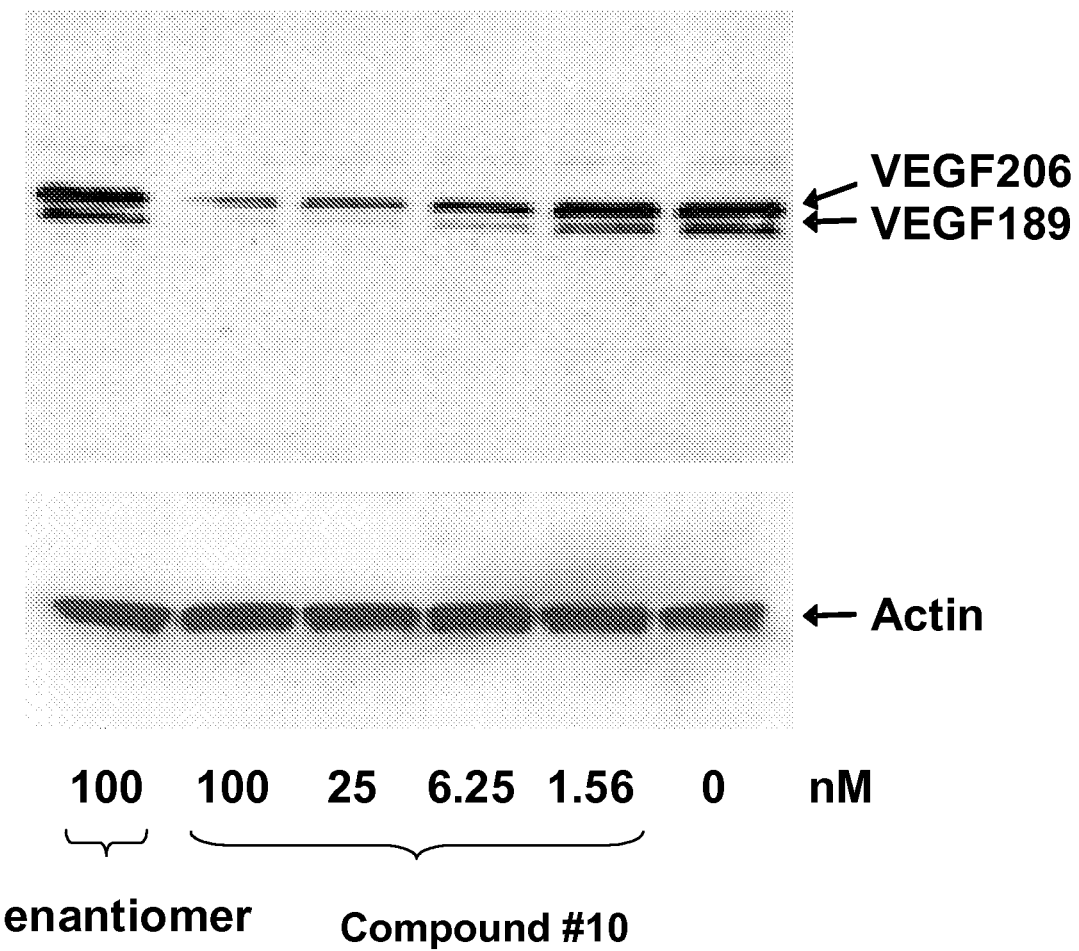
Figure 5:
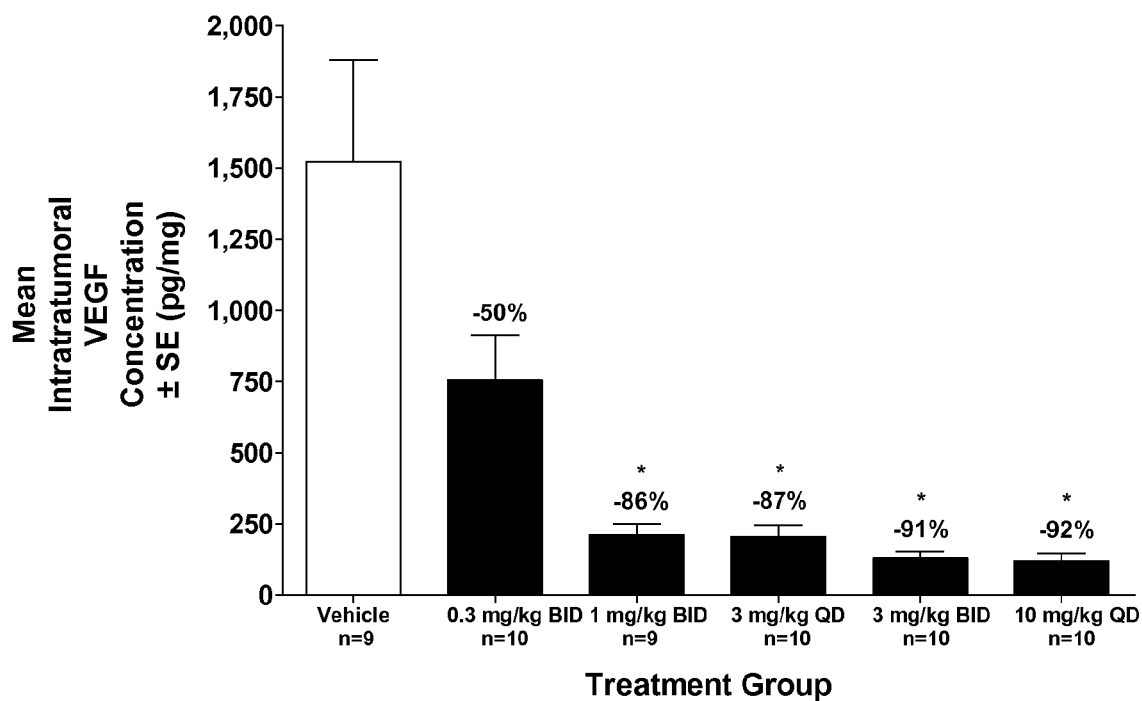
Figure 6:
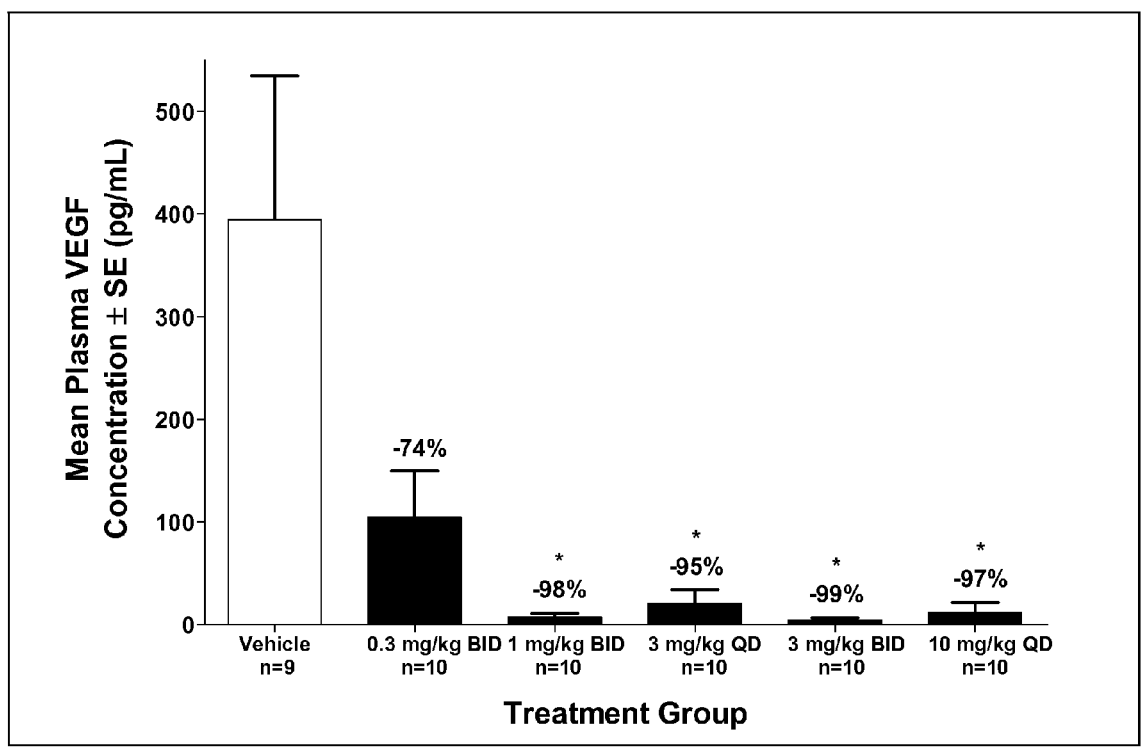
Figure 7:
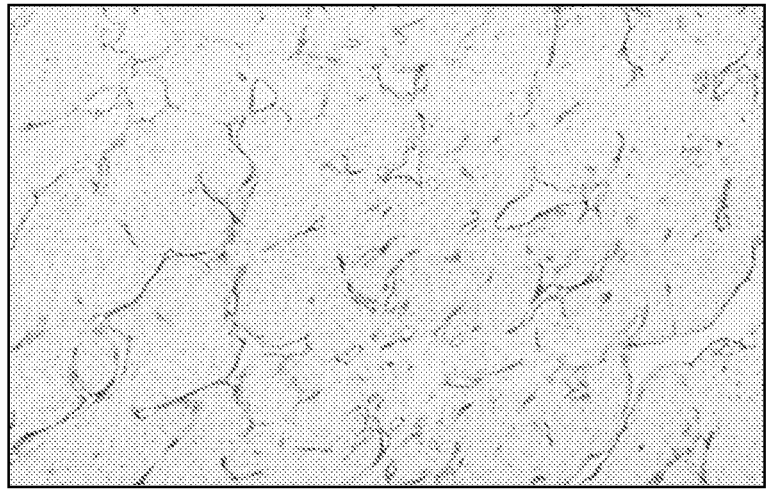
Figure 7:
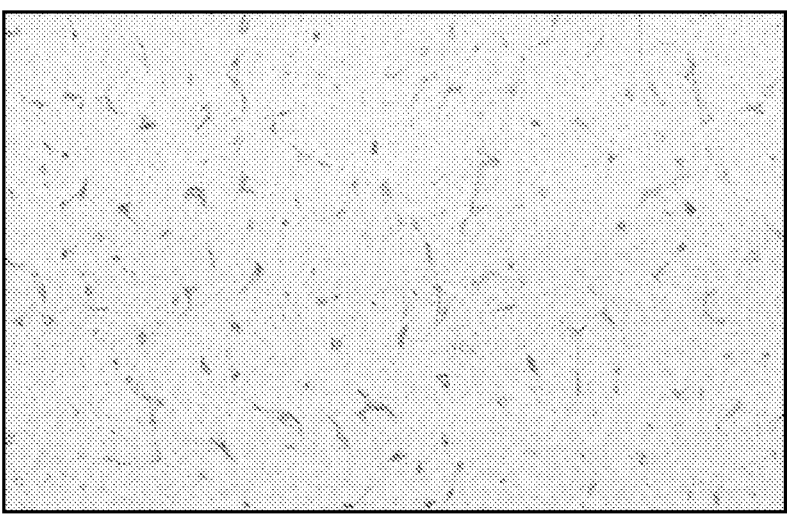
Figure 8:
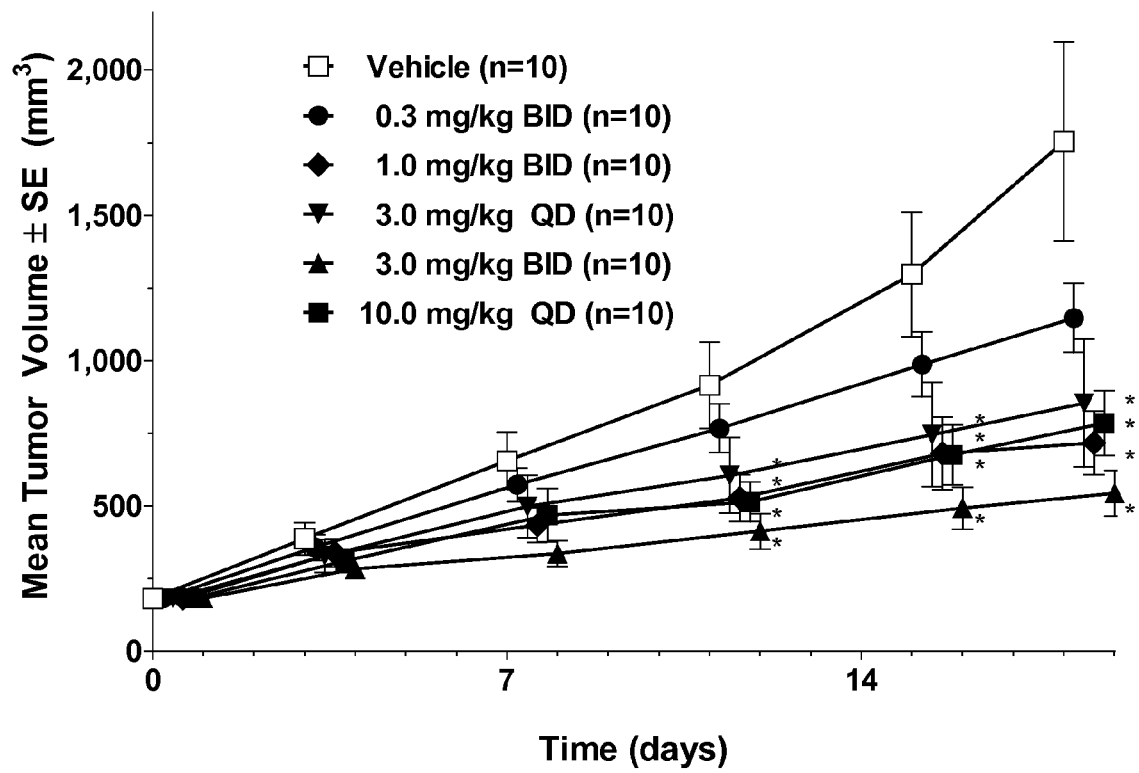
Figure 9:
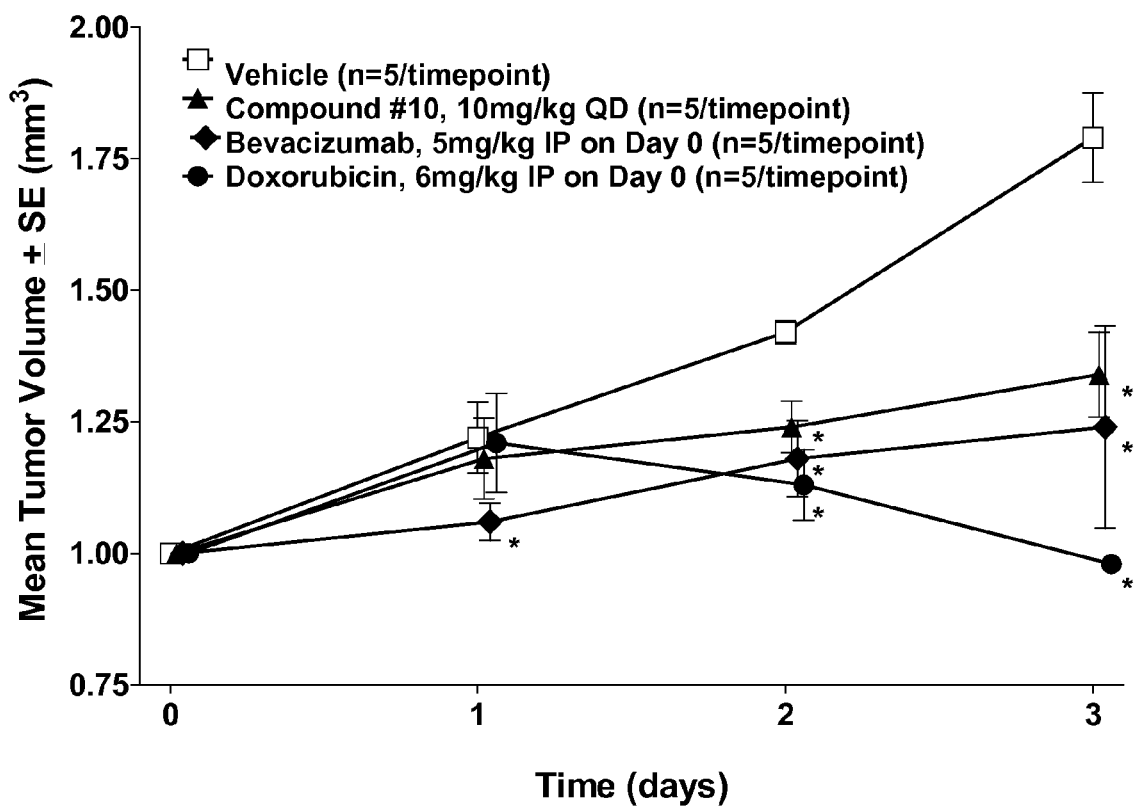
Figure 10:
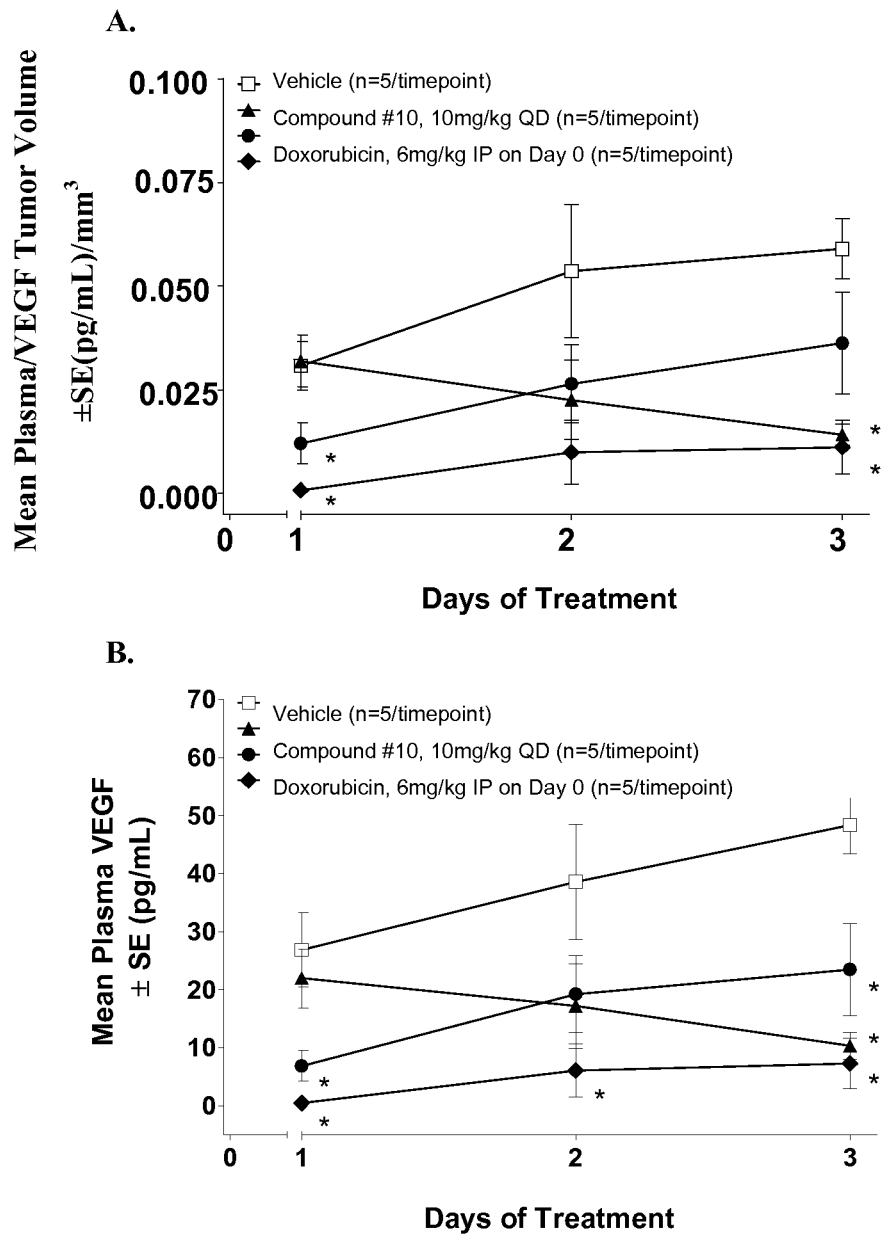
Figure 11:
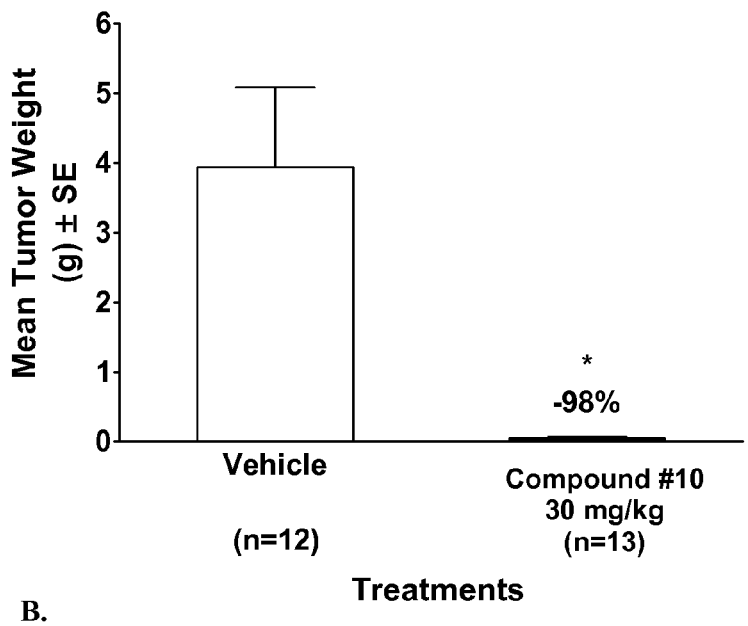
Figure 11:
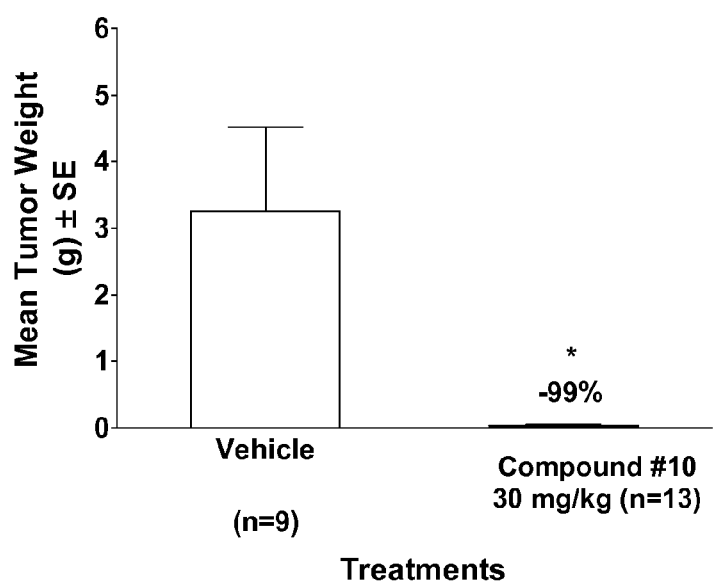
Figure 12:
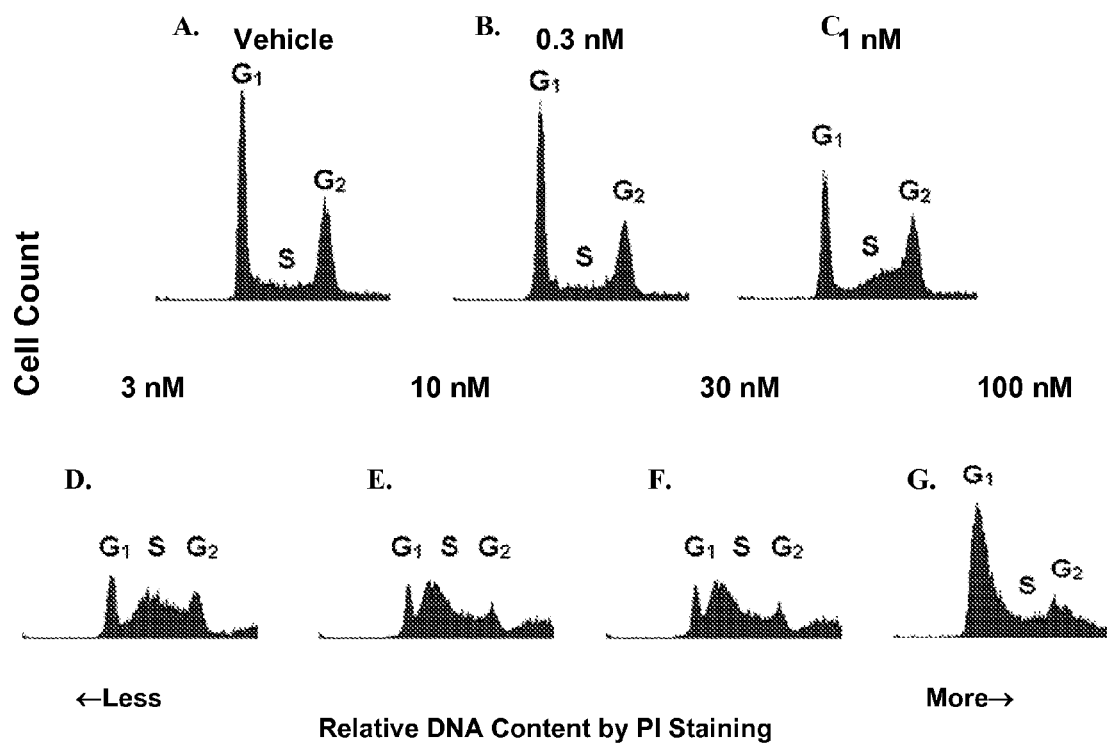
Figure 13:
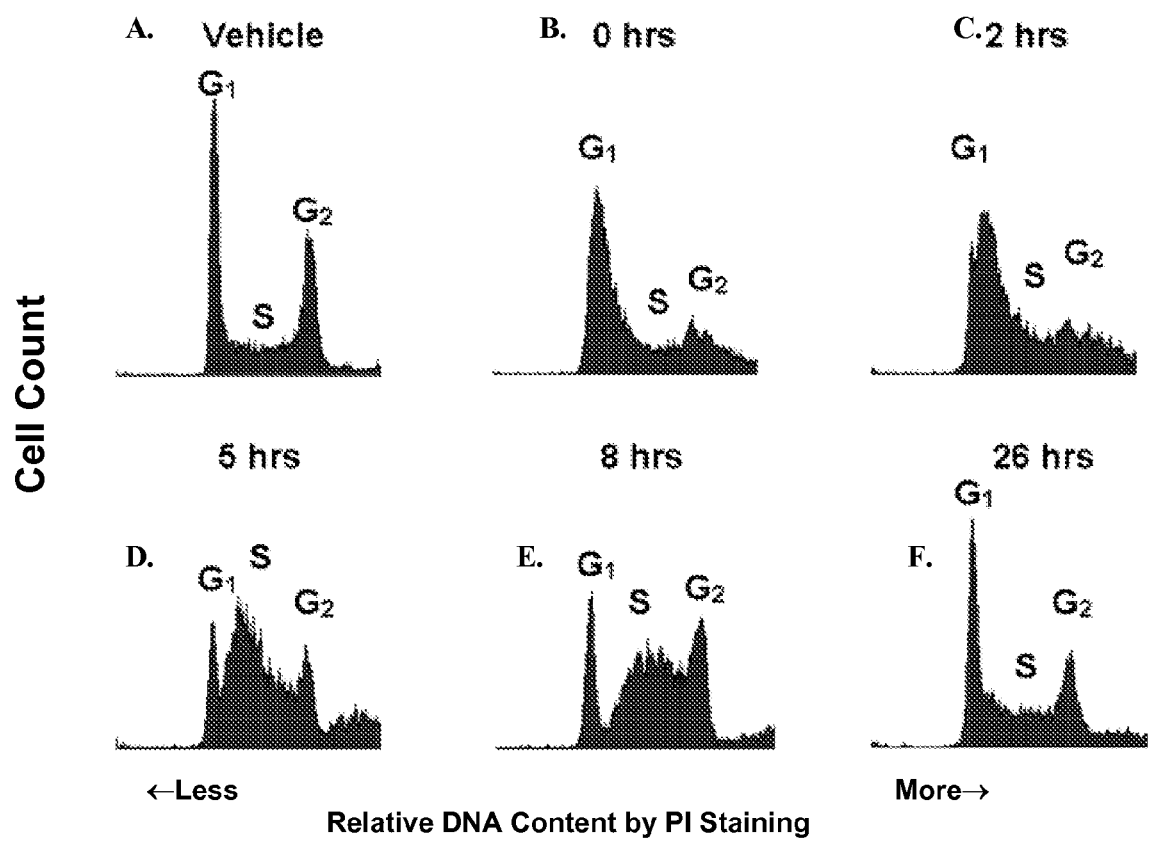
Figure 14:
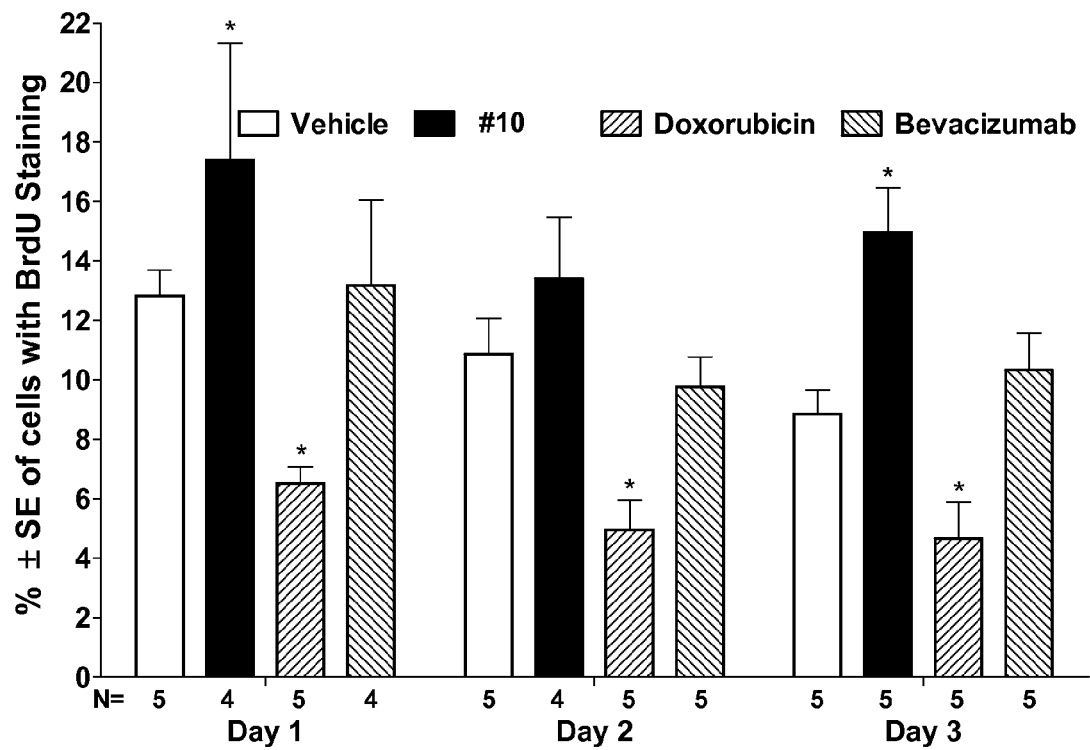
Figure 15:
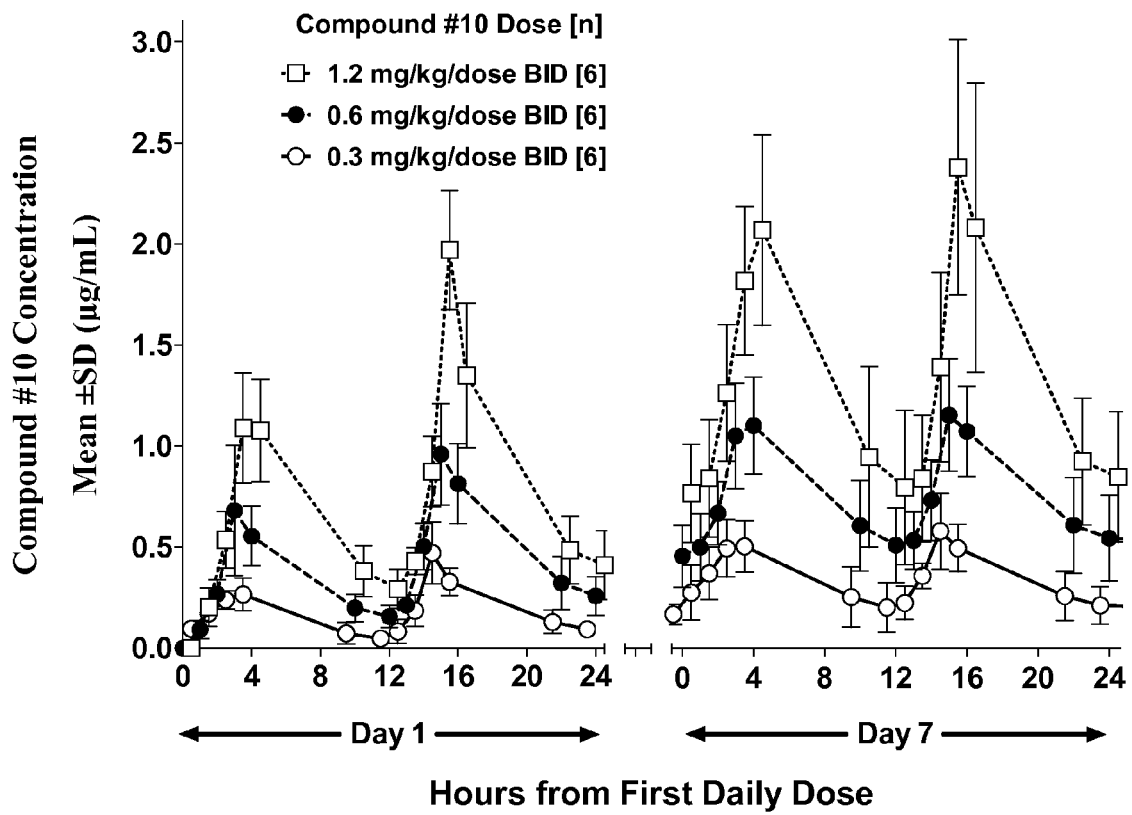
Figure 16:
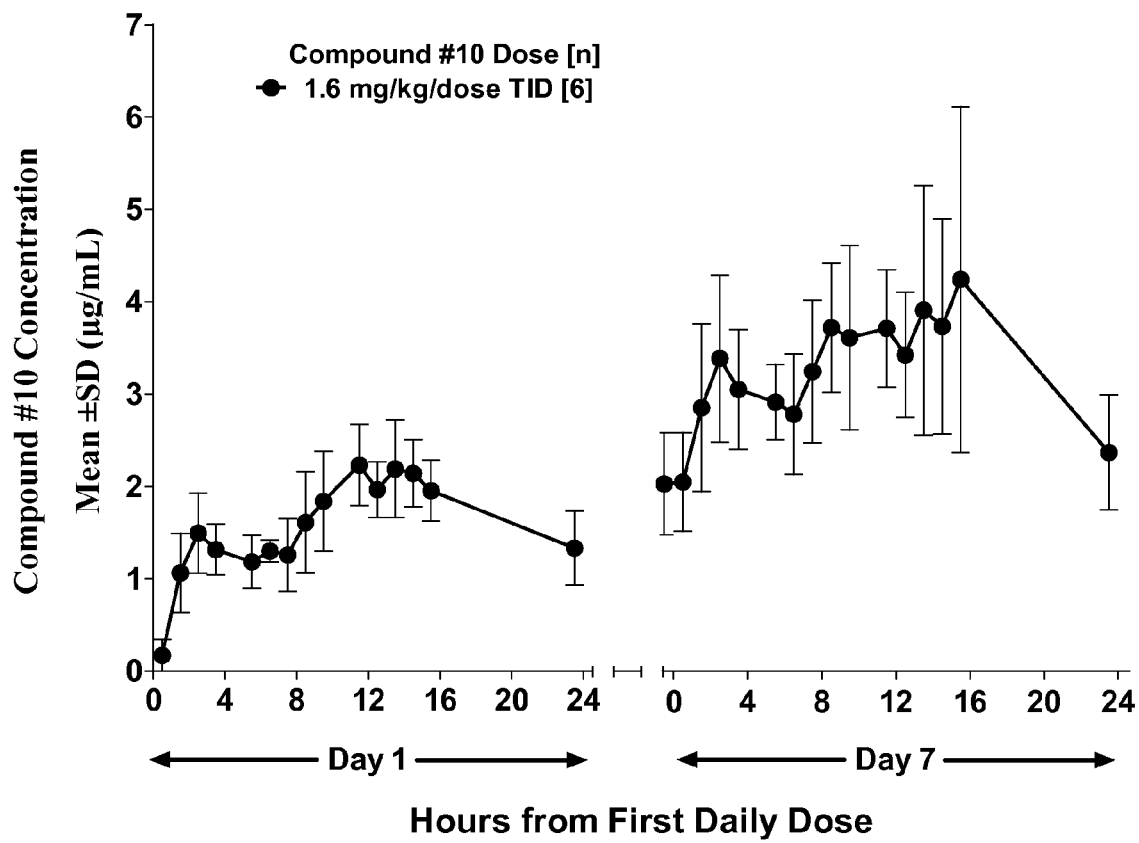
Figure 17:
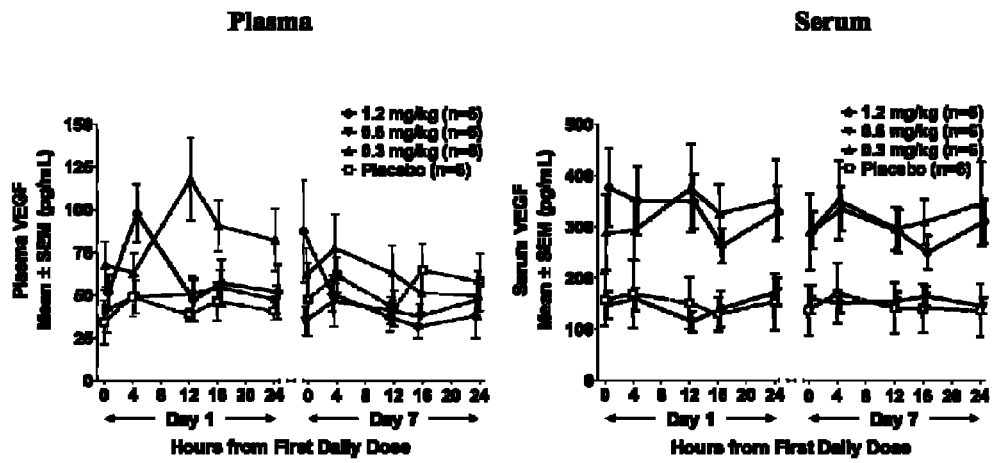
Figure 17:
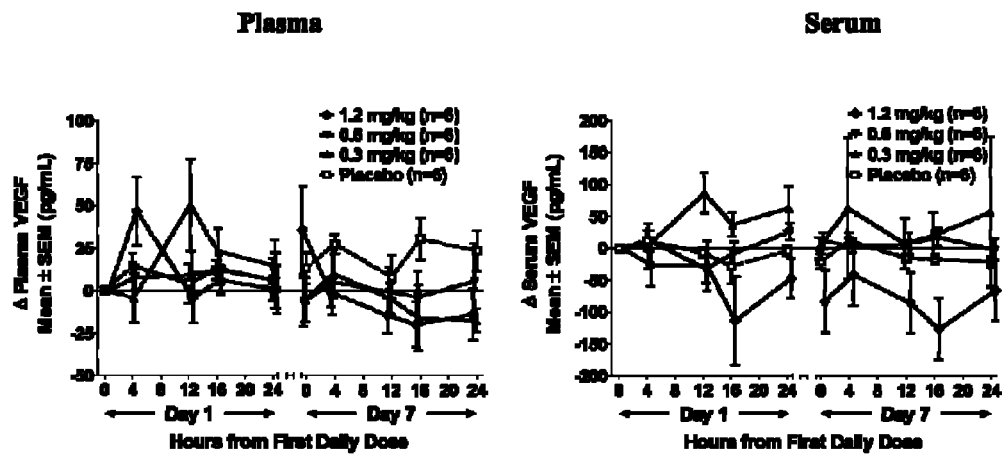
Figure 18:
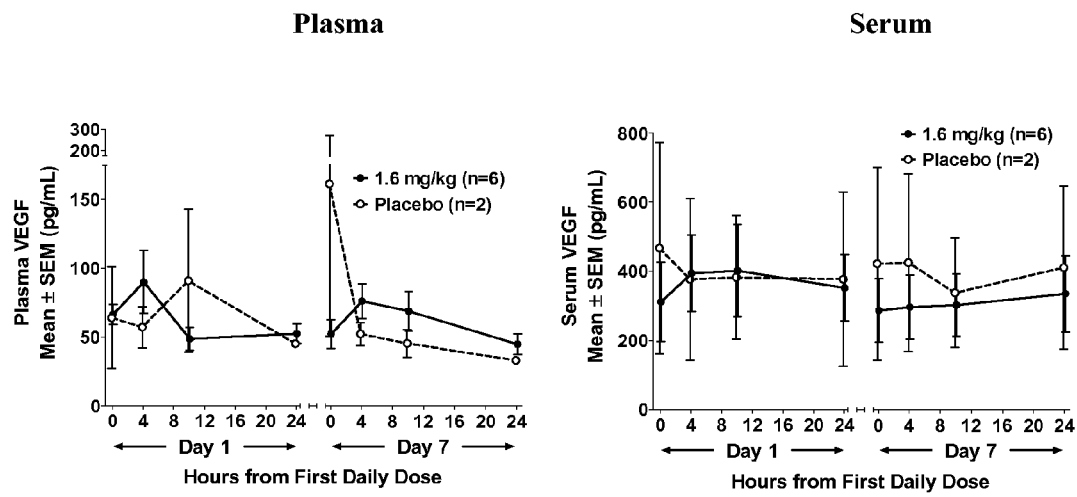
Figure 18:
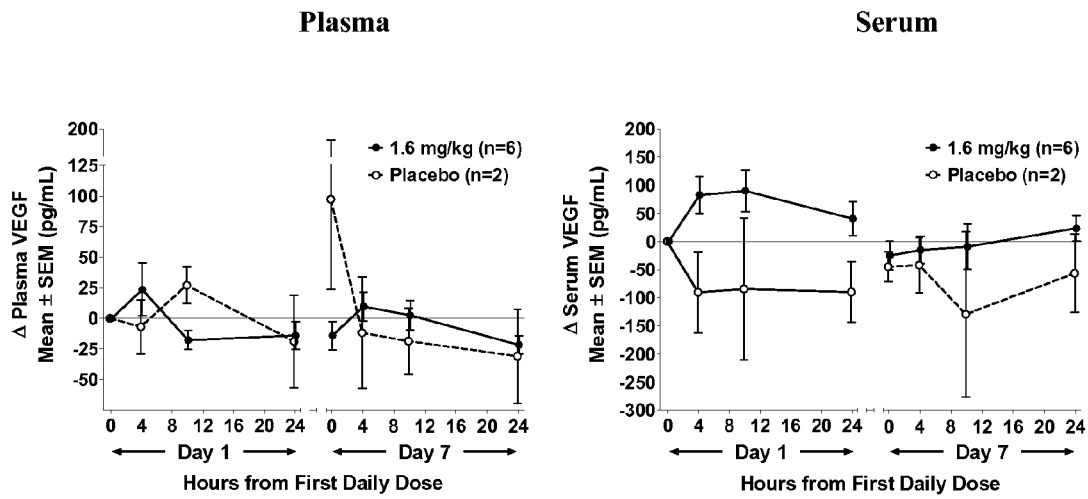
Figure 19:
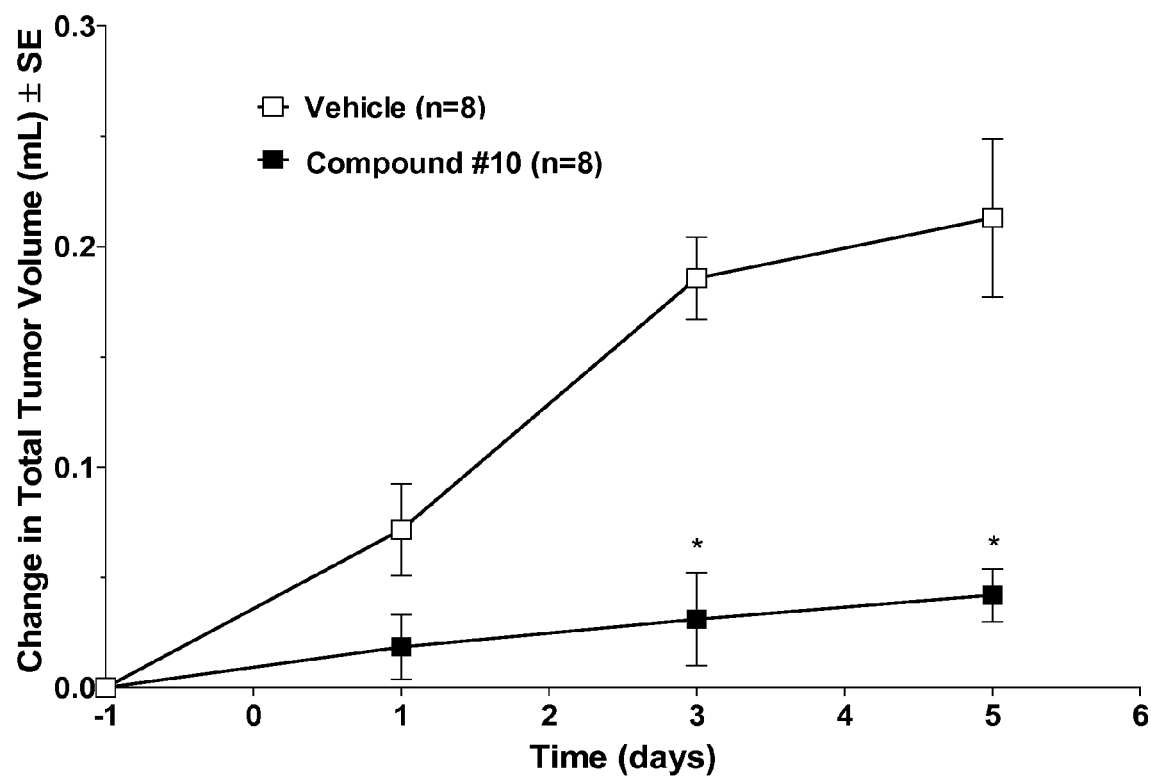
Figure 20:
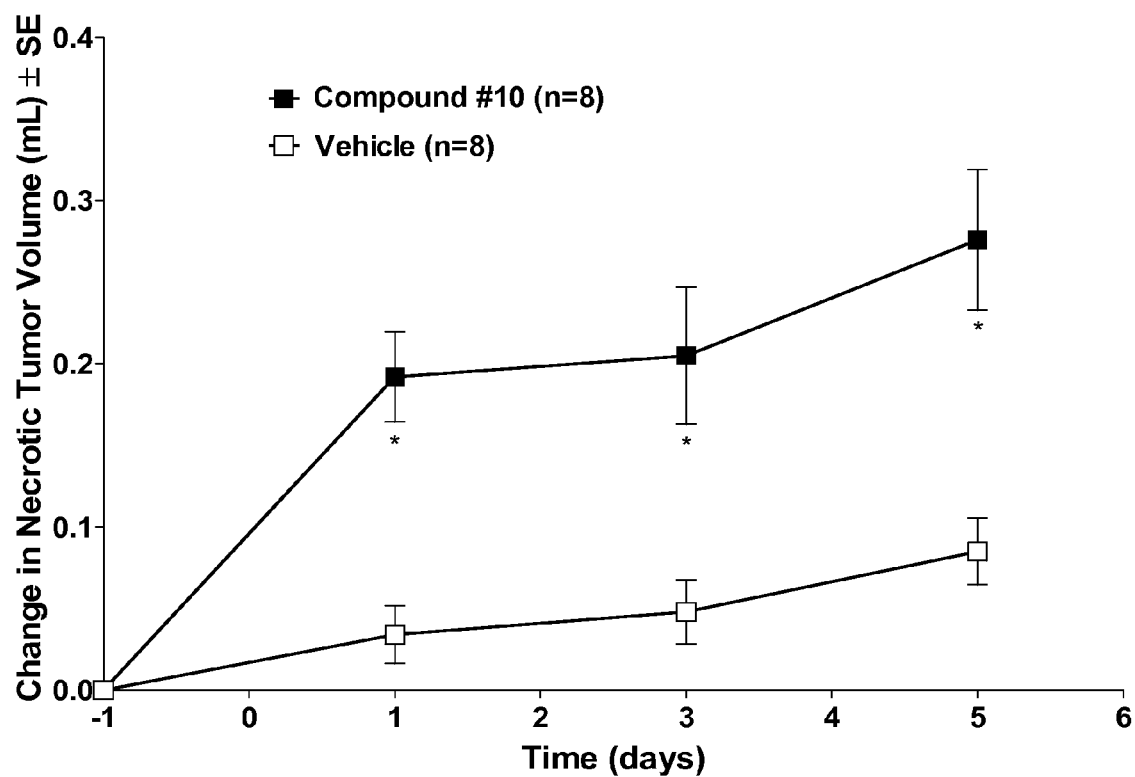
Figure 21:
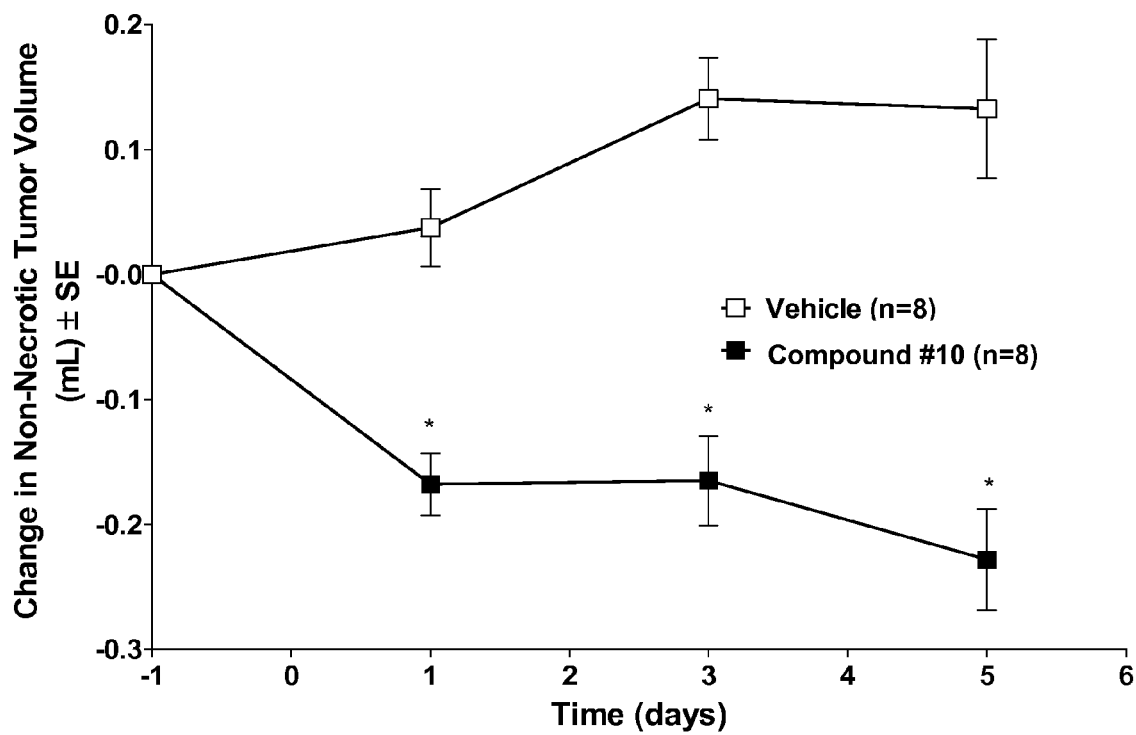
Figure 22:
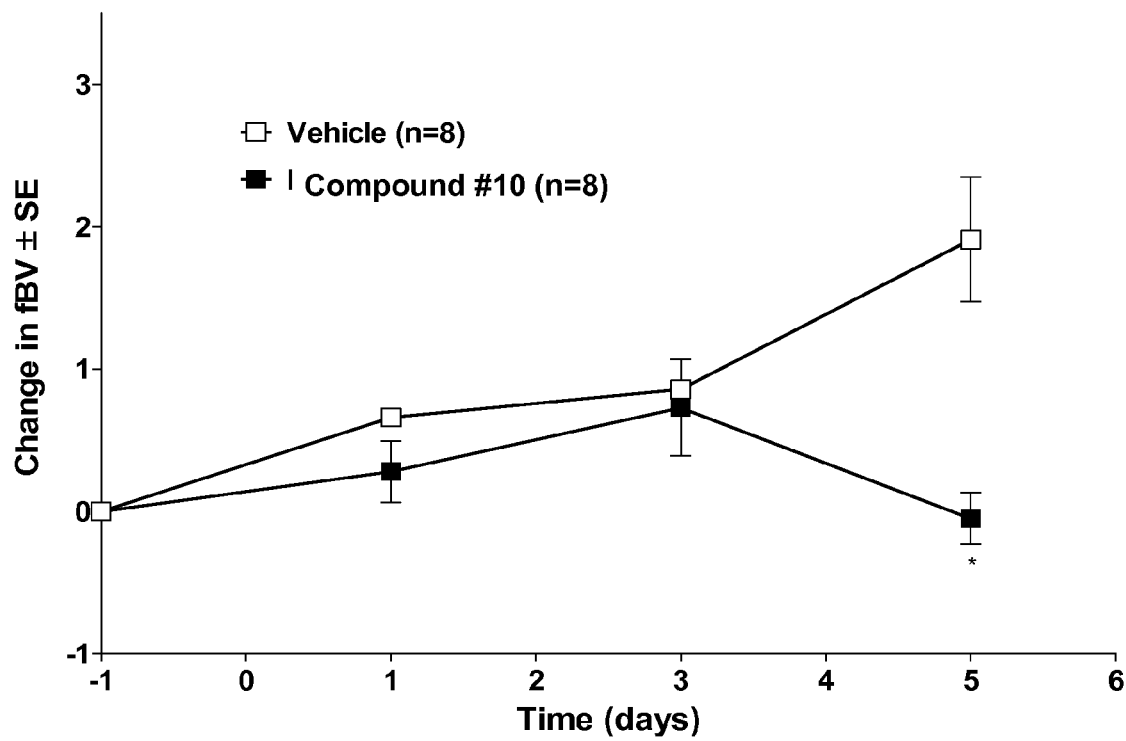
Figure 23:
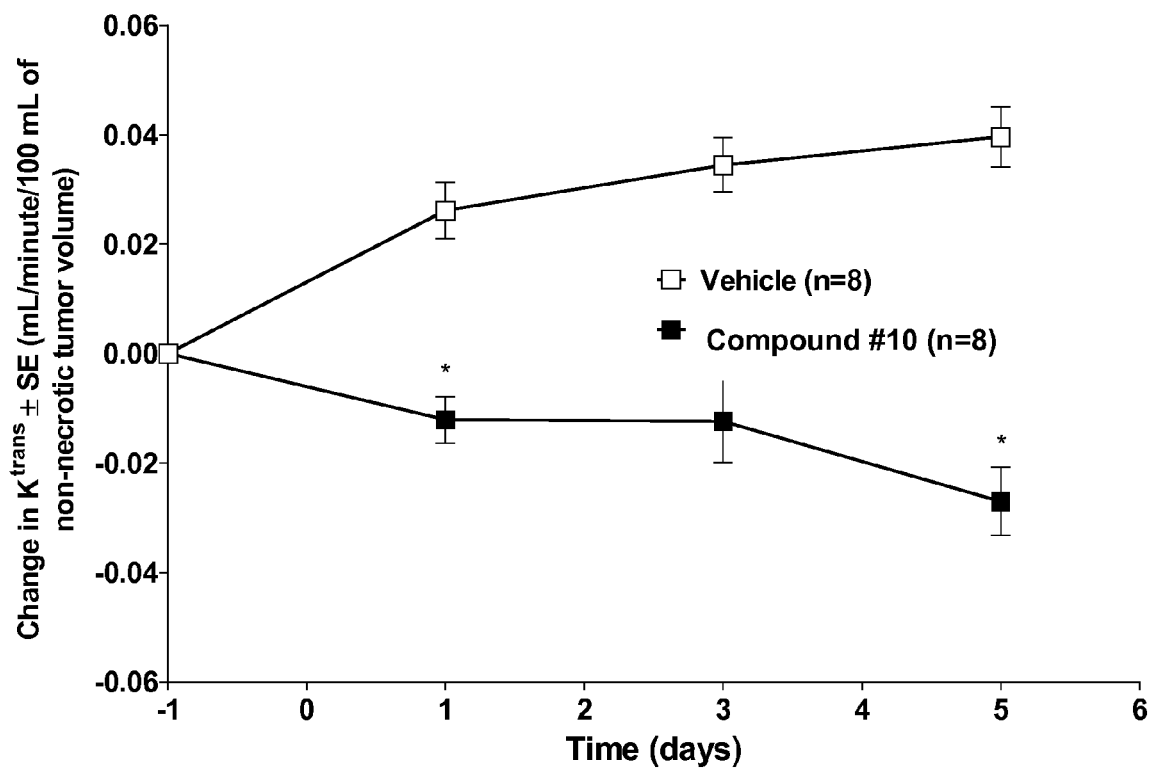
Figure 24:
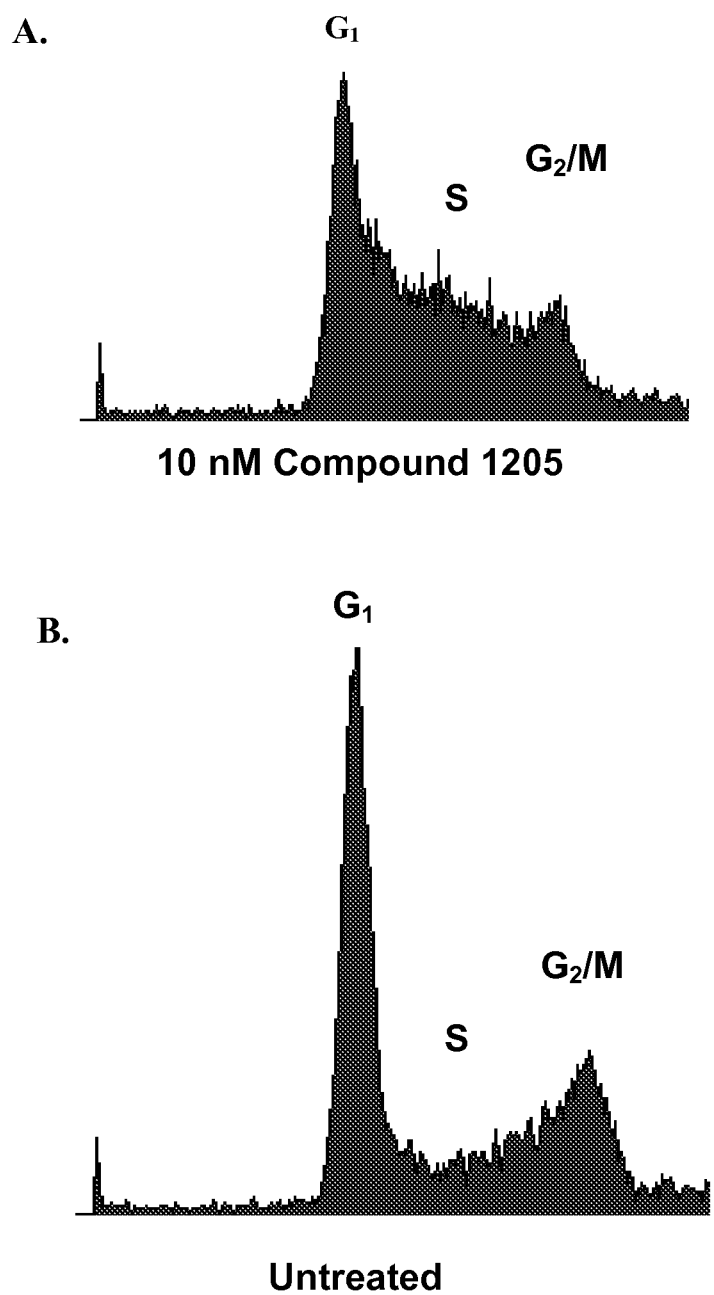
Figure 25:
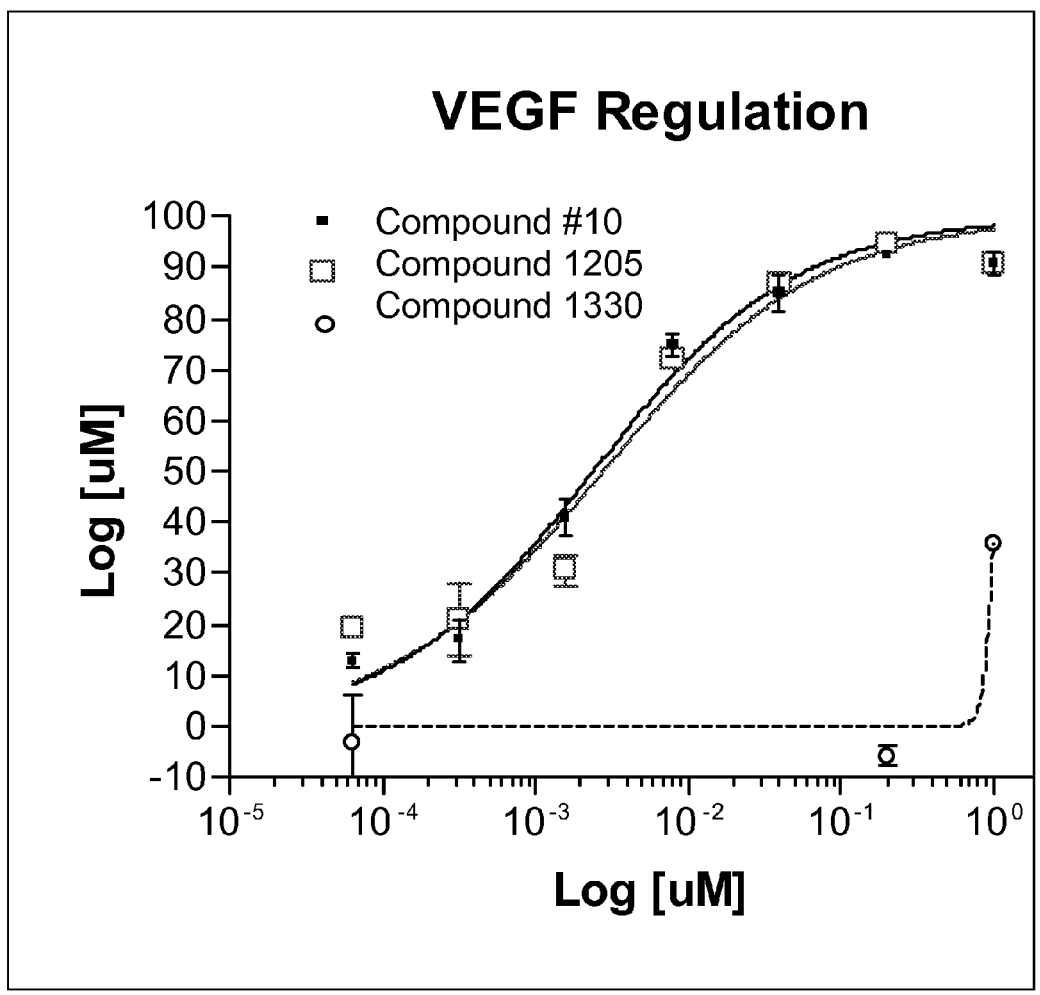
Figure 26:
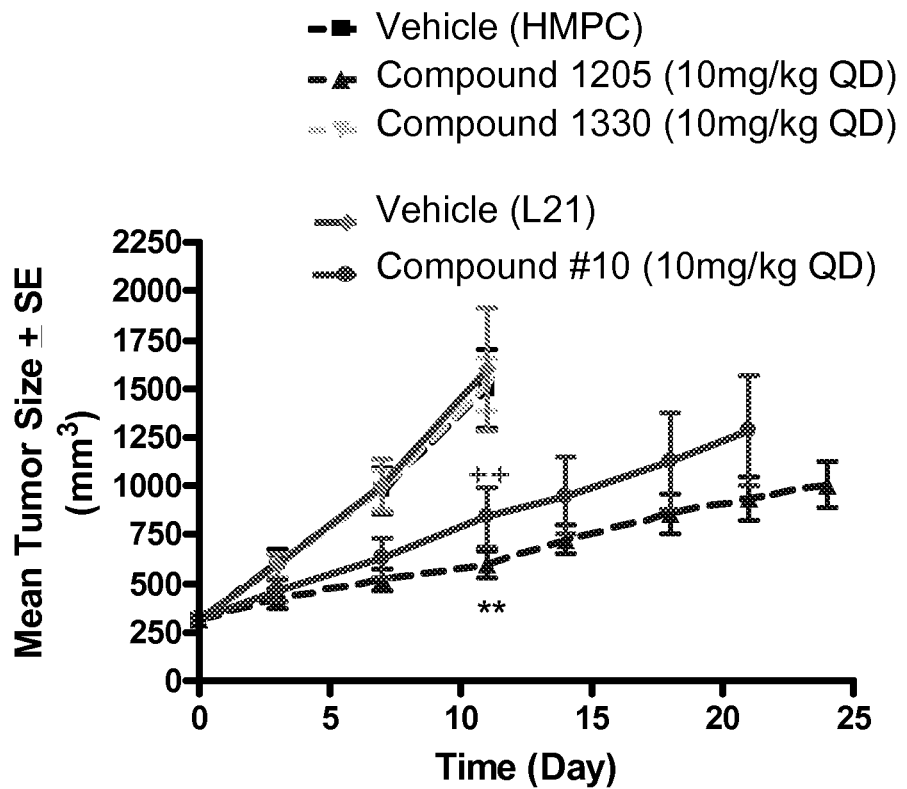
Figure 27:
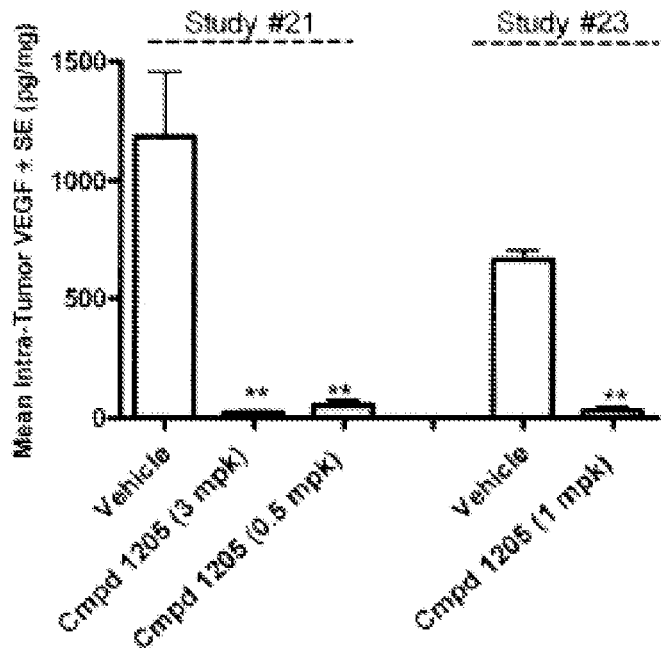
Figure 27:
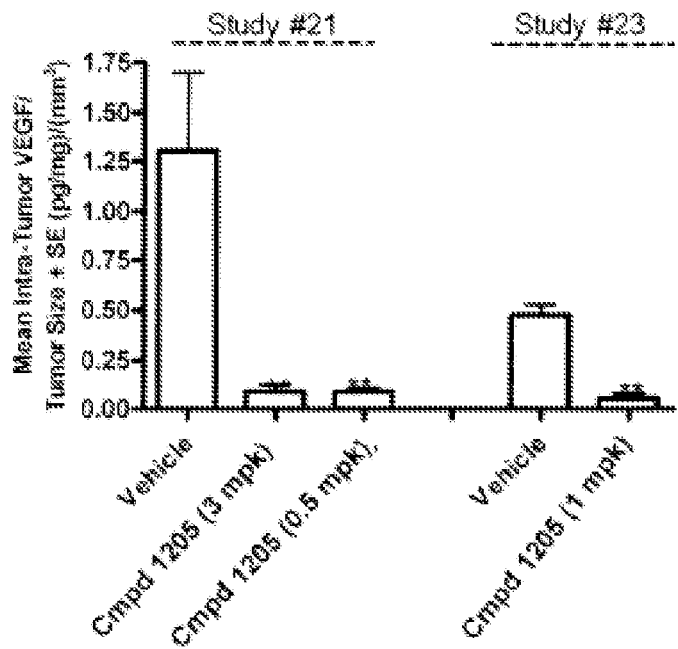
Figure 28:
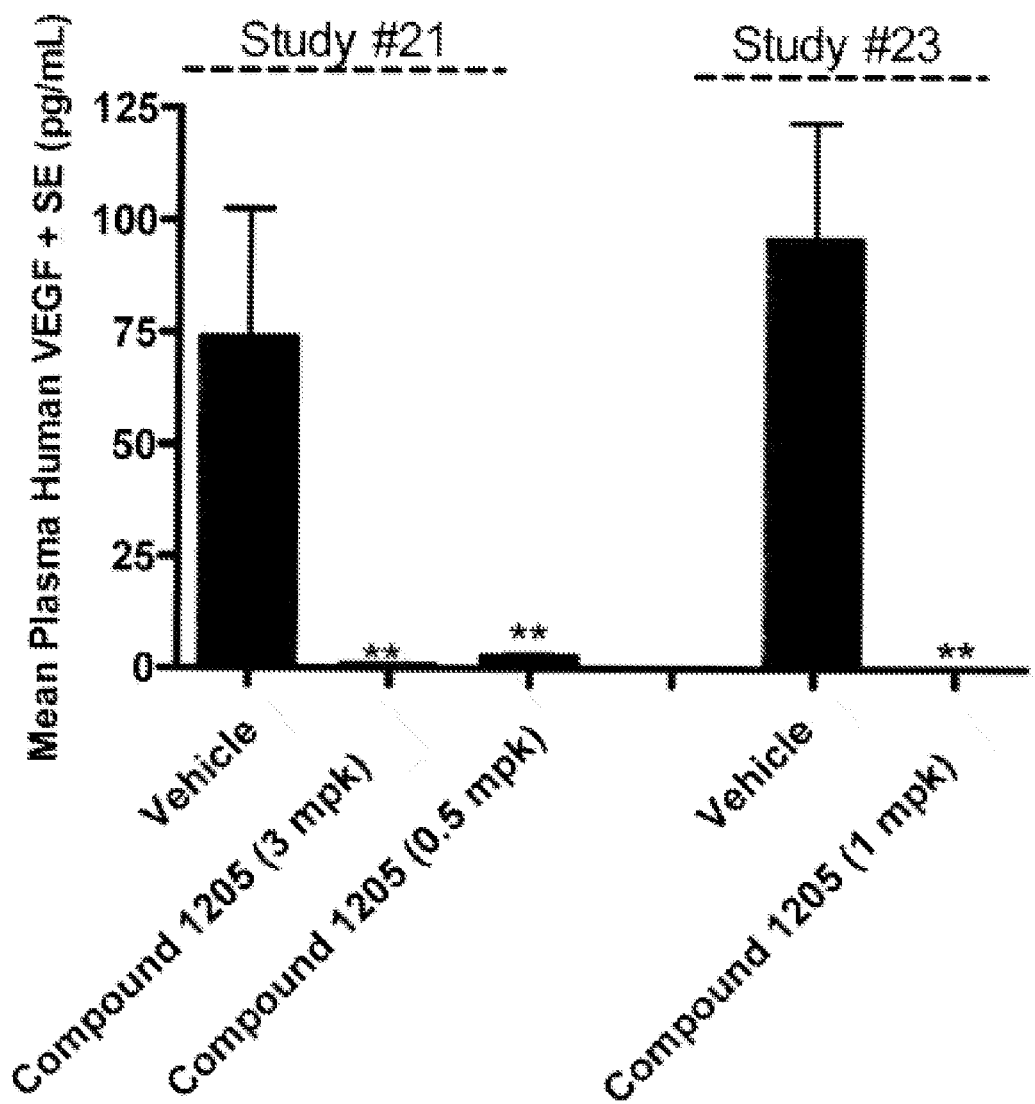
Figure 29:
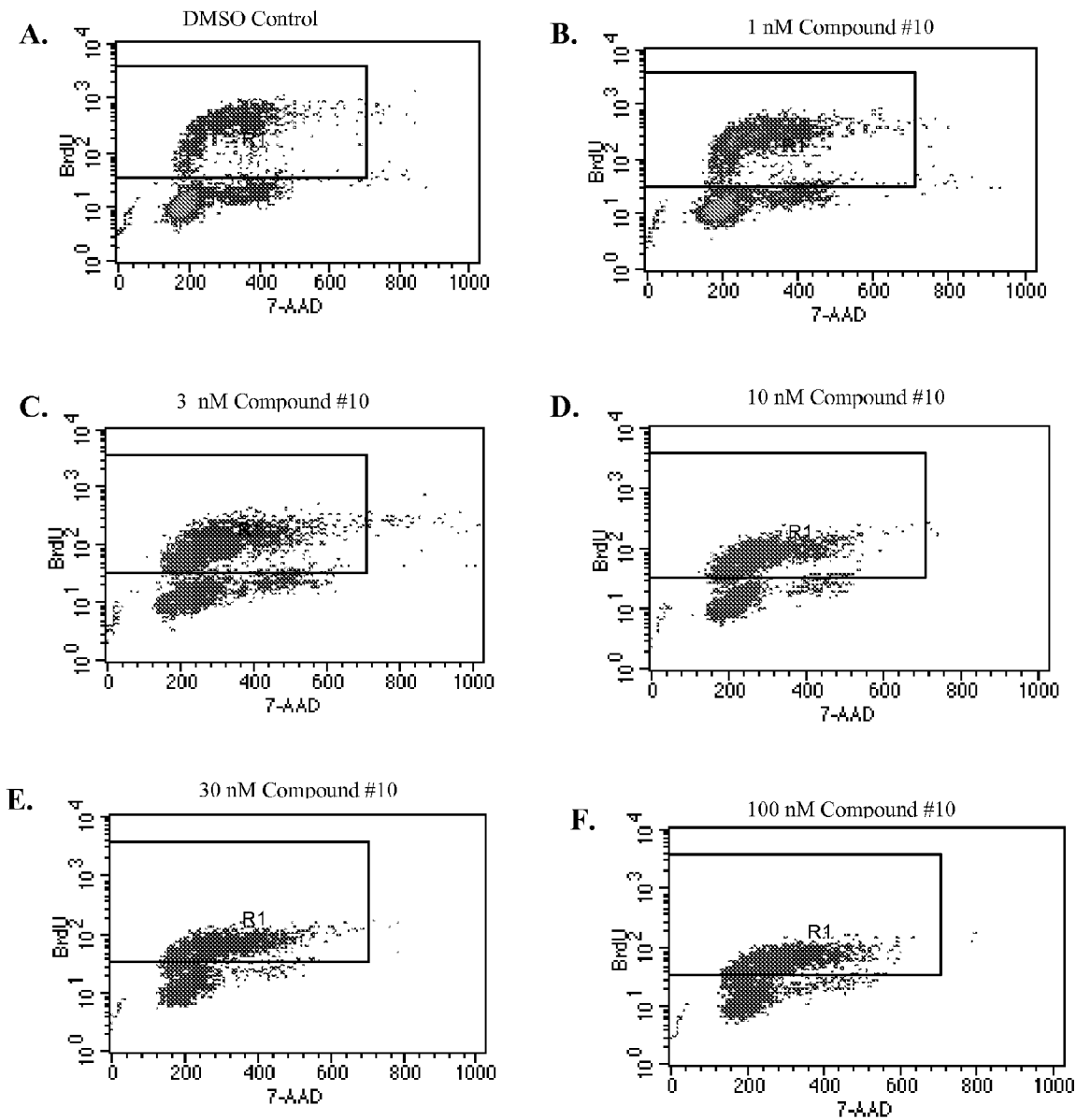
Figure 30:
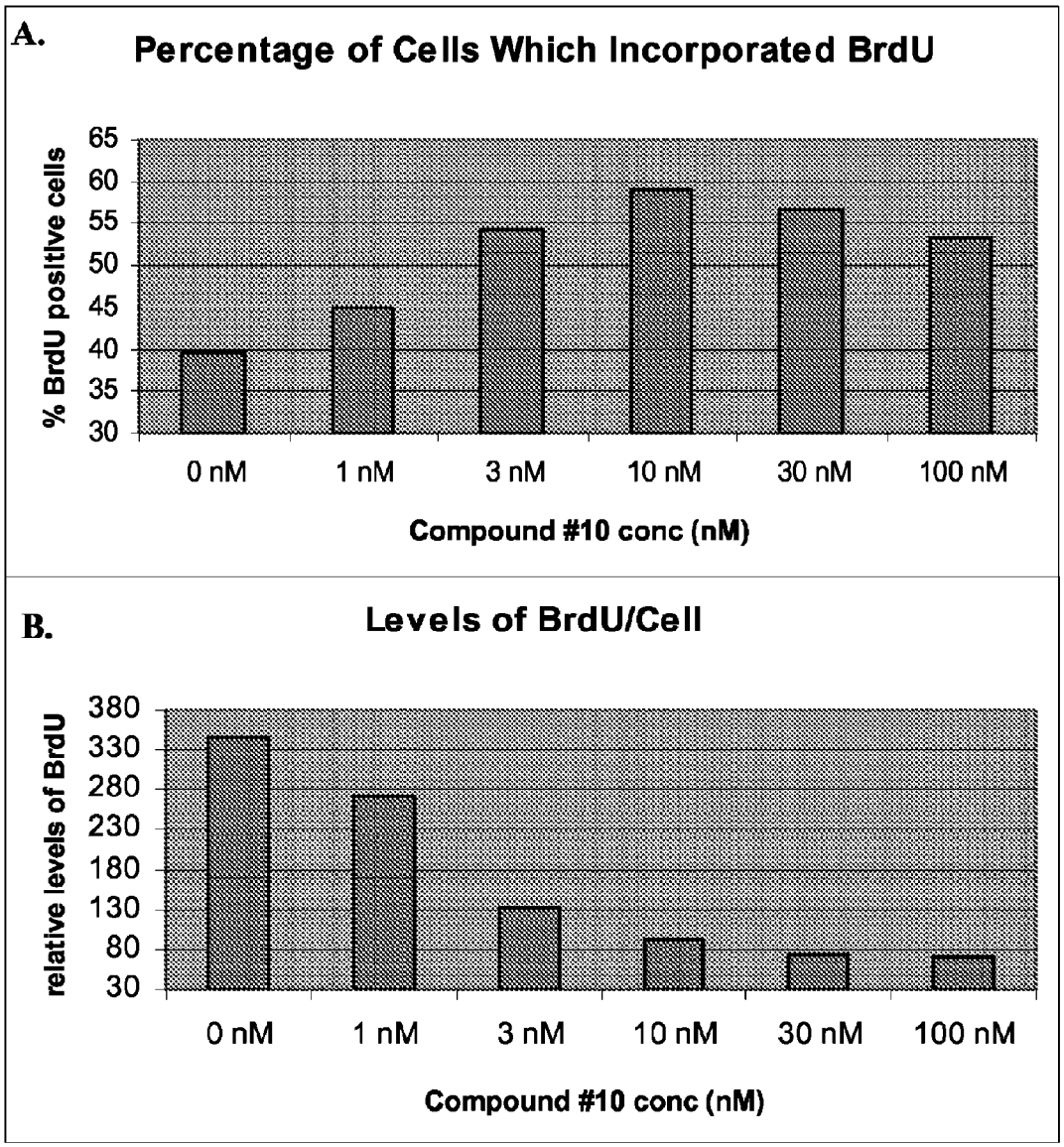
Figure 31C:
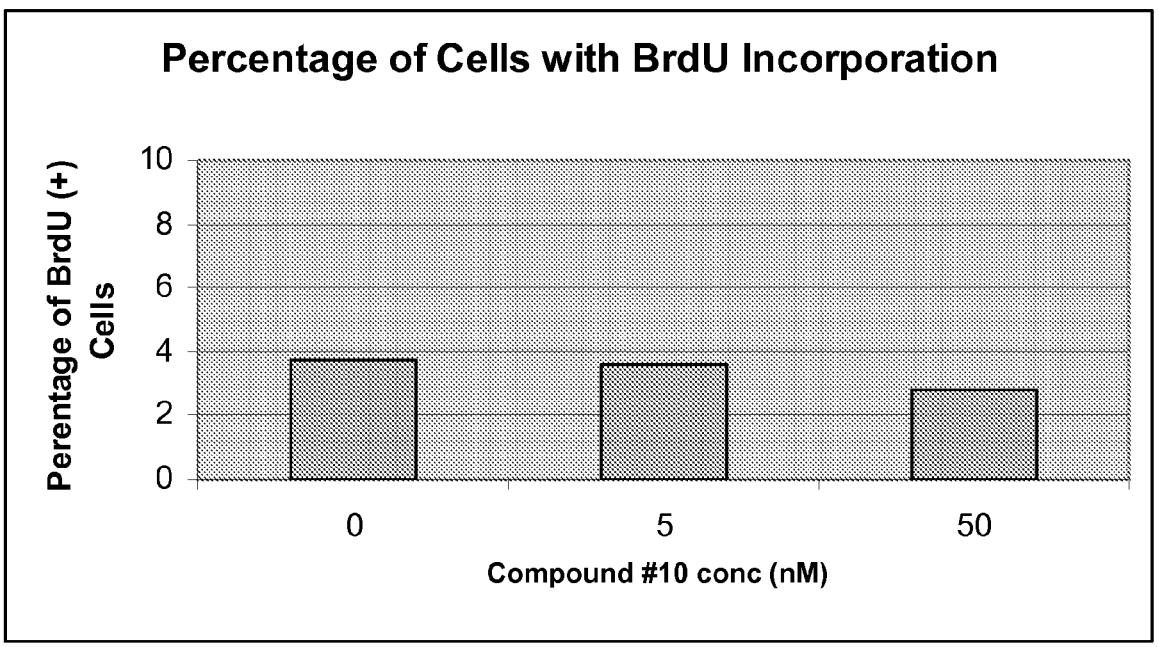
Figure 32C:
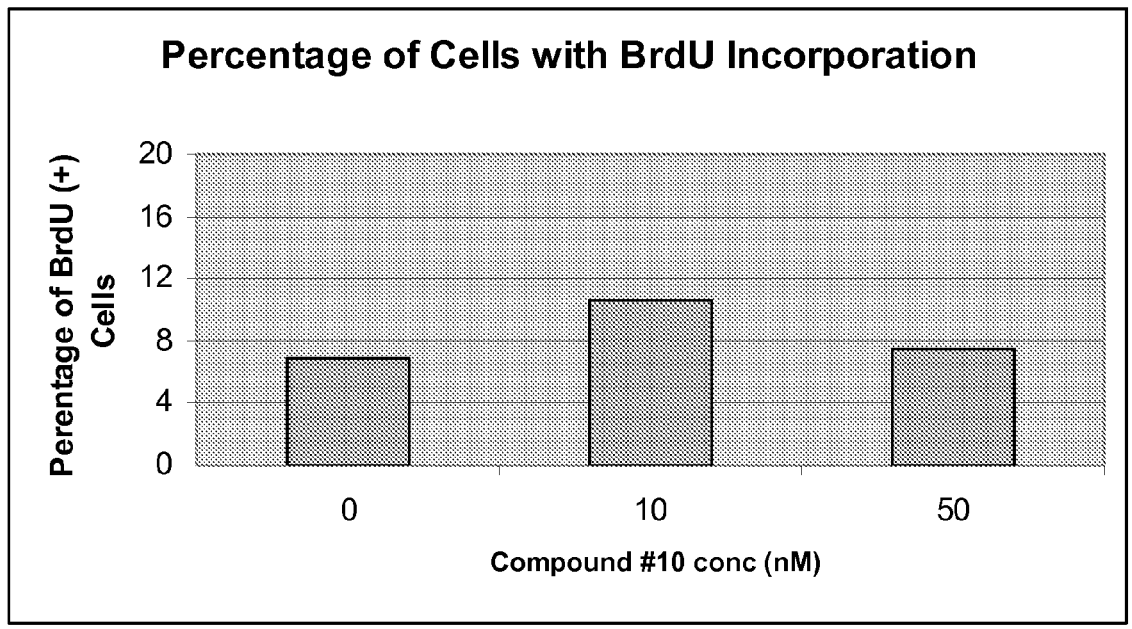
Figure 33:
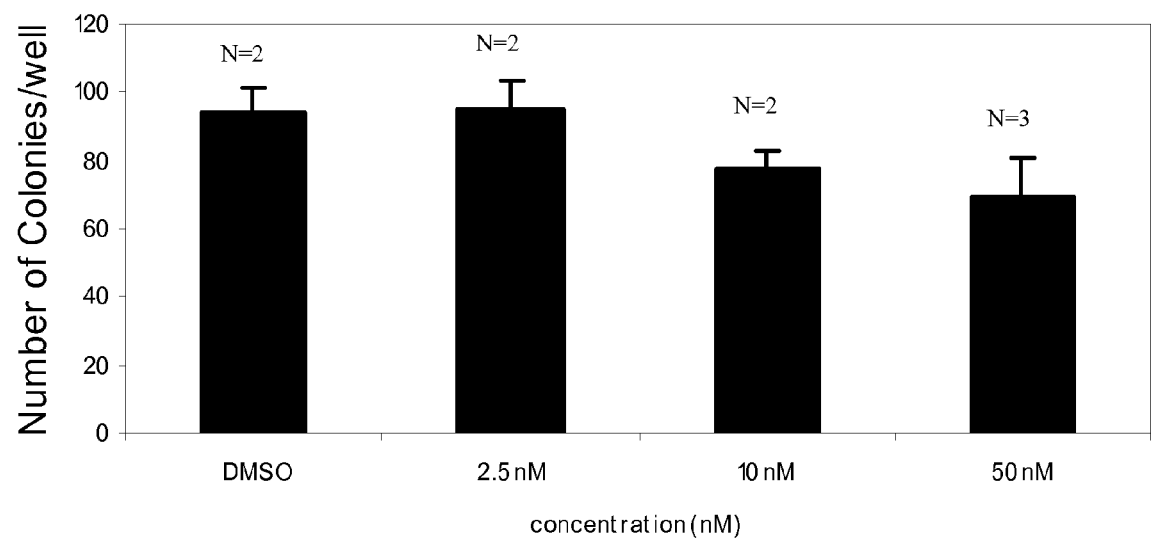
Figure 34:
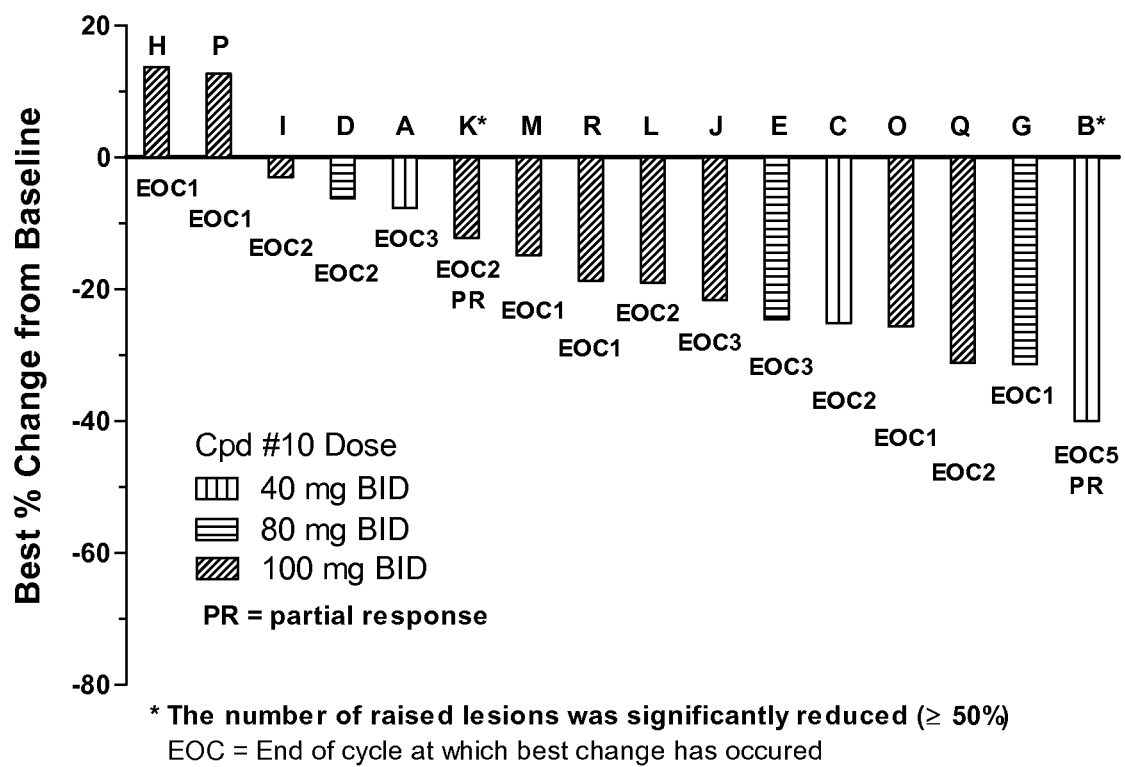
Figure 35:
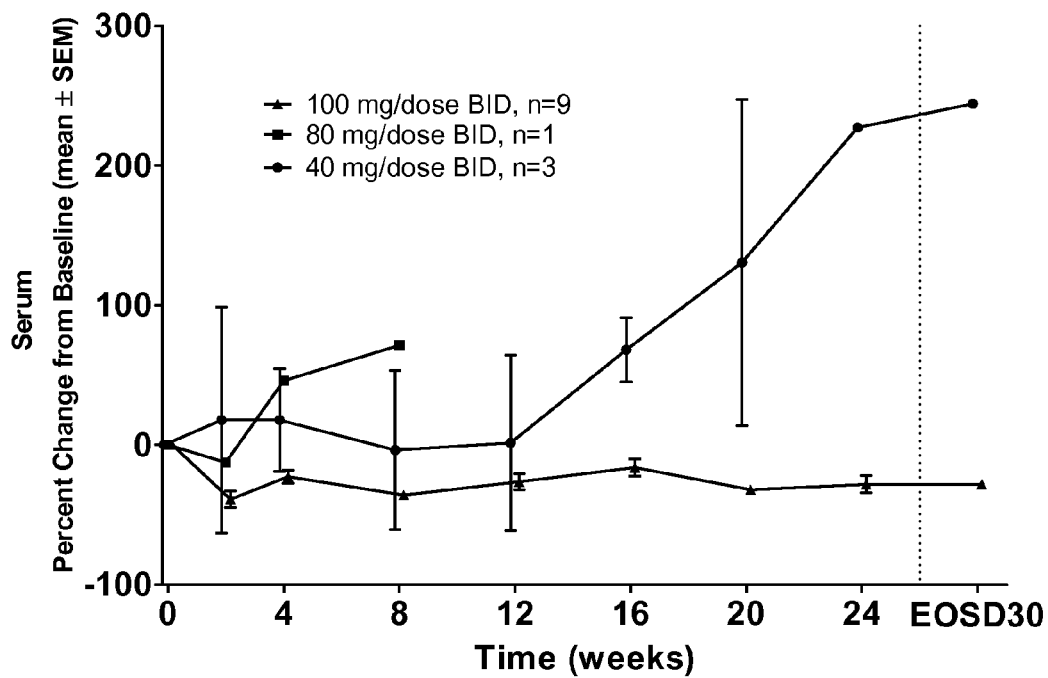
FIG. 35A shows the effect of Compound #10 administration on the clinical endpoint of circulating serum VEGF-A levels in patients. The administration of Compound #10 provides a dose responsive reduction in serum VEGF-A levels in patients.
FIG. 35B shows the effect of Compound #10 administration on the clinical endpoint of circulating plasma VEGF-A levels in patients. The administration of Compound #10 provides a dose responsive reduction in plasma VEGF-A levels in patients.
Figure 35:
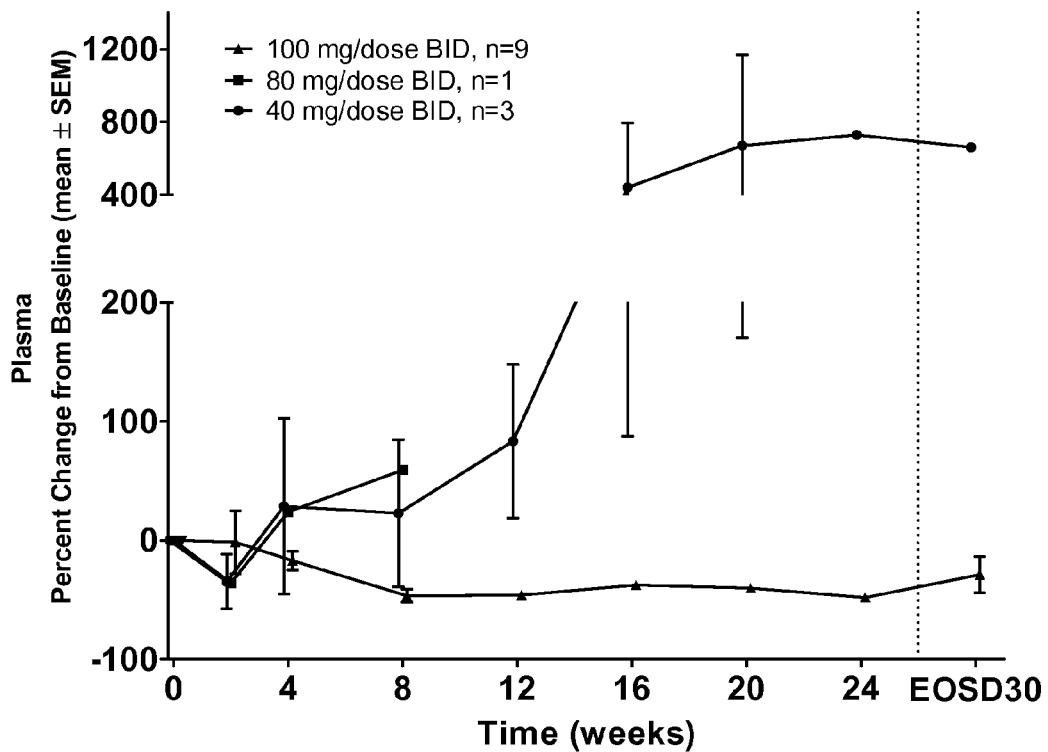

The recently developed mouse model of KS is used to test the anti-tumor efficacy of the agent of a Compound in culture and in mice. In a specific embodiment, the Compound is Compound #10 or Compound #1205. The effect of the drug on the KS-like tumors in mice is evaluated using immune histochemistry. This will validate biological endpoints for future clinical studies.

Experimental Design

In vitro protocol: To test the efficacy of the drug in culture, two human KS cell lines, TIVE-L1 and TIVE-L2 (An et al., 2006; J. Virol. 80(10): 4833-46) are treated with drug at escalating doses and VEGF secretion, cell survival, colony formation and other biochemical markers are tested. TIVE cells (Telomerase-Immortalized human umbilical Vein Endothelial) cells, which, unlike other KS cell lines, maintain KSHV indefinitely. TIVE-L1 and TIVE-L2 are clonal derivatives of KSHV-infected, telomerase-immortalized human endothelial cells.

In vivo Protocol: To test the efficacy of the drug in vivo, TIVE-L1 and TIVE-L2 xenograft tumors are treated using the regimen described below. TIVE-L1 and TIVE-L2 readily form tumors, which resemble KS in their lymphatic endothelial linage as well as KSHV gene expression pattern. The KS-like human cell lines TIVE-L1 and TIVE-E1 are subcutaneously engrafted at 5×10⁵ cells per mouse onto C.B.17 SCID mice. Treatment is initiated when tumors are palpable. Rapamycin is used as the positive control (3 mg/kg/day intraperitoneal (IP) 3× per week for 2 weeks). Mice are treated with a Compound at 10 mg/kg dose or vehicle by oral gavage for the duration of the study (see Table 31).

TABLE 31

| | Group Designation | | |
|---|---|---|---|
| Treatment | Dose (mg/kg) | Regimen | No. of Mice |
| 1 Vehicle (L21) | 0 | QD | 10 |
| 2 Compound | 10 | QD | 10 |
| 3 Rapamycin | 3 | 3X/week for 2 weeks | 10 |

Abbreviations:
IP = intraperitoneal dosing;
L21 = 35% Labrasol ®, 35% Labrafac ® CC and 30% Solutol ® HS 15;
PO = oral dosing;
QD = once-per-day dosing.

A Compound is formulated and stored at room temperature in ambient humidity in glass containers protected from light. For a Compound, vehicles consist of L21 (35% Labrasol®, 35% Labrafac® CC and 30% Solutol® HS15). Rapamycin is purchased and formulated for administration. For rapamycin, vehicles consist of 10% PEG 400/10% Tween-80/8% ethanol.

Each animal is observed at the time of dosing for mortality and signs of pain or distress; findings of overt toxicity are recorded as they are observed. Body weights of the mice are measured the day that dosing is initiated and at least once a week thereafter. Observations are made on animals that die or are sacrificed at an unscheduled interval. Animals are sacrificed if moribund.

To quantify tumor incidence and growth rate, repeated measurements ANOVA are used. There may be 10 treated mice per group, as previous studies have shown that it is adequate to detect a 50% reduction on tumor incidence or tumor growth with p<0.05 after 30 days. When there is a statistically significant effect on tumor size (comparing a Compound with vehicle), all mice in the study are sacrificed and the tumor collected for histology. If the vehicle-treated mice reach the Institutional Animal Care and Use Committee (IACUC) endpoint (ie, the size of tumor that requires euthanasia according to local IACUC guidelines), all mice are sacrificed at that time.

At necropsy, the tumors are collected for subsequent histochemical analysis. The anti-tumor effect of the drug is scored by histology by looking at tumor structure (H&E stain), proliferative index (Ki-67), apoptosis (TUNEL) and KSHV protein expression (LANA, K8.1).

The anti-endothelial effect is scored by immunohistochemistry, specifically LYVE-1, CD31 and mouse cyclin D. This allows the identification of direct anti-KS, i.e. human effects.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for treating a Kaposi sarcoma (KS), comprising administering to a human having the KS an effective amount of a compound having Formula (II):

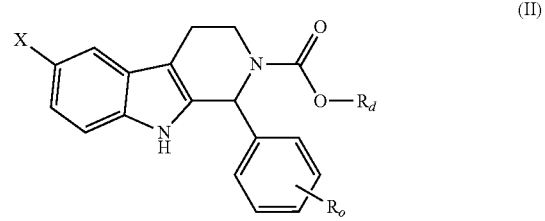

(II)

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_6$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, —C(O)—$R_b$, —(O)O—$R_b$, alkylsulfonyl, morpholinyl or tetrahydropyranyl; $C_1$ to $C_8$ alkyl optionally substituted with one or more substituents independently selected from the group consisting of hydroxyl, halogen and amino; —C(O)R$_n$; or —OR$_a$;

R$_a$ is hydrogen; C$_2$ to C$_8$ alkenyl; —C(O)—R$_n$; —C(O)O—R$_b$; —C(O)—NH—R$_b$; C$_1$ to C$_8$ alkyl optionally substituted with one or more substituents independently selected from the group consisting of hydroxyl, halogen, C$_1$ to C$_4$ alkoxy, (C$_1$ to C$_4$)alkyl-O—(C$_1$ to C$_4$)alkyl-O—, amino, alkylamino, dialkylamino, acetamide, —C(O)—R$_b$, —C(O)O—R$_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene and tetrazole;

wherein amino is optionally substituted with C$_1$ to C$_4$ alkoxycarbonyl, imidazole, isothiazole, pyrazole, pyridine, pyrazine, pyrimidine, pyrrole, thiazole or sulfonyl substituted with C$_1$ to C$_6$ alkyl, wherein pyridine and thiazole are each optionally substituted with C$_1$ to C$_4$ alkyl;

wherein alkylamino and dialkylamino are each optionally substituted on alkyl with hydroxyl, C$_1$ to C$_4$ alkoxy, imidazole, pyrazole, pyrrole or tetrazole; and, wherein morpholinyl, thiomorpholinyl, pyrrolidinyl, piperidinyl, piperazinyl and oxiranyl are each optionally substituted with —C(O)—R$_n$, —C(O)O—R$_n$ or C$_1$ to C$_4$ alkyl, wherein C$_1$ to C$_4$ alkyl is optionally substituted with hydroxyl;

R$_b$ is hydroxyl; amino; alkylamino, optionally substituted on alkyl with hydroxyl, amino, alkylamino or C$_1$ to C$_4$ alkoxy; C$_1$ to C$_4$ alkoxy; C$_2$ to C$_8$ alkenyl; C$_2$ to C$_8$ alkynyl; aryl optionally substituted with one or more substituents independently selected from the group consisting of halogen and C$_1$ to C$_4$ alkoxy; furan; or C$_1$ to C$_8$ alkyl optionally substituted with one or more substituents independently selected from the group consisting of C$_1$ to C$_4$ alkoxy, aryl, amino, morpholinyl, piperidinyl and piperazinyl;

R$_d$ is aryl optionally substituted with one or more substituents independently selected from the group consisting of halogen, nitro, C$_1$ to C$_6$ alkyl, —C(O)O—R$_e$, and —OR$_e$;

R$_e$ is hydrogen; C$_1$ to C$_6$ alkyl optionally substituted with one or more substituents independently selected from the group consisting of halogen and alkoxy; or phenyl, wherein phenyl is optionally substituted with one or more substituents independently selected from the group consisting of halogen and alkoxy; and R$_n$ is hydroxyl, C$_1$ to C$_4$ alkoxy, amino or C$_1$ to C$_6$ alkyl;

wherein administering the compound to the human produces one or more of the results selected from the group consisting of:

(i) decrease in the number of previously existing KS lesions in the human relative to the number of KS lesions observed prior to administration of the compound;

(ii) decrease in the number of raised KS lesions in the human relative to the number of raised KS lesions observed prior to administration of the compound;

(iii) complete flattening of one or more previously raised KS lesions in the human; and (iv) decrease in the sum of perpendicular diameters of a KS lesion in the human, relative to the sum of perpendicular diameters in the KS lesion observed prior to administration of the compound.

2. The method of claim 1, wherein the KS is classic Kaposi sarcoma.

3. The method of claim 1, wherein the KS is endemic Kaposi sarcoma.

4. The method of claim 1, wherein the KS is AIDS-related Kaposi sarcoma.

5. The method of claim 1, wherein the KS is iatrogenic Kaposi sarcoma.

6. The method of claim 1, wherein the effective amount is in a range of from about 0.001 mg per kg per day to about 1500 mg per kg per day.

7. The method of claim 1, wherein the compound is administered during or within about 30 minutes after a meal.

8. The method of claim 1, wherein the effective amount of the compound is administered two times per day at a time interval of from about 12 hours to about 18 hours between doses.

9. The method of claim 8, wherein the effective amount of the compound is administered two times per day at a time interval of about 12 hours between doses.

10. The method of claim 1, wherein the effective amount of the compound is administered three times per day at a time interval of from about 8 hours to about 12 hours between doses.

11. The method of claim 10, wherein the effective amount of the compound is administered three times per day at a time interval of about 8 hours between doses.

12. The method of claim 1, wherein the compound has the Formula (II):

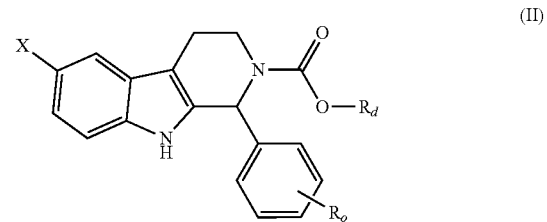

or a pharmaceutically acceptable salt, racemate or stereoisomer thereof, wherein, X is halogen;

R$_o$ is halogen, C$_1$ to C$_8$ alkyl optionally substituted with one or more substituents independently selected from the group consisting of hydroxyl, halogen and amino, or —OR$_a$;

R$_a$ is hydrogen, C$_1$ to C$_8$ alkyl optionally substituted with one or more substituents independently selected from the group consisting of hydroxyl and halogen; and R$_d$ is phenyl optionally substituted with one or more —O(C$_1$-C$_6$ alkyl) or halogen substituents.

13. The method of claim 1, wherein the compound has the Formula (II):

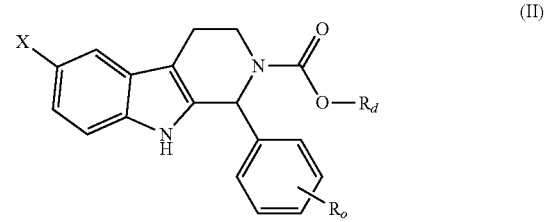

or a pharmaceutically acceptable salt, racemate or stereoisomer thereof, wherein, X is halogen;

R$_o$ is halogen, C$_1$ to C$_8$ alkyl optionally substituted with one or more substituents independently selected from the group consisting of hydroxyl, halogen and amino, or —OR$_a$;

R$_a$ is hydrogen, or C$_1$ to C$_8$ alkyl optionally substituted with one or more substituents independently selected from the group consisting of hydroxyl and halogen; and R$_d$ is phenyl optionally substituted with one or more halogen substituents.

14. The method of claim 1, wherein the compound has the Formula (III):

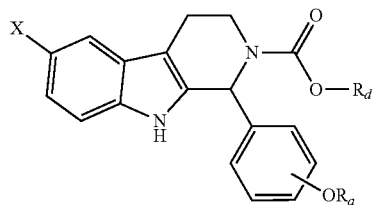

(III)

or a pharmaceutically acceptable salt, racemate or stereoisomer thereof, wherein, X is halogen;

R$_a$ is hydrogen, C$_1$ to C$_8$ alkyl optionally substituted with one or more substituents independently selected from the group consisting of hydroxyl and halogen; and R$_d$ is phenyl substituted with one or more halogen substituents.

15. The method of claim 1, wherein the compound has the Formula (IV):

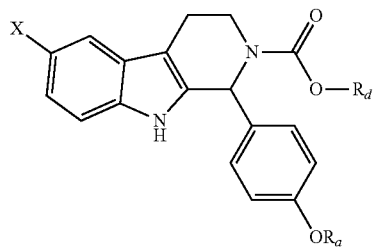

(IV)

or a pharmaceutically acceptable salt, racemate or stereoisomer thereof, wherein, X is halogen;

R$_a$ is hydrogen, C$_1$ to C$_8$ alkyl optionally substituted with one or more substituents independently selected from the group consisting of hydroxyl and halogen; and R$_d$ is phenyl substituted with one or more halogen substituents.

16. The method of claim 1, wherein the compound has the Formula (IV):

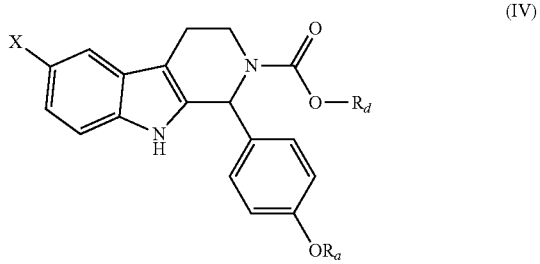

(IV)

or a pharmaceutically acceptable salt, racemate or stereoisomer thereof, wherein, X is halogen;

R$_a$ is hydrogen, C$_1$ to C$_8$ alkyl optionally substituted with one or more substituents independently selected from the group consisting of hydroxyl and halogen; and R$_d$ is phenyl substituted on a para position with a halogen substituent.

17. A method for treating a Kaposi sarcoma (KS), comprising administering to a human having the KS an effective amount of a compound selected from the group consisting of:

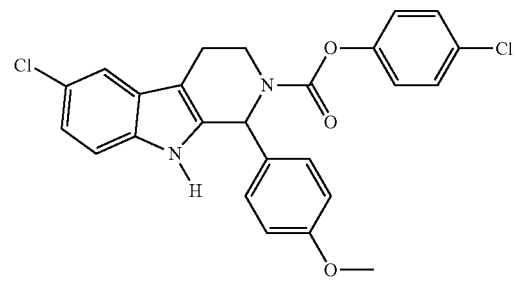

10

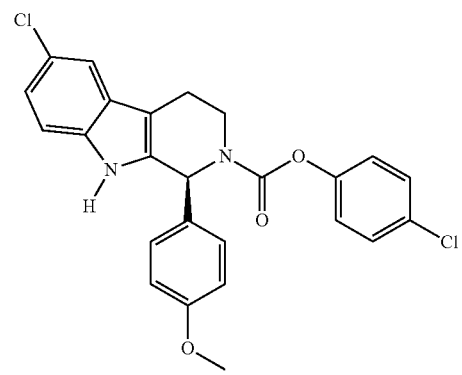

10

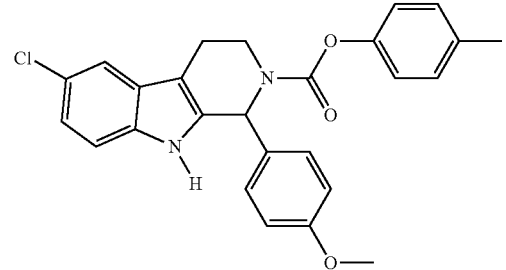

17

399
-continued
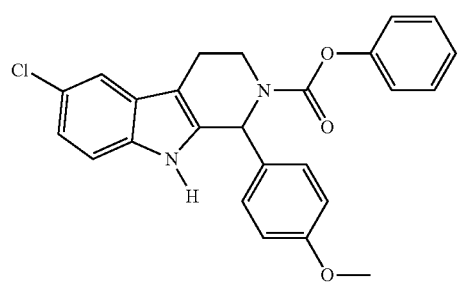
60
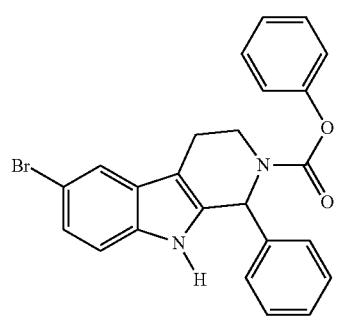
76
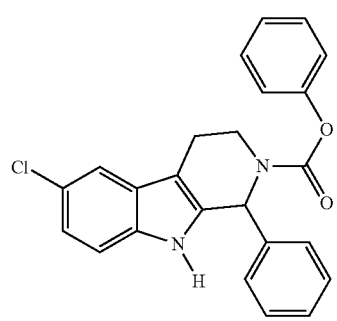
121
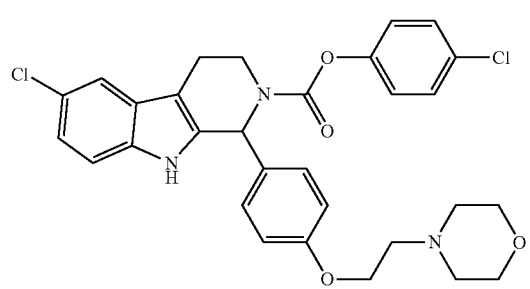
331
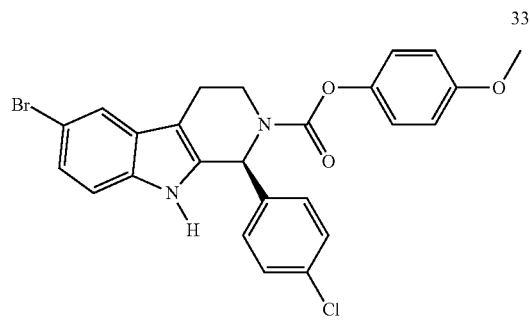
332
400
-continued
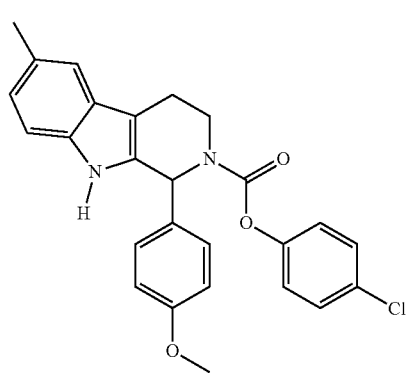
341
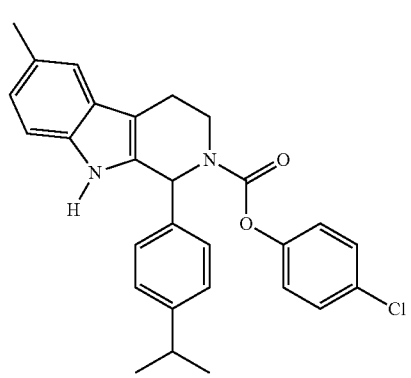
344
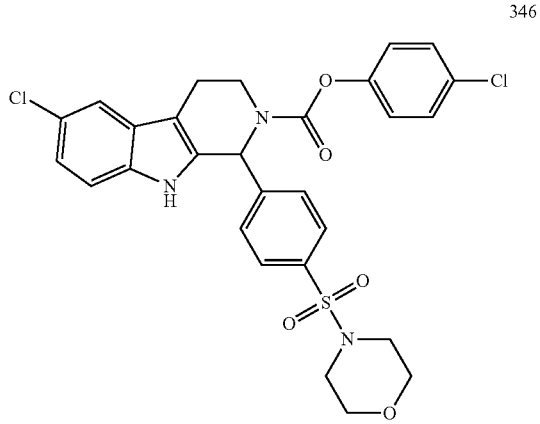
346
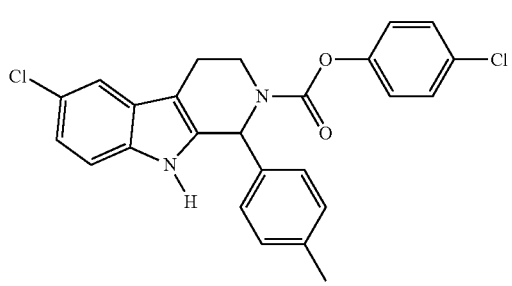
347

348
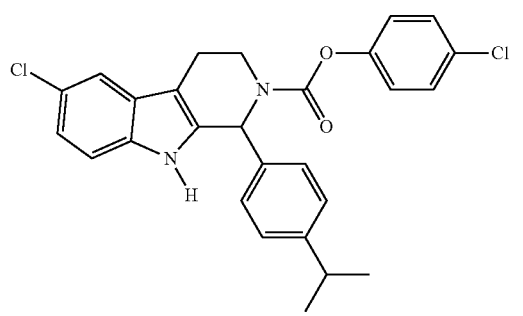
350
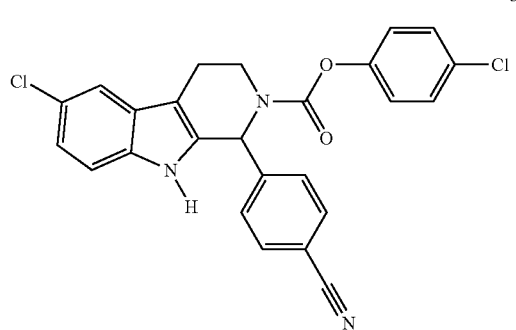
351
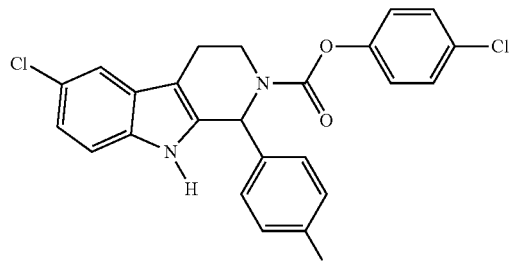
353
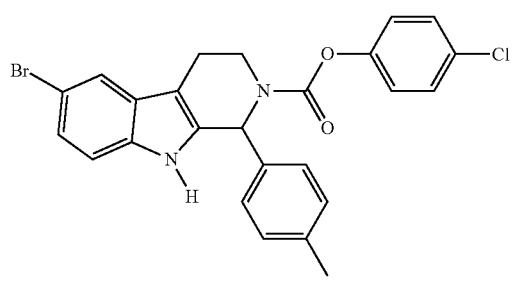
354
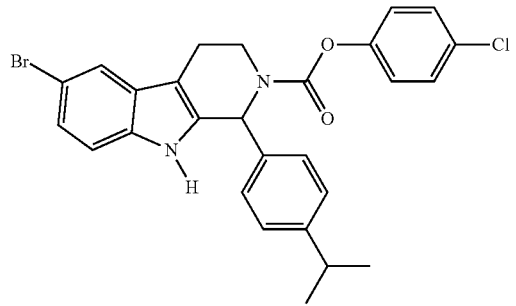
355
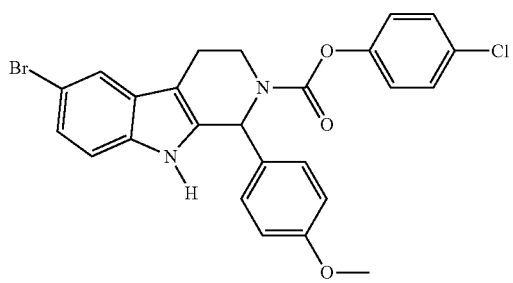
359
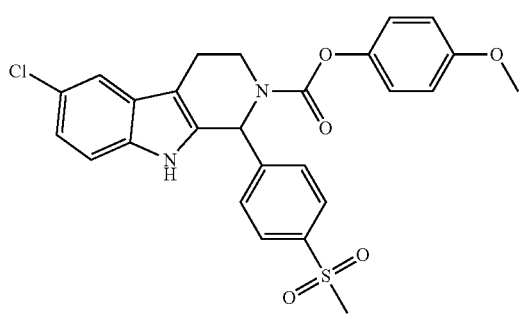
360
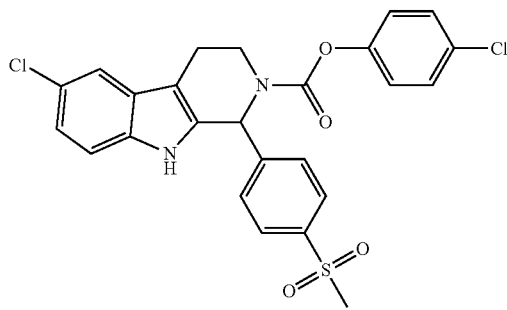
366
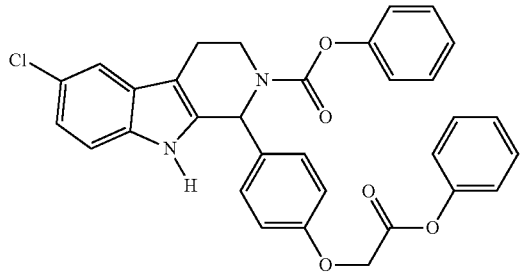
388
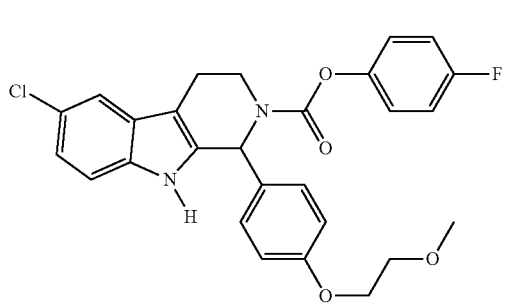

403
-continued
391
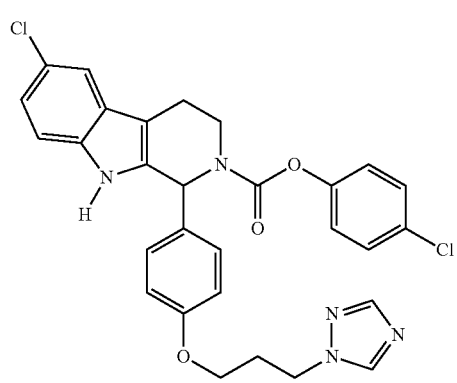
395
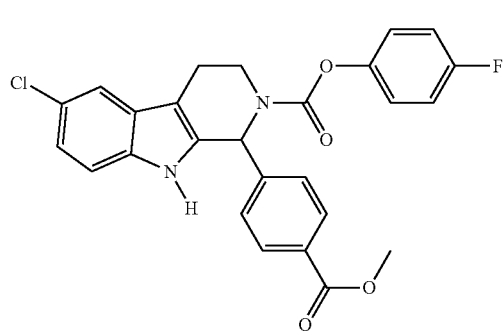
397
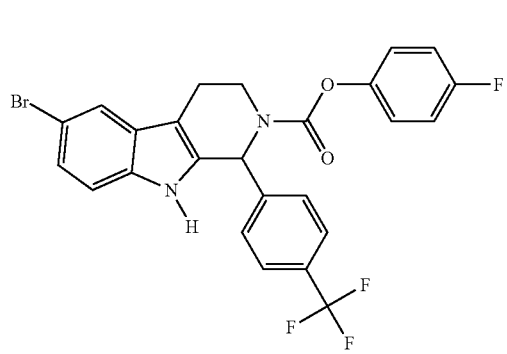
398
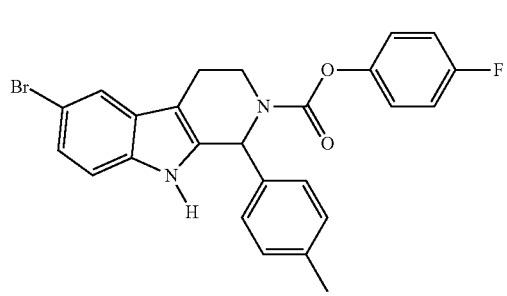
400
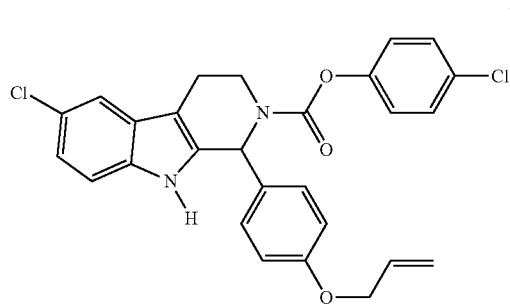
404
-continued
401
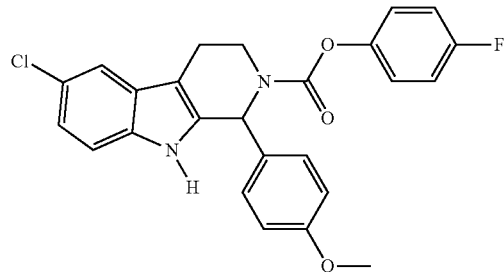
403
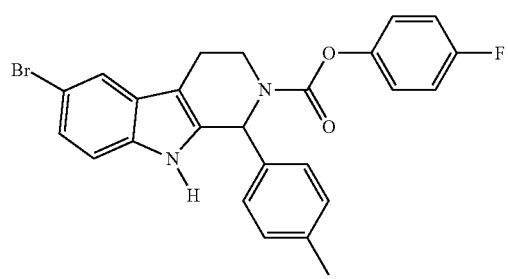
405
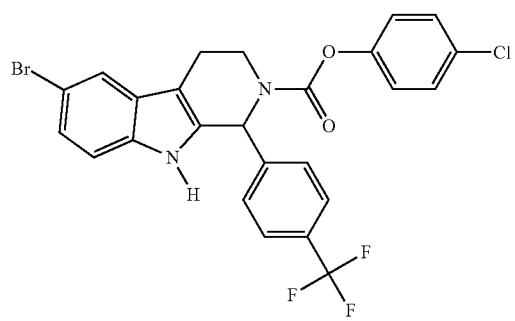
409
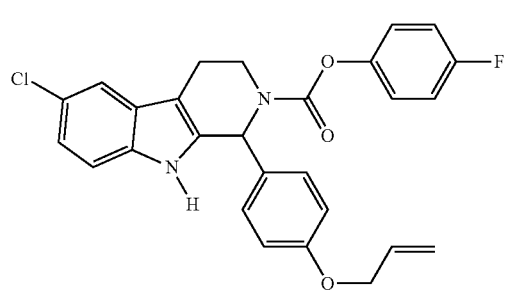
410
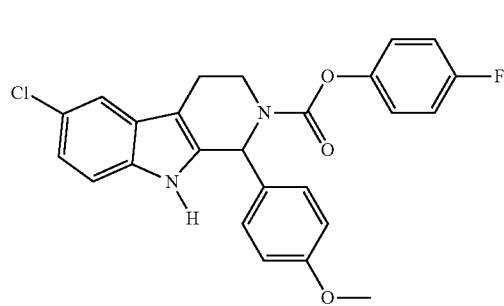

413
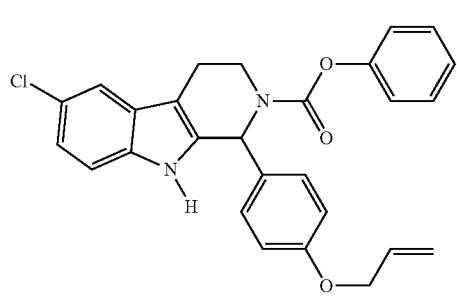
415
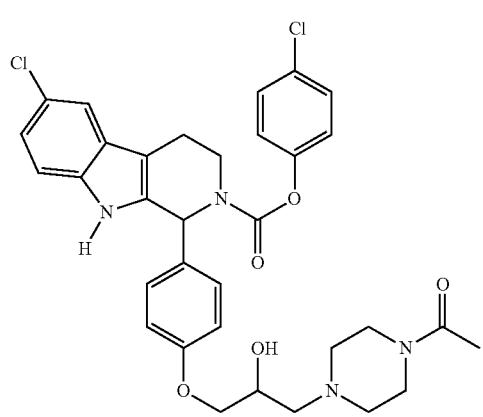
417
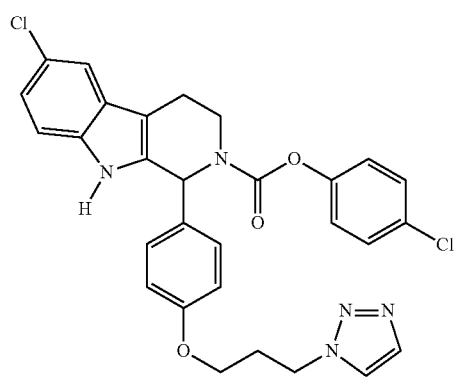
418
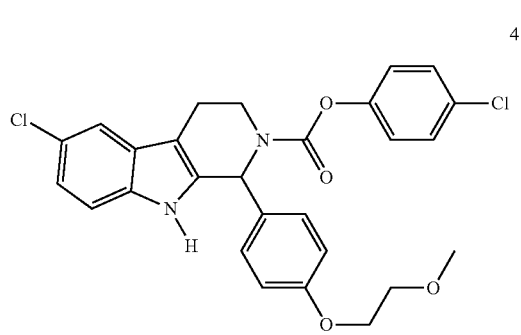
421
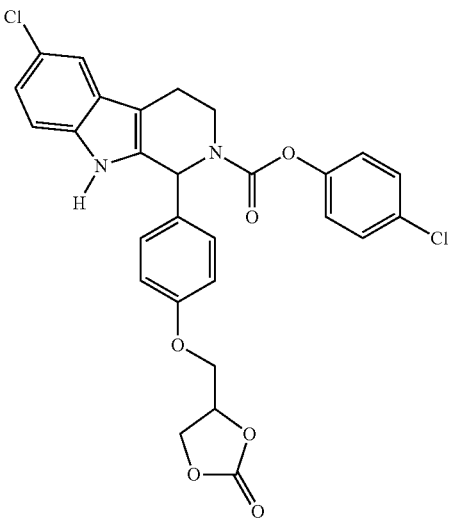
422
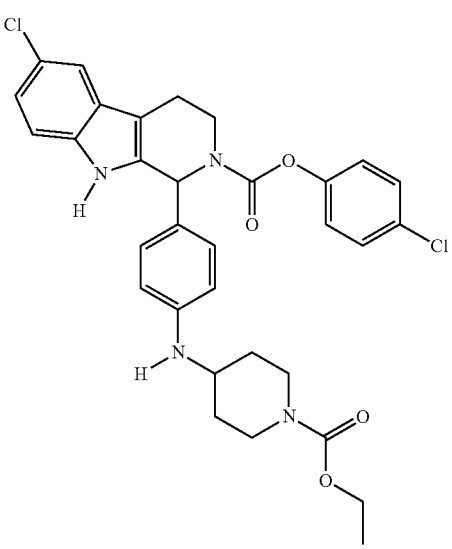
426
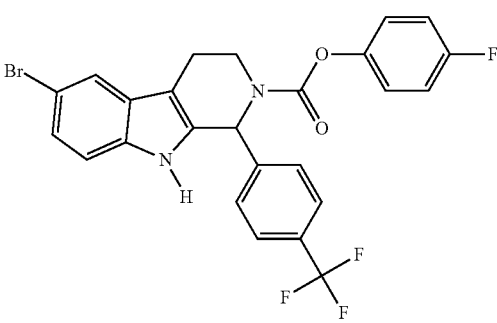

427 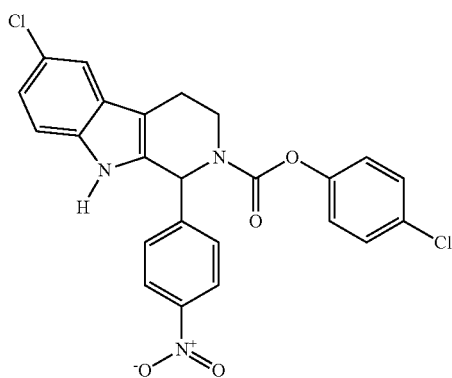
428 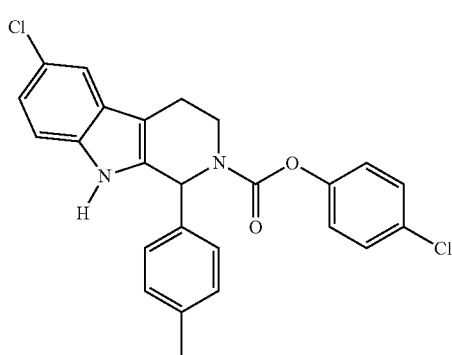
429 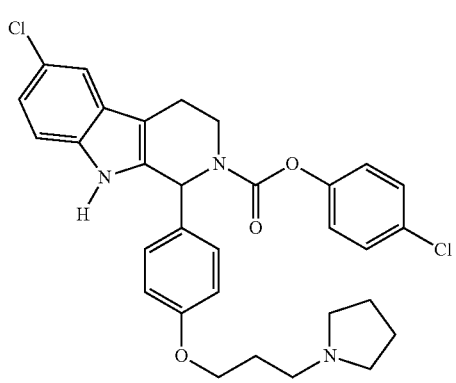
432 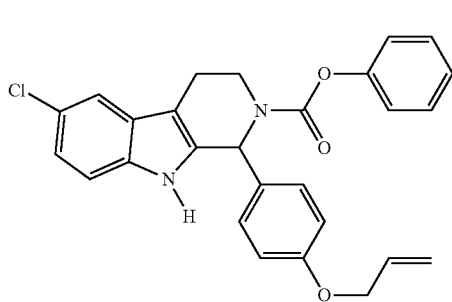
433 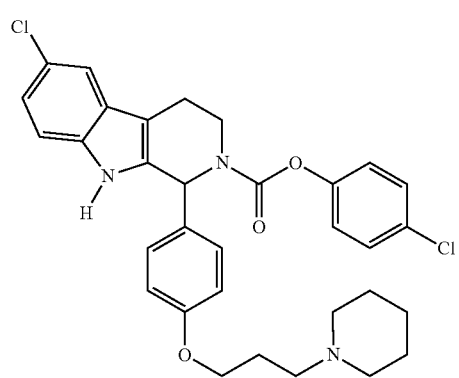
436 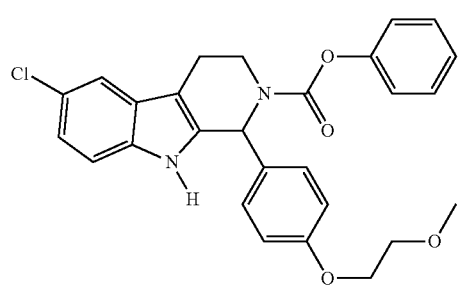
437 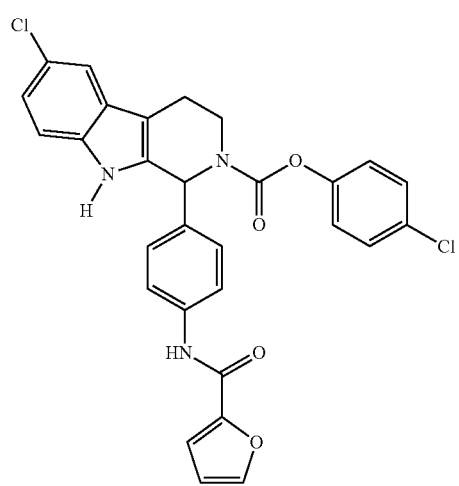
440 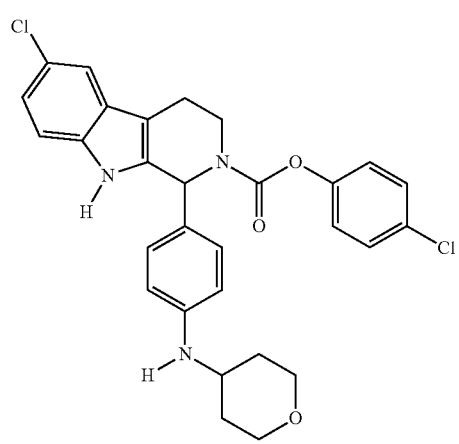

444
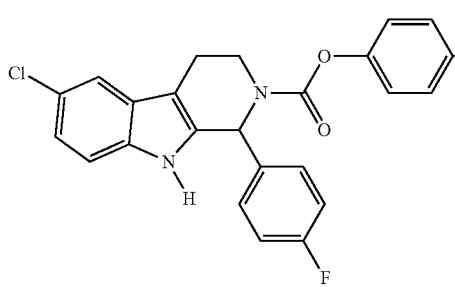
446
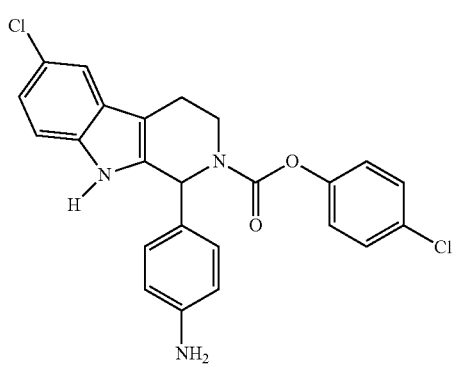
448
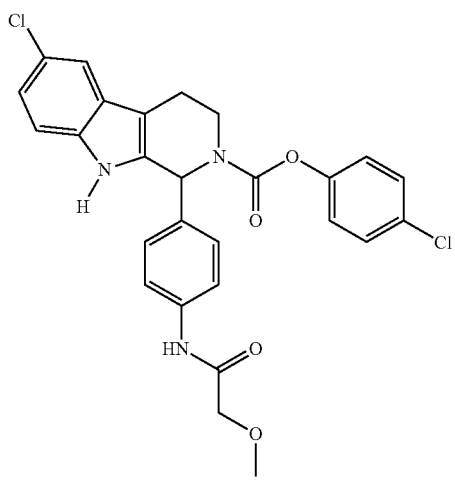
450
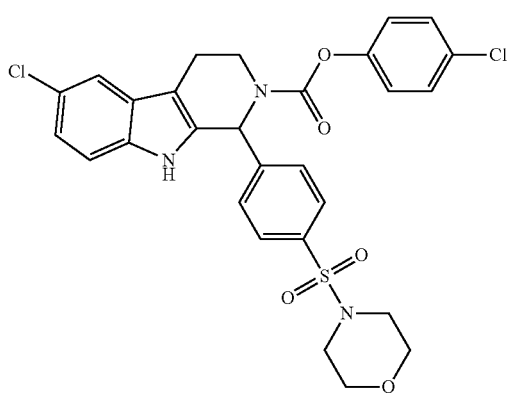
452
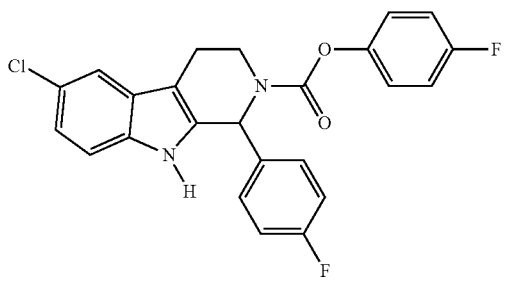
454
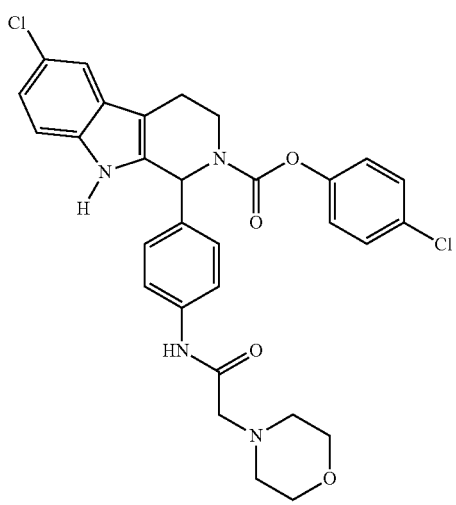
455
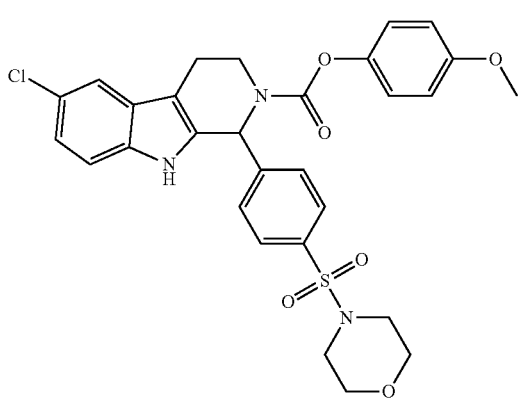
460
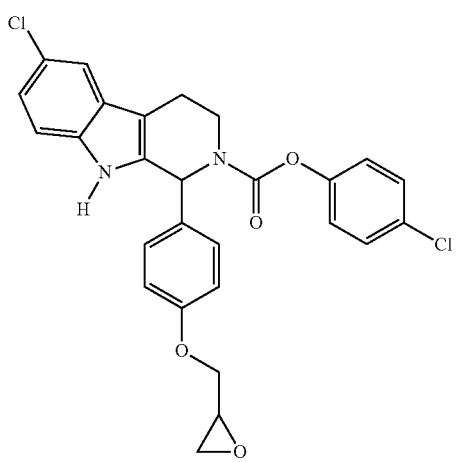

411
-continued
462
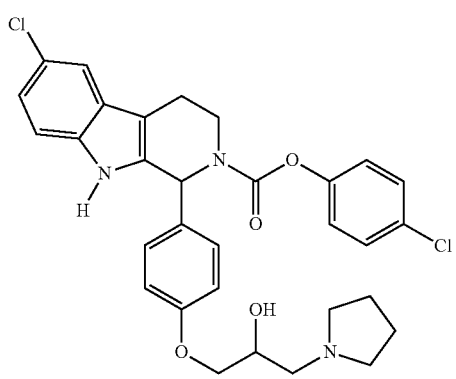
463
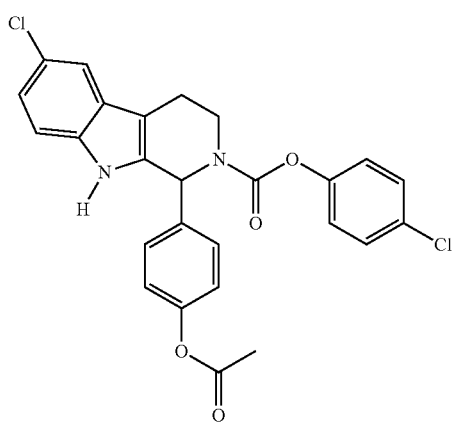
465
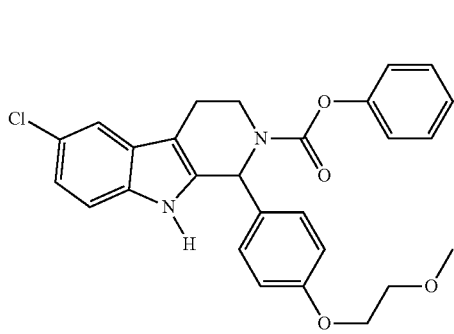
467
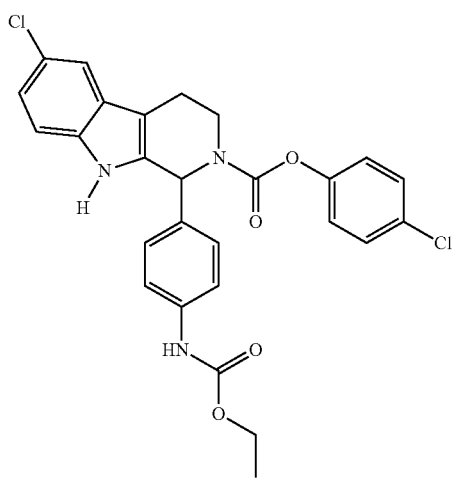
412
-continued
468
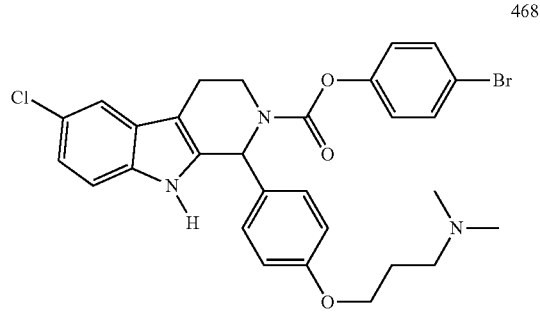
470
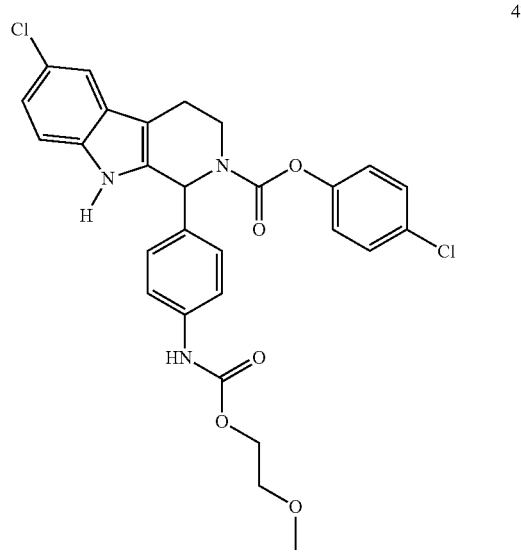
471
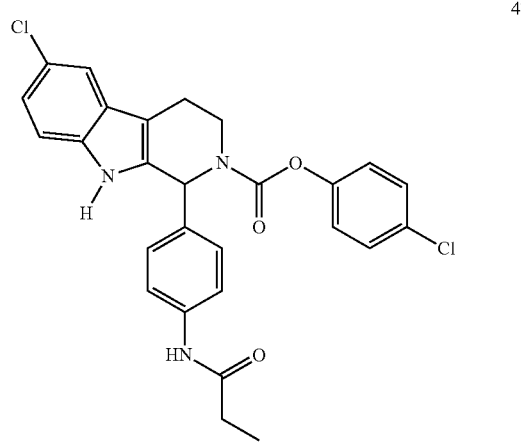
479
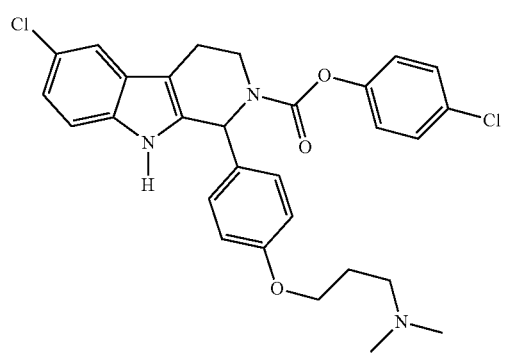

413
-continued
482
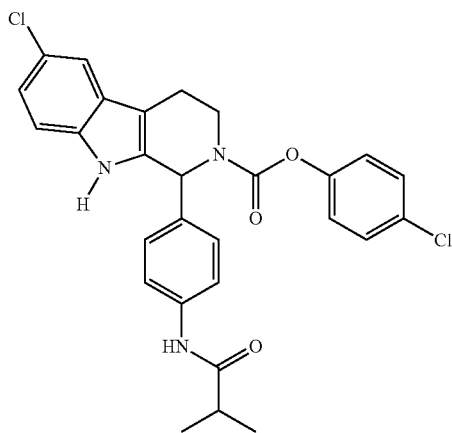
489
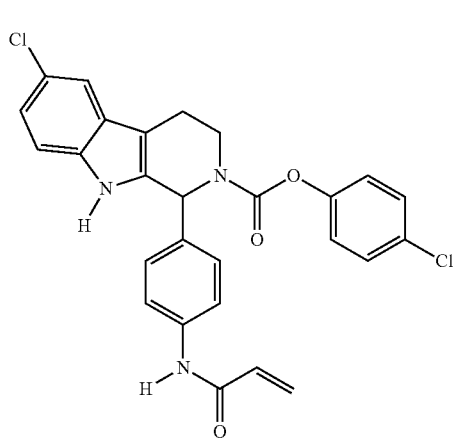
491
414
-continued
493
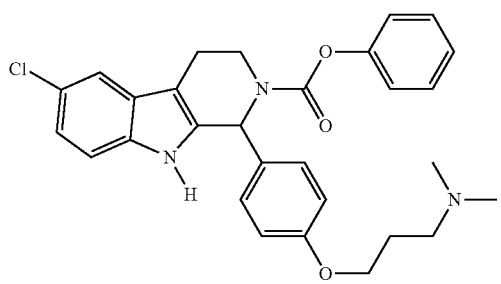
500
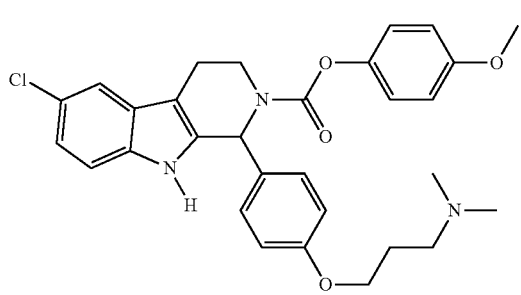
501
502
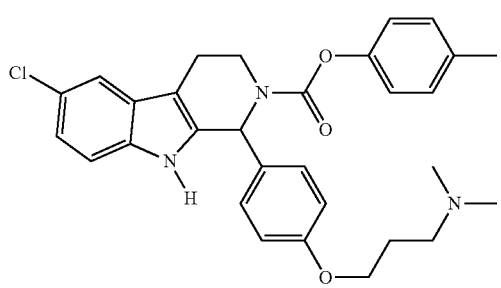

-continued
519
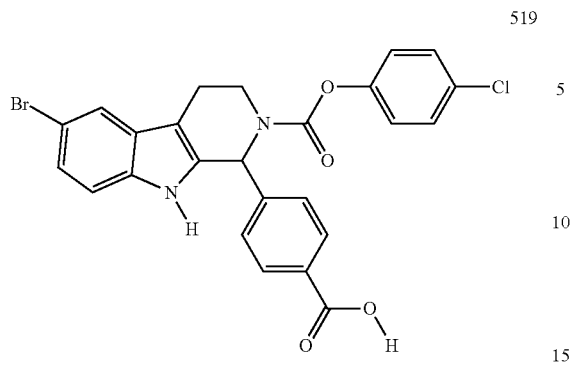
544
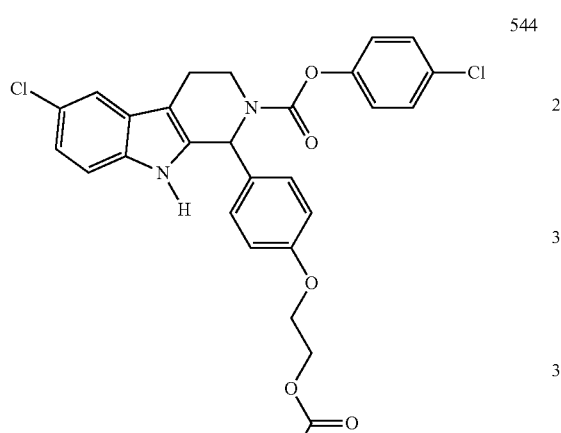
570
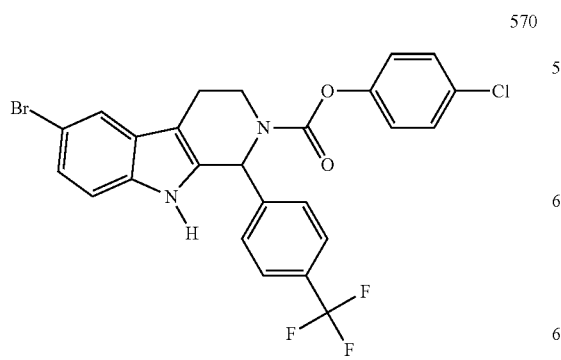
-continued
571
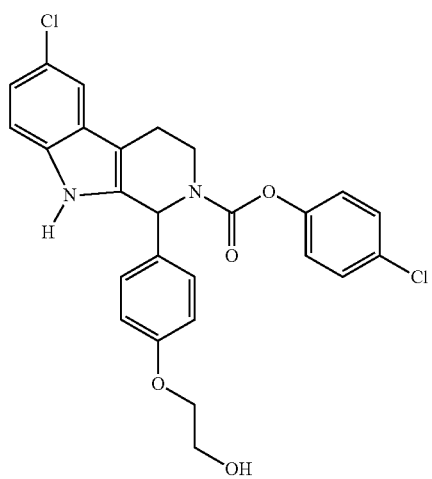
572
575
576
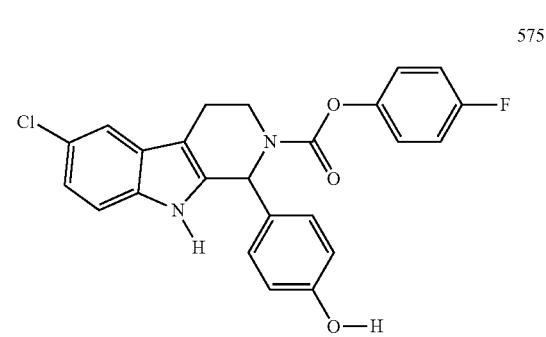
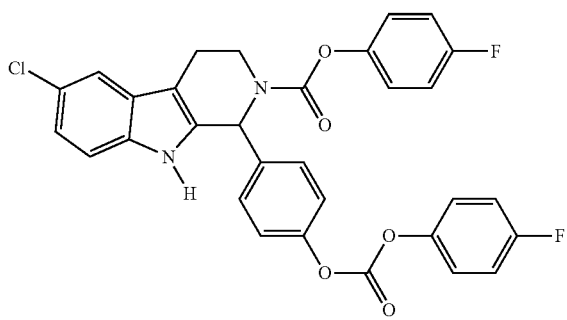

-continued
577
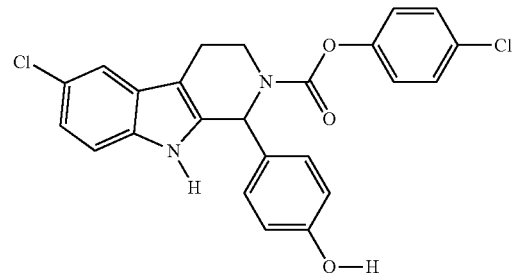
578
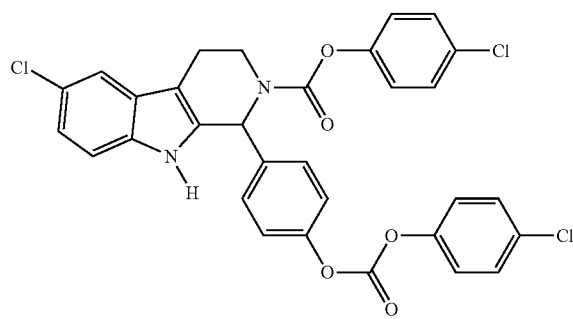
579
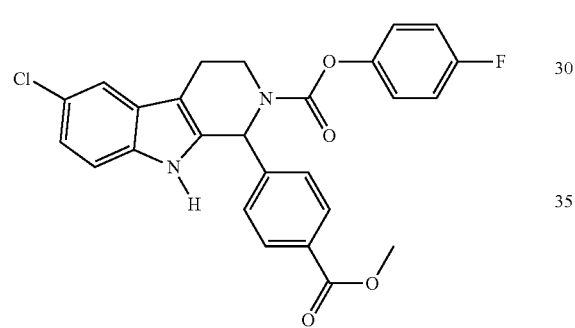
580
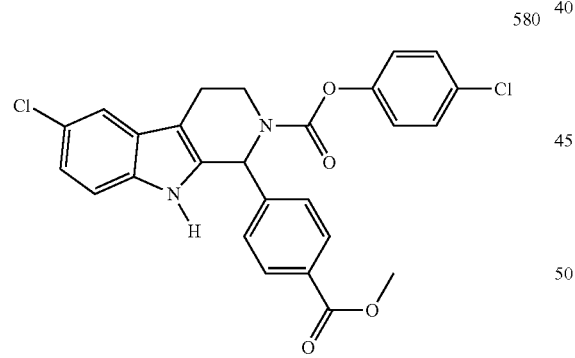
581
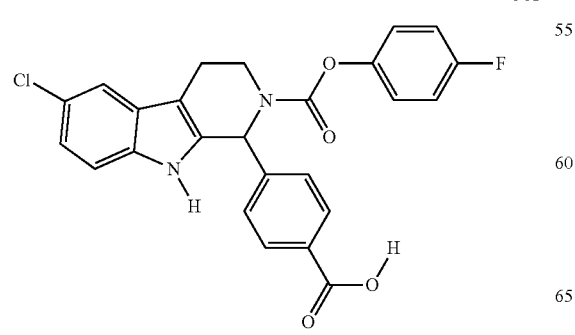
-continued
587
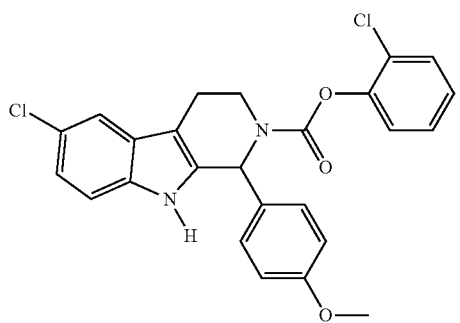
588
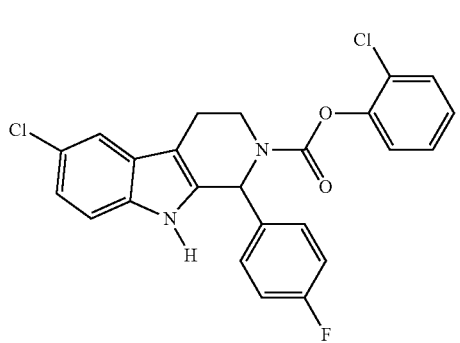
589
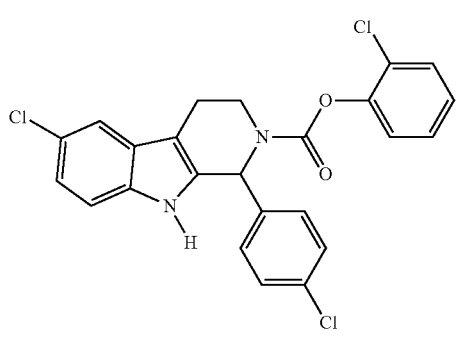
590
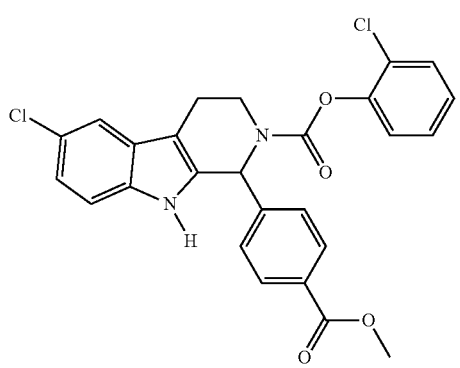

591
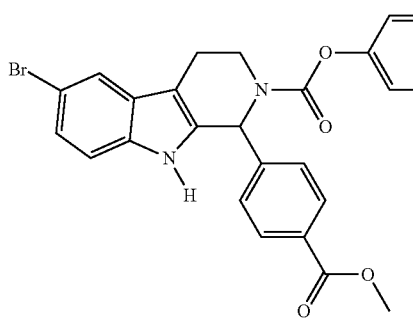
592
614
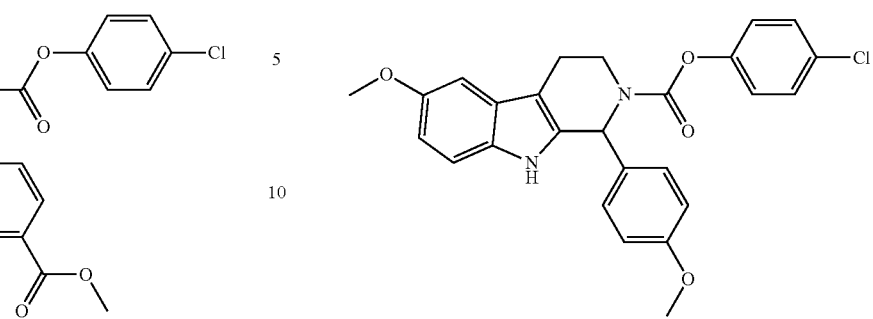
616
617
593
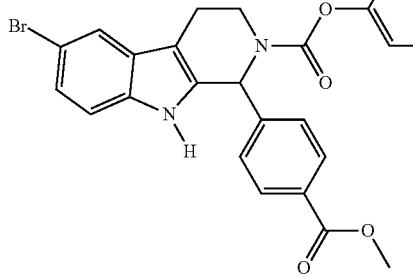
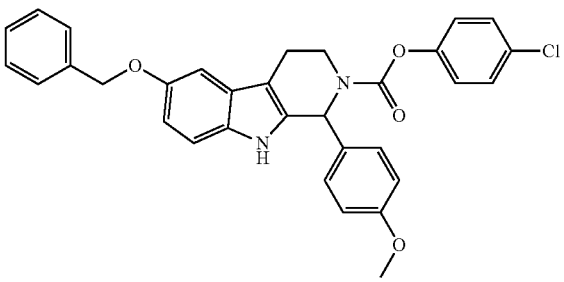
626
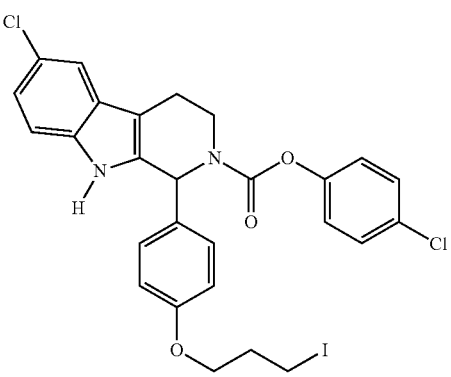
627
594
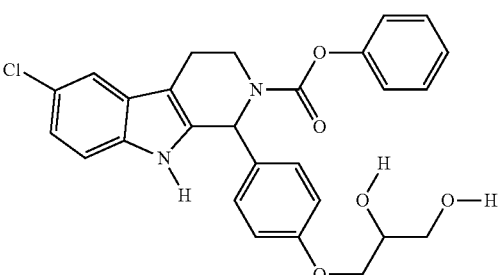
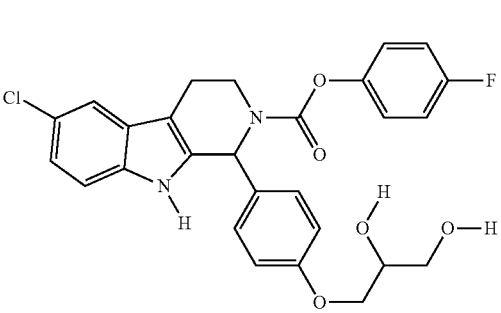

628
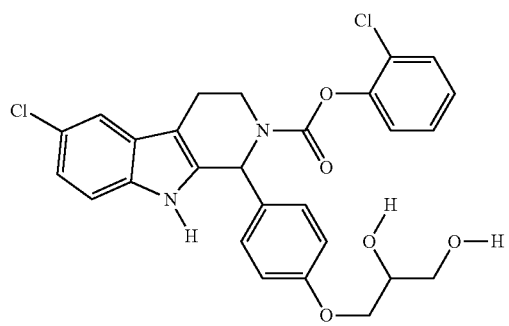
629
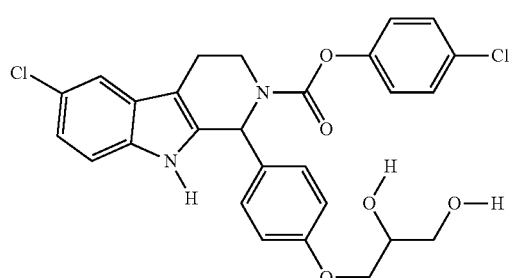
630
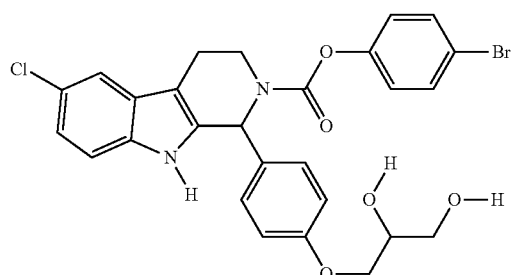
631
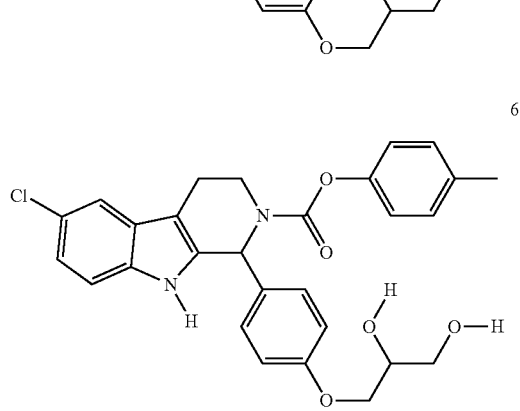
632
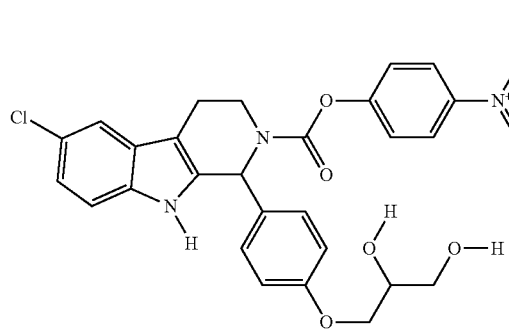
635
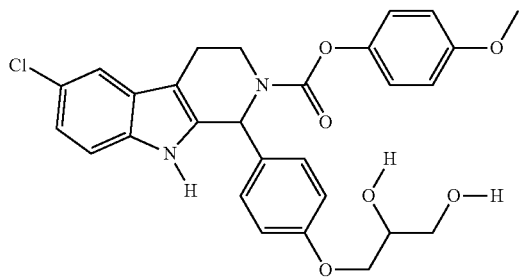
637
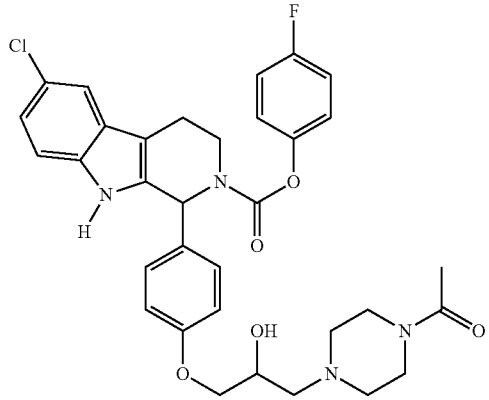
638
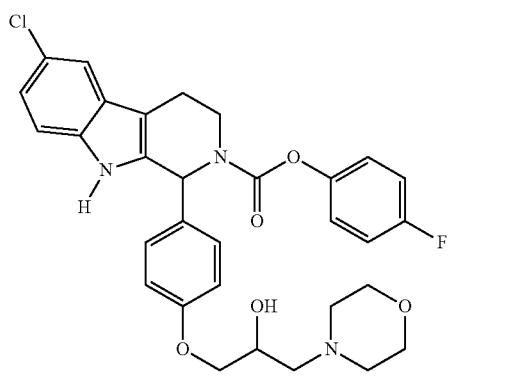
660
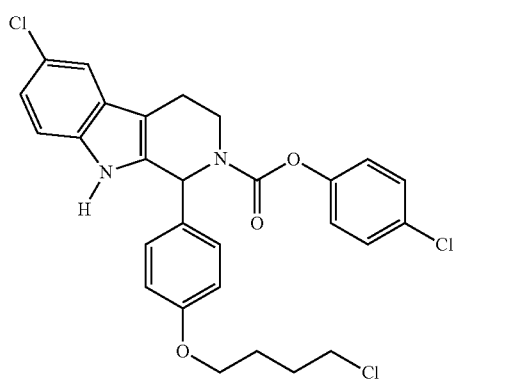

| 670 | 675 |
|---|---|
| 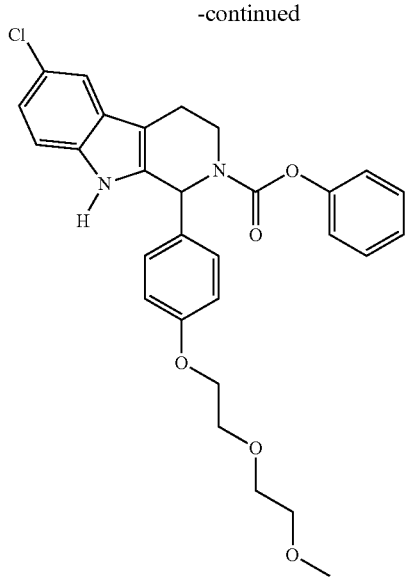 | 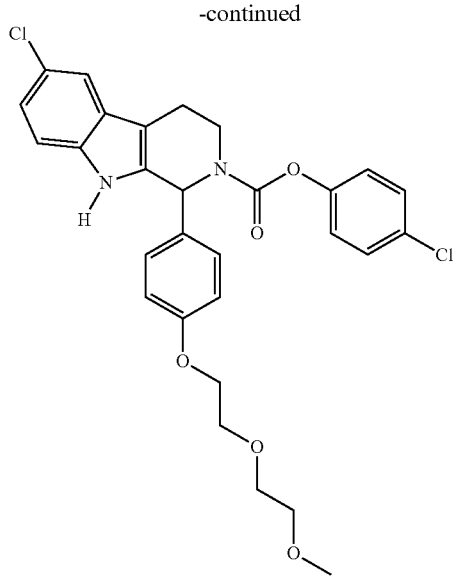 |
| 673 | 677 |
|---|---|
| 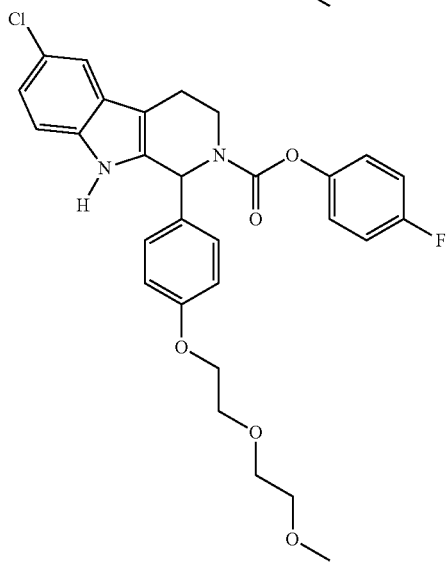 | 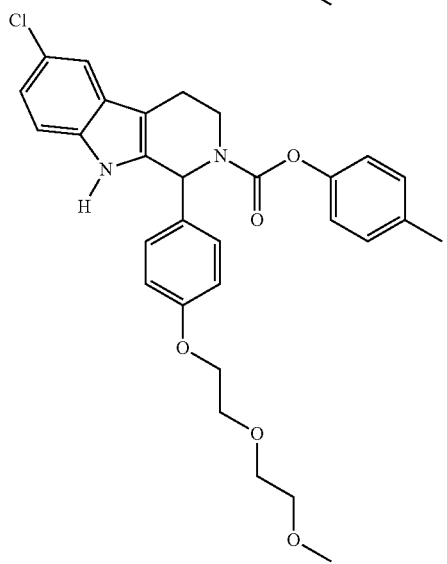 |
| 674 | 678 |
|---|---|
| 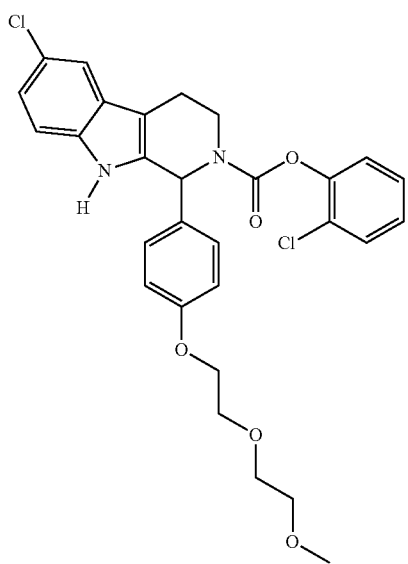 | 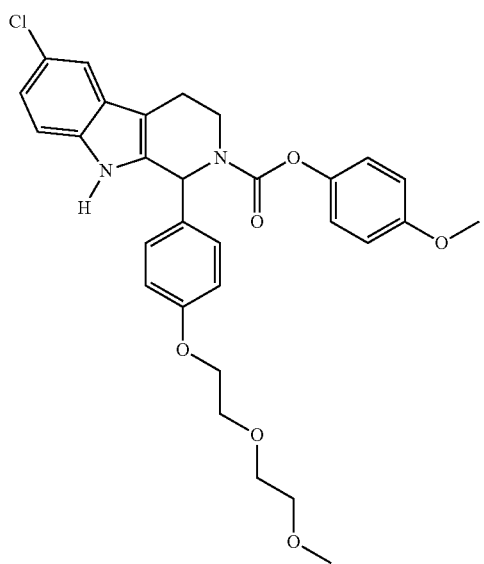 |

680
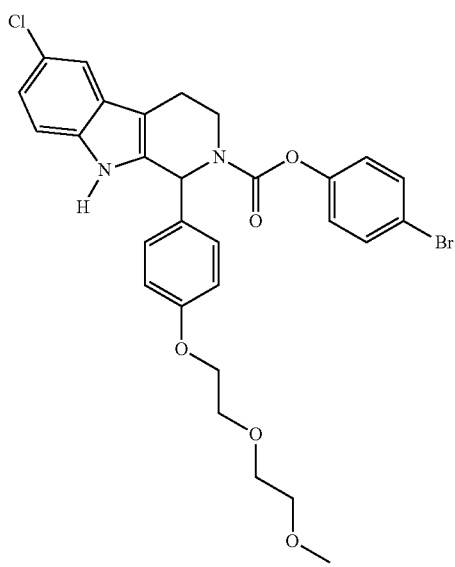
681
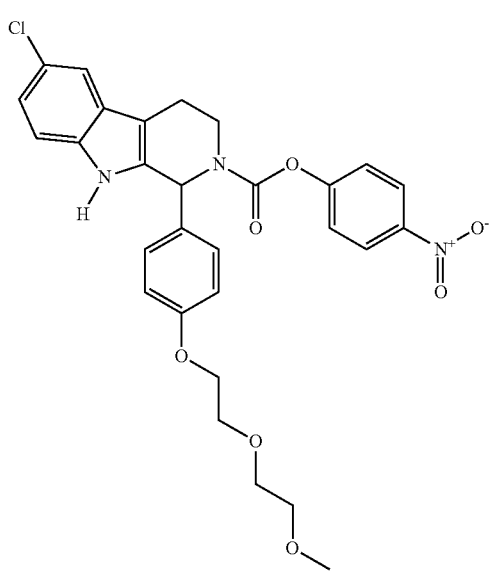
698
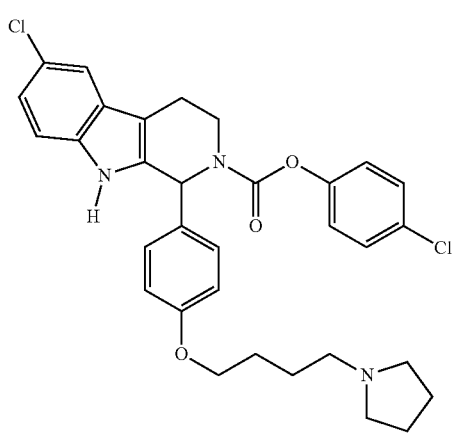
699
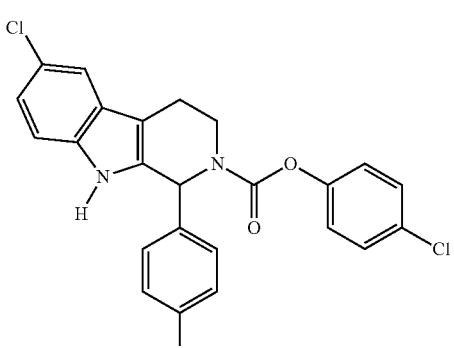
700
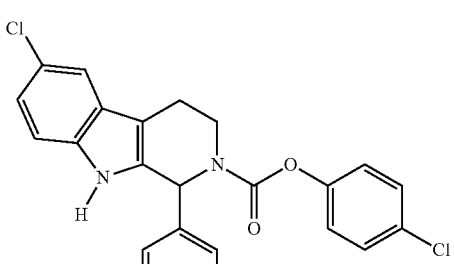
701
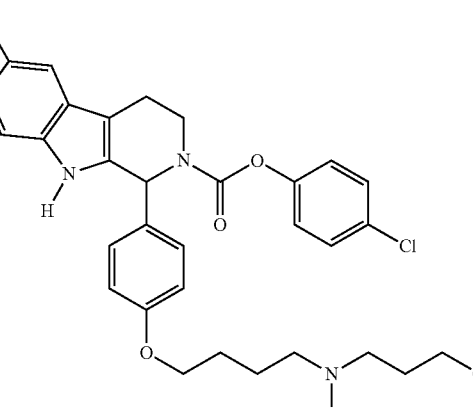
702
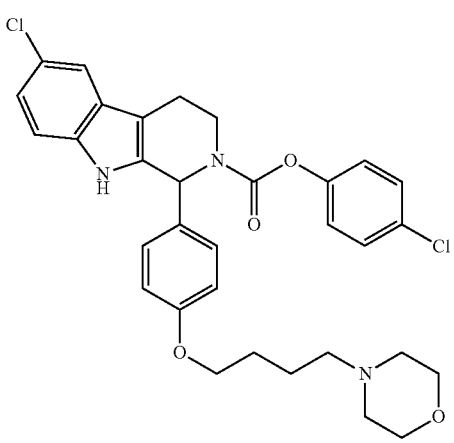

427
-continued
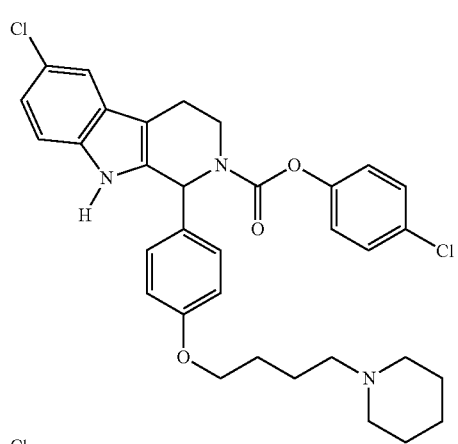
703
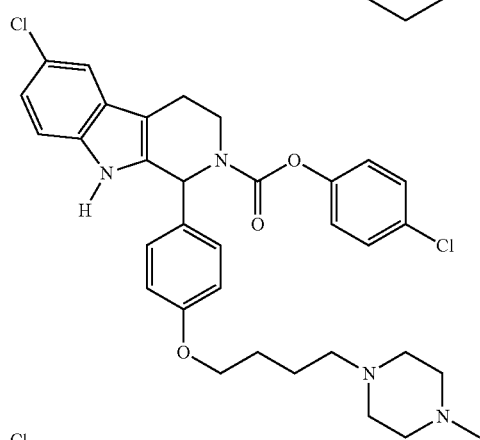
704
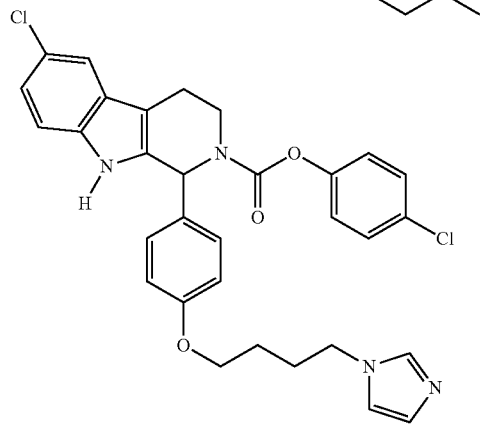
705
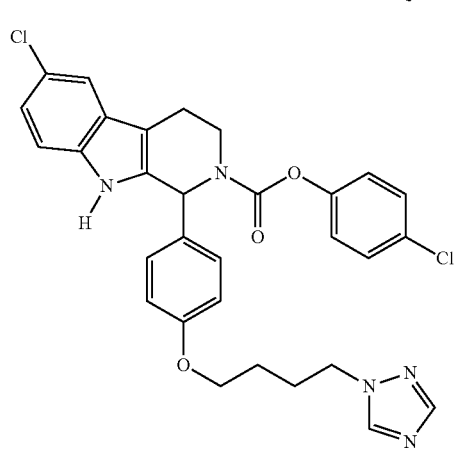
706
428
-continued
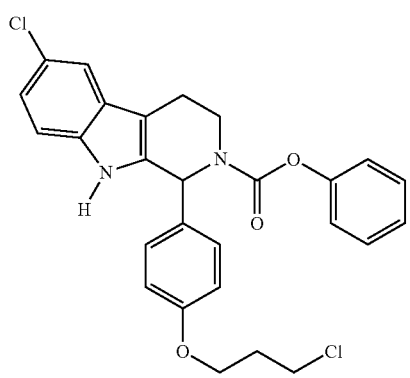
710
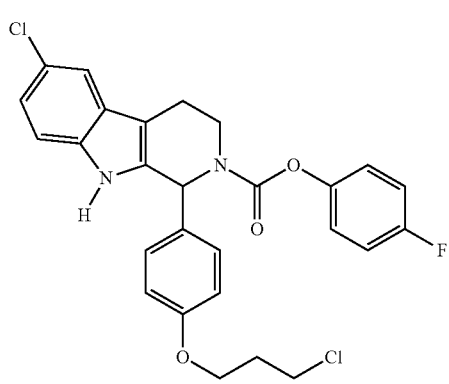
712
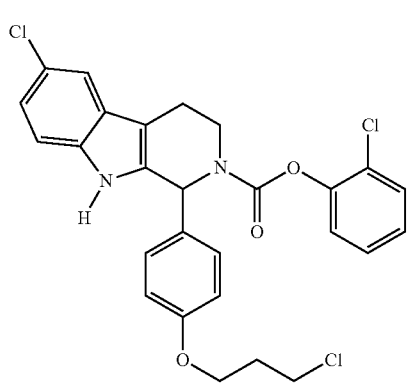
713
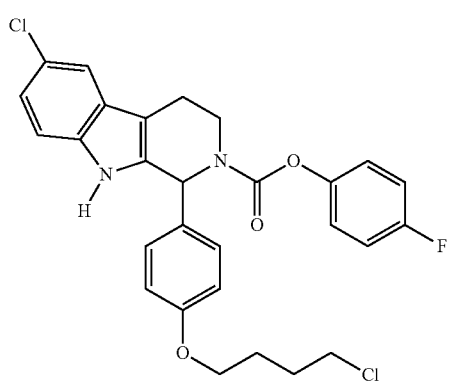
719

429
723
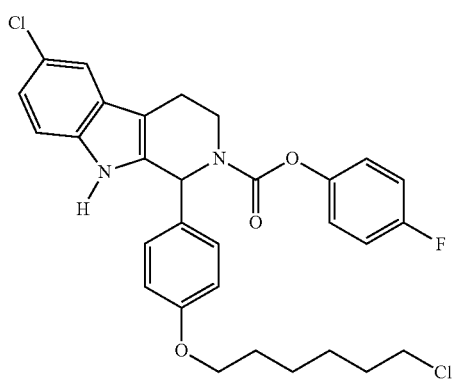
735
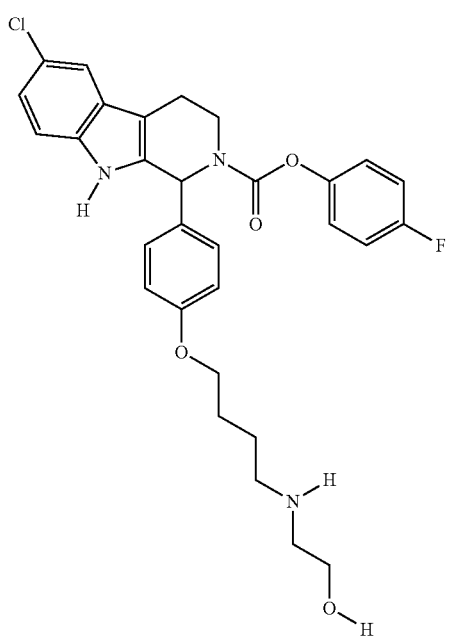
736
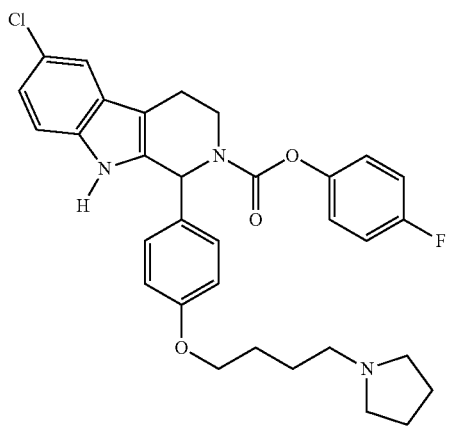
430
737
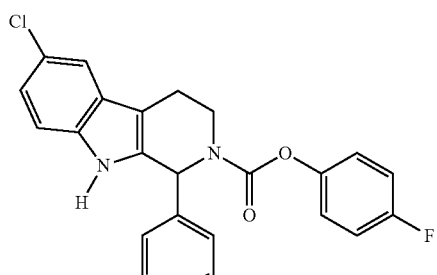
738
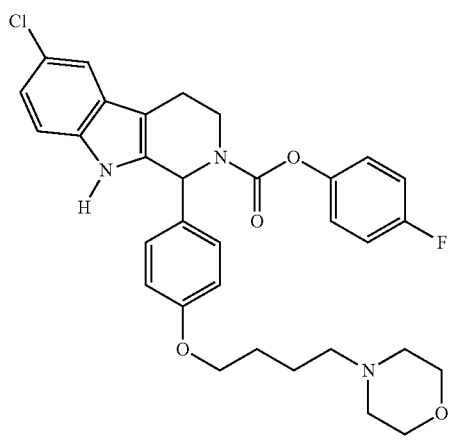
739
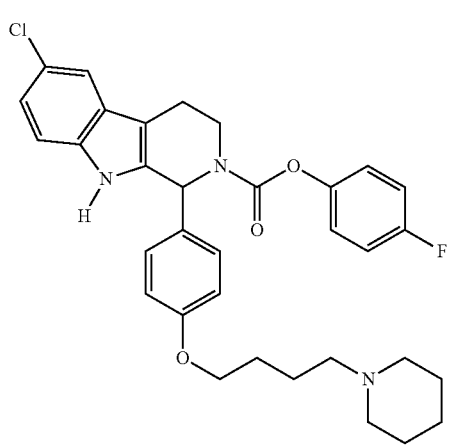

431
-continued
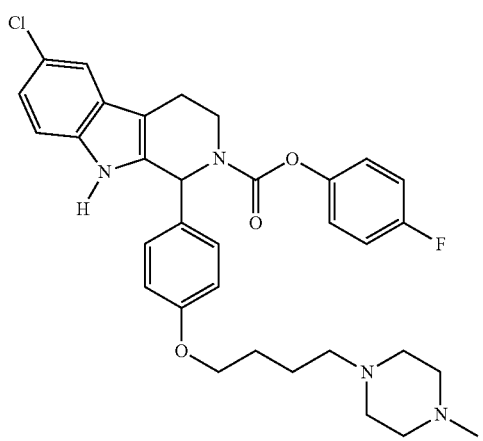
740
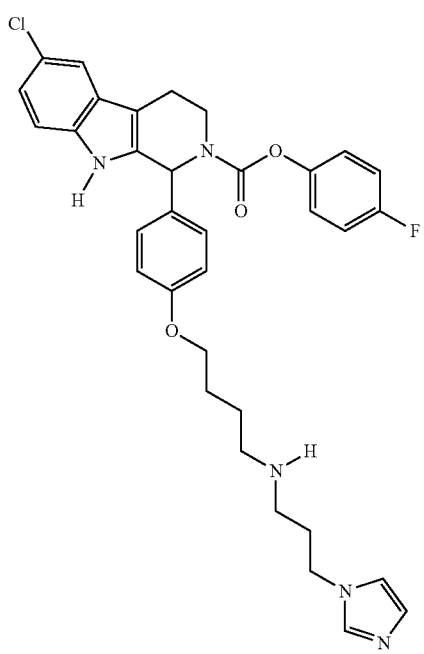
741
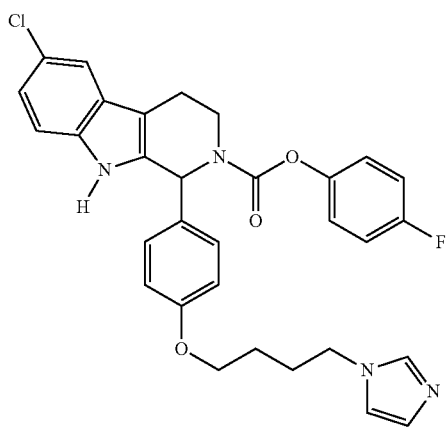
742
432
-continued
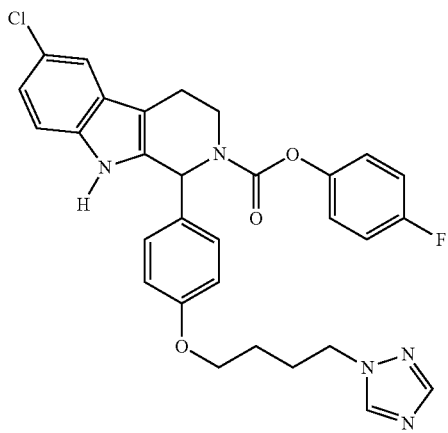
743
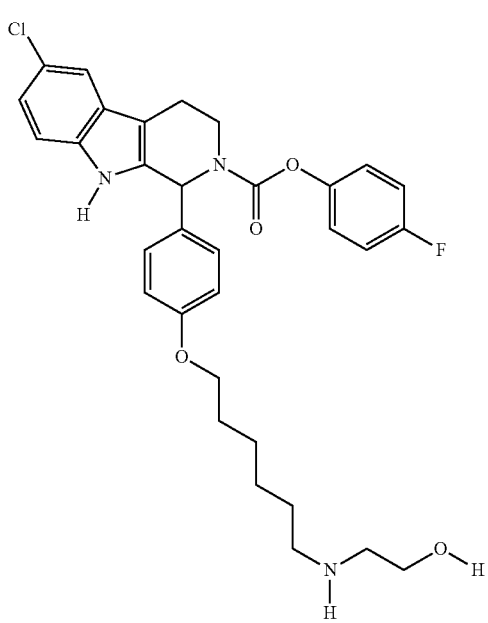
772
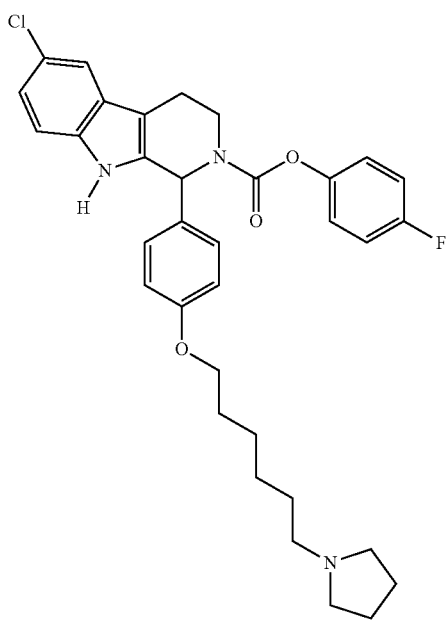
773

433
-continued
434
-continued
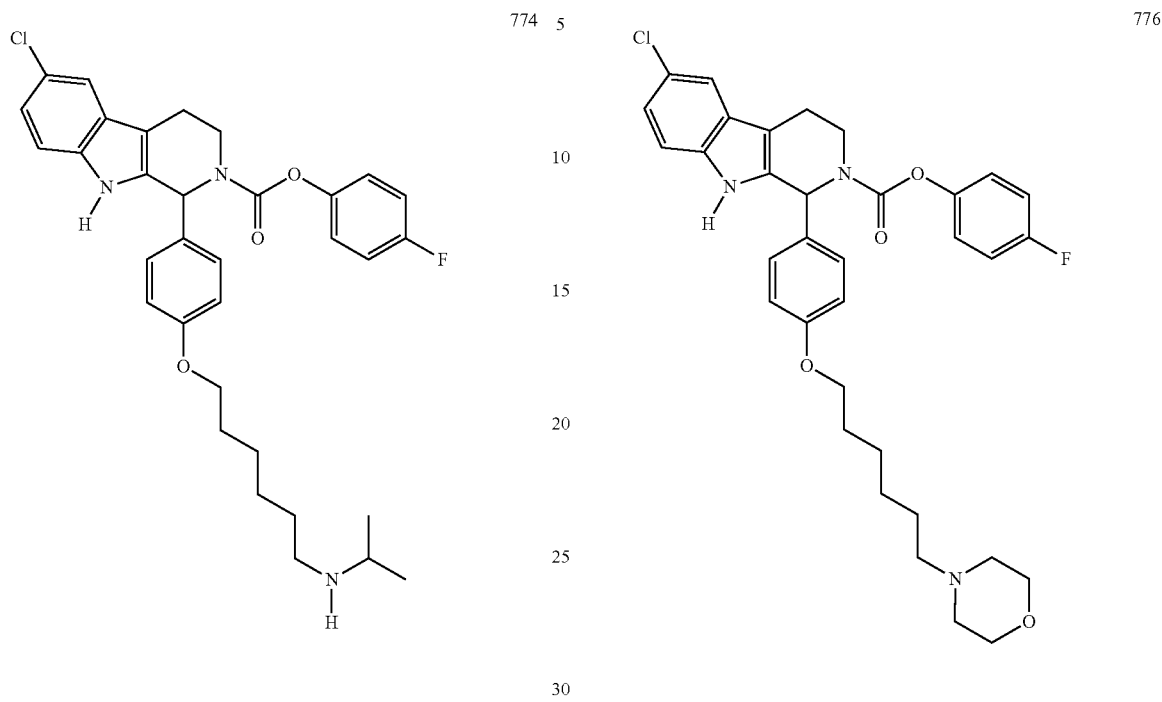
774
776
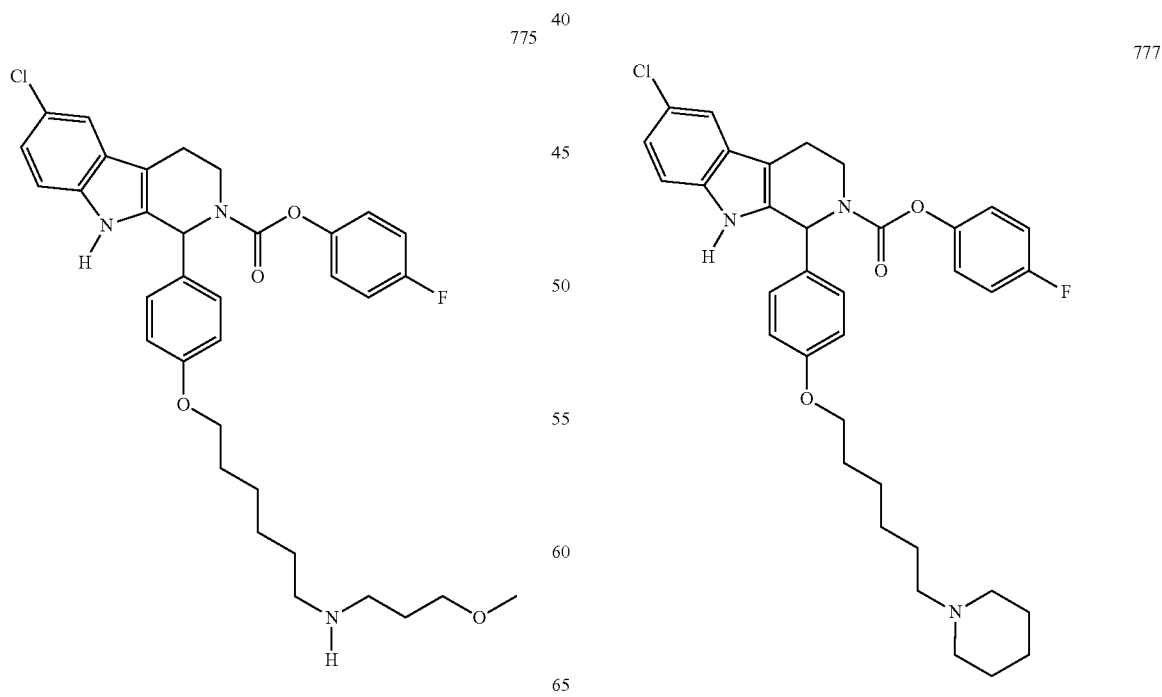
775
777

435
-continued
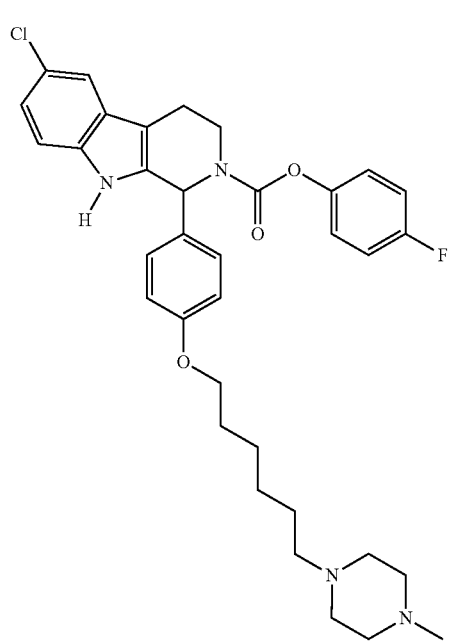
778
436
-continued
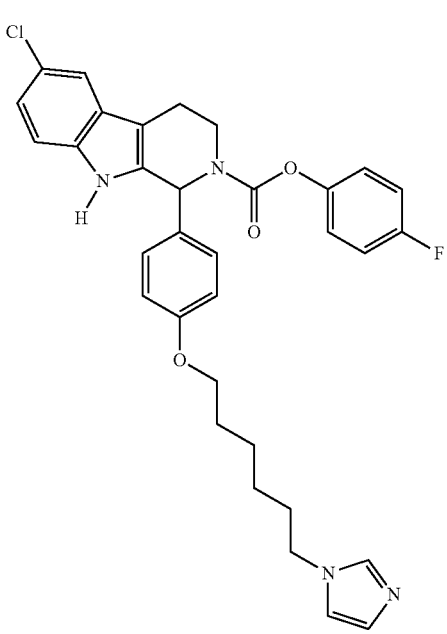
780
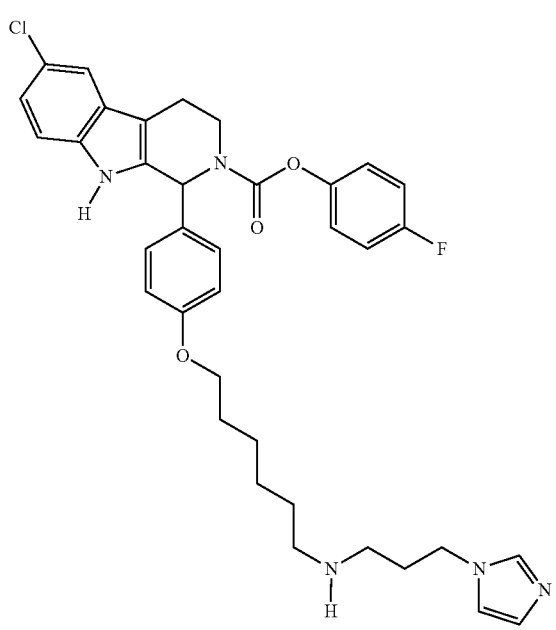
779
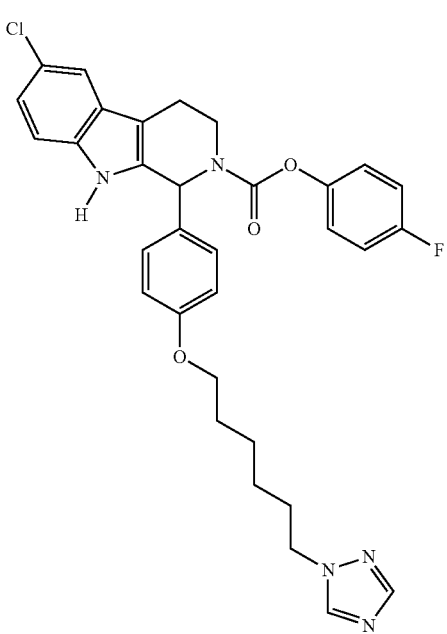
781

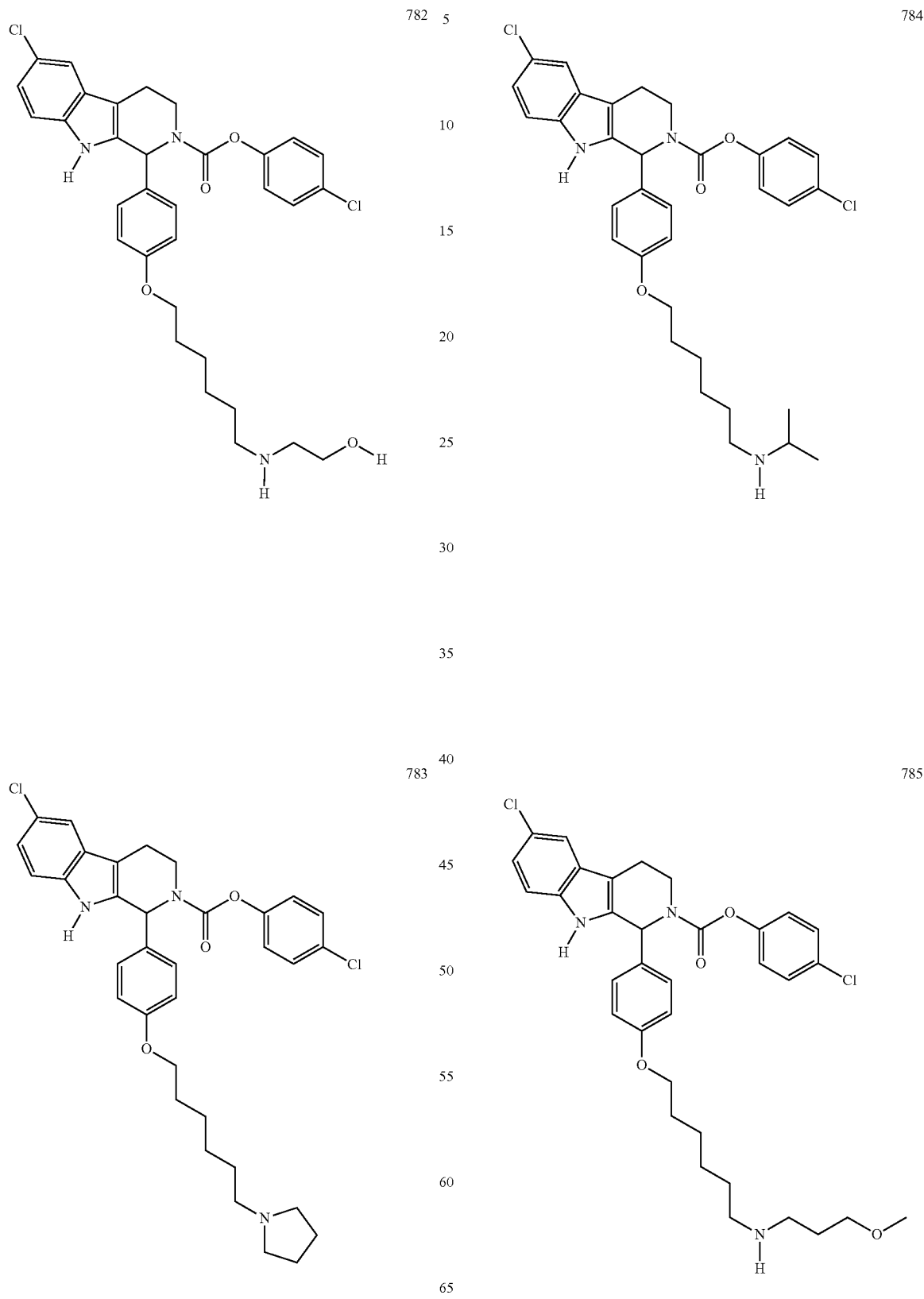

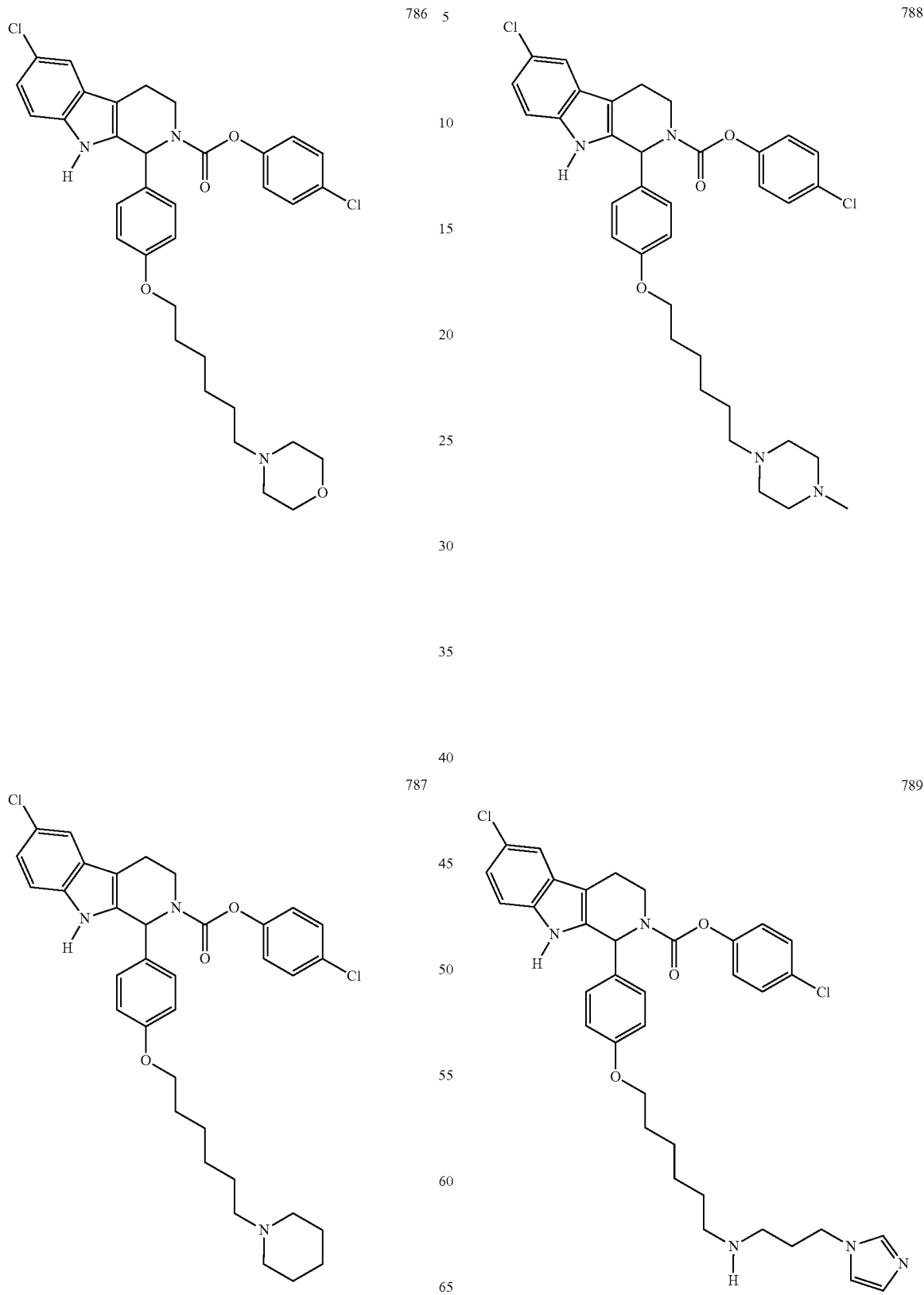

790
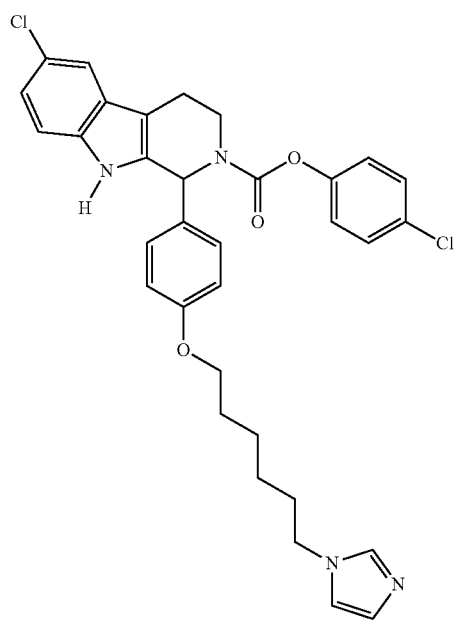
791
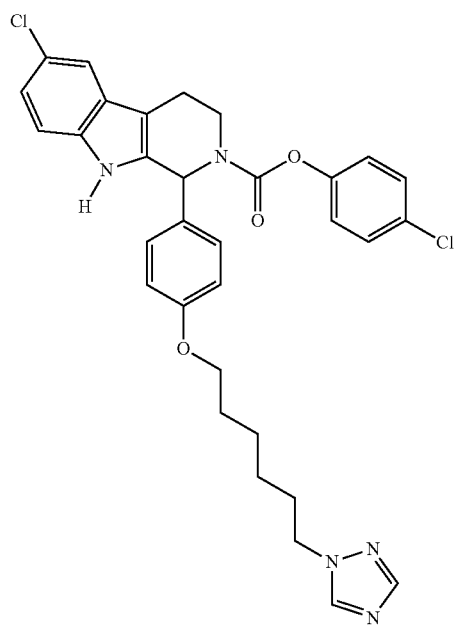
833
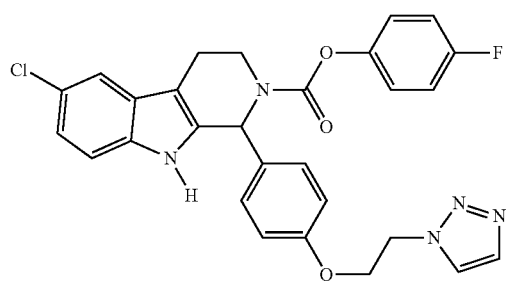
834
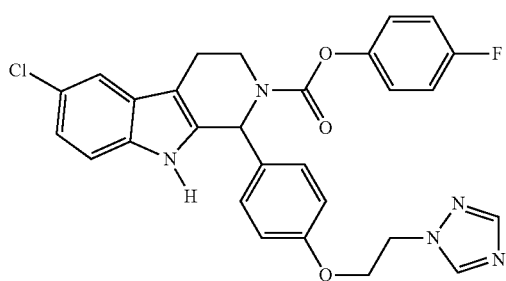
835
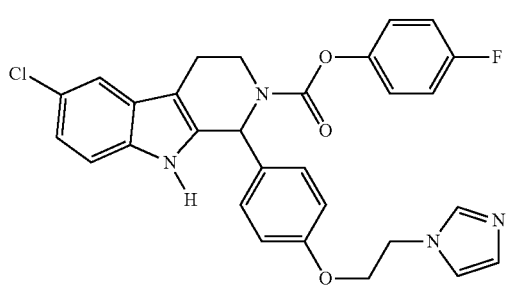
836
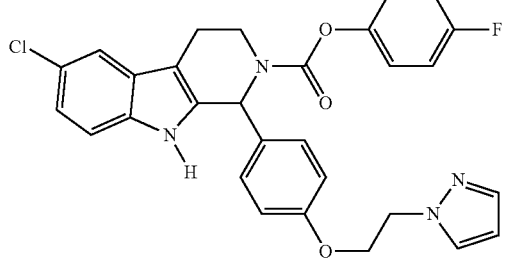
837
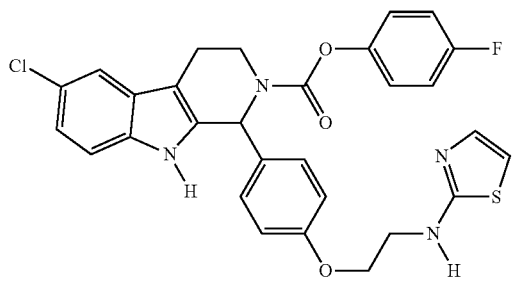
838
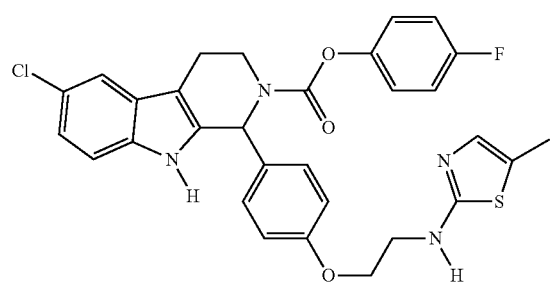

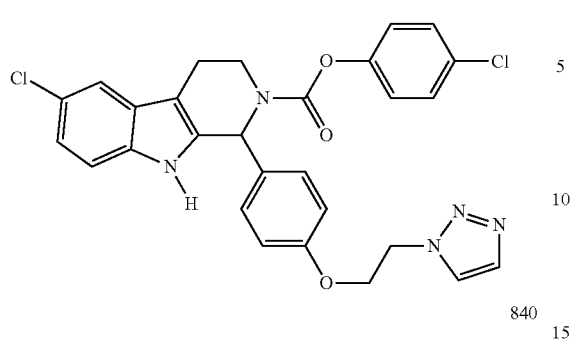
839
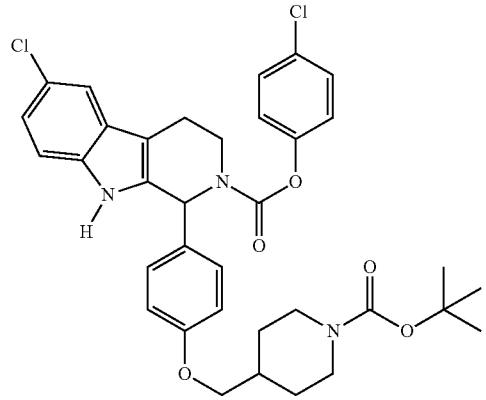
845
840
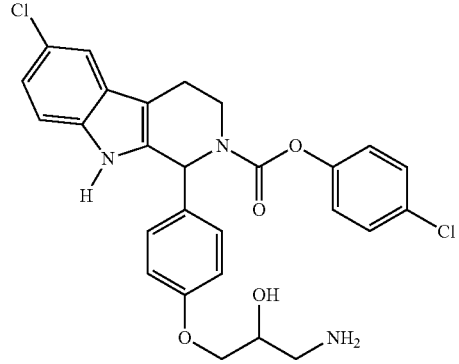
846
841
847
842
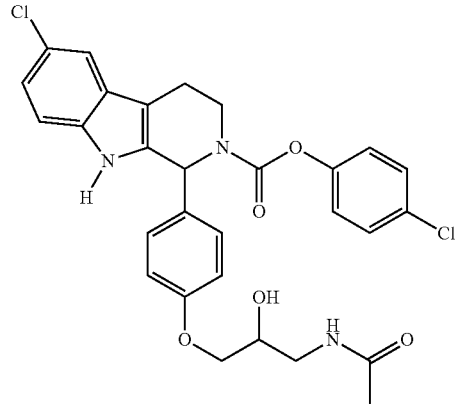
848
843
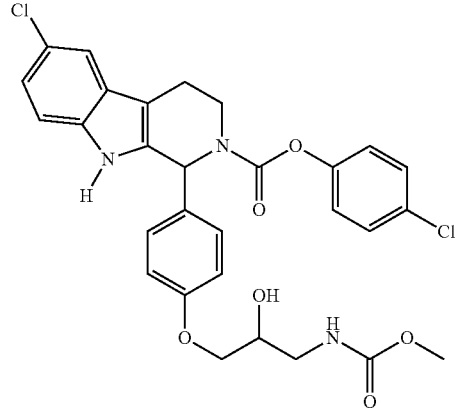

445
-continued
849
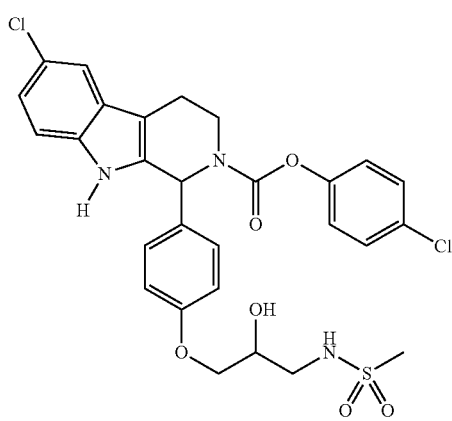
850
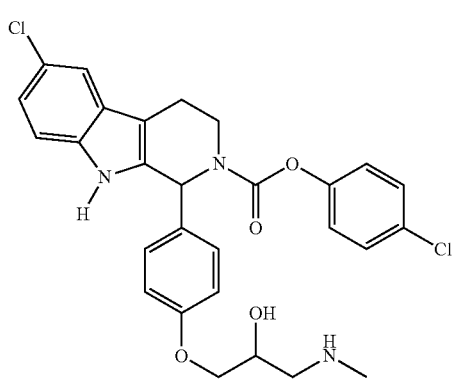
867
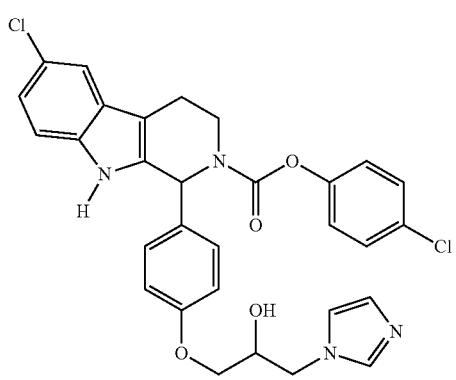
882
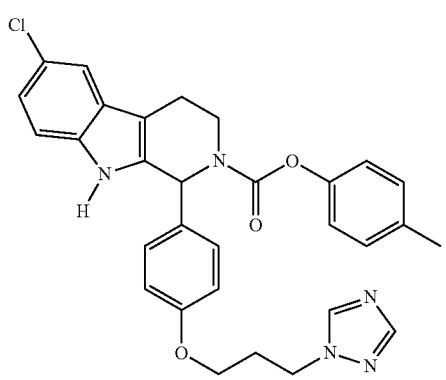
446
-continued
888
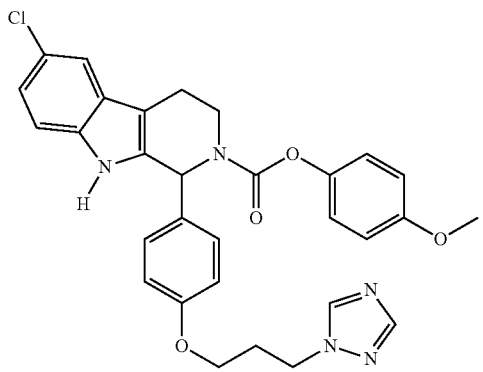
889
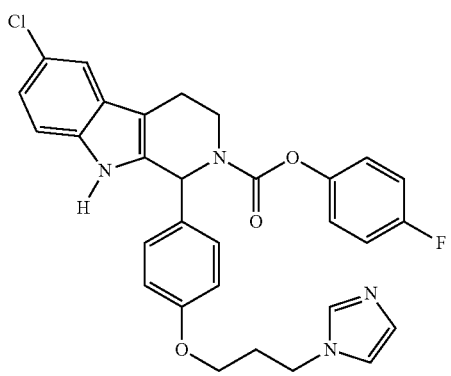
891
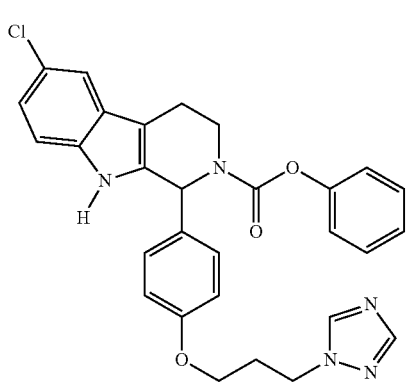
892
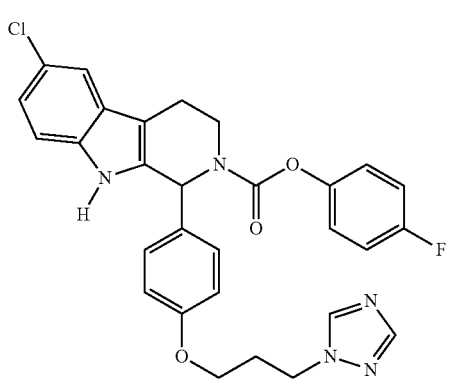

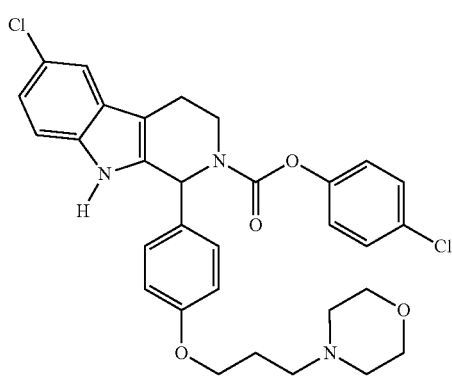
894
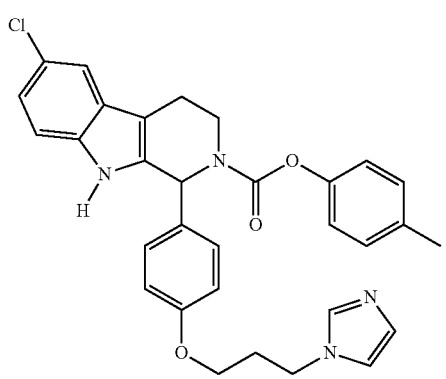
900
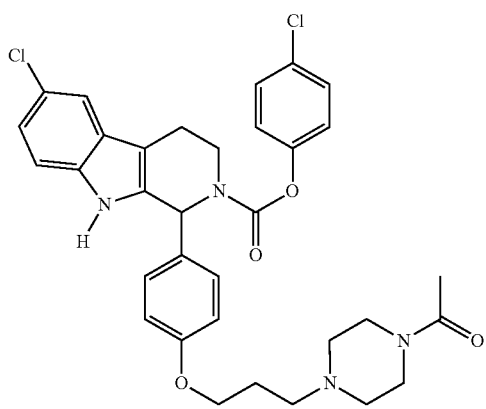
903
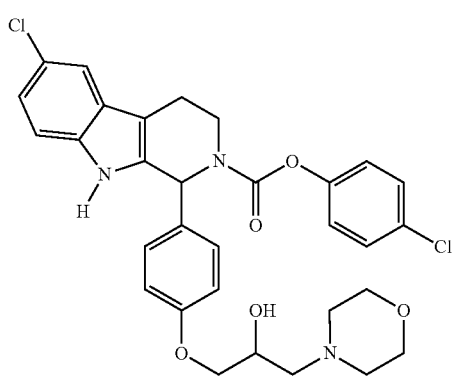
904
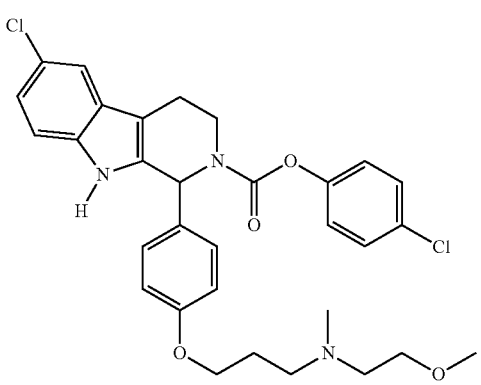
908
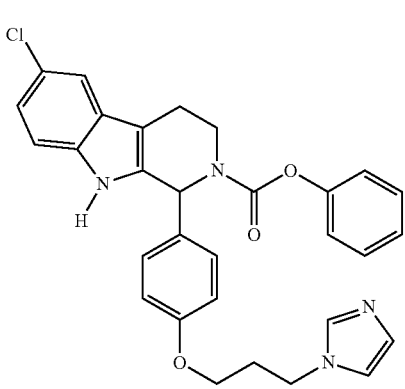
911
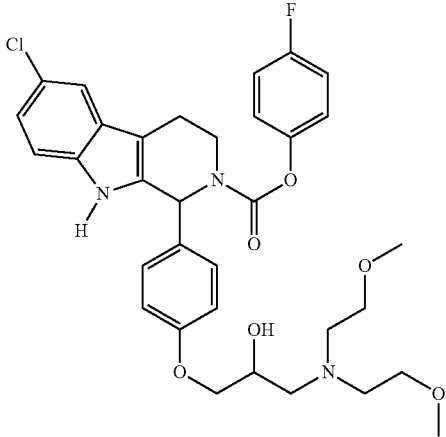
913
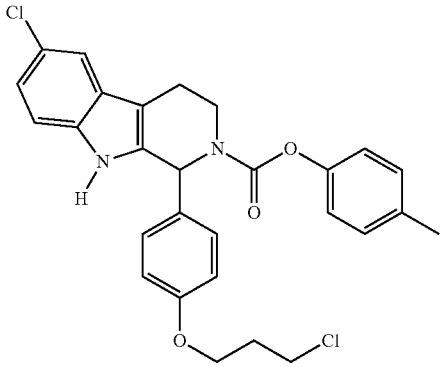
915

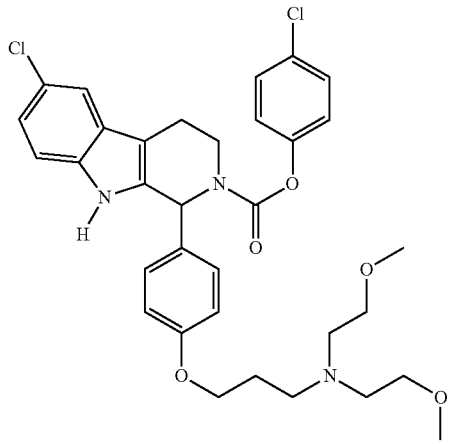
916
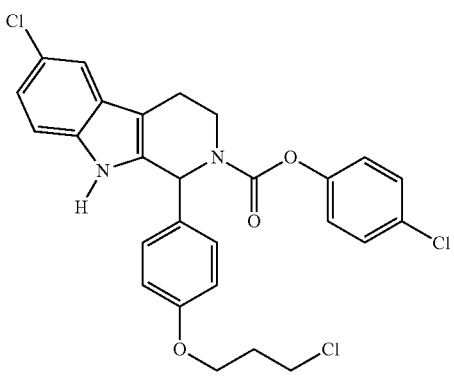
921
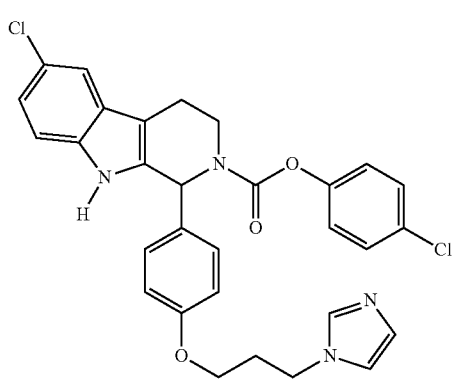
917
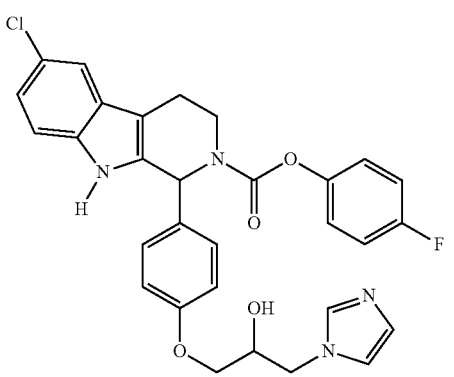
922
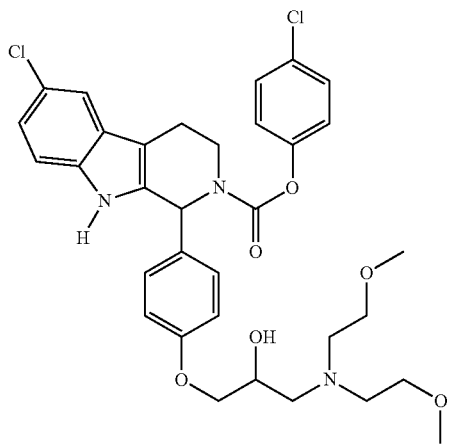
918
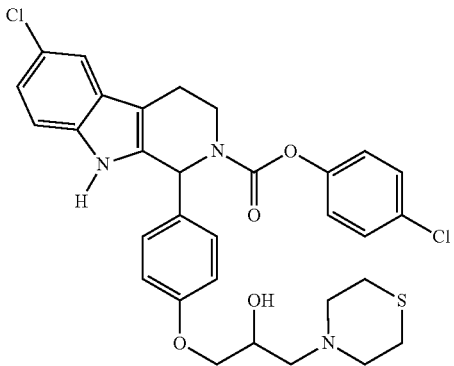
923
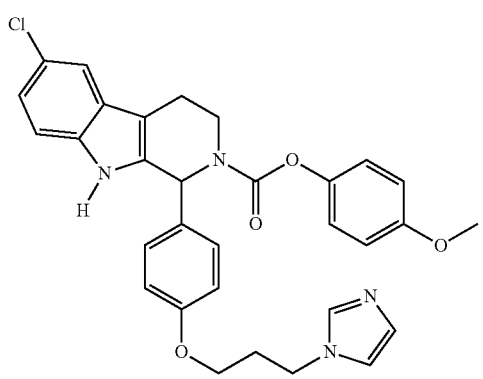
920
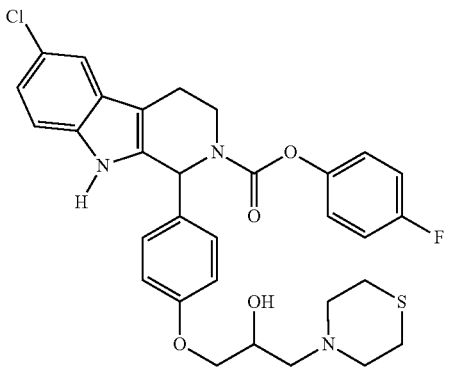
925

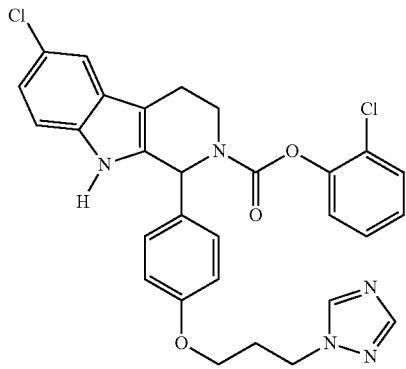
926
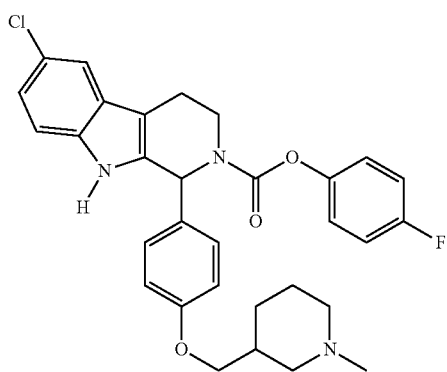
932
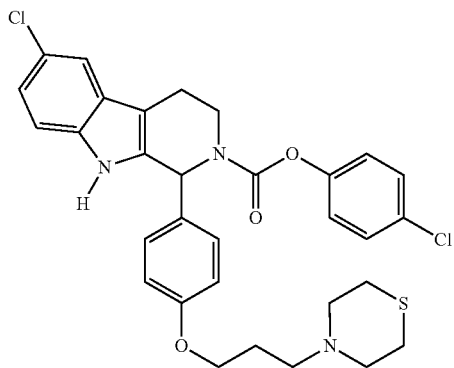
933
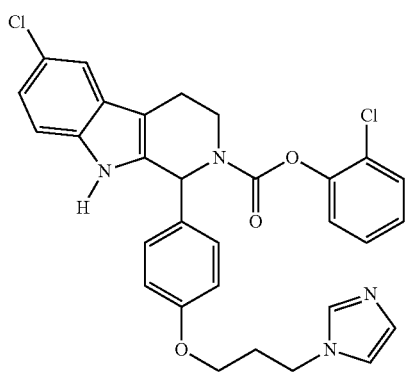
934
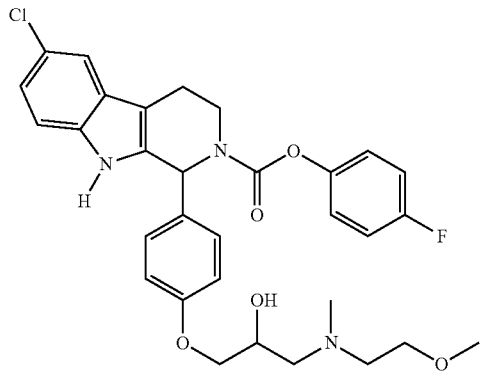
936
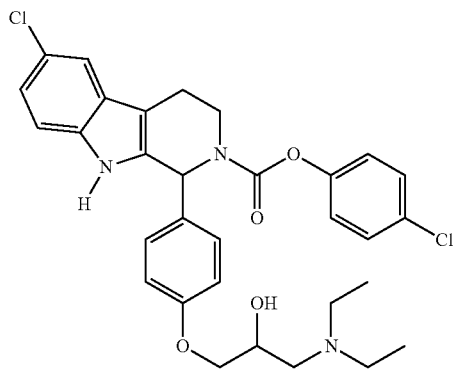
938
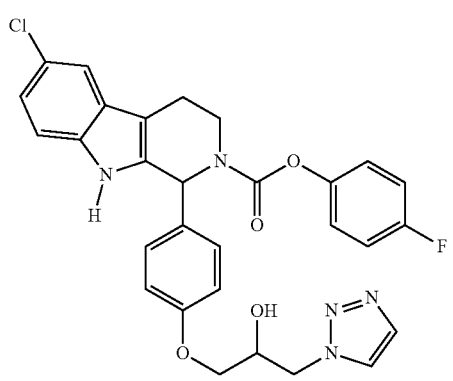
941
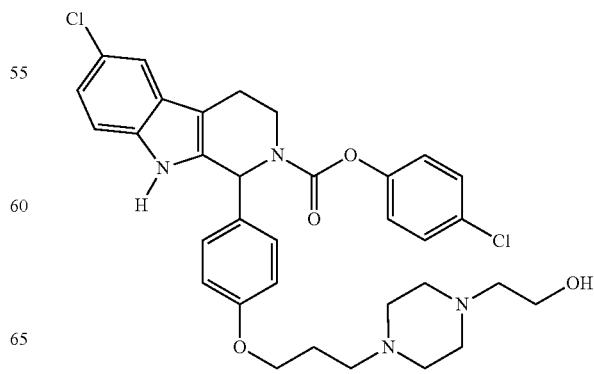
942

453
-continued
944
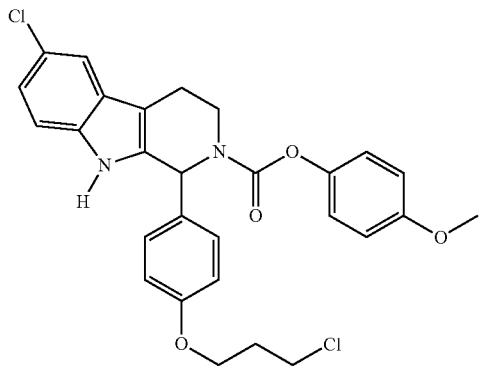
946
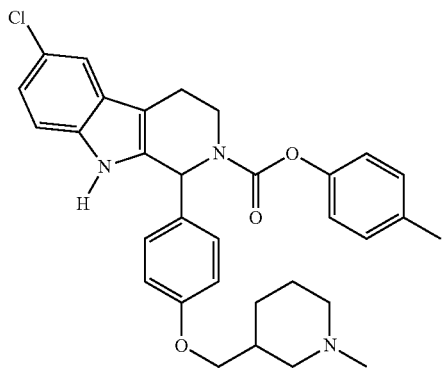
951
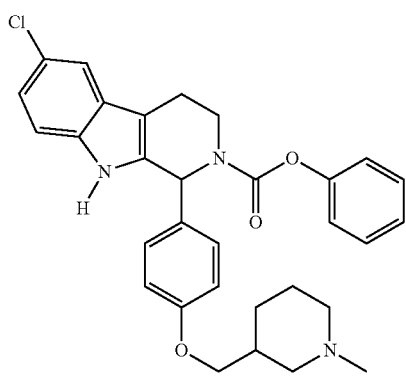
952
454
-continued
953
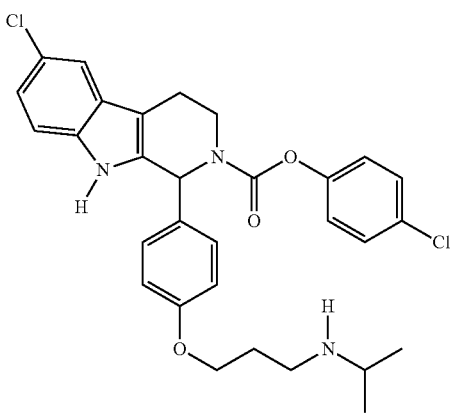
958
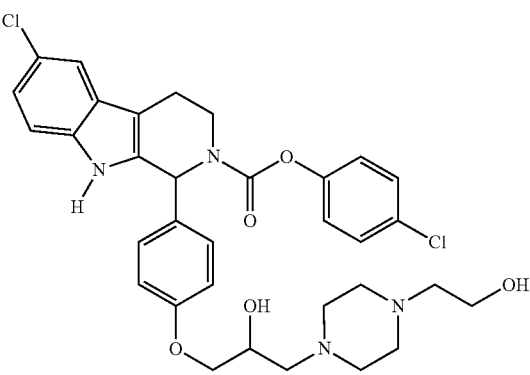
960
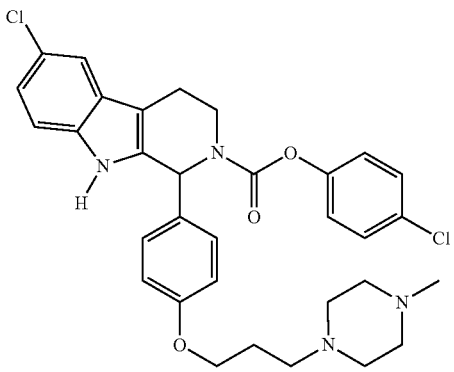
961

455
-continued
963
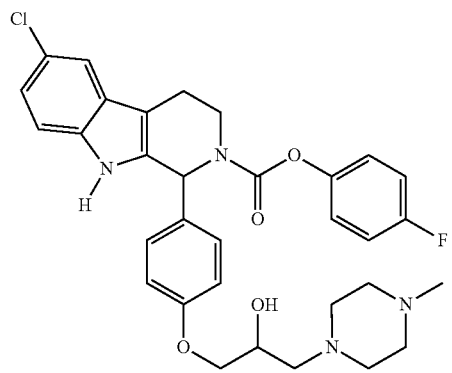
964
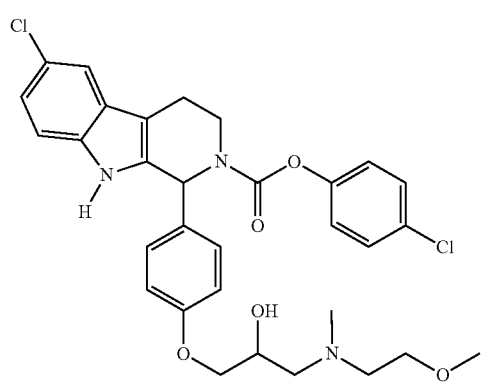
966
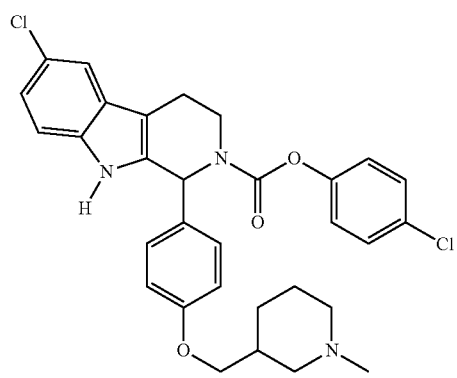
967
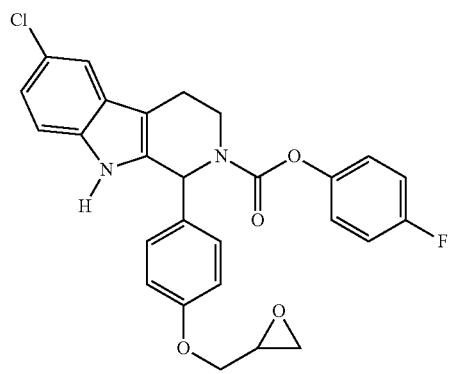
456
-continued
970
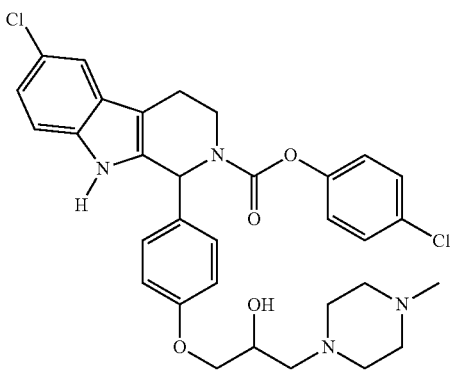
973
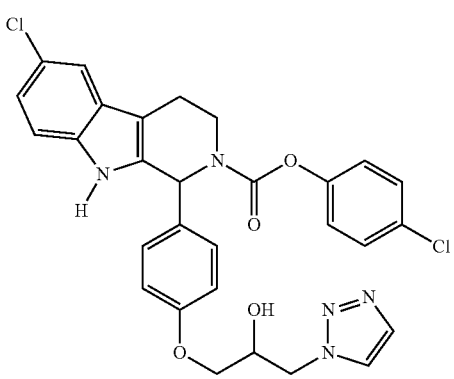
974
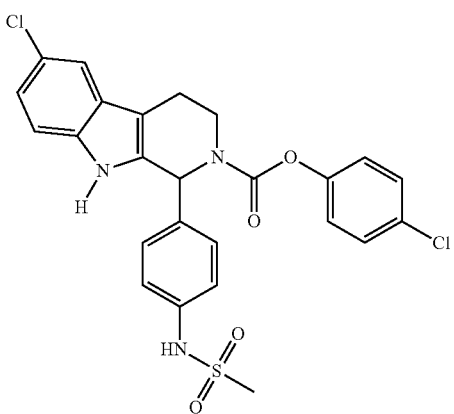
976
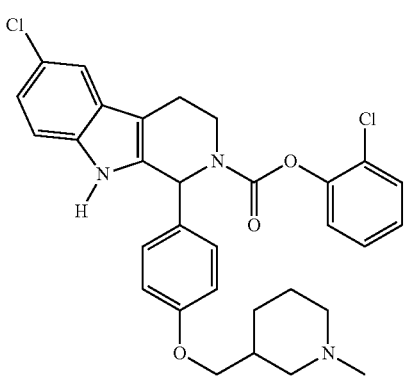

457
-continued
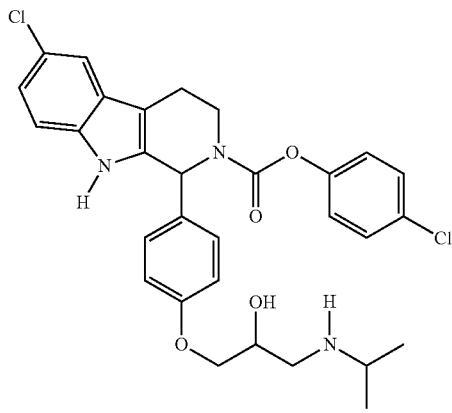
977
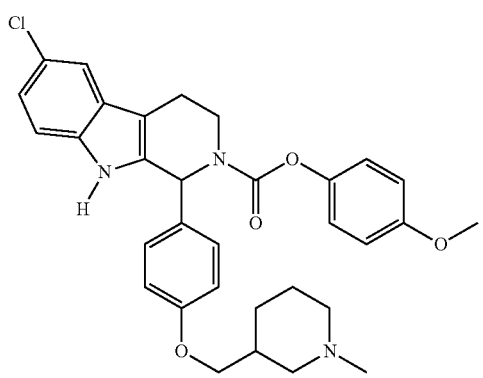
981
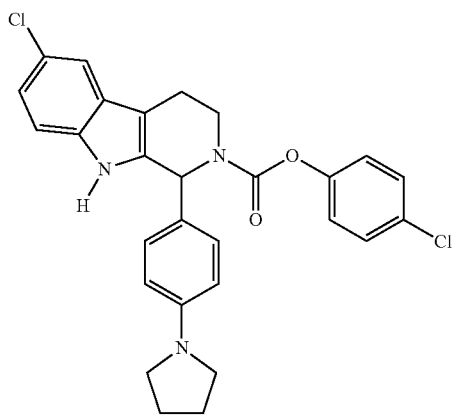
984
458
-continued
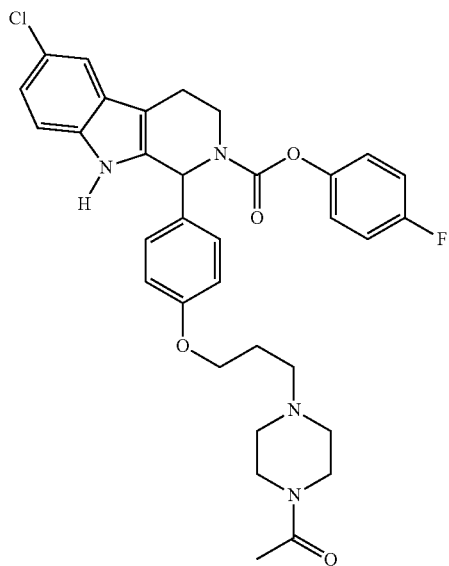
988
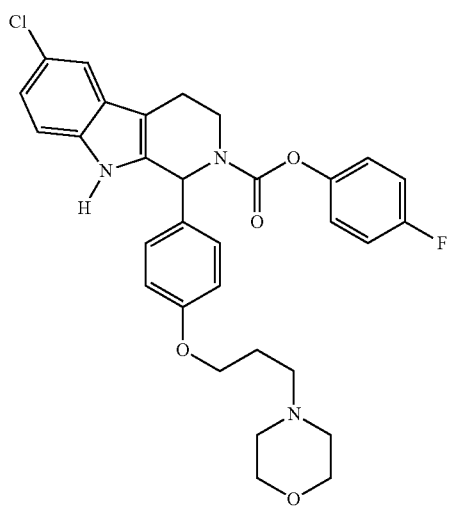
989
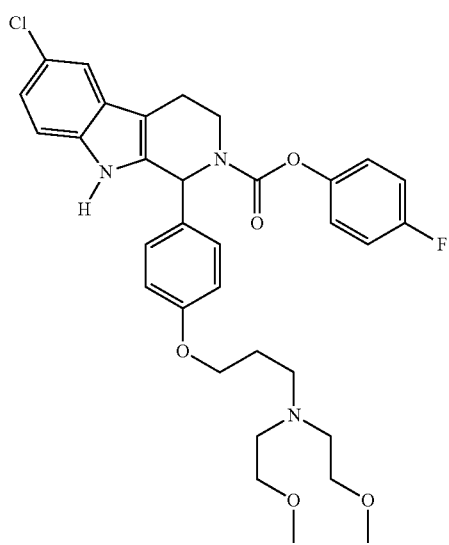
990

459
-continued
991
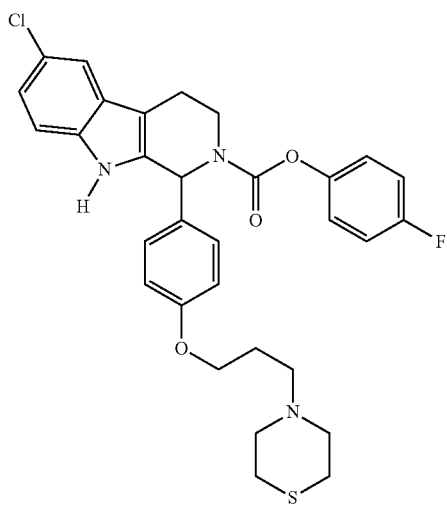
992
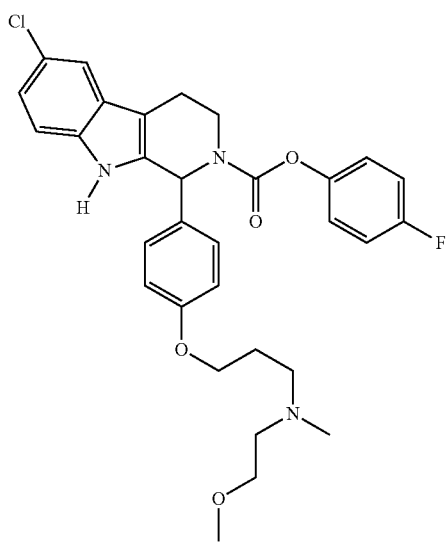
993
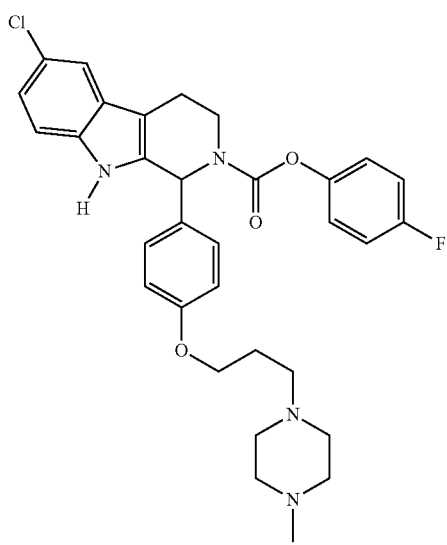
460
-continued
994
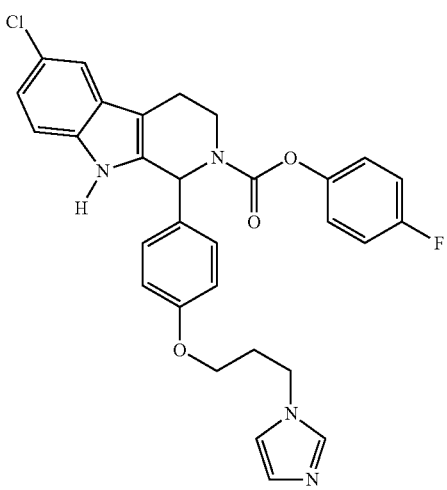
995
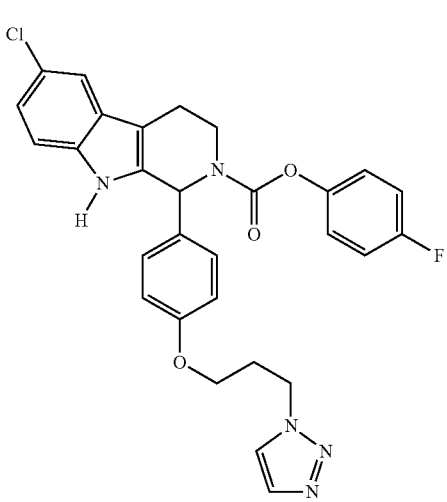
996
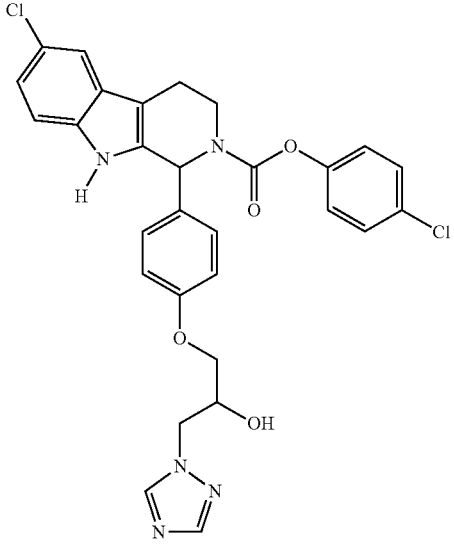

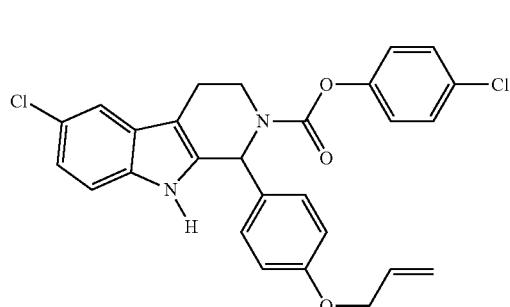
999
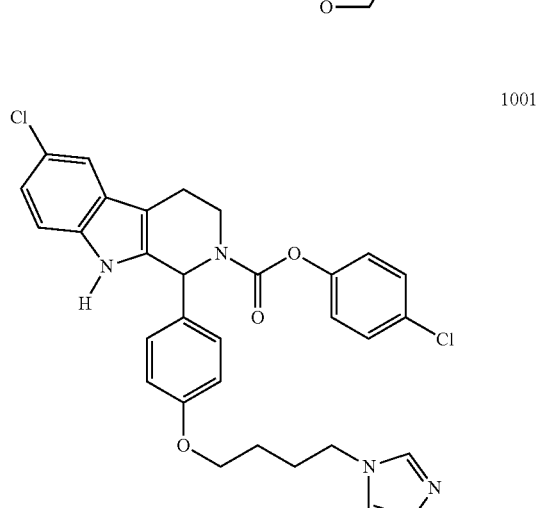
1001
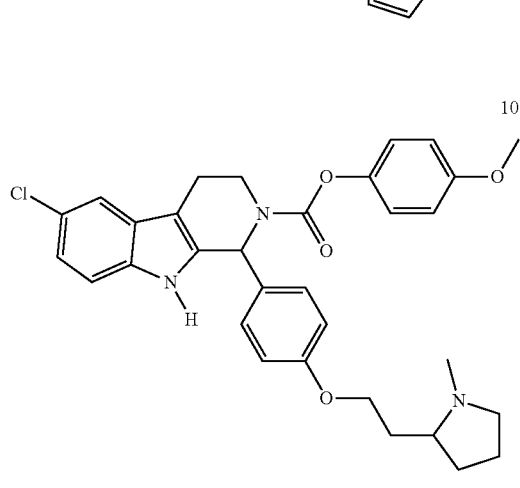
1005
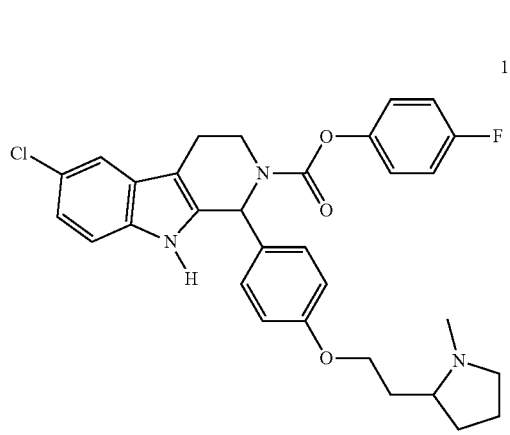
1008
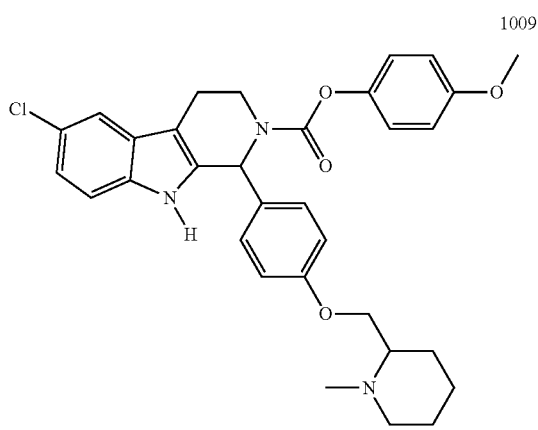
1009
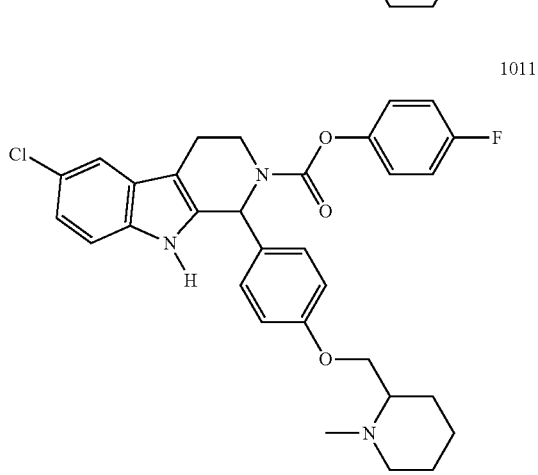
1011
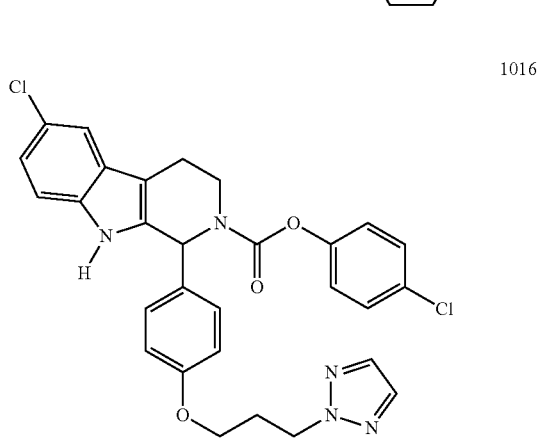
1016
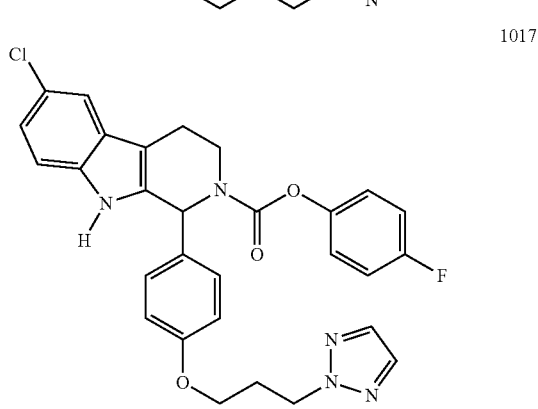
1017

1021
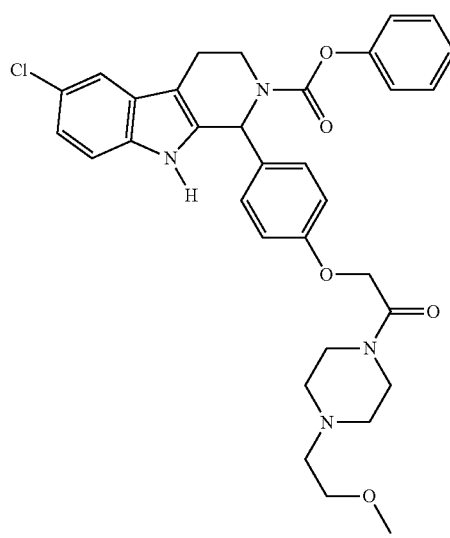
1022
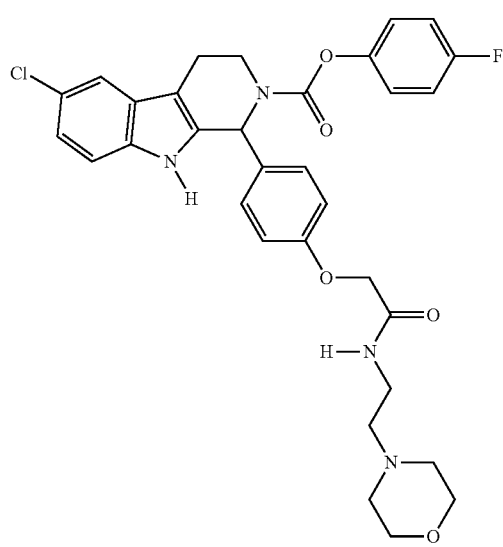
1023
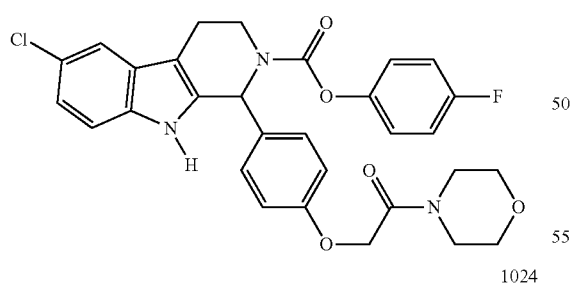
1024
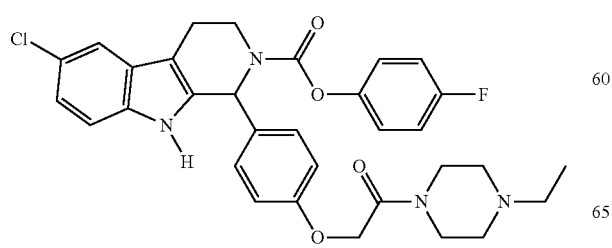
1025
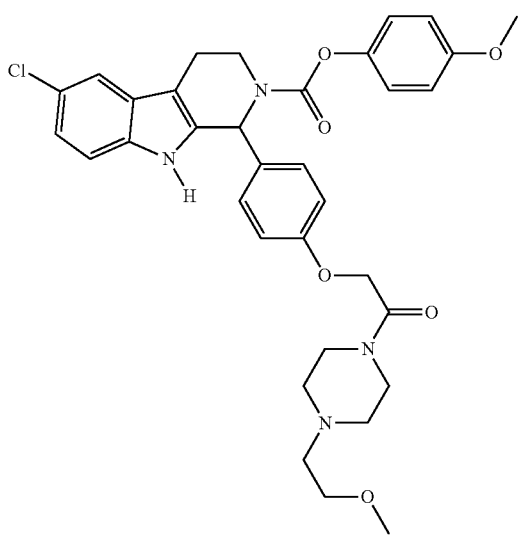
1026
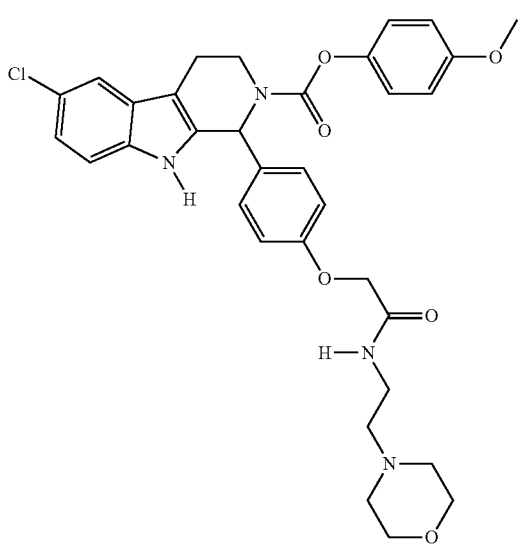
1027
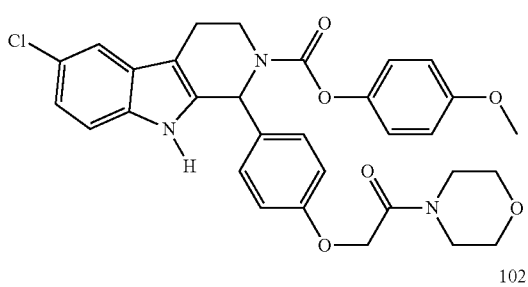
1028
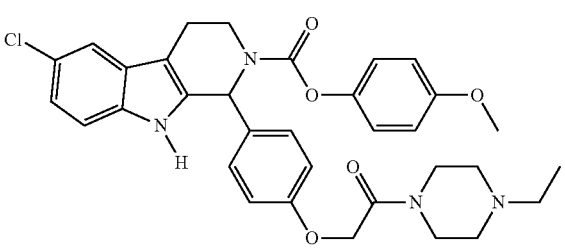

1029
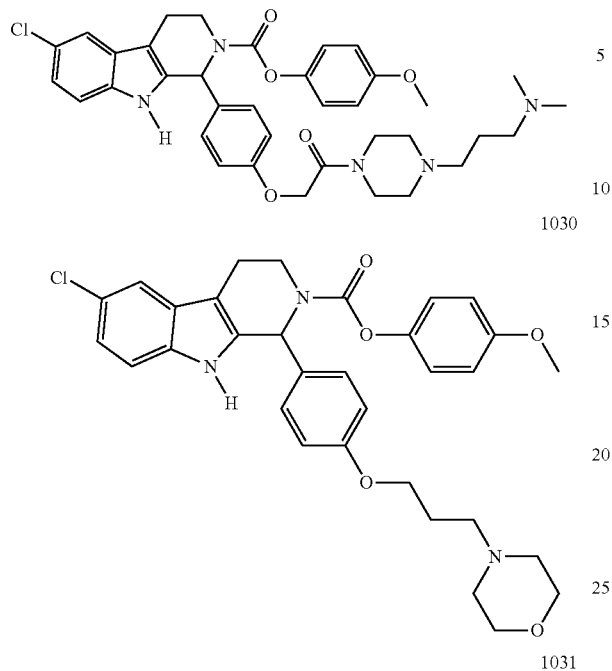
1030
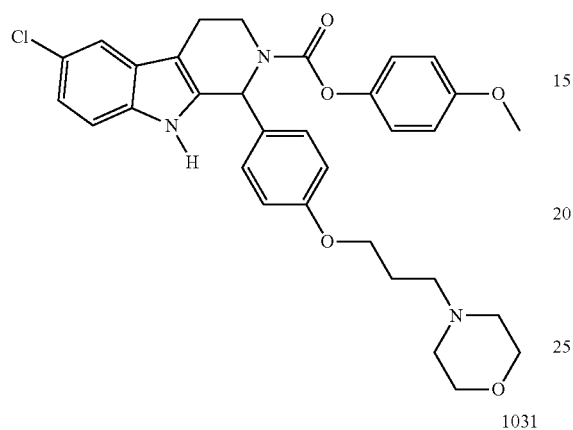
1031
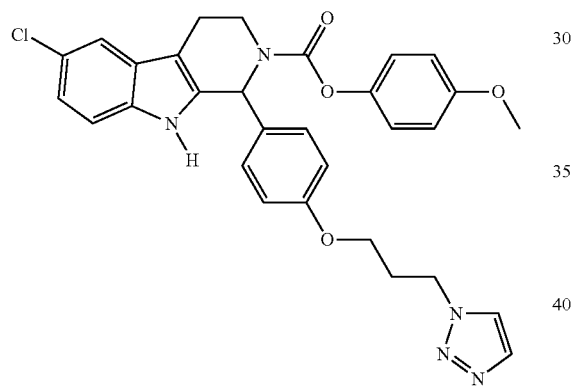
1050
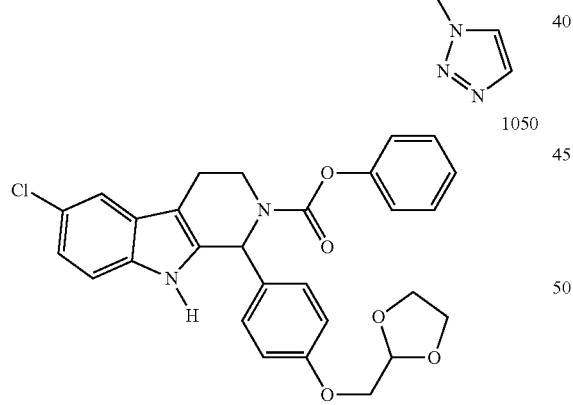
1051
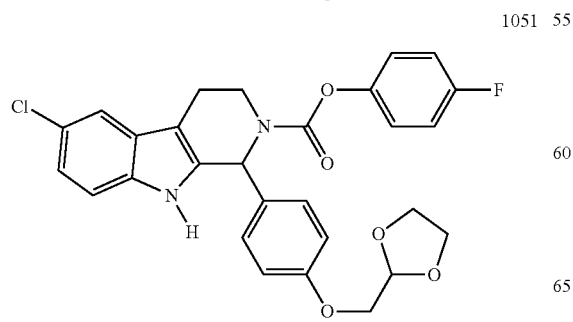
1052
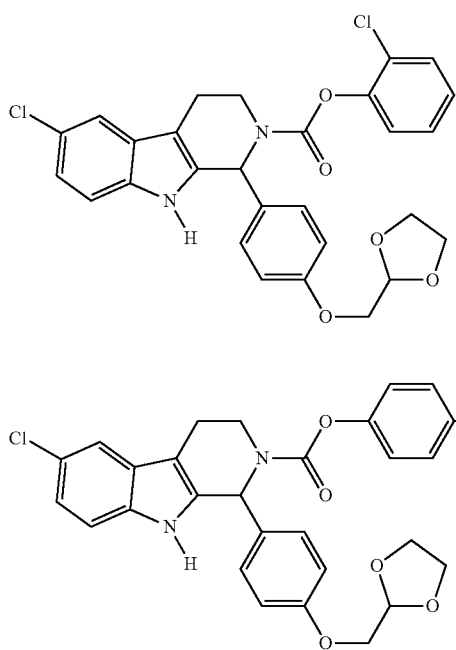
1053
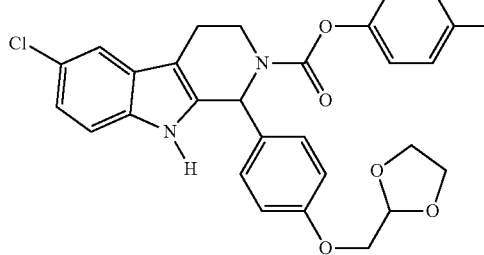
1054
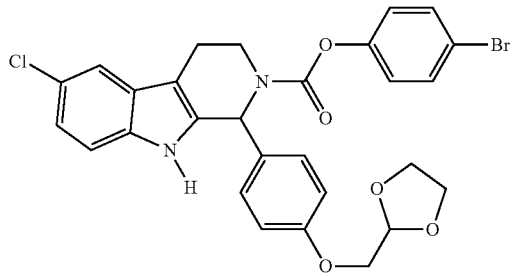
1055
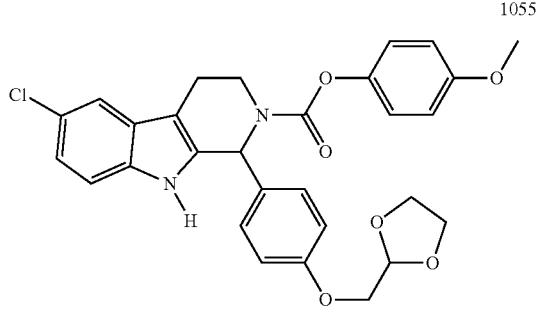
1058
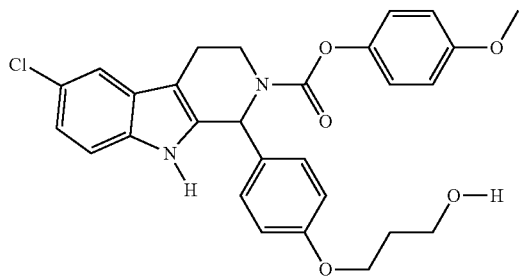

467
-continued
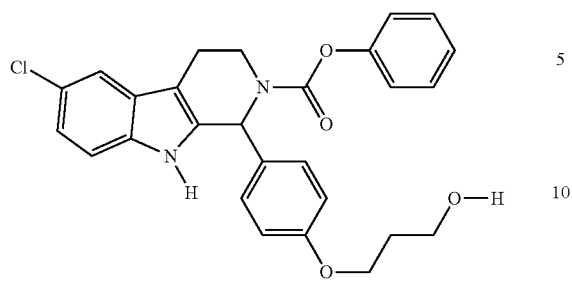
1062
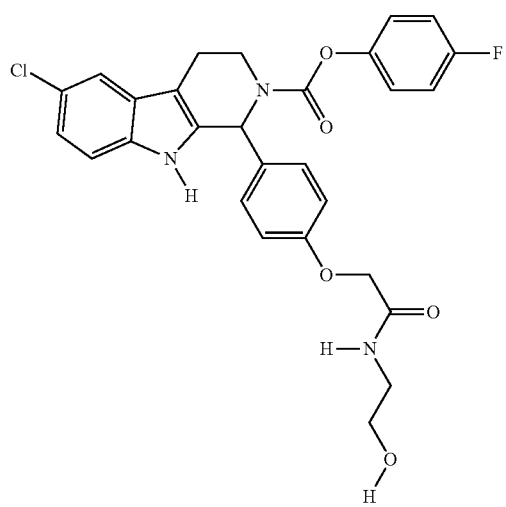
1063
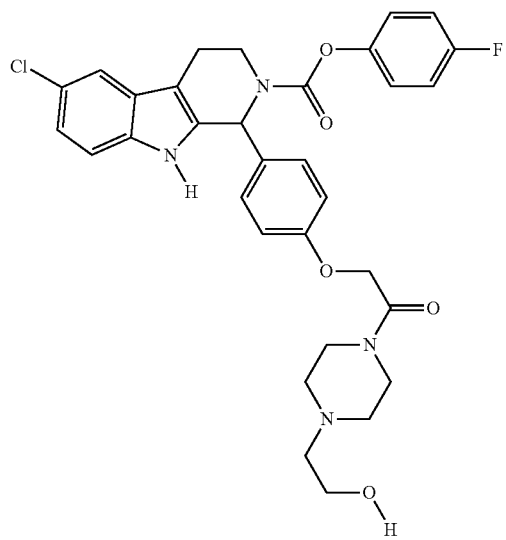
1064
468
-continued
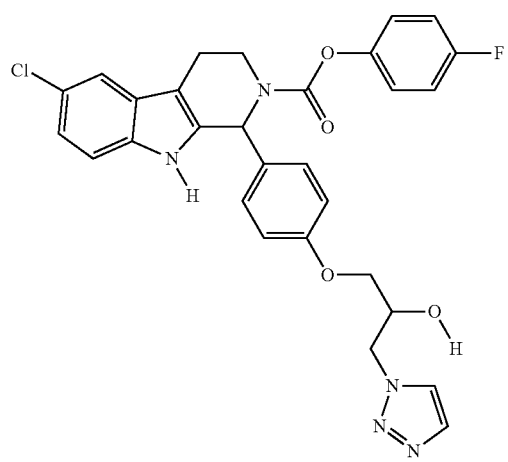
1066
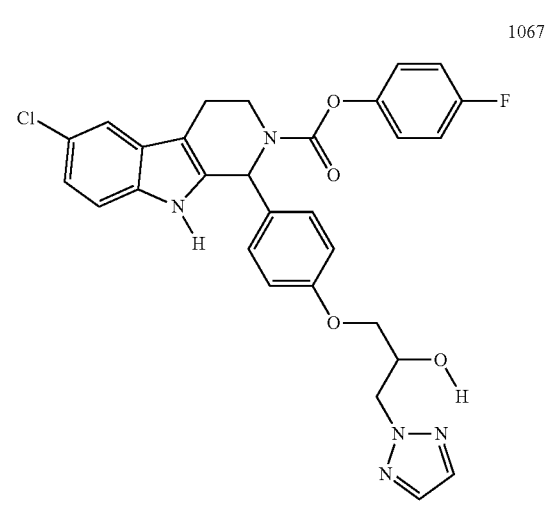
1067
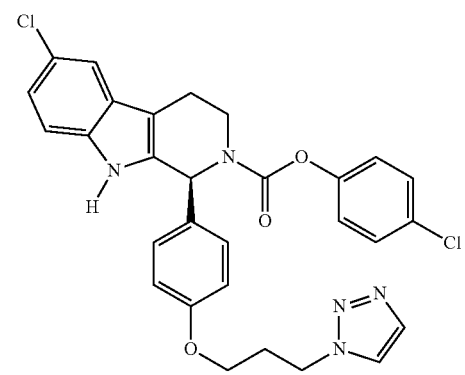
1068

469
-continued
1069
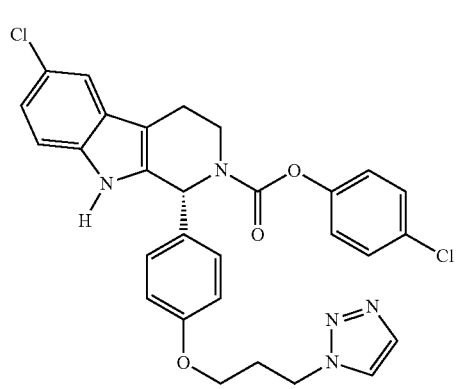
1070
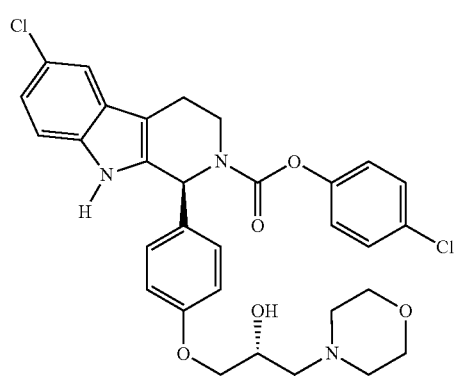
1071
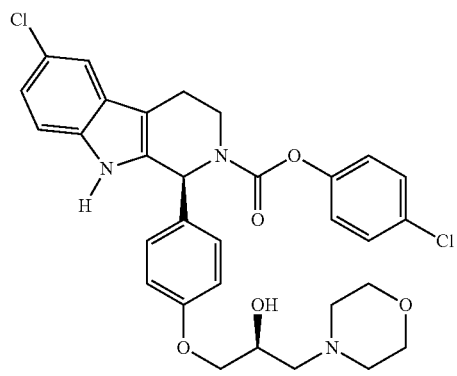
1075
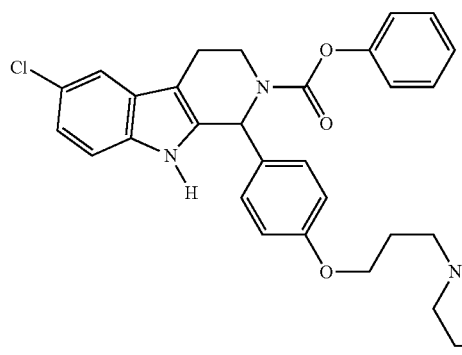
470
-continued
1076
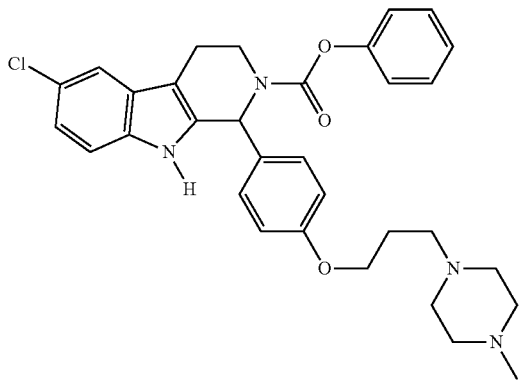
1077
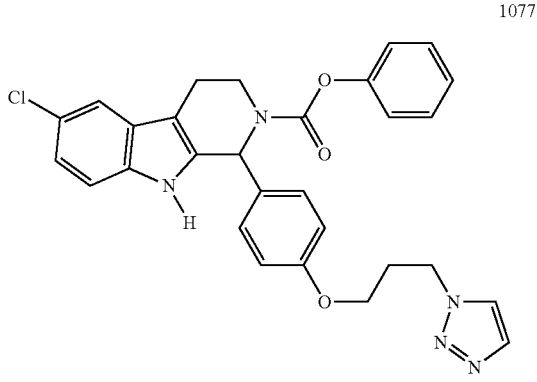
1078
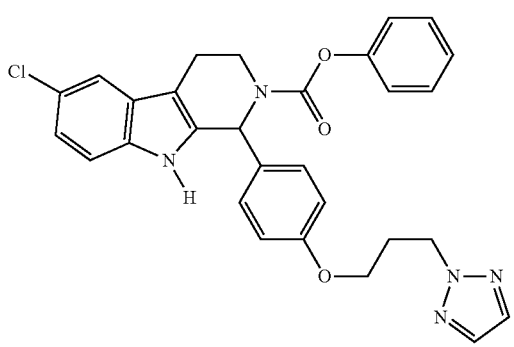
1086
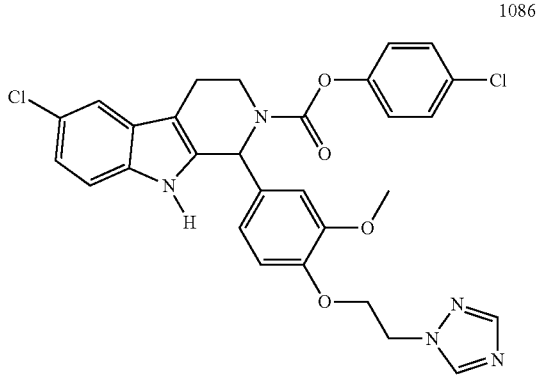

1087
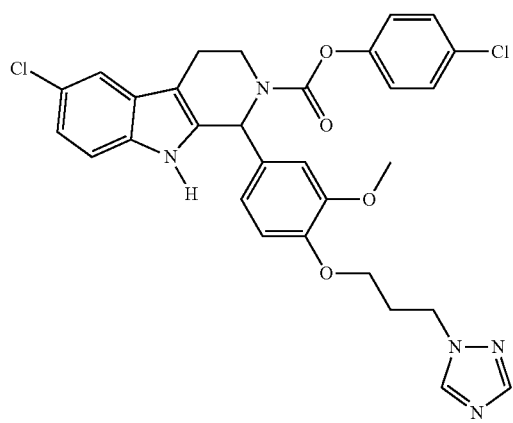
1088
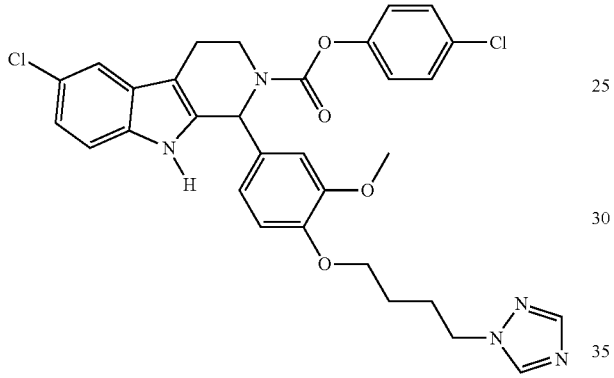
1089
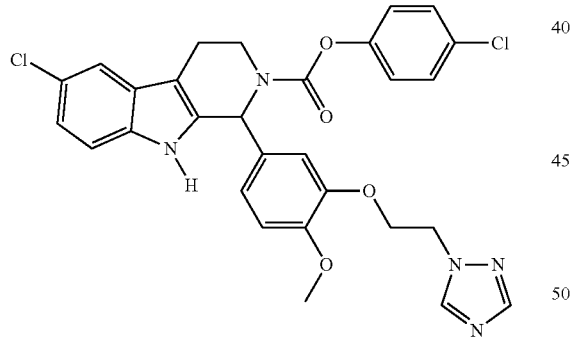
1090
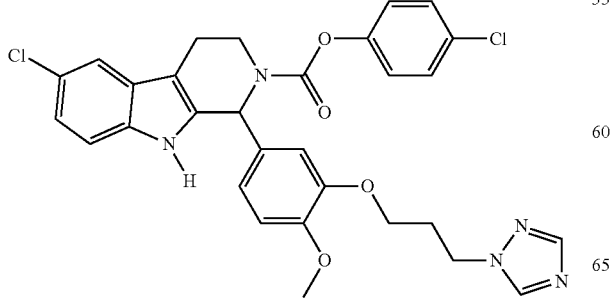
1091
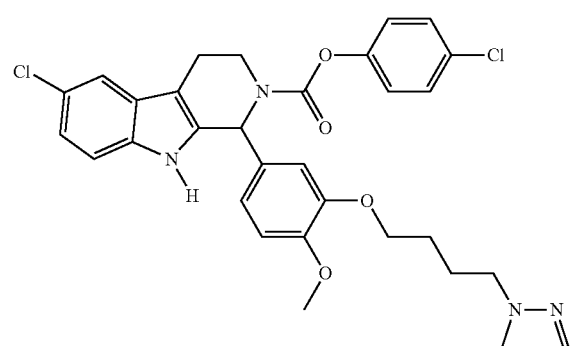
1092
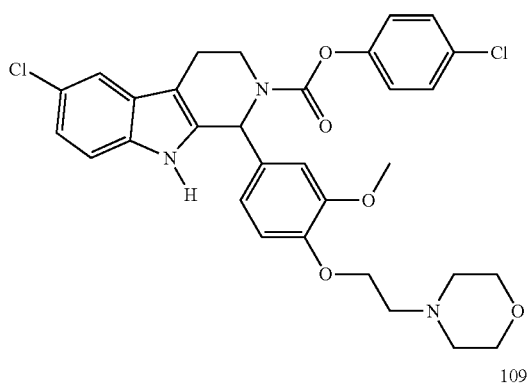
1093
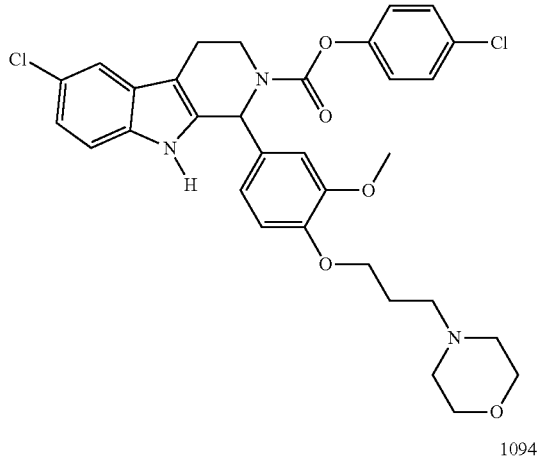
1094

-continued
1095
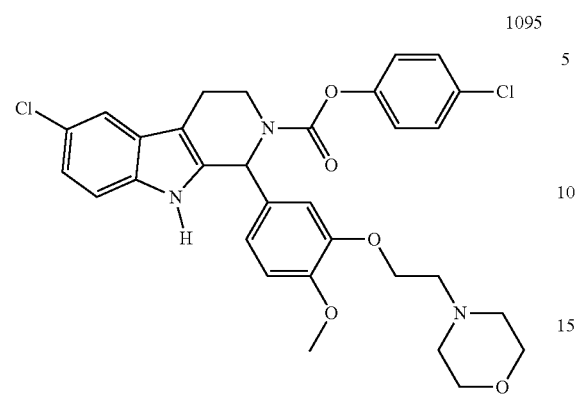
1096
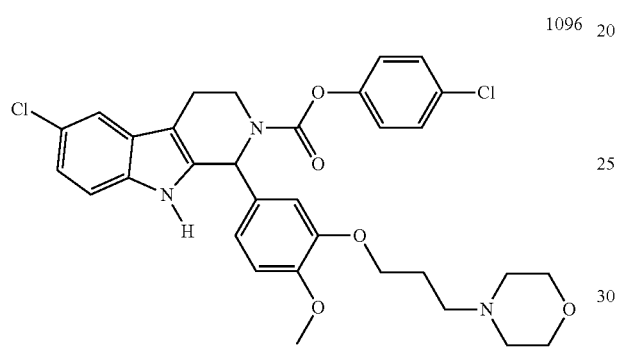
1097
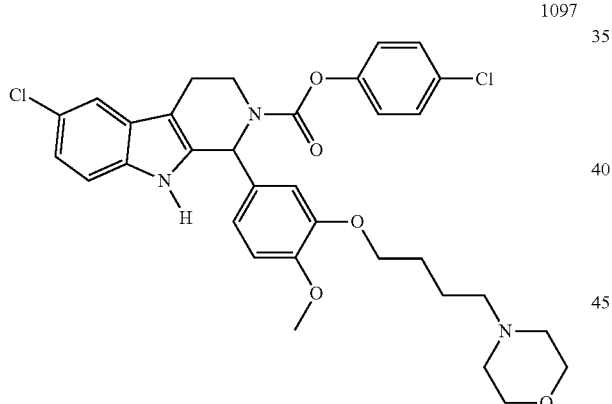
1098
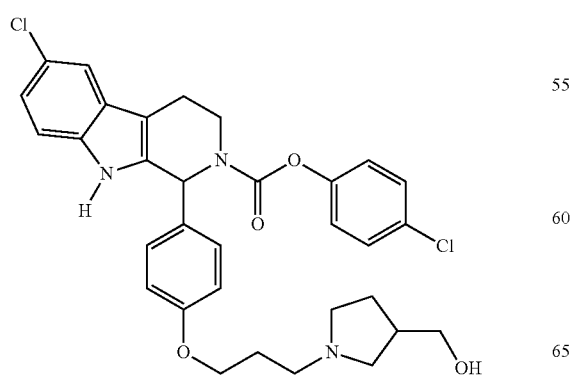
-continued
1099
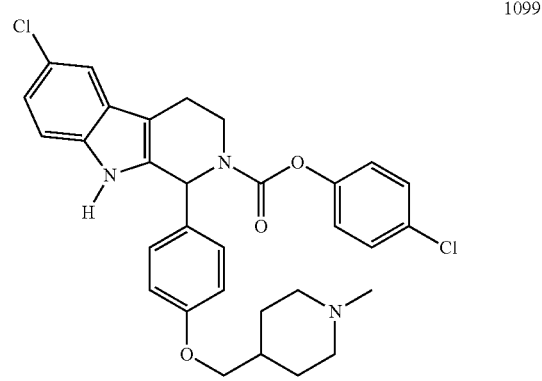
1108
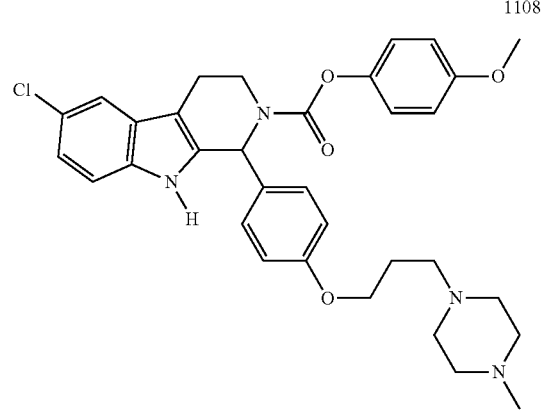
1110
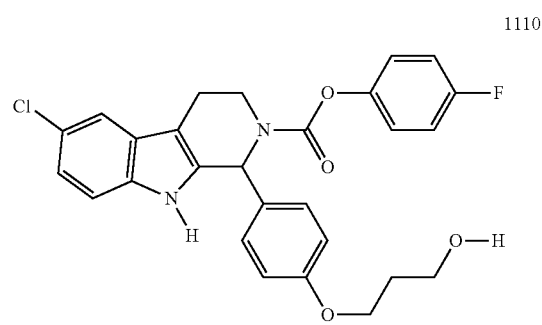
1111
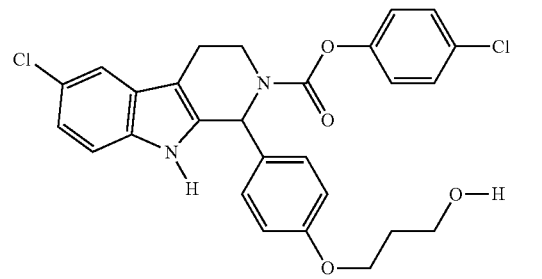

-continued
1113
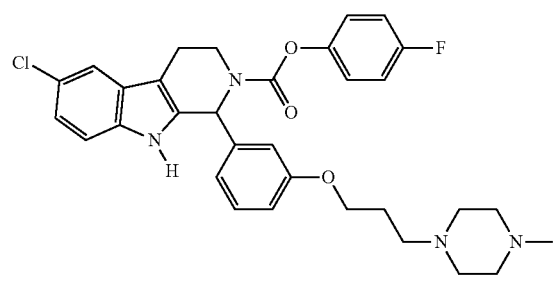
1115
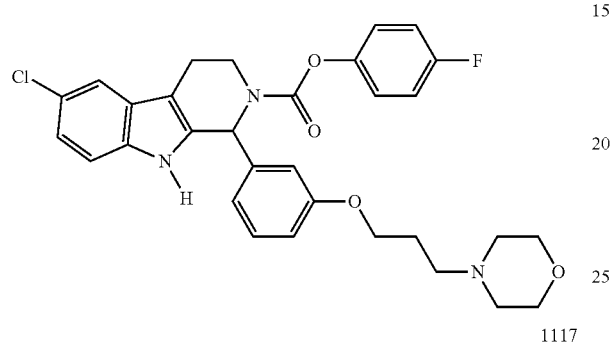
1117
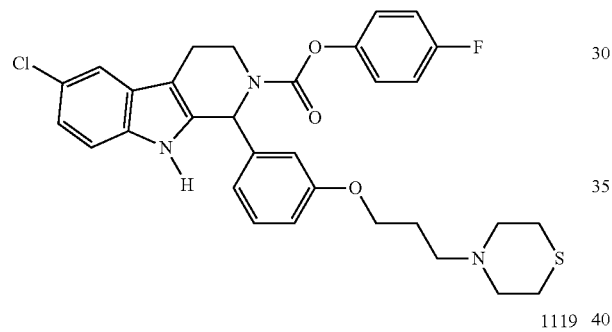
1119
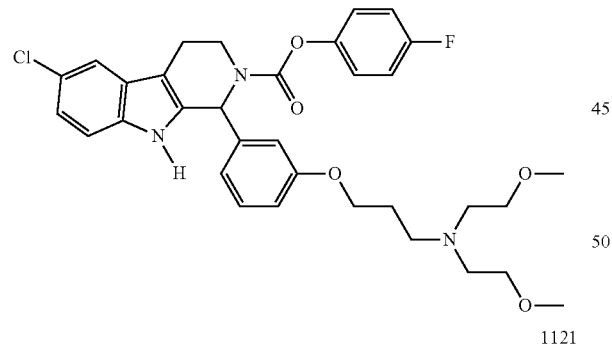
1121
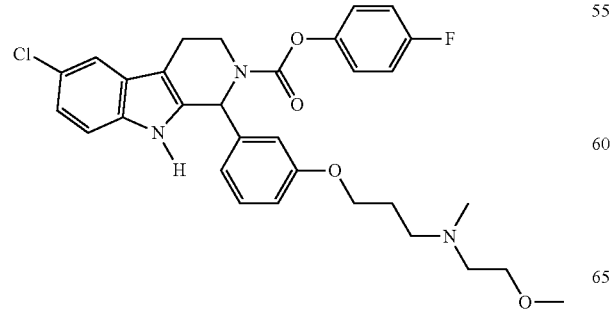
-continued
1123
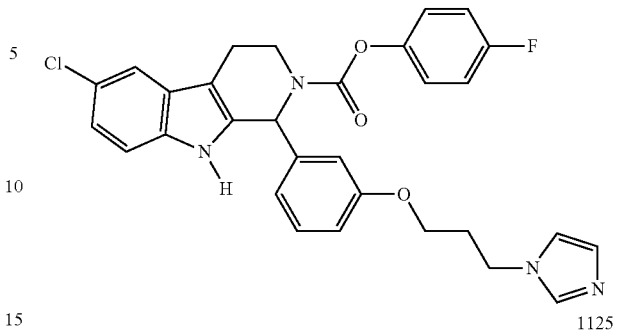
1125
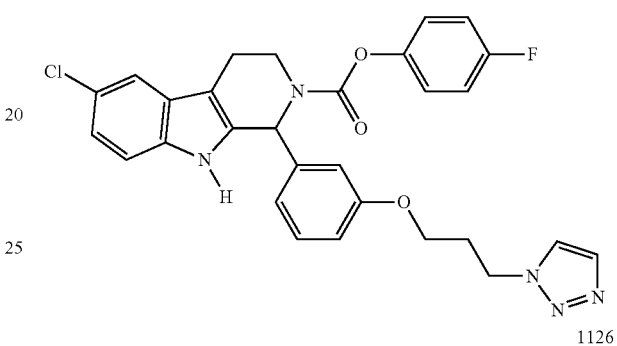
1126
1127
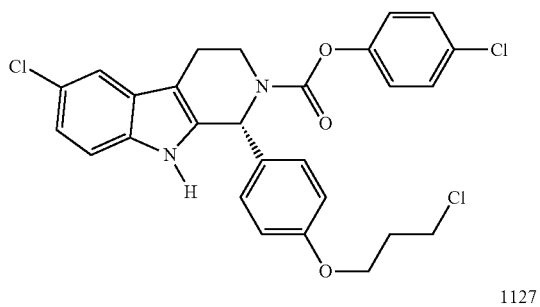
1128
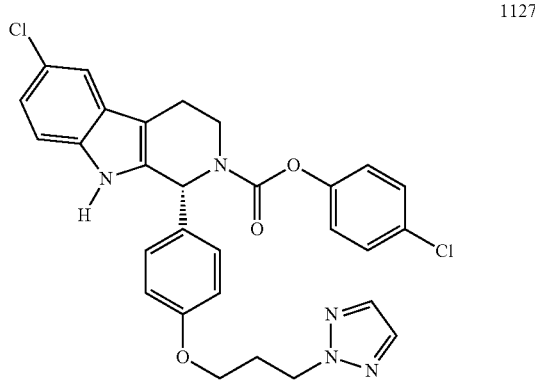

1129
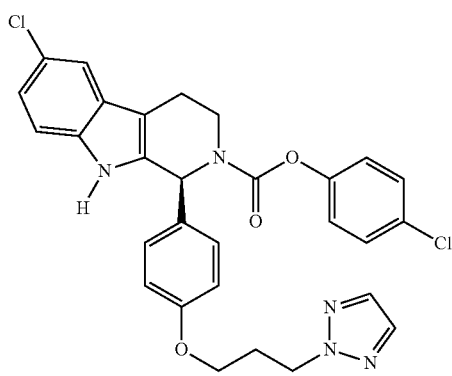
1130
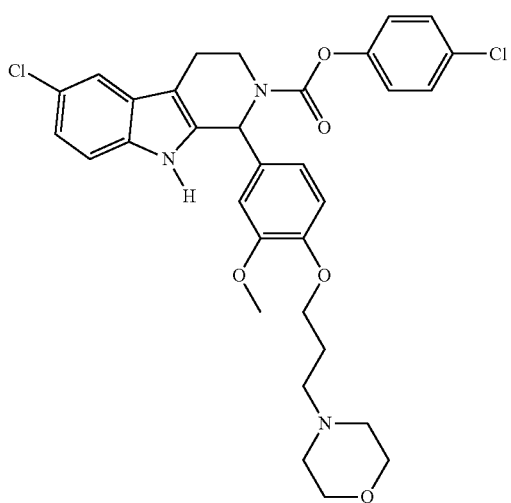
1131
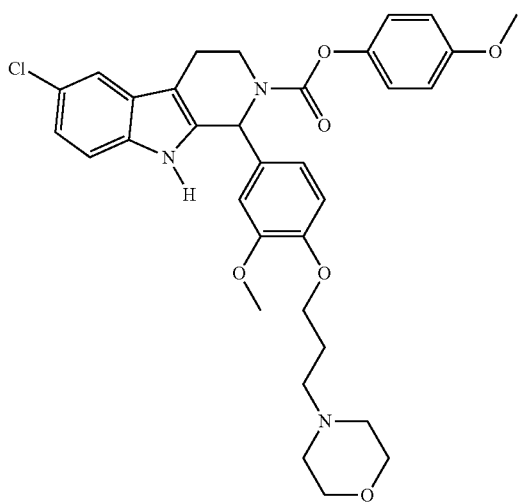
1132
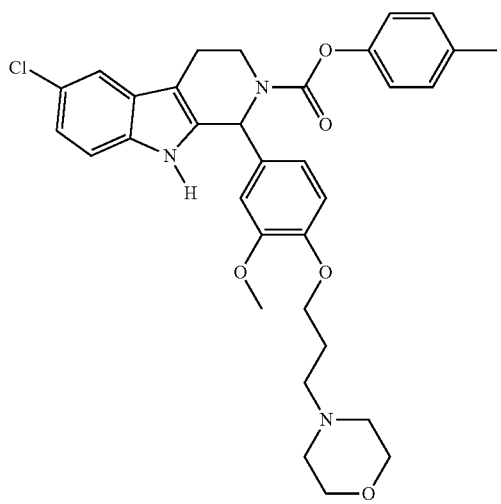
1133
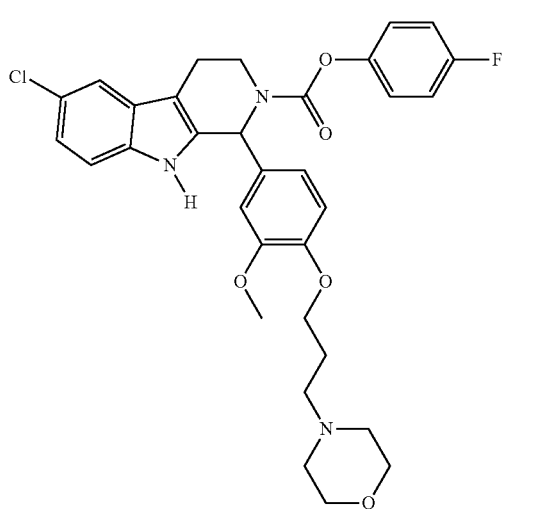
1134
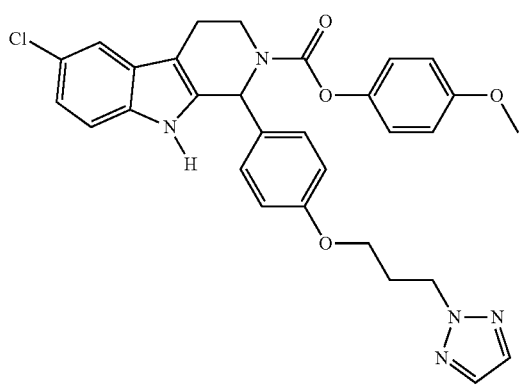

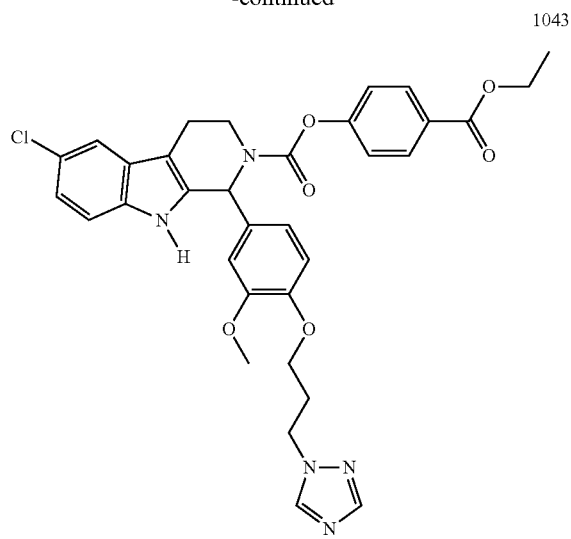
1043
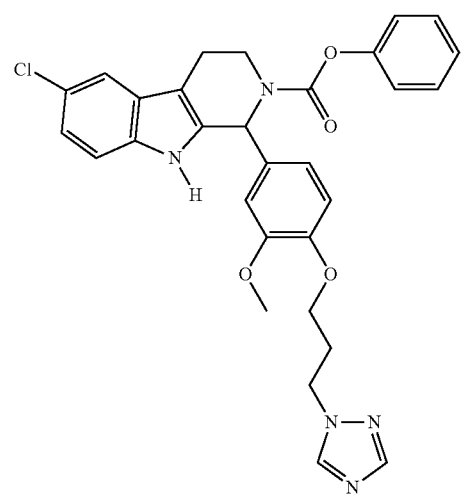
1150
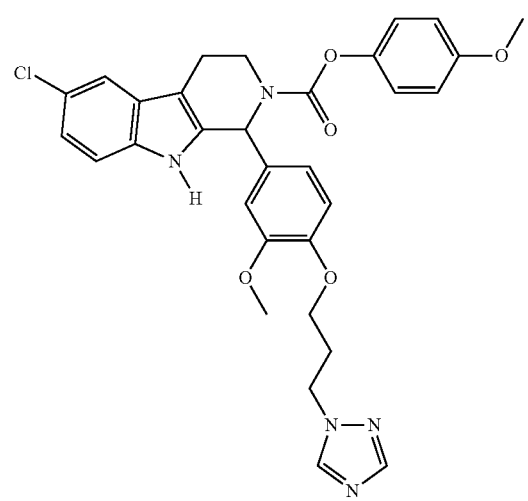
1151
1144
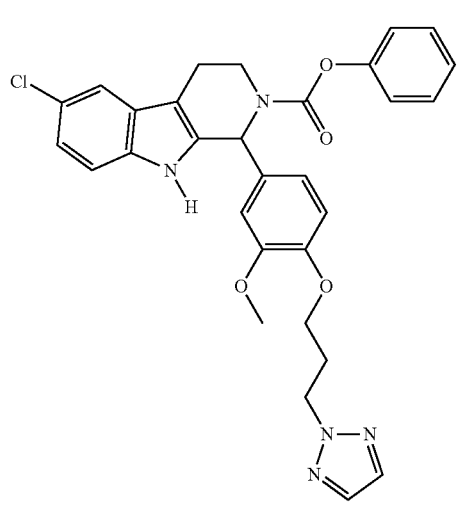
1145
1152

481
-continued
1155
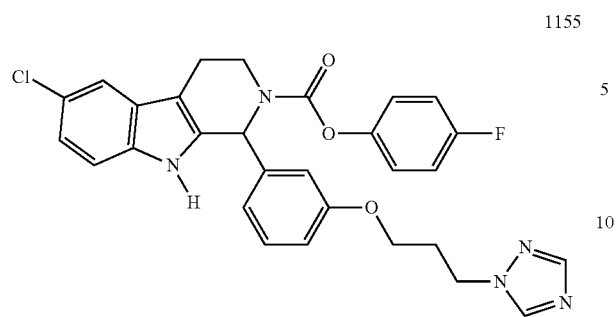
1159
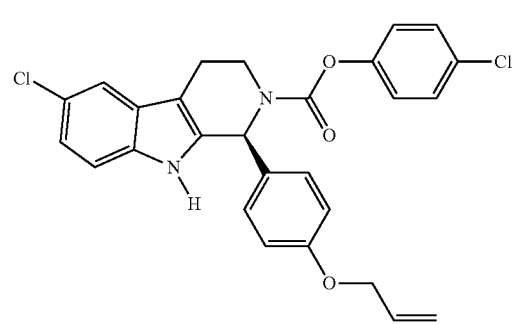
1160
1161
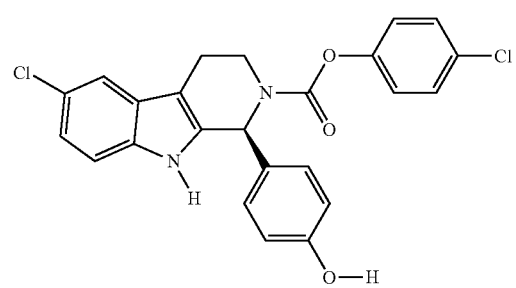
482
-continued
1162
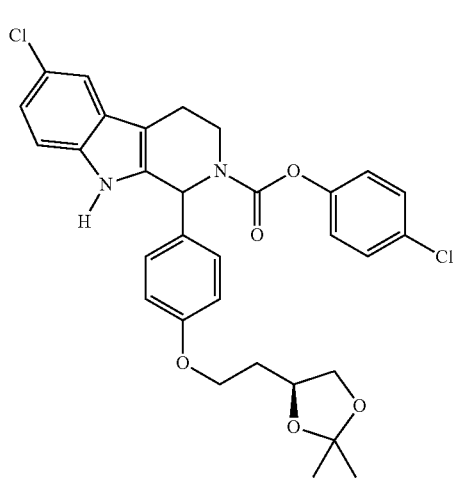
1168
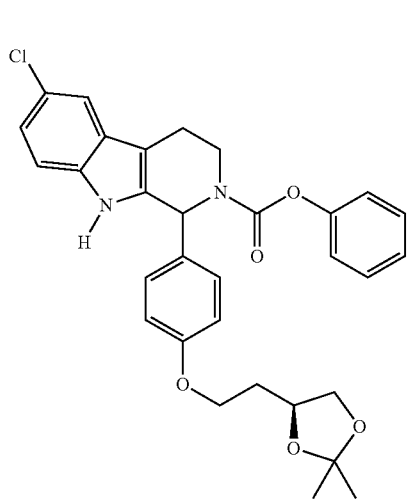
1169
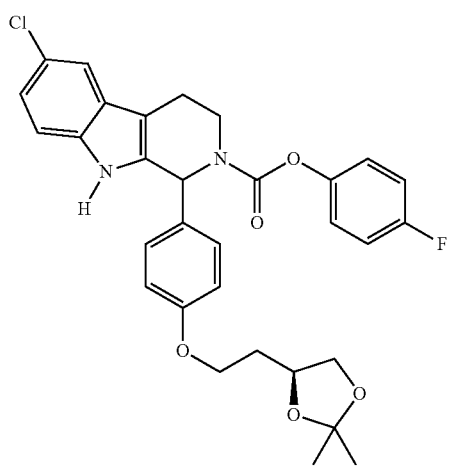

483
-continued
1170
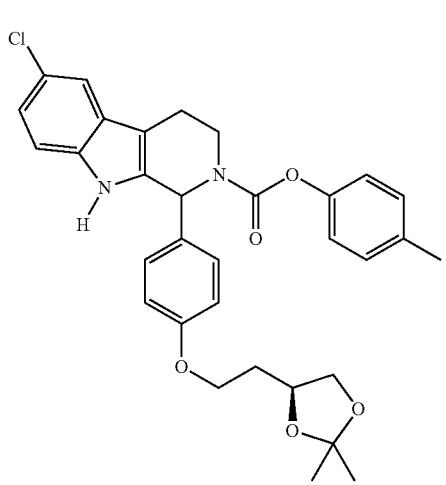
1171
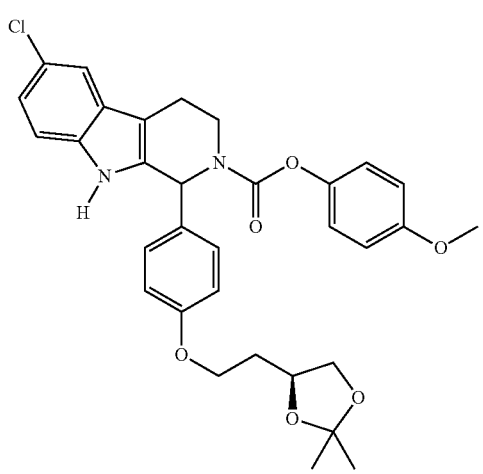
1172
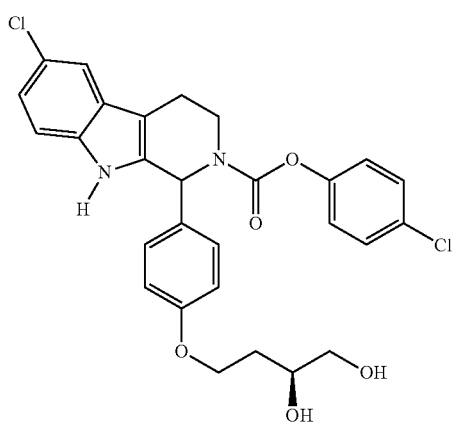
484
-continued
1178
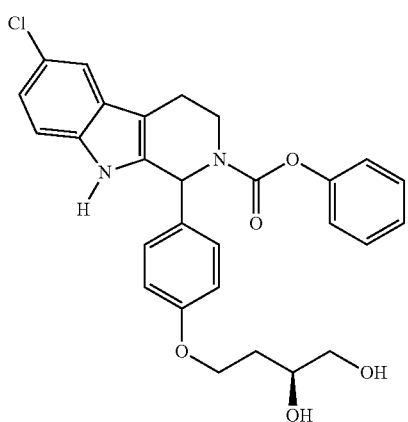
1179
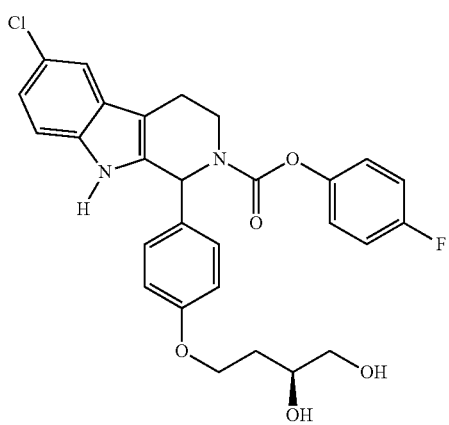
1180
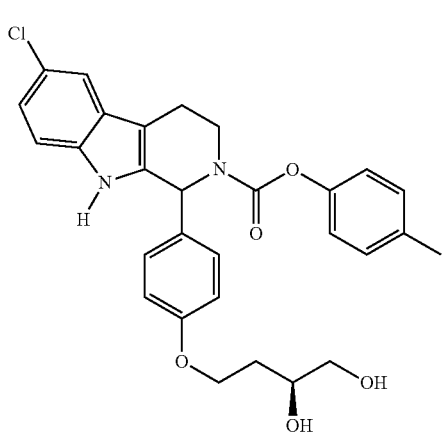

485
-continued
1181
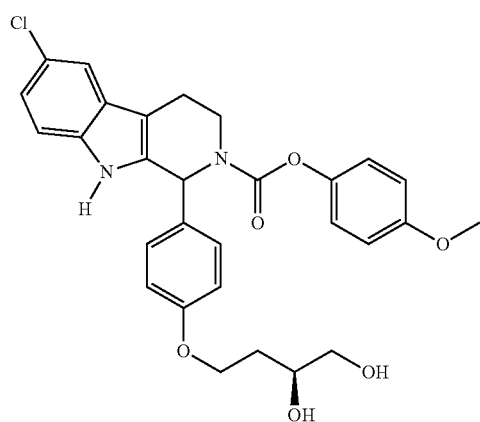
1182
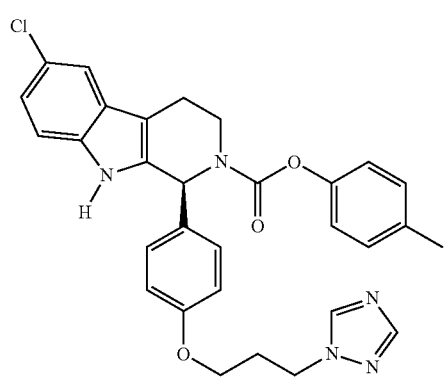
1183
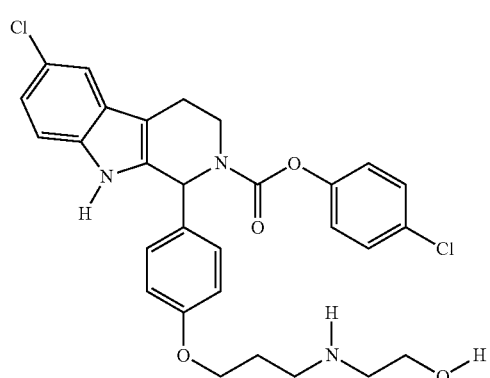
1184
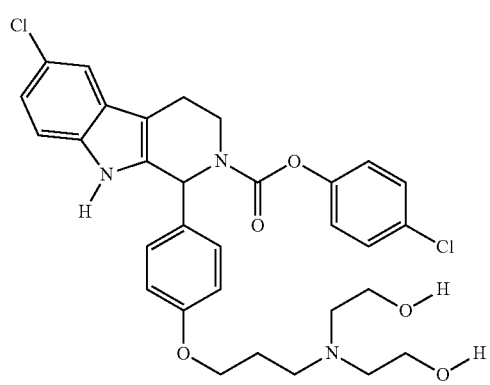
486
-continued
1194
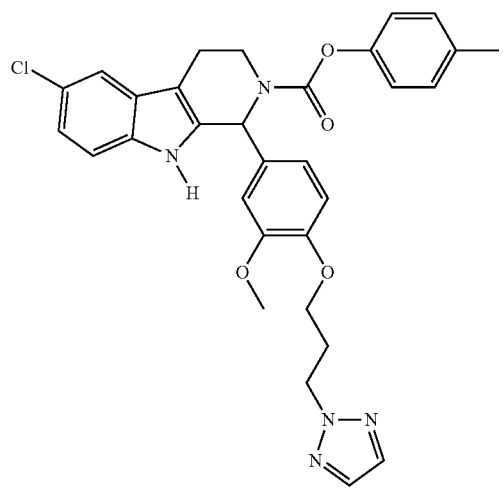
1195
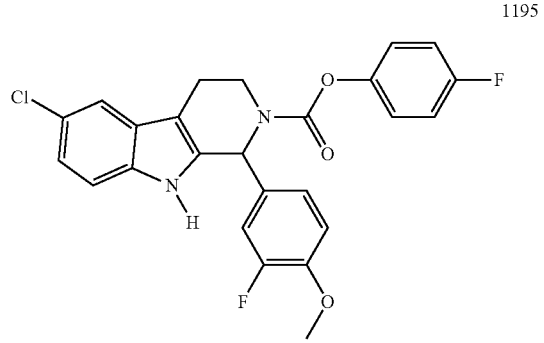
1196
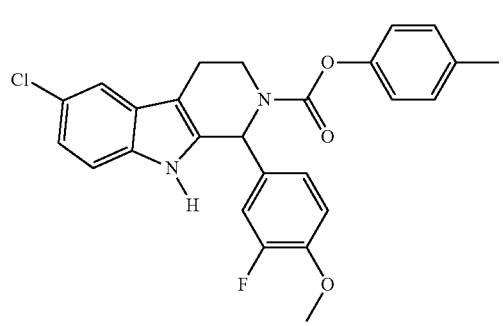
1197
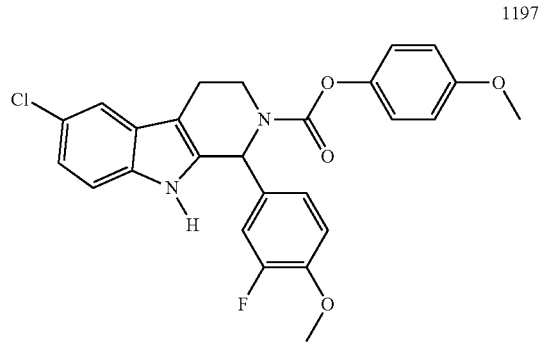

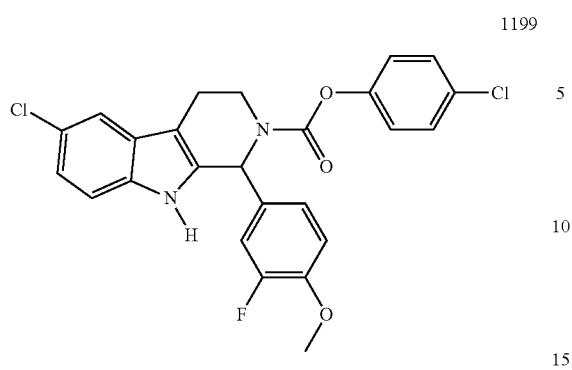
1199
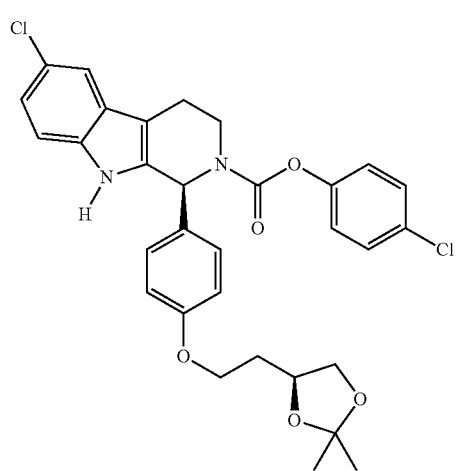
1203
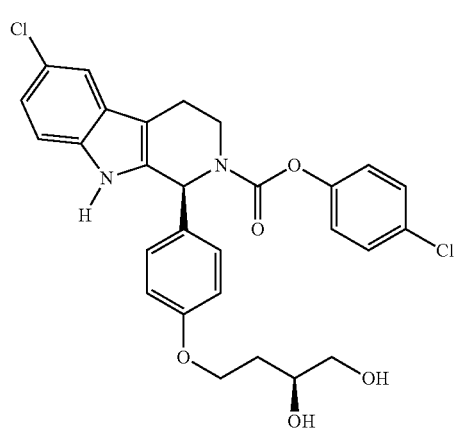
1205
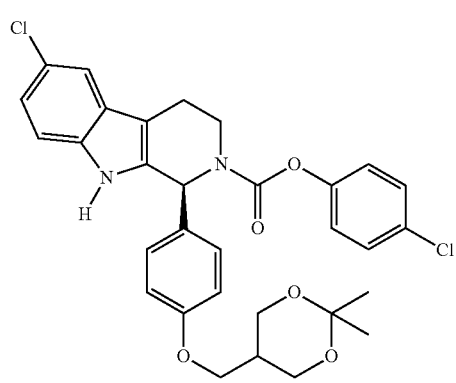
1207
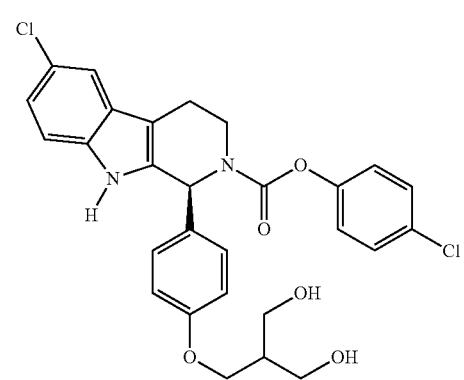
1209
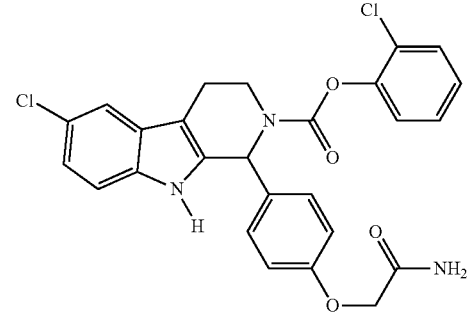
1213
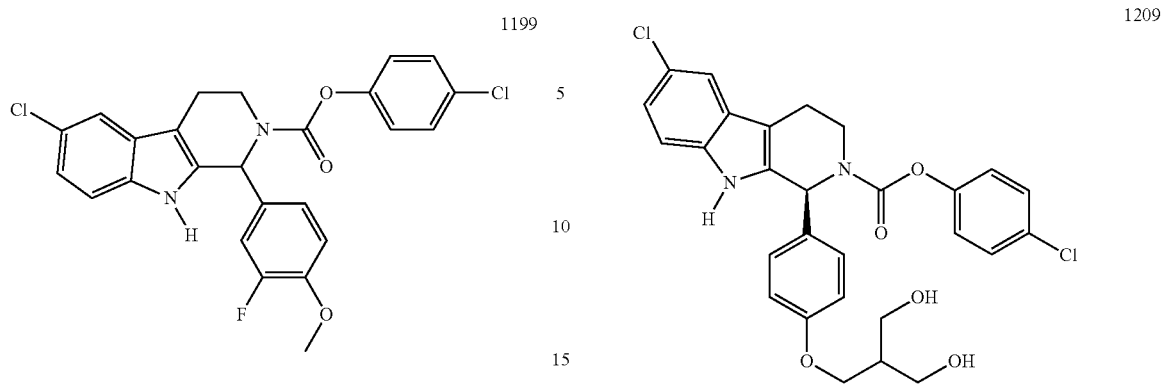
1216
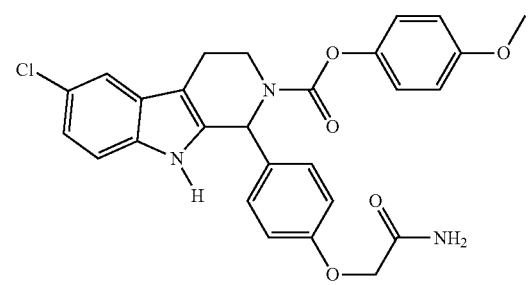
1223

489
-continued
1224
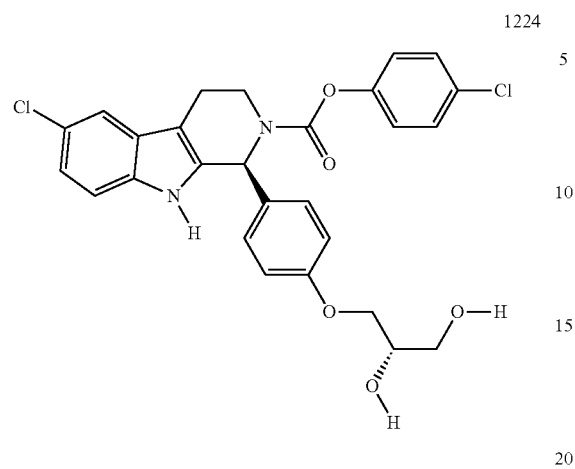
1225
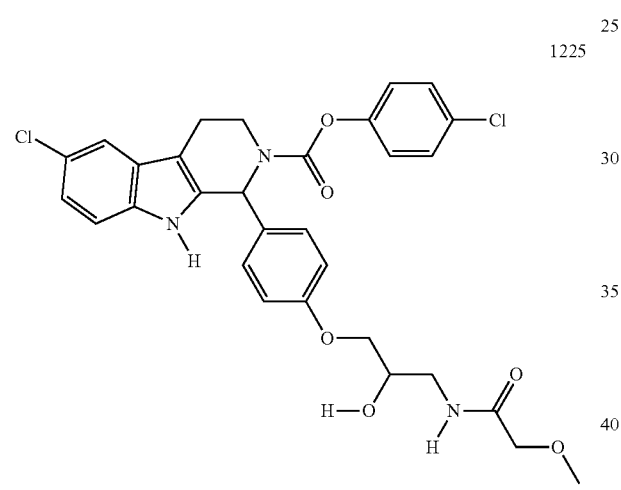
1227
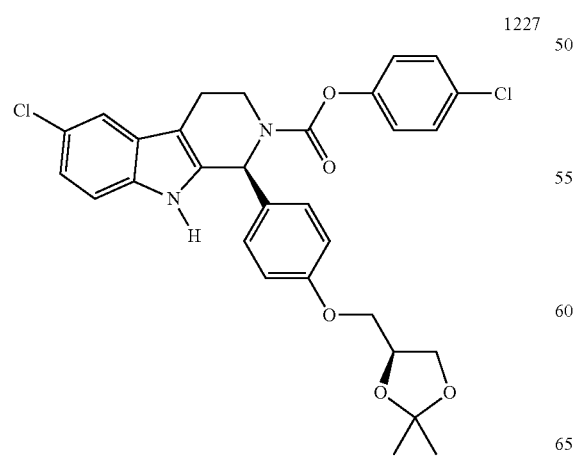
490
-continued
1228
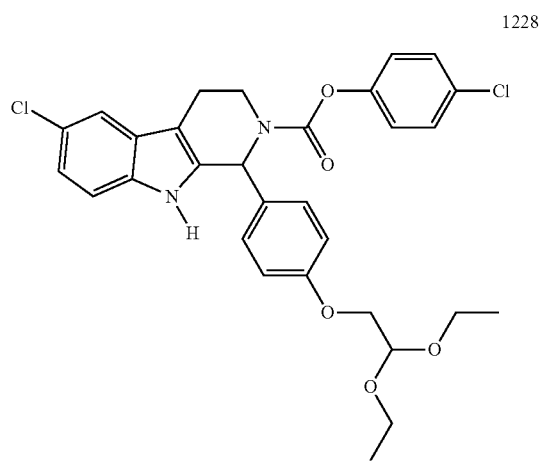
1229
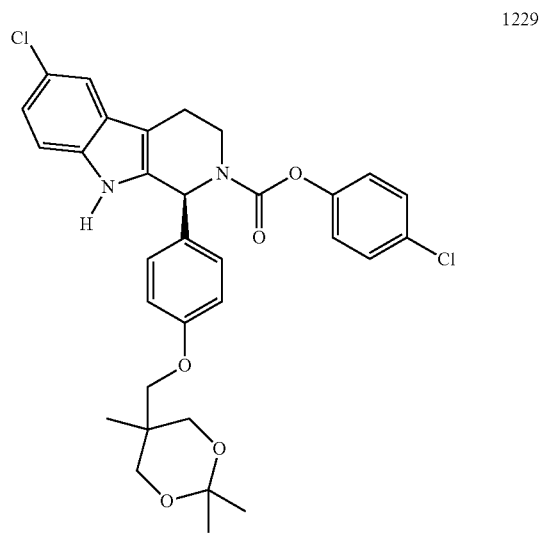
1230
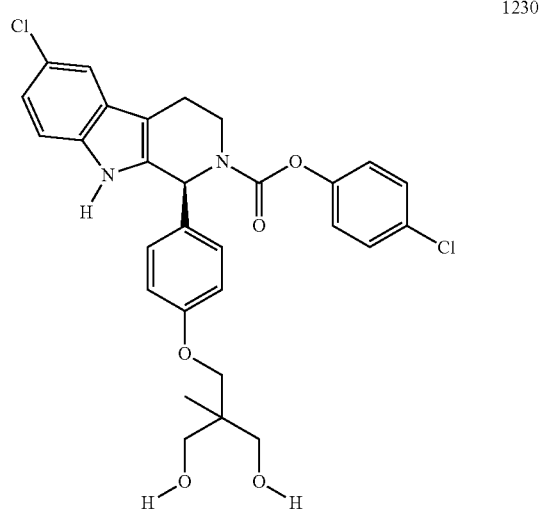

491
-continued
1231
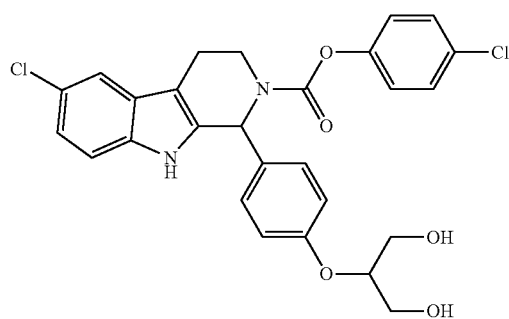
1234
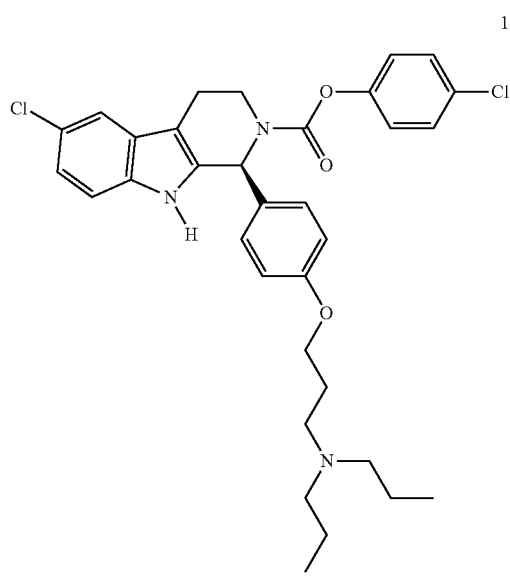
1235
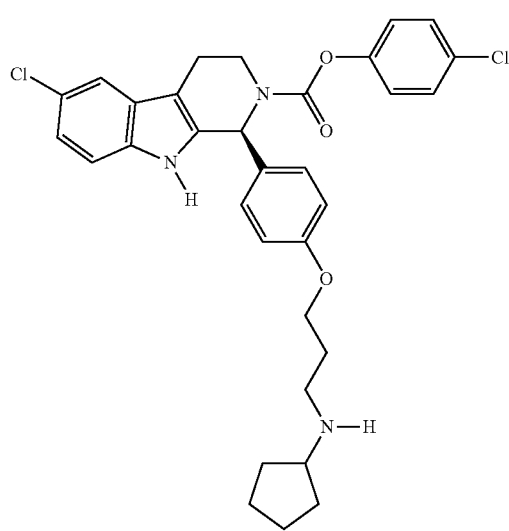
492
-continued
1250
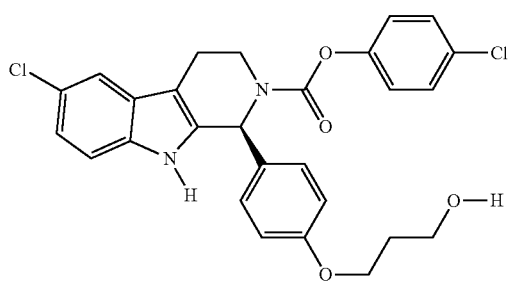
1255
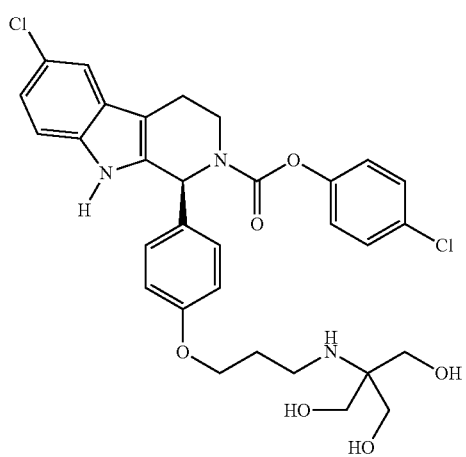
1257
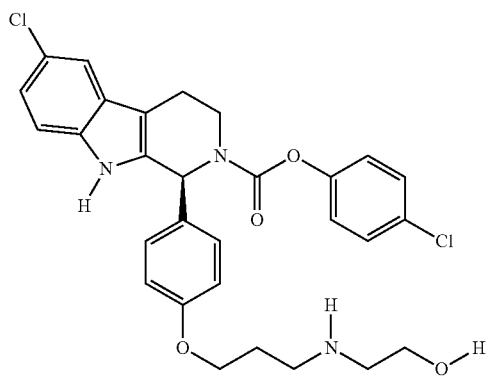
1258
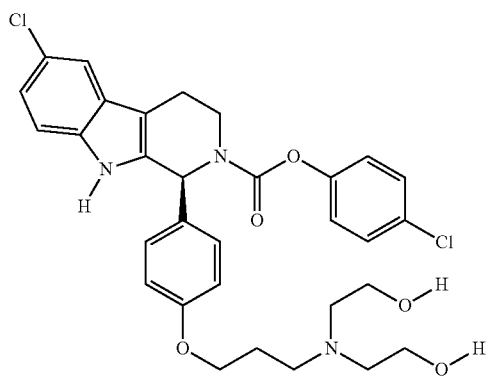

1259
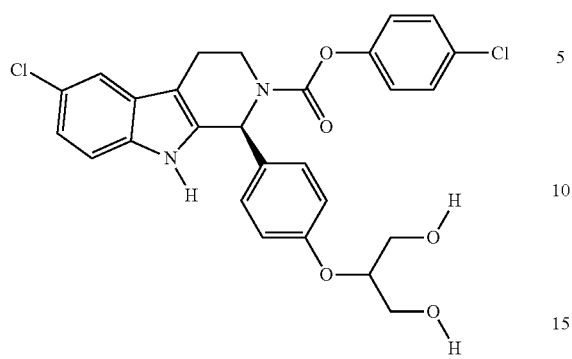
1260
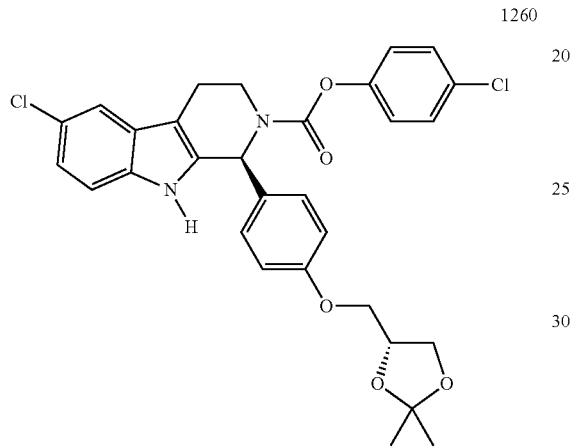
1263
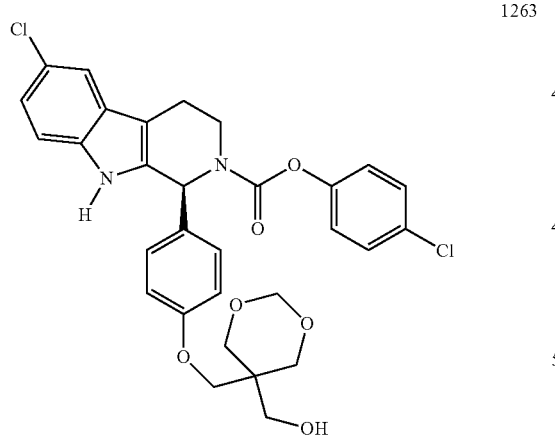
1265
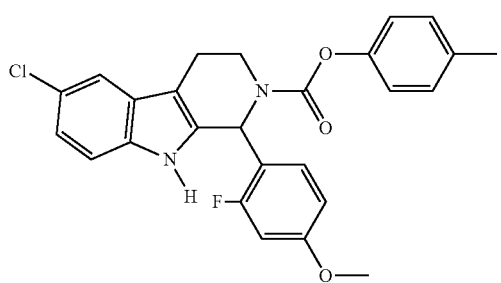
1266
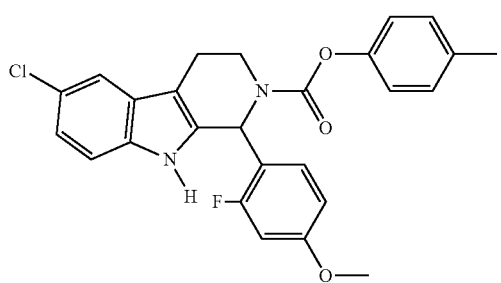
1267
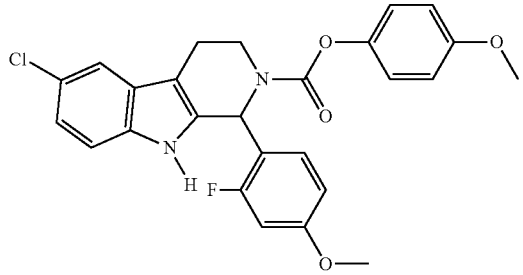
1269
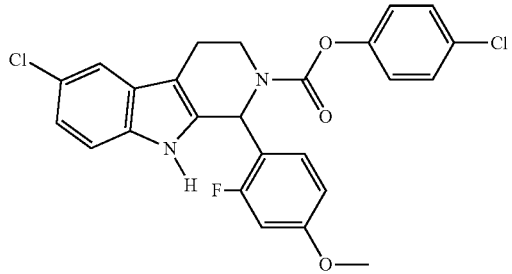
1276
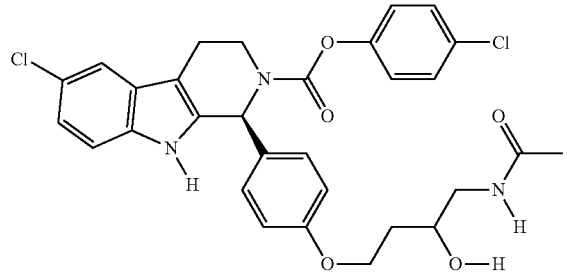
1277
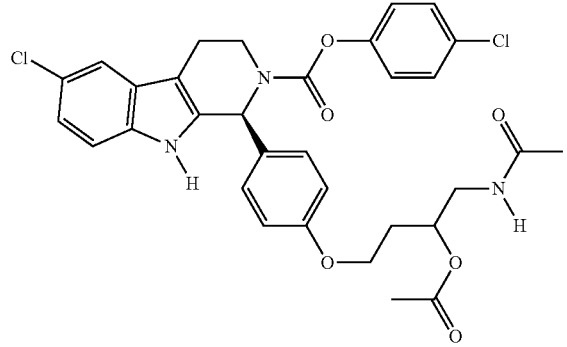

1278
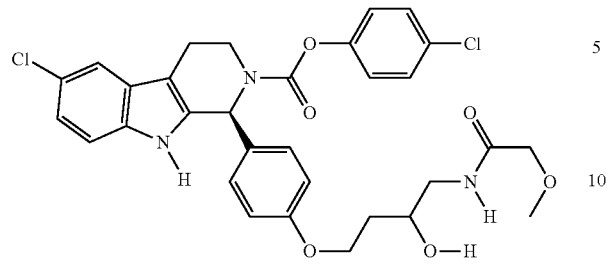
1288
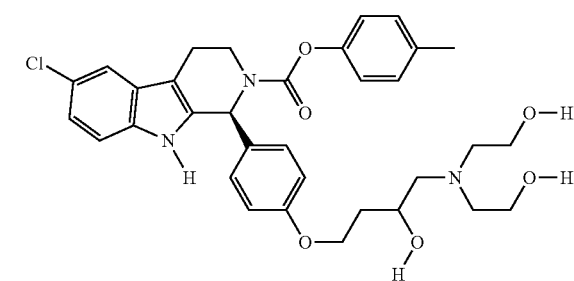
1279
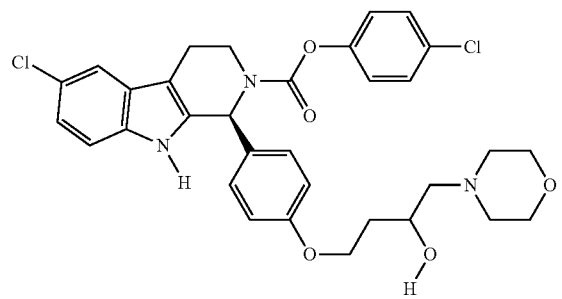
1289
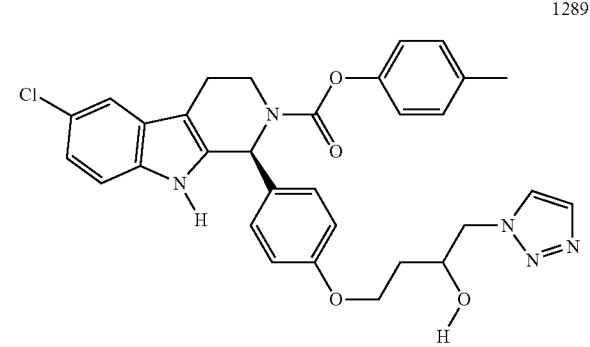
1280
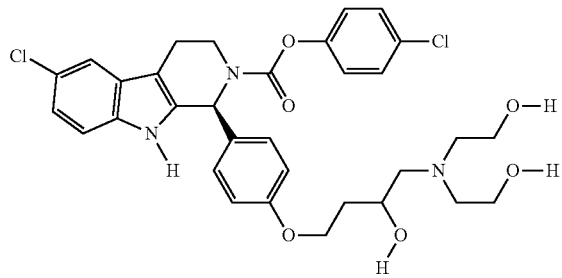
1290
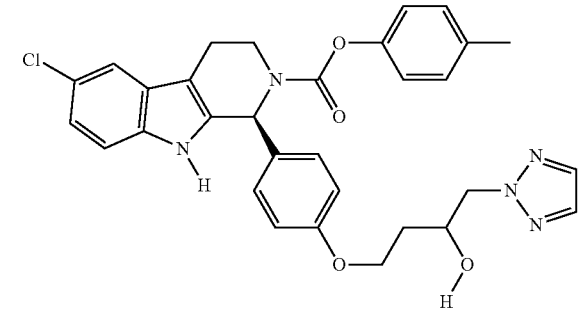
1281
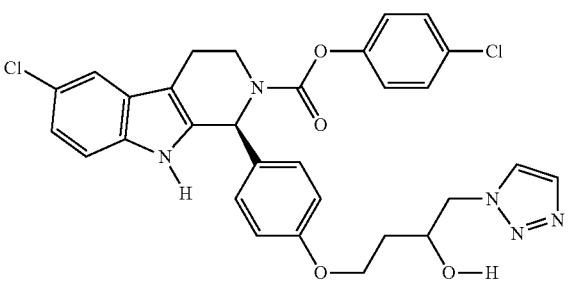
1291
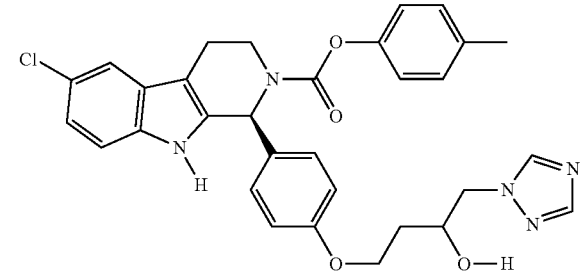
1282
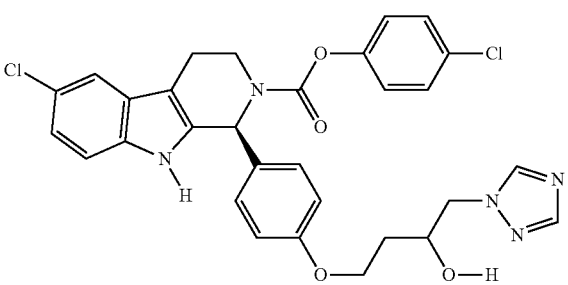
1292
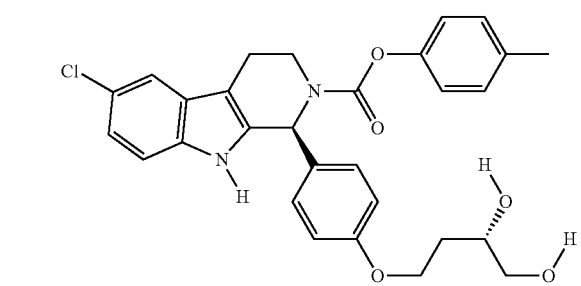

497
-continued
1293
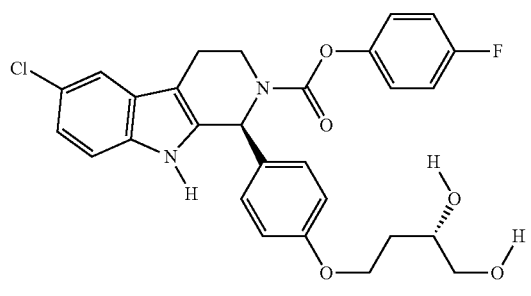
1297
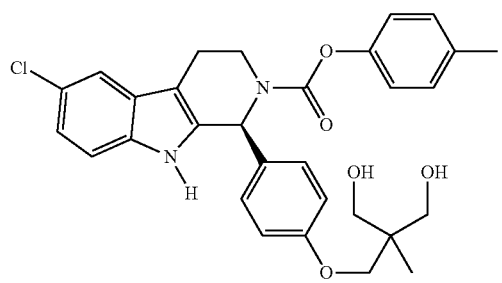
1299
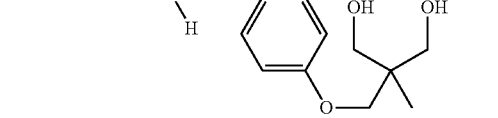
1300
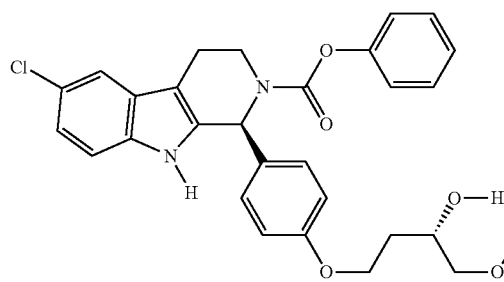
1301
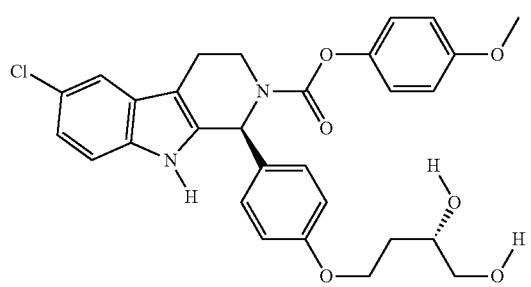
498
-continued
1302
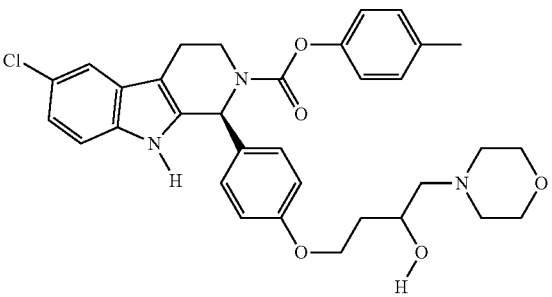
1328
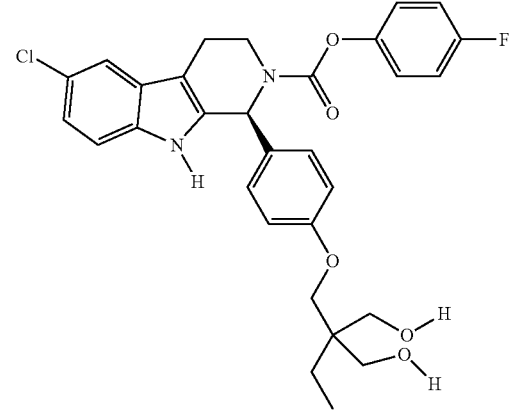
1329
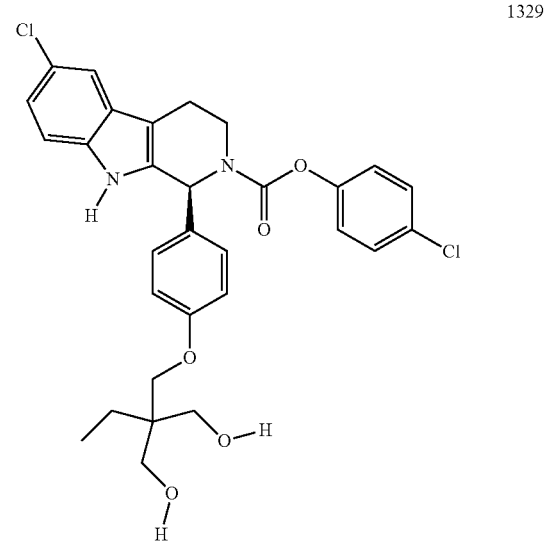

499
-continued
1330
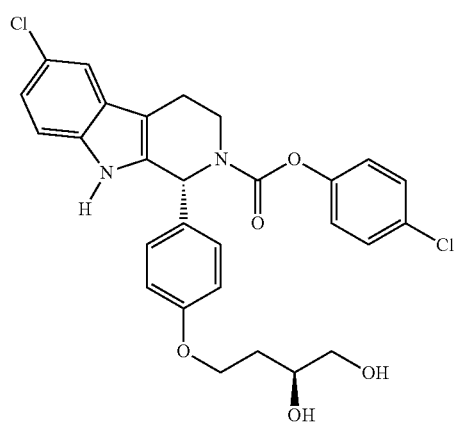
1331
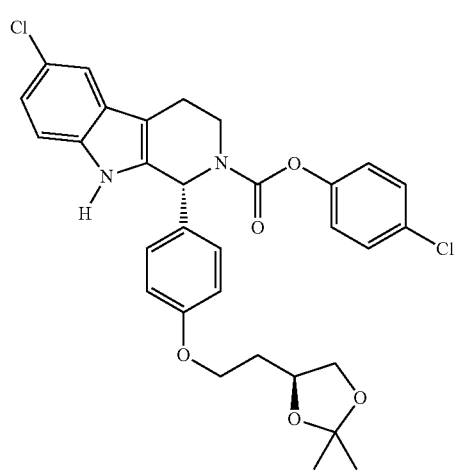
1332
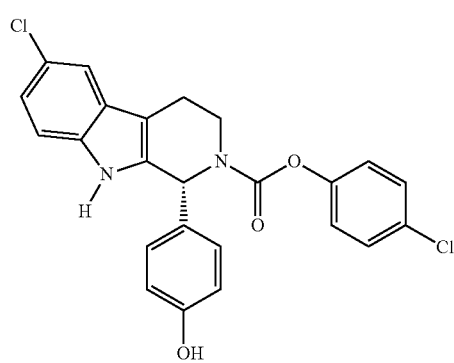
1333
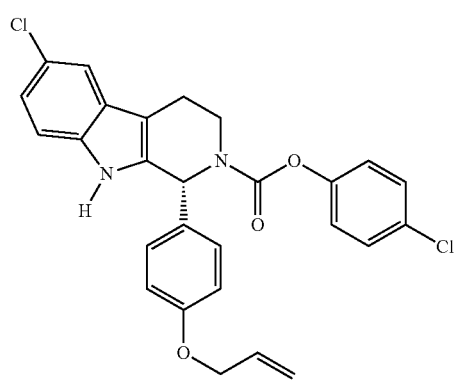
500
-continued
1335
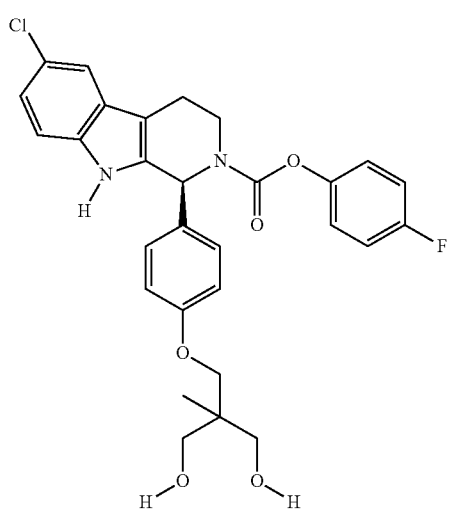
1336
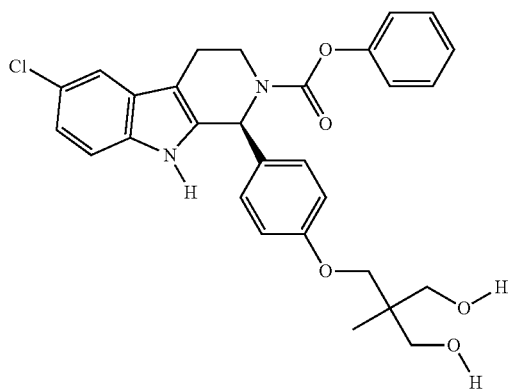
1337
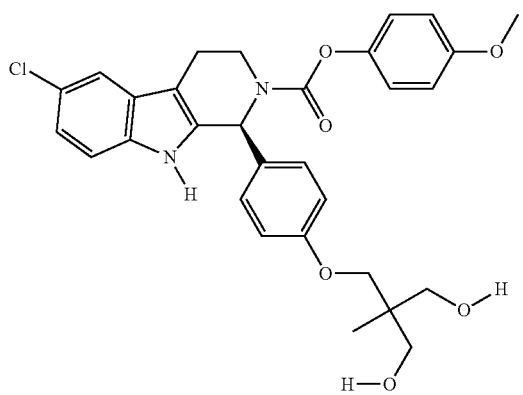

1343
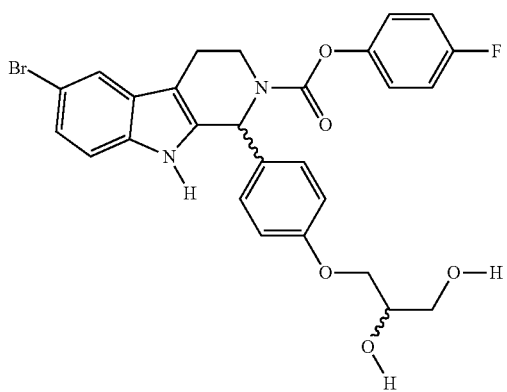
1344
1348
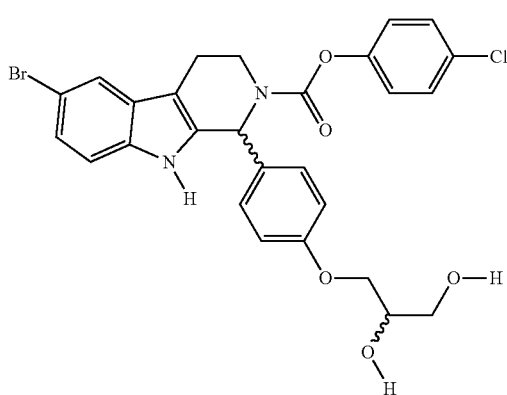
1349
1352
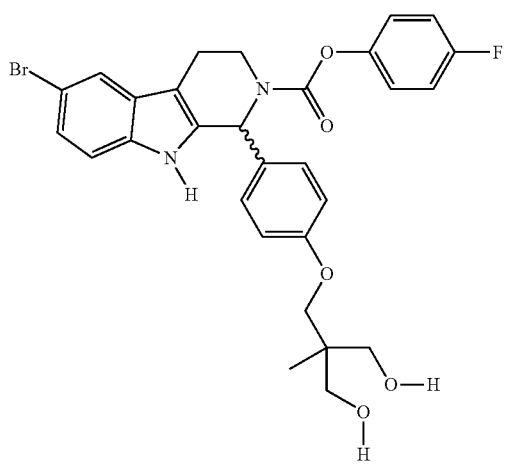
1353
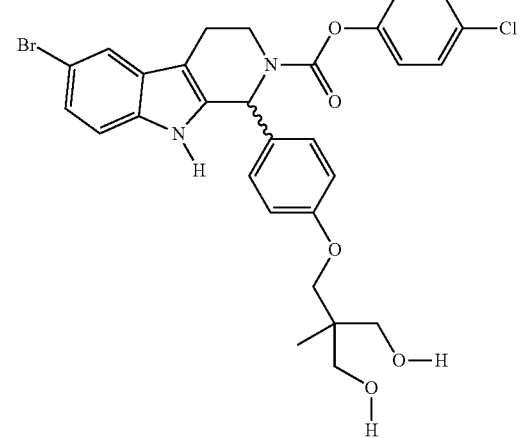
1357
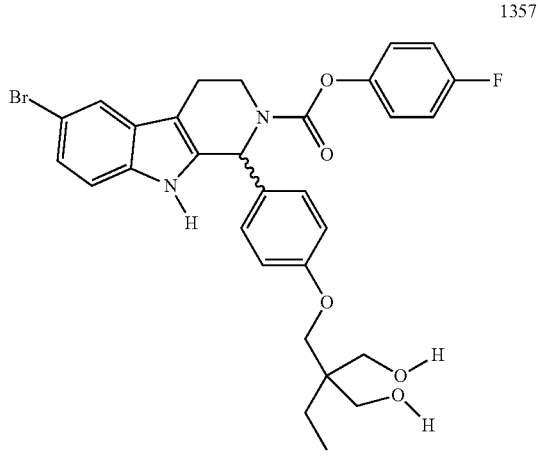

503
-continued
1358
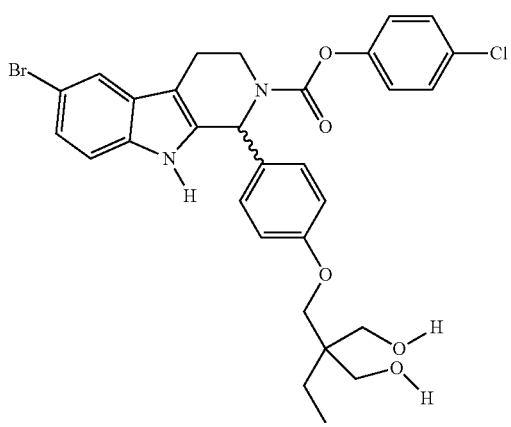
1361
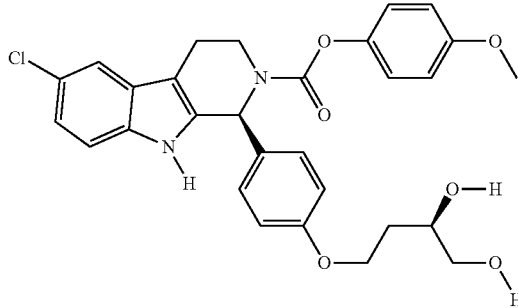
1362
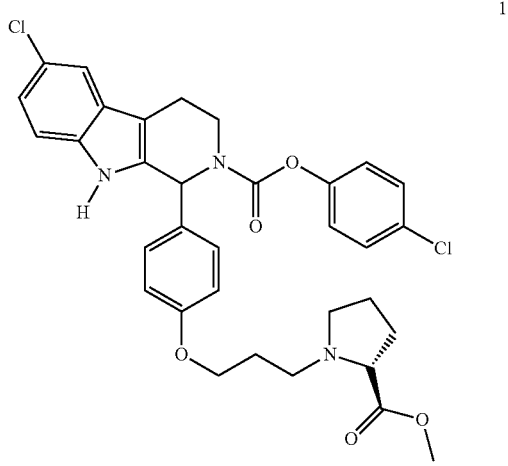
1364
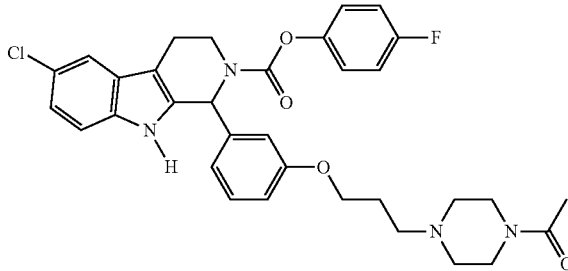
504
-continued
1391
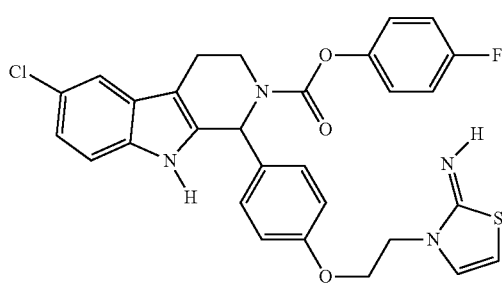
1392
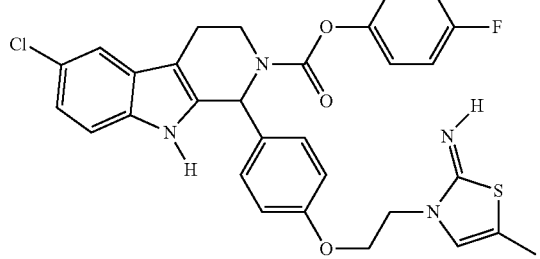
1393
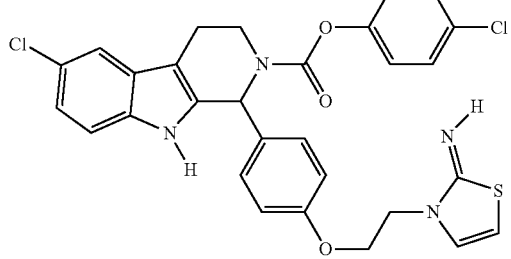
1394
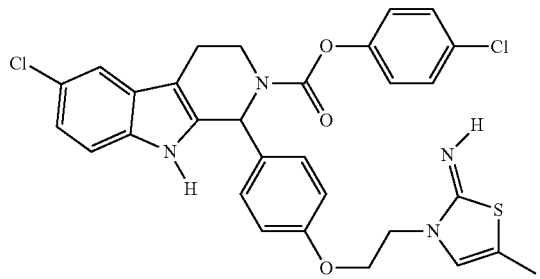
1413
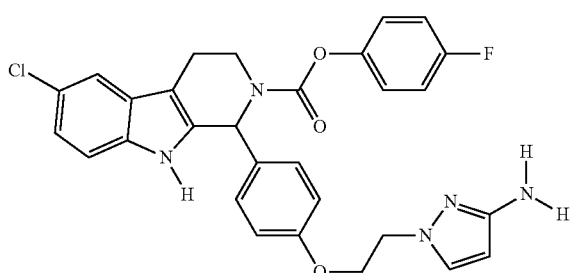

505
-continued
1414
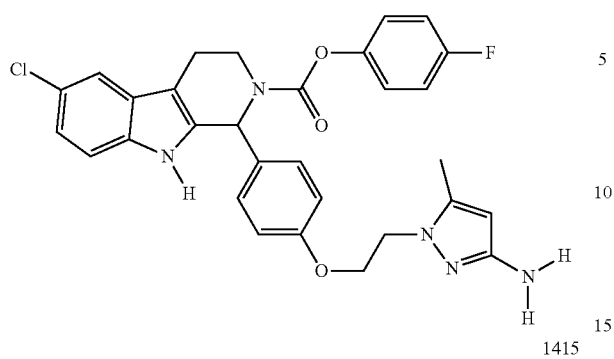
1415
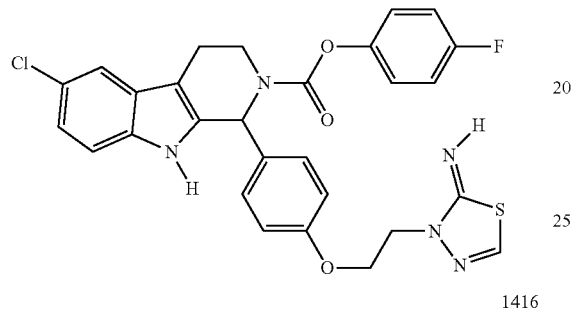
1416
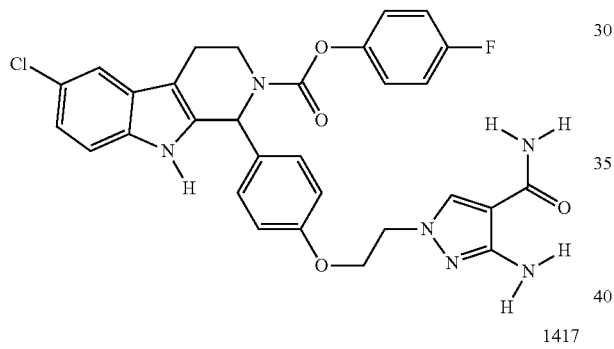
1417
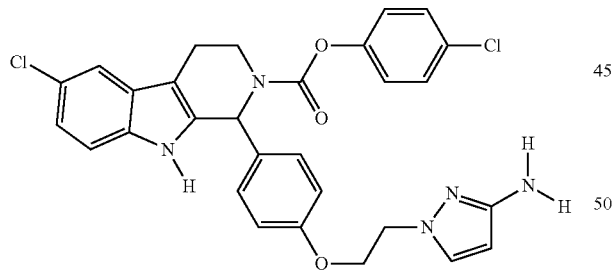
1418
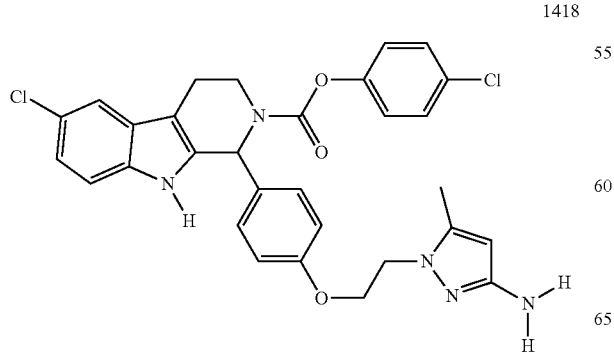
506
-continued
1419
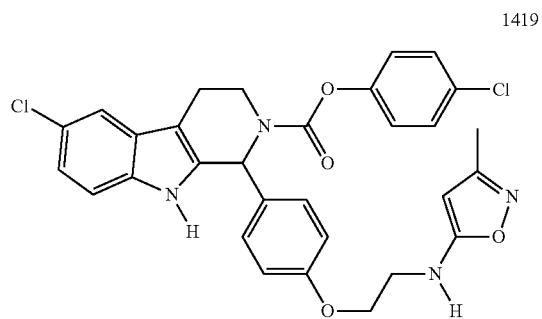
1420
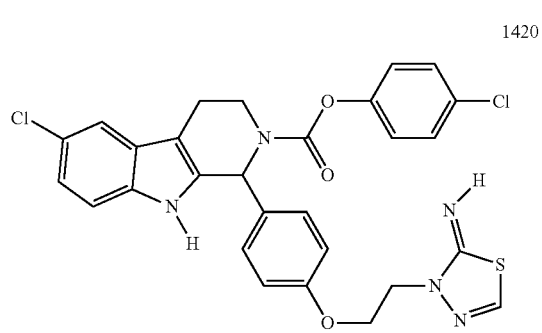
1421
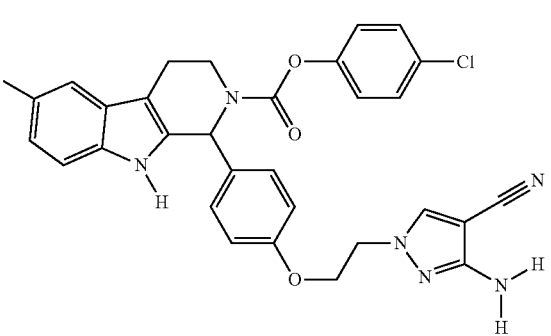
1422
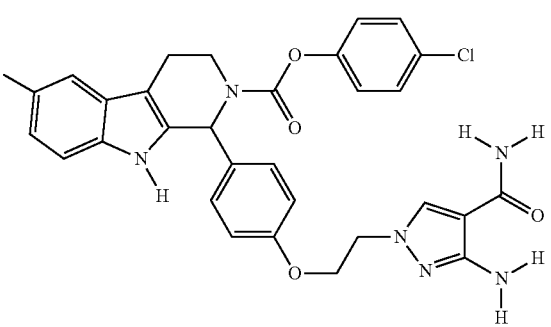

507
-continued
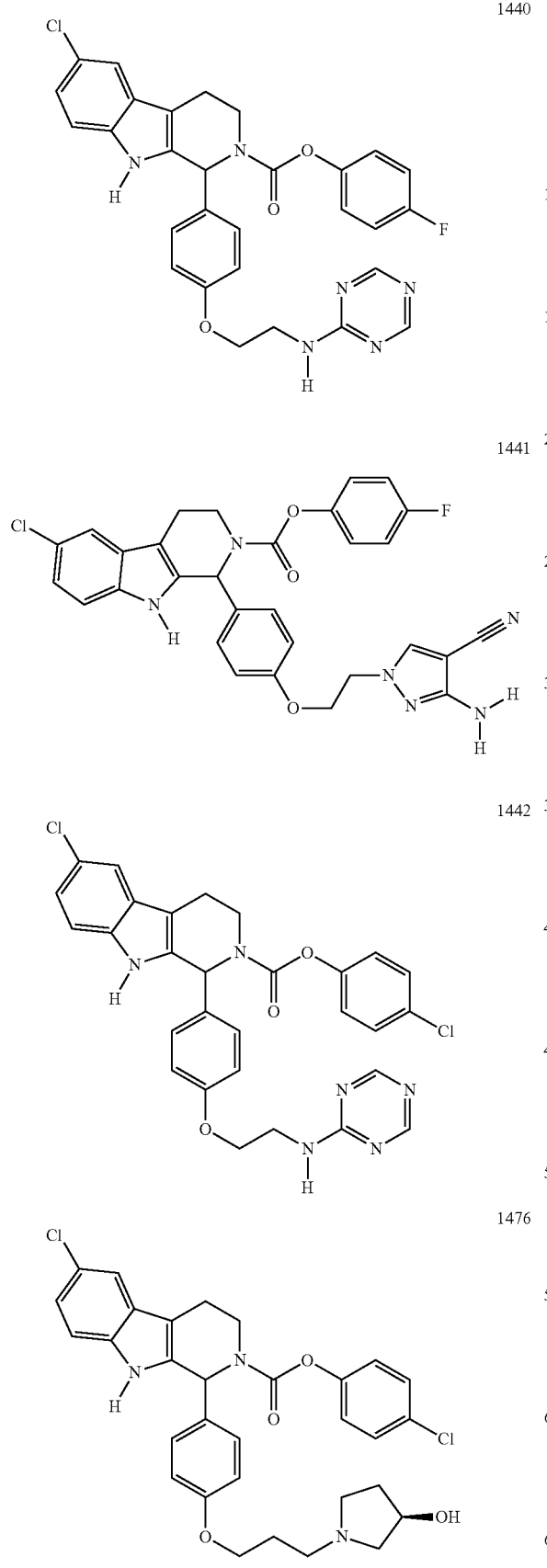
508
-continued
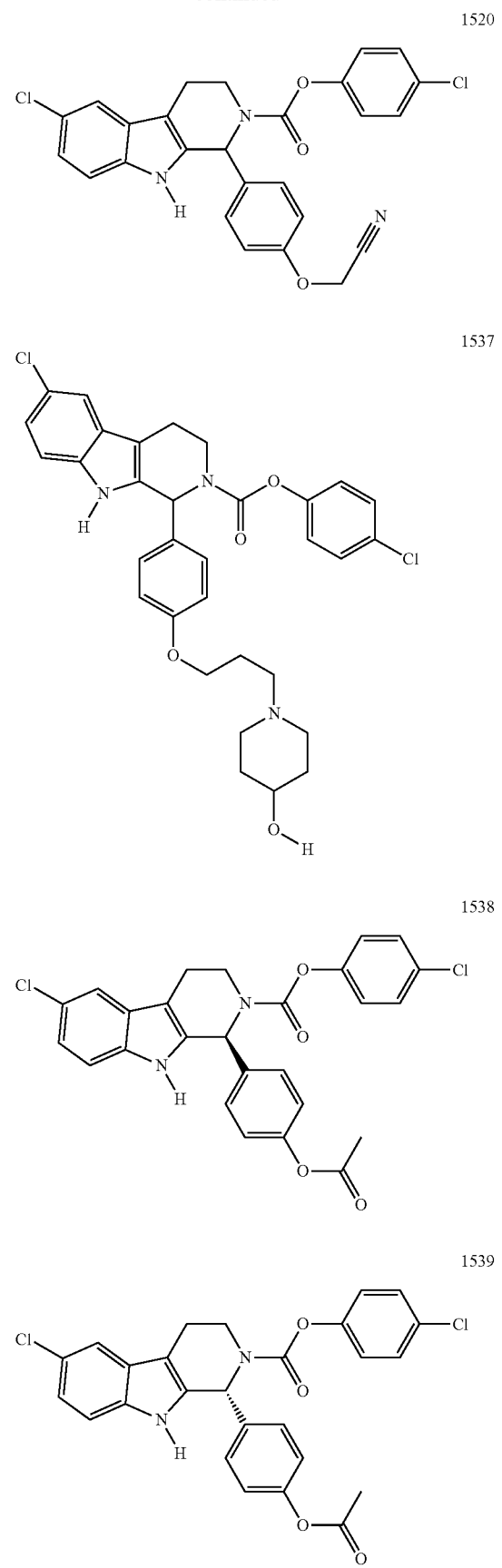

509
-continued
1546
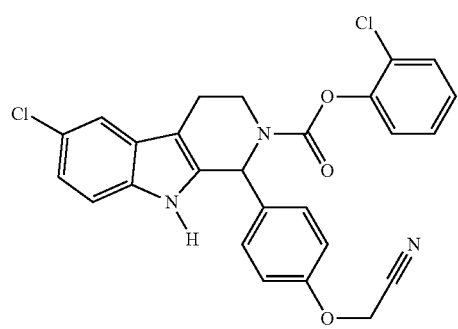
1547
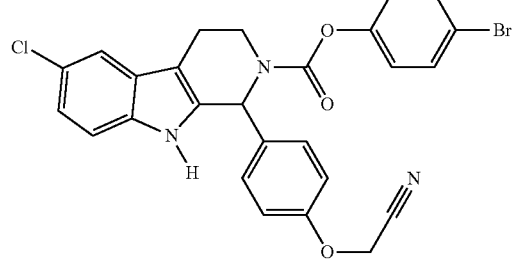
1548
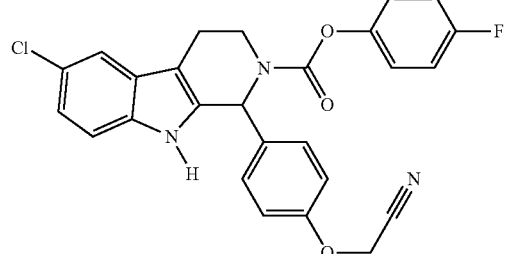
1549
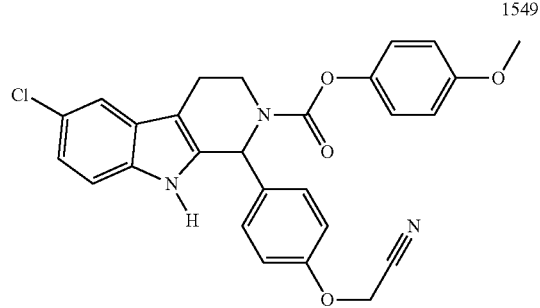
1551
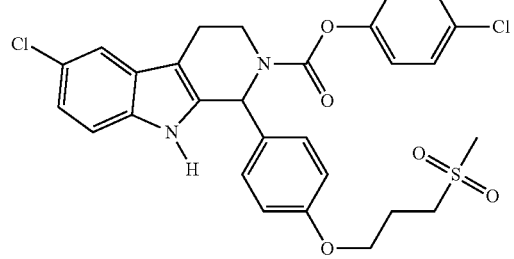
510
-continued
1552
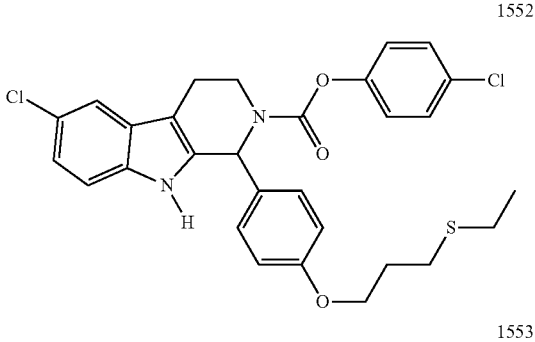
1553
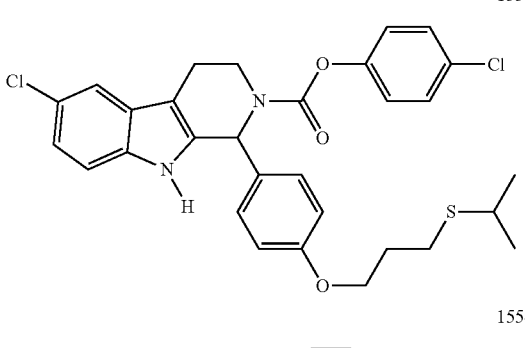
1554
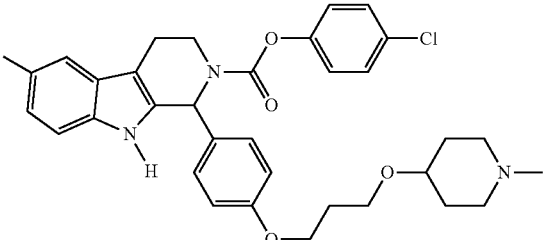
1555
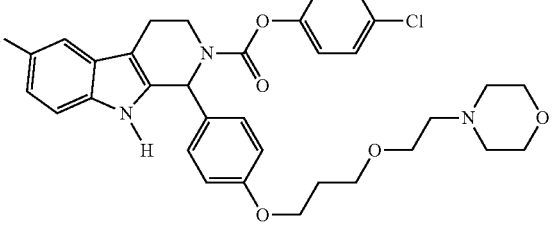
1557
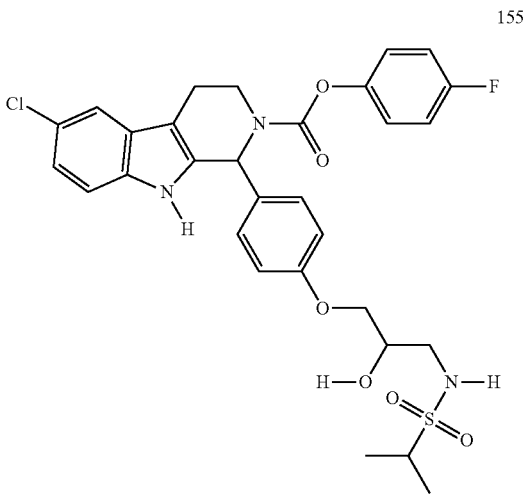

1558
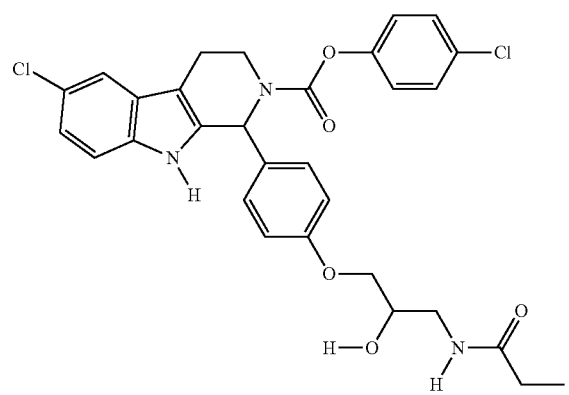
1559
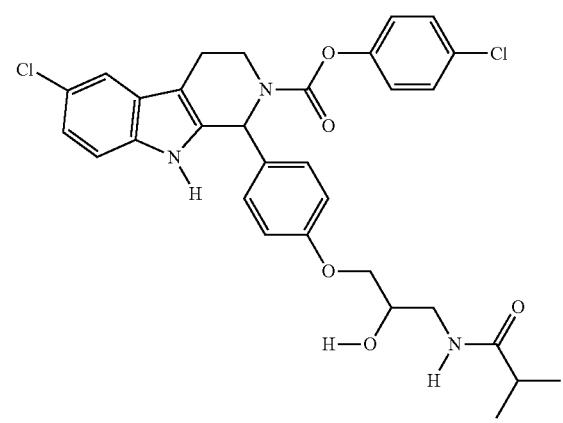
1560
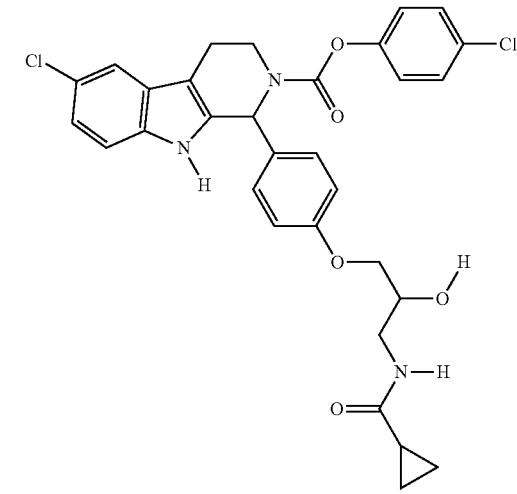
1561
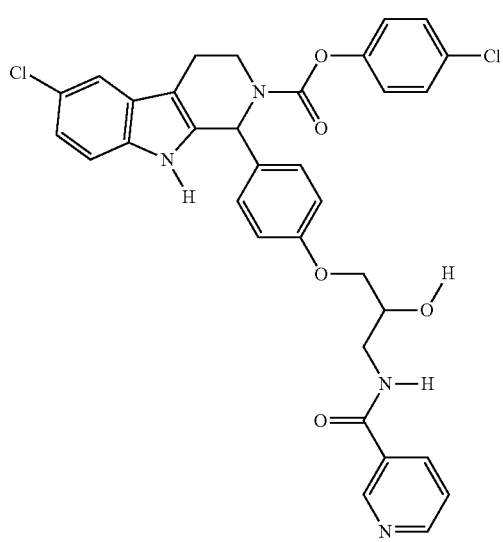
1562
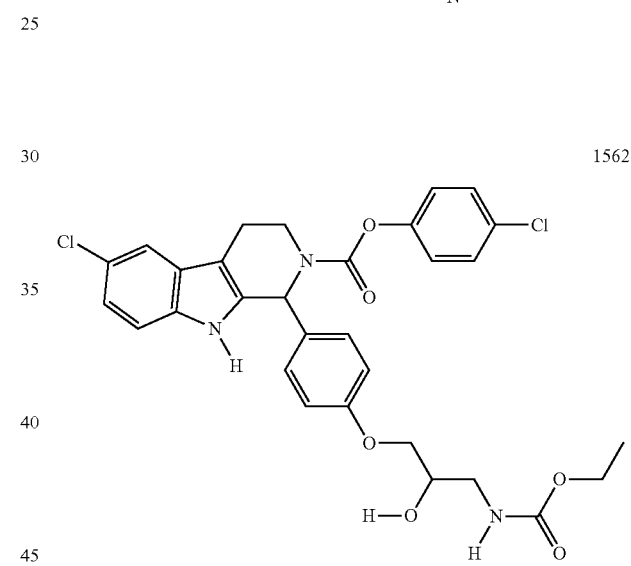
1563
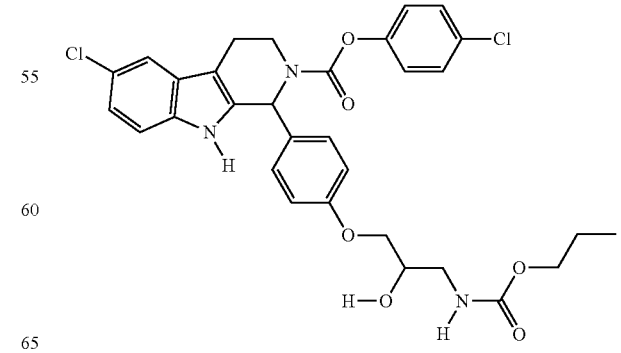

1564
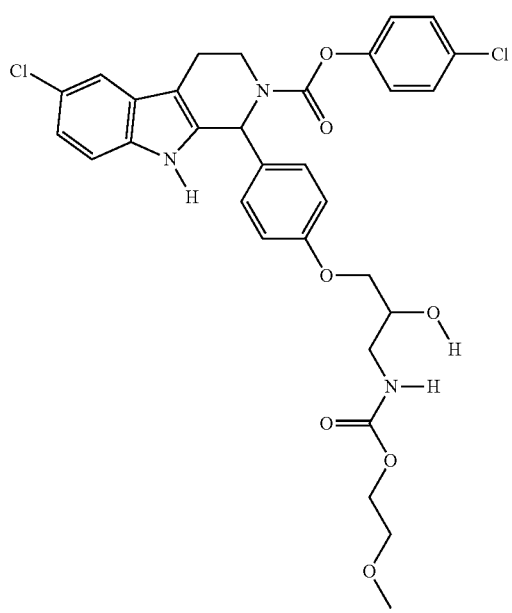
1565
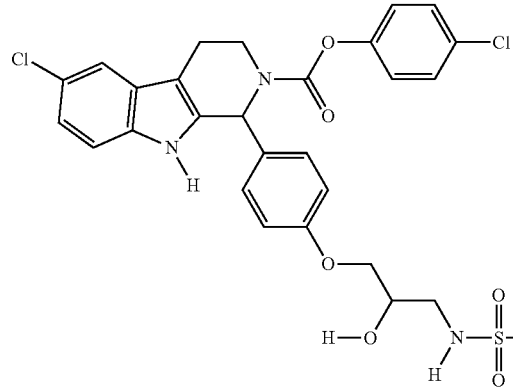
1566
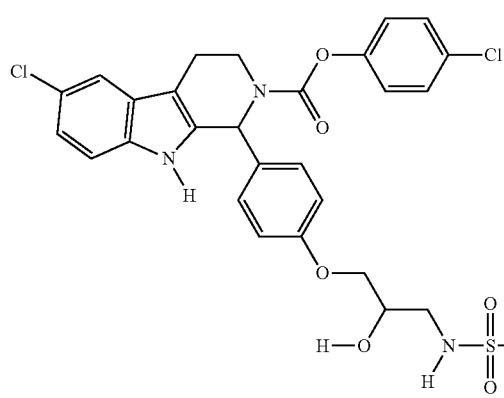
1567
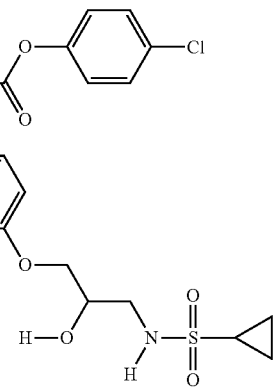
1568
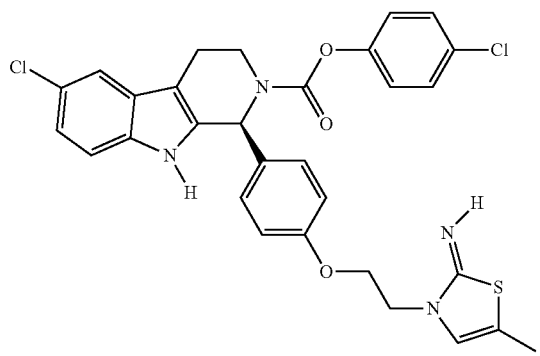
1569
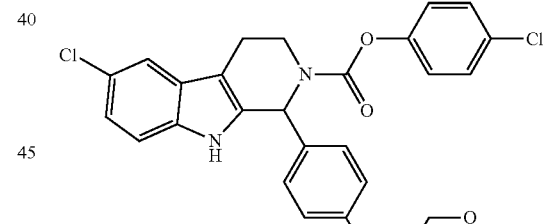
1570
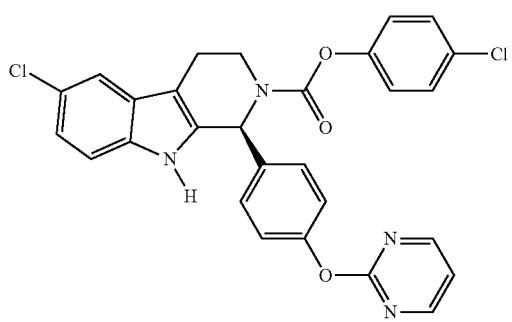

1571
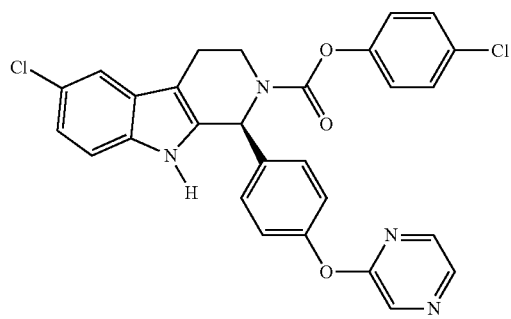
1572
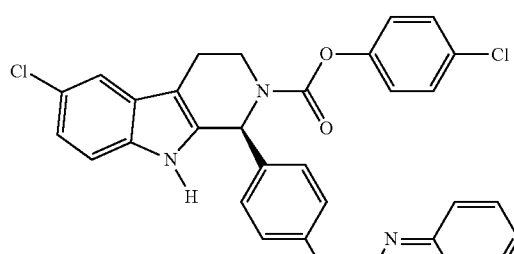
1577
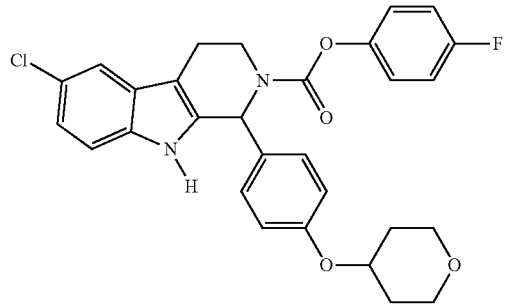
1578
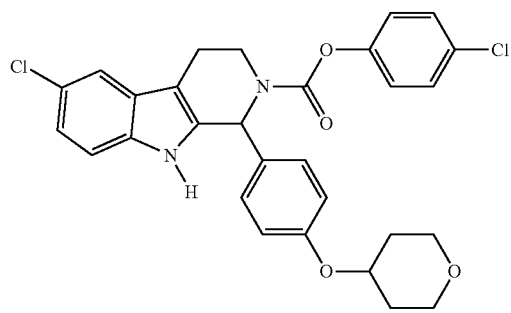
1580
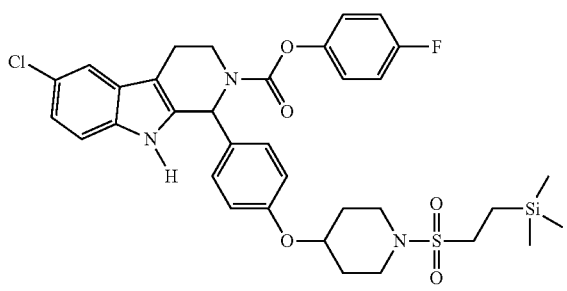
1581
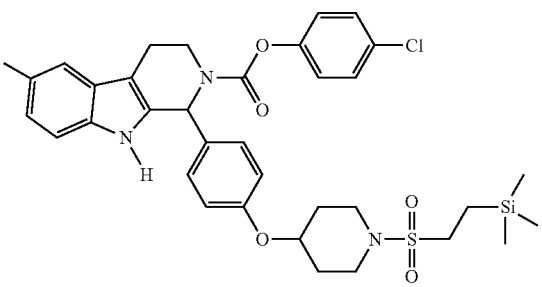
1604
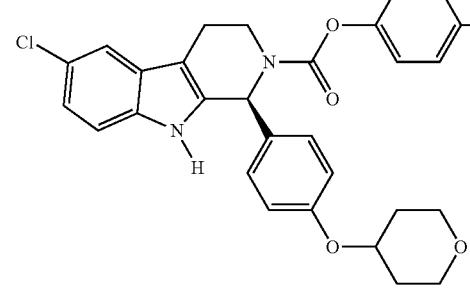
1605
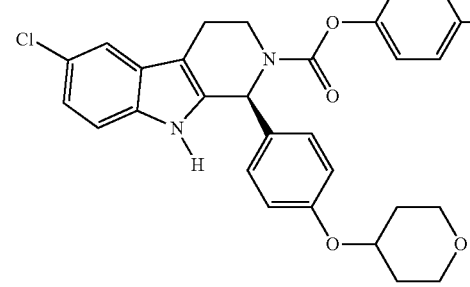
1607
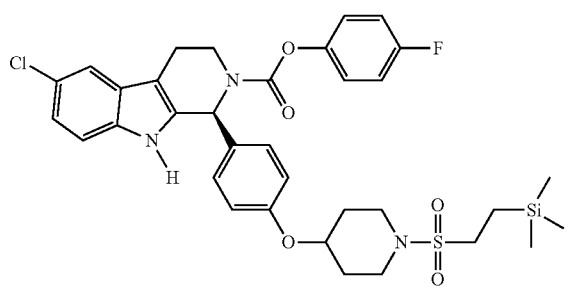

1611
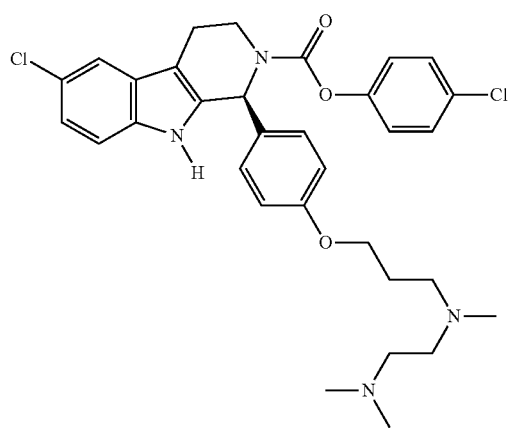
1612
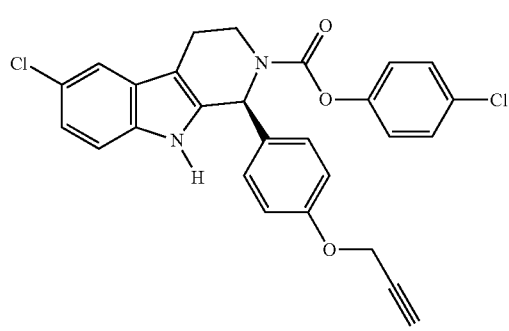
1613
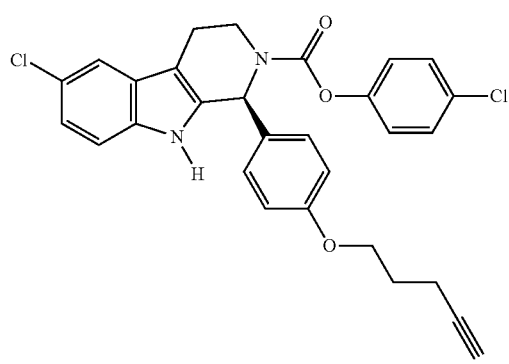
1614
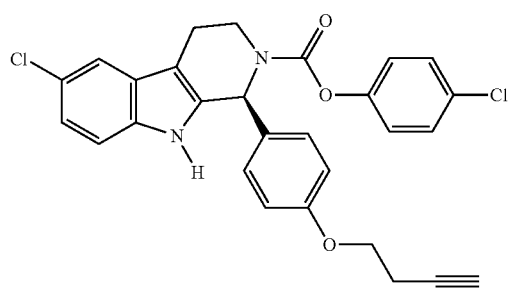
1625
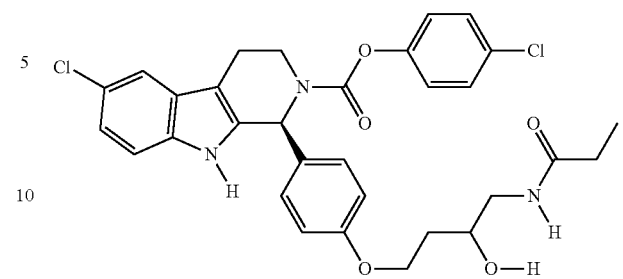
1626
1627
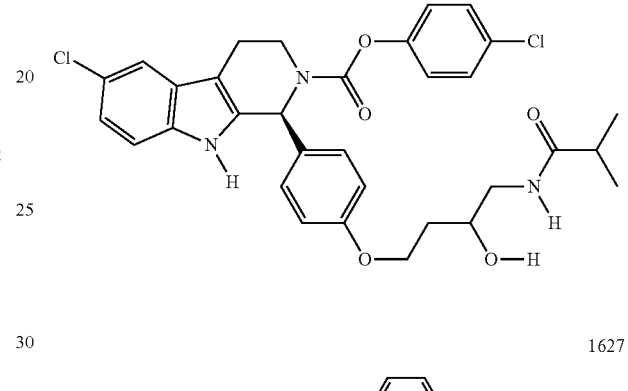
1628
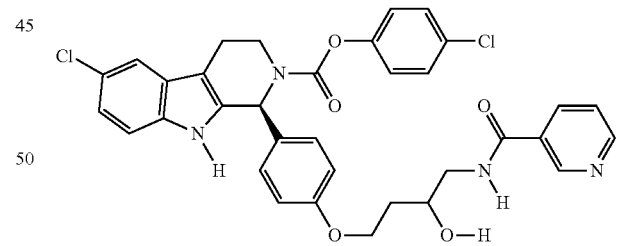
1629
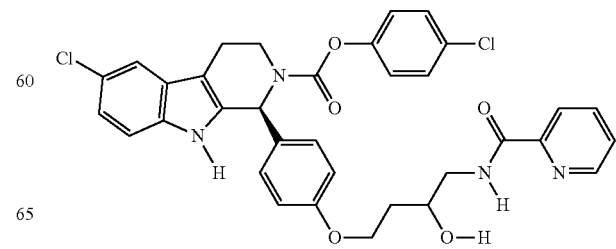

1635
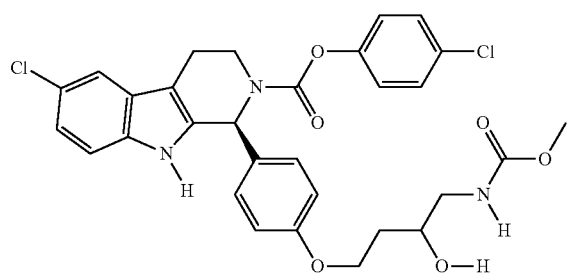
1636
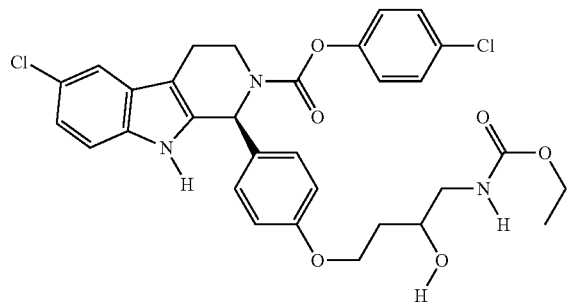
1637
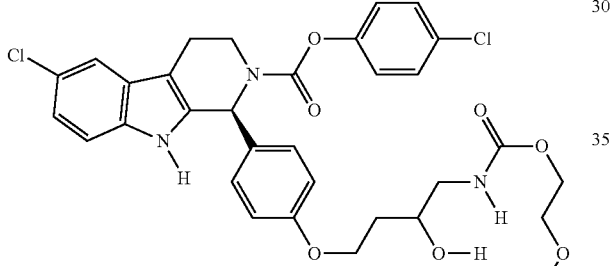
1638
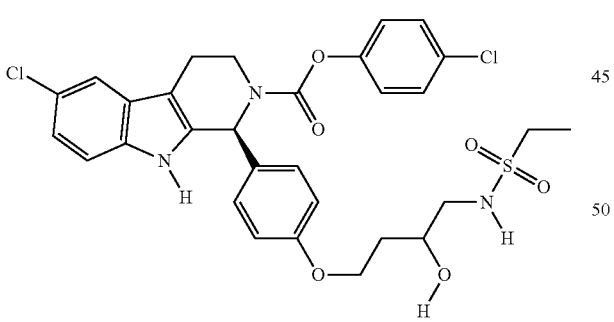
1639
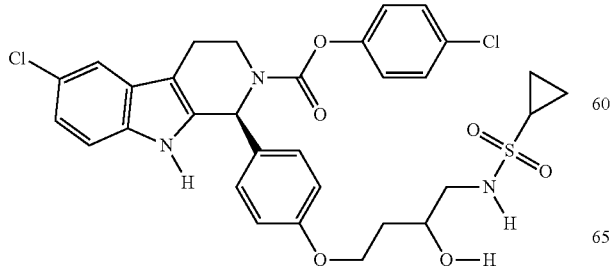
1640
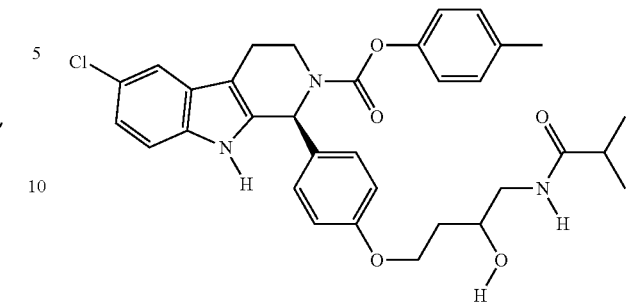
1641
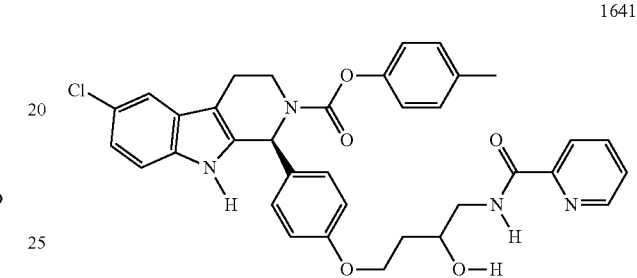
1642
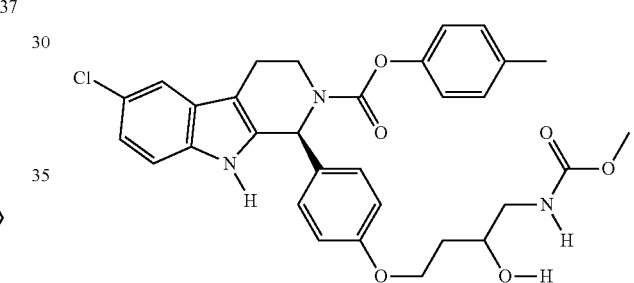
1643
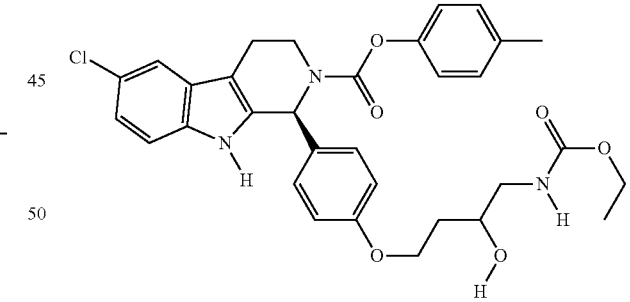
1644
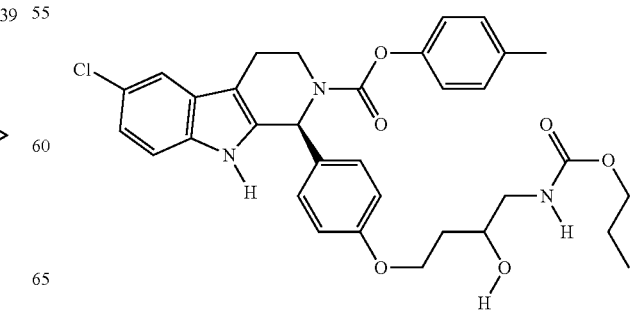

521
-continued
1645
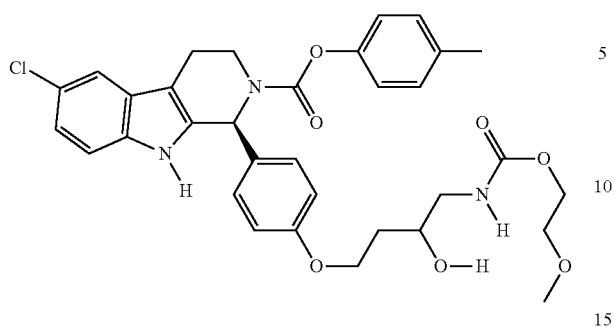
1646
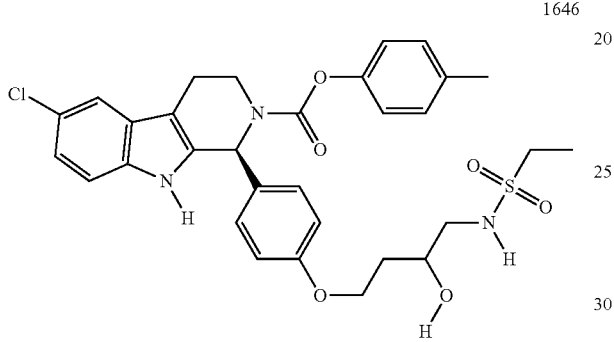
1647
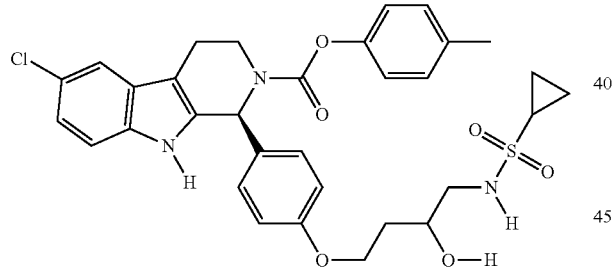
1648
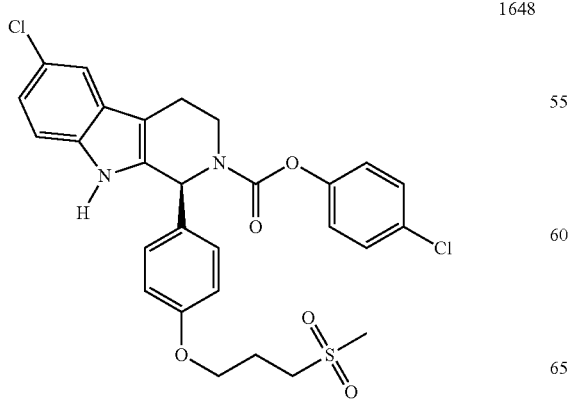
522
-continued
1652
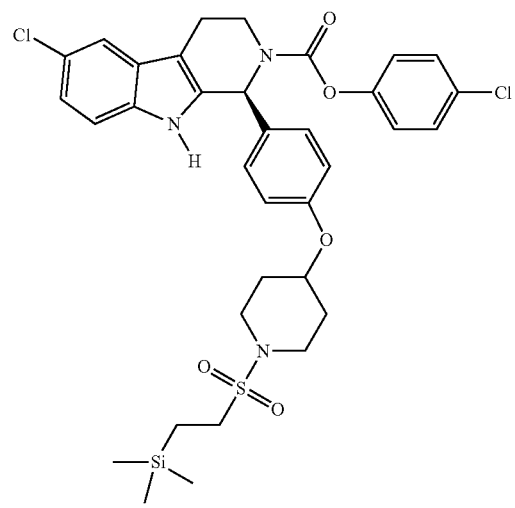
1658
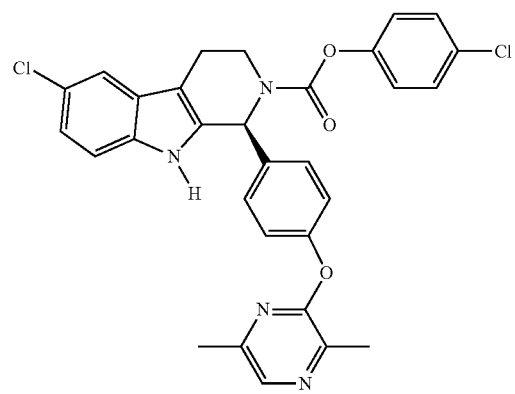
1659
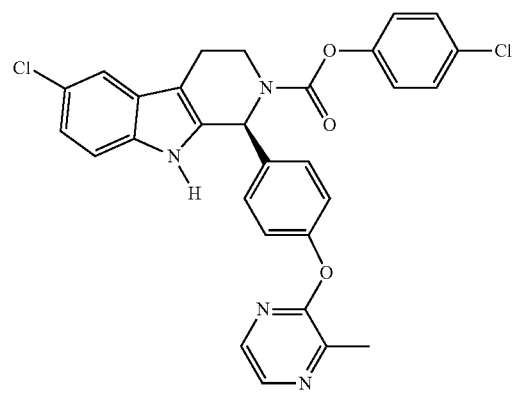

523
-continued
524
-continued
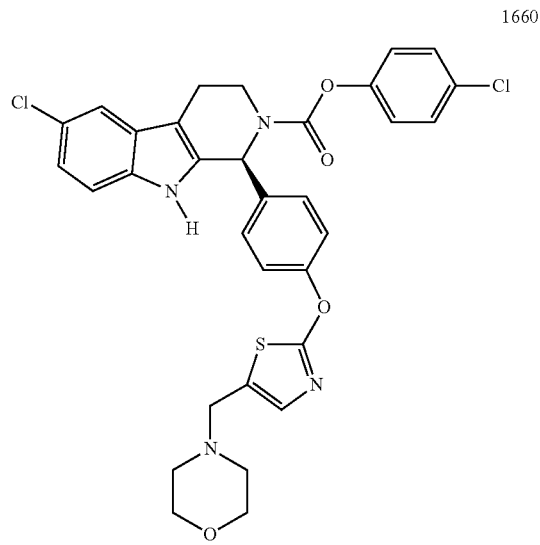
1660
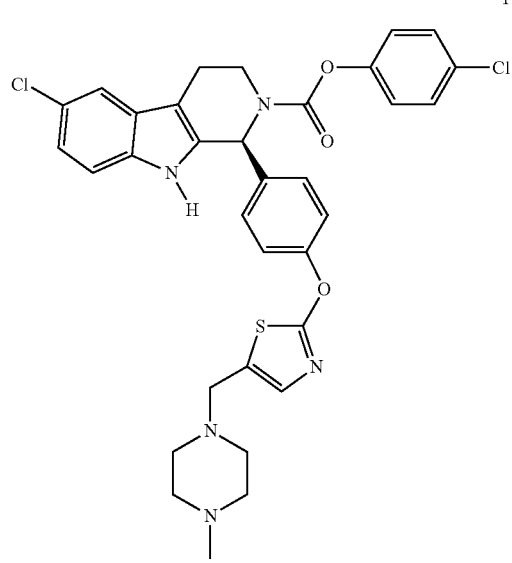
1661
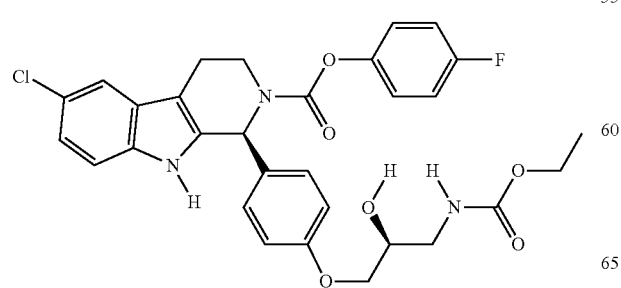
1663
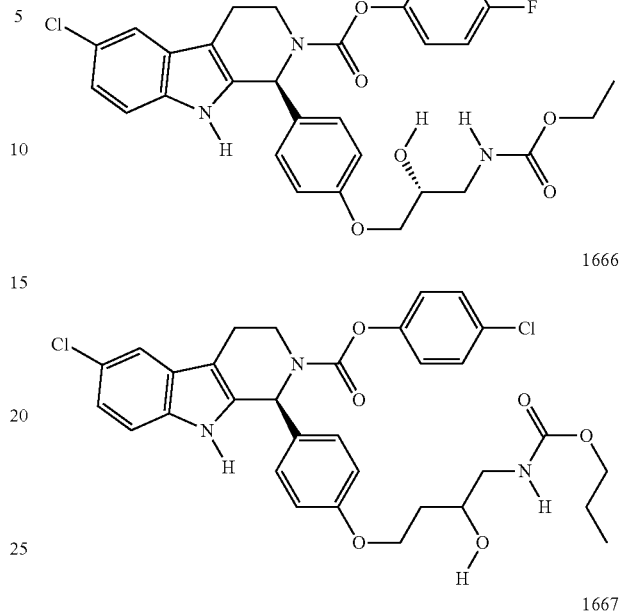
1664
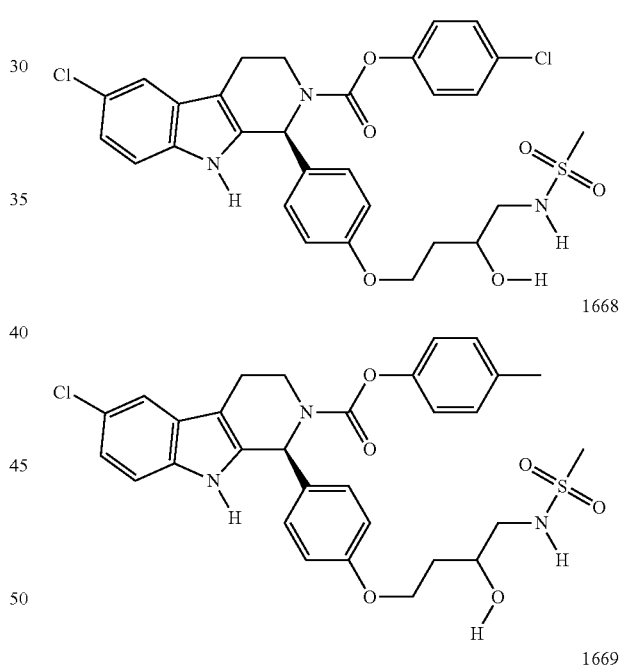
1666
1667
1668
1669
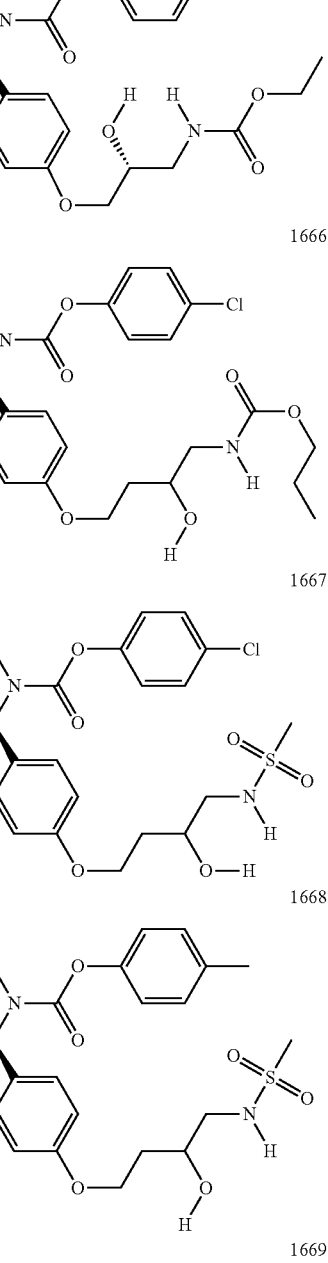
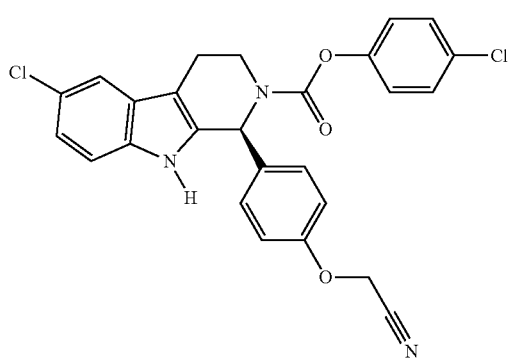

1671
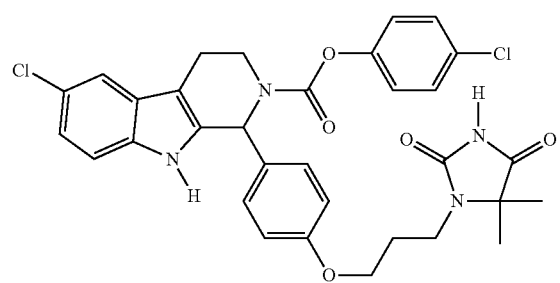
1672
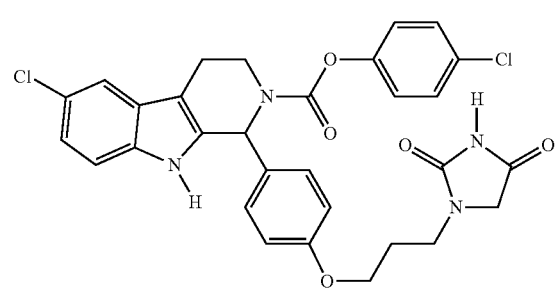
1673
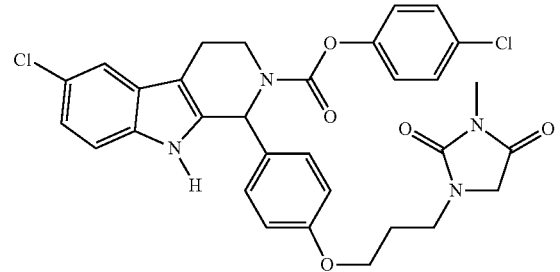
1674
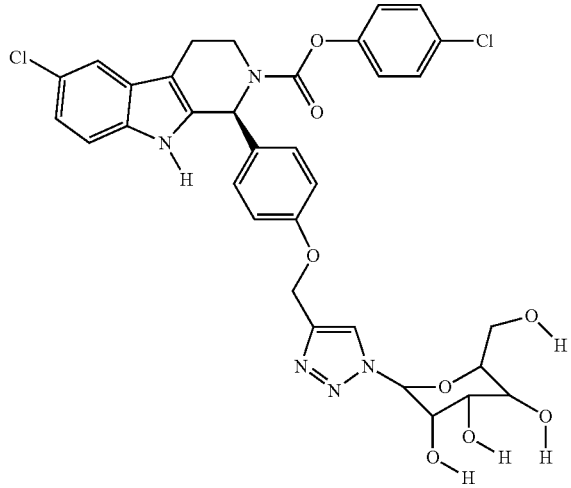
1675
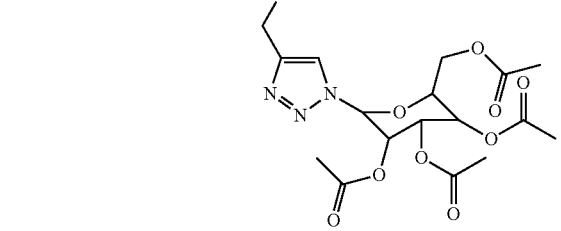
1676
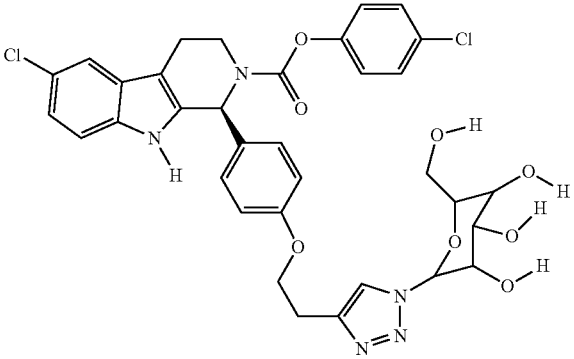
1677
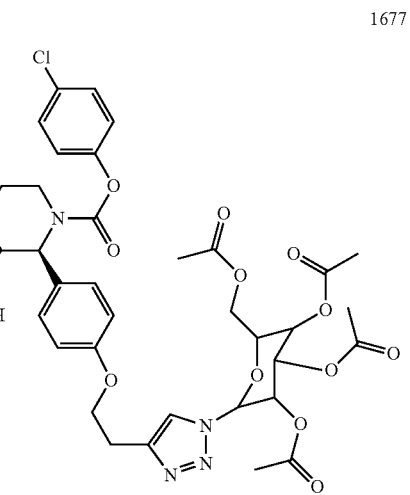

527
-continued
1681
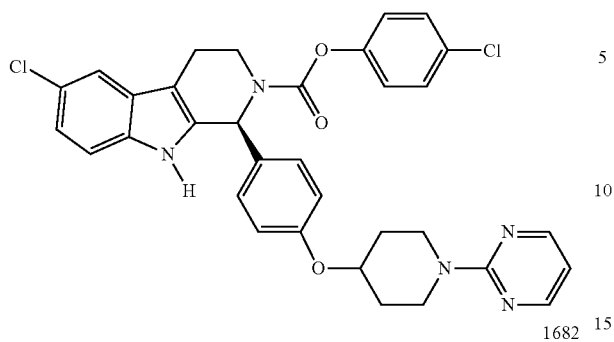
1682
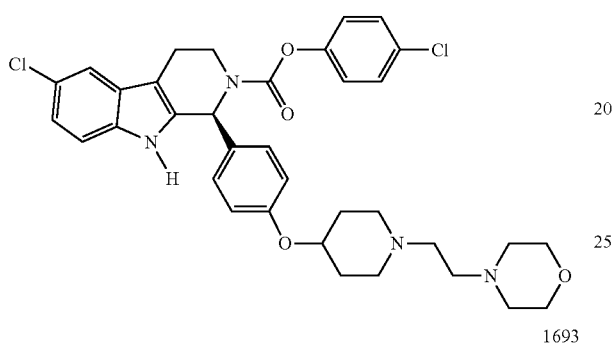
1693
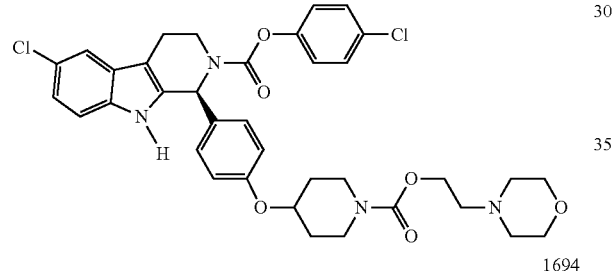
1694
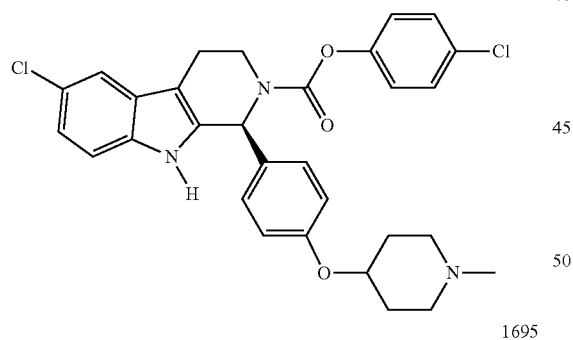
1695
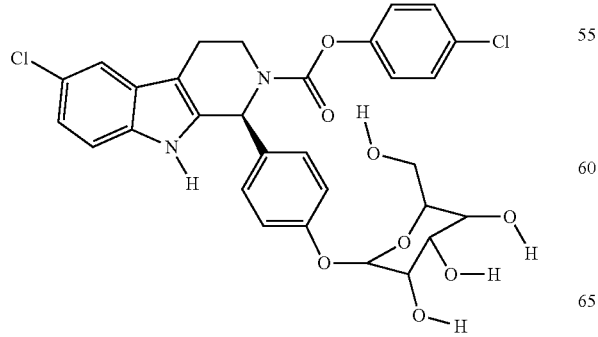
528
-continued
1698
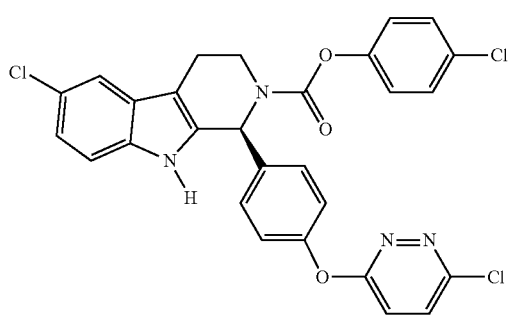
1701
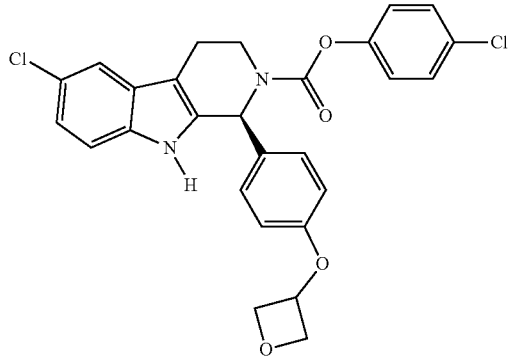
1702
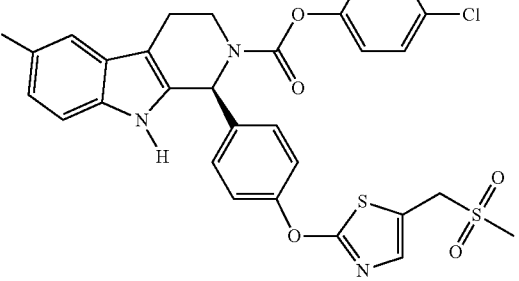
1703
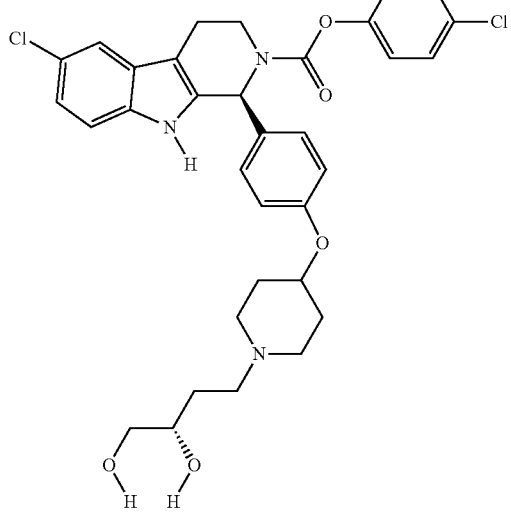

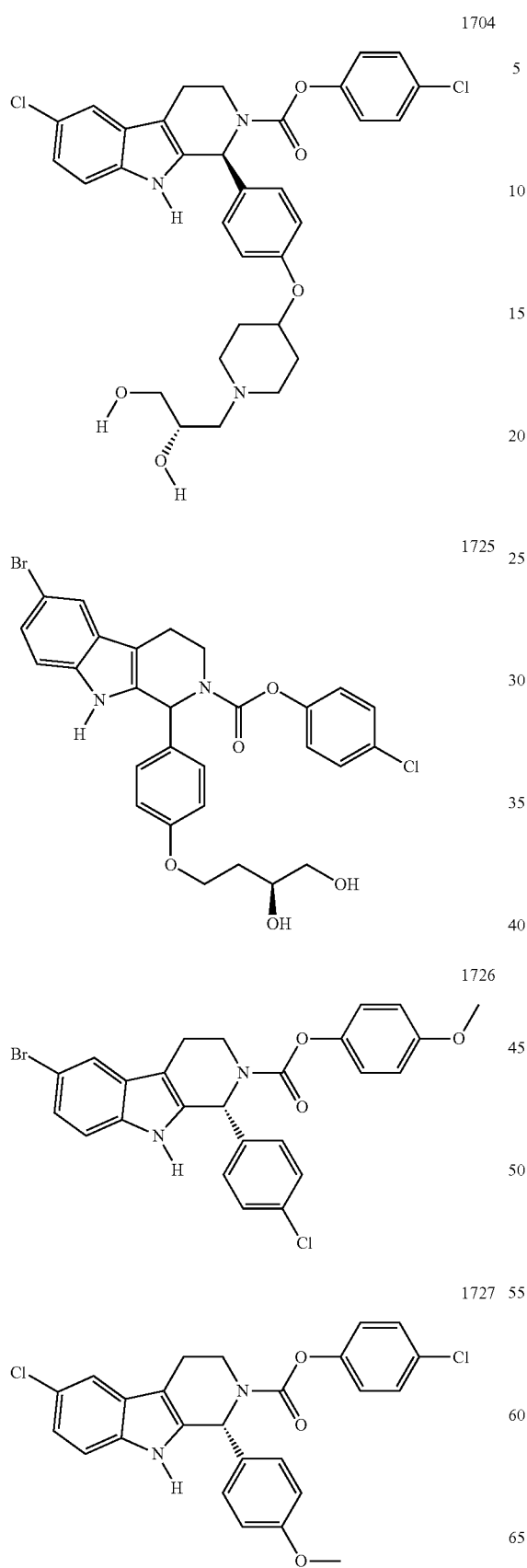
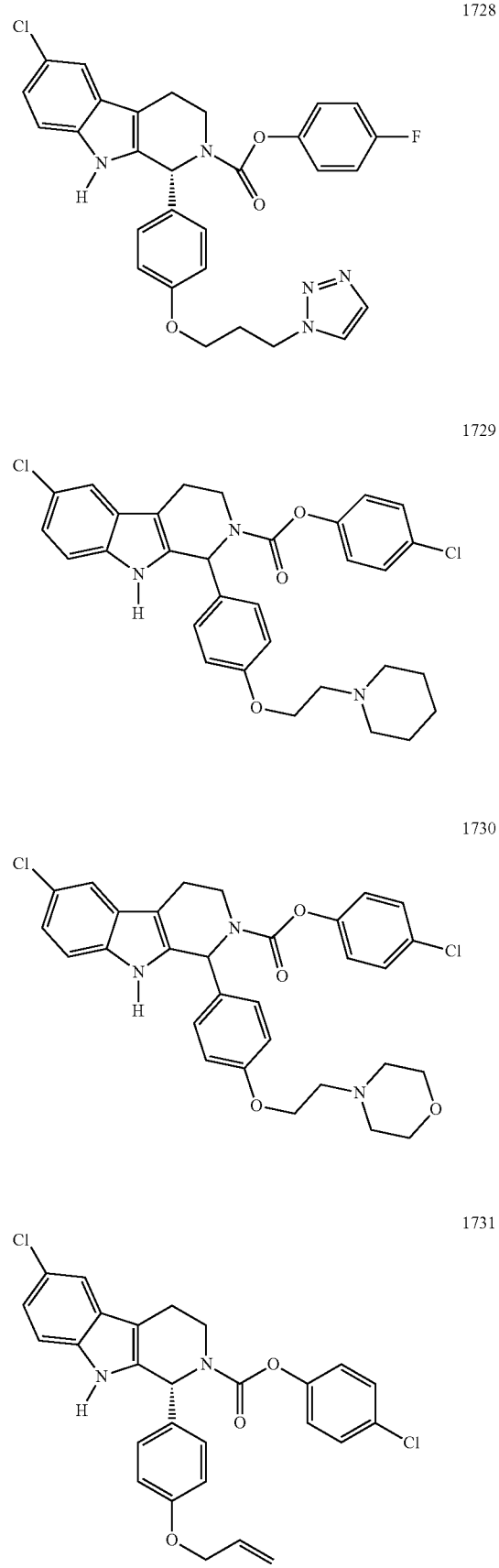

531
-continued
1732
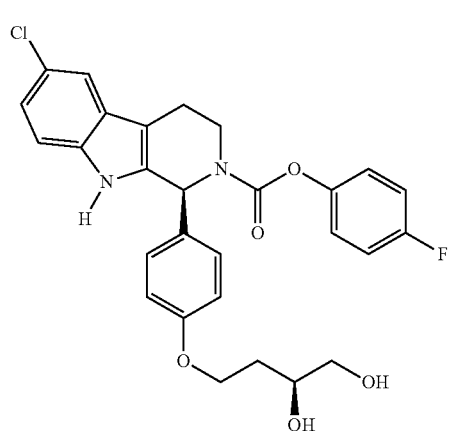
1733
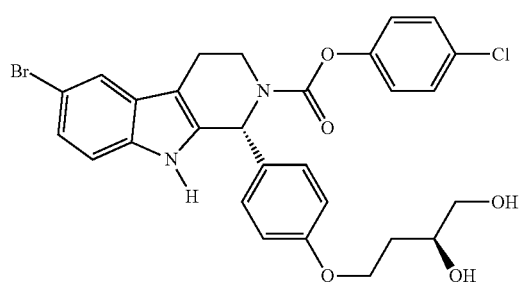
1734
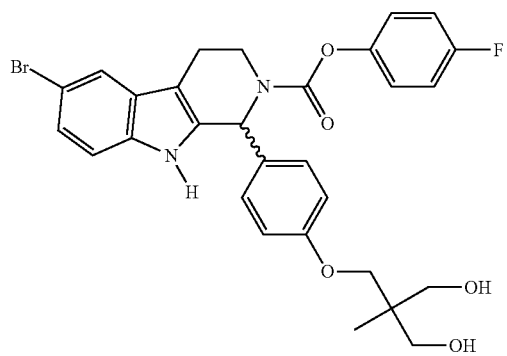
1735
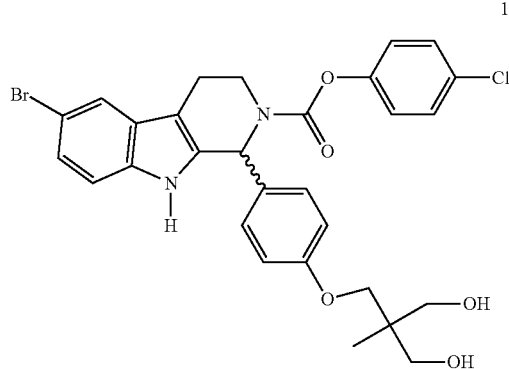
532
-continued
1736
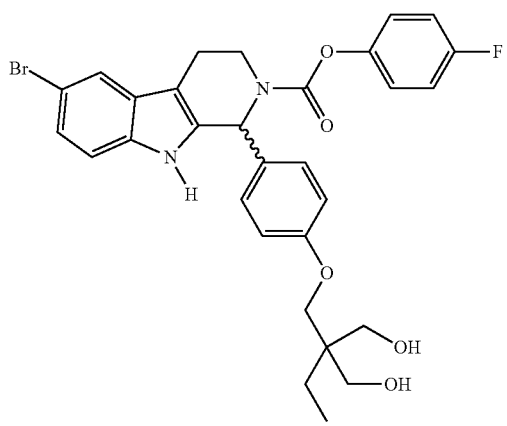
1737
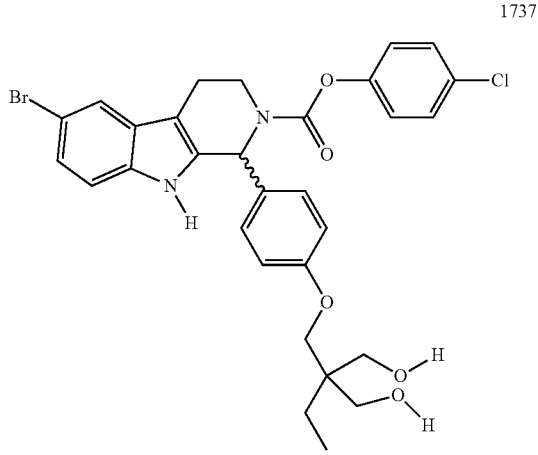
1738
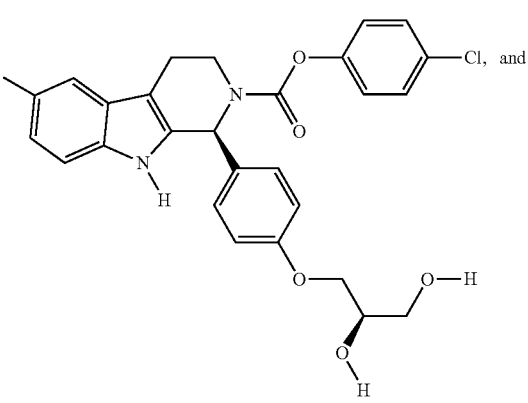, and -continued

1739

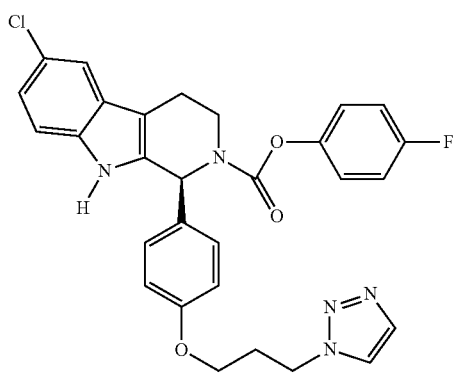

or a pharmaceutically acceptable salt, racemate or stereoisomer thereof;

wherein administering the compound to the human produces one or more of the results selected from the group consisting of:

(i) decrease in the number of previously existing KS lesions in the human relative to the number of KS lesions observed prior to administration of the compound;

(ii) decrease in the number of raised KS lesions in the human relative to the number of raised KS lesions observed prior to administration of the compound;

(iii) complete flattening of one or more previously raised KS lesions in the human; and (iv) decrease in the sum of perpendicular diameters of a KS lesion in the human, relative to the sum of perpendicular diameters in the KS lesion observed prior to administration of the compound.

18. The method of any one of claims 1 and 12-17, wherein said compound is a stereoisomer having a chiral carbon atom at the substituted carbon atom in the beta-position to the nitrogen atom of the five-membered ring of the tricyclic core, and said compound is an (S) stereoisomer at said chiral carbon atom.

* * * * *